US012734327B2

(12) United States Patent
Poltorak

(10) Patent No.: US 12,734,327 B2
(45) Date of Patent: Sep. 15, 2026

(54) SYSTEM AND METHOD OF IMPROVING SLEEP

(71) Applicant: Neuroenhancement Lab, LLC, Suffern, NY (US)

(72) Inventor: Alexander Poltorak, Monsey, NY (US)

(73) Assignee: NeuroLight, Inc., Pomona, NY (US)

( * ) Notice: Subject to any disclaimer, the term of this patent is extended or adjusted under 35 U.S.C. 154(b) by 1026 days.

(21) Appl. No.: 17/952,284

(22) Filed: Sep. 25, 2022

(65) Prior Publication Data

US 2023/0048571 A1 Feb. 16, 2023

Related U.S. Application Data

(63) Continuation of application No. 16/572,153, filed on Sep. 16, 2019, now Pat. No. 11,452,839.

(Continued)

(51) Int. Cl.

| | |
|---|---|
| ***A61M 21/02*** | (2006.01) |
| ***A61B 5/00*** | (2006.01) |
| ***A61B 5/369*** | (2021.01) |
| ***A61B 5/372*** | (2021.01) |
| ***A61M 21/00*** | (2006.01) |
| ***A61N 1/04*** | (2006.01) |
| ***A61N 1/05*** | (2006.01) |
| ***A61N 1/36*** | (2006.01) |
| ***A61N 2/00*** | (2006.01) |
| ***A61N 5/06*** | (2006.01) |
| ***G16H 20/30*** | (2018.01) |

(Continued)

(52) U.S. Cl.

CPC ............. *A61M 21/02* (2013.01); *A61B 5/372* (2021.01); *A61B 5/4809* (2013.01); *A61B 5/0006* (2013.01)

(58) Field of Classification Search

CPC .......... A61M 21/02; A61M 2021/0016; A61M 2021/0022; A61M 2021/0044; A61M 2021/005; A61M 2021/0055; A61M 2021/0072; A61M 2230/60; A61M 2021/0027; A61M 2021/0077; A61M 2205/507; A61M 2230/08; A61M 2230/10; A61B 5/372; A61B 5/4809; A61B 5/0006; A61B 5/369; A61B 5/4812; A61N 1/36025; A61N 1/36031; A61N 2/006; A61N 5/0618; A61N 1/0456; A61N 1/0526; G16H 20/30; G16H 50/20; G16H 70/60

See application file for complete search history.

(56) References Cited

U.S. PATENT DOCUMENTS

| | | | |
|---|---|---|---|
| 3,951,134 | A | 4/1976 | Malech |
| 4,172,014 | A | 10/1979 | Sequeira, Jr. et al. |

(Continued)

FOREIGN PATENT DOCUMENTS

| | | |
|---|---|---|
| EP | 1304073 | 4/2003 |
| WO | WO2000025668 A1 | 9/2003 |
| WO | WO2001087153 A1 | 9/2003 |

*Primary Examiner* — Carrie R Dorna
*Assistant Examiner* — Joshua Daryl D Lannu
(74) *Attorney, Agent, or Firm* — Hoffberg & Associates; Steven M. Hoffberg

(57) ABSTRACT

A method of transplanting a sleep state of a first subject (donor) to a second subject (recipient) comprising: capturing a sleep state of the first subject represented by brain activity patterns; and transplanting the sleep state of the first subject in the second subject by inducing the brain activity patterns in the second subject.

20 Claims, 10 Drawing Sheets

Related U.S. Application Data

(60) Provisional application No. 62/731,674, filed on Sep. 14, 2018.

(51) Int. Cl.
*G16H 50/20* (2018.01)
*G16H 70/60* (2018.01)

(56) References Cited

U.S. PATENT DOCUMENTS 4,296,756 A 10/1981 Dunning et al.
4,367,527 A 1/1983 Desjacques
4,407,299 A 10/1983 Culver
4,408,616 A 10/1983 Duffy et al.
4,421,122 A 12/1983 Duffy
4,437,064 A 3/1984 Overton, Jr. et al.
4,493,327 A 1/1985 Bergelson et al.
4,550,736 A 11/1985 Broughton et al.
4,557,270 A 12/1985 John
4,562,540 A 12/1985 Devaney
4,579,125 A 4/1986 Strobl et al.
4,583,190 A 4/1986 Salb
4,585,011 A 4/1986 Broughton et al.
4,591,787 A 5/1986 Hoenig
4,594,662 A 6/1986 Devaney
4,610,259 A 9/1986 Cohen et al.
4,613,817 A 9/1986 Hoenig
4,649,482 A 3/1987 Raviv et al.
4,689,559 A 8/1987 Hastings et al.
4,693,000 A 9/1987 Hoenig
4,700,135 A 10/1987 Hoenig
4,705,049 A 11/1987 John
4,733,180 A 3/1988 Hoenig et al.
4,736,307 A 4/1988 Salb
4,736,751 A 4/1988 Gevins et al.
4,744,029 A 5/1988 Raviv et al.
4,749,946 A 6/1988 Hoenig
4,753,246 A 6/1988 Freeman
4,761,611 A 8/1988 Hoenig
4,776,345 A 10/1988 Cohen et al.
4,792,145 A 12/1988 Eisenberg et al.
4,794,533 A 12/1988 Cohen
4,801,882 A 1/1989 Daalmans
4,846,190 A 7/1989 John
4,862,359 A 8/1989 Trivedi et al.
4,883,067 A 11/1989 Knispel et al.
4,907,597 A 3/1990 Chamoun
4,913,152 A 4/1990 Ko et al.
4,924,875 A 5/1990 Chamoun
4,937,525 A 6/1990 Daalmans
4,940,058 A 7/1990 Taff et al.
4,947,480 A 8/1990 Lewis
4,949,725 A 8/1990 Raviv et al.
4,951,674 A 8/1990 Zanakis et al.
4,974,602 A 12/1990 Abraham-Fuchs et al.
4,977,505 A 12/1990 Pelizzari et al.
4,982,157 A 1/1991 Seifert
4,983,912 A 1/1991 Roehrlein et al.
4,996,479 A 2/1991 Hoenig
5,008,622 A 4/1991 Overton, Jr. et al.
5,010,891 A 4/1991 Chamoun
5,012,190 A 4/1991 Dossel
5,020,538 A 6/1991 Morgan et al.
5,020,540 A 6/1991 Chamoun
5,027,817 A 7/1991 John
5,029,082 A 7/1991 Shen et al.
5,059,814 A 10/1991 Mead et al.
5,061,680 A 10/1991 Paulson et al.
5,069,218 A 12/1991 Ikeda
5,070,399 A 12/1991 Martel
5,083,571 A 1/1992 Prichep
5,088,497 A 2/1992 Ikeda
5,092,341 A 3/1992 Kelen
5,092,835 A 3/1992 Schurig et al.
5,095,270 A 3/1992 Ludeke
5,105,354 A 4/1992 Nishimura
5,109,862 A 5/1992 Kelen et al.
5,118,606 A 6/1992 Lynch et al.
5,126,315 A 6/1992 Nishino et al.
RE34,015 E 8/1992 Duffy
5,136,687 A 8/1992 Edelman et al.
5,158,932 A 10/1992 Hinshaw et al.
5,159,703 A 10/1992 Lowery
5,159,928 A 11/1992 Keppel
5,166,614 A 11/1992 Yokosawa et al.
5,187,327 A 2/1993 Ohta et al.
5,198,977 A 3/1993 Salb
5,213,338 A 5/1993 Brotz
5,215,086 A 6/1993 Terry, Jr. et al.
5,218,530 A 6/1993 Jastrzebski et al.
5,224,203 A 6/1993 Skeirik
5,230,344 A 7/1993 Ozdamar et al.
5,230,346 A 7/1993 Leuchter et al.
5,231,988 A 8/1993 Wernicke et al.
5,233,517 A 8/1993 Jindra
5,241,967 A 9/1993 Yasushi et al.
5,243,281 A 9/1993 Ahonen et al.
5,243,517 A 9/1993 Schmidt et al.
5,263,488 A 11/1993 Van Veen et al.
5,265,611 A 11/1993 Hoenig et al.
5,269,315 A 12/1993 Leuchter et al.
5,269,325 A 12/1993 Robinson et al.
5,273,038 A 12/1993 Beavin
5,280,791 A 1/1994 Lavie
5,282,474 A 2/1994 Valdes Sosa et al.
5,283,523 A 2/1994 Uhl et al.
5,287,859 A 2/1994 John
5,291,888 A 3/1994 Tucker
5,293,187 A 3/1994 Knapp et al.
5,299,569 A 4/1994 Wernicke et al.
5,303,705 A 4/1994 Nenov
5,306,228 A 4/1994 Rubins
5,307,807 A 5/1994 Valdes Sosa et al.
5,309,095 A 5/1994 Ahonen et al.
5,309,917 A 5/1994 Wang et al.
5,309,923 A 5/1994 Leuchter et al.
5,311,129 A 5/1994 Ludwig et al.
5,320,109 A 6/1994 Chamoun et al.
5,323,777 A 6/1994 Ahonen et al.
5,325,862 A 7/1994 Lewis et al.
5,326,745 A 7/1994 Nishino et al.
5,331,970 A 7/1994 Gevins et al.
5,335,657 A 8/1994 Terry, Jr. et al.
5,339,811 A 8/1994 Ohta et al.
5,339,826 A 8/1994 Schmidt et al.
5,343,871 A 9/1994 Bittman et al.
5,359,363 A 10/1994 Kuban et al.
5,377,100 A 12/1994 Pope et al.
5,384,588 A 1/1995 Martin et al.
5,406,956 A 4/1995 Farwell
5,406,957 A 4/1995 Tansey
5,409,445 A 4/1995 Rubins
5,417,211 A 5/1995 Abraham-Fuchs et al.
5,418,512 A 5/1995 Ohta et al.
5,422,689 A 6/1995 Knapp et al.
5,442,289 A 8/1995 DiIorio et al.
5,443,073 A 8/1995 Wang et al.
5,447,154 A 9/1995 Cinquin et al.
5,447,166 A 9/1995 Gevins
5,458,117 A 10/1995 Chamoun et al.
5,458,142 A 10/1995 Farmer et al.
5,459,536 A 10/1995 Shalon et al.
5,461,699 A 10/1995 Arbabi et al.
5,469,057 A 11/1995 Robinson
5,474,082 A 12/1995 Junker
5,476,438 A 12/1995 Edrich et al.
5,491,492 A 2/1996 Knapp et al.
5,496,798 A 3/1996 Sakai et al.
5,503,149 A 4/1996 Beavin
5,513,649 A 5/1996 Gevins et al.
5,515,301 A 5/1996 Corby, Jr. et al.
5,522,863 A 6/1996 Spano et al.
5,546,943 A 8/1996 Gould
5,552,375 A 9/1996 Nishino et al.

(56) References Cited

U.S. PATENT DOCUMENTS 5,555,889 A 9/1996 Karagueuzian et al.
5,568,816 A 10/1996 Gevins et al.
5,571,150 A 11/1996 Wernicke et al.
5,579,241 A 11/1996 Corby, Jr. et al.
5,594,849 A 1/1997 Kuc et al.
5,600,243 A 2/1997 Colclough
5,601,081 A 2/1997 Tomita et al.
5,611,350 A 3/1997 John
5,617,856 A 4/1997 Tamura et al.
5,619,995 A 4/1997 Lobodzinski
5,622,168 A 4/1997 Keusch et al.
5,626,145 A 5/1997 Clapp et al.
5,632,272 A 5/1997 Diab et al.
5,640,493 A 6/1997 Skeirik
5,643,325 A 7/1997 Karagueuzian et al.
5,649,061 A 7/1997 Smyth
5,650,726 A 7/1997 Gasnier et al.
5,656,937 A 8/1997 Cantor
5,662,109 A 9/1997 Hutson
5,671,740 A 9/1997 Tomita et al.
5,678,561 A 10/1997 Karagueuzian et al.
5,682,889 A 11/1997 Tomita et al.
5,685,313 A 11/1997 Mayevsky
5,692,517 A 12/1997 Junker
5,694,939 A 12/1997 Cowings
5,699,808 A 12/1997 John
5,701,909 A 12/1997 Amir et al.
5,706,402 A 1/1998 Bell
5,706,811 A 1/1998 Takeda et al.
5,711,305 A 1/1998 Swanson et al.
5,715,821 A 2/1998 Faupel
5,719,561 A 2/1998 Gonzales
5,720,619 A 2/1998 Fisslinger
5,722,418 A 3/1998 Bro
5,724,987 A 3/1998 Gevins et al.
5,729,046 A 3/1998 Nishino et al.
5,730,146 A 3/1998 Itil et al.
5,736,543 A 4/1998 Rogers et al.
5,737,485 A 4/1998 Flanagan et al.
5,740,812 A 4/1998 Cowan
5,742,748 A 4/1998 Sever, Jr.
5,743,854 A 4/1998 Dobson et al.
5,743,860 A 4/1998 Hively et al.
5,747,492 A 5/1998 Lynch et al.
5,752,514 A 5/1998 Okamura et al.
5,752,521 A 5/1998 Dardik
5,752,911 A 5/1998 Canedo et al.
5,755,227 A 5/1998 Tomita et al.
5,755,739 A 5/1998 Sun et al.
5,761,332 A 6/1998 Wischmann et al.
5,762,611 A 6/1998 Lewis et al.
5,767,043 A 6/1998 Cantor et al.
5,771,261 A 6/1998 Anbar
5,771,893 A 6/1998 Kassai et al.
5,771,894 A 6/1998 Richards et al.
5,771,897 A 6/1998 Zufrin
5,791,342 A 8/1998 Woodard
5,794,623 A 8/1998 Forbes
5,795,304 A 8/1998 Sun et al.
5,797,840 A 8/1998 Akselrod et al.
5,797,853 A 8/1998 Musha et al.
5,810,737 A 9/1998 Dardik
5,813,993 A 9/1998 Kaplan et al.
5,815,413 A 9/1998 Hively et al.
5,816,247 A 10/1998 Maynard
5,825,830 A 10/1998 Kopf
5,827,195 A 10/1998 Lander
5,840,040 A 11/1998 Altschuler et al.
5,842,986 A 12/1998 Avrin et al.
5,845,639 A 12/1998 Hochman et al.
5,846,189 A 12/1998 Pincus
5,846,208 A 12/1998 Pichlmayr et al.
5,853,005 A 12/1998 Scanlon
5,857,978 A 1/1999 Hively et al.
5,859,533 A 1/1999 Gasnier et al.
5,871,517 A 2/1999 Abrams et al.
5,877,801 A 3/1999 Martin et al.
5,884,626 A 3/1999 Kuroda et al.
5,885,976 A 3/1999 Sandyk
5,891,131 A 4/1999 Rajan et al.
5,899,867 A 5/1999 Collura
5,911,581 A 6/1999 Reynolds et al.
5,916,171 A 6/1999 Mayevsky
5,921,245 A 7/1999 O'Donnell, Jr.
5,928,272 A 7/1999 Adkins et al.
5,938,598 A 8/1999 Takeda et al.
5,938,688 A 8/1999 Schiff
5,954,662 A 9/1999 Swanson et al.
5,970,499 A 10/1999 Smith et al.
5,971,923 A 10/1999 Finger
5,983,129 A 11/1999 Cowan et al.
5,995,868 A 11/1999 Dorfmeister et al.
5,999,856 A 12/1999 Kennedy
6,002,254 A 12/1999 Kassai et al.
6,002,952 A 12/1999 Diab et al.
6,011,990 A 1/2000 Schultz et al.
6,011,991 A 1/2000 Mardirossian
6,016,444 A 1/2000 John
6,021,345 A 2/2000 Karagueuzian et al.
6,023,161 A 2/2000 Dantsker et al.
6,026,173 A 2/2000 Svenson et al.
6,032,072 A 2/2000 Greenwald et al.
6,042,548 A 3/2000 Giuffre
6,044,292 A 3/2000 Heyrend et al.
6,050,940 A 4/2000 Braun et al.
6,050,962 A 4/2000 Kramer et al.
6,052,619 A 4/2000 John
6,053,739 A 4/2000 Stewart et al.
6,057,846 A 5/2000 Sever, Jr.
6,066,084 A 5/2000 Edrich et al.
6,067,462 A 5/2000 Diab et al.
6,067,467 A 5/2000 John
6,069,369 A 5/2000 Nishino et al.
6,070,098 A 5/2000 Moore-Ede et al.
6,071,246 A 6/2000 Sturzebecher et al.
6,080,164 A 6/2000 Oshio et al.
6,081,735 A 6/2000 Diab et al.
6,088,611 A 7/2000 Lauterbur et al.
6,092,058 A 7/2000 Smyth
6,097,980 A 8/2000 Monastra et al.
6,097,981 A 8/2000 Freer
6,099,319 A 8/2000 Zaltman et al.
6,104,956 A 8/2000 Naritoku et al.
6,115,631 A 9/2000 Heyrend et al.
6,117,075 A 9/2000 Barnea
6,129,681 A 10/2000 Kuroda et al.
6,132,724 A 10/2000 Blum
6,144,872 A 11/2000 Graetz
6,149,586 A 11/2000 Elkind
6,154,026 A 11/2000 Dantsker et al.
6,155,966 A 12/2000 Parker
6,155,993 A 12/2000 Scott
6,157,850 A 12/2000 Diab et al.
6,157,857 A 12/2000 Dimpfel
6,161,031 A 12/2000 Hochman et al.
6,167,298 A 12/2000 Levin
6,167,311 A 12/2000 Rezai
6,171,239 B1 1/2001 Humphrey
6,171,258 B1 1/2001 Karakasoglu et al.
6,182,013 B1 1/2001 Malinverno et al.
6,188,924 B1 2/2001 Swanson et al.
6,195,576 B1 2/2001 John
6,196,972 B1 3/2001 Moehring
6,205,359 B1 3/2001 Boveja
6,208,902 B1 3/2001 Boveja
6,224,549 B1 5/2001 Drongelen
6,226,418 B1 5/2001 Miller et al.
6,230,037 B1 5/2001 Tsukada et al.
6,236,872 B1 5/2001 Diab et al.
6,239,145 B1 5/2001 Utsumi et al.
6,240,308 B1 5/2001 Hardy et al.
6,241,686 B1 6/2001 Balkin et al.
6,248,126 B1 6/2001 Lesser et al.
6,259,399 B1 7/2001 Krasner

(56) References Cited

U.S. PATENT DOCUMENTS 6,263,189 B1 7/2001 Reagor
6,266,453 B1 7/2001 Hibbard et al.
6,269,270 B1 7/2001 Boveja
6,272,370 B1 8/2001 Gillies et al.
6,280,393 B1 8/2001 Granger et al.
6,287,328 B1 9/2001 Snyder et al.
6,290,638 B1 9/2001 Canedo et al.
6,292,688 B1 9/2001 Patton
6,293,904 B1 9/2001 Blazey et al.
6,294,917 B1 9/2001 Nichols
6,298,259 B1 10/2001 Kucharczyk et al.
6,305,943 B1 10/2001 Pougatchev et al.
6,306,077 B1 10/2001 Prabhu et al.
6,309,342 B1 10/2001 Blazey et al.
6,309,361 B1 10/2001 Thornton
6,315,736 B1 11/2001 Tsutsumi et al.
6,317,627 B1 11/2001 Ennen et al.
6,319,205 B1 11/2001 Goor et al.
6,322,515 B1 11/2001 Goor et al.
6,325,475 B1 12/2001 Hayes et al.
6,325,761 B1 12/2001 Jay
6,331,164 B1 12/2001 Shaw et al.
6,332,087 B1 12/2001 Svenson et al.
6,338,713 B1 1/2002 Chamoun et al.
6,339,725 B1 1/2002 Naritoku et al.
6,341,236 B1 1/2002 Osorio et al.
6,343,229 B1 1/2002 Siebler et al.
6,354,087 B1 3/2002 Nakahara et al.
6,354,299 B1 3/2002 Fischell et al.
6,356,079 B1 3/2002 Mizoguchi et al.
6,356,781 B1 3/2002 Lee et al.
6,356,788 B2 3/2002 Boveja
6,358,201 B1 3/2002 Childre et al.
6,364,845 B1 4/2002 Duffy et al.
6,366,813 B1 4/2002 DiLorenzo
6,366,814 B1 4/2002 Boveja et al.
6,370,414 B1 4/2002 Robinson
6,370,423 B1 4/2002 Guerrero et al.
6,374,131 B1 4/2002 Tomita et al.
6,375,614 B1 4/2002 Braun et al.
6,377,833 B1 4/2002 Albert
6,385,479 B1 5/2002 Sibbitt et al.
6,385,486 B1 5/2002 John et al.
6,390,979 B1 5/2002 Njemanze
6,393,363 B1 5/2002 Wilt et al.
6,394,963 B1 5/2002 Blazey et al.
6,402,520 B1 6/2002 Freer
6,402,689 B1 6/2002 Scarantino et al.
6,408,107 B1 6/2002 Miller et al.
6,418,344 B1 7/2002 Rezai et al.
6,419,629 B1 7/2002 Balkin et al.
6,427,086 B1 7/2002 Fischell et al.
6,428,490 B1 8/2002 Kramer et al.
6,430,443 B1 8/2002 Karell
6,435,878 B1 8/2002 Reynolds et al.
6,442,421 B1 8/2002 Le Van Quyen et al.
6,442,948 B1 9/2002 Takeda
6,466,816 B2 10/2002 Granger et al.
6,470,220 B1 10/2002 Kraus, Jr. et al.
6,475,163 B1 11/2002 Smits et al.
6,482,165 B1 11/2002 Patton et al.
6,487,441 B1 11/2002 Swanson et al.
6,488,617 B1 12/2002 Katz
6,490,472 B1 12/2002 Li et al.
6,493,577 B1 12/2002 Williams
6,496,724 B1 12/2002 Levendowski et al.
6,497,658 B2 12/2002 Roizen et al.
6,497,699 B1 12/2002 Ludvig et al.
6,503,085 B1 1/2003 Elkind
6,507,754 B2 1/2003 Le Van Quyen et al.
6,510,340 B1 1/2003 Jordan
6,511,424 B1 1/2003 Moore-Ede et al.
6,516,246 B2 2/2003 Derakhshan
6,520,905 B1 2/2003 Surve et al.
6,520,921 B1 2/2003 Patton et al.
6,522,906 B1 2/2003 Salisbury, Jr. et al.
6,524,249 B2 2/2003 Moehring et al.
6,526,297 B1 2/2003 Merilainen
6,526,415 B2 2/2003 Smith et al.
6,527,715 B2 3/2003 Balkin et al.
6,527,730 B2 3/2003 Blazey et al.
6,529,759 B1 3/2003 Tucker et al.
6,529,773 B1 3/2003 Dewan
6,530,884 B2 3/2003 Balkin et al.
6,534,986 B2 3/2003 Nichols
6,538,436 B1 3/2003 Simola et al.
6,539,245 B2 3/2003 Tsukada et al.
6,539,263 B1 3/2003 Schiff et al.
6,544,170 B1 4/2003 Kajihara et al.
6,546,378 B1 4/2003 Cook
6,547,736 B1 4/2003 Moehring et al.
6,547,746 B1 4/2003 Marino
6,549,804 B1 4/2003 Osorio et al.
6,551,243 B2 4/2003 Bocionek et al.
6,553,252 B2 4/2003 Balkin et al.
6,556,695 B1 4/2003 Packer et al.
6,556,861 B1 4/2003 Prichep
6,556,868 B2 4/2003 Naritoku et al.
6,557,558 B1 5/2003 Tajima et al.
6,560,486 B1 5/2003 Osorio et al.
6,565,518 B2 5/2003 Blazey et al.
6,574,573 B1 6/2003 Asano
6,587,727 B2 7/2003 Osorio et al.
6,587,729 B2 7/2003 O'Loughlin et al.
6,591,132 B2 7/2003 Gotman et al.
6,591,137 B1 7/2003 Fischell et al.
6,594,524 B2 7/2003 Esteller et al.
6,597,954 B1 7/2003 Pless et al.
6,602,202 B2 8/2003 John et al.
6,603,502 B2 8/2003 Martin et al.
6,609,030 B1 8/2003 Rezai et al.
6,611,698 B1 8/2003 Yamashita et al.
6,615,158 B2 9/2003 Wenzel et al.
6,616,611 B1 9/2003 Moehring
6,622,036 B1 9/2003 Suffin
6,622,047 B2 9/2003 Barrett et al.
6,625,485 B2 9/2003 Levendowski et al.
6,626,676 B2 9/2003 Freer
6,633,686 B1 10/2003 Bakircioglu et al.
6,644,976 B2 11/2003 Kullok et al.
6,648,822 B2 11/2003 Hamamoto et al.
6,648,880 B2 11/2003 Chauvet et al.
6,650,917 B2 11/2003 Diab et al.
6,652,458 B2 11/2003 Blazey et al.
6,652,470 B2 11/2003 Patton et al.
6,654,632 B2 11/2003 Lange et al.
6,654,729 B1 11/2003 Hickman et al.
6,656,137 B1 12/2003 Tyldsley et al.
6,658,287 B1 12/2003 Litt et al.
6,663,571 B1 12/2003 Njemanze
6,665,552 B2 12/2003 Yokosawa et al.
6,665,553 B2 12/2003 Kandori et al.
6,665,562 B2 12/2003 Gluckman et al.
6,671,555 B2 12/2003 Gielen et al.
6,671,556 B2 12/2003 Osorio et al.
6,678,548 B1 1/2004 Echauz et al.
6,684,098 B2 1/2004 Oshio et al.
6,684,105 B2 1/2004 Cohen et al.
6,687,525 B2 2/2004 Llinas et al.
6,695,761 B2 2/2004 Oschman et al.
6,697,660 B1 2/2004 Robinson
RE38,476 E 3/2004 Diab et al.
6,699,194 B1 3/2004 Diab et al.
6,701,173 B2 3/2004 Nowinski et al.
6,703,838 B2 3/2004 Conti
6,708,051 B1 3/2004 Durousseau
6,708,064 B2 3/2004 Rezai
6,708,184 B2 3/2004 Smith et al.
6,709,399 B1 3/2004 Shen et al.
6,725,080 B2 4/2004 Melkent et al.
6,726,624 B2 4/2004 Keirsbilck et al.
6,728,424 B1 4/2004 Zhu et al.
6,728,564 B2 4/2004 Lahteenmaki
6,731,975 B1 5/2004 Viertio-Oja et al.

(56) References Cited

U.S. PATENT DOCUMENTS 6,735,460 B2 5/2004 Tsukada et al.
6,735,467 B2 5/2004 Wilson
6,735,475 B1 5/2004 Whitehurst et al.
6,740,032 B2 5/2004 Balkin et al.
6,743,167 B2 6/2004 Balkin et al.
6,743,182 B2 6/2004 Miller et al.
6,745,060 B2 6/2004 Diab et al.
6,745,156 B2 6/2004 Cook
6,746,409 B2 6/2004 Keirsbilck et al.
6,751,499 B2 6/2004 Lange et al.
6,758,813 B2 7/2004 Meadows
6,768,920 B2 7/2004 Lange et al.
6,773,400 B2 8/2004 Njemanze
6,774,929 B1 8/2004 Kopp
6,775,405 B1 8/2004 Zhu
6,782,292 B2 8/2004 Whitehurst
6,785,409 B1 8/2004 Suri
6,788,975 B1 9/2004 Whitehurst et al.
6,791,331 B2 9/2004 Conti
6,795,724 B2 9/2004 Hogan
6,798,898 B1 9/2004 Fedorovskaya et al.
6,801,648 B2 10/2004 Cheng
6,801,803 B2 10/2004 Viertio-Oja
6,804,558 B2 10/2004 Haller et al.
6,804,661 B2 10/2004 Cook
6,815,949 B2 11/2004 Kandori et al.
6,816,744 B2 11/2004 Garfield et al.
6,819,956 B2 11/2004 DiLorenzo
6,826,426 B2 11/2004 Lange et al.
6,843,774 B2 1/2005 Foust et al.
6,853,186 B2 2/2005 Li
6,856,830 B2 2/2005 He
6,863,127 B2 3/2005 Clark et al.
6,865,494 B2 3/2005 Duensing et al.
6,873,872 B2 3/2005 Gluckman et al.
6,875,174 B2 4/2005 Braun et al.
6,876,196 B1 4/2005 Taulu et al.
6,879,859 B1 4/2005 Boveja
6,882,881 B1 4/2005 Lesser et al.
6,885,192 B2 4/2005 Clarke et al.
6,885,886 B2 4/2005 Bauch et al.
6,886,964 B2 5/2005 Gardiner et al.
6,893,407 B1 5/2005 Brooks et al.
6,896,655 B2 5/2005 Patton et al.
RE38,749 E 6/2005 Dardik
6,907,280 B2 6/2005 Becerra et al.
6,915,241 B2 7/2005 Kohlmorgen et al.
6,920,357 B2 7/2005 Osorio et al.
6,926,921 B2 8/2005 Stasiak et al.
6,928,354 B2 8/2005 Ryu et al.
6,931,274 B2 8/2005 Williams
6,931,275 B2 8/2005 Collura
6,936,012 B2 8/2005 Wells
6,947,790 B2 9/2005 Gevins et al.
6,950,697 B2 9/2005 Jordan
6,950,698 B2 9/2005 Sarkela et al.
6,959,215 B2 10/2005 Gliner et al.
6,961,618 B2 11/2005 Osorio et al.
6,963,770 B2 11/2005 Scarantino et al.
6,963,771 B2 11/2005 Scarantino et al.
6,978,179 B1 12/2005 Flagg et al.
6,980,863 B2 12/2005 van Venrooij et al.
6,981,947 B2 1/2006 Melker
6,983,184 B2 1/2006 Price
6,983,264 B2 1/2006 Shimizu
6,985,769 B2 1/2006 Jordan
6,988,056 B2 1/2006 Cook
6,990,377 B2 1/2006 Gliner et al.
6,993,380 B1 1/2006 Modarres
6,996,261 B2 2/2006 deCharms
6,996,549 B2 2/2006 Zhang et al.
7,003,352 B1 2/2006 Whitehurst
7,006,872 B2 2/2006 Gielen et al.
7,010,340 B2 3/2006 Scarantino et al.
7,010,351 B2 3/2006 Firlik et al.
7,011,410 B2 3/2006 Bolger et al.
7,011,814 B2 3/2006 Suddarth et al.
7,014,613 B2 3/2006 John et al.
7,016,722 B2 3/2006 Prichep
7,022,083 B2 4/2006 Tanaka et al.
7,023,206 B2 4/2006 Viehland et al.
7,024,247 B2 4/2006 Gliner et al.
7,030,617 B2 4/2006 Conti
7,035,686 B2 4/2006 Hogan
7,037,260 B2 5/2006 Keirsbilck et al.
7,038,450 B2 5/2006 Romalis et al.
7,039,266 B1 5/2006 Doty
7,039,547 B2 5/2006 Wilson
7,043,293 B1 5/2006 Baura
7,053,610 B2 5/2006 Clarke et al.
7,054,454 B2 5/2006 Causevic et al.
7,062,391 B2 6/2006 Wilson
7,063,535 B2 6/2006 Stamm et al.
7,070,571 B2 7/2006 Kramer et al.
7,079,977 B2 7/2006 Osorio et al.
7,089,927 B2 8/2006 John et al.
7,092,748 B2 8/2006 Valdes Sosa et al.
7,099,714 B2 8/2006 Houben
7,104,947 B2 9/2006 Riehl
7,104,963 B2 9/2006 Melker et al.
7,105,824 B2 9/2006 Stoddart et al.
7,107,090 B2 9/2006 Salisbury, Jr. et al.
7,116,102 B2 10/2006 Clarke et al.
7,117,026 B2 10/2006 Shao et al.
7,119,553 B2 10/2006 Yang et al.
7,120,486 B2 10/2006 Leuthardt et al.
7,123,955 B1 10/2006 Gao et al.
7,127,100 B2 10/2006 Wenzel et al.
7,128,713 B2 10/2006 Moehring et al.
7,130,673 B2 10/2006 Tolvanen-Laakso et al.
7,130,675 B2 10/2006 Ewing et al.
7,130,691 B2 10/2006 Falci
7,145,333 B2 12/2006 Romalis et al.
7,146,211 B2 12/2006 Frei et al.
7,146,217 B2 12/2006 Firlik et al.
7,146,218 B2 12/2006 Esteller et al.
7,149,572 B2 12/2006 Frei et al.
7,149,773 B2 12/2006 Haller et al.
7,150,710 B2 12/2006 Haber et al.
7,150,715 B2 12/2006 Collura et al.
7,150,717 B2 12/2006 Katura et al.
7,150,718 B2 12/2006 Okada et al.
7,151,961 B1 12/2006 Whitehurst et al.
7,155,279 B2 12/2006 Whitehurst et al.
7,163,512 B1 1/2007 Childre et al.
7,164,941 B2 1/2007 Misczynski et al.
7,167,751 B1 1/2007 Whitehurst et al.
7,170,294 B2 1/2007 Kasevich
7,171,252 B1 1/2007 Scarantino et al.
7,171,339 B2 1/2007 Repucci et al.
7,174,206 B2 2/2007 Frei et al.
7,176,680 B1 2/2007 Veryaskin
7,177,675 B2 2/2007 Suffin et al.
7,177,678 B1 2/2007 Osorio et al.
7,181,505 B2 2/2007 Haller et al.
7,183,381 B2 2/2007 Varadhachary et al.
7,184,837 B2 2/2007 Goetz
7,186,209 B2 3/2007 Jacobson et al.
7,187,169 B2 3/2007 Clarke et al.
7,190,826 B2 3/2007 Russell et al.
7,190,995 B2 3/2007 Chervin et al.
7,193,413 B2 3/2007 Kandori et al.
7,196,514 B2 3/2007 Li
7,197,352 B2 3/2007 Gott et al.
7,199,708 B2 4/2007 Terauchi et al.
7,203,548 B2 4/2007 Whitehurst et al.
7,207,948 B2 4/2007 Coyle
7,209,787 B2 4/2007 DiLorenzo
7,209,788 B2 4/2007 Nicolelis et al.
7,212,851 B2 5/2007 Donoghue et al.
7,215,986 B2 5/2007 Diab et al.
7,215,994 B2 5/2007 Huiku
7,218,104 B2 5/2007 Clarke et al.
7,221,981 B2 5/2007 Gliner

(56) References Cited

U.S. PATENT DOCUMENTS 7,222,964 B2 5/2007 Gotze et al.
7,224,282 B2 5/2007 Terauchi et al.
7,225,013 B2 5/2007 Geva et al.
7,228,167 B2 6/2007 Kara et al.
7,228,169 B2 6/2007 Viertio-Oja et al.
7,228,171 B2 6/2007 Lesser et al.
7,228,178 B2 6/2007 Carroll et al.
7,231,245 B2 6/2007 Greenwald et al.
7,231,254 B2 6/2007 DiLorenzo
7,236,830 B2 6/2007 Gliner
7,236,831 B2 6/2007 Firlik et al.
7,239,731 B1 7/2007 Semenov et al.
7,239,926 B2 7/2007 Goetz
7,242,983 B2 7/2007 Frei et al.
7,242,984 B2 7/2007 DiLorenzo
7,252,090 B2 8/2007 Goetz
7,254,433 B2 8/2007 Diab et al.
7,254,439 B2 8/2007 Misczynski et al.
7,254,500 B2 8/2007 Makeig et al.
7,257,439 B2 8/2007 Llinas
7,258,659 B2 8/2007 Anninou et al.
7,260,430 B2 8/2007 Wu et al.
7,267,644 B2 9/2007 Thomas et al.
7,267,652 B2 9/2007 Coyle et al.
7,269,455 B2 9/2007 Pineda
7,269,456 B2 9/2007 Collura
7,269,516 B2 9/2007 Brunner et al.
7,276,916 B2 10/2007 Hammer
7,277,758 B2 10/2007 DiLorenzo
7,278,966 B2 10/2007 Hjelt et al.
7,280,861 B2 10/2007 Thomas et al.
7,280,867 B2 10/2007 Frei et al.
7,280,870 B2 10/2007 Nurmikko et al.
7,282,030 B2 10/2007 Frei et al.
7,283,861 B2 10/2007 Bystritsky
7,286,871 B2 10/2007 Cohen
7,288,066 B2 10/2007 Drew
7,292,890 B2 11/2007 Whitehurst et al.
7,295,019 B2 11/2007 Yang et al.
7,297,110 B2 11/2007 Goyal et al.
7,299,088 B1 11/2007 Thakor et al.
7,299,096 B2 11/2007 Balzer et al.
7,302,298 B2 11/2007 Lowry et al.
7,305,268 B2 12/2007 Gliner et al.
7,309,315 B2 12/2007 Kullok et al.
7,313,442 B2 12/2007 Velasco et al.
7,321,837 B2 1/2008 Osorio et al.
7,324,845 B2 1/2008 Mietus et al.
7,324,851 B1 1/2008 DiLorenzo
7,328,053 B1 2/2008 Diab et al.
7,330,032 B2 2/2008 Donnangelo
7,333,619 B2 2/2008 Causevic et al.
7,333,851 B2 2/2008 Echauz et al.
7,334,892 B2 2/2008 Goodall et al.
7,338,171 B2 3/2008 Hsieh et al.
7,338,455 B2 3/2008 White et al.
7,340,125 B1 3/2008 Doty
7,340,289 B2 3/2008 Kandori et al.
7,343,198 B2 3/2008 Behbehani et al.
7,346,382 B2 3/2008 McIntyre et al.
7,346,395 B2 3/2008 Lozano et al.
7,353,064 B2 4/2008 Gliner et al.
7,353,065 B2 4/2008 Morrell
7,355,597 B2 4/2008 Laidlaw et al.
7,359,837 B2 4/2008 Drew
7,363,164 B2 4/2008 Little et al.
7,366,571 B2 4/2008 Armstrong
7,367,807 B1 5/2008 Pennebaker
7,367,949 B2 5/2008 Korhonen et al.
7,369,896 B2 5/2008 Gesotti
7,371,365 B2 5/2008 Poduslo et al.
7,373,198 B2 5/2008 Bibian et al.
7,376,453 B1 5/2008 Diab et al.
7,376,459 B2 5/2008 Rosenfeld
7,378,056 B2 5/2008 Black
7,381,185 B2 6/2008 Zhirnov et al.
7,383,070 B2 6/2008 Diab et al.
7,383,237 B2 6/2008 Zhang et al.
7,386,347 B2 6/2008 Chung et al.
7,389,144 B1 6/2008 Osorio et al.
7,392,079 B2 6/2008 Donoghue et al.
7,394,246 B2 7/2008 Chieh et al.
7,395,292 B2 7/2008 Johnson
7,396,333 B2 7/2008 Stahmann et al.
7,399,282 B2 7/2008 John et al.
7,400,984 B2 7/2008 Kandori et al.
7,403,809 B2 7/2008 Tsukada et al.
7,403,814 B2 7/2008 Cox et al.
7,403,815 B2 7/2008 Katz et al.
7,403,820 B2 7/2008 DiLorenzo
7,407,485 B2 8/2008 Huiku
7,409,321 B2 8/2008 Repucci et al.
7,418,290 B2 8/2008 Devlin et al.
7,420,033 B2 9/2008 Varadhachary et al.
7,422,555 B2 9/2008 Zabara
7,429,247 B2 9/2008 Okada et al.
7,437,196 B2 10/2008 Wyler et al.
7,440,789 B2 10/2008 Hannula et al.
7,440,806 B1 10/2008 Whitehurst et al.
7,444,184 B2 10/2008 Boveja et al.
7,450,986 B2 11/2008 Nguyen et al.
7,453,263 B2 11/2008 Kim et al.
7,454,240 B2 11/2008 Diab et al.
7,454,243 B2 11/2008 Silberstein
7,454,245 B2 11/2008 Armstrong et al.
7,454,387 B2 11/2008 Abercrombie et al.
7,457,653 B2 11/2008 Fujimaki
7,457,665 B1 11/2008 Osorio et al.
7,461,045 B1 12/2008 Chaovalitwongse et al.
7,462,151 B2 12/2008 Childre et al.
7,462,155 B2 12/2008 England
7,463,024 B2 12/2008 Simola et al.
7,463,142 B2 12/2008 Lindsay
7,463,927 B1 12/2008 Chaouat
7,466,132 B2 12/2008 Clarke et al.
7,468,040 B2 12/2008 Hartley et al.
7,468,350 B2 12/2008 Gong et al.
7,469,697 B2 12/2008 Lee et al.
7,471,971 B2 12/2008 Diab et al.
7,471,978 B2 12/2008 John et al.
7,478,108 B2 1/2009 Townsend et al.
7,482,298 B2 1/2009 Nepela
7,483,747 B2 1/2009 Gliner et al.
7,486,986 B1 2/2009 Osorio et al.
7,488,294 B2 2/2009 Torch
7,489,958 B2 2/2009 Diab et al.
7,489,964 B2 2/2009 Suffin et al.
7,490,085 B2 2/2009 Walker et al.
7,491,173 B2 2/2009 Heim
7,493,171 B1 2/2009 Whitehurst et al.
7,493,172 B2 2/2009 Whitehurst et al.
7,496,393 B2 2/2009 Diab et al.
7,497,828 B1 3/2009 Wilk et al.
7,499,741 B2 3/2009 Diab et al.
7,499,745 B2 3/2009 Littrup et al.
7,499,752 B2 3/2009 Maschino et al.
7,499,894 B2 3/2009 Marom et al.
7,502,720 B2 3/2009 Taulu
7,509,154 B2 3/2009 Diab et al.
7,509,161 B2 3/2009 Viertio-Oja
7,509,163 B1 3/2009 Luo et al.
7,510,531 B2 3/2009 Lee et al.
7,510,699 B2 3/2009 Black et al.
7,515,054 B2 4/2009 Torch
7,530,955 B2 5/2009 Diab et al.
7,537,568 B2 5/2009 Moehring
7,539,528 B2 5/2009 Xiong et al.
7,539,532 B2 5/2009 Tran
7,539,533 B2 5/2009 Tran
7,539,543 B2 5/2009 Schiff et al.
7,547,284 B2 6/2009 Brainard, II
7,553,810 B2 6/2009 Gong et al.
7,558,622 B2 7/2009 Tran
7,559,903 B2 7/2009 Moussavi et al.

(56) References Cited

U.S. PATENT DOCUMENTS 7,561,918 B2 7/2009 Armstrong et al.
7,565,193 B2 7/2009 Laken
7,565,199 B2 7/2009 Sheffield et al.
7,565,200 B2 7/2009 Wyler et al.
7,565,809 B2 7/2009 Takeda
7,567,693 B2 7/2009 deCharms
7,570,054 B1 8/2009 Lin
7,570,991 B2 8/2009 Milgramm et al.
7,572,225 B2 8/2009 Stahmann et al.
7,573,264 B2 8/2009 Xu et al.
7,573,268 B2 8/2009 Volegov et al.
7,574,007 B2 8/2009 Shaw et al.
7,574,254 B2 8/2009 Milgramm et al.
7,577,472 B2 8/2009 Li et al.
7,577,481 B2 8/2009 Firlik et al.
7,580,798 B2 8/2009 Brunner et al.
7,582,062 B2 9/2009 Magill et al.
7,583,857 B2 9/2009 Xu et al.
7,593,767 B1 9/2009 Modarres
7,594,122 B2 9/2009 Milgramm et al.
7,594,889 B2 9/2009 St. Ores et al.
7,596,535 B2 9/2009 de Voir et al.
7,597,665 B2 10/2009 Wilk et al.
7,603,168 B2 10/2009 Bibian et al.
7,603,174 B2 10/2009 De Ridder
7,604,603 B2 10/2009 Sackner et al.
7,606,405 B2 10/2009 Sawyer et al.
7,608,579 B2 10/2009 Gong et al.
7,610,083 B2 10/2009 Drew et al.
7,610,094 B2 10/2009 Stahmann et al.
7,610,096 B2 10/2009 McDonald, III
7,610,100 B2 10/2009 Jaax et al.
7,613,502 B2 11/2009 Yamamoto et al.
7,613,519 B2 11/2009 De Ridder
7,613,520 B2 11/2009 De Ridder
7,617,002 B2 11/2009 Goetz
7,618,381 B2 11/2009 Krebs et al.
7,620,455 B2 11/2009 Maschino
7,620,456 B2 11/2009 Gliner et al.
7,623,912 B2 11/2009 Akselrod et al.
7,623,927 B2 11/2009 Rezai
7,623,928 B2 11/2009 DiLorenzo
7,624,293 B2 11/2009 Osorio et al.
7,625,340 B2 12/2009 Sarkela
7,627,370 B2 12/2009 Marks
7,629,889 B2 12/2009 Sachanandani et al.
7,630,757 B2 12/2009 Dorfmeister et al.
7,634,317 B2 12/2009 Ben-David et al.
7,640,055 B2 12/2009 Geva et al.
7,643,655 B2 1/2010 Liang et al.
7,643,881 B2 1/2010 Armstrong
7,647,097 B2 1/2010 Flaherty et al.
7,647,098 B2 1/2010 Prichep
7,648,498 B2 1/2010 Hempel
7,649,351 B2 1/2010 Kajola et al.
7,653,433 B2 1/2010 Lozano et al.
7,654,948 B2 2/2010 Kaplan et al.
7,657,316 B2 2/2010 Jaax et al.
7,668,579 B2 2/2010 Lynn
7,668,591 B2 2/2010 Lee et al.
7,670,838 B2 3/2010 Deisseroth et al.
7,672,707 B2 3/2010 Takeda
7,672,717 B1 3/2010 Zikov et al.
7,672,730 B2 3/2010 Firlik et al.
7,676,263 B2 3/2010 Harris et al.
7,678,047 B2 3/2010 Shiomi et al.
7,678,061 B2 3/2010 Lee et al.
7,678,767 B2 3/2010 Gong et al.
7,680,526 B2 3/2010 McIntyre et al.
7,680,540 B2 3/2010 Jensen et al.
7,684,856 B2 3/2010 Virtanen et al.
7,684,858 B2 3/2010 He et al.
7,684,866 B2 3/2010 Fowler et al.
7,684,867 B2 3/2010 Jaax et al.
7,697,979 B2 4/2010 Martinerie et al.
7,702,387 B2 4/2010 Stevenson et al.
7,702,502 B2 4/2010 Ricci et al.
7,706,871 B2 4/2010 Devlin et al.
7,706,992 B2 4/2010 Ricci et al.
7,711,417 B2 5/2010 John et al.
7,711,432 B2 5/2010 Thimineur et al.
7,714,936 B1 5/2010 Martin et al.
7,715,894 B2 5/2010 Dunseath et al.
7,715,910 B2 5/2010 Hargrove et al.
7,715,919 B2 5/2010 Osorio et al.
7,720,519 B2 5/2010 Ruohonen
7,720,530 B2 5/2010 Causevic
7,725,174 B2 5/2010 Kern et al.
7,725,192 B2 5/2010 Eskandar et al.
7,727,161 B2 6/2010 Coyle et al.
7,729,740 B2 6/2010 Kraus, Jr. et al.
7,729,753 B2 6/2010 Kremliovsky et al.
7,729,755 B2 6/2010 Laken
7,729,773 B2 6/2010 Sloan
7,733,224 B2 6/2010 Tran
7,733,973 B2 6/2010 Moriya et al.
7,734,334 B2 6/2010 Mietus et al.
7,734,340 B2 6/2010 De Ridder
7,734,355 B2 6/2010 Cohen et al.
7,736,382 B2 6/2010 Webb et al.
7,737,687 B2 6/2010 Na et al.
7,738,683 B2 6/2010 Cahill et al.
7,740,592 B2 6/2010 Graham et al.
7,742,820 B2 6/2010 Wyler et al.
7,746,979 B2 6/2010 Dilmanian et al.
7,747,318 B2 6/2010 John et al.
7,747,325 B2 6/2010 Dilorenzo
7,747,326 B2 6/2010 Velasco et al.
7,747,551 B2 6/2010 Snyder
7,749,155 B1 7/2010 Anderson et al.
7,751,877 B2 7/2010 Flaherty et al.
7,751,878 B1 7/2010 Merkle et al.
7,753,836 B2 7/2010 Peterchev
7,754,190 B2 7/2010 Suffin
7,756,564 B2 7/2010 Matsui et al.
7,756,568 B2 7/2010 Scarantino et al.
7,756,584 B2 7/2010 Sheffield et al.
7,757,690 B2 7/2010 Stahmann et al.
7,758,503 B2 7/2010 Lynn et al.
7,763,588 B2 7/2010 van Praag et al.
7,764,987 B2 7/2010 Dorr et al.
7,765,088 B2 7/2010 Drew
7,766,827 B2 8/2010 Balkin et al.
7,769,424 B2 8/2010 Sato
7,769,431 B2 8/2010 Scarantino et al.
7,769,461 B2 8/2010 Whitehurst et al.
7,769,464 B2 8/2010 Gerber et al.
7,771,341 B2 8/2010 Rogers
7,771,364 B2 8/2010 Arbel et al.
7,774,052 B2 8/2010 Burton et al.
7,774,064 B2 8/2010 Meyer et al.
7,775,993 B2 8/2010 Heruth et al.
7,778,490 B2 8/2010 Quist
7,778,692 B2 8/2010 Scarantino et al.
7,778,693 B2 8/2010 Barbour et al.
7,783,362 B2 8/2010 Whitehurst et al.
7,787,937 B2 8/2010 Scarantino et al.
7,787,946 B2 8/2010 Stahmann et al.
7,792,575 B2 9/2010 Fujimaki et al.
7,794,403 B2 9/2010 Schaafsma
7,794,406 B2 9/2010 Reisfeld et al.
7,797,040 B2 9/2010 Pesaran et al.
7,800,493 B2 9/2010 Terauchi et al.
7,801,591 B1 9/2010 Shusterman
7,801,592 B2 9/2010 Shan et al.
7,801,593 B2 9/2010 Behbehani et al.
7,801,601 B2 9/2010 Maschino et al.
7,801,686 B2 9/2010 Hyde et al.
7,803,118 B2 9/2010 Reisfeld et al.
7,803,119 B2 9/2010 Reisfeld
7,804,441 B1 9/2010 DeChiaro, Jr.
7,805,203 B2 9/2010 Ben-David et al.
7,809,433 B2 10/2010 Keenan
7,809,434 B2 10/2010 Kofol et al.

(56) References Cited

U.S. PATENT DOCUMENTS 7,811,279 B2 10/2010 John
7,819,794 B2 10/2010 Becker
7,819,812 B2 10/2010 John et al.
7,822,481 B2 10/2010 Gerber et al.
D627,476 S 11/2010 Gaw et al.
7,829,562 B2 11/2010 Shamloo et al.
7,831,302 B2 11/2010 Thomas
7,831,305 B2 11/2010 Gliner
7,834,627 B2 11/2010 Sakai et al.
7,835,787 B2 11/2010 Sajda et al.
7,840,039 B2 11/2010 Fuchs
7,840,248 B2 11/2010 Fuchs et al.
7,840,250 B2 11/2010 Tucker
7,840,257 B2 11/2010 Chance
7,840,280 B2 11/2010 Parnis et al.
7,841,986 B2 11/2010 He et al.
7,844,324 B2 11/2010 Sarkela et al.
7,848,803 B1 12/2010 Jaax et al.
7,852,087 B2 12/2010 Wilt et al.
7,853,321 B2 12/2010 Jaax et al.
7,853,322 B2 12/2010 Bourget et al.
7,853,323 B2 12/2010 Goetz
7,853,329 B2 12/2010 DiLorenzo
7,856,264 B2 12/2010 Firlik et al.
7,860,548 B2 12/2010 McIntyre et al.
7,860,552 B2 12/2010 Borsook et al.
7,860,561 B1 12/2010 Modarres
7,860,570 B2 12/2010 Whitehurst et al.
7,863,272 B2 1/2011 Oksenberg et al.
7,865,234 B1 1/2011 Modarres
7,865,235 B2 1/2011 Le et al.
7,865,244 B2 1/2011 Giftakis et al.
7,869,867 B2 1/2011 Armstrong et al.
7,869,884 B2 1/2011 Scott et al.
7,869,885 B2 1/2011 Begnaud et al.
7,872,235 B2 1/2011 Rousso et al.
7,873,411 B2 1/2011 Eda et al.
7,876,938 B2 1/2011 Huang et al.
7,878,965 B2 2/2011 Haber et al.
7,879,043 B2 2/2011 Meneghini et al.
7,881,760 B2 2/2011 Matsui et al.
7,881,770 B2 2/2011 Melkent et al.
7,881,780 B2 2/2011 Flaherty
7,882,135 B2 2/2011 Brunner et al.
7,884,101 B2 2/2011 Teegarden et al.
7,887,493 B2 2/2011 Stahmann et al.
7,890,155 B2 2/2011 Burns et al.
7,890,176 B2 2/2011 Jaax et al.
7,890,185 B2 2/2011 Cohen et al.
7,891,814 B2 2/2011 Harada et al.
7,892,764 B2 2/2011 Xiong et al.
7,894,890 B2 2/2011 Sun et al.
7,894,903 B2 2/2011 John
7,895,033 B2 2/2011 Joublin et al.
7,896,807 B2 3/2011 Clancy et al.
7,899,524 B2 3/2011 Kozel
7,899,525 B2 3/2011 John et al.
7,899,539 B2 3/2011 Whitehurst et al.
7,899,545 B2 3/2011 John
7,901,211 B2 3/2011 Pennebaker
7,904,134 B2 3/2011 McIntyre et al.
7,904,139 B2 3/2011 Chance
7,904,144 B2 3/2011 Causevic et al.
7,904,151 B2 3/2011 Ben-David et al.
7,904,175 B2 3/2011 Scott et al.
7,904,507 B2 3/2011 Jung et al.
7,907,994 B2 3/2011 Stolarski et al.
7,907,998 B2 3/2011 Arad
7,908,008 B2 3/2011 Ben-David et al.
7,908,009 B2 3/2011 Wyler et al.
7,909,771 B2 3/2011 Meyer et al.
7,912,530 B2 3/2011 Seki et al.
7,917,199 B2 3/2011 Drew et al.
7,917,206 B2 3/2011 Frei et al.
7,917,221 B2 3/2011 Tass
7,917,225 B2 3/2011 Wyler et al.
7,918,779 B2 4/2011 Haber et al.
7,920,914 B2 4/2011 Shieh et al.
7,920,915 B2 4/2011 Mann et al.
7,920,916 B2 4/2011 Johnson et al.
7,925,353 B1 4/2011 Whitehurst et al.
7,929,693 B2 4/2011 Terauchi et al.
7,930,035 B2 4/2011 DiLorenzo
7,932,225 B2 4/2011 Gong et al.
7,933,645 B2 4/2011 Strychacz et al.
7,933,646 B2 4/2011 Frei et al.
7,933,727 B2 4/2011 Taulu et al.
7,937,138 B2 5/2011 Liley
7,937,152 B1 5/2011 Lozano
7,937,222 B2 5/2011 Donadille et al.
7,938,782 B2 5/2011 Stahmann et al.
7,938,785 B2 5/2011 Aguilar et al.
7,941,209 B2 5/2011 Hughes et al.
7,942,824 B1 5/2011 Kayyali et al.
7,944,551 B2 5/2011 Addison et al.
7,945,304 B2 5/2011 Feinberg
7,945,316 B2 5/2011 Giftakis et al.
7,945,330 B2 5/2011 Gliner et al.
7,957,796 B2 6/2011 Maschino
7,957,797 B2 6/2011 Bourget et al.
7,957,806 B2 6/2011 Stevenson et al.
7,957,809 B2 6/2011 Bourget et al.
7,961,922 B2 6/2011 Spence et al.
7,962,204 B2 6/2011 Suffin et al.
7,962,214 B2 6/2011 Byerman et al.
7,962,219 B2 6/2011 Jaax et al.
7,962,220 B2 6/2011 Kolafa et al.
7,970,734 B2 6/2011 Townsend et al.
7,972,278 B2 7/2011 Graham et al.
7,974,688 B2 7/2011 Armstrong et al.
7,974,693 B2 7/2011 Ben-David et al.
7,974,696 B1 7/2011 DiLorenzo
7,974,697 B2 7/2011 Maschino et al.
7,974,701 B2 7/2011 Armstrong
7,974,787 B2 7/2011 Hyde et al.
7,976,465 B2 7/2011 Frei et al.
7,983,740 B2 7/2011 Culver et al.
7,983,741 B2 7/2011 Chance
7,983,757 B2 7/2011 Miyazawa et al.
7,983,762 B2 7/2011 Gliner et al.
7,986,991 B2 7/2011 Prichep
7,988,613 B2 8/2011 Becker
7,988,969 B2 8/2011 Poduslo et al.
7,991,461 B2 8/2011 Flaherty et al.
7,991,477 B2 8/2011 McDonald, III
7,993,279 B2 8/2011 Hartley et al.
7,996,075 B2 8/2011 Korzinov et al.
7,996,079 B2 8/2011 Armstrong
8,000,767 B2 8/2011 Eden et al.
8,000,773 B2 8/2011 Rousso et al.
8,000,788 B2 8/2011 Giftakis et al.
8,000,793 B2 8/2011 Libbus
8,000,794 B2 8/2011 Lozano
8,000,795 B2 8/2011 Lozano
8,001,179 B2 8/2011 Jung et al.
8,002,553 B2 8/2011 Hatlestad et al.
8,005,534 B2 8/2011 Greenwald et al.
8,005,624 B1 8/2011 Starr
8,005,894 B2 8/2011 Jung et al.
8,010,178 B2 8/2011 Seki et al.
8,010,347 B2 8/2011 Ricci et al.
8,012,107 B2 9/2011 Einav et al.
8,014,847 B2 9/2011 Shastri et al.
8,014,870 B2 9/2011 Seidman
8,016,597 B2 9/2011 Becker et al.
8,019,400 B2 9/2011 Diab et al.
8,019,410 B1 9/2011 Bharmi et al.
8,024,029 B2 9/2011 Drew et al.
8,024,032 B1 9/2011 Osorio et al.
8,025,404 B2 9/2011 Bolger et al.
8,027,730 B2 9/2011 John
8,029,553 B2 10/2011 Nemenov
8,031,076 B2 10/2011 Sachanandani et al.
8,032,209 B2 10/2011 He et al.

(56) References Cited

U.S. PATENT DOCUMENTS 8,032,229 B2 10/2011 Gerber et al.
8,032,486 B2 10/2011 Townsend et al.
8,033,996 B2 10/2011 Behar
8,036,434 B2 10/2011 Hewett et al.
8,036,728 B2 10/2011 Diab et al.
8,036,736 B2 10/2011 Snyder et al.
8,036,745 B2 10/2011 Ben-David et al.
8,041,136 B2 10/2011 Causevic
8,041,418 B2 10/2011 Giftakis et al.
8,041,419 B2 10/2011 Giftakis et al.
8,046,041 B2 10/2011 Diab et al.
8,046,042 B2 10/2011 Diab et al.
8,046,076 B2 10/2011 Whitehurst et al.
8,050,768 B2 11/2011 Firlik et al.
8,055,348 B2 11/2011 Heruth et al.
8,055,591 B2 11/2011 Jung et al.
8,059,879 B2 11/2011 Tsukimoto
8,060,181 B2 11/2011 Rodriguez Ponce et al.
8,060,194 B2 11/2011 Flaherty
8,064,994 B2 11/2011 Pardo et al.
8,065,011 B2 11/2011 Echauz et al.
8,065,012 B2 11/2011 Firlik et al.
8,065,017 B2 11/2011 Cornejo Cruz et al.
8,065,240 B2 11/2011 Jung et al.
8,065,360 B2 11/2011 Jung et al.
8,066,637 B2 11/2011 Childre et al.
8,066,647 B2 11/2011 Armitstead
8,068,904 B2 11/2011 Sun et al.
8,068,911 B2 11/2011 Giftakis et al.
8,069,125 B2 11/2011 Jung et al.
8,073,534 B2 12/2011 Low
8,073,546 B2 12/2011 Sheffield et al.
8,073,631 B2 12/2011 Wilber et al.
8,075,499 B2 12/2011 Nathan et al.
8,079,953 B2 12/2011 Braun et al.
8,082,031 B2 12/2011 Ochs
8,082,033 B2 12/2011 Rezai et al.
8,082,215 B2 12/2011 Jung et al.
8,083,786 B2 12/2011 Gafni et al.
8,086,294 B2 12/2011 Echauz et al.
8,086,296 B2 12/2011 Bystritsky
8,086,563 B2 12/2011 Jung et al.
8,088,057 B2 1/2012 Honeycutt et al.
8,089,283 B2 1/2012 Kaplan et al.
8,090,164 B2 1/2012 Bullitt et al.
8,092,549 B2 1/2012 Hillis et al.
8,095,209 B2 1/2012 Flaherty
8,095,210 B2 1/2012 Burdick et al.
8,097,926 B2 1/2012 De Graff et al.
8,099,299 B2 1/2012 Sirohey et al.
8,103,333 B2 1/2012 Tran
8,108,033 B2 1/2012 Drew et al.
8,108,036 B2 1/2012 Tran
8,108,038 B2 1/2012 Giftakis et al.
8,108,039 B2 1/2012 Saliga et al.
8,108,042 B1 1/2012 Johnson et al.
8,112,148 B2 2/2012 Giftakis et al.
8,112,153 B2 2/2012 Giftakis et al.
8,114,021 B2 2/2012 Robertson et al.
8,116,874 B2 2/2012 Tass
8,116,877 B2 2/2012 Lozano
8,116,883 B2 2/2012 Williams et al.
8,121,361 B2 2/2012 Ernst et al.
8,121,673 B2 2/2012 Tran
8,121,694 B2 2/2012 Molnar et al.
8,121,695 B2 2/2012 Gliner et al.
8,126,228 B2 2/2012 Fueyo et al.
8,126,243 B2 2/2012 Hamada et al.
8,126,528 B2 2/2012 Diab et al.
8,126,542 B2 2/2012 Grey
8,126,567 B2 2/2012 Gerber et al.
8,126,568 B2 2/2012 Gliner
8,128,572 B2 3/2012 Diab et al.
8,131,354 B2 3/2012 Arad
8,131,526 B2 3/2012 Neville
8,133,172 B2 3/2012 Shachar et al.
8,135,472 B2 3/2012 Fowler et al.
8,135,957 B2 3/2012 Dinges et al.
8,137,269 B2 3/2012 Sheikhzadeh-Nadjar et al.
8,137,270 B2 3/2012 Keenan et al.
8,140,152 B2 3/2012 John et al.
8,145,295 B2 3/2012 Boyden et al.
8,145,310 B2 3/2012 Dong et al.
8,148,417 B2 4/2012 Teegarden et al.
8,148,418 B2 4/2012 Teegarden et al.
8,150,508 B2 4/2012 Craig
8,150,523 B2 4/2012 Schiff et al.
8,150,524 B2 4/2012 Maschino et al.
8,150,796 B2 4/2012 Jung et al.
8,152,732 B2 4/2012 Lynn et al.
8,155,726 B2 4/2012 Seki et al.
8,155,736 B2 4/2012 Sullivan et al.
8,160,273 B2 4/2012 Visser et al.
8,160,317 B2 4/2012 Amunts et al.
8,160,680 B2 4/2012 Boyden et al.
8,160,689 B2 4/2012 Jadidi
8,160,696 B2 4/2012 Bendett et al.
8,165,687 B2 4/2012 Cornejo Cruz et al.
8,167,784 B1 5/2012 Honeycutt et al.
8,167,826 B2 5/2012 Oohashi et al.
8,170,315 B2 5/2012 Mistretta et al.
8,170,347 B2 5/2012 Ancelin
8,172,759 B2 5/2012 Bukhman
8,172,766 B1 5/2012 Kayyali et al.
8,174,430 B1 5/2012 DeChiaro, Jr.
8,175,359 B2 5/2012 O'Halloran et al.
8,175,360 B2 5/2012 Razifar et al.
8,175,686 B2 5/2012 Utsugi et al.
8,175,696 B2 5/2012 Liley et al.
8,175,700 B2 5/2012 Johnson et al.
8,177,724 B2 5/2012 Derchak et al.
8,177,726 B2 5/2012 John
8,177,727 B2 5/2012 Kwak
8,180,125 B2 5/2012 Avinash et al.
8,180,148 B2 5/2012 Cover et al.
8,180,420 B2 5/2012 Diab et al.
8,180,436 B2 5/2012 Boyden et al.
8,180,601 B2 5/2012 Butson et al.
8,185,186 B2 5/2012 Ross et al.
8,185,207 B2 5/2012 Molnar et al.
8,185,382 B2 5/2012 Joublin et al.
8,187,181 B2 5/2012 Osorio et al.
8,187,201 B2 5/2012 Lynn
8,188,749 B2 5/2012 Wilt et al.
8,190,227 B2 5/2012 Diab et al.
8,190,248 B2 5/2012 Besio et al.
8,190,249 B1 5/2012 Gharieb et al.
8,190,251 B2 5/2012 Molnar et al.
8,190,264 B2 5/2012 Lozano et al.
8,195,295 B2 6/2012 Stevenson et al.
8,195,298 B2 6/2012 Lozano
8,195,300 B2 6/2012 Gliner et al.
8,195,593 B2 6/2012 Jung et al.
8,197,395 B2 6/2012 Jassemidis et al.
8,197,437 B2 6/2012 Kalafut et al.
8,199,982 B2 6/2012 Fueyo et al.
8,199,985 B2 6/2012 Jakobsson et al.
8,200,319 B2 6/2012 Pu et al.
8,200,340 B2 6/2012 Skelton et al.
8,204,583 B2 6/2012 Sackellares et al.
8,204,603 B2 6/2012 Maschino
8,209,009 B2 6/2012 Giftakis et al.
8,209,018 B2 6/2012 Osorio et al.
8,209,019 B2 6/2012 Giftakis et al.
8,209,224 B2 6/2012 Pradeep et al.
8,211,035 B2 7/2012 Melker et al.
8,212,556 B1 7/2012 Schwindt et al.
8,213,670 B2 7/2012 Lai
8,214,007 B2 7/2012 Baker et al.
8,214,035 B2 7/2012 Giftakis et al.
8,219,188 B2 7/2012 Craig
8,221,330 B2 7/2012 Sarkela et al.
8,222,378 B2 7/2012 Masure
8,223,023 B2 7/2012 Sachanandani et al.

(56) References Cited

U.S. PATENT DOCUMENTS 8,224,431 B2 7/2012 Drew
8,224,433 B2 7/2012 Suffin et al.
8,224,444 B2 7/2012 Ben-David et al.
8,224,451 B2 7/2012 Jaax et al.
8,229,540 B2 7/2012 Sami et al.
8,229,559 B2 7/2012 Westendorp et al.
8,233,682 B2 7/2012 Fessler et al.
8,233,689 B2 7/2012 Razifar et al.
8,233,965 B2 7/2012 Bjornerud et al.
8,233,990 B2 7/2012 Goetz
8,235,907 B2 8/2012 Wilk et al.
8,236,005 B2 8/2012 Meneghini et al.
8,236,038 B2 8/2012 Nofzinger
8,239,014 B2 8/2012 Ochs
8,239,028 B2 8/2012 Scott
8,239,029 B2 8/2012 De Ridder
8,239,030 B1 8/2012 Hagedorn et al.
8,241,213 B2 8/2012 Lynn et al.
8,244,340 B2 8/2012 Wu et al.
8,244,341 B2 8/2012 Hinrikus et al.
8,244,347 B2 8/2012 Lozano
8,244,475 B2 8/2012 Aguilar et al.
8,244,552 B2 8/2012 Firminger et al.
8,244,553 B2 8/2012 Firminger et al.
8,248,069 B2 8/2012 Buracas
8,249,316 B2 8/2012 Hu et al.
8,249,698 B2 8/2012 Mugler et al.
8,249,718 B2 8/2012 Skelton et al.
8,249,815 B2 8/2012 Taylor
8,260,426 B2 9/2012 Armstrong et al.
8,262,714 B2 9/2012 Hulvershorn et al.
8,263,574 B2 9/2012 Schaller et al.
8,267,851 B1 9/2012 Kroll
8,270,814 B2 9/2012 Pradeep et al.
8,271,077 B1 9/2012 Rotenberg
8,280,502 B2 10/2012 Hargrove et al.
8,280,503 B2 10/2012 Linderman
8,280,505 B2 10/2012 Craig
8,280,514 B2 10/2012 Lozano et al.
8,280,517 B2 10/2012 Skelton et al.
8,285,351 B2 10/2012 Johnson et al.
8,285,368 B2 10/2012 Chen et al.
8,290,575 B2 10/2012 Tarassenko et al.
8,290,596 B2 10/2012 Wei et al.
8,295,914 B2 10/2012 Kalafut et al.
8,295,934 B2 10/2012 Leyde
8,295,935 B2 10/2012 Okun et al.
8,296,108 B2 10/2012 Tanaka
8,298,078 B2 10/2012 Sutton et al.
8,298,140 B2 10/2012 Beck-Nielsen et al.
8,301,222 B2 10/2012 Rongen et al.
8,301,232 B2 10/2012 Albert et al.
8,301,233 B2 10/2012 Zhang et al.
8,301,257 B2 10/2012 Hsu et al.
8,303,636 B2 11/2012 Schiffer
8,304,246 B2 11/2012 Cook et al.
8,305,078 B2 11/2012 Savukov et al.
8,306,607 B1 11/2012 Levi et al.
8,306,610 B2 11/2012 Mirow
8,306,627 B2 11/2012 Armstrong
8,308,646 B2 11/2012 Belohlavek et al.
8,308,661 B2 11/2012 Miesel et al.
8,311,622 B2 11/2012 Snyder et al.
8,311,747 B2 11/2012 Taylor
8,311,748 B2 11/2012 Taylor et al.
8,311,750 B2 11/2012 Taylor
8,313,441 B2 11/2012 Dalton
8,314,707 B2 11/2012 Kobetski et al.
8,315,703 B2 11/2012 Lozano
8,315,704 B2 11/2012 Jaax et al.
8,315,710 B2 11/2012 Skelton et al.
8,315,812 B2 11/2012 Taylor
8,315,813 B2 11/2012 Taylor et al.
8,315,814 B2 11/2012 Taylor et al.
8,315,962 B1 11/2012 Horne
8,315,970 B2 11/2012 Zalay et al.
8,320,649 B2 11/2012 Shahaf et al.
8,321,150 B2 11/2012 Taylor
8,323,188 B2 12/2012 Tran
8,323,189 B2 12/2012 Tran et al.
8,323,204 B2 12/2012 Stahmann et al.
8,326,418 B2 12/2012 Sommer et al.
8,326,420 B2 12/2012 Skelton et al.
8,326,433 B2 12/2012 Blum et al.
8,328,718 B2 12/2012 Tran
8,332,017 B2 12/2012 Tarassenko et al.
8,332,024 B2 12/2012 Rapoport et al.
8,332,038 B2 12/2012 Heruth et al.
8,332,041 B2 12/2012 Skelton et al.
8,332,191 B2 12/2012 Rosthal et al.
8,334,690 B2 12/2012 Kitching et al.
8,335,561 B1 12/2012 Modarres
8,335,664 B2 12/2012 Eberle
8,335,715 B2 12/2012 Pradeep et al.
8,335,716 B2 12/2012 Pradeep et al.
8,337,404 B2 12/2012 Osorio
8,340,752 B2 12/2012 Cox et al.
8,340,753 B2 12/2012 Hardt
8,340,771 B2 12/2012 Thimineur et al.
8,343,026 B2 1/2013 Gardiner et al.
8,343,027 B1 1/2013 DiMino et al.
8,343,066 B1 1/2013 Eagleman et al.
8,346,331 B2 1/2013 Bunce et al.
8,346,342 B2 1/2013 Kalafut
8,346,349 B2 1/2013 Guttag et al.
8,346,354 B2 1/2013 Hyde et al.
8,346,365 B2 1/2013 Lozano
8,350,804 B1 1/2013 Moll
8,352,023 B2 1/2013 John et al.
8,352,031 B2 1/2013 Rousso et al.
8,353,837 B2 1/2013 John et al.
8,354,438 B2 1/2013 Chez
8,354,881 B2 1/2013 Denison
8,355,768 B2 1/2013 Masmanidis et al.
8,356,004 B2 1/2013 Jung et al.
8,356,594 B2 1/2013 Ujhazy et al.
8,358,818 B2 1/2013 Miga et al.
8,359,080 B2 1/2013 Diab et al.
8,362,780 B2 1/2013 Rosthal et al.
8,364,226 B2 1/2013 Diab et al.
8,364,254 B2 1/2013 Jacquin et al.
8,364,255 B2 1/2013 Isenhart et al.
8,364,271 B2 1/2013 De Ridder
8,364,272 B2 1/2013 Goetz
8,369,940 B2 2/2013 Sun et al.
8,374,411 B2 2/2013 Ernst et al.
8,374,412 B2 2/2013 Kimura
8,374,690 B2 2/2013 Ma
8,374,696 B2 2/2013 Sanchez et al.
8,374,701 B2 2/2013 Hyde et al.
8,374,703 B2 2/2013 Imran
8,376,965 B2 2/2013 Schuette et al.
8,379,947 B2 2/2013 Garg et al.
8,379,952 B2 2/2013 McIntyre et al.
8,380,289 B2 2/2013 Zellers et al.
8,380,290 B2 2/2013 Scarantino et al.
8,380,296 B2 2/2013 Lee et al.
8,380,314 B2 2/2013 Panken et al.
8,380,316 B2 2/2013 Hagedorn et al.
8,380,658 B2 2/2013 Jung et al.
8,382,667 B2 2/2013 Osorio
8,386,188 B2 2/2013 Taylor et al.
8,386,244 B2 2/2013 Ricci et al.
8,386,312 B2 2/2013 Pradeep et al.
8,386,313 B2 2/2013 Pradeep et al.
RE44,097 E 3/2013 Wilber et al.
8,388,529 B2 3/2013 Fueyo et al.
8,388,530 B2 3/2013 Shusterman
8,388,555 B2 3/2013 Panken et al.
8,391,942 B2 3/2013 Benni
8,391,956 B2 3/2013 Zellers et al.
8,391,966 B2 3/2013 Luo et al.
8,392,250 B2 3/2013 Pradeep et al.
8,392,251 B2 3/2013 Pradeep et al.

(56) References Cited

U.S. PATENT DOCUMENTS 8,392,253 B2 3/2013 Pradeep et al.
8,392,254 B2 3/2013 Pradeep et al.
8,392,255 B2 3/2013 Pradeep et al.
8,396,542 B2 3/2013 Johnson et al.
8,396,545 B2 3/2013 Berridge et al.
8,396,546 B2 3/2013 Hirata et al.
8,396,557 B2 3/2013 DiLorenzo
8,396,565 B2 3/2013 Singhal et al.
8,396,744 B2 3/2013 Pradeep et al.
8,398,692 B2 3/2013 Deisseroth et al.
8,401,624 B2 3/2013 Govari
8,401,626 B2 3/2013 Mietus et al.
8,401,634 B2 3/2013 Whitehurst et al.
8,401,654 B1 3/2013 Foster et al.
8,401,655 B2 3/2013 De Ridder
8,401,666 B2 3/2013 Skelton et al.
8,403,848 B2 3/2013 Mietus et al.
8,406,838 B2 3/2013 Kato
8,406,841 B2 3/2013 Lin et al.
8,406,848 B2 3/2013 Wu et al.
8,406,862 B2 3/2013 Hopenfeld
8,406,890 B2 3/2013 Goetz
8,412,334 B2 4/2013 Whitehurst et al.
8,412,335 B2 4/2013 Gliner et al.
8,412,337 B2 4/2013 Lozano
8,412,338 B2 4/2013 Faltys
8,412,655 B2 4/2013 Colman et al.
8,415,123 B2 4/2013 Pilla et al.
8,417,344 B2 4/2013 Colborn et al.
8,423,118 B2 4/2013 Wenzel et al.
8,423,125 B2 4/2013 Rousso et al.
8,423,144 B2 4/2013 Tass et al.
8,423,155 B1 4/2013 Jaax et al.
8,423,297 B2 4/2013 Wilber
8,425,415 B2 4/2013 Tran
8,425,583 B2 4/2013 Nofzinger
8,428,696 B2 4/2013 Foo
8,428,703 B2 4/2013 Hopenfeld
8,428,704 B2 4/2013 Johnson et al.
8,428,726 B2 4/2013 Ignagni et al.
8,429,225 B2 4/2013 Jung et al.
8,430,805 B2 4/2013 Burnett et al.
8,430,816 B2 4/2013 Avinash et al.
8,431,537 B2 4/2013 Gong et al.
8,433,388 B2 4/2013 Blunt et al.
8,433,410 B2 4/2013 Stevenson et al.
8,433,414 B2 4/2013 Gliner et al.
8,433,418 B2 4/2013 DeRidder
8,435,166 B2 5/2013 Burnett et al.
8,437,843 B1 5/2013 Kayyali et al.
8,437,844 B2 5/2013 Syed Momen et al.
8,437,861 B2 5/2013 Skelton et al.
8,439,845 B2 5/2013 Folkerts et al.
8,442,626 B2 5/2013 Zavoronkovs et al.
8,444,571 B2 5/2013 Folkerts et al.
8,445,021 B2 5/2013 Akhtari et al.
8,445,851 B2 5/2013 Rousso et al.
8,447,392 B2 5/2013 Llinas
8,447,407 B2 5/2013 Talathi et al.
8,447,411 B2 5/2013 Skelton et al.
8,449,471 B2 5/2013 Tran
8,452,387 B2 5/2013 Osorio et al.
8,452,544 B2 5/2013 Hymel
8,454,555 B2 6/2013 Struijk et al.
8,456,164 B2 6/2013 Subbarao
8,456,166 B2 6/2013 DePavia et al.
8,456,309 B2 6/2013 Sachanandani et al.
8,457,730 B2 6/2013 Makinen
8,457,746 B2 6/2013 Libbus
8,457,747 B2 6/2013 Terry, Jr.
8,461,988 B2 6/2013 Tran
8,463,006 B2 6/2013 Prokoski
8,463,007 B2 6/2013 Steinberg et al.
8,463,349 B2 6/2013 Diab et al.
8,463,370 B2 6/2013 Korhonen et al.
8,463,374 B2 6/2013 Hudson et al.
8,463,378 B2 6/2013 Tass
8,463,386 B2 6/2013 Tass
8,463,387 B2 6/2013 De Ridder
8,464,288 B2 6/2013 Pradeep et al.
8,465,408 B2 6/2013 Phillips et al.
8,467,877 B2 6/2013 Imran
8,467,878 B2 6/2013 Lozano et al.
8,473,024 B2 6/2013 Causevic et al.
8,473,044 B2 6/2013 Lee et al.
8,473,306 B2 6/2013 Seely
8,473,345 B2 6/2013 Pradeep et al.
8,475,354 B2 7/2013 Phillips et al.
8,475,368 B2 7/2013 Tran et al.
8,475,371 B2 7/2013 Derchak et al.
8,475,387 B2 7/2013 Derchak et al.
8,475,506 B1 7/2013 Bendett et al.
8,478,389 B1 7/2013 Brockway et al.
8,478,394 B2 7/2013 Prichep et al.
8,478,402 B2 7/2013 Wahlstrand et al.
8,478,417 B2 7/2013 Drew et al.
8,478,428 B2 7/2013 Cowley
8,480,554 B2 7/2013 Phillips et al.
8,483,795 B2 7/2013 Okada
8,483,815 B2 7/2013 Liley
8,483,816 B1 7/2013 Payton et al.
8,484,081 B2 7/2013 Pradeep et al.
8,484,270 B2 7/2013 Kurtz et al.
8,485,979 B2 7/2013 Giftakis et al.
8,487,760 B2 7/2013 Kangas et al.
8,489,185 B2 7/2013 Kilgard et al.
8,492,336 B2 7/2013 Masure
8,494,610 B2 7/2013 Pradeep et al.
8,494,829 B2 7/2013 Teixeira
8,494,857 B2 7/2013 Pakhomov
8,494,905 B2 7/2013 Pradeep et al.
8,496,594 B2 7/2013 Taylor et al.
8,498,697 B2 7/2013 Yong et al.
8,498,699 B2 7/2013 Wells et al.
8,498,708 B2 7/2013 Bentwich
RE44,408 E 8/2013 Lindsay
8,500,282 B2 8/2013 Bolger et al.
8,500,636 B2 8/2013 Tran
8,504,150 B2 8/2013 Skelton
8,506,469 B2 8/2013 Dietrich et al.
8,509,879 B2 8/2013 Durkin et al.
8,509,881 B2 8/2013 Thiagarajan et al.
8,509,885 B2 8/2013 Snyder et al.
8,509,904 B2 8/2013 Rickert et al.
8,512,219 B2 8/2013 Ferren et al.
8,512,221 B2 8/2013 Kaplan et al.
8,512,240 B1 8/2013 Zuckerman-Stark et al.
8,515,535 B2 8/2013 Hopper et al.
8,515,538 B1 8/2013 Osorio et al.
8,515,541 B1 8/2013 Jaax et al.
8,515,549 B2 8/2013 Panken et al.
8,515,550 B2 8/2013 Skelton et al.
8,517,909 B2 8/2013 Honeycutt et al.
8,517,912 B2 8/2013 Clare
8,519,705 B2 8/2013 Savukov et al.
8,519,853 B2 8/2013 Eskandarian et al.
8,520,974 B2 8/2013 Fujita et al.
8,521,284 B2 8/2013 Kim et al.
8,523,779 B2 9/2013 Taylor et al.
8,525,673 B2 9/2013 Tran
8,525,687 B2 9/2013 Tran
8,527,029 B2 9/2013 Okada
8,527,035 B2 9/2013 Diamond
8,527,435 B1 9/2013 Han et al.
8,529,463 B2 9/2013 Della Santina et al.
8,531,291 B2 9/2013 Tran
8,532,756 B2 9/2013 Schalk et al.
8,532,757 B2 9/2013 Molnar et al.
8,533,042 B2 9/2013 Pradeep et al.
8,536,667 B2 9/2013 de Graff et al.
8,538,108 B2 9/2013 Shekhar et al.
8,538,512 B1 9/2013 Bibian et al.
8,538,513 B2 9/2013 Molnar et al.
8,538,514 B2 9/2013 Sun et al.

(56) References Cited

U.S. PATENT DOCUMENTS 8,538,523 B2 9/2013 Sommer et al.
8,538,536 B2 9/2013 Rezai et al.
8,538,543 B2 9/2013 McIntyre et al.
8,538,700 B2 9/2013 Badri et al.
8,538,705 B2 9/2013 Greenwald
8,542,900 B2 9/2013 Tolkowsky et al.
8,542,916 B2 9/2013 Tognoli et al.
8,543,189 B2 9/2013 Paitel et al.
8,543,199 B2 9/2013 Snyder et al.
8,543,214 B2 9/2013 Osorio et al.
8,543,219 B2 9/2013 Tass
8,545,378 B2 10/2013 Peterchev
8,545,416 B1 10/2013 Kayyali et al.
8,545,420 B2 10/2013 Einav et al.
8,545,436 B2 10/2013 Robertson et al.
8,548,583 B2 10/2013 Rousso et al.
8,548,594 B2 10/2013 Thimineur et al.
8,548,604 B2 10/2013 Whitehurst et al.
8,548,786 B2 10/2013 Plenz
8,548,852 B2 10/2013 Pradeep et al.
8,553,956 B2 10/2013 Wu et al.
8,554,311 B2 10/2013 Warner et al.
8,554,325 B2 10/2013 Molnar et al.
8,559,645 B2 10/2013 Corona-Strauss et al.
8,560,034 B1 10/2013 Diab et al.
8,560,041 B2 10/2013 Flaherty et al.
8,560,073 B2 10/2013 Osorio
8,562,525 B2 10/2013 Nakashima et al.
8,562,526 B2 10/2013 Heneghan et al.
8,562,527 B2 10/2013 Braun et al.
8,562,536 B2 10/2013 Osorio et al.
8,562,540 B2 10/2013 Goodall et al.
8,562,548 B2 10/2013 Shimada et al.
8,562,660 B2 10/2013 Peyman
8,562,951 B2 10/2013 Suffin et al.
8,565,606 B2 10/2013 Kim et al.
8,565,864 B2 10/2013 Drew et al.
8,565,867 B2 10/2013 Armstrong et al.
8,565,883 B2 10/2013 Lozano
8,565,886 B2 10/2013 Nelson et al.
8,568,231 B2 10/2013 Solanki et al.
8,568,329 B2 10/2013 Lee et al.
8,571,293 B2 10/2013 Ernst et al.
8,571,629 B2 10/2013 Faro et al.
8,571,642 B2 10/2013 Gill et al.
8,571,643 B2 10/2013 Osorio et al.
8,571,653 B2 10/2013 Ben-David et al.
8,574,164 B2 11/2013 Mashiach
8,574,279 B2 11/2013 Schiffer
8,577,103 B2 11/2013 Vija et al.
8,577,464 B2 11/2013 Mashiach
8,577,465 B2 11/2013 Mashiach
8,577,466 B2 11/2013 Mashiach
8,577,467 B2 11/2013 Mashiach et al.
8,577,468 B2 11/2013 Mashiach et al.
8,577,472 B2 11/2013 Mashiach et al.
8,577,478 B2 11/2013 Mashiach et al.
8,579,786 B2 11/2013 Osorio et al.
8,579,793 B1 11/2013 Honeycutt et al.
8,579,795 B2 11/2013 Martel
8,579,834 B2 11/2013 Davis et al.
8,583,238 B1 11/2013 Heldman et al.
8,583,252 B2 11/2013 Skelton et al.
8,585,568 B2 11/2013 Phillips et al.
8,586,019 B2 11/2013 Satchi-Fainaro et al.
8,586,932 B2 11/2013 Rousso et al.
8,587,304 B2 11/2013 Budker et al.
8,588,486 B2 11/2013 Virtue et al.
8,588,552 B2 11/2013 Garg et al.
8,588,899 B2 11/2013 Schiff
8,588,929 B2 11/2013 Skelton et al.
8,588,933 B2 11/2013 Floyd et al.
8,588,941 B2 11/2013 Mashiach
8,589,316 B2 11/2013 Lujan et al.
8,591,419 B2 11/2013 Tyler
8,591,498 B2 11/2013 John
8,593,141 B1 11/2013 Radparvar et al.
8,593,154 B2 11/2013 Ross
8,594,798 B2 11/2013 Osorio et al.
8,594,800 B2 11/2013 Butson et al.
8,594,950 B2 11/2013 Taylor
8,597,171 B2 12/2013 Altman et al.
8,597,193 B2 12/2013 Grunwald et al.
8,600,493 B2 12/2013 Tanner et al.
8,600,502 B2 12/2013 Lovett et al.
8,600,513 B2 12/2013 Aur et al.
8,600,521 B2 12/2013 Armstrong et al.
8,600,696 B2 12/2013 Zafiris
8,603,790 B2 12/2013 Deisseroth et al.
8,606,349 B2 12/2013 Rousso et al.
8,606,351 B2 12/2013 Wheeler
8,606,356 B2 12/2013 Lee et al.
8,606,360 B2 12/2013 Butson et al.
8,606,361 B2 12/2013 Gliner et al.
8,606,530 B2 12/2013 Taylor
8,606,592 B2 12/2013 Hyde et al.
8,612,005 B2 12/2013 Rezai et al.
8,613,695 B2 12/2013 Von Ohlsen et al.
8,613,905 B2 12/2013 El-Agnaf
8,614,254 B2 12/2013 Llinas et al.
8,614,873 B1 12/2013 Beran
8,615,293 B2 12/2013 Jacobson et al.
8,615,309 B2 12/2013 Craig
8,615,479 B2 12/2013 Jung et al.
8,615,664 B2 12/2013 Jung et al.
8,618,799 B1 12/2013 Radparvar et al.
8,620,206 B2 12/2013 Brown et al.
8,620,419 B2 12/2013 Rotenberg et al.
8,626,264 B1 1/2014 Beran
8,626,301 B2 1/2014 Libbus
8,628,328 B2 1/2014 Palacios
8,628,480 B2 1/2014 Derchak
8,630,699 B2 1/2014 Baker et al.
8,630,705 B2 1/2014 Mann et al.
8,630,812 B2 1/2014 Taylor
8,632,465 B1 1/2014 Brockway
8,632,750 B2 1/2014 Suffin et al.
8,634,616 B2 1/2014 Den Harder et al.
8,634,922 B1 1/2014 Osorio et al.
8,635,105 B2 1/2014 Pradeep et al.
8,636,640 B2 1/2014 Chang
8,638,950 B2 1/2014 Anderson et al.
8,641,632 B2 2/2014 Quintin et al.
8,641,646 B2 2/2014 Colborn
8,644,754 B2 2/2014 Brown
8,644,910 B2 2/2014 Rousso et al.
8,644,914 B2 2/2014 Hunt
8,644,921 B2 2/2014 Wilson
8,644,945 B2 2/2014 Skelton et al.
8,644,946 B2 2/2014 Butson et al.
8,644,954 B2 2/2014 Jaax et al.
8,644,957 B2 2/2014 Mashiach
8,647,278 B2 2/2014 Ji et al.
8,648,017 B2 2/2014 Umansky et al.
8,649,845 B2 2/2014 McIntyre et al.
8,649,866 B2 2/2014 Brooke
8,649,871 B2 2/2014 Frei et al.
8,652,038 B2 2/2014 Tran et al.
8,652,187 B2 2/2014 Wells et al.
8,652,189 B2 2/2014 Gafni et al.
8,655,428 B2 2/2014 Pradeep et al.
8,655,437 B2 2/2014 Pradeep et al.
8,655,817 B2 2/2014 Hasey et al.
8,657,732 B2 2/2014 Vasishta
8,657,756 B2 2/2014 Stahmann et al.
8,658,149 B2 2/2014 Satchi-Fainaro et al.
8,660,642 B2 2/2014 Ferren et al.
8,660,649 B2 2/2014 Ruffini et al.
8,660,666 B2 2/2014 Craig
8,660,799 B2 2/2014 Watson et al.
8,664,258 B2 3/2014 Teegarden et al.
8,666,099 B2 3/2014 Nielsen et al.
8,666,467 B2 3/2014 Lynn et al.
8,666,478 B2 3/2014 Violette et al.

(56) References Cited

U.S. PATENT DOCUMENTS 8,666,501 B2 3/2014 Kilgard et al.
8,668,496 B2 3/2014 Nolen
8,670,603 B2 3/2014 Tolkowsky et al.
8,672,852 B2 3/2014 Gavish
8,675,936 B2 3/2014 Vija et al.
8,675,945 B2 3/2014 Barnhorst et al.
8,675,983 B2 3/2014 Yahil
8,676,324 B2 3/2014 Simon et al.
8,676,325 B2 3/2014 Lindenthaler et al.
8,676,330 B2 3/2014 Simon et al.
8,679,009 B2 3/2014 Osorio
8,680,119 B2 3/2014 Teegarden et al.
8,680,991 B2 3/2014 Tran
8,682,422 B2 3/2014 Hopenfeld
8,682,441 B2 3/2014 De Ridder
8,682,449 B2 3/2014 Simon
8,682,687 B2 3/2014 Hyde et al.
8,684,742 B2 4/2014 Siefert
8,684,900 B2 4/2014 Tran
8,684,921 B2 4/2014 Osorio
8,684,922 B2 4/2014 Tran
8,684,926 B2 4/2014 Arndt
8,688,209 B2 4/2014 Verbitskiy
8,690,748 B1 4/2014 Fu
8,693,756 B2 4/2014 Tolkowsky et al.
8,693,765 B2 4/2014 Mercier et al.
8,694,087 B2 4/2014 Schiff
8,694,089 B2 4/2014 Arad
8,694,092 B2 4/2014 Ferren et al.
8,694,107 B2 4/2014 Falci
8,694,118 B2 4/2014 Armstrong
8,694,157 B2 4/2014 Wenderow et al.
8,696,722 B2 4/2014 Deisseroth et al.
8,696,724 B2 4/2014 Rogers
8,698,639 B2 4/2014 Fung et al.
8,700,137 B2 4/2014 Albert
8,700,141 B2 4/2014 Causevic
8,700,142 B2 4/2014 John et al.
8,700,163 B2 4/2014 Terry, Jr. et al.
8,700,167 B2 4/2014 Sabel
8,700,174 B2 4/2014 Skelton et al.
8,700,183 B2 4/2014 Mashiach
8,703,114 B2 4/2014 Satchi-Fainaro et al.
8,706,183 B2 4/2014 Cui et al.
8,706,205 B2 4/2014 Shahaf et al.
8,706,206 B2 4/2014 Kanai et al.
8,706,207 B2 4/2014 Flint
8,706,237 B2 4/2014 Giftakis et al.
8,706,241 B2 4/2014 Firlik et al.
8,706,518 B2 4/2014 Hyde et al.
8,708,903 B2 4/2014 Tran
8,708,934 B2 4/2014 Skelton et al.
8,711,655 B2 4/2014 Gzara et al.
8,712,507 B2 4/2014 Cazares et al.
8,712,512 B2 4/2014 Doidge et al.
8,712,513 B1 4/2014 Modarres
8,712,547 B2 4/2014 Whitehurst et al.
8,716,447 B2 5/2014 Deisseroth et al.
8,717,430 B2 5/2014 Simon et al.
8,718,747 B2 5/2014 Bjornerud et al.
8,718,776 B2 5/2014 Mashiach et al.
8,718,777 B2 5/2014 Lowry et al.
8,718,779 B2 5/2014 Whitehurst et al.
8,721,695 B2 5/2014 Tass et al.
8,724,871 B1 5/2014 Biagiotti et al.
8,725,238 B2 5/2014 Liu et al.
8,725,243 B2 5/2014 Dilorenzo et al.
8,725,311 B1 5/2014 Breed
8,725,668 B2 5/2014 Georgopoulos
8,725,669 B1 5/2014 Fu
8,725,796 B2 5/2014 Serena
8,727,978 B2 5/2014 Tran et al.
8,728,001 B2 5/2014 Lynn
8,729,040 B2 5/2014 Deisseroth et al.
8,731,650 B2 5/2014 Sajda et al.
8,731,656 B2 5/2014 Bourget et al.
8,731,987 B2 5/2014 Chen et al.
8,733,290 B2 5/2014 Gerashchenko
8,734,356 B2 5/2014 Taylor
8,734,357 B2 5/2014 Taylor
8,734,498 B2 5/2014 DiMauro et al.
8,738,121 B2 5/2014 Virag et al.
8,738,126 B2 5/2014 Craig
8,738,136 B2 5/2014 Frei et al.
8,738,140 B2 5/2014 De Ridder
8,738,395 B2 5/2014 Hyde et al.
8,744,562 B2 6/2014 Giftakis et al.
8,744,563 B2 6/2014 Yoshida
8,747,313 B2 6/2014 Tran et al.
8,747,336 B2 6/2014 Tran
8,747,382 B2 6/2014 D'Souza et al.
8,750,971 B2 6/2014 Tran
8,750,974 B2 6/2014 Baker et al.
8,750,992 B2 6/2014 Hopper et al.
8,751,008 B2 6/2014 Carlton et al.
8,751,011 B2 6/2014 Skelton et al.
8,753,296 B2 6/2014 Einav et al.
8,754,238 B2 6/2014 Teegarden et al.
8,755,854 B2 6/2014 Addison et al.
8,755,856 B2 6/2014 Diab et al.
8,755,868 B2 6/2014 Yazicioglu
8,755,869 B2 6/2014 Zhang et al.
8,755,871 B2 6/2014 Weng et al.
8,755,877 B2 6/2014 Zoica
8,755,901 B2 6/2014 Skelton et al.
8,756,017 B2 6/2014 Hu et al.
8,758,274 B2 6/2014 Sahasrabudhe et al.
8,761,438 B2 6/2014 Lee et al.
8,761,866 B2 6/2014 Chance
8,761,868 B2 6/2014 Giftakis et al.
8,761,869 B2 6/2014 Leuthardt et al.
8,761,889 B2 6/2014 Wingeier et al.
8,762,065 B2 6/2014 DiLorenzo
8,762,202 B2 6/2014 Pradeep et al.
8,764,651 B2 7/2014 Tran
8,764,652 B2 7/2014 Lee et al.
8,764,653 B2 7/2014 Kaminska et al.
8,764,673 B2 7/2014 McCraty et al.
8,768,022 B2 7/2014 Miga et al.
8,768,427 B2 7/2014 Sjaaheim et al.
8,768,431 B2 7/2014 Ross et al.
8,768,446 B2 7/2014 Drew et al.
8,768,447 B2 7/2014 Ermes et al.
8,768,449 B2 7/2014 Pesaran et al.
8,768,471 B2 7/2014 Colborn et al.
8,768,477 B2 7/2014 Spitzer et al.
8,768,718 B2 7/2014 Cazares et al.
8,771,194 B2 7/2014 John et al.
8,774,923 B2 7/2014 Rom
8,775,340 B2 7/2014 Waxman et al.
8,781,193 B2 7/2014 Steinberg et al.
8,781,197 B2 7/2014 Wang et al.
8,781,557 B2 7/2014 Dean et al.
8,781,563 B2 7/2014 Foo
8,781,595 B2 7/2014 Grevious et al.
8,781,597 B2 7/2014 DiLorenzo
8,781,796 B2 7/2014 Mott et al.
8,784,109 B2 7/2014 Gottfried
8,784,322 B2 7/2014 Kim et al.
8,785,441 B2 7/2014 Teegarden et al.
8,786,624 B2 7/2014 Echauz et al.
8,787,637 B2 7/2014 Duchesnay et al.
8,788,030 B1 7/2014 Payton et al.
8,788,033 B2 7/2014 Rossi
8,788,044 B2 7/2014 John
8,788,055 B2 7/2014 Gerber et al.
8,788,057 B2 7/2014 Stevenson et al.
8,790,255 B2 7/2014 Behar
8,790,272 B2 7/2014 Sackner et al.
8,790,297 B2 7/2014 Bromander et al.
8,792,972 B2 7/2014 Zaidel et al.
8,792,974 B2 7/2014 Rothman
8,792,991 B2 7/2014 Gerber et al.
8,795,175 B2 8/2014 Funane et al.

(56) References Cited

U.S. PATENT DOCUMENTS 8,798,717 B2 8/2014 Roscher
8,798,728 B2 8/2014 Drew et al.
8,798,735 B1 8/2014 Bibian et al.
8,798,736 B2 8/2014 Sullivan et al.
8,798,773 B2 8/2014 Mashiach
8,801,620 B2 8/2014 Melker et al.
8,805,516 B2 8/2014 Bentwich
8,805,518 B2 8/2014 King et al.
8,812,126 B2 8/2014 Butson et al.
8,812,237 B2 8/2014 Wilt et al.
8,812,245 B2 8/2014 Taylor
8,812,246 B2 8/2014 Taylor
8,814,923 B2 8/2014 Nissila et al.
8,815,582 B2 8/2014 Deisseroth et al.
8,821,376 B2 9/2014 Tolkowsky
8,821,408 B2 9/2014 Hu et al.
8,821,559 B2 9/2014 DiMauro et al.
8,825,149 B2 9/2014 Kraus et al.
8,825,166 B2 9/2014 John
8,825,167 B2 9/2014 Tass et al.
8,825,428 B2 9/2014 Addison et al.
8,827,912 B2 9/2014 Bukhman
8,827,917 B2 9/2014 Watson et al.
8,829,908 B2 9/2014 Roshtal et al.
8,831,705 B2 9/2014 Dobak
8,831,731 B2 9/2014 Blum et al.
8,831,732 B2 9/2014 Frei et al.
8,834,392 B2 9/2014 Panken et al.
8,834,546 B2 9/2014 Deisseroth et al.
8,838,201 B2 9/2014 Mori et al.
8,838,225 B2 9/2014 Ahonen et al.
8,838,226 B2 9/2014 Bibian et al.
8,838,227 B2 9/2014 Causevic et al.
8,838,247 B2 9/2014 Hagedorn et al.
8,843,199 B2 9/2014 Kim et al.
8,843,201 B1 9/2014 Heldman et al.
8,843,210 B2 9/2014 Simon et al.
8,845,545 B2 9/2014 Folkerts et al.
8,849,390 B2 9/2014 Echauz et al.
8,849,392 B2 9/2014 Lozano
8,849,407 B1 9/2014 Danilov et al.
8,849,409 B2 9/2014 Colborn et al.
8,849,632 B2 9/2014 Sparks et al.
8,849,681 B2 9/2014 Hargrove et al.
8,852,073 B2 10/2014 Genereux et al.
8,852,100 B2 10/2014 Osorio
8,852,103 B2 10/2014 Rothberg et al.
8,855,758 B2 10/2014 Rodriquez-Villegas et al.
8,855,773 B2 10/2014 Kokones et al.
8,855,775 B2 10/2014 Leyde
8,858,440 B2 10/2014 Tyler
8,858,449 B2 10/2014 Inan et al.
8,861,819 B2 10/2014 Lee et al.
8,862,196 B2 10/2014 Lynn
8,862,210 B2 10/2014 Yazicioglu et al.
8,862,236 B2 10/2014 Wolpaw et al.
8,862,581 B2 10/2014 Zhang et al.
8,864,310 B2 10/2014 Gross et al.
8,864,806 B2 10/2014 Wells et al.
8,868,148 B2 10/2014 Engelbrecht et al.
8,868,163 B2 10/2014 Guttag et al.
8,868,172 B2 10/2014 Leyde et al.
8,868,173 B2 10/2014 Nelson et al.
8,868,174 B2 10/2014 Sato et al.
8,868,175 B2 10/2014 Arad
8,868,177 B2 10/2014 Simon et al.
8,868,189 B2 10/2014 Stevenson et al.
8,868,201 B2 10/2014 Roberts et al.
8,870,737 B2 10/2014 Phillips et al.
8,871,797 B2 10/2014 Teegarden et al.
8,872,640 B2 10/2014 Horseman
8,874,205 B2 10/2014 Simon et al.
8,874,218 B2 10/2014 Terry, Jr.
8,874,227 B2 10/2014 Simon et al.
8,874,439 B2 10/2014 Kim et al.
8,880,207 B2 11/2014 Abeyratne et al.
8,880,576 B2 11/2014 Ochs et al.
8,886,299 B2 11/2014 Yazicioglu et al.
8,886,302 B2 11/2014 Skelton et al.
8,888,672 B2 11/2014 Phillips et al.
8,888,673 B2 11/2014 Phillips et al.
8,888,702 B2 11/2014 Osorio
8,888,708 B2 11/2014 Diab et al.
8,888,723 B2 11/2014 Einav
8,892,207 B2 11/2014 Nelson et al.
8,893,120 B2 11/2014 Pinsky et al.
8,898,037 B2 11/2014 Watson et al.
8,900,284 B2 12/2014 DiMauro et al.
8,902,070 B2 12/2014 Kobetski et al.
8,903,479 B2 12/2014 Zoicas
8,903,483 B2 12/2014 Sun et al.
8,903,486 B2 12/2014 Bourget et al.
8,903,494 B2 12/2014 Goldwasser et al.
8,906,360 B2 12/2014 Deisseroth et al.
8,907,668 B2 12/2014 Okada
8,909,345 B1 12/2014 Danilov et al.
8,910,638 B2 12/2014 Boyden et al.
8,913,810 B2 12/2014 Panin et al.
8,914,100 B2 12/2014 Adachi et al.
8,914,115 B2 12/2014 Giftakis et al.
8,914,119 B2 12/2014 Wu et al.
8,914,122 B2 12/2014 Simon et al.
8,915,741 B2 12/2014 Hatlestad et al.
8,915,871 B2 12/2014 Einav
8,918,162 B2 12/2014 Prokoski
8,918,176 B2 12/2014 Nelson et al.
8,918,178 B2 12/2014 Simon et al.
8,918,183 B2 12/2014 Carlton et al.
8,921,320 B2 12/2014 Paul et al.
8,922,376 B2 12/2014 Kangas et al.
8,922,788 B2 12/2014 Addison et al.
8,923,958 B2 12/2014 Gupta et al.
8,924,235 B2 12/2014 Seely
RE45,336 E 1/2015 Teegarden et al.
RE45,337 E 1/2015 Teegarden et al.
8,926,959 B2 1/2015 Deisseroth et al.
8,929,991 B2 1/2015 Fowler et al.
8,929,999 B2 1/2015 Maschiach
8,932,218 B1 1/2015 Thompson
8,932,227 B2 1/2015 Lynn
8,932,562 B2 1/2015 Deisseroth et al.
8,933,696 B2 1/2015 Nishikawa
8,934,685 B2 1/2015 Avinash et al.
8,934,965 B2 1/2015 Rogers et al.
8,934,967 B2 1/2015 Kilgard et al.
8,934,979 B2 1/2015 Moffitt
8,934,986 B2 1/2015 Goetz
8,936,629 B2 1/2015 Boyden et al.
8,936,630 B2 1/2015 Denison et al.
8,938,102 B2 1/2015 Carroll
8,938,289 B2 1/2015 Einav et al.
8,938,290 B2 1/2015 Wingeier et al.
8,938,301 B2 1/2015 Hagedorn
8,939,903 B2 1/2015 Roberts et al.
8,942,777 B2 1/2015 Diab et al.
8,942,813 B1 1/2015 Hagedorn et al.
8,942,817 B2 1/2015 Hyde et al.
8,945,006 B2 2/2015 Osorio
8,948,834 B2 2/2015 Diab et al.
8,948,849 B2 2/2015 Diamond et al.
8,948,855 B2 2/2015 Osorio et al.
8,948,860 B2 2/2015 Causevic
8,951,189 B2 2/2015 Osorio
8,951,190 B2 2/2015 Chmiel et al.
8,951,192 B2 2/2015 Osorio
8,951,203 B2 2/2015 Patangay et al.
8,954,139 B2 2/2015 Hopenfeld et al.
8,954,146 B2 2/2015 Hopper et al.
8,954,293 B2 2/2015 Klinkenbusch
8,955,010 B2 2/2015 Pradeep et al.
8,955,974 B2 2/2015 Gross et al.
8,956,277 B2 2/2015 Mishelevich
8,956,363 B2 2/2015 Schneider et al.
8,958,868 B2 2/2015 Ghovanloo et al.

(56) References Cited

U.S. PATENT DOCUMENTS 8,958,870 B2 2/2015 Gerber et al.
8,958,882 B1 2/2015 Hagedorn
8,961,187 B2 2/2015 Boers et al.
8,961,385 B2 2/2015 Pilla et al.
8,961,386 B2 2/2015 Phillips et al.
8,962,042 B2 2/2015 Geng
8,962,589 B2 2/2015 Deisseroth et al.
8,964,298 B2 2/2015 Haddick et al.
8,965,492 B2 2/2015 Baker et al.
8,965,513 B2 2/2015 Wingeier et al.
8,965,514 B2 2/2015 Bikson et al.
8,968,172 B2 3/2015 Wang et al.
8,968,176 B2 3/2015 Altman et al.
8,968,195 B2 3/2015 Tran
8,968,376 B2 3/2015 Wells et al.
8,971,936 B2 3/2015 Derchak
8,972,004 B2 3/2015 Simon et al.
8,972,013 B2 3/2015 Maschino
8,974,365 B2 3/2015 Best
8,977,024 B1 3/2015 Rex et al.
8,977,110 B2 3/2015 Pradeep et al.
8,977,362 B2 3/2015 Saab
8,980,891 B2 3/2015 Stirn et al.
8,983,155 B2 3/2015 McIntyre et al.
8,983,591 B2 3/2015 Leininger et al.
8,983,620 B2 3/2015 Cinbis
8,983,628 B2 3/2015 Simon et al.
8,983,629 B2 3/2015 Simon et al.
8,985,119 B1 3/2015 Webb et al.
8,986,207 B2 3/2015 Li et al.
8,989,835 B2 3/2015 Badower et al.
8,989,836 B2 3/2015 Machon et al.
8,989,863 B2 3/2015 Osorio
8,989,867 B2 3/2015 Chow et al.
8,989,868 B2 3/2015 Mashiach et al.
8,989,871 B2 3/2015 Ollivier
8,992,230 B2 3/2015 Tuchschmid et al.
8,993,623 B2 3/2015 Goodenowe
8,996,112 B2 3/2015 Brooke
8,996,120 B1 3/2015 Calle et al.
8,998,828 B2 4/2015 Reichow et al.
9,002,458 B2 4/2015 Pal et al.
9,002,471 B2 4/2015 Stevenson et al.
9,002,477 B2 4/2015 Burnett
9,004,687 B2 4/2015 Stack
9,005,102 B2 4/2015 Burnett et al.
9,005,126 B2 4/2015 Beach et al.
9,005,649 B2 4/2015 Ho et al.
9,008,367 B2 4/2015 Tolkowsky et al.
9,008,754 B2 4/2015 Steinberg et al.
9,008,771 B2 4/2015 Dong et al.
9,008,780 B2 4/2015 Nudo et al.
9,008,970 B2 4/2015 Donderici et al.
9,011,329 B2 4/2015 Ferren et al.
9,014,216 B2 4/2015 Lazar et al.
9,014,453 B2 4/2015 Steinberg et al.
9,014,804 B2 4/2015 Giftakis et al.
9,014,811 B2 4/2015 Pal et al.
9,014,819 B2 4/2015 Lee et al.
9,014,823 B2 4/2015 Simon et al.
9,015,057 B2 4/2015 Phillips et al.
9,015,087 B2 4/2015 Li et al.
9,020,576 B2 4/2015 Nagatani
9,020,582 B2 4/2015 Osorio et al.
9,020,585 B2 4/2015 John et al.
9,020,586 B2 4/2015 Yamada et al.
9,020,598 B2 4/2015 Simon et al.
9,020,612 B1 4/2015 Danilov et al.
9,020,789 B2 4/2015 Butson et al.
9,022,930 B2 5/2015 Sachanandani et al.
9,022,936 B2 5/2015 Rothberg et al.
9,025,845 B2 5/2015 Carroll
9,026,194 B2 5/2015 Okada
9,026,202 B2 5/2015 Albert
9,026,217 B2 5/2015 Kokones et al.
9,026,218 B2 5/2015 Lozano et al.
9,026,372 B2 5/2015 O'Donnell, Jr. et al.
9,028,405 B2 5/2015 Tran
9,028,412 B2 5/2015 Rothberg et al.
9,031,644 B2 5/2015 Johnson et al.
9,031,653 B2 5/2015 Mashiach
9,031,655 B2 5/2015 Osorio et al.
9,031,658 B2 5/2015 Chiao et al.
9,033,884 B2 5/2015 Rothberg et al.
9,034,055 B2 5/2015 Vinjamuri et al.
9,034,911 B2 5/2015 Selvey et al.
9,034,923 B2 5/2015 Goodenowe
9,035,657 B2 5/2015 Zhang et al.
9,036,844 B1 5/2015 Suhami et al.
9,037,224 B1 5/2015 Fu
9,037,225 B1 5/2015 Saliga et al.
9,037,254 B2 5/2015 John
9,037,256 B2 5/2015 Bokil
9,037,530 B2 5/2015 Tan et al.
9,042,074 B1 5/2015 Beran
9,042,201 B2 5/2015 Tyler et al.
9,042,952 B2 5/2015 Lynn et al.
9,042,958 B2 5/2015 Karmarkar et al.
9,042,988 B2 5/2015 DiLorenzo
9,043,001 B2 5/2015 Simon et al.
9,044,188 B2 6/2015 DiLorenzo et al.
9,044,612 B2 6/2015 Mashiach et al.
9,050,469 B1 6/2015 Osorio et al.
9,050,470 B2 6/2015 Carlton et al.
9,050,471 B2 6/2015 Skelton et al.
9,053,516 B2 6/2015 Stempora
9,053,534 B2 6/2015 Ross et al.
9,055,871 B2 6/2015 Inan et al.
9,055,974 B2 6/2015 Goetz
9,056,195 B2 6/2015 Sabesan
9,058,473 B2 6/2015 Navratil et al.
9,060,671 B2 6/2015 Badower et al.
9,060,683 B2 6/2015 Tran
9,060,695 B2 6/2015 Peters
9,060,722 B2 6/2015 Teixeira
9,060,746 B2 6/2015 Weng et al.
9,061,132 B1 6/2015 Zweber et al.
9,061,133 B2 6/2015 Wurster et al.
9,061,151 B2 6/2015 Mashiach et al.
9,061,153 B1 6/2015 Lebovitz et al.
9,063,183 B2 6/2015 Toda et al.
9,063,643 B2 6/2015 Sparks et al.
9,064,036 B2 6/2015 Hyde et al.
9,067,052 B2 6/2015 Moses et al.
9,067,054 B2 6/2015 Simon et al.
9,067,070 B2 6/2015 Connor
9,069,031 B2 6/2015 Guedes et al.
9,069,097 B2 6/2015 Zhang et al.
9,070,492 B2 6/2015 Yarmush et al.
9,072,449 B2 7/2015 Semenov
9,072,482 B2 7/2015 Sarkela et al.
9,072,832 B2 7/2015 Frei et al.
9,072,870 B2 7/2015 Wu et al.
9,072,905 B2 7/2015 Kokones et al.
9,074,976 B2 7/2015 Adolphi et al.
9,076,212 B2 7/2015 Ernst et al.
9,078,564 B2 7/2015 Taylor
9,078,577 B2 7/2015 He et al.
9,078,584 B2 7/2015 Jorge et al.
9,079,039 B2 7/2015 Carlson et al.
9,079,940 B2 7/2015 Deisseroth et al.
9,081,488 B2 7/2015 Soederstroem
9,081,882 B2 7/2015 Taylor
9,081,890 B2 7/2015 An et al.
9,082,169 B2 7/2015 Thomson et al.
9,084,584 B2 7/2015 Weiland et al.
9,084,885 B2 7/2015 Deisseroth et al.
9,084,896 B2 7/2015 Kokones et al.
9,084,900 B2 7/2015 Hershey et al.
9,087,147 B1 7/2015 Fonte
9,089,310 B2 7/2015 Isenhart et al.
9,089,400 B2 7/2015 Nofzinger
9,089,683 B2 7/2015 Mishelevich
9,089,707 B2 7/2015 Kilgard et al.

(56) References Cited

U.S. PATENT DOCUMENTS 9,089,713 B2 7/2015 John
9,089,719 B2 7/2015 Simon et al.
9,091,785 B2 7/2015 Donderici et al.
9,092,556 B2 7/2015 Amble et al.
9,092,895 B2 7/2015 Ross et al.
9,095,266 B1 8/2015 Fu
9,095,268 B2 8/2015 Kurtz et al.
9,095,295 B2 8/2015 Eagleman et al.
9,095,303 B2 8/2015 Osorio
9,095,314 B2 8/2015 Osorio et al.
9,095,618 B2 8/2015 Satchi-Fainaro et al.
9,095,713 B2 8/2015 Foster et al.
9,100,758 B2 8/2015 Adachi et al.
9,101,263 B2 8/2015 Jung et al.
9,101,276 B2 8/2015 Georgopoulos
9,101,279 B2 8/2015 Ritchey et al.
9,101,690 B2 8/2015 Deisseroth et al.
9,101,759 B2 8/2015 Delp et al.
9,101,766 B2 8/2015 Nekhendzy
9,102,717 B2 8/2015 Huang et al.
9,107,586 B2 8/2015 Tran
9,107,595 B1 8/2015 Smyth
9,108,041 B2 8/2015 Craig
9,113,777 B2 8/2015 Mittal
9,113,801 B2 8/2015 DiLorenzo
9,113,803 B2 8/2015 Zhang
9,113,830 B2 8/2015 Galen et al.
9,116,201 B2 8/2015 Shah et al.
9,116,835 B1 8/2015 Smyth
9,118,775 B2 8/2015 Lim et al.
9,119,533 B2 9/2015 Ghaffari
9,119,551 B2 9/2015 Qi et al.
9,119,583 B2 9/2015 Tass
9,119,597 B2 9/2015 Dripps et al.
9,119,598 B2 9/2015 Engelbrecht et al.
9,121,964 B2 9/2015 Lewis et al.
9,125,574 B2 9/2015 Zia et al.
9,125,581 B2 9/2015 Wu et al.
9,125,788 B2 9/2015 Tee et al.
9,126,050 B2 9/2015 Simon et al.
9,131,864 B2 9/2015 Korenberg
9,133,024 B2 9/2015 Phan et al.
9,133,709 B2 9/2015 Huh et al.
9,135,221 B2 9/2015 Shahaf et al.
9,135,400 B2 9/2015 McIntyre et al.
9,138,156 B2 9/2015 Wu et al.
9,138,175 B2 9/2015 Ernst et al.
9,138,183 B2 9/2015 McKenna et al.
9,138,579 B2 9/2015 Wolpaw et al.
9,138,580 B2 9/2015 Ignagni et al.
9,142,145 B2 9/2015 Tuchschmid et al.
9,142,185 B2 9/2015 Fateh
9,144,392 B2 9/2015 Santosh et al.
RE45,766 E 10/2015 Lindsay
9,149,195 B2 10/2015 Hadley
9,149,197 B2 10/2015 Taylor
9,149,210 B2 10/2015 Sahasrabudhe et al.
9,149,214 B2 10/2015 Adachi et al.
9,149,226 B2 10/2015 Jadidi
9,149,255 B2 10/2015 Rothberg et al.
9,149,577 B2 10/2015 Robertson et al.
9,149,599 B2 10/2015 Walter et al.
9,149,719 B2 10/2015 Guan et al.
9,152,757 B2 10/2015 Taylor
9,155,373 B2 10/2015 Allen et al.
9,155,484 B2 10/2015 Baker et al.
9,155,487 B2 10/2015 Linderman et al.
9,155,521 B2 10/2015 Rothberg et al.
9,161,715 B2 10/2015 Jung et al.
9,162,051 B2 10/2015 Morrell
9,162,052 B2 10/2015 Morrell
9,165,472 B2 10/2015 Hagedorn et al.
9,167,970 B2 10/2015 Gratton et al.
9,167,974 B2 10/2015 Taylor
9,167,976 B2 10/2015 Wingeier et al.
9,167,977 B2 10/2015 Wingeier et al.
9,167,978 B2 10/2015 Wingeier et al.
9,167,979 B2 10/2015 Skidmore et al.
9,171,353 B2 10/2015 Vija et al.
9,171,366 B2 10/2015 Declerck et al.
9,173,582 B2 11/2015 Popovic et al.
9,173,609 B2 11/2015 Nelson
9,173,610 B2 11/2015 Navakatikyan
9,174,045 B2 11/2015 Simon et al.
9,174,055 B2 11/2015 Davis et al.
9,174,066 B2 11/2015 Simon et al.
9,175,095 B2 11/2015 Deisseroth et al.
9,177,379 B1 11/2015 Biagiotti et al.
9,177,416 B2 11/2015 Sharp
9,179,850 B2 11/2015 Wingeier et al.
9,179,854 B2 11/2015 Doidge et al.
9,179,855 B2 11/2015 Burdea et al.
9,179,858 B2 11/2015 Hasson et al.
9,179,875 B2 11/2015 Hua
9,179,876 B2 11/2015 Ochs et al.
9,183,351 B2 11/2015 Shusterman
9,186,060 B2 11/2015 De Graff et al.
9,186,106 B2 11/2015 Osorio
9,186,503 B2 11/2015 Lindenthaler et al.
9,186,510 B2 11/2015 Gliner et al.
9,187,745 B2 11/2015 Deisseroth et al.
9,192,300 B2 11/2015 Jung et al.
9,192,309 B1 11/2015 Hopenfeld et al.
9,198,563 B2 12/2015 Ferren et al.
9,198,612 B2 12/2015 Fueyo et al.
9,198,621 B2 12/2015 Fernstrom et al.
9,198,624 B2 12/2015 Funane et al.
9,198,637 B2 12/2015 Rothberg et al.
9,198,707 B2 12/2015 Mckay et al.
9,198,733 B2 12/2015 Neal, II et al.
9,204,796 B2 12/2015 Tran
9,204,835 B2 12/2015 Parsey et al.
9,204,838 B2 12/2015 Osorio
9,204,998 B2 12/2015 Kilgard et al.
9,208,430 B2 12/2015 Solari
9,208,557 B2 12/2015 Pautot
9,208,558 B2 12/2015 Dean et al.
9,211,076 B2 12/2015 Kim
9,211,077 B2 12/2015 Jung et al.
9,211,212 B2 12/2015 Nofzinger et al.
9,211,411 B2 12/2015 Wu et al.
9,211,417 B2 12/2015 Heldman et al.
9,213,074 B2 12/2015 van der Kouwe et al.
9,213,076 B2 12/2015 Liu
9,215,298 B2 12/2015 Schiff
9,215,978 B2 12/2015 Knight et al.
9,220,910 B2 12/2015 Colborn
9,220,917 B2 12/2015 Boyden et al.
9,221,755 B2 12/2015 Teegarden et al.
9,226,672 B2 1/2016 Taylor
9,227,056 B1 1/2016 Heldman et al.
9,229,080 B2 1/2016 Lin
9,230,065 B2 1/2016 Hasegawa et al.
9,230,539 B2 1/2016 Pakhomov
9,232,910 B2 1/2016 Alshaer et al.
9,232,984 B2 1/2016 Guthart et al.
9,233,244 B2 1/2016 Pal et al.
9,233,245 B2 1/2016 Lamensdorf et al.
9,233,246 B2 1/2016 Simon et al.
9,233,258 B2 1/2016 Simon et al.
9,235,679 B2 1/2016 Taylor
9,235,685 B2 1/2016 McIntyre et al.
9,238,142 B2 1/2016 Heldman et al.
9,238,150 B2 1/2016 Deisseroth et al.
9,241,647 B2 1/2016 Osorio et al.
9,241,665 B2 1/2016 deCharms
9,242,067 B2 1/2016 Shore et al.
9,242,092 B2 1/2016 Simon et al.
9,247,890 B2 2/2016 Turnbull et al.
9,247,911 B2 2/2016 Galloway et al.
9,247,924 B2 2/2016 Rothberg et al.
9,248,003 B2 2/2016 Wright et al.
9,248,280 B2 2/2016 Moffitt et al.
9,248,286 B2 2/2016 Simon et al.

(56) References Cited

U.S. PATENT DOCUMENTS 9,248,288 B2 2/2016 Panken et al.
9,248,290 B2 2/2016 Mashiach
9,248,291 B2 2/2016 Mashiach
9,248,296 B2 2/2016 Carcieri et al.
9,249,200 B2 2/2016 Deisseroth et al.
9,249,234 B2 2/2016 Deisseroth et al.
9,251,566 B1 2/2016 Bajic
9,254,097 B2 2/2016 Espy et al.
9,254,099 B2 2/2016 Connor
9,254,383 B2 2/2016 Simon et al.
9,254,387 B2 2/2016 Blum et al.
9,256,982 B2 2/2016 Sharp et al.
9,259,177 B2 2/2016 Drew et al.
9,259,482 B2 2/2016 Satchi-Fainaro et al.
9,259,591 B2 2/2016 Brown et al.
9,261,573 B1 2/2016 Radparvar et al.
9,265,458 B2 2/2016 Stack
9,265,660 B2 2/2016 Kilgard et al.
9,265,661 B2 2/2016 Kilgard et al.
9,265,662 B2 2/2016 Kilgard et al.
9,265,663 B2 2/2016 Kilgard et al.
9,265,931 B2 2/2016 Morrell
9,265,943 B2 2/2016 Yun et al.
9,265,946 B2 2/2016 Morrell
9,265,965 B2 2/2016 Fox et al.
9,265,974 B2 2/2016 You et al.
9,268,014 B2 2/2016 Rothberg et al.
9,268,015 B2 2/2016 Rothberg et al.
9,268,902 B2 2/2016 Taylor et al.
9,271,651 B2 3/2016 Avinash et al.
9,271,657 B2 3/2016 Taylor
9,271,660 B2 3/2016 Luo et al.
9,271,674 B2 3/2016 Deisseroth et al.
9,271,679 B2 3/2016 Cho et al.
9,272,091 B2 3/2016 Skelton et al.
9,272,139 B2 3/2016 Hamilton et al.
9,272,145 B2 3/2016 Kilgard et al.
9,272,153 B2 3/2016 Blum et al.
9,273,035 B2 3/2016 Teegarden et al.
9,275,191 B2 3/2016 Dean et al.
9,275,451 B2 3/2016 Ben-Haim et al.
9,277,871 B2 3/2016 Keenan et al.
9,277,873 B2 3/2016 Sarma et al.
9,278,159 B2 3/2016 Deisseroth et al.
9,278,231 B2 3/2016 Vasishta
9,280,784 B2 3/2016 Barnett et al.
9,282,927 B2 3/2016 Hyde et al.
9,282,930 B2 3/2016 Machon et al.
9,282,934 B2 3/2016 Liley et al.
9,283,279 B2 3/2016 Satchi-Fainaro et al.
9,283,394 B2 3/2016 Whitehurst et al.
9,284,353 B2 3/2016 Deisseroth et al.
9,285,249 B2 3/2016 Schober et al.
9,289,143 B2 3/2016 Wingeier et al.
9,289,595 B2 3/2016 Floyd et al.
9,289,599 B2 3/2016 Craig
9,289,603 B1 3/2016 Giuffrida et al.
9,289,609 B2 3/2016 Moffitt
9,292,471 B2 3/2016 Fung et al.
9,292,858 B2 3/2016 Marci et al.
9,292,920 B2 3/2016 Dean et al.
9,295,838 B2 3/2016 Starr et al.
9,296,382 B2 3/2016 Fung et al.
9,302,069 B2 4/2016 Tass et al.
9,302,093 B2 4/2016 Mashiach
9,302,103 B1 4/2016 Nirenberg
9,302,109 B2 4/2016 Sabesan
9,302,110 B2 4/2016 Kokones et al.
9,302,114 B2 4/2016 Rossi
9,302,116 B2 4/2016 Vo-Dinh et al.
9,305,376 B2 4/2016 Lee et al.
9,307,925 B2 4/2016 Russell et al.
9,307,944 B2 4/2016 Colman et al.
9,308,372 B2 4/2016 Sparks et al.
9,308,392 B2 4/2016 Deisseroth et al.
9,309,296 B2 4/2016 Deisseroth et al.
9,310,985 B2 4/2016 Blum et al.
9,311,335 B2 4/2016 Simon
9,314,190 B1 4/2016 Giuffrida et al.
9,314,613 B2 4/2016 Mashiach
9,314,633 B2 4/2016 Osorio et al.
9,314,635 B2 4/2016 Libbus
9,320,449 B2 4/2016 Gu
9,320,450 B2 4/2016 Badower
9,320,451 B2 4/2016 Feldkamp et al.
9,320,900 B2 4/2016 DiLorenzo
9,320,913 B2 4/2016 Dimino et al.
9,320,914 B2 4/2016 Toselli et al.
9,322,895 B2 4/2016 Santosh et al.
9,326,705 B2 5/2016 Derchak
9,326,720 B2 5/2016 McLaughlin
9,326,742 B2 5/2016 Hirschman et al.
9,327,069 B2 5/2016 Foster et al.
9,327,070 B2 5/2016 Skelton et al.
9,328,107 B2 5/2016 Teegarden et al.
9,329,758 B2 5/2016 Guzak et al.
9,330,206 B2 5/2016 Dean et al.
9,330,523 B2 5/2016 Sutton et al.
9,331,841 B2 5/2016 Kim et al.
9,332,939 B2 5/2016 Osorio
9,333,334 B2 5/2016 Jeffery et al.
9,333,347 B2 5/2016 Simon et al.
9,333,350 B2 5/2016 Rise et al.
9,336,302 B1 5/2016 Swamy
9,336,535 B2 5/2016 Pradeep et al.
9,336,611 B2 5/2016 Bilgic et al.
9,339,200 B2 5/2016 Fonte
9,339,227 B2 5/2016 D'arcy et al.
9,339,641 B2 5/2016 Rajguru et al.
9,339,654 B2 5/2016 Kilgard et al.
9,340,589 B2 5/2016 Deisseroth et al.
9,345,412 B2 5/2016 Horne
9,345,609 B2 5/2016 Hyde et al.
9,345,886 B2 5/2016 Kilgard et al.
9,345,901 B2 5/2016 Peterchev
9,348,974 B2 5/2016 Goetz
9,349,178 B1 5/2016 Itu et al.
9,351,640 B2 5/2016 Tran
9,351,651 B2 5/2016 Nagasaka
9,352,145 B2 5/2016 Whitehurst et al.
9,352,152 B2 5/2016 Lindenthaler et al.
9,352,156 B2 5/2016 Lane et al.
9,357,240 B2 5/2016 Pradeep et al.
9,357,298 B2 5/2016 Hiroe
9,357,941 B2 6/2016 Simon
9,357,949 B2 6/2016 Drew
9,357,970 B2 6/2016 Clark et al.
9,358,361 B2 6/2016 Hyde et al.
9,358,381 B2 6/2016 Simon et al.
9,358,392 B2 6/2016 Mashiach
9,358,393 B1 6/2016 Lozano
9,358,398 B2 6/2016 Moffitt et al.
9,359,449 B2 6/2016 Deisseroth et al.
9,360,472 B2 6/2016 Deisseroth et al.
9,364,462 B2 6/2016 Simpson, Jr.
9,364,665 B2 6/2016 Bokil et al.
9,364,674 B2 6/2016 Cook et al.
9,364,679 B2 6/2016 John
9,365,628 B2 6/2016 Deisseroth et al.
9,367,131 B2 6/2016 Klappert et al.
9,367,738 B2 6/2016 Harumatsu et al.
9,368,018 B2 6/2016 Kangas et al.
9,368,265 B2 6/2016 Park et al.
9,370,309 B2 6/2016 Ko et al.
9,370,667 B2 6/2016 Schmidt
9,375,145 B2 6/2016 Chin et al.
9,375,151 B1 6/2016 Hopenfeld et al.
9,375,171 B2 6/2016 Teixeira
9,375,564 B2 6/2016 Wingeier et al.
9,375,571 B2 6/2016 Errico et al.
9,375,573 B2 6/2016 Dilorenzo
9,377,348 B2 6/2016 Kataoka
9,377,515 B2 6/2016 Kim et al.
9,380,976 B2 7/2016 Stack

(56) References Cited

U.S. PATENT DOCUMENTS 9,381,346 B2 7/2016 Lee et al.
9,381,352 B2 7/2016 Yun et al.
9,383,208 B2 7/2016 Mohanty
9,387,320 B2 7/2016 Wingeier et al.
9,387,338 B2 7/2016 Burnett
9,390,233 B2 7/2016 Fueyo et al.
9,392,955 B2 7/2016 Folkerts et al.
9,393,406 B2 7/2016 Ollivier
9,393,418 B2 7/2016 Giuffrida et al.
9,394,347 B2 7/2016 Deisseroth et al.
9,395,425 B2 7/2016 Diamond et al.
9,396,533 B2 7/2016 Skidmore
9,396,669 B2 7/2016 Karkanias et al.
9,398,873 B2 7/2016 Van Dooren et al.
9,399,126 B2 7/2016 Pal et al.
9,399,133 B2 7/2016 Besio
9,399,134 B2 7/2016 Simon et al.
9,399,144 B2 7/2016 Howard
9,401,021 B1 7/2016 Biagiotti et al.
9,401,033 B2 7/2016 Bajic
9,402,558 B2 8/2016 John et al.
9,402,994 B2 8/2016 Chow et al.
9,403,000 B2 8/2016 Lyons et al.
9,403,001 B2 8/2016 Simon et al.
9,403,009 B2 8/2016 Mashiach
9,403,010 B2 8/2016 Fried et al.
9,403,038 B2 8/2016 Tyler
9,405,366 B2 8/2016 Segal
9,408,530 B2 8/2016 Ferren et al.
9,409,013 B2 8/2016 Mashiach et al.
9,409,022 B2 8/2016 Jaax et al.
9,409,028 B2 8/2016 Whitehurst et al.
9,410,885 B2 8/2016 Schober et al.
9,411,033 B2 8/2016 He et al.
9,411,935 B2 8/2016 Moffitt et al.
9,412,076 B2 8/2016 Sapiro et al.
9,412,233 B1 8/2016 Bagherzadeh et al.
9,414,029 B2 8/2016 Miyazaki et al.
9,414,749 B2 8/2016 Semenov
9,414,763 B2 8/2016 Semenov
9,414,764 B2 8/2016 Semenov
9,414,776 B2 8/2016 Sillay et al.
9,414,780 B2 8/2016 Rhoads
9,414,907 B2 8/2016 Wortz et al.
9,415,215 B2 8/2016 Mashiach
9,415,216 B2 8/2016 Mashiach
9,415,219 B2 8/2016 Simon et al.
9,415,222 B2 8/2016 DiLorenzo
9,415,233 B2 8/2016 Pilla et al.
9,418,368 B2 8/2016 Jung et al.
9,420,970 B2 8/2016 Dagum
9,421,258 B2 8/2016 Deisseroth et al.
9,421,372 B2 8/2016 Mashiach et al.
9,421,373 B2 8/2016 DiLorenzo
9,421,379 B2 8/2016 Zhu
9,424,761 B2 8/2016 Tuchschmid et al.
9,427,474 B2 8/2016 Satchi-Fainaro et al.
9,427,581 B2 8/2016 Simon et al.
9,427,585 B2 8/2016 Gliner
9,427,598 B2 8/2016 Pilla et al.
9,430,615 B2 8/2016 Michaelis et al.
9,432,777 B2 8/2016 Lunner et al.
9,433,797 B2 9/2016 Pilla et al.
9,434,692 B2 9/2016 Xiong et al.
9,436,989 B2 9/2016 Uber, III
9,438,650 B2 9/2016 Serena
9,439,150 B2 9/2016 Carlson et al.
9,440,063 B2 9/2016 Ho et al.
9,440,064 B2 9/2016 Wingeier et al.
9,440,070 B2 9/2016 Goldwasser et al.
9,440,084 B2 9/2016 Davis et al.
9,440,089 B2 9/2016 Pilla et al.
9,440,646 B2 9/2016 Fung et al.
9,442,088 B2 9/2016 Feldkamp et al.
9,442,525 B2 9/2016 Choi et al.
9,443,141 B2 9/2016 Mirowski et al.
9,444,998 B2 9/2016 Kim et al.
9,445,713 B2 9/2016 Douglas et al.
9,445,730 B2 9/2016 Snyder et al.
9,445,739 B1 9/2016 Payton et al.
9,445,763 B2 9/2016 Davis et al.
9,446,238 B2 9/2016 Lozano
9,448,289 B2 9/2016 Wang et al.
9,449,147 B2 9/2016 Taylor
9,451,303 B2 9/2016 Kothuri et al.
9,451,734 B2 9/2016 Onuma et al.
9,451,883 B2 9/2016 Gallant et al.
9,451,886 B2 9/2016 Teixeira
9,451,899 B2 9/2016 Ritchey et al.
9,452,287 B2 9/2016 Rosenbluth et al.
9,453,215 B2 9/2016 Deisseroth et al.
9,454,646 B2 9/2016 Siefert
9,458,208 B2 10/2016 Deisseroth et al.
9,459,597 B2 10/2016 Kahn et al.
9,460,400 B2 10/2016 De Bruin et al.
9,462,733 B2 10/2016 Hokari
9,462,956 B2 10/2016 Pandia et al.
9,462,975 B2 10/2016 Sackner et al.
9,462,977 B2 10/2016 Horseman
9,463,327 B2 10/2016 Lempka et al.
9,468,541 B2 10/2016 Contreras-Vidal et al.
9,468,761 B2 10/2016 Frei et al.
9,470,728 B2 10/2016 George et al.
9,471,978 B2 10/2016 Chen et al.
9,472,000 B2 10/2016 Dempsey et al.
9,474,481 B2 10/2016 Dagum
9,474,852 B2 10/2016 Lozano et al.
9,474,903 B2 10/2016 Chen et al.
9,475,502 B2 10/2016 Fung et al.
RE46,189 E 11/2016 Prichep et al.
RE46,209 E 11/2016 Gong et al.
9,480,402 B2 11/2016 Leuthardt et al.
9,480,425 B2 11/2016 Culver et al.
9,480,812 B1 11/2016 Thompson
9,480,841 B2 11/2016 Hershey et al.
9,480,845 B2 11/2016 Harris et al.
9,480,854 B2 11/2016 Von Ohlsen et al.
9,483,117 B2 11/2016 Karkkainen et al.
9,483,613 B2 11/2016 Fueyo et al.
9,486,168 B2 11/2016 Bonmassar et al.
9,486,381 B2 11/2016 Juto et al.
9,486,389 B2 11/2016 Tass
9,486,618 B2 11/2016 Wingeier et al.
9,486,632 B2 11/2016 Saab
9,489,854 B2 11/2016 Haruta et al.
9,492,084 B2 11/2016 Behar et al.
9,492,114 B2 11/2016 Reiman
9,492,120 B2 11/2016 Horseman
9,492,313 B2 11/2016 Nofzinger
9,492,656 B2 11/2016 Chow et al.
9,492,678 B2 11/2016 Chow
9,495,684 B2 11/2016 Jung et al.
9,497,017 B1 11/2016 Kim et al.
9,498,134 B1 11/2016 Trobaugh et al.
9,498,628 B2 11/2016 Kaemmerer et al.
9,498,634 B2 11/2016 De Ridder
9,500,722 B2 11/2016 Takahashi
9,501,829 B2 11/2016 Carlton et al.
9,504,390 B2 11/2016 Osorio
9,504,410 B2 11/2016 Gal
9,504,420 B2 11/2016 Davis et al.
9,504,788 B2 11/2016 Hyde et al.
9,505,402 B2 11/2016 Fung et al.
9,505,817 B2 11/2016 Deisseroth et al.
9,510,790 B2 12/2016 Kang et al.
9,513,398 B2 12/2016 Wilson et al.
9,517,020 B2 12/2016 Shacham-Diamand et al.
9,517,031 B2 12/2016 Jung
9,517,222 B2 12/2016 Goodenowe
9,519,981 B2 12/2016 Sudarsky et al.
9,521,958 B2 12/2016 Nagasaka et al.
9,522,085 B2 12/2016 Kilgard et al.
9,522,278 B1 12/2016 Heldman et al.
9,522,282 B2 12/2016 Chow et al.

(56) References Cited

U.S. PATENT DOCUMENTS 9,522,288 B2 12/2016 Deisseroth et al.
9,526,419 B2 12/2016 Derchak et al.
9,526,902 B2 12/2016 Blum et al.
9,526,906 B2 12/2016 Mashiach
9,526,913 B2 12/2016 Vo-Dinh et al.
9,526,914 B2 12/2016 Vo-Dinh et al.
9,533,113 B2 1/2017 Lain et al.
9,533,144 B2 1/2017 Bahmer
9,533,147 B2 1/2017 Osorio
9,533,148 B2 1/2017 Carcieri
9,533,150 B2 1/2017 Nudo et al.
9,533,151 B2 1/2017 Craig
9,534,044 B2 1/2017 El-Agnaf
9,538,635 B1 1/2017 Beran
9,538,948 B2 1/2017 Dagum
9,538,951 B2 1/2017 Osorio
9,539,118 B2 1/2017 Leuthardt et al.
9,541,383 B2 1/2017 Abovitz et al.
9,545,221 B2 1/2017 Adhikari et al.
9,545,222 B2 1/2017 Derchak et al.
9,545,225 B2 1/2017 Cavuoto et al.
9,545,226 B2 1/2017 Osorio
9,545,285 B2 1/2017 Ghaffari et al.
9,545,510 B2 1/2017 Kokones et al.
9,545,515 B2 1/2017 Wolpaw et al.
9,549,691 B2 1/2017 Tran
9,550,064 B2 1/2017 Mashiach
9,556,149 B2 1/2017 Krishnan et al.
9,556,487 B2 1/2017 Umansky et al.
9,557,439 B2 1/2017 Wilson et al.
9,558,558 B2 1/2017 Stehle et al.
9,560,458 B2 1/2017 Lunner et al.
9,560,967 B2 2/2017 Hyde et al.
9,560,984 B2 2/2017 Pradeep et al.
9,560,986 B2 2/2017 Varcoe
9,561,380 B2 2/2017 Carcieri et al.
9,562,988 B2 2/2017 Wilson et al.
9,563,273 B2 2/2017 Mann
9,563,740 B2 2/2017 Abdelghani et al.
9,563,950 B2 2/2017 Raj
9,566,426 B2 2/2017 Simon et al.
9,567,327 B2 2/2017 Xiong et al.
9,568,564 B2 2/2017 Ma et al.
9,568,635 B2 2/2017 Suhami
9,572,996 B2 2/2017 Tass et al.
9,577,992 B2 2/2017 Zizi et al.
9,578,425 B2 2/2017 Hakansson
9,579,035 B2 2/2017 Sarkela
9,579,048 B2 2/2017 Rayner et al.
9,579,247 B2 2/2017 Juto et al.
9,579,457 B2 2/2017 Osorio
9,579,506 B2 2/2017 Osorio
9,582,072 B2 2/2017 Connor
9,582,152 B2 2/2017 Gulaka et al.
9,582,925 B2 2/2017 Durand et al.
9,584,928 B2 2/2017 Laudanski et al.
9,585,581 B1 3/2017 Mullins et al.
9,585,723 B2 3/2017 Taylor
9,586,047 B2 3/2017 Osorio et al.
9,586,053 B2 3/2017 Moffitt et al.
9,588,203 B2 3/2017 Zhu et al.
9,588,490 B2 3/2017 Tsang
9,590,986 B2 3/2017 Zizi et al.
9,592,003 B2 3/2017 Osorio et al.
9,592,004 B2 3/2017 DiLorenzo et al.
9,592,384 B2 3/2017 Tass
9,592,387 B2 3/2017 Skelton et al.
9,592,389 B2 3/2017 Moffitt
9,592,409 B2 3/2017 Yoo et al.
9,596,224 B2 3/2017 Woods et al.
9,597,493 B2 3/2017 Wingeier et al.
9,597,494 B2 3/2017 Wingeier et al.
9,597,501 B1 3/2017 Danilov et al.
9,597,504 B1 3/2017 Danilov et al.
9,600,138 B2 3/2017 Thomas et al.
9,600,778 B2 3/2017 Sapiro et al.
9,604,056 B2 3/2017 Starr et al.
9,604,067 B2 3/2017 Kothandaraman et al.
9,604,073 B2 3/2017 Deisseroth et al.
9,607,023 B1 3/2017 Swamy
9,607,377 B2 3/2017 Lovberg et al.
9,609,453 B2 3/2017 Jabri
9,610,442 B2 4/2017 Yoo et al.
9,610,456 B2 4/2017 Linke et al.
9,610,459 B2 4/2017 Burnett et al.
9,612,295 B2 4/2017 Toda et al.
9,613,184 B2 4/2017 Giftakis et al.
9,613,186 B2 4/2017 Fonte
9,615,746 B2 4/2017 Horseman
9,615,749 B2 4/2017 Clifton et al.
9,615,789 B2 4/2017 Deisseroth et al.
9,616,166 B2 4/2017 Kalafut et al.
9,616,227 B2 4/2017 Lindenthaler et al.
9,618,591 B1 4/2017 Radparvar et al.
9,622,660 B2 4/2017 Le et al.
9,622,672 B2 4/2017 Yoshida et al.
9,622,675 B2 4/2017 Leyde et al.
9,622,676 B2 4/2017 Masmanidis et al.
9,622,700 B2 4/2017 Sahasrabudhe et al.
9,622,702 B2 4/2017 Badower et al.
9,622,703 B2 4/2017 Badower et al.
9,623,240 B2 4/2017 Simon et al.
9,623,241 B2 4/2017 Wagner et al.
9,626,756 B2 4/2017 Dean et al.
9,629,548 B2 4/2017 Sachanandani et al.
9,629,568 B2 4/2017 Hagedorn et al.
9,629,976 B1 4/2017 Acton
9,630,004 B2 4/2017 Rajguru et al.
9,630,008 B2 4/2017 McLaughlin et al.
9,630,011 B2 4/2017 Lipani
9,630,029 B2 4/2017 Wurster et al.
9,636,019 B2 5/2017 Hendler et al.
9,636,185 B2 5/2017 Quaid et al.
9,640,167 B2 5/2017 DeFranks et al.
9,641,665 B2 5/2017 Lee et al.
9,642,552 B2 5/2017 Hua
9,642,553 B2 5/2017 Hokari
9,642,554 B2 5/2017 Simola et al.
9,642,699 B2 5/2017 Wortz et al.
9,643,015 B2 5/2017 Moffitt et al.
9,643,017 B2 5/2017 Carcieri et al.
9,643,019 B2 5/2017 Higgins et al.
9,646,248 B1 5/2017 Benvenuto et al.
9,649,030 B2 5/2017 Gross et al.
9,649,036 B2 5/2017 Teixeira
9,649,439 B2 5/2017 John
9,649,493 B2 5/2017 Mashiach
9,649,494 B2 5/2017 Gerber et al.
9,649,501 B2 5/2017 Best
9,651,368 B2 5/2017 Abovitz et al.
9,651,706 B2 5/2017 Mandviwala et al.
9,652,626 B2 5/2017 Son et al.
9,652,871 B2 5/2017 Han et al.
9,655,573 B2 5/2017 Majewski et al.
9,655,669 B2 5/2017 Palti et al.
9,656,069 B1 5/2017 Danilov et al.
9,656,075 B2 5/2017 Osorio
9,656,078 B1 5/2017 Danilov et al.
9,656,096 B2 5/2017 Pilla
9,659,186 B2 5/2017 Pinsky et al.
9,659,229 B2 5/2017 Clifton et al.
9,662,049 B2 5/2017 Scarantino et al.
9,662,069 B2 5/2017 De Graff et al.
9,662,083 B2 5/2017 Sakaue
9,662,490 B2 5/2017 Tracey et al.
9,662,492 B1 5/2017 Tucker et al.
9,662,502 B2 5/2017 Giuffrida et al.
9,664,856 B2 5/2017 Nagasaka
9,665,824 B2 5/2017 Chang et al.
9,665,987 B2 5/2017 Fateh
9,668,694 B2 6/2017 Badower
9,669,185 B2 6/2017 Nofzinger
9,669,239 B2 6/2017 Carpentier
9,672,302 B2 6/2017 Dean et al.

(56) References Cited

U.S. PATENT DOCUMENTS 9,672,617 B2 6/2017 Dean et al.
9,674,621 B2 6/2017 Bahmer
9,675,254 B2 6/2017 Semenov
9,675,255 B2 6/2017 Semenov
9,675,292 B2 6/2017 Fadem
9,675,794 B2 6/2017 Miller
9,675,809 B2 6/2017 Chow
9,681,814 B2 6/2017 Galloway et al.
9,681,820 B2 6/2017 Wagner
9,682,232 B2 6/2017 Shore et al.
9,682,241 B2 6/2017 Hyde et al.
9,684,051 B2 6/2017 Nieminen et al.
9,684,335 B2 6/2017 Kim et al.
9,685,600 B2 6/2017 Washington, II et al.
9,687,187 B2 6/2017 Dagum
9,687,562 B2 6/2017 Satchi-Fainaro et al.
9,693,684 B2 7/2017 Lopez et al.
9,693,724 B2 7/2017 Dagum
9,693,725 B2 7/2017 Soza
9,693,734 B2 7/2017 Horseman
9,694,155 B2 7/2017 Panova et al.
9,694,178 B2 7/2017 Ruffini et al.
9,694,197 B2 7/2017 Segal
9,697,330 B2 7/2017 Taylor
9,697,336 B2 7/2017 Hyde et al.
9,700,256 B2 7/2017 Osorio et al.
9,700,716 B2 7/2017 Faltys et al.
9,700,723 B2 7/2017 Sabesan
9,704,205 B2 7/2017 Akutagawa et al.
9,706,910 B1 7/2017 Blaha et al.
9,706,925 B2 7/2017 Taylor
9,706,957 B2 7/2017 Wu et al.
9,706,963 B2 7/2017 Gupta et al.
9,707,372 B2 7/2017 Smith
9,707,390 B2 7/2017 Ahmed
9,707,391 B2 7/2017 Ahmed
9,707,396 B2 7/2017 Su et al.
9,710,788 B2 7/2017 Horseman
9,712,736 B2 7/2017 Kearns et al.
9,713,428 B2 7/2017 Chon et al.
9,713,433 B2 7/2017 Gadot et al.
9,713,444 B2 7/2017 Severson
9,713,712 B2 7/2017 Wingeier et al.
9,715,032 B2 7/2017 Song et al.
9,717,461 B2 8/2017 Yu et al.
9,717,904 B2 8/2017 Simon et al.
9,717,920 B1 8/2017 Heldman et al.
9,724,517 B2 8/2017 Giftakis et al.
9,729,252 B2 8/2017 Tyler et al.
9,732,039 B2 8/2017 Xiong et al.
9,734,589 B2 8/2017 Yu et al.
9,734,601 B2 8/2017 Bresler et al.
9,734,632 B2 8/2017 Thomas et al.
9,737,230 B2 8/2017 Sarma et al.
9,740,710 B2 8/2017 Han et al.
9,740,946 B2 8/2017 Varkuti et al.
9,741,114 B2 8/2017 Varkuti
9,743,197 B2 8/2017 Petersen et al.
9,743,835 B2 8/2017 Taylor
9,744,358 B2 8/2017 Hehrmann et al.
9,763,592 B2 9/2017 Le et al.
2001/0003799 A1 6/2001 Boveja
2001/0009975 A1 7/2001 Tsukada et al.
2001/0014818 A1 8/2001 Kennedy
2001/0020127 A1 9/2001 Oshio et al.
2001/0021800 A1 9/2001 Balkin et al.
2001/0029391 A1 10/2001 Gluckman et al.
2001/0049480 A1 12/2001 John et al.
2001/0051774 A1 12/2001 Littrup et al.
2001/0051787 A1 12/2001 Haller et al.
2002/0000808 A1 1/2002 Nichols
2002/0005784 A1 1/2002 Balkin et al.
2002/0006875 A1 1/2002 Mcfetridge
2002/0013612 A1 1/2002 Whitehurst
2002/0013613 A1 1/2002 Haller et al.
2002/0016552 A1 2/2002 Granger et al.
2002/0017905 A1 2/2002 Conti
2002/0017994 A1 2/2002 Balkin et al.
2002/0024450 A1 2/2002 Townsend et al.
2002/0032375 A1 3/2002 Bauch et al.
2002/0033454 A1 3/2002 Cheng et al.
2002/0035317 A1 3/2002 Cheng et al.
2002/0035338 A1 3/2002 Dear et al.
2002/0037095 A1 3/2002 Cheng
2002/0042563 A1 4/2002 Becerra et al.
2002/0052539 A1 5/2002 Haller et al.
2002/0055675 A1 5/2002 Llinas et al.
2002/0058867 A1 5/2002 Breiter et al.
2002/0059159 A1 5/2002 Cook
2002/0072776 A1 6/2002 Osorio et al.
2002/0072782 A1 6/2002 Osorio et al.
2002/0077536 A1 6/2002 Diab et al.
2002/0082513 A1 6/2002 Ennen et al.
2002/0082665 A1 6/2002 Haller et al.
2002/0085174 A1 7/2002 Bolger et al.
2002/0087201 A1 7/2002 Firlik et al.
2002/0091319 A1 7/2002 Moehring et al.
2002/0091335 A1 7/2002 John et al.
2002/0091419 A1 7/2002 Firlik et al.
2002/0095099 A1 7/2002 Quyen et al.
2002/0097332 A1 7/2002 Martin et al.
2002/0099273 A1 7/2002 Bocionek et al.
2002/0099295 A1 7/2002 Gil et al.
2002/0099306 A1 7/2002 Shaw et al.
2002/0099412 A1 7/2002 Fischell et al.
2002/0099417 A1 7/2002 Naritoku et al.
2002/0099418 A1 7/2002 Naritoku et al.
2002/0103428 A1 8/2002 deCharms
2002/0103429 A1 8/2002 deCharms
2002/0103512 A1 8/2002 Echauz et al.
2002/0107454 A1 8/2002 Collura et al.
2002/0112732 A1 8/2002 Blazey et al.
2002/0117176 A1 8/2002 Mantzaridis et al.
2002/0128540 A1 9/2002 Kim et al.
2002/0128544 A1 9/2002 Diab et al.
2002/0128638 A1 9/2002 Chauvet et al.
2002/0138013 A1 9/2002 Guerrero et al.
2002/0151771 A1 10/2002 Braun et al.
2002/0151939 A1 10/2002 Rezai
2002/0158631 A1 10/2002 Kandori et al.
2002/0173714 A1 11/2002 Tsukada et al.
2002/0177882 A1 11/2002 DiLorenzo
2002/0182574 A1 12/2002 Freer
2002/0183607 A1 12/2002 Bauch et al.
2002/0183644 A1 12/2002 Levendowski et al.
2002/0188330 A1 12/2002 Gielen et al.
2002/0193670 A1 12/2002 Garfield et al.
2003/0001098 A1 1/2003 Stoddart et al.
2003/0004429 A1 1/2003 Price
2003/0009078 A1 1/2003 Fedorovskaya et al.
2003/0009096 A1 1/2003 Lahteenmaki
2003/0013981 A1 1/2003 Gevins et al.
2003/0018277 A1 1/2003 He
2003/0018278 A1 1/2003 Jordan
2003/0023183 A1 1/2003 Williams
2003/0023282 A1 1/2003 Barrett et al.
2003/0028081 A1 2/2003 Blazey et al.
2003/0028121 A1 2/2003 Blazey et al.
2003/0028348 A1 2/2003 Wenzel et al.
2003/0031357 A1 2/2003 Wenzel et al.
2003/0032870 A1 2/2003 Farwell
2003/0032888 A1 2/2003 Dewan
2003/0032889 A1 2/2003 Wells
2003/0035301 A1 2/2003 Gardiner et al.
2003/0036689 A1 2/2003 Diab et al.
2003/0040660 A1 2/2003 Jackowski et al.
2003/0045914 A1 3/2003 Cohen et al.
2003/0046018 A1 3/2003 Kohlmorgen et al.
2003/0055355 A1 3/2003 Viertio-Oja
2003/0068605 A1 4/2003 Kullok et al.
2003/0070685 A1 4/2003 Patton et al.
2003/0074032 A1 4/2003 Gliner
2003/0081818 A1 5/2003 Fujimaki
2003/0083596 A1 5/2003 Kramer et al.

(56) References Cited

U.S. PATENT DOCUMENTS

2003/0083716 A1 5/2003 Nicolelis et al.
2003/0088274 A1 5/2003 Gliner et al.
2003/0093004 A1 5/2003 Sosa et al.
2003/0093005 A1 5/2003 Tucker
2003/0093129 A1 5/2003 Nicolelis et al.
2003/0097159 A1 5/2003 Schiff et al.
2003/0097161 A1 5/2003 Firlik et al.
2003/0100844 A1 5/2003 Miller et al.
2003/0105408 A1 6/2003 Gotman et al.
2003/0114886 A1 6/2003 Gluckman et al.
2003/0120140 A1 6/2003 Bango
2003/0120172 A1 6/2003 Foust et al.
2003/0125786 A1 7/2003 Gliner et al.
2003/0128801 A1 7/2003 Eisenberg et al.
2003/0130706 A1 7/2003 Sheffield et al.
2003/0130709 A1 7/2003 D.C. et al.
2003/0135128 A1 7/2003 Suffin et al.
2003/0139681 A1 7/2003 Melker et al.
2003/0144601 A1 7/2003 Prichep
2003/0149351 A1 8/2003 Nowinski et al.
2003/0149678 A1 8/2003 Cook
2003/0153818 A1 8/2003 Bocionek et al.
2003/0158466 A1 8/2003 Lynn et al.
2003/0158495 A1 8/2003 Hogan
2003/0158496 A1 8/2003 Keirsbilck et al.
2003/0158497 A1 8/2003 Graham et al.
2003/0158587 A1 8/2003 Esteller et al.
2003/0160622 A1 8/2003 Duensing et al.
2003/0163027 A1 8/2003 Balkin et al.
2003/0163028 A1 8/2003 Balkin et al.
2003/0167019 A1 9/2003 Viertio-Oja et al.
2003/0171658 A1 9/2003 Keirsbilck et al.
2003/0171685 A1 9/2003 Lesser et al.
2003/0171689 A1 9/2003 Millan et al.
2003/0176804 A1 9/2003 Melker
2003/0181791 A1 9/2003 Thomas et al.
2003/0181821 A1 9/2003 Greenwald et al.
2003/0181954 A1 9/2003 Rezai
2003/0181955 A1 9/2003 Gielen et al.
2003/0185408 A1 10/2003 Causevic et al.
2003/0187359 A1 10/2003 Njemanze
2003/0195429 A1 10/2003 Wilson
2003/0195574 A1 10/2003 Osorio et al.
2003/0199749 A1 10/2003 Lowery, Jr. et al.
2003/0204135 A1 10/2003 Bystritsky
2003/0216654 A1 11/2003 Xu et al.
2003/0225335 A1 12/2003 Njemanze
2003/0225340 A1 12/2003 Collura
2003/0229291 A1 12/2003 Collura
2003/0233039 A1 12/2003 Shao et al.
2003/0233250 A1 12/2003 Joffe et al.
2003/0234781 A1 12/2003 Laidlaw et al.
2003/0236458 A1 12/2003 Hochman
2003/0236557 A1 12/2003 Whitehurst et al.
2003/0236558 A1 12/2003 Whitehurst et al.
2004/0002635 A1 1/2004 Hargrove et al.
2004/0006265 A1 1/2004 Alhussiny
2004/0006376 A1 1/2004 Falci
2004/0010203 A1 1/2004 Bibian et al.
2004/0015204 A1 1/2004 Whitehurst et al.
2004/0015205 A1 1/2004 Whitehurst et al.
2004/0019257 A1 1/2004 Meadows
2004/0019370 A1 1/2004 Gliner et al.
2004/0024287 A1 2/2004 Patton et al.
2004/0030585 A1 2/2004 Sariel
2004/0034299 A1 2/2004 Kandori et al.
2004/0039268 A1 2/2004 Barbour et al.
2004/0049124 A1 3/2004 Kullok et al.
2004/0049484 A1 3/2004 Kamba
2004/0059203 A1 3/2004 Guerrero et al.
2004/0059241 A1 3/2004 Suffin
2004/0064020 A1 4/2004 Diab et al.
2004/0064066 A1 4/2004 John et al.
2004/0068164 A1 4/2004 Diab et al.
2004/0068172 A1 4/2004 Nowinski et al.
2004/0068199 A1 4/2004 Echauz et al.
2004/0072133 A1 4/2004 Kullok et al.
2004/0073098 A1 4/2004 Geva et al.
2004/0073129 A1 4/2004 Caldwell et al.
2004/0073273 A1 4/2004 Gluckman et al.
2004/0077960 A1 4/2004 Tanaka et al.
2004/0077967 A1 4/2004 Jordan
2004/0078056 A1 4/2004 Zangen et al.
2004/0079372 A1 4/2004 John et al.
2004/0082862 A1 4/2004 Chance
2004/0082876 A1 4/2004 Viertio-Oja et al.
2004/0088732 A1 5/2004 Martin et al.
2004/0092809 A1 5/2004 DeCharms
2004/0096395 A1 5/2004 Xiong et al.
2004/0097802 A1 5/2004 Cohen
2004/0101146 A1 5/2004 Laitinen et al.
2004/0116784 A1 6/2004 Gavish
2004/0116791 A1 6/2004 Miyauchi
2004/0116798 A1 6/2004 Cancro et al.
2004/0116825 A1 6/2004 Sturzebecher
2004/0117098 A1 6/2004 Ryu et al.
2004/0122787 A1 6/2004 Avinash et al.
2004/0122790 A1 6/2004 Walker et al.
2004/0127803 A1 7/2004 Berkes et al.
2004/0131998 A1 7/2004 Marom et al.
2004/0133118 A1 7/2004 Llinas
2004/0133119 A1 7/2004 Osorio et al.
2004/0133120 A1 7/2004 Frei et al.
2004/0133248 A1 7/2004 Frei et al.
2004/0133390 A1 7/2004 Osorio et al.
2004/0138516 A1 7/2004 Osorio et al.
2004/0138517 A1 7/2004 Osorio et al.
2004/0138518 A1 7/2004 Rise et al.
2004/0138536 A1 7/2004 Frei et al.
2004/0138578 A1* 7/2004 Pineda .................. A61N 2/006 600/544
2004/0138580 A1 7/2004 Frei et al.
2004/0138581 A1 7/2004 Frei et al.
2004/0138647 A1 7/2004 Osorio et al.
2004/0138711 A1 7/2004 Osorio et al.
2004/0138721 A1 7/2004 Osorio et al.
2004/0140811 A1 7/2004 Conti
2004/0143170 A1 7/2004 DuRousseau
2004/0144925 A1 7/2004 Stoddart et al.
2004/0145370 A1 7/2004 Conti
2004/0151368 A1 8/2004 Cruickshank et al.
2004/0152958 A1 8/2004 Frei et al.
2004/0152995 A1 8/2004 Cox et al.
2004/0153129 A1 8/2004 Pless et al.
2004/0158119 A1 8/2004 Osorio et al.
2004/0158298 A1 8/2004 Gliner et al.
2004/0158300 A1 8/2004 Gardiner
2004/0166536 A1 8/2004 Kerkman et al.
2004/0167418 A1 8/2004 Nguyen et al.
2004/0172089 A1 9/2004 Whitehurst et al.
2004/0172091 A1 9/2004 Rezai
2004/0172094 A1 9/2004 Cohen et al.
2004/0181162 A1 9/2004 Wilson
2004/0184024 A1 9/2004 Katura et al.
2004/0186542 A1 9/2004 van Venrooij et al.
2004/0193037 A1 9/2004 Tsukada et al.
2004/0193068 A1 9/2004 Burton et al.
2004/0193220 A1 9/2004 Whitehurst et al.
2004/0195512 A1 10/2004 Crosetto
2004/0199482 A1 10/2004 Wilson
2004/0204636 A1 10/2004 Diab et al.
2004/0204637 A1 10/2004 Diab et al.
2004/0204656 A1 10/2004 Tolvanen-Laakso et al.
2004/0204659 A1 10/2004 John et al.
2004/0210127 A1 10/2004 Kandori et al.
2004/0210146 A1 10/2004 Diab et al.
2004/0210156 A1 10/2004 Hogan
2004/0215082 A1 10/2004 Chance
2004/0220494 A1 11/2004 Sturzebecher
2004/0220782 A1 11/2004 Cook
2004/0225179 A1 11/2004 Kaplan et al.
2004/0230105 A1 11/2004 Geva et al.
2004/0243017 A1 12/2004 Causevic
2004/0243182 A1 12/2004 Cohen et al.

(56) References Cited

U.S. PATENT DOCUMENTS

2004/0254493 A1 12/2004 Chervin et al.
2004/0260169 A1 12/2004 Sternnickel
2004/0260356 A1 12/2004 Kara et al.
2004/0263162 A1 12/2004 Kandori et al.
2004/0267152 A1 12/2004 Pineda
2005/0004489 A1 1/2005 Sarkela et al.
2005/0007091 A1 1/2005 Makeig et al.
2005/0010091 A1 1/2005 Woods et al.
2005/0010116 A1 1/2005 Korhonen et al.
2005/0015205 A1 1/2005 Repucci et al.
2005/0018858 A1 1/2005 John
2005/0019734 A1 1/2005 Peled
2005/0020483 A1 1/2005 Oksenberg et al.
2005/0020918 A1 1/2005 Wilk et al.
2005/0021105 A1 1/2005 Firlik et al.
2005/0025704 A1 2/2005 Keirsbilck et al.
2005/0027284 A1 2/2005 Lozano et al.
2005/0032827 A1 2/2005 Oksenberg et al.
2005/0033122 A1 2/2005 Balkin et al.
2005/0033154 A1 2/2005 deCharms
2005/0033174 A1 2/2005 Moehring et al.
2005/0033379 A1 2/2005 Lozano et al.
2005/0038354 A1 2/2005 Miller et al.
2005/0043774 A1 2/2005 Devlin et al.
2005/0049651 A1 3/2005 Whitehurst et al.
2005/0059689 A1 3/2005 Oksenberg et al.
2005/0059874 A1 3/2005 Fuchs et al.
2005/0060001 A1 3/2005 Singhal et al.
2005/0060007 A1 3/2005 Goetz
2005/0060008 A1 3/2005 Goetz
2005/0060009 A1 3/2005 Goetz
2005/0060010 A1 3/2005 Goetz
2005/0065412 A1 3/2005 Shiomi et al.
2005/0065427 A1 3/2005 Magill et al.
2005/0075568 A1 4/2005 Moehring
2005/0079474 A1 4/2005 Lowe
2005/0079636 A1 4/2005 White et al.
2005/0080124 A1 4/2005 Teegarden et al.
2005/0080349 A1 4/2005 Okada et al.
2005/0080828 A1 4/2005 Johnson
2005/0085744 A1 4/2005 Beverina et al.
2005/0096311 A1 5/2005 Suffin et al.
2005/0096517 A1 5/2005 Diab et al.
2005/0106713 A1 5/2005 Phan et al.
2005/0107654 A1 5/2005 Riehl
2005/0113713 A1 5/2005 Foust et al.
2005/0118286 A1 6/2005 Suffin et al.
2005/0119547 A1 6/2005 Shastri et al.
2005/0119586 A1 6/2005 Coyle et al.
2005/0124848 A1 6/2005 Holzner
2005/0124851 A1 6/2005 Patton et al.
2005/0124863 A1 6/2005 Cook
2005/0131311 A1 6/2005 Leuthardt et al.
2005/0135102 A1 6/2005 Gardiner et al.
2005/0136002 A1 6/2005 Fossheim et al.
2005/0137494 A1 6/2005 Viertio-Oja
2005/0137645 A1 6/2005 Voipio et al.
2005/0144042 A1 6/2005 Joffe et al.
2005/0148828 A1 7/2005 Lindsay
2005/0148893 A1 7/2005 Misczynski et al.
2005/0148894 A1 7/2005 Misczynski et al.
2005/0148895 A1 7/2005 Misczynski et al.
2005/0149123 A1 7/2005 Lesser et al.
2005/0149157 A1 7/2005 Hunter et al.
2005/0153268 A1 7/2005 Junkin et al.
2005/0154290 A1 7/2005 Langleben
2005/0154419 A1 7/2005 Whitehurst et al.
2005/0154425 A1 7/2005 Boveja et al.
2005/0154426 A1 7/2005 Boveja et al.
2005/0156602 A1 7/2005 Conti
2005/0159670 A1 7/2005 Sneddon
2005/0159671 A1 7/2005 Sneddon
2005/0165458 A1 7/2005 Boveja et al.
2005/0167588 A1 8/2005 Donnangelo
2005/0171410 A1 8/2005 Hjelt et al.
2005/0182287 A1 8/2005 Becker
2005/0182288 A1 8/2005 Zabara
2005/0182389 A1 8/2005 LaPorte et al.
2005/0182450 A1 8/2005 Hunter et al.
2005/0182453 A1 8/2005 Whitehurst et al.
2005/0182456 A1 8/2005 Ziobro et al.
2005/0182467 A1 8/2005 Hunter et al.
2005/0182468 A1 8/2005 Hunter et al.
2005/0182469 A1 8/2005 Hunter et al.
2005/0187600 A1 8/2005 Hunter et al.
2005/0192514 A1 9/2005 Kearby et al.
2005/0192644 A1 9/2005 Boveja et al.
2005/0192647 A1 9/2005 Hunter et al.
2005/0197590 A1 9/2005 Osorio et al.
2005/0197675 A1 9/2005 David et al.
2005/0197678 A1 9/2005 Boveja et al.
2005/0209512 A1 9/2005 Heruth et al.
2005/0209517 A1 9/2005 Diab et al.
2005/0209654 A1 9/2005 Boveja et al.
2005/0209664 A1 9/2005 Hunter et al.
2005/0209665 A1 9/2005 Hunter et al.
2005/0209666 A1 9/2005 Hunter et al.
2005/0215889 A1 9/2005 Patterson
2005/0216070 A1 9/2005 Boveja et al.
2005/0216071 A1 9/2005 Devlin et al.
2005/0222522 A1 10/2005 Heruth et al.
2005/0222639 A1 10/2005 Seifritz et al.
2005/0228451 A1 10/2005 Jaax et al.
2005/0228785 A1 10/2005 Wolcott et al.
2005/0240087 A1 10/2005 Keenan et al.
2005/0240229 A1 10/2005 Whitehurst et al.
2005/0240253 A1 10/2005 Tyler et al.
2005/0244045 A1 11/2005 Eriksson
2005/0245796 A1 11/2005 Woods et al.
2005/0251055 A1 11/2005 Zhirnov et al.
2005/0251220 A1 11/2005 Barrett et al.
2005/0256378 A1 11/2005 Takai et al.
2005/0256385 A1 11/2005 Diab et al.
2005/0256418 A1 11/2005 Mietus et al.
2005/0267011 A1 12/2005 Deisseroth et al.
2005/0267343 A1 12/2005 Woods et al.
2005/0267344 A1 12/2005 Woods et al.
2005/0267362 A1 12/2005 Mietus et al.
2005/0267542 A1 12/2005 David et al.
2005/0273017 A1 12/2005 Gordon
2005/0277813 A1 12/2005 Katz et al.
2005/0277912 A1 12/2005 John
2005/0283053 A1 12/2005 deCharms
2005/0283090 A1 12/2005 Wells
2006/0004298 A1 1/2006 Kennedy et al.
2006/0004422 A1 1/2006 De Ridder
2006/0009704 A1 1/2006 Okada et al.
2006/0009815 A1 1/2006 Boveja et al.
2006/0014753 A1 1/2006 Shamloo et al.
2006/0015034 A1 1/2006 Martinerie et al.
2006/0015153 A1 1/2006 Gliner et al.
2006/0018525 A1 1/2006 Barbour
2006/0020184 A1 1/2006 Woods et al.
2006/0036152 A1 2/2006 Kozel
2006/0036153 A1 2/2006 Laken
2006/0041201 A1 2/2006 Behbehani et al.
2006/0047187 A1 3/2006 Goyal et al.
2006/0047216 A1 3/2006 Dorr et al.
2006/0047324 A1 3/2006 Tass
2006/0047325 A1 3/2006 Thimineur et al.
2006/0051814 A1 3/2006 Jackowski et al.
2006/0052386 A1 3/2006 Wieloch et al.
2006/0052657 A9 3/2006 Zabara
2006/0052706 A1 3/2006 Hynynen et al.
2006/0058590 A1 3/2006 Shaw et al.
2006/0058683 A1 3/2006 Chance
2006/0058856 A1 3/2006 Morrell
2006/0061544 A1 3/2006 Min et al.
2006/0064138 A1 3/2006 Velasco et al.
2006/0064139 A1 3/2006 Chung et al.
2006/0064140 A1 3/2006 Whitehurst et al.
2006/0069059 A1 3/2006 Schaller et al.
2006/0069415 A1 3/2006 Cameron et al.
2006/0074290 A1 4/2006 Chen et al.

(56) References Cited

U.S. PATENT DOCUMENTS

2006/0074298 A1 4/2006 Borsook et al.
2006/0074334 A1 4/2006 Coyle
2006/0074822 A1 4/2006 Eda et al.
2006/0078183 A1 4/2006 deCharms
2006/0079936 A1 4/2006 Boveja et al.
2006/0082727 A1 4/2006 Bolger et al.
2006/0084858 A1 4/2006 Marks
2006/0084877 A1 4/2006 Ujhazy et al.
2006/0087746 A1 4/2006 Lipow
2006/0089541 A1 4/2006 Braun et al.
2006/0089549 A1 4/2006 Diab et al.
2006/0094968 A1 5/2006 Drew
2006/0094970 A1 5/2006 Drew
2006/0094971 A1 5/2006 Drew
2006/0094972 A1 5/2006 Drew
2006/0095091 A1 5/2006 Drew
2006/0095092 A1 5/2006 Drew
2006/0100526 A1 5/2006 Yamamoto et al.
2006/0100530 A1 5/2006 Kliot et al.
2006/0100671 A1 5/2006 Ridder
2006/0102171 A1 5/2006 Gavish
2006/0106274 A1 5/2006 Thomas et al.
2006/0106326 A1 5/2006 Krebs et al.
2006/0106430 A1 5/2006 Fowler et al.
2006/0106434 A1 5/2006 Padgitt et al.
2006/0111644 A1 5/2006 Guttag et al.
2006/0116556 A1 6/2006 Duhamel
2006/0122481 A1 6/2006 Sievenpiper et al.
2006/0129022 A1 6/2006 Venza et al.
2006/0129202 A1 6/2006 Armstrong
2006/0129277 A1 6/2006 Wu et al.
2006/0129324 A1 6/2006 Rabinoff et al.
2006/0135879 A1 6/2006 Liley
2006/0135880 A1 6/2006 Sarkela
2006/0136135 A1 6/2006 Little et al.
2006/0142802 A1 6/2006 Armstrong
2006/0149144 A1 7/2006 Lynn et al.
2006/0149160 A1 7/2006 Kofol et al.
2006/0149337 A1 7/2006 John
2006/0152227 A1 7/2006 Hammer
2006/0153396 A1 7/2006 John
2006/0155206 A1 7/2006 Lynn
2006/0155207 A1 7/2006 Lynn et al.
2006/0155348 A1 7/2006 deCharms
2006/0155495 A1 7/2006 Osorio et al.
2006/0161071 A1 7/2006 Lynn et al.
2006/0161075 A1 7/2006 Kurtz
2006/0161217 A1 7/2006 Jaax et al.
2006/0161218 A1 7/2006 Danilov
2006/0161384 A1 7/2006 Osorio et al.
2006/0167370 A1 7/2006 Greenwald et al.
2006/0167497 A1 7/2006 Armstrong et al.
2006/0167564 A1 7/2006 Flaherty et al.
2006/0167722 A1 7/2006 Mrf Struys et al.
2006/0170424 A1 8/2006 Kasevich
2006/0173259 A1 8/2006 Flaherty et al.
2006/0173364 A1 8/2006 Clancy et al.
2006/0173493 A1 8/2006 Armstrong et al.
2006/0173494 A1 8/2006 Armstrong et al.
2006/0173495 A1 8/2006 Armstrong et al.
2006/0173510 A1 8/2006 Besio et al.
2006/0176062 A1 8/2006 Yang et al.
2006/0178709 A1 8/2006 Foster et al.
2006/0184058 A1 8/2006 Silberstein
2006/0184059 A1 8/2006 Jadidi
2006/0188134 A1 8/2006 Quist
2006/0189866 A1 8/2006 Thomas et al.
2006/0189880 A1 8/2006 Lynn et al.
2006/0189882 A1 8/2006 Thomas
2006/0189899 A1 8/2006 Flaherty et al.
2006/0191543 A1 8/2006 Becker et al.
2006/0195039 A1 8/2006 Drew et al.
2006/0195154 A1 8/2006 Jaax et al.
2006/0195155 A1 8/2006 Firlik et al.
2006/0200013 A1 9/2006 Smith et al.
2006/0200016 A1 9/2006 Diab et al.
2006/0200034 A1 9/2006 Ricci et al.
2006/0200035 A1 9/2006 Ricci et al.
2006/0200206 A1 9/2006 Firlik et al.
2006/0204532 A1 9/2006 John
2006/0206033 A1 9/2006 Guerrero et al.
2006/0206108 A1 9/2006 Hempel
2006/0206155 A1 9/2006 Ben-David et al.
2006/0206165 A1 9/2006 Jaax et al.
2006/0206174 A1 9/2006 Honeycutt et al.
2006/0212090 A1 9/2006 Lozano et al.
2006/0212091 A1 9/2006 Lozano et al.
2006/0217609 A1 9/2006 Diab et al.
2006/0217781 A1 9/2006 John
2006/0217816 A1 9/2006 Pesaran et al.
2006/0224216 A1 10/2006 Pless et al.
2006/0224421 A1 10/2006 St. Ores et al.
2006/0225437 A1 10/2006 Kazami
2006/0229164 A1 10/2006 Einav
2006/0233390 A1 10/2006 Causevic et al.
2006/0235315 A1 10/2006 Akselrod et al.
2006/0235324 A1 10/2006 Lynn
2006/0235484 A1 10/2006 Jaax et al.
2006/0235489 A1 10/2006 Drew et al.
2006/0239482 A1 10/2006 Hatoum
2006/0241373 A1 10/2006 Strychacz et al.
2006/0241382 A1 10/2006 Li et al.
2006/0241562 A1 10/2006 John et al.
2006/0241718 A1 10/2006 Tyler et al.
2006/0247728 A1 11/2006 Foster et al.
2006/0251303 A1 11/2006 He et al.
2006/0252978 A1 11/2006 Vesely et al.
2006/0252979 A1 11/2006 Vesely et al.
2006/0258896 A1 11/2006 Haber et al.
2006/0258950 A1 11/2006 Hargrove et al.
2006/0259077 A1 11/2006 Pardo et al.
2006/0265022 A1 11/2006 John et al.
2006/0276695 A9 12/2006 Lynn et al.
2006/0281543 A1 12/2006 Sutton et al.
2006/0281980 A1 12/2006 Randlov et al.
2006/0282123 A1 12/2006 Hunter et al.
2006/0287691 A1 12/2006 Drew
2006/0293578 A1 12/2006 Rennaker
2006/0293721 A1 12/2006 Tarver et al.
2006/0293723 A1 12/2006 Whitehurst et al.
2007/0000372 A1 1/2007 Rezai et al.
2007/0005115 A1 1/2007 Lozano et al.
2007/0005391 A1 1/2007 Repucci et al.
2007/0007454 A1 1/2007 Stoddart et al.
2007/0008172 A1 1/2007 Hewett et al.
2007/0014454 A1 1/2007 Sawyer et al.
2007/0015985 A1 1/2007 Tolvanen-Laakso et al.
2007/0016095 A1 1/2007 Low et al.
2007/0016264 A1 1/2007 Falci
2007/0019846 A1 1/2007 Bullitt et al.
2007/0021673 A1 1/2007 Arbel et al.
2007/0021675 A1 1/2007 Childre et al.
2007/0021800 A1 1/2007 Whitehurst et al.
2007/0025608 A1 2/2007 Armstrong
2007/0027486 A1 2/2007 Armstrong
2007/0027498 A1 2/2007 Maschino et al.
2007/0027499 A1 2/2007 Maschino et al.
2007/0027500 A1 2/2007 Maschino et al.
2007/0027501 A1 2/2007 Jensen et al.
2007/0031798 A1 2/2007 Gottfried
2007/0032733 A1 2/2007 Burton
2007/0032737 A1 2/2007 Causevic et al.
2007/0032834 A1 2/2007 Gliner et al.
2007/0036355 A1 2/2007 Terauchi et al.
2007/0036402 A1 2/2007 Cahill et al.
2007/0038067 A1 2/2007 Kandori et al.
2007/0038264 A1 2/2007 Jaax et al.
2007/0038382 A1 2/2007 Keenan
2007/0043392 A1 2/2007 Gliner et al.
2007/0043401 A1 2/2007 John
2007/0049844 A1 3/2007 Rosenfeld
2007/0049988 A1 3/2007 Carbunaru et al.
2007/0050715 A1 3/2007 Behar
2007/0055145 A1 3/2007 Zelnik et al.

(56) References Cited

U.S. PATENT DOCUMENTS

2007/0060830 A1 3/2007 Le et al.
2007/0060831 A1 3/2007 Le et al.
2007/0060954 A1 3/2007 Cameron et al.
2007/0060974 A1 3/2007 Lozano
2007/0060984 A1 3/2007 Webb et al.
2007/0066403 A1 3/2007 Conkwright
2007/0066914 A1 3/2007 Le et al.
2007/0066915 A1 3/2007 Frei et al.
2007/0066997 A1 3/2007 He et al.
2007/0067003 A1 3/2007 Sanchez et al.
2007/0067004 A1 3/2007 Boveja et al.
2007/0072857 A1 3/2007 Teegarden et al.
2007/0078134 A1 4/2007 Teegarden et al.
2007/0081712 A1 4/2007 Huang et al.
2007/0083128 A1 4/2007 Cote et al.
2007/0093721 A1 4/2007 Lynn et al.
2007/0093870 A1 4/2007 Maschino
2007/0100246 A1 5/2007 Hyde
2007/0100251 A1 5/2007 Prichep
2007/0100278 A1 5/2007 Frei et al.
2007/0100377 A1 5/2007 Armstrong et al.
2007/0100378 A1 5/2007 Maschino
2007/0100389 A1 5/2007 Jaax et al.
2007/0100392 A1 5/2007 Maschino et al.
2007/0100398 A1 5/2007 Sloan
2007/0100666 A1 5/2007 Stivoric et al.
2007/0112404 A1 5/2007 Mann et al.
2007/0118197 A1 5/2007 Loeb
2007/0127793 A1 6/2007 Beckett et al.
2007/0129647 A1 6/2007 Lynn
2007/0129769 A1 6/2007 Bourget et al.
2007/0129774 A1 6/2007 Bourget et al.
2007/0135724 A1 6/2007 Ujhazy et al.
2007/0135728 A1 6/2007 Snyder et al.
2007/0138886 A1 6/2007 Krebs et al.
2007/0142862 A1 6/2007 Dilorenzo
2007/0142873 A1 6/2007 Esteller et al.
2007/0142874 A1 6/2007 John
2007/0149860 A1 6/2007 Lynn et al.
2007/0150024 A1 6/2007 Leyde et al.
2007/0150025 A1 6/2007 Dilorenzo et al.
2007/0150026 A1 6/2007 Bourget et al.
2007/0150029 A1 6/2007 Bourget et al.
2007/0156180 A1 7/2007 Jaax et al.
2007/0156457 A1 7/2007 Brown
2007/0159185 A1 7/2007 Yang et al.
2007/0161919 A1 7/2007 DiLorenzo
2007/0162085 A1 7/2007 DiLorenzo
2007/0162086 A1 7/2007 DiLorenzo
2007/0165915 A1 7/2007 Fuchs
2007/0167694 A1 7/2007 Causevic et al.
2007/0167723 A1 7/2007 Park et al.
2007/0167853 A1 7/2007 Melker et al.
2007/0167858 A1 7/2007 Virtanen et al.
2007/0167991 A1 7/2007 DiLorenzo
2007/0173733 A1 7/2007 Le et al.
2007/0173902 A1 7/2007 Maschino et al.
2007/0179395 A1 8/2007 Sotos et al.
2007/0179396 A1 8/2007 Le et al.
2007/0179534 A1 8/2007 Firlik et al.
2007/0179558 A1 8/2007 Gliner et al.
2007/0179734 A1 8/2007 Chmiel et al.
2007/0184507 A1 8/2007 Jackowski et al.
2007/0191688 A1 8/2007 Lynn
2007/0191691 A1 8/2007 Polanco
2007/0191697 A1 8/2007 Lynn et al.
2007/0191704 A1 8/2007 DeCharms
2007/0191727 A1 8/2007 Fadem
2007/0197930 A1 8/2007 Sarkela
2007/0198063 A1 8/2007 Hunter et al.
2007/0203401 A1 8/2007 Gordon et al.
2007/0203448 A1 8/2007 Melker et al.
2007/0208212 A1 9/2007 DiLorenzo
2007/0208269 A1 9/2007 Mumford et al.
2007/0209669 A1 9/2007 Derchak
2007/0213785 A1 9/2007 Osorio et al.
2007/0213786 A1 9/2007 Sackellares et al.
2007/0225581 A1 9/2007 Diab et al.
2007/0225674 A1 9/2007 Molnar et al.
2007/0225774 A1 9/2007 Eskandar et al.
2007/0225932 A1 9/2007 Halford
2007/0233192 A1 10/2007 Craig
2007/0233193 A1 10/2007 Craig
2007/0238934 A1 10/2007 Viswanathan
2007/0239059 A1 10/2007 McIver
2007/0244387 A1 10/2007 Rodriguez Ponce et al.
2007/0244407 A1 10/2007 Osorio
2007/0249918 A1 10/2007 Diab et al.
2007/0249949 A1 10/2007 Hadley
2007/0249952 A1 10/2007 Rubin et al.
2007/0250119 A1 10/2007 Tyler et al.
2007/0250138 A1 10/2007 Nofzinger
2007/0255122 A1 11/2007 Vol et al.
2007/0255135 A1 11/2007 Kalafut et al.
2007/0255155 A1 11/2007 Drew et al.
2007/0255320 A1 11/2007 Inman et al.
2007/0255379 A1 11/2007 Williams et al.
2007/0255531 A1 11/2007 Drew
2007/0259323 A1 11/2007 Brown et al.
2007/0260151 A1 11/2007 Clifford
2007/0265508 A1 11/2007 Sheikhzadeh-Nadjar et al.
2007/0265533 A1 11/2007 Tran
2007/0273504 A1 11/2007 Tran
2007/0273611 A1 11/2007 Torch
2007/0276270 A1 11/2007 Tran
2007/0276278 A1 11/2007 Coyle et al.
2007/0276279 A1 11/2007 Echauz et al.
2007/0276441 A1 11/2007 Goetz
2007/0276609 A1 11/2007 Greenwald
2007/0280508 A1 12/2007 Ernst et al.
2007/0282228 A1 12/2007 Einav et al.
2007/0287896 A1 12/2007 Derchak et al.
2007/0291832 A1 12/2007 Diab et al.
2007/0293760 A1 12/2007 Schaafsma
2007/0299370 A1 12/2007 Bystritsky
2007/0299371 A1 12/2007 Einav et al.
2008/0001600 A1 1/2008 deCharms
2008/0001735 A1 1/2008 Tran
2008/0004514 A1 1/2008 Diab et al.
2008/0004550 A1 1/2008 Einav et al.
2008/0004904 A1 1/2008 Tran
2008/0009685 A1 1/2008 Kim et al.
2008/0009772 A1 1/2008 Tyler et al.
2008/0013747 A1 1/2008 Tran
2008/0015458 A1 1/2008 Buarque de Macedo et al.
2008/0015459 A1 1/2008 Llinas
2008/0021332 A1 1/2008 Brainard
2008/0021336 A1 1/2008 Dobak
2008/0021340 A1 1/2008 Sarkela
2008/0021341 A1 1/2008 Harris et al.
2008/0021342 A1 1/2008 Echauz et al.
2008/0021345 A1 1/2008 Kern et al.
2008/0027347 A1 1/2008 Harris et al.
2008/0027348 A1 1/2008 Harris et al.
2008/0027515 A1 1/2008 Harris et al.
2008/0033266 A1 2/2008 Diab et al.
2008/0033291 A1 2/2008 Rousso et al.
2008/0033297 A1 2/2008 Sliwa
2008/0033502 A1 2/2008 Harris et al.
2008/0033503 A1 2/2008 Fowler et al.
2008/0033508 A1 2/2008 Frei et al.
2008/0033513 A1 2/2008 Man et al.
2008/0036752 A1 2/2008 Diab et al.
2008/0039677 A1 2/2008 Adams
2008/0039698 A1 2/2008 Burton
2008/0039737 A1 2/2008 Breiter et al.
2008/0039904 A1 2/2008 Bulkes et al.
2008/0042067 A1 2/2008 Rousso et al.
2008/0045775 A1 2/2008 Lozano
2008/0045823 A1 2/2008 Diab et al.
2008/0045844 A1 2/2008 Arbel et al.
2008/0046012 A1 2/2008 Covalin et al.
2008/0046035 A1 2/2008 Fowler et al.
2008/0049376 A1 2/2008 Stevenson et al.

(56) References Cited

U.S. PATENT DOCUMENTS

2008/0051669 A1 2/2008 Meyer et al.
2008/0051858 A1 2/2008 Haber et al.
2008/0058664 A1 3/2008 Mirro
2008/0058668 A1 3/2008 Seyed Momen et al.
2008/0058773 A1 3/2008 John
2008/0064934 A1 3/2008 Frei et al.
2008/0065183 A1 3/2008 Whitehurst et al.
2008/0069446 A1 3/2008 Ancelin
2008/0071150 A1 3/2008 Miesel et al.
2008/0071326 A1 3/2008 Heruth et al.
2008/0074307 A1 3/2008 Boric-Lubecke et al.
2008/0077010 A1 3/2008 Cohen-Solal et al.
2008/0077015 A1 3/2008 Boric-Lubecke et al.
2008/0077191 A1 3/2008 Morrell
2008/0081963 A1 4/2008 Naghavi et al.
2008/0082018 A1 4/2008 Sackner et al.
2008/0086182 A1 4/2008 Ben-David et al.
2008/0091118 A1 4/2008 Georgopoulos
2008/0091240 A1 4/2008 Ben-David et al.
2008/0097197 A1 4/2008 Kalafut et al.
2008/0097235 A1 4/2008 Ofek et al.
2008/0097553 A1 4/2008 John
2008/0097785 A1 4/2008 Ali
2008/0103547 A1 5/2008 Okun et al.
2008/0103548 A1 5/2008 Fowler et al.
2008/0109050 A1 5/2008 John
2008/0119716 A1 5/2008 Boric-Lubecke et al.
2008/0119747 A1 5/2008 Mietus et al.
2008/0119763 A1 5/2008 Wiener
2008/0119900 A1 5/2008 DiLorenzo
2008/0123927 A1 5/2008 Miga et al.
2008/0125669 A1 5/2008 Suffin et al.
2008/0125829 A1 5/2008 Velasco et al.
2008/0125830 A1 5/2008 Morrell
2008/0125831 A1 5/2008 Morrell
2008/0128626 A1 6/2008 Rousso et al.
2008/0132383 A1 6/2008 Einav et al.
2008/0139953 A1 6/2008 Baker et al.
2008/0140141 A1 6/2008 Ben-David et al.
2008/0140149 A1 6/2008 John et al.
2008/0140403 A1 6/2008 Hughes et al.
2008/0147137 A1 6/2008 Cohen et al.
2008/0154111 A1 6/2008 Wu et al.
2008/0154126 A1 6/2008 Culver et al.
2008/0154148 A1 6/2008 Chung et al.
2008/0154331 A1 6/2008 John et al.
2008/0154332 A1 6/2008 Rezai
2008/0157980 A1 7/2008 Sachanandani et al.
2008/0161700 A1 7/2008 Sachanandani et al.
2008/0161879 A1 7/2008 Firlik et al.
2008/0161880 A1 7/2008 Firlik et al.
2008/0161881 A1 7/2008 Firlik et al.
2008/0161886 A1 7/2008 Stevenson et al.
2008/0161894 A1 7/2008 Ben-David et al.
2008/0162182 A1 7/2008 Cazares et al.
2008/0167535 A1 7/2008 Stivoric et al.
2008/0167540 A1 7/2008 Korhonen et al.
2008/0167569 A1 7/2008 Ermes et al.
2008/0167571 A1 7/2008 Gevins
2008/0177195 A1 7/2008 Armitstead
2008/0177196 A1 7/2008 Burdick et al.
2008/0177197 A1 7/2008 Lee et al.
2008/0183072 A1 7/2008 Robertson et al.
2008/0183097 A1 7/2008 Leyde et al.
2008/0188765 A1 8/2008 Stolarski et al.
2008/0194981 A1 8/2008 Sarkela et al.
2008/0195166 A1 8/2008 Sun et al.
2008/0200831 A1 8/2008 Sturzebecher
2008/0208072 A1 8/2008 Fadem et al.
2008/0208073 A1 8/2008 Causevic
2008/0208280 A1 8/2008 Lindenthaler et al.
2008/0208285 A1 8/2008 Fowler et al.
2008/0214902 A1 9/2008 Lee et al.
2008/0215112 A1 9/2008 Firlik et al.
2008/0219917 A1 9/2008 Koruga
2008/0221400 A1 9/2008 Lee et al.
2008/0221401 A1 9/2008 Derchak et al.
2008/0221441 A1 9/2008 Bjornerud et al.
2008/0221472 A1 9/2008 Lee et al.
2008/0221969 A1 9/2008 Lee et al.
2008/0228077 A1 9/2008 Wilk et al.
2008/0228100 A1 9/2008 Navakatikyan
2008/0228239 A1 9/2008 Tyler et al.
2008/0229408 A1 9/2008 Dinges et al.
2008/0230702 A1 9/2008 Rousso et al.
2008/0230705 A1 9/2008 Rousso et al.
2008/0234113 A1 9/2008 Einav
2008/0234601 A1 9/2008 Wexelman
2008/0235469 A1 9/2008 Drew
2008/0241804 A1 10/2008 Pennebaker
2008/0242521 A1 10/2008 Einav
2008/0242976 A1 10/2008 Robertson et al.
2008/0243005 A1 10/2008 Jung et al.
2008/0243014 A1 10/2008 Moussavi et al.
2008/0243017 A1 10/2008 Moussavi et al.
2008/0243021 A1 10/2008 Causevic et al.
2008/0247618 A1 10/2008 Laine et al.
2008/0249430 A1 10/2008 John et al.
2008/0249589 A1 10/2008 Cornejo Cruz et al.
2008/0255469 A1 10/2008 Shieh et al.
2008/0255816 A1 10/2008 Neville
2008/0255949 A1 10/2008 Genco et al.
2008/0257349 A1 10/2008 Hedner et al.
2008/0260212 A1 10/2008 Moskal et al.
2008/0262327 A1 10/2008 Kato
2008/0262367 A1 10/2008 Mugler et al.
2008/0262371 A1 10/2008 Causevic
2008/0269542 A1 10/2008 Zabara
2008/0269812 A1 10/2008 Gerber et al.
2008/0269833 A1 10/2008 Scott et al.
2008/0269834 A1 10/2008 Byerman et al.
2008/0269840 A1 10/2008 Scott et al.
2008/0269843 A1 10/2008 Gerber et al.
2008/0275327 A1 11/2008 Faarbaek et al.
2008/0275340 A1 11/2008 Beach et al.
2008/0275526 A1 11/2008 Lozano
2008/0279436 A1 11/2008 Razifar et al.
2008/0281238 A1 11/2008 Oohashi et al.
2008/0281381 A1 11/2008 Gerber et al.
2008/0281667 A1 11/2008 Chen et al.
2008/0286453 A1 11/2008 Koruga
2008/0287774 A1 11/2008 Katz-Brull
2008/0287821 A1 11/2008 Jung et al.
2008/0288018 A1 11/2008 Rezai et al.
2008/0294019 A1 11/2008 Tran
2008/0294063 A1 11/2008 Bibian et al.
2008/0298653 A1 12/2008 Amunts et al.
2008/0298659 A1 12/2008 Spence et al.
2008/0304691 A1 12/2008 Lai
2008/0304731 A1 12/2008 Kimura
2008/0306365 A1 12/2008 Bunce et al.
2008/0310697 A1 12/2008 Razifar et al.
2008/0311549 A1 12/2008 Belitsiotis
2008/0317317 A1 12/2008 Shekhar et al.
2008/0319326 A1 12/2008 Behbehani et al.
2008/0319505 A1 12/2008 Boyden et al.
2009/0005654 A1 1/2009 Jung et al.
2009/0005667 A1 1/2009 Cui et al.
2009/0005675 A1 1/2009 Grunwald et al.
2009/0006001 A1 1/2009 Niculescu et al.
2009/0009284 A1 1/2009 Sako
2009/0012387 A1 1/2009 Hanson et al.
2009/0018407 A1 1/2009 Jung et al.
2009/0018419 A1 1/2009 Torch
2009/0018429 A1 1/2009 Saliga et al.
2009/0018431 A1 1/2009 Feiweier et al.
2009/0018432 A1 1/2009 He et al.
2009/0018462 A1 1/2009 Bell
2009/0022825 A1 1/2009 Kerkman et al.
2009/0024007 A1 1/2009 Lee et al.
2009/0024050 A1 1/2009 Jung et al.
2009/0030476 A1 1/2009 Hargrove
2009/0030930 A1 1/2009 Pradeep et al.
2009/0033333 A1 2/2009 Gribova et al.

(56) References Cited

U.S. PATENT DOCUMENTS

2009/0036781 A1 2/2009 Utsugi et al.
2009/0036791 A1 2/2009 Plenz
2009/0036950 A1 2/2009 Armstrong et al.
2009/0039889 A1 2/2009 Wilt et al.
2009/0043221 A1 2/2009 Kaplan et al.
2009/0048507 A1 2/2009 Feiweier et al.
2009/0048530 A1 2/2009 Sarkela et al.
2009/0054788 A1 2/2009 Hauger et al.
2009/0054800 A1 2/2009 Martinerie et al.
2009/0054801 A1 2/2009 Hinrikus et al.
2009/0054946 A1 2/2009 Sommer et al.
2009/0054958 A1 2/2009 Nofzinger
2009/0058660 A1 3/2009 Torch
2009/0062660 A1 3/2009 Chance
2009/0062670 A1 3/2009 Sterling et al.
2009/0062676 A1 3/2009 Kruglikov et al.
2009/0062679 A1 3/2009 Tan et al.
2009/0062680 A1 3/2009 Sandford
2009/0062696 A1 3/2009 Nathan et al.
2009/0062698 A1 3/2009 Einav et al.
2009/0069707 A1 3/2009 Sandford
2009/0074279 A1 3/2009 Razifar et al.
2009/0076339 A1 3/2009 Quintin et al.
2009/0076399 A1 3/2009 Arbel et al.
2009/0076400 A1 3/2009 Diab et al.
2009/0076406 A1 3/2009 Graham et al.
2009/0076407 A1 3/2009 John et al.
2009/0076567 A1 3/2009 Fowler et al.
2009/0078875 A1 3/2009 Rousso et al.
2009/0082688 A1 3/2009 Wagner
2009/0082689 A1 3/2009 Guttag et al.
2009/0082690 A1 3/2009 Phillips et al.
2009/0082829 A1 3/2009 Panken et al.
2009/0083071 A1 3/2009 Phillips et al.
2009/0088658 A1 4/2009 Luo et al.
2009/0088680 A1 4/2009 Aravanis et al.
2009/0093403 A1 4/2009 Zhang et al.
2009/0093862 A1 4/2009 Gliner et al.
2009/0094305 A1 4/2009 Johnson
2009/0099474 A1 4/2009 Pineda et al.
2009/0099627 A1 4/2009 Molnar et al.
2009/0099783 A1 4/2009 Reisberg
2009/0105785 A1 4/2009 Wei et al.
2009/0112117 A1 4/2009 Rewari
2009/0112273 A1 4/2009 Wingeier et al.
2009/0112277 A1 4/2009 Wingeier et al.
2009/0112278 A1 4/2009 Wingeier et al.
2009/0112279 A1 4/2009 Wingeier et al.
2009/0112280 A1 4/2009 Wingeier et al.
2009/0112281 A1 4/2009 Miyazawa et al.
2009/0112523 A1 4/2009 Townsend et al.
2009/0118593 A1 5/2009 Jung et al.
2009/0118610 A1 5/2009 Karmarkar et al.
2009/0118622 A1 5/2009 Durkin et al.
2009/0118636 A1 5/2009 Collura
2009/0118780 A1 5/2009 DiLorenzo
2009/0118786 A1 5/2009 Meadows et al.
2009/0118787 A1 5/2009 Moffitt et al.
2009/0119154 A1 5/2009 Jung et al.
2009/0124869 A1 5/2009 Hu et al.
2009/0124921 A1 5/2009 Milgramm et al.
2009/0124922 A1 5/2009 Milgramm et al.
2009/0124923 A1 5/2009 Sackellares et al.
2009/0131995 A1 5/2009 Sloan et al.
2009/0132275 A1 5/2009 Jung et al.
2009/0137915 A1 5/2009 Childre et al.
2009/0137923 A1 5/2009 Suffin et al.
2009/0143654 A1 6/2009 Funane et al.
2009/0148019 A1 6/2009 Hamada et al.
2009/0149148 A1 6/2009 Kurtz et al.
2009/0149736 A1 6/2009 Skidmore et al.
2009/0156907 A1 6/2009 Jung et al.
2009/0156954 A1 6/2009 Cox et al.
2009/0156955 A1 6/2009 Jung et al.
2009/0156956 A1 6/2009 Milgramm et al.
2009/0157323 A1 6/2009 Jung et al.
2009/0157481 A1 6/2009 Jung et al.
2009/0157482 A1 6/2009 Jung et al.
2009/0157625 A1 6/2009 Jung et al.
2009/0157660 A1 6/2009 Jung et al.
2009/0157662 A1 6/2009 Suffin et al.
2009/0157751 A1 6/2009 Jung et al.
2009/0157813 A1 6/2009 Jung et al.
2009/0163777 A1 6/2009 Jung et al.
2009/0163980 A1 6/2009 Stevenson
2009/0163981 A1 6/2009 Stevenson et al.
2009/0163982 A1 6/2009 deCharms
2009/0164131 A1 6/2009 Jung et al.
2009/0164132 A1 6/2009 Jung et al.
2009/0164302 A1 6/2009 Jung et al.
2009/0164401 A1 6/2009 Jung et al.
2009/0164403 A1 6/2009 Jung et al.
2009/0164458 A1 6/2009 Jung et al.
2009/0164503 A1 6/2009 Jung et al.
2009/0164549 A1 6/2009 Jung et al.
2009/0171164 A1 7/2009 Jung et al.
2009/0171232 A1 7/2009 Hu et al.
2009/0171240 A1 7/2009 Aguilar et al.
2009/0171405 A1 7/2009 Craig
2009/0172540 A1 7/2009 Jung et al.
2009/0177050 A1 7/2009 Griffiths et al.
2009/0177090 A1 7/2009 Grunwald et al.
2009/0177108 A1 7/2009 Shieh et al.
2009/0177144 A1 7/2009 Masmanidis et al.
2009/0179642 A1 7/2009 deCharms
2009/0182211 A1 7/2009 Diab et al.
2009/0187230 A1 7/2009 Dilorenzo
2009/0191131 A1 7/2009 Fossheim et al.
2009/0192394 A1 7/2009 Guttag et al.
2009/0192556 A1 7/2009 Wu et al.
2009/0198144 A1 8/2009 Phillips et al.
2009/0198145 A1 8/2009 Chow
2009/0204015 A1 8/2009 Phillips et al.
2009/0209831 A1 8/2009 Kucharczyk et al.
2009/0209835 A1 8/2009 Diab et al.
2009/0209845 A1 8/2009 Christen et al.
2009/0210018 A1 8/2009 Lozano
2009/0216091 A1 8/2009 Arndt
2009/0216146 A1 8/2009 Teicher et al.
2009/0216288 A1 8/2009 Schiff et al.
2009/0220425 A1 9/2009 Moxon et al.
2009/0220429 A1 9/2009 Johnsen et al.
2009/0221904 A1 9/2009 Shealy et al.
2009/0221928 A1 9/2009 Einav et al.
2009/0221930 A1 9/2009 Laken
2009/0227876 A1 9/2009 Tran
2009/0227877 A1 9/2009 Tran
2009/0227882 A1 9/2009 Foo
2009/0227889 A2 9/2009 John et al.
2009/0234419 A1 9/2009 Maschino et al.
2009/0240119 A1 9/2009 Schwaibold et al.
2009/0243756 A1 10/2009 Stevenson et al.
2009/0246138 A1 10/2009 Santosh et al.
2009/0247893 A1 10/2009 Lapinlampi et al.
2009/0247894 A1 10/2009 Causevic
2009/0259277 A1 10/2009 Cornejo Cruz et al.
2009/0261832 A1 10/2009 DePavia et al.
2009/0264785 A1 10/2009 Causevic et al.
2009/0264789 A1 10/2009 Molnar et al.
2009/0264952 A1 10/2009 Jassemidis et al.
2009/0264954 A1 10/2009 Rise et al.
2009/0264955 A1 10/2009 Giftakis et al.
2009/0264956 A1 10/2009 Rise et al.
2009/0264957 A1 10/2009 Giftakis et al.
2009/0264958 A1 10/2009 Hsu et al.
2009/0264967 A1 10/2009 Giftakis et al.
2009/0267758 A1 10/2009 Hyde et al.
2009/0270687 A1 10/2009 Hyde et al.
2009/0270688 A1 10/2009 Hyde et al.
2009/0270692 A1 10/2009 Hyde et al.
2009/0270693 A1 10/2009 Hyde et al.
2009/0270694 A1 10/2009 Hyde et al.
2009/0270754 A1 10/2009 Moridaira
2009/0270758 A1 10/2009 Eagleman et al.

(56) References Cited

U.S. PATENT DOCUMENTS

2009/0270786 A1 10/2009 Hyde et al.
2009/0270944 A1 10/2009 Whitehurst et al.
2009/0271011 A1 10/2009 Hyde et al.
2009/0271120 A1 10/2009 Hyde et al.
2009/0271122 A1 10/2009 Hyde et al.
2009/0271347 A1 10/2009 Hyde et al.
2009/0275853 A1 11/2009 Sarkela
2009/0276011 A1 11/2009 Hyde et al.
2009/0276012 A1 11/2009 Hyde et al.
2009/0280153 A1 11/2009 Hunter et al.
2009/0281400 A1 11/2009 McCraty et al.
2009/0281448 A1 11/2009 Wright et al.
2009/0281594 A1 11/2009 King et al.
2009/0287035 A1 11/2009 Dietrich et al.
2009/0287107 A1 11/2009 Beck-Nielsen et al.
2009/0287108 A1 11/2009 Levy
2009/0287271 A1 11/2009 Blum et al.
2009/0287272 A1 11/2009 Kokones et al.
2009/0287273 A1 11/2009 Carlton et al.
2009/0287274 A1 11/2009 De Ridder
2009/0287467 A1 11/2009 Sparks et al.
2009/0290767 A1 11/2009 Jung et al.
2009/0290772 A1 11/2009 Avinash et al.
2009/0292180 A1 11/2009 Mirow
2009/0292478 A1 11/2009 Avinash et al.
2009/0292551 A1 11/2009 Sirohey et al.
2009/0292713 A1 11/2009 Jung et al.
2009/0292724 A1 11/2009 Jung et al.
2009/0297000 A1 12/2009 Shahaf et al.
2009/0299126 A1 12/2009 Fowler et al.
2009/0299169 A1 12/2009 deCharms
2009/0299435 A1 12/2009 Gliner et al.
2009/0304582 A1 12/2009 Rousso et al.
2009/0306491 A1 12/2009 Haggers
2009/0306531 A1 12/2009 Leuthardt et al.
2009/0306532 A1 12/2009 Tucker
2009/0306534 A1 12/2009 Pizzagalli
2009/0306741 A1 12/2009 Hogle et al.
2009/0311655 A1 12/2009 Karkanias et al.
2009/0312595 A1 12/2009 Leuthardt et al.
2009/0312624 A1 12/2009 Berridge et al.
2009/0312646 A1 12/2009 Binder et al.
2009/0312663 A1 12/2009 John et al.
2009/0312664 A1 12/2009 Rodriguez Villegas et al.
2009/0312668 A1 12/2009 Leuthardt et al.
2009/0312808 A1 12/2009 Tyler et al.
2009/0312817 A1 12/2009 Hogle et al.
2009/0312998 A1 12/2009 Berckmans et al.
2009/0316925 A1 12/2009 Eisenfeld et al.
2009/0316968 A1 12/2009 Fueyo et al.
2009/0316969 A1 12/2009 Fueyo et al.
2009/0318773 A1 12/2009 Jung et al.
2009/0318779 A1 12/2009 Tran
2009/0318794 A1 12/2009 DeCharms
2009/0319000 A1 12/2009 Firlik et al.
2009/0319001 A1 12/2009 Schiff
2009/0319002 A1 12/2009 Simon
2009/0319004 A1 12/2009 Sabel
2009/0322331 A1 12/2009 Buracas
2009/0323049 A1 12/2009 Addison et al.
2009/0326353 A1 12/2009 Watson et al.
2009/0326604 A1 12/2009 Tyler et al.
2009/0326605 A1 12/2009 Morrell
2009/0327068 A1 12/2009 Pradeep et al.
2010/0003656 A1 1/2010 Kilgard et al.
2010/0004500 A1 1/2010 Gliner et al.
2010/0004705 A1 1/2010 Kilgard et al.
2010/0004717 A1 1/2010 Kilgard et al.
2010/0004762 A1 1/2010 Leuthardt et al.
2010/0004977 A1 1/2010 Marci et al.
2010/0010289 A1 1/2010 Clare
2010/0010316 A1 1/2010 Fueyo et al.
2010/0010363 A1 1/2010 Fueyo et al.
2010/0010364 A1 1/2010 Verbitskiy
2010/0010365 A1 1/2010 Terao et al.
2010/0010366 A1 1/2010 Silberstein
2010/0010383 A1 1/2010 Skelton et al.
2010/0010388 A1 1/2010 Panken et al.
2010/0010391 A1 1/2010 Skelton et al.
2010/0010392 A1 1/2010 Skelton et al.
2010/0010571 A1 1/2010 Skelton et al.
2010/0010572 A1 1/2010 Skelton et al.
2010/0010573 A1 1/2010 Skelton et al.
2010/0010574 A1 1/2010 Skelton et al.
2010/0010575 A1 1/2010 Skelton et al.
2010/0010576 A1 1/2010 Skelton et al.
2010/0010577 A1 1/2010 Skelton et al.
2010/0010578 A1 1/2010 Skelton et al.
2010/0010579 A1 1/2010 Skelton et al.
2010/0010580 A1 1/2010 Skelton et al.
2010/0010584 A1 1/2010 Skelton et al.
2010/0010585 A1 1/2010 Davis et al.
2010/0010587 A1 1/2010 Skelton et al.
2010/0010588 A1 1/2010 Skelton et al.
2010/0010589 A1 1/2010 Skelton et al.
2010/0010590 A1 1/2010 Skelton et al.
2010/0010844 A1 1/2010 Isaksen
2010/0014730 A1 1/2010 Hahn et al.
2010/0014732 A1 1/2010 Vija et al.
2010/0015583 A1 1/2010 Leuthardt et al.
2010/0016783 A1 1/2010 Bourke, Jr. et al.
2010/0017001 A1 1/2010 Leuthardt et al.
2010/0021378 A1 1/2010 Rousso et al.
2010/0022820 A1 1/2010 Leuthardt et al.
2010/0023089 A1 1/2010 DiLorenzo
2010/0028841 A1 2/2010 Eatough et al.
2010/0030073 A1 2/2010 Kalafut
2010/0030089 A1 2/2010 Hyde et al.
2010/0030097 A1 2/2010 Silberstein
2010/0030287 A1 2/2010 Jaax et al.
2010/0036211 A1 2/2010 La Rue et al.
2010/0036233 A1 2/2010 Zhu et al.
2010/0036276 A1 2/2010 Ochs
2010/0036453 A1 2/2010 Hulvershorn et al.
2010/0041949 A1 2/2010 Tolkowsky
2010/0041958 A1 2/2010 Leuthardt et al.
2010/0041962 A1 2/2010 Causevic et al.
2010/0041964 A1 2/2010 Hyde et al.
2010/0042011 A1 2/2010 Doidge et al.
2010/0042578 A1 2/2010 Leuthardt et al.
2010/0043795 A1 2/2010 Ujhazy et al.
2010/0045467 A1 2/2010 Sachanandani et al.
2010/0049069 A1 2/2010 Tarassenko et al.
2010/0049075 A1 2/2010 Bolger et al.
2010/0049276 A1 2/2010 Blum et al.
2010/0049482 A1 2/2010 He et al.
2010/0056276 A1 3/2010 Silberstein
2010/0056854 A1 3/2010 Chang
2010/0056939 A1 3/2010 Tarassenko et al.
2010/0057159 A1 3/2010 Lozano
2010/0057160 A1 3/2010 De Ridder
2010/0057655 A1 3/2010 Jacobson et al.
2010/0063368 A1 3/2010 Leuthardt et al.
2010/0063563 A1 3/2010 Craig
2010/0068751 A1 3/2010 Eberle
2010/0069724 A1 3/2010 Leuthardt et al.
2010/0069739 A1 3/2010 deCharms
2010/0069762 A1 3/2010 Mietus et al.
2010/0069775 A1 3/2010 Milgramm et al.
2010/0069777 A1 3/2010 Marks
2010/0069780 A1 3/2010 Schuette et al.
2010/0070001 A1 3/2010 Goetz
2010/0076249 A1 3/2010 Leuthardt et al.
2010/0076253 A1 3/2010 Altman et al.
2010/0076274 A1 3/2010 Severson
2010/0076333 A9 3/2010 Burton et al.
2010/0076334 A1 3/2010 Rothblatt
2010/0076338 A1 3/2010 Kwak
2010/0076525 A1 3/2010 Skelton et al.
2010/0079292 A1 4/2010 Lynn et al.
2010/0080432 A1 4/2010 Lilja et al.
2010/0081860 A1 4/2010 Leuthardt et al.
2010/0081861 A1 4/2010 Leuthardt et al.
2010/0082506 A1 4/2010 Avinash et al.

(56) References Cited

U.S. PATENT DOCUMENTS

2010/0087719 A1 4/2010 Benni
2010/0087900 A1 4/2010 Flint
2010/0090835 A1 4/2010 Liu et al.
2010/0092934 A1 4/2010 Silberstein
2010/0094103 A1 4/2010 Kaplan et al.
2010/0094152 A1 4/2010 Semmlow
2010/0094154 A1 4/2010 Schalk et al.
2010/0094155 A1 4/2010 Prichep
2010/0098289 A1 4/2010 Tognoli et al.
2010/0099954 A1 4/2010 Dickinson et al.
2010/0099975 A1 4/2010 Faro et al.
2010/0100036 A1 4/2010 Leuthardt et al.
2010/0100164 A1 4/2010 Johnson et al.
2010/0106041 A1 4/2010 Ghovanloo et al.
2010/0106043 A1 4/2010 Robinson et al.
2010/0106044 A1 4/2010 Linderman
2010/0106217 A1 4/2010 Colborn
2010/0113959 A1 5/2010 Pascual-Leone et al.
2010/0114190 A1 5/2010 Bendett et al.
2010/0114192 A1 5/2010 Jaax et al.
2010/0114193 A1 5/2010 Lozano et al.
2010/0114237 A1 5/2010 Giftakis et al.
2010/0114272 A1 5/2010 Haidarliu et al.
2010/0114813 A1 5/2010 Zalay et al.
2010/0121415 A1 5/2010 Skelton et al.
2010/0125219 A1 5/2010 Harris et al.
2010/0125304 A1 5/2010 Faltys
2010/0125561 A1 5/2010 Leuthardt et al.
2010/0130811 A1 5/2010 Leuthardt et al.
2010/0130812 A1 5/2010 Martel
2010/0130869 A1 5/2010 Hauger et al.
2010/0130878 A1 5/2010 Lasso et al.
2010/0131030 A1 5/2010 Firlik et al.
2010/0131034 A1 5/2010 Gliner et al.
2010/0132448 A1 6/2010 Donadille et al.
2010/0134113 A1 6/2010 Depavia et al.
2010/0135556 A1 6/2010 Razifar et al.
2010/0137728 A1 6/2010 Govari
2010/0137937 A1 6/2010 John et al.
2010/0142774 A1 6/2010 Ben-Haim et al.
2010/0143256 A1 6/2010 Suffin et al.
2010/0145215 A1 6/2010 Pradeep et al.
2010/0145219 A1 6/2010 Grey
2010/0145427 A1 6/2010 Gliner et al.
2010/0145428 A1 6/2010 Cameron et al.
2010/0152621 A1 6/2010 Janna et al.
2010/0160737 A1 6/2010 Shachar et al.
2010/0163027 A1 7/2010 Hyde et al.
2010/0163028 A1 7/2010 Hyde et al.
2010/0163035 A1 7/2010 Hyde et al.
2010/0165593 A1 7/2010 Townsend et al.
2010/0168053 A1 7/2010 Kurtz
2010/0168525 A1 7/2010 Hyde et al.
2010/0168529 A1 7/2010 Hyde et al.
2010/0168602 A1 7/2010 Hyde et al.
2010/0172567 A1 7/2010 Prokoski
2010/0174161 A1 7/2010 Lynn
2010/0174533 A1 7/2010 Pakhomov
2010/0179415 A1 7/2010 Wenzel et al.
2010/0179447 A1 7/2010 Hunt
2010/0185113 A1 7/2010 Peot et al.
2010/0189318 A1 7/2010 Chang et al.
2010/0191095 A1 7/2010 Felblinger et al.
2010/0191124 A1 7/2010 Prokoski
2010/0191139 A1 7/2010 Jacquin et al.
2010/0191304 A1 7/2010 Scott
2010/0191305 A1 7/2010 Imran et al.
2010/0195770 A1 8/2010 Ricci et al.
2010/0197610 A1 8/2010 Lian et al.
2010/0197993 A1 8/2010 Vasishta
2010/0198090 A1 8/2010 Hudson et al.
2010/0198098 A1 8/2010 Osorio et al.
2010/0198101 A1 8/2010 Song et al.
2010/0198282 A1 8/2010 Rogers
2010/0198296 A1 8/2010 Ignagni et al.
2010/0198519 A1 8/2010 Wilt et al.
2010/0204604 A1 8/2010 Liley et al.
2010/0204614 A1 8/2010 Lindquist et al.
2010/0204748 A1 8/2010 Lozano et al.
2010/0204749 A1 8/2010 Thimineur et al.
2010/0204750 A1 8/2010 Hargrove et al.
2010/0217100 A1 8/2010 LeBoeuf et al.
2010/0217146 A1 8/2010 Osvath
2010/0217341 A1 8/2010 John et al.
2010/0217348 A1 8/2010 DiLorenzo
2010/0219820 A1 9/2010 Skidmore et al.
2010/0222640 A1 9/2010 Anderson et al.
2010/0222694 A1 9/2010 Causevic
2010/0222845 A1 9/2010 Goetz
2010/0224188 A1 9/2010 John et al.
2010/0231221 A1 9/2010 Rosthal et al.
2010/0231327 A1 9/2010 Johnson et al.
2010/0234705 A1 9/2010 Lynn
2010/0234752 A1 9/2010 Sullivan et al.
2010/0234753 A1 9/2010 Ma
2010/0238763 A1 9/2010 Gzara et al.
2010/0241020 A1 9/2010 Zaidel et al.
2010/0241195 A1 9/2010 Meadows et al.
2010/0241449 A1 9/2010 Firminger et al.
2010/0245093 A1 9/2010 Kobetski et al.
2010/0248275 A1 9/2010 Jackowski et al.
2010/0249573 A1 9/2010 Marks
2010/0249627 A1 9/2010 Zhang et al.
2010/0249635 A1 9/2010 Van Der Reijden
2010/0249638 A1 9/2010 Liley
2010/0256592 A1 10/2010 Gerber et al.
2010/0258126 A1 10/2010 Ujhazy et al.
2010/0260402 A1 10/2010 Axelsson et al.
2010/0261977 A1 10/2010 Seely
2010/0261993 A1 10/2010 van der Kouwe et al.
2010/0262377 A1 10/2010 Jensen
2010/0268055 A1 10/2010 Jung et al.
2010/0268057 A1 10/2010 Firminger et al.
2010/0268108 A1 10/2010 Firminger et al.
2010/0268288 A1 10/2010 Hunter et al.
2010/0274106 A1 10/2010 Heruth et al.
2010/0274141 A1 10/2010 Patangay et al.
2010/0274147 A1 10/2010 Patangay et al.
2010/0274303 A1 10/2010 Bukhman
2010/0274305 A1 10/2010 Gliner et al.
2010/0274308 A1 10/2010 Scott
2010/0274577 A1 10/2010 Firminger et al.
2010/0274578 A1 10/2010 Firminger et al.
2010/0280332 A1 11/2010 Hyde et al.
2010/0280334 A1 11/2010 Carlson et al.
2010/0280335 A1 11/2010 Carlson et al.
2010/0280372 A1 11/2010 Poolman et al.
2010/0280403 A1 11/2010 Erdogmus et al.
2010/0280500 A1 11/2010 Skelton et al.
2010/0280571 A1 11/2010 Sloan
2010/0280574 A1 11/2010 Carlson et al.
2010/0280579 A1 11/2010 Denison et al.
2010/0286549 A1 11/2010 John et al.
2010/0286747 A1 11/2010 Sabesan et al.
2010/0292602 A1 11/2010 Worrell et al.
2010/0292752 A1 11/2010 Bardakjian et al.
2010/0293002 A1 11/2010 Firminger et al.
2010/0293115 A1 11/2010 Seyed Momen
2010/0298624 A1 11/2010 Becker
2010/0298735 A1 11/2010 Suffin
2010/0303101 A1 12/2010 Lazar et al.
2010/0305962 A1 12/2010 Firminger et al.
2010/0305963 A1 12/2010 Firminger et al.
2010/0312188 A1 12/2010 Robertson et al.
2010/0312579 A1 12/2010 Firminger et al.
2010/0318025 A1 12/2010 John
2010/0318160 A1 12/2010 Stevenson et al.
2010/0322488 A1 12/2010 Virtue et al.
2010/0322497 A1 12/2010 Dempsey et al.
2010/0324441 A1 12/2010 Hargrove et al.
2010/0331649 A1 12/2010 Chou
2010/0331715 A1 12/2010 Addison et al.
2010/0331976 A1 12/2010 Pesaran et al.
2011/0004115 A1 1/2011 Shahaf et al.

(56) References Cited

U.S. PATENT DOCUMENTS

2011/0004270 A1 1/2011 Sheffield et al.
2011/0004283 A1 1/2011 Stevenson et al.
2011/0004412 A1 1/2011 Shahaf et al.
2011/0007129 A1 1/2011 Martin et al.
2011/0009715 A1 1/2011 O' Reilly et al.
2011/0009729 A1 1/2011 Shin et al.
2011/0009752 A1 1/2011 Chen et al.
2011/0009777 A1 1/2011 Reichow et al.
2011/0009920 A1 1/2011 Whitehurst et al.
2011/0009928 A1 1/2011 Gerber et al.
2011/0015209 A1 1/2011 Shamloo et al.
2011/0015469 A1 1/2011 Walter et al.
2011/0015501 A1 1/2011 Lynn et al.
2011/0015515 A1 1/2011 deCharms
2011/0015536 A1 1/2011 Milgramm et al.
2011/0015539 A1 1/2011 deCharms
2011/0021899 A1 1/2011 Arps et al.
2011/0021970 A1 1/2011 Vo-Dinh et al.
2011/0022981 A1 1/2011 Mahajan et al.
2011/0028798 A1 2/2011 Hyde et al.
2011/0028799 A1 2/2011 Hyde et al.
2011/0028802 A1 2/2011 Addison et al.
2011/0028825 A1 2/2011 Douglas et al.
2011/0028827 A1 2/2011 Sitaram et al.
2011/0028859 A1 2/2011 Chian
2011/0029038 A1 2/2011 Hyde et al.
2011/0029044 A1 2/2011 Hyde et al.
2011/0034812 A1 2/2011 Patangay et al.
2011/0034821 A1 2/2011 Ekpar
2011/0034822 A1 2/2011 Phillips et al.
2011/0034912 A1 2/2011 de Graff et al.
2011/0035231 A1 2/2011 Firminger et al.
2011/0038515 A1 2/2011 Jacquin et al.
2011/0038850 A1 2/2011 Bagnol et al.
2011/0040202 A1 2/2011 Luo et al.
2011/0040356 A1 2/2011 Schiffer
2011/0040546 A1 2/2011 Gerber et al.
2011/0040547 A1 2/2011 Gerber et al.
2011/0040713 A1 2/2011 Colman et al.
2011/0043759 A1 2/2011 Bushinsky
2011/0046451 A1 2/2011 Horn et al.
2011/0046473 A1 2/2011 Pradeep et al.
2011/0046491 A1 2/2011 Diamond
2011/0050232 A1 3/2011 Wilt et al.
2011/0054272 A1 3/2011 Derchak
2011/0054279 A1 3/2011 Reisfeld et al.
2011/0054345 A1 3/2011 Nagatani
2011/0054562 A1 3/2011 Gliner
2011/0054569 A1 3/2011 Zitnik et al.
2011/0060382 A1 3/2011 Jaax et al.
2011/0066005 A1 3/2011 Rotenberg
2011/0066041 A1 3/2011 Pandia et al.
2011/0066042 A1 3/2011 Pandia et al.
2011/0066053 A1 3/2011 Yazicioglu
2011/0074396 A1 3/2011 Liao et al.
2011/0077503 A1 3/2011 Bonilha et al.
2011/0077538 A1 3/2011 Liu et al.
2011/0077548 A1 3/2011 Torch
2011/0077721 A1 3/2011 Whitehurst et al.
2011/0082154 A1 4/2011 Oksenberg et al.
2011/0082360 A1 4/2011 Fuchs et al.
2011/0082381 A1 4/2011 Uthman et al.
2011/0082522 A1 4/2011 Bourget et al.
2011/0087125 A1 4/2011 Causevic
2011/0087127 A1 4/2011 Sarkela et al.
2011/0092800 A1 4/2011 Yoo et al.
2011/0092834 A1 4/2011 Yazicioglu et al.
2011/0092839 A1 4/2011 Alshaer et al.
2011/0092882 A1 4/2011 Firlik et al.
2011/0093033 A1 4/2011 Nekhendzy
2011/0098583 A1 4/2011 Pandia et al.
2011/0098778 A1 4/2011 Thimineur et al.
2011/0105859 A1 5/2011 Popovic et al.
2011/0105915 A1 5/2011 Bauer et al.
2011/0105938 A1 5/2011 Hardt
2011/0105998 A1 5/2011 Zhang et al.
2011/0106206 A1 5/2011 Schiff
2011/0106750 A1 5/2011 Pradeep et al.
2011/0110868 A1 5/2011 Akhtari et al.
2011/0112379 A1 5/2011 Li et al.
2011/0112381 A1 5/2011 Sun et al.
2011/0112394 A1 5/2011 Mishelevich
2011/0112426 A1 5/2011 Causevic
2011/0112427 A1 5/2011 Phillips et al.
2011/0112590 A1 5/2011 Wu et al.
2011/0115624 A1 5/2011 Tran
2011/0118536 A1 5/2011 Phillips et al.
2011/0118618 A1 5/2011 John et al.
2011/0118619 A1 5/2011 Burton et al.
2011/0119212 A1 5/2011 De Bruin et al.
2011/0125046 A1 5/2011 Burton et al.
2011/0125048 A1 5/2011 Causevic et al.
2011/0125077 A1 5/2011 Denison et al.
2011/0125078 A1 5/2011 Denison et al.
2011/0125203 A1 5/2011 Simon et al.
2011/0125238 A1 5/2011 Nofzinger
2011/0129129 A1 6/2011 Avinash et al.
2011/0130615 A1 6/2011 Mishelevich
2011/0130643 A1 6/2011 Derchak et al.
2011/0130675 A1 6/2011 Bibian et al.
2011/0137371 A1 6/2011 Giftakis et al.
2011/0137381 A1 6/2011 Lee et al.
2011/0144520 A1 6/2011 Causevic et al.
2011/0144521 A1 6/2011 Molnar et al.
2011/0150253 A1 6/2011 Corona-Strauss et al.
2011/0152284 A1 6/2011 Wieloch et al.
2011/0152710 A1 6/2011 Kim et al.
2011/0152729 A1 6/2011 Oohashi et al.
2011/0152967 A1 6/2011 Simon et al.
2011/0152988 A1 6/2011 Whitehurst et al.
2011/0160543 A1 6/2011 Parsey et al.
2011/0160607 A1 6/2011 John et al.
2011/0160608 A1 6/2011 Hargrove
2011/0160795 A1 6/2011 Osorio
2011/0160796 A1 6/2011 Lane et al.
2011/0161011 A1 6/2011 Hasson et al.
2011/0162645 A1 7/2011 John et al.
2011/0166430 A1 7/2011 Harris et al.
2011/0166471 A1 7/2011 Drew et al.
2011/0166546 A1 7/2011 Jaax et al.
2011/0172500 A1 7/2011 Van Dooren et al.
2011/0172509 A1 7/2011 Chance
2011/0172553 A1 7/2011 John et al.
2011/0172554 A1 7/2011 Leyde et al.
2011/0172562 A1 7/2011 Sahasrabudhe et al.
2011/0172564 A1 7/2011 Drew
2011/0172567 A1 7/2011 Panken et al.
2011/0172725 A1 7/2011 Wells et al.
2011/0172732 A1 7/2011 Maschino
2011/0172738 A1 7/2011 Davis et al.
2011/0172739 A1 7/2011 Mann et al.
2011/0172743 A1 7/2011 Davis et al.
2011/0172927 A1 7/2011 Sahasrabudhe et al.
2011/0178359 A1 7/2011 Hirschman et al.
2011/0178441 A1 7/2011 Tyler
2011/0178442 A1 7/2011 Mishelevich
2011/0178581 A1 7/2011 Haber et al.
2011/0181422 A1 7/2011 Tran
2011/0182501 A1 7/2011 Mercier et al.
2011/0184305 A1 7/2011 Liley
2011/0184487 A1 7/2011 Alberts et al.
2011/0184650 A1 7/2011 Hymel
2011/0190569 A1 8/2011 Simon et al.
2011/0190600 A1 8/2011 McKenna et al.
2011/0190846 A1 8/2011 Ruffini et al.
2011/0191275 A1 8/2011 Lujan et al.
2011/0191350 A1 8/2011 Zhang et al.
2011/0196693 A1 8/2011 Hargrove et al.
2011/0201944 A1 8/2011 Higgins et al.
2011/0207988 A1 8/2011 Ruohonen et al.
2011/0208012 A1 8/2011 Gerber et al.
2011/0208094 A1 8/2011 Mishelevich
2011/0208264 A1 8/2011 Gliner et al.
2011/0208539 A1 8/2011 Lynn

(56) References Cited

U.S. PATENT DOCUMENTS

2011/0213200 A1 9/2011 Mishelevich
2011/0213222 A1 9/2011 Leyde et al.
2011/0217240 A1 9/2011 Ferris
2011/0218405 A1 9/2011 Avinash et al.
2011/0218453 A1 9/2011 Hirata et al.
2011/0218456 A1 9/2011 Graham et al.
2011/0218950 A1 9/2011 Mirowski et al.
2011/0224569 A1 9/2011 Isenhart et al.
2011/0224570 A1 9/2011 Causevic
2011/0224571 A1 9/2011 Pascual-Leone et al.
2011/0224602 A1 9/2011 Struijk et al.
2011/0224749 A1 9/2011 Ben-David et al.
2011/0229005 A1 9/2011 Den Harder et al.
2011/0230701 A1 9/2011 Simon et al.
2011/0230738 A1 9/2011 Chance
2011/0230755 A1 9/2011 MacFarlane et al.
2011/0230938 A1 9/2011 Simon et al.
2011/0238130 A1 9/2011 Bourget et al.
2011/0238136 A1 9/2011 Bourget et al.
2011/0245709 A1 10/2011 Greenwald
2011/0245734 A1 10/2011 Wagner et al.
2011/0251583 A1 10/2011 Miyazawa et al.
2011/0251985 A1 10/2011 Waxman et al.
2011/0256520 A1 10/2011 Siefert
2011/0257501 A1 10/2011 Huys et al.
2011/0257517 A1 10/2011 Guttag et al.
2011/0257519 A1 10/2011 Bjornerud et al.
2011/0263962 A1 10/2011 Marks
2011/0263968 A1 10/2011 Quattrocki-Knight et al.
2011/0263995 A1 10/2011 Chen
2011/0264182 A1 10/2011 Cowley
2011/0270074 A1 11/2011 deCharms
2011/0270095 A1 11/2011 Bukhman
2011/0270096 A1 11/2011 Osorio et al.
2011/0270117 A1 11/2011 Warwick et al.
2011/0270346 A1 11/2011 Frei et al.
2011/0270347 A1 11/2011 Frei et al.
2011/0270348 A1 11/2011 Goetz
2011/0270579 A1 11/2011 Watson et al.
2011/0270914 A1 11/2011 Jung et al.
2011/0275927 A1 11/2011 Wagner et al.
2011/0276107 A1 11/2011 Simon et al.
2011/0276112 A1 11/2011 Simon et al.
2011/0282225 A1 11/2011 Anderson et al.
2011/0282230 A9 11/2011 Liley
2011/0282234 A1 11/2011 Ochs
2011/0288119 A1 11/2011 Chesworth et al.
2011/0288400 A1 11/2011 Russell et al.
2011/0288424 A1 11/2011 Kanai et al.
2011/0288431 A1 11/2011 Alshaer et al.
2011/0293193 A1 12/2011 Garg et al.
2011/0295142 A1 12/2011 Chakravarthy et al.
2011/0295143 A1 12/2011 Leuthardt et al.
2011/0295166 A1 12/2011 Dalton
2011/0295338 A1 12/2011 Rickert et al.
2011/0295344 A1 12/2011 Wells et al.
2011/0295345 A1 12/2011 Wells et al.
2011/0295346 A1 12/2011 Wells et al.
2011/0295347 A1 12/2011 Wells et al.
2011/0298706 A1 12/2011 Mann
2011/0301436 A1 12/2011 Teixeira
2011/0301439 A1 12/2011 Albert et al.
2011/0301441 A1 12/2011 Bandic et al.
2011/0301448 A1 12/2011 deCharms
2011/0301486 A1 12/2011 Van Hek et al.
2011/0301487 A1 12/2011 Abeyratne et al.
2011/0301488 A1 12/2011 Schuette et al.
2011/0301529 A1 12/2011 Zhang et al.
2011/0306845 A1 12/2011 Osorio
2011/0306846 A1 12/2011 Osorio
2011/0307029 A1 12/2011 Hargrove
2011/0307030 A1 12/2011 John
2011/0307079 A1 12/2011 Oweiss et al.
2011/0308789 A1 12/2011 Zhang et al.
2011/0311021 A1 12/2011 Tsukagoshi
2011/0311489 A1 12/2011 Deisseroth et al.
2011/0313268 A1 12/2011 Kokones et al.
2011/0313274 A1 12/2011 Subbarao
2011/0313308 A1 12/2011 Zavoronkovs et al.
2011/0313487 A1 12/2011 Kokones et al.
2011/0313760 A1 12/2011 Ricci et al.
2011/0319482 A1 12/2011 Blower et al.
2011/0319724 A1 12/2011 Cox
2011/0319726 A1 12/2011 Sachanandani et al.
2011/0319975 A1 12/2011 Ho et al.
2012/0003615 A1 1/2012 Ochs
2012/0004518 A1 1/2012 D'Souza et al.
2012/0004561 A1 1/2012 John
2012/0004564 A1 1/2012 Dobak
2012/0004579 A1 1/2012 Luo et al.
2012/0004749 A1 1/2012 Abeyratne et al.
2012/0010493 A1 1/2012 Semenov
2012/0010536 A1 1/2012 Bolger et al.
2012/0011927 A1 1/2012 Badri et al.
2012/0016218 A1 1/2012 Lau et al.
2012/0016252 A1 1/2012 Melker et al.
2012/0016336 A1 1/2012 Whitehurst et al.
2012/0016430 A1 1/2012 Lozano
2012/0016432 A1 1/2012 Westendorp et al.
2012/0016435 A1 1/2012 Rom
2012/0021394 A1 1/2012 deCharms
2012/0022336 A1 1/2012 Teixeira
2012/0022340 A1 1/2012 Heruth et al.
2012/0022343 A1 1/2012 Shastri et al.
2012/0022350 A1 1/2012 Teixeira
2012/0022351 A1 1/2012 Starr
2012/0022365 A1 1/2012 Mansfield
2012/0022384 A1 1/2012 Teixeira
2012/0022392 A1 1/2012 Leuthardt et al.
2012/0022611 A1 1/2012 Firlik et al.
2012/0022844 A1 1/2012 Teixeira
2012/0022884 A1 1/2012 Chillemi
2012/0029320 A1 2/2012 Watson et al.
2012/0029378 A1 2/2012 Low
2012/0029379 A1 2/2012 Sivadas
2012/0029591 A1 2/2012 Simon et al.
2012/0029601 A1 2/2012 Simon et al.
2012/0035428 A1 2/2012 Roberts et al.
2012/0035431 A1 2/2012 Sun et al.
2012/0035433 A1 2/2012 Chance
2012/0035698 A1 2/2012 Johnson et al.
2012/0035765 A1 2/2012 Sato et al.
2012/0036004 A1 2/2012 Pradeep et al.
2012/0041279 A1 2/2012 Freeman et al.
2012/0041318 A1 2/2012 Taylor
2012/0041319 A1 2/2012 Taylor et al.
2012/0041320 A1 2/2012 Taylor
2012/0041321 A1 2/2012 Taylor et al.
2012/0041322 A1 2/2012 Taylor et al.
2012/0041323 A1 2/2012 Taylor et al.
2012/0041324 A1 2/2012 Taylor et al.
2012/0041330 A1 2/2012 Prichep et al.
2012/0041498 A1 2/2012 Gliner et al.
2012/0041735 A1 2/2012 Taylor
2012/0041739 A1 2/2012 Taylor
2012/0046531 A1 2/2012 Hua
2012/0046535 A1 2/2012 Lin et al.
2012/0046711 A1 2/2012 Osorio
2012/0046715 A1 2/2012 Moffitt et al.
2012/0046971 A1 2/2012 Walker et al.
2012/0052469 A1 3/2012 Sobel et al.
2012/0052905 A1 3/2012 Lim et al.
2012/0053394 A1 3/2012 Honeycutt
2012/0053433 A1 3/2012 Chamoun et al.
2012/0053449 A1 3/2012 Moses et al.
2012/0053473 A1 3/2012 Johnson et al.
2012/0053476 A1 3/2012 Hopenfeld
2012/0053478 A1 3/2012 Johnson et al.
2012/0053479 A1 3/2012 Hopenfeld
2012/0053483 A1 3/2012 Doidge et al.
2012/0053491 A1 3/2012 Nathan et al.
2012/0053508 A1 3/2012 Wu et al.
2012/0053919 A1 3/2012 Taylor
2012/0053921 A1 3/2012 Taylor

(56) References Cited

U.S. PATENT DOCUMENTS

2012/0059246 A1 3/2012 Taylor
2012/0059273 A1 3/2012 Meggiolaro et al.
2012/0059431 A1 3/2012 Williams et al.
2012/0060851 A1 3/2012 Amberg
2012/0065536 A1 3/2012 Causevic et al.
2012/0070044 A1 3/2012 Avinash et al.
2012/0071771 A1 3/2012 Behar
2012/0078115 A1 3/2012 Lonky
2012/0078323 A1 3/2012 Osorio
2012/0078327 A1 3/2012 Sloan et al.
2012/0080305 A1 4/2012 Koruga
2012/0083668 A1 4/2012 Pradeep et al.
2012/0083690 A1 4/2012 Semenov
2012/0083700 A1 4/2012 Osorio
2012/0083701 A1 4/2012 Osorio
2012/0083708 A1 4/2012 Rajdev et al.
2012/0088987 A1 4/2012 Braun et al.
2012/0088992 A1 4/2012 Armitstead
2012/0089004 A1 4/2012 Hsu et al.
2012/0089205 A1 4/2012 Boyden et al.
2012/0092156 A1 4/2012 Tran
2012/0092157 A1 4/2012 Tran
2012/0095352 A1 4/2012 Tran
2012/0095357 A1 4/2012 Tran
2012/0100514 A1 4/2012 Desain et al.
2012/0101326 A1 4/2012 Simon et al.
2012/0101387 A1 4/2012 Ji et al.
2012/0101401 A1 4/2012 Faul et al.
2012/0101402 A1 4/2012 Nguyen
2012/0101430 A1 4/2012 Robertson et al.
2012/0101544 A1 4/2012 Hoberman et al.
2012/0108909 A1 5/2012 Slobounov et al.
2012/0108918 A1 5/2012 Jarvik et al.
2012/0108995 A1 5/2012 Pradeep et al.
2012/0108997 A1 5/2012 Guan et al.
2012/0108998 A1 5/2012 Molnar et al.
2012/0108999 A1 5/2012 Leininger et al.
2012/0109020 A1 5/2012 Wagner et al.
2012/0116149 A1 5/2012 Pilla et al.
2012/0116179 A1 5/2012 Drew et al.
2012/0116235 A1 5/2012 Trumble et al.
2012/0116244 A1 5/2012 McIntyre et al.
2012/0116475 A1 5/2012 Nelson et al.
2012/0116741 A1 5/2012 Choi et al.
2012/0123232 A1 5/2012 Najarian et al.
2012/0123290 A1 5/2012 Kidmose et al.
2012/0125337 A1 5/2012 Asanoi
2012/0128683 A1 5/2012 Shantha
2012/0130204 A1 5/2012 Basta et al.
2012/0130228 A1 5/2012 Zellers et al.
2012/0130229 A1 5/2012 Zellers et al.
2012/0130300 A1 5/2012 Stavchansky et al.
2012/0130641 A1 5/2012 Morrison et al.
2012/0136242 A1 5/2012 Qi et al.
2012/0136274 A1 5/2012 Burdea et al.
2012/0136605 A1 5/2012 Addison et al.
2012/0143038 A1 6/2012 Georgopoulos
2012/0143074 A1 6/2012 Shin et al.
2012/0143075 A1 6/2012 Tansey
2012/0143104 A1 6/2012 Tee et al.
2012/0143285 A1 6/2012 Wang et al.
2012/0145152 A1 6/2012 Lain et al.
2012/0149042 A1 6/2012 Jackowski et al.
2012/0149997 A1 6/2012 Diab et al.
2012/0150255 A1 6/2012 Lindenthaler et al.
2012/0150257 A1 6/2012 Aur et al.
2012/0150262 A1 6/2012 Gliner et al.
2012/0150516 A1 6/2012 Taylor et al.
2012/0150545 A1 6/2012 Simon
2012/0157804 A1 6/2012 Rogers et al.
2012/0157963 A1 6/2012 Imran
2012/0158092 A1 6/2012 Thimineur et al.
2012/0159656 A1 6/2012 Gerber et al.
2012/0162002 A1 6/2012 Semenov
2012/0163689 A1 6/2012 Bottger et al.
2012/0164613 A1 6/2012 Jung et al.
2012/0165624 A1 6/2012 Diab et al.
2012/0165631 A1 6/2012 Diab et al.
2012/0165696 A1 6/2012 Arns
2012/0165898 A1 6/2012 Moffitt
2012/0165899 A1 6/2012 Gliner
2012/0165904 A1 6/2012 Lee et al.
2012/0172682 A1 7/2012 Linderman et al.
2012/0172689 A1 7/2012 Albert et al.
2012/0172743 A1 7/2012 Aguilar et al.
2012/0177716 A1 7/2012 Ho et al.
2012/0179071 A1 7/2012 Skelton
2012/0179228 A1 7/2012 DeCharms
2012/0184801 A1 7/2012 Simon et al.
2012/0184826 A1 7/2012 Keenan et al.
2012/0185020 A1 7/2012 Simon et al.
2012/0191000 A1 7/2012 Adachi et al.
2012/0191158 A1 7/2012 Craig
2012/0191542 A1 7/2012 Nurmi
2012/0195860 A1 8/2012 Walker et al.
2012/0197092 A1 8/2012 Luo et al.
2012/0197153 A1 8/2012 Kraus et al.
2012/0197163 A1 8/2012 Mishelevich
2012/0197322 A1 8/2012 Skelton et al.
2012/0203079 A1 8/2012 McLaughlin
2012/0203087 A1 8/2012 McKenna et al.
2012/0203130 A1 8/2012 Bernhard
2012/0203131 A1 8/2012 DiLorenzo
2012/0203133 A1 8/2012 Jadidi
2012/0203725 A1 8/2012 Stoica
2012/0207362 A1 8/2012 Fueyo et al.
2012/0209126 A1 8/2012 Amos et al.
2012/0209136 A1 8/2012 Ma
2012/0209139 A1 8/2012 John
2012/0209346 A1 8/2012 Bikson et al.
2012/0212353 A1 8/2012 Fung et al.
2012/0215114 A1 8/2012 Gratton et al.
2012/0215448 A1 8/2012 Hu et al.
2012/0219195 A1 8/2012 Wu et al.
2012/0219507 A1 8/2012 Santosh et al.
2012/0220843 A1 8/2012 Diab et al.
2012/0220889 A1 8/2012 Sullivan et al.
2012/0221310 A1 8/2012 Sarrafzadeh et al.
2012/0226091 A1 9/2012 Mishelevich
2012/0226130 A1 9/2012 De Graff et al.
2012/0226185 A1 9/2012 Chung et al.
2012/0226334 A1 9/2012 Gardiner et al.
2012/0232327 A1 9/2012 Lozano et al.
2012/0232376 A1 9/2012 Crevecoeur et al.
2012/0232433 A1 9/2012 Mishelevich
2012/0238890 A1 9/2012 Baker et al.
2012/0242501 A1 9/2012 Tran et al.
2012/0245464 A1 9/2012 Tran
2012/0245474 A1 9/2012 Ofek et al.
2012/0245481 A1 9/2012 Blanco et al.
2012/0245493 A1 9/2012 Mishelevich
2012/0245655 A1 9/2012 Spitzer et al.
2012/0249274 A1 10/2012 Toda et al.
2012/0253101 A1 10/2012 Wang et al.
2012/0253141 A1 10/2012 Addison et al.
2012/0253168 A1 10/2012 Hu et al.
2012/0253219 A1 10/2012 Suffin et al.
2012/0253249 A1 10/2012 Wilson
2012/0253261 A1 10/2012 Poletto et al.
2012/0253421 A1 10/2012 Gliner et al.
2012/0253429 A1 10/2012 Schiffer
2012/0253434 A1 10/2012 Nissila et al.
2012/0253442 A1 10/2012 Gliner et al.
2012/0259249 A1 10/2012 Khuri-Yakub et al.
2012/0262250 A1 10/2012 Stevenson et al.
2012/0262558 A1 10/2012 Boger et al.
2012/0263393 A1 10/2012 Yahil
2012/0265080 A1 10/2012 Yu et al.
2012/0265262 A1 10/2012 Osorio
2012/0265267 A1 10/2012 Blum et al.
2012/0265270 A1 10/2012 Cornejo Cruz et al.
2012/0265271 A1 10/2012 Goetz
2012/0268272 A1 10/2012 Lee et al.
2012/0269385 A1 10/2012 Lee et al.

(56) References Cited

U.S. PATENT DOCUMENTS

2012/0271148 A1 10/2012 Nelson
2012/0271151 A1 10/2012 LaVoilette et al.
2012/0271183 A1 10/2012 Sachanandani et al.
2012/0271189 A1 10/2012 Nelson et al.
2012/0271190 A1 10/2012 Mortensen et al.
2012/0271374 A1 10/2012 Nelson et al.
2012/0271375 A1 10/2012 Wu et al.
2012/0271376 A1 10/2012 Kokones et al.
2012/0271377 A1 10/2012 Hagedorn et al.
2012/0271380 A1 10/2012 Roberts et al.
2012/0277545 A1 11/2012 Teixeira
2012/0277548 A1 11/2012 Burton
2012/0277816 A1 11/2012 Zhang et al.
2012/0277833 A1 11/2012 Gerber et al.
2012/0283502 A1 11/2012 Mishelevich et al.
2012/0283604 A1 11/2012 Mishelevich
2012/0288143 A1 11/2012 Ernst et al.
2012/0289854 A1 11/2012 Yamada et al.
2012/0289869 A1 11/2012 Tyler
2012/0290058 A1 11/2012 Langevin et al.
2012/0296182 A1 11/2012 Hornero Sanchez et al.
2012/0296241 A1 11/2012 Mishelevich
2012/0296253 A1 11/2012 Mathews et al.
2012/0296569 A1 11/2012 Shahaf et al.
2012/0302842 A1 11/2012 Kurtz et al.
2012/0302845 A1 11/2012 Lynn et al.
2012/0302856 A1 11/2012 Chang et al.
2012/0302867 A1 11/2012 Ichimura
2012/0302894 A1 11/2012 Diab et al.
2012/0302912 A1 11/2012 Moffitt et al.
2012/0303080 A1 11/2012 Ben-David et al.
2012/0303087 A1 11/2012 Moffitt et al.
2012/0310050 A1 12/2012 Osorio
2012/0310100 A1 12/2012 Galen et al.
2012/0310105 A1 12/2012 Feingold et al.
2012/0310106 A1 12/2012 Cavuoto
2012/0310107 A1 12/2012 Doidge et al.
2012/0310298 A1 12/2012 Besio et al.
2012/0316622 A1 12/2012 Whitehurst et al.
2012/0316630 A1 12/2012 Firlik et al.
2012/0316793 A1 12/2012 Jung et al.
2012/0321152 A1 12/2012 Carroll
2012/0321160 A1 12/2012 Carroll
2012/0321759 A1 12/2012 Marinkovich et al.
2012/0323108 A1 12/2012 Carroll
2012/0323132 A1 12/2012 Warner et al.
2012/0330109 A1 12/2012 Tran
2012/0330369 A1 12/2012 Osorio et al.
2013/0006124 A1 1/2013 Eyal et al.
2013/0006332 A1 1/2013 Sommer et al.
2013/0009783 A1 1/2013 Tran
2013/0011819 A1 1/2013 Horseman
2013/0012786 A1 1/2013 Horseman
2013/0012787 A1 1/2013 Horseman
2013/0012788 A1 1/2013 Horseman
2013/0012789 A1 1/2013 Horseman
2013/0012790 A1 1/2013 Horseman
2013/0012802 A1 1/2013 Horseman
2013/0012804 A1 1/2013 deCharms
2013/0012830 A1 1/2013 Leininger et al.
2013/0013327 A1 1/2013 Horseman
2013/0013339 A1 1/2013 Goldman et al.
2013/0013667 A1 1/2013 Serena
2013/0018435 A1 1/2013 De Ridder
2013/0018438 A1 1/2013 Chow
2013/0018439 A1 1/2013 Chow et al.
2013/0018440 A1 1/2013 Chow et al.
2013/0018592 A1 1/2013 Mollicone et al.
2013/0018596 A1 1/2013 Bottger et al.
2013/0019325 A1 1/2013 Deisseroth et al.
2013/0023783 A1 1/2013 Snyder et al.
2013/0028496 A1 1/2013 Panin et al.
2013/0030241 A1 1/2013 Smith
2013/0030257 A1 1/2013 Nakata et al.
2013/0031038 A1 1/2013 Horne
2013/0034837 A1 2/2013 Clapp et al.
2013/0035579 A1 2/2013 Le et al.
2013/0039498 A1 2/2013 Adachi et al.
2013/0041235 A1 2/2013 Rogers et al.
2013/0041281 A1 2/2013 Park et al.
2013/0046151 A1 2/2013 Bsoul et al.
2013/0046193 A1 2/2013 Guttag et al.
2013/0046358 A1 2/2013 Leyde
2013/0046715 A1 2/2013 Castermans et al.
2013/0053656 A1 2/2013 Mollicone et al.
2013/0054214 A1 2/2013 Taylor
2013/0054215 A1 2/2013 Stubna et al.
2013/0058548 A1 3/2013 Garg et al.
2013/0060110 A1 3/2013 Lynn et al.
2013/0060125 A1 3/2013 Zeman et al.
2013/0060158 A1 3/2013 Perez-Velazquez et al.
2013/0063434 A1 3/2013 Miga et al.
2013/0063550 A1 3/2013 Ritchey et al.
2013/0064438 A1 3/2013 Taylor et al.
2013/0066350 A1 3/2013 Mishelevich
2013/0066391 A1 3/2013 Hulvershorn et al.
2013/0066392 A1 3/2013 Simon et al.
2013/0066394 A1 3/2013 Saab
2013/0066395 A1 3/2013 Simon et al.
2013/0066618 A1 3/2013 Taylor et al.
2013/0069780 A1 3/2013 Tran et al.
2013/0070929 A1 3/2013 Adachi et al.
2013/0072292 A1 3/2013 Sutton et al.
2013/0072775 A1 3/2013 Rogers et al.
2013/0072780 A1 3/2013 Espy et al.
2013/0072807 A1 3/2013 Tran
2013/0072996 A1 3/2013 Kilgard et al.
2013/0073022 A1 3/2013 Ollivier
2013/0076885 A1 3/2013 Kobetski et al.
2013/0079606 A1 3/2013 McGonigle et al.
2013/0079621 A1 3/2013 Shoham et al.
2013/0079647 A1 3/2013 McGonigle et al.
2013/0079656 A1 3/2013 Dripps et al.
2013/0079657 A1 3/2013 Ochs et al.
2013/0080127 A1 3/2013 Shahaf et al.
2013/0080489 A1 3/2013 Ochs et al.
2013/0085678 A1 4/2013 Jung et al.
2013/0089503 A1 4/2013 Deisseroth et al.
2013/0090454 A1 4/2013 Deisseroth et al.
2013/0090706 A1 4/2013 Nudo et al.
2013/0091941 A1 4/2013 Huh et al.
2013/0095459 A1 4/2013 Tran
2013/0096391 A1 4/2013 Osorio et al.
2013/0096393 A1 4/2013 Osorio et al.
2013/0096394 A1 4/2013 Gupta et al.
2013/0096408 A1 4/2013 He et al.
2013/0096441 A1 4/2013 Osorio
2013/0096453 A1 4/2013 Chung et al.
2013/0096454 A1 4/2013 Jang et al.
2013/0096839 A1 4/2013 Osorio et al.
2013/0096840 A1 4/2013 Osorio et al.
2013/0102833 A1 4/2013 John et al.
2013/0102877 A1 4/2013 Mori et al.
2013/0102897 A1 4/2013 Kalafut et al.
2013/0102907 A1 4/2013 Funane et al.
2013/0102919 A1 4/2013 Schiff
2013/0104066 A1 4/2013 Soederstroem
2013/0109995 A1 5/2013 Rothman et al.
2013/0109996 A1 5/2013 Turnbull et al.
2013/0110616 A1 5/2013 Bakalash et al.
2013/0113816 A1 5/2013 Sudarsky et al.
2013/0116520 A1 5/2013 Roham et al.
2013/0116540 A1 5/2013 Li et al.
2013/0116561 A1 5/2013 Rothberg et al.
2013/0116578 A1 5/2013 An et al.
2013/0116588 A1 5/2013 Yazicioglu et al.
2013/0116748 A1 5/2013 Bokil et al.
2013/0118494 A1 5/2013 Ujhazy et al.
2013/0120246 A1 5/2013 Schuette et al.
2013/0121984 A1 5/2013 Haslett et al.
2013/0123568 A1 5/2013 Hamilton et al.
2013/0123584 A1 5/2013 Sun et al.
2013/0123607 A1 5/2013 Leuthardt et al.
2013/0123684 A1 5/2013 Giuffrida et al.

(56) References Cited

U.S. PATENT DOCUMENTS

2013/0127708 A1 5/2013 Jung et al.
2013/0127980 A1 5/2013 Haddick et al.
2013/0130799 A1 5/2013 Van Hulle et al.
2013/0131438 A1 5/2013 Brewer et al.
2013/0131461 A1 5/2013 Jorge et al.
2013/0131537 A1 5/2013 Tam
2013/0131746 A1 5/2013 Simon et al.
2013/0131753 A1 5/2013 Simon et al.
2013/0131755 A1 5/2013 Panken et al.
2013/0132029 A1 5/2013 Mollicone et al.
2013/0137717 A1 5/2013 Chesworth et al.
2013/0137936 A1 5/2013 Baker, Jr. et al.
2013/0137938 A1 5/2013 Peters
2013/0138002 A1 5/2013 Weng et al.
2013/0138176 A1 5/2013 Goetz
2013/0138177 A1 5/2013 DeRidder
2013/0141103 A1 6/2013 Roshtal et al.
2013/0144106 A1 6/2013 Phillips et al.
2013/0144107 A1 6/2013 Phillips et al.
2013/0144108 A1 6/2013 Phillips et al.
2013/0144183 A1 6/2013 John et al.
2013/0144192 A1 6/2013 Mischelevich et al.
2013/0144353 A1 6/2013 Lozano
2013/0144537 A1 6/2013 Schalk et al.
2013/0150650 A1 6/2013 Phillips et al.
2013/0150651 A1 6/2013 Phillips et al.
2013/0150659 A1 6/2013 Shaw et al.
2013/0150702 A1 6/2013 Hokari
2013/0150921 A1 6/2013 Singhal et al.
2013/0151163 A1 6/2013 Taylor et al.
2013/0158883 A1 6/2013 Hasegawa et al.
2013/0159041 A1 6/2013 Jayaraman et al.
2013/0165766 A1 6/2013 Nishikawa et al.
2013/0165804 A1 6/2013 Johnson et al.
2013/0165812 A1 6/2013 Aksenova et al.
2013/0165846 A1 6/2013 Peyman
2013/0165996 A1 6/2013 Meadows et al.
2013/0167360 A1 7/2013 Masmanidis et al.
2013/0172663 A1 7/2013 Leonard
2013/0172686 A1 7/2013 Addison et al.
2013/0172691 A1 7/2013 Tran
2013/0172716 A1 7/2013 Lozano et al.
2013/0172763 A1 7/2013 Wheeler
2013/0172767 A1 7/2013 Dripps et al.
2013/0172772 A1 7/2013 Alshaer et al.
2013/0172774 A1 7/2013 Crowder et al.
2013/0178693 A1 7/2013 Neuvonen et al.
2013/0178718 A1 7/2013 Tran et al.
2013/0178733 A1 7/2013 Langleben
2013/0178913 A1 7/2013 Lozano
2013/0182860 A1 7/2013 Adachi et al.
2013/0184218 A1 7/2013 Paul et al.
2013/0184516 A1 7/2013 Genereux et al.
2013/0184552 A1 7/2013 Westermann et al.
2013/0184558 A1 7/2013 Gallant et al.
2013/0184597 A1 7/2013 Hopenfeld
2013/0184603 A1 7/2013 Rothman
2013/0184639 A1 7/2013 Whitehurst et al.
2013/0184728 A1 7/2013 Mishelevich
2013/0184781 A1 7/2013 Eskandar et al.
2013/0184786 A1 7/2013 Goetz
2013/0184792 A1 7/2013 Simon et al.
2013/0184997 A1 7/2013 Mott
2013/0185144 A1 7/2013 Pradeep et al.
2013/0185145 A1 7/2013 Pradeep et al.
2013/0188830 A1 7/2013 Ernst et al.
2013/0188854 A1 7/2013 Bilgic et al.
2013/0189663 A1 7/2013 Tuchschmid et al.
2013/0190577 A1 7/2013 Brunner et al.
2013/0190642 A1 7/2013 Muesch et al.
2013/0197321 A1 8/2013 Wilson
2013/0197322 A1 8/2013 Tran
2013/0197328 A1 8/2013 Diab et al.
2013/0197339 A1 8/2013 Bardakjian et al.
2013/0197401 A1 8/2013 Sato et al.
2013/0197944 A1 8/2013 Drew et al.
2013/0203019 A1 8/2013 Nolen
2013/0204085 A1 8/2013 Alexander et al.
2013/0204122 A1 8/2013 Hendler et al.
2013/0204144 A1 8/2013 Colborn et al.
2013/0204150 A1 8/2013 Similowski et al.
2013/0211183 A1 8/2013 Schiffer
2013/0211224 A1 8/2013 Isenhart et al.
2013/0211238 A1 8/2013 DeCharms
2013/0211276 A1 8/2013 Luo et al.
2013/0211291 A1 8/2013 Tran
2013/0211728 A1 8/2013 Taylor et al.
2013/0217982 A1 8/2013 Behzadi
2013/0218043 A1 8/2013 Yoshida
2013/0218053 A1 8/2013 Kaiser et al.
2013/0218232 A1 8/2013 Giftakis et al.
2013/0218233 A1 8/2013 Warschewske et al.
2013/0218819 A1 8/2013 Lujan et al.
2013/0221961 A1 8/2013 Liu
2013/0223709 A1 8/2013 Wagner
2013/0225940 A1 8/2013 Fujita et al.
2013/0225953 A1 8/2013 Oliviero et al.
2013/0225992 A1 8/2013 Osorio
2013/0226261 A1 8/2013 Sparks et al.
2013/0226408 A1 8/2013 Fung et al.
2013/0226464 A1 8/2013 Marci et al.
2013/0231574 A1 9/2013 Tran
2013/0231580 A1 9/2013 Chen et al.
2013/0231709 A1 9/2013 Lozano
2013/0231716 A1 9/2013 Skelton et al.
2013/0231721 A1 9/2013 DeCharms
2013/0231947 A1 9/2013 Shusterman
2013/0234823 A1 9/2013 Kahn et al.
2013/0235550 A1 9/2013 Stevenson et al.
2013/0237541 A1 9/2013 Teegarden et al.
2013/0237874 A1 9/2013 Zoicas
2013/0238049 A1 9/2013 Simon et al.
2013/0238050 A1 9/2013 Simon et al.
2013/0238053 A1 9/2013 Ignagni et al.
2013/0238063 A1 9/2013 Nofzinger
2013/0242262 A1 9/2013 Lewis
2013/0243287 A1 9/2013 Thomson et al.
2013/0244323 A1 9/2013 Deisseroth et al.
2013/0245416 A1 9/2013 Yarmush et al.
2013/0245422 A1 9/2013 D'arcy et al.
2013/0245424 A1 9/2013 deCharms
2013/0245464 A1 9/2013 Colborn et al.
2013/0245466 A1 9/2013 Sachanandani et al.
2013/0245485 A1 9/2013 Mashour et al.
2013/0245486 A1 9/2013 Simon et al.
2013/0245711 A1 9/2013 Simon et al.
2013/0245712 A1 9/2013 Simon et al.
2013/0245886 A1 9/2013 Fung et al.
2013/0251641 A1 9/2013 Akhtari et al.
2013/0253363 A1 9/2013 Juffali et al.
2013/0253612 A1 9/2013 Chow
2013/0255586 A1 10/2013 Gerashchenko
2013/0261490 A1 10/2013 Truccolo et al.
2013/0261506 A1 10/2013 Mishelevich
2013/0261703 A1 10/2013 Chow et al.
2013/0266163 A1 10/2013 Morikawa et al.
2013/0267760 A1 10/2013 Jin
2013/0267866 A1 10/2013 Nakashima et al.
2013/0267928 A1 10/2013 Imran et al.
2013/0274562 A1 10/2013 Ghaffari et al.
2013/0274580 A1 10/2013 Madsen et al.
2013/0274586 A1 10/2013 Miyazaki et al.
2013/0274625 A1 10/2013 Sarma et al.
2013/0275159 A1 10/2013 Seely
2013/0281758 A1 10/2013 Solvason et al.
2013/0281759 A1 10/2013 Hagedorn et al.
2013/0281811 A1 10/2013 Imran
2013/0281879 A1 10/2013 Raniere
2013/0281890 A1 10/2013 Mishelevich
2013/0282075 A1 10/2013 De Ridder
2013/0282339 A1 10/2013 Ricci et al.
2013/0289360 A1 10/2013 Hyde et al.
2013/0289364 A1 10/2013 Colman et al.
2013/0289385 A1 10/2013 Lozano et al.

(56) References Cited

U.S. PATENT DOCUMENTS

2013/0289386 A1 10/2013 Deisseroth et al.
2013/0289401 A1 10/2013 Colbaugh et al.
2013/0289413 A1 10/2013 Ochs et al.
2013/0289417 A1 10/2013 Grunwald et al.
2013/0289424 A1 10/2013 Brockway et al.
2013/0289433 A1 10/2013 Jin et al.
2013/0289653 A1 10/2013 Kilgard et al.
2013/0289669 A1 10/2013 Deisseroth et al.
2013/0293844 A1 11/2013 Gross et al.
2013/0295016 A1 11/2013 Gerber et al.
2013/0296406 A1 11/2013 Deisseroth et al.
2013/0296637 A1 11/2013 Kilgard et al.
2013/0300573 A1 11/2013 Brown et al.
2013/0303828 A1 11/2013 Hargrove
2013/0303934 A1 11/2013 Collura
2013/0304153 A1 11/2013 Hargrove et al.
2013/0304159 A1 11/2013 Simon et al.
2013/0304472 A1 11/2013 Pakhomov
2013/0308099 A1 11/2013 Stack
2013/0309278 A1 11/2013 Peyman
2013/0310422 A1 11/2013 Brown et al.
2013/0310660 A1 11/2013 Zuckerman-Stark et al.
2013/0310909 A1 11/2013 Simon et al.
2013/0314243 A1 11/2013 Le
2013/0317380 A1 11/2013 Liley et al.
2013/0317382 A1 11/2013 Le
2013/0317384 A1 11/2013 Le
2013/0317474 A1 11/2013 Rezai et al.
2013/0317568 A1 11/2013 Skelton
2013/0317580 A1 11/2013 Simon et al.
2013/0318546 A1 11/2013 Kothuri et al.
2013/0324880 A1 12/2013 Adachi et al.
2013/0330428 A1 12/2013 Geng
2013/0338449 A1 12/2013 Warwick et al.
2013/0338450 A1 12/2013 Osorio et al.
2013/0338459 A1 12/2013 Lynn et al.
2013/0338518 A1 12/2013 Zoica
2013/0338526 A1 12/2013 Howard
2013/0338738 A1 12/2013 Garcia Molina et al.
2013/0338803 A1 12/2013 Maoz et al.
2013/0339043 A1 12/2013 Bakar et al.
2013/0344465 A1 12/2013 Dickinson et al.
2013/0345522 A1 12/2013 Sun et al.
2013/0345523 A1 12/2013 Diab et al.
2014/0000630 A1 1/2014 Ford
2014/0003696 A1 1/2014 Taghva
2014/0005518 A1 1/2014 Ko et al.
2014/0005743 A1 1/2014 Giuffrida et al.
2014/0005744 A1 1/2014 Hershey et al.
2014/0005988 A1 1/2014 Brockway
2014/0012061 A1 1/2014 Song et al.
2014/0012110 A1 1/2014 Watson et al.
2014/0012133 A1 1/2014 Sverdlik et al.
2014/0012153 A1 1/2014 Greenwald
2014/0015852 A1 1/2014 Kantartzis et al.
2014/0018649 A1 1/2014 Jespersen et al.
2014/0018792 A1 1/2014 Gang et al.
2014/0019165 A1 1/2014 Horseman
2014/0023999 A1 1/2014 Greder
2014/0025133 A1 1/2014 Lozano
2014/0025396 A1 1/2014 Horseman
2014/0025397 A1 1/2014 Horseman
2014/0029830 A1 1/2014 Vija et al.
2014/0031703 A1 1/2014 Rayner et al.
2014/0031889 A1 1/2014 Mashiach
2014/0031903 A1 1/2014 Mashiach
2014/0032512 A1 1/2014 Drew et al.
2014/0038147 A1 2/2014 Morrow
2014/0039279 A1 2/2014 Jarvik et al.
2014/0039290 A1 2/2014 De Graff et al.
2014/0039336 A1 2/2014 Osorio et al.
2014/0039571 A1 2/2014 Wolpaw et al.
2014/0039577 A1 2/2014 Kothandaraman et al.
2014/0039578 A1 2/2014 Whitehurst et al.
2014/0039975 A1 2/2014 Hill
2014/0046203 A1 2/2014 Osorio et al.
2014/0046208 A1 2/2014 Sejdic et al.
2014/0046407 A1 2/2014 Ben-Ezra et al.
2014/0051044 A1 2/2014 Badower et al.
2014/0051960 A1 2/2014 Badower et al.
2014/0051961 A1 2/2014 Badower et al.
2014/0052213 A1 2/2014 Osorio
2014/0055284 A1 2/2014 Tran et al.
2014/0056815 A1 2/2014 Peyman
2014/0057232 A1 2/2014 Wetmore et al.
2014/0058189 A1 2/2014 Stubbeman
2014/0058218 A1 2/2014 Randlov et al.
2014/0058219 A1 2/2014 Kiraly
2014/0058241 A1 2/2014 Apparies et al.
2014/0058289 A1 2/2014 Panken et al.
2014/0058292 A1 2/2014 Alford et al.
2014/0058528 A1 2/2014 Contreras-Vidal et al.
2014/0062472 A1 3/2014 Nishikawa
2014/0063054 A1 3/2014 Osterhout et al.
2014/0063055 A1 3/2014 Osterhout et al.
2014/0066739 A1 3/2014 He et al.
2014/0066763 A2 3/2014 Rothberg et al.
2014/0066796 A1 3/2014 Davis et al.
2014/0067740 A1 3/2014 Solari
2014/0070958 A1 3/2014 Foo
2014/0072127 A1 3/2014 Adachi et al.
2014/0072130 A1 3/2014 Adachi et al.
2014/0073863 A1 3/2014 Engelbrecht et al.
2014/0073864 A1 3/2014 Engelbrecht et al.
2014/0073866 A1 3/2014 Engelbrecht et al.
2014/0073870 A1 3/2014 Engelbrecht et al.
2014/0073875 A1 3/2014 Engelbrecht et al.
2014/0073876 A1 3/2014 Rodriguez-Llorente et al.
2014/0073877 A1 3/2014 Wooder
2014/0073878 A1 3/2014 Engelbrecht et al.
2014/0073898 A1 3/2014 Engelbrecht et al.
2014/0073948 A1 3/2014 Engelbrecht et al.
2014/0073949 A1 3/2014 Engelbrecht et al.
2014/0073951 A1 3/2014 Engelbrecht et al.
2014/0073953 A1 3/2014 Engelbrecht et al.
2014/0073954 A1 3/2014 Engelbrecht et al.
2014/0073955 A1 3/2014 Engelbrecht et al.
2014/0073956 A1 3/2014 Engelbrecht et al.
2014/0073960 A1 3/2014 Rodriguez-Llorente et al.
2014/0073961 A1 3/2014 Rodriguez-Llorente et al.
2014/0073963 A1 3/2014 Engelbrecht et al.
2014/0073965 A1 3/2014 Engelbrecht et al.
2014/0073966 A1 3/2014 Engelbrecht et al.
2014/0073967 A1 3/2014 Engelbrecht et al.
2014/0073968 A1 3/2014 Engelbrecht et al.
2014/0073974 A1 3/2014 Engelbrecht
2014/0073975 A1 3/2014 Engelbrecht et al.
2014/0074060 A1 3/2014 Imran
2014/0074179 A1 3/2014 Heldman et al.
2014/0074180 A1 3/2014 Heldman et al.
2014/0074188 A1 3/2014 Armstrong et al.
2014/0077612 A1 3/2014 Onuma et al.
2014/0077946 A1 3/2014 Tran
2014/0081071 A1 3/2014 Simon et al.
2014/0081114 A1 3/2014 Shachar et al.
2014/0081115 A1 3/2014 Gu
2014/0081347 A1 3/2014 Nelson et al.
2014/0081353 A1 3/2014 Cook et al.
2014/0088341 A1 3/2014 Altman et al.
2014/0088377 A1 3/2014 Manzke et al.
2014/0094710 A1 4/2014 Sarma et al.
2014/0094719 A1 4/2014 Mishelevich
2014/0094720 A1 4/2014 Tyler
2014/0098981 A1 4/2014 Lunner et al.
2014/0100467 A1 4/2014 Baker et al.
2014/0100633 A1 4/2014 Mann et al.
2014/0101084 A1 4/2014 Li et al.
2014/0104059 A1 4/2014 Tran
2014/0105436 A1 4/2014 Adachi et al.
2014/0107397 A1 4/2014 Simon et al.
2014/0107398 A1 4/2014 Simon et al.
2014/0107401 A1 4/2014 Anderson et al.
2014/0107464 A1 4/2014 Aksenova et al.
2014/0107519 A1 4/2014 Musha et al.

(56) References Cited

U.S. PATENT DOCUMENTS

2014/0107521 A1 4/2014 Galan
2014/0107525 A1 4/2014 Tass
2014/0107728 A1 4/2014 Fried et al.
2014/0107935 A1 4/2014 Taylor
2014/0111335 A1 4/2014 Kleiss et al.
2014/0113367 A1 4/2014 Deisseroth et al.
2014/0114165 A1 4/2014 Walker et al.
2014/0114205 A1 4/2014 Braun et al.
2014/0114207 A1 4/2014 Patterson
2014/0114242 A1 4/2014 Eckle
2014/0114889 A1 4/2014 Dagum
2014/0119621 A1 5/2014 Uber
2014/0121446 A1 5/2014 Phillips et al.
2014/0121476 A1 5/2014 Tran et al.
2014/0121554 A1 5/2014 Sarma et al.
2014/0121565 A1 5/2014 Kim
2014/0122379 A1 5/2014 Moffitt et al.
2014/0128762 A1 5/2014 Han et al.
2014/0128763 A1 5/2014 Fadem
2014/0128764 A1 5/2014 Gandhi
2014/0128938 A1 5/2014 Craig
2014/0133720 A1 5/2014 Lee et al.
2014/0133722 A1 5/2014 Lee et al.
2014/0135642 A1 5/2014 Ekpar
2014/0135680 A1 5/2014 Peyman
2014/0135873 A1 5/2014 An et al.
2014/0135879 A1 5/2014 Flint
2014/0135886 A1 5/2014 Cook et al.
2014/0136585 A1 5/2014 Brockway
2014/0140567 A1 5/2014 LeBoeuf et al.
2014/0142448 A1 5/2014 Bae et al.
2014/0142653 A1 5/2014 Osorio
2014/0142654 A1 5/2014 Simon et al.
2014/0142669 A1 5/2014 Cook et al.
2014/0143064 A1 5/2014 Tran
2014/0148479 A1 5/2014 Chesworth et al.
2014/0148657 A1 5/2014 Hendler et al.
2014/0148693 A1 5/2014 Taylor
2014/0148716 A1 5/2014 Hopenfeld et al.
2014/0148723 A1 5/2014 Nierenberg et al.
2014/0148726 A1 5/2014 Wagner
2014/0148872 A1 5/2014 Goldwasser et al.
2014/0151563 A1 6/2014 Rousso et al.
2014/0152673 A1 6/2014 Lynn et al.
2014/0154647 A1 6/2014 Nolen
2014/0154650 A1 6/2014 Stack
2014/0155430 A1 6/2014 Chesworth et al.
2014/0155706 A1 6/2014 Kochs et al.
2014/0155714 A1 6/2014 Gavish
2014/0155730 A1 6/2014 Bansal et al.
2014/0155740 A1 6/2014 Semenov
2014/0155770 A1 6/2014 Taylor
2014/0155772 A1 6/2014 Frei et al.
2014/0155952 A1 6/2014 Lozano et al.
2014/0156000 A1 6/2014 Campin et al.
2014/0159862 A1 6/2014 Yang et al.
2014/0161352 A1 6/2014 Buyens et al.
2014/0163328 A1 6/2014 Geva et al.
2014/0163330 A1 6/2014 Horseman
2014/0163331 A1 6/2014 Horseman
2014/0163332 A1 6/2014 Horseman
2014/0163333 A1 6/2014 Horseman
2014/0163335 A1 6/2014 Horseman
2014/0163336 A1 6/2014 Horseman
2014/0163337 A1 6/2014 Horseman
2014/0163368 A1 6/2014 Rousso et al.
2014/0163385 A1 6/2014 Kelleher et al.
2014/0163409 A1 6/2014 Arndt
2014/0163425 A1 6/2014 Tran
2014/0163627 A1 6/2014 Starr et al.
2014/0163643 A1 6/2014 Craig
2014/0163893 A1 6/2014 Harumatsu et al.
2014/0163897 A1 6/2014 Lynn et al.
2014/0171749 A1 6/2014 Chin et al.
2014/0171757 A1 6/2014 Kawato et al.
2014/0171819 A1 6/2014 Patterson
2014/0171820 A1 6/2014 Causevic
2014/0174277 A1 6/2014 Mann
2014/0175261 A1 6/2014 Addison et al.
2014/0176944 A1 6/2014 Addison et al.
2014/0179980 A1 6/2014 Phillips et al.
2014/0180088 A1 6/2014 Rothberg et al.
2014/0180092 A1 6/2014 Rothberg et al.
2014/0180093 A1 6/2014 Rothberg et al.
2014/0180094 A1 6/2014 Rothberg et al.
2014/0180095 A1 6/2014 Rothberg et al.
2014/0180096 A1 6/2014 Rothberg et al.
2014/0180097 A1 6/2014 Rothberg et al.
2014/0180099 A1 6/2014 Rothberg et al.
2014/0180100 A1 6/2014 Rothberg et al.
2014/0180112 A1 6/2014 Rothberg et al.
2014/0180113 A1 6/2014 Rothberg et al.
2014/0180145 A1 6/2014 Kanai et al.
2014/0180153 A1 6/2014 Zia et al.
2014/0180160 A1 6/2014 Brown et al.
2014/0180161 A1 6/2014 Bolger et al.
2014/0180176 A1 6/2014 Rothberg et al.
2014/0180177 A1 6/2014 Rothberg et al.
2014/0180194 A1 6/2014 Lozano
2014/0180358 A1 6/2014 Giftakis et al.
2014/0180597 A1 6/2014 Brown et al.
2014/0184550 A1 7/2014 Hennessey et al.
2014/0187901 A1 7/2014 Cui et al.
2014/0187994 A1 7/2014 Thornton
2014/0188006 A1 7/2014 Alshaer et al.
2014/0188770 A1 7/2014 Agrafioti et al.
2014/0193336 A1 7/2014 Rousso et al.
2014/0194702 A1 7/2014 Tran
2014/0194720 A1 7/2014 Hua
2014/0194726 A1 7/2014 Mishelevich et al.
2014/0194758 A1 7/2014 Korenberg
2014/0194759 A1 7/2014 Weiland et al.
2014/0194768 A1 7/2014 Nierenberg et al.
2014/0194769 A1 7/2014 Nierenberg et al.
2014/0194780 A1 7/2014 Alshaer et al.
2014/0194793 A1 7/2014 Nakata et al.
2014/0200414 A1 7/2014 Osorio
2014/0200432 A1 7/2014 Banerji et al.
2014/0200623 A1 7/2014 Lindenthaler et al.
2014/0203797 A1 7/2014 Stivoric et al.
2014/0206981 A1 7/2014 Nagasaka
2014/0207224 A1 7/2014 Simon
2014/0207432 A1 7/2014 Taylor
2014/0211593 A1 7/2014 Tyler et al.
2014/0213842 A1 7/2014 Simon et al.
2014/0213843 A1 7/2014 Pilla et al.
2014/0213844 A1 7/2014 Pilla et al.
2014/0213937 A1 7/2014 Bianchi et al.
2014/0213961 A1 7/2014 Whitehurst et al.
2014/0214135 A1 7/2014 Ben-David et al.
2014/0214330 A1 7/2014 Iyer et al.
2014/0214335 A1 7/2014 Siefert
2014/0221726 A1 8/2014 Pilla et al.
2014/0221866 A1 8/2014 Quy
2014/0222113 A1 8/2014 Gliner et al.
2014/0222406 A1 8/2014 Taylor
2014/0226131 A1 8/2014 Lopez et al.
2014/0226888 A1 8/2014 Skidmore
2014/0228620 A1 8/2014 Vasishta
2014/0228649 A1 8/2014 Rayner et al.
2014/0228651 A1 8/2014 Causevic et al.
2014/0228653 A1 8/2014 Kiraly
2014/0228702 A1 8/2014 Shahaf et al.
2014/0232516 A1 8/2014 Stivoric et al.
2014/0235826 A1 8/2014 Deisseroth et al.
2014/0235965 A1 8/2014 Tran
2014/0236039 A1 8/2014 Strokova Aksenova et al.
2014/0236077 A1 8/2014 Robertson et al.
2014/0236272 A1 8/2014 Simon et al.
2014/0236492 A1 8/2014 Taylor
2014/0237073 A1 8/2014 Schiff
2014/0243608 A1 8/2014 Hunt
2014/0243613 A1 8/2014 Osorio
2014/0243614 A1 8/2014 Rothberg et al.

(56) References Cited

U.S. PATENT DOCUMENTS

2014/0243621 A1 8/2014 Weng et al.
2014/0243628 A1 8/2014 Ochs et al.
2014/0243647 A1 8/2014 Clark et al.
2014/0243652 A1 8/2014 Pashko
2014/0243663 A1 8/2014 Taylor
2014/0243694 A1 8/2014 Baker et al.
2014/0243714 A1 8/2014 Ward et al.
2014/0243926 A1 8/2014 Carcieri
2014/0243934 A1 8/2014 Vo-Dinh et al.
2014/0245191 A1 8/2014 Serena
2014/0247970 A1 9/2014 Taylor
2014/0249360 A1 9/2014 Jaeger et al.
2014/0249396 A1 9/2014 Shacham-Diamand et al.
2014/0249429 A1 9/2014 Tran
2014/0249445 A1 9/2014 Deadwyler et al.
2014/0249447 A1 9/2014 Sereno et al.
2014/0249454 A1 9/2014 Carpentier
2014/0249608 A1 9/2014 Rogers
2014/0249791 A1 9/2014 Taylor
2014/0249792 A1 9/2014 Taylor
2014/0257047 A1 9/2014 Sillay et al.
2014/0257073 A1 9/2014 Machon et al.
2014/0257118 A1 9/2014 DiLorenzo et al.
2014/0257128 A1 9/2014 Moxon et al.
2014/0257132 A1 9/2014 Kilgard et al.
2014/0257147 A1 9/2014 John et al.
2014/0257430 A1 9/2014 Kilgard et al.
2014/0257437 A1 9/2014 Simon et al.
2014/0257438 A1 9/2014 Simon et al.
2014/0266696 A1 9/2014 Addison et al.
2014/0266787 A1 9/2014 Tran
2014/0270438 A1 9/2014 Declerck et al.
2014/0271483 A1 9/2014 Satchi-Fainaro et al.
2014/0275716 A1 9/2014 Connor
2014/0275741 A1 9/2014 Vandenbelt et al.
2014/0275807 A1 9/2014 Redei
2014/0275847 A1 9/2014 Perryman et al.
2014/0275851 A1 9/2014 Amble et al.
2014/0275886 A1 9/2014 Teixeira
2014/0275889 A1 9/2014 Addison et al.
2014/0275891 A1 9/2014 Muehlemann et al.
2014/0275944 A1 9/2014 Semenov
2014/0276012 A1 9/2014 Semenov
2014/0276013 A1 9/2014 Muehlemann et al.
2014/0276014 A1 9/2014 Khanicheh et al.
2014/0276090 A1 9/2014 Breed
2014/0276123 A1 9/2014 Yang
2014/0276130 A1 9/2014 Mirelman et al.
2014/0276181 A1 9/2014 Sun et al.
2014/0276183 A1 9/2014 Badower
2014/0276185 A1 9/2014 Carlson et al.
2014/0276187 A1 9/2014 Iasemidis et al.
2014/0276194 A1 9/2014 Osorio
2014/0276549 A1 9/2014 Osorio
2014/0276702 A1 9/2014 McKay et al.
2014/0276944 A1 9/2014 Farritor et al.
2014/0277255 A1 9/2014 Sabesan
2014/0277256 A1 9/2014 Osorio
2014/0277282 A1 9/2014 Jaax
2014/0277286 A1 9/2014 Cinbis
2014/0277582 A1 9/2014 Leuthardt et al.
2014/0279341 A1 9/2014 Bhardwaj et al.
2014/0279746 A1 9/2014 De Bruin et al.
2014/0288381 A1 9/2014 Faarbaek et al.
2014/0288614 A1 9/2014 Hagedorn et al.
2014/0288620 A1 9/2014 DiLorenzo
2014/0288953 A1 9/2014 Lynn et al.
2014/0289172 A1 9/2014 Rothman et al.
2014/0296646 A1 10/2014 Wingeier et al.
2014/0296655 A1 10/2014 Akhbardeh et al.
2014/0296724 A1 10/2014 Guttag et al.
2014/0296733 A1 10/2014 Omurtag et al.
2014/0296750 A1 10/2014 Einav et al.
2014/0297397 A1 10/2014 Bakalash et al.
2014/0300532 A1 10/2014 Karkkainen et al.
2014/0303424 A1 10/2014 Glass
2014/0303425 A1 10/2014 Pilla et al.
2014/0303452 A1 10/2014 Ghaffari
2014/0303453 A1 10/2014 Seely et al.
2014/0303454 A1 10/2014 Clifton et al.
2014/0303486 A1 10/2014 Baumgartner et al.
2014/0303508 A1 10/2014 Plotnik-Peleg et al.
2014/0303511 A1 10/2014 Sajda et al.
2014/0304773 A1 10/2014 Woods et al.
2014/0309484 A1 10/2014 Chang
2014/0309614 A1 10/2014 Frei et al.
2014/0309881 A1 10/2014 Fung et al.
2014/0309943 A1 10/2014 Grundlehner et al.
2014/0313303 A1 10/2014 Davis et al.
2014/0315169 A1 10/2014 Bohbot
2014/0316191 A1 10/2014 de Zambotti et al.
2014/0316192 A1 10/2014 de Zambotti et al.
2014/0316217 A1 10/2014 Purdon et al.
2014/0316221 A1 10/2014 Rothman
2014/0316230 A1 10/2014 Denison et al.
2014/0316235 A1 10/2014 Davis et al.
2014/0316243 A1 10/2014 Niedermeyer
2014/0316248 A1 10/2014 deCharms
2014/0316278 A1 10/2014 Addison et al.
2014/0323849 A1 10/2014 Deisseroth et al.
2014/0323899 A1 10/2014 Silberstein
2014/0323900 A1 10/2014 Bibian et al.
2014/0323924 A1 10/2014 Mishelevich
2014/0323946 A1 10/2014 Bourke, Jr. et al.
2014/0324118 A1 10/2014 Simon et al.
2014/0324138 A1 10/2014 Wentz et al.
2014/0328487 A1 11/2014 Hiroe
2014/0330093 A1 11/2014 Pedro
2014/0330102 A1 11/2014 Zbrzeski et al.
2014/0330157 A1 11/2014 Snook
2014/0330159 A1 11/2014 Costa et al.
2014/0330268 A1 11/2014 Palti et al.
2014/0330334 A1 11/2014 Errico et al.
2014/0330335 A1 11/2014 Errico et al.
2014/0330336 A1 11/2014 Errico et al.
2014/0330337 A1 11/2014 Linke et al.
2014/0330345 A1 11/2014 John
2014/0330357 A1 11/2014 Stevenson et al.
2014/0330394 A1 11/2014 Leuthardt et al.
2014/0330404 A1 11/2014 Abdelghani et al.
2014/0330580 A1 11/2014 Grima et al.
2014/0335489 A1 11/2014 DeCharms
2014/0336473 A1 11/2014 Greco
2014/0336489 A1 11/2014 Angotzi et al.
2014/0336514 A1 11/2014 Peyman
2014/0336547 A1 11/2014 Tass et al.
2014/0336730 A1 11/2014 Simon et al.
2014/0340084 A1 11/2014 Alon
2014/0343354 A1* 11/2014 Larson ................ A61B 5/4812 600/28
2014/0343397 A1 11/2014 Kim et al.
2014/0343399 A1 11/2014 Posse
2014/0343408 A1 11/2014 Tolkowsky
2014/0343463 A1 11/2014 Mishelevich
2014/0343882 A1 11/2014 Taulu et al.
2014/0347265 A1 11/2014 Aimone et al.
2014/0347491 A1 11/2014 Connor
2014/0348183 A1 11/2014 Kim et al.
2014/0348412 A1 11/2014 Taylor
2014/0350353 A1 11/2014 Connor
2014/0350369 A1 11/2014 Budiman et al.
2014/0350380 A1 11/2014 Eidelberg
2014/0350431 A1 11/2014 Hagedorn
2014/0350436 A1 11/2014 Nathan et al.
2014/0350634 A1 11/2014 Grill et al.
2014/0350636 A1 11/2014 King et al.
2014/0350864 A1 11/2014 Fang et al.
2014/0354278 A1 12/2014 Subbarao
2014/0355859 A1 12/2014 Taylor et al.
2014/0357507 A1 12/2014 Umansky et al.
2014/0357932 A1 12/2014 Lozano
2014/0357935 A1 12/2014 Ilmoniemi et al.
2014/0357936 A1 12/2014 Simon et al.
2014/0357962 A1 12/2014 Harrington et al.

(56) References Cited

U.S. PATENT DOCUMENTS

2014/0358024 A1 12/2014 Nelson et al.
2014/0358025 A1 12/2014 Parhi et al.
2014/0358067 A1 12/2014 Deisseroth et al.
2014/0358193 A1 12/2014 Lyons et al.
2014/0358199 A1 12/2014 Lim
2014/0364721 A1 12/2014 Lee et al.
2014/0364746 A1 12/2014 Addison et al.
2014/0369537 A1 12/2014 Pontoppidan et al.
2014/0370479 A1 12/2014 Gazzaley
2014/0371515 A1 12/2014 John
2014/0371516 A1 12/2014 Tsai et al.
2014/0371544 A1 12/2014 Wu et al.
2014/0371573 A1 12/2014 Komoto et al.
2014/0371599 A1 12/2014 Wu et al.
2014/0371611 A1 12/2014 Kim
2014/0371984 A1 12/2014 Fung et al.
2014/0378809 A1 12/2014 Weitnauer et al.
2014/0378810 A1 12/2014 Davis et al.
2014/0378815 A1 12/2014 Huang et al.
2014/0378830 A1 12/2014 Li
2014/0378851 A1 12/2014 Frei et al.
2014/0378941 A1 12/2014 Su et al.
2014/0379620 A1 12/2014 Sarrafzadeh et al.
2015/0002815 A1 1/2015 Gross et al.
2015/0003698 A1 1/2015 Davis et al.
2015/0003699 A1 1/2015 Davis et al.
2015/0005592 A1 1/2015 Osorio
2015/0005594 A1 1/2015 Chamoun et al.
2015/0005640 A1 1/2015 Davis et al.
2015/0005644 A1 1/2015 Rhoads
2015/0005646 A1 1/2015 Balakrishnan et al.
2015/0005660 A1 1/2015 Kraus et al.
2015/0005680 A1 1/2015 Lipani
2015/0005839 A1 1/2015 Sabesan et al.
2015/0005840 A1 1/2015 Pal et al.
2015/0005841 A1 1/2015 Pal et al.
2015/0006186 A1 1/2015 Davis et al.
2015/0008916 A1 1/2015 Le Prado et al.
2015/0010223 A1 1/2015 Sapiro et al.
2015/0011866 A1 1/2015 Baumgartner
2015/0011877 A1 1/2015 Baumgartner
2015/0011907 A1 1/2015 Purdon et al.
2015/0012054 A1 1/2015 Kilgard et al.
2015/0012057 A1 1/2015 Carlson et al.
2015/0012111 A1 1/2015 Contreras-Vidal et al.
2015/0012466 A1 1/2015 Sapiro et al.
2015/0016618 A1 1/2015 Adachi et al.
2015/0017115 A1 1/2015 Satchi-Fainaro et al.
2015/0018665 A1 1/2015 Jasanoff et al.
2015/0018699 A1 1/2015 Zeng et al.
2015/0018702 A1 1/2015 Galloway et al.
2015/0018705 A1 1/2015 Barlow et al.
2015/0018706 A1 1/2015 Segal
2015/0018758 A1 1/2015 John
2015/0018893 A1 1/2015 Kilgard et al.
2015/0018905 A1 1/2015 Nofzinger et al.
2015/0019241 A1 1/2015 Bennett et al.
2015/0019266 A1 1/2015 Stempora
2015/0024356 A1 1/2015 Hillyer et al.
2015/0025351 A1 1/2015 Govari
2015/0025408 A1 1/2015 Wingeier et al.
2015/0025410 A1 1/2015 Wolpaw et al.
2015/0025421 A1 1/2015 Wagner et al.
2015/0025422 A1 1/2015 Tyler
2015/0025610 A1 1/2015 Wingeier et al.
2015/0025917 A1 1/2015 Stempora
2015/0026446 A1 1/2015 Kim et al.
2015/0029087 A1 1/2015 Klappert et al.
2015/0030220 A1 1/2015 Cho et al.
2015/0032017 A1 1/2015 Babaeizadeh et al.
2015/0032044 A9 1/2015 Peyman
2015/0032178 A1 1/2015 Simon et al.
2015/0033245 A1 1/2015 Klappert et al.
2015/0033258 A1 1/2015 Klappert et al.
2015/0033259 A1 1/2015 Klappert et al.
2015/0033262 A1 1/2015 Klappert et al.
2015/0033266 A1 1/2015 Klappert et al.
2015/0033363 A1 1/2015 Pinsky et al.
2015/0035959 A1 2/2015 Amble et al.
2015/0038804 A1 2/2015 Younes
2015/0038812 A1 2/2015 Ayaz et al.
2015/0038822 A1 2/2015 Wingeier et al.
2015/0038869 A1 2/2015 Simon et al.
2015/0039066 A1 2/2015 Wingeier et al.
2015/0039110 A1 2/2015 Abeyratne et al.
2015/0042477 A1 2/2015 Kobetski et al.
2015/0044138 A1 2/2015 Lansbergen et al.
2015/0045606 A1 2/2015 Hagedorn et al.
2015/0045607 A1 2/2015 Hakansson
2015/0045686 A1 2/2015 Lynn
2015/0051655 A1 2/2015 Kilgard et al.
2015/0051656 A1 2/2015 Kilgard et al.
2015/0051657 A1 2/2015 Kilgard et al.
2015/0051658 A1 2/2015 Kilgard et al.
2015/0051659 A1 2/2015 Kilgard et al.
2015/0051663 A1 2/2015 Hagedorn
2015/0051668 A1 2/2015 Bahmer
2015/0057512 A1 2/2015 Kapoor
2015/0057715 A1 2/2015 Kilgard et al.
2015/0065803 A1 3/2015 Douglas et al.
2015/0065831 A1 3/2015 Popovic et al.
2015/0065838 A1 3/2015 Wingeier et al.
2015/0065839 A1 3/2015 Farah et al.
2015/0065845 A1 3/2015 Takiguchi
2015/0066124 A1 3/2015 Stevenson et al.
2015/0068069 A1 3/2015 Tran et al.
2015/0069846 A1 3/2015 Hokari
2015/0071907 A1 3/2015 Crombez et al.
2015/0072394 A1 3/2015 Deisseroth et al.
2015/0073141 A1 3/2015 Teegarden et al.
2015/0073237 A1 3/2015 Osorio
2015/0073249 A1 3/2015 Musha
2015/0073294 A1 3/2015 Zhang et al.
2015/0073306 A1 3/2015 Abeyratne et al.
2015/0073505 A1 3/2015 Errico et al.
2015/0073722 A1 3/2015 Taylor et al.
2015/0080327 A1 3/2015 Paul et al.
2015/0080671 A1 3/2015 Christensen et al.
2015/0080674 A1 3/2015 Drew et al.
2015/0080695 A1 3/2015 Rogers et al.
2015/0080703 A1 3/2015 Reiman
2015/0080746 A1 3/2015 Bleich et al.
2015/0080753 A1 3/2015 Miyazaki et al.
2015/0080985 A1 3/2015 Yun et al.
2015/0081226 A1 3/2015 Baki
2015/0081299 A1 3/2015 Jasinschi et al.
2015/0087931 A1 3/2015 Banerjee et al.
2015/0088015 A1 3/2015 Taylor
2015/0088024 A1 3/2015 Sackellares et al.
2015/0088093 A1 3/2015 Goetz
2015/0088120 A1 3/2015 Garcia et al.
2015/0088224 A1 3/2015 Goldwasser et al.
2015/0088228 A1 3/2015 Moffitt
2015/0088478 A1 3/2015 Taylor
2015/0091730 A1 4/2015 Kangas et al.
2015/0091791 A1 4/2015 Segal
2015/0092949 A1 4/2015 Adachi et al.
2015/0093729 A1 4/2015 Plans et al.
2015/0094962 A1 4/2015 Hoegh et al.
2015/0096564 A1 4/2015 Cosnek
2015/0099941 A1 4/2015 Tran
2015/0099946 A1 4/2015 Sahin
2015/0099959 A1 4/2015 Bonmassar et al.
2015/0099962 A1 4/2015 Weiss et al.
2015/0103360 A1 4/2015 Addison et al.
2015/0105631 A1 4/2015 Tran et al.
2015/0105641 A1 4/2015 Austin et al.
2015/0105701 A1 4/2015 Mayer et al.
2015/0105837 A1 4/2015 Aguilar Domingo
2015/0105844 A1 4/2015 Tass et al.
2015/0112222 A1 4/2015 Sun et al.
2015/0112403 A1 4/2015 Ruffini et al.
2015/0112409 A1 4/2015 Hagedorn
2015/0112899 A1 4/2015 Dagum

(56) References Cited

U.S. PATENT DOCUMENTS

2015/0119652 A1 4/2015 Hyde et al.
2015/0119658 A1 4/2015 Osorio
2015/0119689 A1 4/2015 Pascual-Leone et al.
2015/0119698 A1 4/2015 Eyal et al.
2015/0119743 A1 4/2015 Maksym et al.
2015/0119745 A1 4/2015 Similowski et al.
2015/0119746 A1 4/2015 Conradsen
2015/0119794 A1 4/2015 Peyman
2015/0119898 A1 4/2015 Desalles et al.
2015/0119956 A1 4/2015 Libbus et al.
2015/0120007 A1 4/2015 Guez et al.
2015/0123653 A1 5/2015 Nagasaka
2015/0124220 A1 5/2015 Gross et al.
2015/0126821 A1 5/2015 Kempfner et al.
2015/0126845 A1 5/2015 Jin et al.
2015/0126848 A1 5/2015 Baker et al.
2015/0126873 A1 5/2015 Connor
2015/0133716 A1 5/2015 Suhami et al.
2015/0133811 A1 5/2015 Suzuki et al.
2015/0133812 A1 5/2015 deCharms
2015/0133830 A1 5/2015 Dirks et al.
2015/0134031 A1 5/2015 Moffitt et al.
2015/0134264 A1 5/2015 Tansey
2015/0137817 A1 5/2015 Wilson et al.
2015/0137988 A1 5/2015 Gravenstein et al.
2015/0140528 A1 5/2015 Sikstrom et al.
2015/0141529 A1 5/2015 Hargrove
2015/0141773 A1 5/2015 Einav et al.
2015/0141789 A1 5/2015 Knight et al.
2015/0141794 A1 5/2015 Foo
2015/0142082 A1 5/2015 Simon et al.
2015/0145519 A1 5/2015 Lee et al.
2015/0145676 A1 5/2015 Adhikari et al.
2015/0148617 A1 5/2015 Friedman
2015/0148619 A1 5/2015 Berg et al.
2015/0148700 A1 5/2015 Mhuircheartaigh et al.
2015/0148878 A1 5/2015 Yoo et al.
2015/0150122 A1 5/2015 Son et al.
2015/0150473 A1 6/2015 Knight et al.
2015/0150475 A1 6/2015 Varcoe
2015/0150530 A1 6/2015 Taylor et al.
2015/0150753 A1 6/2015 Racette
2015/0151142 A1 6/2015 Tyler et al.
2015/0153477 A1 6/2015 Wikelski et al.
2015/0154721 A1 6/2015 Thompson
2015/0154764 A1 6/2015 Xie et al.
2015/0154889 A1 6/2015 Tuchschmid et al.
2015/0157235 A1 6/2015 Jelen et al.
2015/0157266 A1 6/2015 Machon et al.
2015/0157271 A1 6/2015 Zhang
2015/0157859 A1 6/2015 Besio
2015/0161326 A1 6/2015 Taylor et al.
2015/0161348 A1 6/2015 Taylor et al.
2015/0161738 A1 6/2015 Stempora
2015/0164349 A1 6/2015 Gopalakrishnan et al.
2015/0164362 A1 6/2015 Morrow
2015/0164375 A1 6/2015 Schindhelm et al.
2015/0164404 A1 6/2015 Euliano et al.
2015/0164431 A1 6/2015 Terry et al.
2015/0165226 A1 6/2015 Simon et al.
2015/0165239 A1 6/2015 Mishelevich
2015/0167459 A1 6/2015 Sen et al.
2015/0174362 A1 6/2015 Panova et al.
2015/0174398 A1 6/2015 Chow et al.
2015/0174403 A1 6/2015 Pal et al.
2015/0174405 A1 6/2015 Kilgard et al.
2015/0174406 A1 6/2015 Lamensdorf et al.
2015/0174407 A1 6/2015 Osorio
2015/0174418 A1 6/2015 Tyler et al.
2015/0177413 A1 6/2015 Wilt et al.
2015/0178631 A1 6/2015 Thomas et al.
2015/0178978 A1 6/2015 Durand et al.
2015/0181840 A1 7/2015 Tupin, Jr. et al.
2015/0182417 A1 7/2015 Nagatani
2015/0182753 A1 7/2015 Harris et al.
2015/0182756 A1 7/2015 Peyman
2015/0186923 A1 7/2015 Gurumoorthy et al.
2015/0190062 A1 7/2015 Han et al.
2015/0190070 A1 7/2015 Bonmassar et al.
2015/0190077 A1 7/2015 Kim et al.
2015/0190085 A1 7/2015 Nathan et al.
2015/0190094 A1 7/2015 Lee et al.
2015/0190636 A1 7/2015 Simon et al.
2015/0190637 A1 7/2015 Simon et al.
2015/0192532 A1 7/2015 Clevenson et al.
2015/0192776 A1 7/2015 Lee et al.
2015/0196213 A1 7/2015 Pandia et al.
2015/0196246 A1 7/2015 Osorio
2015/0196249 A1 7/2015 Brown et al.
2015/0196800 A1 7/2015 Macri et al.
2015/0199010 A1 7/2015 Coleman et al.
2015/0199121 A1 7/2015 Gulaka et al.
2015/0200046 A1 7/2015 Park et al.
2015/0201849 A1 7/2015 Taylor
2015/0201879 A1 7/2015 Hargrove
2015/0202330 A1 7/2015 Yang et al.
2015/0202428 A1 7/2015 Miller
2015/0202447 A1 7/2015 Afshar et al.
2015/0203822 A1 7/2015 Tremolada et al.
2015/0206051 A1 7/2015 McIntosh et al.
2015/0206174 A1 7/2015 Barnett et al.
2015/0208940 A1 7/2015 Addison et al.
2015/0208975 A1 7/2015 Ghajar
2015/0208978 A1 7/2015 Osorio et al.
2015/0208982 A1 7/2015 Ho et al.
2015/0208994 A1 7/2015 Rapoport
2015/0212168 A1 7/2015 Shah et al.
2015/0213012 A1 7/2015 Marvit et al.
2015/0213019 A1 7/2015 Marvit et al.
2015/0213020 A1 7/2015 Marvit et al.
2015/0213191 A1 7/2015 Abdelghani et al.
2015/0215412 A1 7/2015 Marvit et al.
2015/0216436 A1 8/2015 Bosl et al.
2015/0216439 A1 8/2015 Muraskin et al.
2015/0216468 A1 8/2015 Vidal-Naquet et al.
2015/0216469 A1 8/2015 DiLorenzo et al.
2015/0216762 A1 8/2015 Oohashi et al.
2015/0217082 A1 8/2015 Kang et al.
2015/0219729 A1 8/2015 Takahashi
2015/0219732 A1 8/2015 Diamond et al.
2015/0220486 A1 8/2015 Karakonstantis et al.
2015/0220830 A1 8/2015 Li et al.
2015/0223721 A1 8/2015 De Ridder
2015/0223731 A1 8/2015 Sahin
2015/0223743 A1 8/2015 Pathangay et al.
2015/0223905 A1 8/2015 Karmarkar et al.
2015/0226813 A1 8/2015 Yu et al.
2015/0227702 A1 8/2015 Krishna et al.
2015/0227793 A1 8/2015 Ernst et al.
2015/0230719 A1 8/2015 Berg et al.
2015/0230744 A1 8/2015 Faubert et al.
2015/0230750 A1 8/2015 McDarby et al.
2015/0231330 A1 8/2015 Lozano et al.
2015/0231395 A1 8/2015 Saab
2015/0231397 A1 8/2015 Nudo, Jr. et al.
2015/0231405 A1 8/2015 Okada
2015/0231408 A1 8/2015 Williams et al.
2015/0234477 A1 8/2015 Abovitz et al.
2015/0235088 A1 8/2015 Abovitz et al.
2015/0235370 A1 8/2015 Abovitz et al.
2015/0235441 A1 8/2015 Abovitz et al.
2015/0235447 A1 8/2015 Abovitz et al.
2015/0238104 A1 8/2015 Tass
2015/0238106 A1 8/2015 Lappalainen et al.
2015/0238112 A1 8/2015 Park et al.
2015/0238137 A1 8/2015 Eyal et al.
2015/0238693 A1 8/2015 Skelton et al.
2015/0238761 A1 8/2015 Sabesan
2015/0238765 A1 8/2015 Zhu
2015/0241705 A1 8/2015 Abovitz et al.
2015/0241916 A1 8/2015 Choi et al.
2015/0241959 A1 8/2015 Abovitz et al.
2015/0242575 A1 8/2015 Abovitz et al.
2015/0242608 A1 8/2015 Kim et al.

(56) References Cited

U.S. PATENT DOCUMENTS

2015/0242943 A1 8/2015 Abovitz et al.
2015/0243100 A1 8/2015 Abovitz et al.
2015/0243105 A1 8/2015 Abovitz et al.
2015/0243106 A1 8/2015 Abovitz et al.
2015/0245781 A1 9/2015 Hua
2015/0245800 A1 9/2015 Sorensen et al.
2015/0246238 A1 9/2015 Moses et al.
2015/0247723 A1 9/2015 Abovitz et al.
2015/0247921 A1 9/2015 Rothberg et al.
2015/0247975 A1 9/2015 Abovitz et al.
2015/0247976 A1 9/2015 Abovitz et al.
2015/0248167 A1 9/2015 Turbell et al.
2015/0248169 A1 9/2015 Abovitz et al.
2015/0248170 A1 9/2015 Abovitz et al.
2015/0248470 A1 9/2015 Coleman et al.
2015/0248615 A1 9/2015 Parra et al.
2015/0248764 A1 9/2015 Keskin et al.
2015/0248765 A1 9/2015 Criminisi et al.
2015/0248787 A1 9/2015 Abovitz et al.
2015/0248788 A1 9/2015 Abovitz et al.
2015/0248789 A1 9/2015 Abovitz et al.
2015/0248791 A1 9/2015 Abovitz et al.
2015/0248792 A1 9/2015 Abovitz et al.
2015/0248793 A1 9/2015 Abovitz et al.
2015/0250393 A1 9/2015 Tran
2015/0250401 A1 9/2015 Tveit
2015/0250415 A1 9/2015 Leininger et al.
2015/0251016 A1 9/2015 Vo-Dinh et al.
2015/0253391 A1 9/2015 Toda et al.
2015/0253410 A1 9/2015 Warfield et al.
2015/0254413 A1 9/2015 Soederstroem
2015/0257645 A1 9/2015 Bae et al.
2015/0257648 A1 9/2015 Semenov
2015/0257649 A1 9/2015 Semenov
2015/0257673 A1 9/2015 Lawrence et al.
2015/0257674 A1 9/2015 Jordan et al.
2015/0257700 A1 9/2015 Fu
2015/0257712 A1 9/2015 Sarrafzadeh et al.
2015/0262016 A1 9/2015 Rothblatt
2015/0264492 A1 9/2015 Laudanski et al.
2015/0265164 A1 9/2015 Gopalakrishnan et al.
2015/0265207 A1 9/2015 Wu et al.
2015/0265583 A1 9/2015 Chesworth et al.
2015/0265830 A1 9/2015 Simon et al.
2015/0265836 A1 9/2015 Simon et al.
2015/0269825 A1 9/2015 Tran
2015/0272448 A1 10/2015 Fonte et al.
2015/0272461 A1 10/2015 Morimoto et al.
2015/0272465 A1 10/2015 Ishii
2015/0272496 A1 10/2015 Klappert et al.
2015/0272510 A1 10/2015 Chin
2015/0272652 A1 10/2015 Ghaffari et al.
2015/0273211 A1 10/2015 Ollivier
2015/0273223 A1 10/2015 John
2015/0282705 A1 10/2015 Avital
2015/0282730 A1 10/2015 Knight et al.
2015/0282749 A1 10/2015 Zand et al.
2015/0282755 A1 10/2015 Deriche et al.
2015/0282760 A1 10/2015 Badower et al.
2015/0283019 A1 10/2015 Feingold
2015/0283265 A1 10/2015 Peyman
2015/0283379 A1 10/2015 Venkatesan
2015/0283393 A1 10/2015 Schmidt
2015/0287223 A1 10/2015 Bresler et al.
2015/0289217 A1 10/2015 Ban et al.
2015/0289779 A1 10/2015 Fischl et al.
2015/0289813 A1 10/2015 Lipov
2015/0289929 A1 10/2015 Toth et al.
2015/0290419 A1 10/2015 Kare et al.
2015/0290420 A1 10/2015 Nofzinger
2015/0290453 A1 10/2015 Tyler et al.
2015/0290454 A1 10/2015 Tyler et al.
2015/0293004 A1 10/2015 Adolphi et al.
2015/0294067 A1 10/2015 Kare et al.
2015/0294074 A1 10/2015 Kawato et al.
2015/0294085 A1 10/2015 Kare et al.
2015/0294086 A1 10/2015 Kare et al.
2015/0294445 A1 10/2015 Sakaue
2015/0296288 A1 10/2015 Anastas
2015/0297106 A1 10/2015 Pasley et al.
2015/0297108 A1 10/2015 Chase et al.
2015/0297109 A1 10/2015 Garten et al.
2015/0297139 A1 10/2015 Toth
2015/0297141 A1 10/2015 Siegel et al.
2015/0297444 A1 10/2015 Tass
2015/0297719 A1 10/2015 Deisseroth et al.
2015/0297889 A1 10/2015 Simon et al.
2015/0297893 A1 10/2015 Kokones et al.
2015/0301218 A1 10/2015 Donderici
2015/0304048 A1 10/2015 Kim et al.
2015/0304101 A1 10/2015 Gupta et al.
2015/0305685 A1 10/2015 Shahaf et al.
2015/0305686 A1 10/2015 Coleman et al.
2015/0305689 A1 10/2015 Gourmelon et al.
2015/0305799 A1 10/2015 Trieu
2015/0305800 A1 10/2015 Trieu
2015/0305801 A1 10/2015 Trieu
2015/0306057 A1 10/2015 Goodenowe
2015/0306340 A1 10/2015 Giap et al.
2015/0306390 A1 10/2015 Zalay et al.
2015/0306391 A1 10/2015 Wu et al.
2015/0306392 A1 10/2015 Sabesan
2015/0309563 A1 10/2015 Connor
2015/0309582 A1 10/2015 Gupta
2015/0310862 A1 10/2015 Dauphin et al.
2015/0313496 A1 11/2015 Connor
2015/0313498 A1 11/2015 Coleman et al.
2015/0313535 A1 11/2015 Alshaer et al.
2015/0313539 A1 11/2015 Connor
2015/0313540 A1 11/2015 Deuchar et al.
2015/0313949 A1 11/2015 Cutillo
2015/0313971 A1 11/2015 Haslett et al.
2015/0315554 A1 11/2015 Shekdar et al.
2015/0317447 A1 11/2015 Helleputte et al.
2015/0317796 A1 11/2015 Schett et al.
2015/0320591 A1 11/2015 Smith et al.
2015/0321000 A1 11/2015 Rosenbluth et al.
2015/0324544 A1 11/2015 Maslowski et al.
2015/0324545 A1 11/2015 Fonte
2015/0324692 A1 11/2015 Ritchey et al.
2015/0325151 A1 11/2015 Tuchschmid et al.
2015/0327813 A1 11/2015 Fu
2015/0327837 A1 11/2015 Qi et al.
2015/0328330 A1 11/2015 Satchi-Fainaro et al.
2015/0328455 A1 11/2015 Meadows et al.
2015/0331929 A1 11/2015 El-Saban et al.
2015/0332015 A1 11/2015 Taylor
2015/0335281 A1 11/2015 Scroggins
2015/0335288 A1 11/2015 Toth et al.
2015/0335292 A1 11/2015 Mittal
2015/0335294 A1 11/2015 Witcher et al.
2015/0335295 A1 11/2015 Park et al.
2015/0335303 A1 11/2015 Chandelier et al.
2015/0335876 A1 11/2015 Jeffery et al.
2015/0335877 A1 11/2015 Jeffery et al.
2015/0338915 A1 11/2015 Publicover et al.
2015/0339363 A1 11/2015 Moldoveanu et al.
2015/0339459 A1 11/2015 Taylor
2015/0342472 A1 12/2015 Semenov
2015/0342478 A1 12/2015 Galen et al.
2015/0342493 A1 12/2015 Hardt
2015/0343215 A1 12/2015 De Ridder
2015/0343222 A1 12/2015 Kilgard et al.
2015/0343242 A1 12/2015 Tyler et al.
2015/0351655 A1 12/2015 Coleman
2015/0351690 A1 12/2015 Toth et al.
2015/0351701 A1 12/2015 Moxon et al.
2015/0352362 A1 12/2015 Craig
2015/0352363 A1 12/2015 McIntyre et al.
2015/0359431 A1 12/2015 Bakalash et al.
2015/0359441 A1 12/2015 Giovangrandi et al.
2015/0359450 A1 12/2015 Lee et al.
2015/0359452 A1 12/2015 Giovangrandi et al.
2015/0359467 A1 12/2015 Tran

(56) References Cited

U.S. PATENT DOCUMENTS

2015/0359486 A1 12/2015 Kovacs et al.
2015/0359492 A1 12/2015 Giovangrandi et al.
2015/0360026 A1 12/2015 Wagner
2015/0360030 A1 12/2015 Cartledge et al.
2015/0360039 A1 12/2015 Lempka et al.
2015/0363941 A1 12/2015 Taylor
2015/0366482 A1 12/2015 Lee
2015/0366497 A1 12/2015 Cavuoto et al.
2015/0366503 A1 12/2015 Sjaaheim et al.
2015/0366504 A1 12/2015 Connor
2015/0366516 A1 12/2015 Dripps et al.
2015/0366518 A1 12/2015 Sampson
2015/0366656 A1 12/2015 Wortz et al.
2015/0366659 A1 12/2015 Wortz et al.
2015/0369864 A1 12/2015 Marlow et al.
2015/0370320 A1 12/2015 Connor
2015/0370325 A1 12/2015 Jarosiewicz et al.
2015/0374250 A1 12/2015 Hatano et al.
2015/0374285 A1 12/2015 Chang et al.
2015/0374292 A1 12/2015 Wyeth et al.
2015/0374300 A1 12/2015 Najarian et al.
2015/0374973 A1 12/2015 Morrell
2015/0374983 A1 12/2015 Simon et al.
2015/0374986 A1 12/2015 Bahmer
2015/0374987 A1 12/2015 Bahmer
2015/0374993 A1 12/2015 Morrell
2015/0375006 A1 12/2015 Denison et al.
2015/0379230 A1 12/2015 Taylor
2015/0379370 A1 12/2015 Clifton et al.
2015/0379878 A1 12/2015 Walter et al.
2015/0380009 A1 12/2015 Chang et al.
2016/0000348 A1 1/2016 Kitajo et al.
2016/0000354 A1 1/2016 Hagedorn et al.
2016/0000383 A1 1/2016 Lee et al.
2016/0001065 A1 1/2016 Wingeier et al.
2016/0001096 A1 1/2016 Mishelevich
2016/0001098 A1 1/2016 Wingeier et al.
2016/0002523 A1 1/2016 Huh et al.
2016/0004298 A1 1/2016 Mazed et al.
2016/0004396 A1 1/2016 Gulaka et al.
2016/0004821 A1 1/2016 Fueyo et al.
2016/0004957 A1 1/2016 Solari
2016/0005235 A1 1/2016 Fateh
2016/0005320 A1 1/2016 deCharms et al.
2016/0007899 A1 1/2016 Durkee et al.
2016/0007904 A1 1/2016 Vardy
2016/0007915 A1 1/2016 Berka et al.
2016/0007918 A1 1/2016 Badower et al.
2016/0007945 A1 1/2016 Taylor
2016/0008489 A1 1/2016 Korzus
2016/0008568 A1 1/2016 Attia et al.
2016/0008598 A1 1/2016 McLaughlin et al.
2016/0008600 A1 1/2016 Hershey et al.
2016/0008620 A1 1/2016 Stubbeman
2016/0008632 A1 1/2016 Wetmore et al.
2016/0012011 A1 1/2016 Llinas et al.
2016/0012583 A1 1/2016 Cales et al.
2016/0012749 A1 1/2016 Connor
2016/0015281 A1 1/2016 McKenna et al.
2016/0015289 A1 1/2016 Simon et al.
2016/0015307 A1 1/2016 Kothuri
2016/0015673 A1 1/2016 Goodenowe
2016/0016014 A1 1/2016 Wagner et al.
2016/0019434 A1 1/2016 Caldwell
2016/0019693 A1 1/2016 Silbersweig et al.
2016/0022141 A1 1/2016 Mittal et al.
2016/0022156 A1 1/2016 Kovacs et al.
2016/0022164 A1 1/2016 Brockway et al.
2016/0022165 A1 1/2016 Sackellares et al.
2016/0022167 A1 1/2016 Simon
2016/0022168 A1 1/2016 Luczak et al.
2016/0022206 A1 1/2016 Simon et al.
2016/0022207 A1 1/2016 Roberts et al.
2016/0022981 A1 1/2016 Wingeier et al.
2016/0023016 A1 1/2016 Bonmassar et al.
2016/0026913 A1 1/2016 Moon et al.
2016/0027178 A1 1/2016 Yu et al.
2016/0027293 A1 1/2016 Esteller et al.
2016/0027342 A1 1/2016 Ben-Haim
2016/0027423 A1 1/2016 Deuel et al.
2016/0029896 A1 2/2016 Lee et al.
2016/0029917 A1 2/2016 Baker et al.
2016/0029918 A1 2/2016 Baker et al.
2016/0029946 A1 2/2016 Simon et al.
2016/0029950 A1 2/2016 Chang et al.
2016/0029958 A1 2/2016 Le et al.
2016/0029959 A1 2/2016 Le et al.
2016/0029965 A1 2/2016 Simon
2016/0029998 A1 2/2016 Brister et al.
2016/0030666 A1 2/2016 Lozano et al.
2016/0030702 A1 2/2016 Yang
2016/0030749 A1 2/2016 Carcieri et al.
2016/0030750 A1 2/2016 Bokil et al.
2016/0030834 A1 2/2016 Brown et al.
2016/0031479 A1 2/2016 Fung et al.
2016/0035093 A1 2/2016 Kateb et al.
2016/0038037 A1 2/2016 Kovacs
2016/0038038 A1 2/2016 Kovacs
2016/0038042 A1 2/2016 Mulligan et al.
2016/0038043 A1 2/2016 Mulligan et al.
2016/0038049 A1 2/2016 Geva et al.
2016/0038069 A1 2/2016 Stack
2016/0038091 A1 2/2016 Krishnaswamy et al.
2016/0038559 A1 2/2016 Palmer et al.
2016/0038770 A1 2/2016 Tyler et al.
2016/0040514 A1 2/2016 Rahmani et al.
2016/0044841 A1 2/2016 Chamberlain
2016/0045128 A1 2/2016 Sitt et al.
2016/0045150 A1 2/2016 Leininger et al.
2016/0045162 A1 2/2016 De Graff et al.
2016/0045731 A1 2/2016 Simon et al.
2016/0045756 A1 2/2016 Phillips et al.
2016/0048659 A1 2/2016 Pereira et al.
2016/0048948 A1 2/2016 Bajic
2016/0048965 A1 2/2016 Stehle et al.
2016/0051161 A1 2/2016 Labyt et al.
2016/0051162 A1 2/2016 Durand et al.
2016/0051187 A1 2/2016 Damadian
2016/0051195 A1 2/2016 Pang et al.
2016/0051793 A1 2/2016 Gibson-Horn
2016/0051812 A1 2/2016 Montgomery, Jr. et al.
2016/0051818 A1 2/2016 Simon et al.
2016/0055236 A1 2/2016 Frank et al.
2016/0055304 A1 2/2016 Russell et al.
2016/0055415 A1 2/2016 Baxi
2016/0055842 A1 2/2016 DeFranks et al.
2016/0058301 A1 3/2016 Shusterman
2016/0058304 A1 3/2016 Emblem et al.
2016/0058322 A1 3/2016 Brister et al.
2016/0058354 A1 3/2016 Phan et al.
2016/0058359 A1 3/2016 Osorio
2016/0058366 A1 3/2016 Choi et al.
2016/0058376 A1 3/2016 Baek et al.
2016/0058392 A1 3/2016 Hasson et al.
2016/0058673 A1 3/2016 Francis
2016/0060926 A1 3/2016 Kim et al.
2016/0062459 A1 3/2016 Publicover et al.
2016/0063207 A1 3/2016 Schmidt
2016/0063883 A1 3/2016 Jeyanandarajan
2016/0065724 A1 3/2016 Lee et al.
2016/0065840 A1 3/2016 Kim et al.
2016/0066788 A1 3/2016 Tran et al.
2016/0066789 A1 3/2016 Rogers et al.
2016/0066828 A1 3/2016 Phan et al.
2016/0066838 A1 3/2016 DeCharms
2016/0067485 A1 3/2016 Lindenthaler et al.
2016/0067492 A1 3/2016 Wolpaw et al.
2016/0067494 A1 3/2016 Lipani
2016/0067496 A1 3/2016 Gliner et al.
2016/0067526 A1 3/2016 Yang
2016/0070436 A1 3/2016 Thomas et al.
2016/0073886 A1 3/2016 Connor
2016/0073916 A1 3/2016 Aksenova et al.
2016/0073947 A1 3/2016 Anderson

(56) References Cited

U.S. PATENT DOCUMENTS

2016/0073991 A1 3/2016 Taylor
2016/0074657 A1 3/2016 Kwan et al.
2016/0074660 A1 3/2016 Osorio et al.
2016/0074661 A1 3/2016 Lipani
2016/0077547 A1 3/2016 Aimone et al.
2016/0078780 A1 3/2016 Alexander et al.
2016/0081577 A1 3/2016 Sridhar et al.
2016/0081610 A1 3/2016 Osorio et al.
2016/0081613 A1 3/2016 Braun et al.
2016/0081616 A1 3/2016 Li
2016/0081625 A1 3/2016 Kim et al.
2016/0081793 A1 3/2016 Galstian et al.
2016/0082180 A1 3/2016 Toth et al.
2016/0082319 A1 3/2016 Macri et al.
2016/0084925 A1 3/2016 Le Prado et al.
2016/0085302 A1 3/2016 Publicover et al.
2016/0086622 A1 3/2016 Yamamoto
2016/0087603 A1 3/2016 Ricci et al.
2016/0089031 A1 3/2016 Hu
2016/0091448 A1 3/2016 Soleimani
2016/0095546 A1 4/2016 Sahasrabudhe et al.
2016/0095838 A1 4/2016 Satchi-Fainaro et al.
2016/0096025 A1 4/2016 Moffitt et al.
2016/0097824 A1 4/2016 Fujii et al.
2016/0100769 A1 4/2016 Kim et al.
2016/0101260 A1 4/2016 Austin et al.
2016/0102500 A1 4/2016 Donderici et al.
2016/0103487 A1 4/2016 Crawford et al.
2016/0103963 A1 4/2016 Mishra
2016/0104006 A1 4/2016 Son et al.
2016/0106331 A1 4/2016 Zorick et al.
2016/0106344 A1 4/2016 Nazari
2016/0106513 A1 4/2016 De Stavola et al.
2016/0106950 A1 4/2016 Vasapollo
2016/0106997 A1 4/2016 Arendash et al.
2016/0107309 A1 4/2016 Walsh et al.
2016/0107653 A1 4/2016 Fung et al.
2016/0109851 A1 4/2016 Tsang
2016/0109959 A1 4/2016 Heo
2016/0110517 A1 4/2016 Taylor
2016/0110866 A1 4/2016 Taylor
2016/0110867 A1 4/2016 Taylor
2016/0112022 A1 4/2016 Butts
2016/0112684 A1 4/2016 Connor
2016/0113517 A1 4/2016 Lee et al.
2016/0113528 A1 4/2016 Taylor
2016/0113539 A1 4/2016 Sinharay et al.
2016/0113545 A1 4/2016 Kim et al.
2016/0113567 A1 4/2016 Osvath et al.
2016/0113569 A1 4/2016 Zhao et al.
2016/0113587 A1 4/2016 Kothe et al.
2016/0113726 A1 4/2016 Taylor
2016/0114165 A1 4/2016 Levine et al.
2016/0116472 A1 4/2016 Ay
2016/0116553 A1 4/2016 Kim et al.
2016/0117815 A1 4/2016 Taylor
2016/0117816 A1 4/2016 Taylor
2016/0117819 A1 4/2016 Taylor
2016/0119726 A1 4/2016 Pontoppidan et al.
2016/0120048 A1 4/2016 Seo et al.
2016/0120428 A1 5/2016 Yoshida et al.
2016/0120432 A1 5/2016 Sridhar et al.
2016/0120433 A1 5/2016 Hughes et al.
2016/0120434 A1 5/2016 Park et al.
2016/0120436 A1 5/2016 Silberstein
2016/0120437 A1 5/2016 Graham et al.
2016/0120457 A1 5/2016 Wu et al.
2016/0120464 A1 5/2016 Lau et al.
2016/0120480 A1 5/2016 Turnbull et al.
2016/0121074 A1 5/2016 Ashby
2016/0121114 A1 5/2016 Simon et al.
2016/0121116 A1 5/2016 Simon et al.
2016/0125228 A1 5/2016 Son et al.
2016/0125572 A1 5/2016 Yoo et al.
2016/0128589 A1 5/2016 Tabib-Azar
2016/0128596 A1 5/2016 Morshed et al.
2016/0128597 A1 5/2016 Lin et al.
2016/0128632 A1 5/2016 Wiebe et al.
2016/0128661 A1 5/2016 Taylor
2016/0128864 A1 5/2016 Nofzinger et al.
2016/0129249 A1 5/2016 Yun et al.
2016/0131723 A1 5/2016 Nagasaka
2016/0132654 A1 5/2016 Rothman et al.
2016/0133015 A1 5/2016 Taylor
2016/0135691 A1 5/2016 Dripps et al.
2016/0135727 A1 5/2016 Osorio
2016/0135748 A1 5/2016 Lin et al.
2016/0135754 A1 5/2016 Marshall et al.
2016/0136423 A1 5/2016 Simon et al.
2016/0136427 A1 5/2016 De Ridder
2016/0136429 A1 5/2016 Massoumi et al.
2016/0136430 A1 5/2016 Moffitt et al.
2016/0136443 A1 5/2016 Grandhe et al.
2016/0139215 A1 5/2016 Fujii
2016/0140306 A1 5/2016 Hua et al.
2016/0140313 A1 5/2016 Taylor
2016/0140707 A1 5/2016 Abe et al.
2016/0140834 A1 5/2016 Tran
2016/0140975 A1 5/2016 Kamamoto et al.
2016/0143540 A1 5/2016 Gencer et al.
2016/0143541 A1 5/2016 He et al.
2016/0143554 A1 5/2016 Lim et al.
2016/0143560 A1 5/2016 Grunwald et al.
2016/0143574 A1 5/2016 Jones et al.
2016/0143582 A1 5/2016 Connor
2016/0143594 A1 5/2016 Moorman et al.
2016/0144175 A1 5/2016 Simon et al.
2016/0144186 A1 5/2016 Kaemmerer et al.
2016/0147964 A1 5/2016 Corey et al.
2016/0148077 A1 5/2016 Cox et al.
2016/0148371 A1 5/2016 Itu et al.
2016/0148372 A1 5/2016 Itu et al.
2016/0148400 A1 5/2016 Bajic
2016/0148531 A1 5/2016 Bleich et al.
2016/0150988 A1 6/2016 Prerau et al.
2016/0151014 A1 6/2016 Ujhazy et al.
2016/0151018 A1 6/2016 Machon et al.
2016/0151628 A1 6/2016 Simon et al.
2016/0152233 A1 6/2016 Fung et al.
2016/0155005 A1 6/2016 Varkuti et al.
2016/0157742 A1 6/2016 Huang et al.
2016/0157773 A1 6/2016 Baek et al.
2016/0157777 A1 6/2016 Attal et al.
2016/0157828 A1 6/2016 Sumi et al.
2016/0158553 A1 6/2016 Panken et al.
2016/0158554 A1 6/2016 Graig
2016/0162652 A1 6/2016 Siekmeier
2016/0164813 A1 6/2016 Anderson et al.
2016/0165852 A1 6/2016 Goldfain
2016/0165853 A1 6/2016 Goldfain
2016/0166169 A1 6/2016 Badower et al.
2016/0166197 A1 6/2016 Venkatraman et al.
2016/0166199 A1 6/2016 Sun et al.
2016/0166205 A1 6/2016 Ernst et al.
2016/0166207 A1 6/2016 Falconer
2016/0166208 A1 6/2016 Girouard et al.
2016/0166219 A1 6/2016 Majewski et al.
2016/0167672 A1 6/2016 Krueger
2016/0168137 A1 6/2016 Van Leyen et al.
2016/0170996 A1 6/2016 Frank et al.
2016/0170998 A1 6/2016 Frank et al.
2016/0171514 A1 6/2016 Frank et al.
2016/0174099 A1 6/2016 Goldfain
2016/0174862 A1 6/2016 Yu et al.
2016/0174863 A1 6/2016 Foerster et al.
2016/0174867 A1 6/2016 Hatano et al.
2016/0174907 A1 6/2016 Colman et al.
2016/0175557 A1 6/2016 Tass
2016/0175607 A1 6/2016 Deisseroth et al.
2016/0176053 A1 6/2016 Rognini et al.
2016/0178392 A1 6/2016 Goldfain
2016/0180042 A1 6/2016 Menon et al.
2016/0180054 A1 6/2016 Luo et al.
2016/0180055 A1 6/2016 Fonte

(56) References Cited

U.S. PATENT DOCUMENTS

2016/0183812 A1 6/2016 Zhang et al.
2016/0183828 A1 6/2016 Ouyang et al.
2016/0183861 A1 6/2016 Hayes et al.
2016/0183881 A1 6/2016 Keenan et al.
2016/0184029 A1 6/2016 Peng et al.
2016/0184596 A1 6/2016 Fried et al.
2016/0184599 A1 6/2016 Segal
2016/0187524 A1 6/2016 Suhami
2016/0191517 A1 6/2016 Bae et al.
2016/0192841 A1 7/2016 Inagaki et al.
2016/0192842 A1 7/2016 Inagaki
2016/0192847 A1 7/2016 Inagaki
2016/0192879 A1 7/2016 Yamashita
2016/0193499 A1 7/2016 Kim et al.
2016/0196185 A1 7/2016 Gu et al.
2016/0196393 A1 7/2016 Avinash et al.
2016/0196635 A1 7/2016 Cho et al.
2016/0196758 A1 7/2016 Causevic et al.
2016/0198950 A1 7/2016 Gross et al.
2016/0198963 A1 7/2016 Addison et al.
2016/0198966 A1 7/2016 Uematsu et al.
2016/0198968 A1 7/2016 Plenz et al.
2016/0198973 A1 7/2016 Fukuda et al.
2016/0199241 A1 7/2016 Rapoport
2016/0199577 A1 7/2016 Hyde et al.
2016/0199656 A1 7/2016 Phillips
2016/0199662 A1 7/2016 Wundrich et al.
2016/0202755 A1 7/2016 Connor
2016/0203597 A1 7/2016 Chang et al.
2016/0203726 A1 7/2016 Hibbs et al.
2016/0204937 A1 7/2016 Edwards et al.
2016/0205450 A1 7/2016 Gartseev et al.
2016/0205489 A1 7/2016 Jabri
2016/0206236 A1 7/2016 Dilorenzo et al.
2016/0206241 A1 7/2016 Cho et al.
2016/0206380 A1 7/2016 Sparks et al.
2016/0206581 A1 7/2016 Wittkowski
2016/0206671 A1 7/2016 Geng
2016/0206871 A1 7/2016 Weisend
2016/0206877 A1 7/2016 Hargrove
2016/0206880 A1 7/2016 Koubeissi
2016/0210872 A1 7/2016 Roberts et al.
2016/0213261 A1 7/2016 Fleischer et al.
2016/0213276 A1 7/2016 Gadot et al.
2016/0213314 A1 7/2016 Zuckerman-Stark et al.
2016/0213317 A1 7/2016 Richardson et al.
2016/0213947 A1 7/2016 Han et al.
2016/0216760 A1 7/2016 Trutna et al.
2016/0217586 A1 7/2016 Dickrell et al.
2016/0217595 A1 7/2016 Han et al.
2016/0219345 A1 7/2016 Knight et al.
2016/0220133 A1 8/2016 Inagaki
2016/0220134 A1 8/2016 Inagaki
2016/0220136 A1 8/2016 Schultz
2016/0220163 A1 8/2016 Yamada et al.
2016/0220166 A1 8/2016 Thornton
2016/0220439 A1 8/2016 Wojciechowski et al.
2016/0220821 A1 8/2016 O'Connell et al.
2016/0220836 A1 8/2016 Parks
2016/0220837 A1 8/2016 Jin
2016/0220850 A1 8/2016 Tyler
2016/0222073 A1 8/2016 Deisseroth et al.
2016/0223622 A1 8/2016 Yu et al.
2016/0223627 A1 8/2016 Shah et al.
2016/0223703 A1 8/2016 Wu et al.
2016/0224757 A1 8/2016 Melkonyan
2016/0224803 A1 8/2016 Frank et al.
2016/0228019 A1 8/2016 Grunwald et al.
2016/0228028 A1 8/2016 Van Der Kooi et al.
2016/0228029 A1 8/2016 Ware
2016/0228059 A1 8/2016 Badower
2016/0228064 A1 8/2016 Jung et al.
2016/0228204 A1 8/2016 Quaid et al.
2016/0228640 A1 8/2016 Pindado et al.
2016/0228702 A1 8/2016 Kempe et al.
2016/0228705 A1 8/2016 Crowder et al.
2016/0231401 A1 8/2016 Wang et al.
2016/0232330 A1 8/2016 Dowson
2016/0232625 A1 8/2016 Akutagawa et al.
2016/0232667 A1 8/2016 Taylor
2016/0232811 A9 8/2016 Connor
2016/0235323 A1 8/2016 Tadi et al.
2016/0235324 A1 8/2016 Mershin et al.
2016/0235341 A1 8/2016 Choi et al.
2016/0235351 A1 8/2016 Intrator
2016/0235352 A1 8/2016 DiLorenzo
2016/0235359 A1 8/2016 Cho et al.
2016/0235980 A1 8/2016 Berman et al.
2016/0235983 A1 8/2016 Berman et al.
2016/0238673 A1 8/2016 Honkura
2016/0239084 A1 8/2016 Connor
2016/0239966 A1 8/2016 Parsey et al.
2016/0239968 A1 8/2016 Parsey et al.
2016/0240212 A1 8/2016 Wilson et al.
2016/0240765 A1 8/2016 Washington et al.
2016/0242645 A1 8/2016 Muller
2016/0242659 A1 8/2016 Yamashita et al.
2016/0242665 A1 8/2016 Galloway et al.
2016/0242669 A1 8/2016 Muraskin et al.
2016/0242670 A1 8/2016 Suzuki et al.
2016/0242690 A1 8/2016 Principe et al.
2016/0242699 A1 8/2016 Das et al.
2016/0243362 A1 8/2016 Hehrmann et al.
2016/0243381 A1 8/2016 Alford et al.
2016/0245670 A1 8/2016 Nelson et al.
2016/0245766 A1 8/2016 Nelson et al.
2016/0245952 A1 8/2016 Dupuis et al.
2016/0246939 A1 8/2016 Taylor
2016/0247064 A1 8/2016 Yoo et al.
2016/0248434 A1 8/2016 Govari
2016/0248994 A1 8/2016 Liu
2016/0249826 A1 9/2016 Derchak
2016/0249841 A1 9/2016 Gerber et al.
2016/0249846 A1 9/2016 Yoo et al.
2016/0249857 A1 9/2016 Choi et al.
2016/0249864 A1 9/2016 Kang et al.
2016/0250355 A1 9/2016 Macknik
2016/0250465 A1 9/2016 Simon et al.
2016/0250473 A1 9/2016 Alberts et al.
2016/0256063 A1 9/2016 Friedman et al.
2016/0256086 A1 9/2016 Byrd et al.
2016/0256105 A1 9/2016 Boyle et al.
2016/0256108 A1 9/2016 Yun et al.
2016/0256109 A1 9/2016 Semenov
2016/0256112 A1 9/2016 Brockway et al.
2016/0256118 A1 9/2016 Iyer et al.
2016/0256130 A1 9/2016 Hamilton et al.
2016/0256690 A1 9/2016 Cecchi et al.
2016/0256691 A1 9/2016 Cecchi et al.
2016/0256693 A1 9/2016 Parramon
2016/0257957 A1 9/2016 Greenberg et al.
2016/0259085 A1 9/2016 Wilson et al.
2016/0259905 A1 9/2016 Park et al.
2016/0260216 A1 9/2016 Wu et al.
2016/0261962 A1 9/2016 Petersen et al.
2016/0262623 A1 9/2016 Semenov
2016/0262664 A1 9/2016 Linderman
2016/0262680 A1 9/2016 Martucci et al.
2016/0262685 A1 9/2016 Wagner et al.
2016/0262695 A1 9/2016 Zhang et al.
2016/0262703 A1 9/2016 Maccallum
2016/0263318 A1 9/2016 Osorio
2016/0263376 A1 9/2016 Yoo et al.
2016/0263380 A1 9/2016 Starr et al.
2016/0263393 A1 9/2016 Vo-Dinh et al.
2016/0267809 A1 9/2016 deCharms et al.
2016/0270656 A1 9/2016 Samec et al.
2016/0270723 A1 9/2016 Deisseroth et al.
2016/0274660 A1 9/2016 Publicover et al.
2016/0275536 A1 9/2016 Anderson
2016/0278651 A1 9/2016 Lu et al.
2016/0278653 A1 9/2016 Clark et al.
2016/0278662 A1 9/2016 Brister et al.
2016/0278672 A1 9/2016 Cho et al.

(56) References Cited

U.S. PATENT DOCUMENTS

2016/0278687 A1 9/2016 Xia
2016/0278697 A1 9/2016 John et al.
2016/0278713 A1 9/2016 Shoaran et al.
2016/0278736 A1 9/2016 Hamilton et al.
2016/0278870 A1 9/2016 Quaid et al.
2016/0279021 A1 9/2016 Hyde et al.
2016/0279022 A1 9/2016 Hyde et al.
2016/0279023 A1 9/2016 Hyde et al.
2016/0279024 A1 9/2016 Hyde et al.
2016/0279025 A1 9/2016 Hyde et al.
2016/0279267 A1 9/2016 Deisseroth et al.
2016/0279410 A1 9/2016 Simon et al.
2016/0279417 A1 9/2016 Kilgard et al.
2016/0279435 A1 9/2016 Hyde et al.
2016/0282113 A1 9/2016 Lee
2016/0282941 A1 9/2016 Aksenova et al.
2016/0284082 A1 9/2016 Varkuti
2016/0287117 A1 10/2016 Breakspear et al.
2016/0287118 A1 10/2016 Sarma et al.
2016/0287120 A1 10/2016 Sun et al.
2016/0287142 A1 10/2016 Han et al.
2016/0287157 A1 10/2016 Simpson
2016/0287162 A1 10/2016 Bardakjian et al.
2016/0287166 A1 10/2016 Tran
2016/0287169 A1 10/2016 Kortelainen et al.
2016/0287308 A1 10/2016 Grant et al.
2016/0287334 A1 10/2016 Grant et al.
2016/0287436 A1 10/2016 Wingeier et al.
2016/0287869 A1 10/2016 Errico et al.
2016/0287871 A1 10/2016 Bardakjian et al.
2016/0287889 A1 10/2016 Bokil et al.
2016/0287895 A1 10/2016 Deisseroth et al.
2016/0296157 A1 10/2016 Girouard
2016/0296287 A1 10/2016 Taylor
2016/0296746 A1 10/2016 Wingeier et al.
2016/0298449 A1 10/2016 Orban
2016/0299568 A1 10/2016 Segal
2016/0300252 A1 10/2016 Frank et al.
2016/0300352 A1 10/2016 Raj
2016/0302683 A1 10/2016 Lawrence et al.
2016/0302704 A9 10/2016 Lynn et al.
2016/0302709 A1 10/2016 Mossbridge
2016/0302711 A1 10/2016 Frank et al.
2016/0302720 A1 10/2016 John et al.
2016/0302737 A1 10/2016 Watson et al.
2016/0303322 A1 10/2016 John
2016/0303396 A9 10/2016 Deisseroth et al.
2016/0303397 A1 10/2016 Hirschman et al.
2016/0303402 A1 10/2016 Tyler
2016/0306844 A1 10/2016 Frank et al.
2016/0306942 A1 10/2016 Rapaka et al.
2016/0310031 A1 10/2016 Sarkar
2016/0310070 A1 10/2016 Sabesan
2016/0310071 A1 10/2016 Kim
2016/0313408 A1 10/2016 Hatano et al.
2016/0313417 A1 10/2016 Kawabata et al.
2016/0313418 A1 10/2016 Fujii et al.
2016/0313798 A1 10/2016 Connor
2016/0317056 A1 11/2016 Moon et al.
2016/0317060 A1 11/2016 Connor
2016/0317077 A1 11/2016 Sillay
2016/0317383 A1 11/2016 Stanfield et al.
2016/0317824 A1 11/2016 Moffitt et al.
2016/0320210 A1 11/2016 Nelson et al.
2016/0321742 A1 11/2016 Phillips et al.
2016/0324445 A1 11/2016 Kim et al.
2016/0324457 A1 11/2016 Dagum
2016/0324465 A1 11/2016 Osvath et al.
2016/0324478 A1 11/2016 Goldstein
2016/0324580 A1 11/2016 Esterberg
2016/0324677 A1 11/2016 Hyde et al.
2016/0324942 A1 11/2016 Lester et al.
2016/0325111 A1 11/2016 Bourke, Jr. et al.
2016/0331264 A1 11/2016 Helms-Tillery et al.
2016/0331307 A1 11/2016 Purdon et al.
2016/0331952 A1 11/2016 Faltys et al.
2016/0331970 A1 11/2016 Lozano
2016/0331974 A1 11/2016 Lyons et al.
2016/0331982 A1 11/2016 Chow et al.
2016/0334475 A1 11/2016 Ueno
2016/0334534 A1 11/2016 Mandviwala et al.
2016/0334866 A9 11/2016 Mazed et al.
2016/0338608 A1 11/2016 Nagasaka et al.
2016/0338634 A1 11/2016 Neu et al.
2016/0338644 A1 11/2016 Connor
2016/0338798 A1 11/2016 Vora et al.
2016/0338825 A1 11/2016 Wortz et al.
2016/0339237 A1 11/2016 Ahmed et al.
2016/0339238 A1 11/2016 Ahmed et al.
2016/0339239 A1 11/2016 Yoo et al.
2016/0339242 A1 11/2016 Cook et al.
2016/0339243 A1 11/2016 Wingeier et al.
2016/0339300 A1 11/2016 Todasco
2016/0341684 A1 11/2016 Choi
2016/0342241 A1 11/2016 Chung et al.
2016/0342762 A1 11/2016 Goetz
2016/0345856 A1 12/2016 Semenov
2016/0345895 A1 12/2016 Loetsch et al.
2016/0345901 A1 12/2016 Connor
2016/0345911 A1 12/2016 Leuthardt et al.
2016/0346530 A1 12/2016 Jeffery et al.
2016/0346542 A1 12/2016 Simon et al.
2016/0351069 A1 12/2016 Faubert et al.
2016/0354003 A1 12/2016 Baker et al.
2016/0354027 A1 12/2016 Benson et al.
2016/0356911 A1 12/2016 Wilson et al.
2016/0357003 A1 12/2016 Hauger et al.
2016/0357256 A1 12/2016 Siefert
2016/0360100 A1 12/2016 Kim et al.
2016/0360965 A1 12/2016 Tran
2016/0360970 A1 12/2016 Tzvieli et al.
2016/0361021 A1 12/2016 Salehizadeh et al.
2016/0361027 A1 12/2016 Jang et al.
2016/0361041 A1 12/2016 Barsimantov et al.
2016/0361532 A1 12/2016 Wingeier et al.
2016/0361534 A9 12/2016 Weisend
2016/0361540 A9 12/2016 Simon et al.
2016/0361546 A1 12/2016 Salam et al.
2016/0363483 A1 12/2016 Tzvieli et al.
2016/0364859 A1 12/2016 Taylor
2016/0364860 A1 12/2016 Taylor
2016/0364861 A1 12/2016 Taylor
2016/0366462 A1 12/2016 Klappert et al.
2016/0367138 A1 12/2016 Kim et al.
2016/0367186 A1 12/2016 Freeman et al.
2016/0367195 A1 12/2016 Park et al.
2016/0367198 A1 12/2016 Chon et al.
2016/0367204 A1 12/2016 Won et al.
2016/0367209 A1 12/2016 Odry et al.
2016/0367808 A9 12/2016 Simon et al.
2016/0367812 A1 12/2016 De Ridder
2016/0371387 A1 12/2016 Serena
2016/0371455 A1 12/2016 Taylor
2016/0371721 A1 12/2016 Bogdon et al.
2016/0374581 A1 12/2016 Jensen
2016/0374616 A1 12/2016 Mullins et al.
2016/0374618 A1 12/2016 Giovangrandi
2016/0374990 A1 12/2016 Teegarden et al.
2016/0375245 A1 12/2016 Frei et al.
2016/0375259 A1 12/2016 Davis et al.
2016/0378608 A1 12/2016 Kong et al.
2016/0378965 A1 12/2016 Choe et al.
2017/0000324 A1 1/2017 Samec et al.
2017/0000325 A1 1/2017 Samec et al.
2017/0000326 A1 1/2017 Samec et al.
2017/0000329 A1 1/2017 Samec et al.
2017/0000330 A1 1/2017 Samec et al.
2017/0000331 A1 1/2017 Samec et al.
2017/0000332 A1 1/2017 Samec et al.
2017/0000333 A1 1/2017 Samec et al.
2017/0000334 A1 1/2017 Samec et al.
2017/0000335 A1 1/2017 Samec et al.
2017/0000337 A1 1/2017 Samec et al.
2017/0000340 A1 1/2017 Samec et al.

(56) References Cited

U.S. PATENT DOCUMENTS

2017/0000341 A1 1/2017 Samec et al.
2017/0000342 A1 1/2017 Samec et al.
2017/0000343 A1 1/2017 Samec et al.
2017/0000345 A1 1/2017 Samec et al.
2017/0000404 A1 1/2017 Leininger et al.
2017/0000422 A1 1/2017 Moturu et al.
2017/0000454 A1 1/2017 Samec et al.
2017/0000683 A1 1/2017 Samec et al.
2017/0001016 A1 1/2017 De Ridder
2017/0001032 A1 1/2017 Samec et al.
2017/0006931 A1 1/2017 Guez et al.
2017/0007111 A1 1/2017 Samec et al.
2017/0007115 A1 1/2017 Samec et al.
2017/0007116 A1 1/2017 Samec et al.
2017/0007122 A1 1/2017 Samec et al.
2017/0007123 A1 1/2017 Samec et al.
2017/0007165 A1 1/2017 Jain et al.
2017/0007173 A1 1/2017 Adamczyk et al.
2017/0007182 A1 1/2017 Samec et al.
2017/0007450 A1 1/2017 Samec et al.
2017/0007799 A1 1/2017 Samec et al.
2017/0007820 A9 1/2017 Simon et al.
2017/0007828 A1 1/2017 Monteiro
2017/0007843 A1 1/2017 Samec et al.
2017/0010469 A1 1/2017 Samec et al.
2017/0010470 A1 1/2017 Samec et al.
2017/0013562 A1 1/2017 Lim et al.
2017/0014037 A1 1/2017 Coppola et al.
2017/0014080 A1 1/2017 Macia Barber et al.
2017/0014083 A1 1/2017 Diab et al.
2017/0014625 A1 1/2017 Rosenbluth et al.
2017/0014630 A1 1/2017 Fried et al.
2017/0017083 A1 1/2017 Samec et al.
2017/0020434 A1 1/2017 Walker et al.
2017/0020447 A1 1/2017 Grossman et al.
2017/0020454 A1 1/2017 Keteyian et al.
2017/0020627 A1 1/2017 Tesar et al.
2017/0021158 A1 1/2017 Wingeier et al.
2017/0021161 A1 1/2017 De Ridder
2017/0024886 A1 1/2017 Dickrell et al.
2017/0027467 A1 2/2017 Hagedorn
2017/0027517 A9 2/2017 Le et al.
2017/0027521 A1 2/2017 Geva et al.
2017/0027539 A1 2/2017 Uber
2017/0027651 A1 2/2017 Esterberg
2017/0027812 A1 2/2017 Hyde et al.
2017/0028563 A1 2/2017 Hemken
2017/0031440 A1 2/2017 Randolph
2017/0031441 A1 2/2017 Muller et al.
2017/0032098 A1 2/2017 Ghorbanian et al.
2017/0032221 A1 2/2017 Wu et al.
2017/0032524 A1 2/2017 Dickrell et al.
2017/0032527 A1 2/2017 Murthy et al.
2017/0032544 A1 2/2017 Dempsey et al.
2017/0034638 A1 2/2017 Anastas
2017/0035309 A1 2/2017 Kang et al.
2017/0035317 A1 2/2017 Jung et al.
2017/0035344 A1 2/2017 Tzvieli et al.
2017/0035392 A1 2/2017 Grunwald et al.
2017/0036024 A1 2/2017 Hershey et al.
2017/0039591 A1 2/2017 Knight et al.
2017/0039706 A1 2/2017 Mikhno et al.
2017/0041699 A1 2/2017 Mackellar et al.
2017/0042430 A1 2/2017 Kovacs
2017/0042444 A1 2/2017 Bardy et al.
2017/0042469 A1 2/2017 Prerau et al.
2017/0042474 A1 2/2017 Widge et al.
2017/0042475 A1 2/2017 Verghese et al.
2017/0042476 A1 2/2017 Reiman
2017/0042485 A1 2/2017 Chung et al.
2017/0042713 A1 2/2017 Nurmikko et al.
2017/0042827 A1 2/2017 Margel et al.
2017/0043160 A1 2/2017 Goodall et al.
2017/0043166 A1 2/2017 Choi et al.
2017/0043167 A1 2/2017 Widge et al.
2017/0043178 A1 2/2017 Vo-Dinh et al.
2017/0045601 A1 2/2017 Akhtari
2017/0046052 A1 2/2017 Lee et al.
2017/0046971 A1 2/2017 Moreno
2017/0050046 A1 2/2017 Walder et al.
2017/0052170 A1 2/2017 Shekdar et al.
2017/0053082 A1 2/2017 Pereira et al.
2017/0053088 A1 2/2017 Walker et al.
2017/0053092 A1 2/2017 Taylor
2017/0053461 A1 2/2017 Pal et al.
2017/0053513 A1 2/2017 Savolainen et al.
2017/0053665 A1 2/2017 Quatieri, Jr. et al.
2017/0055839 A1 3/2017 Levinson et al.
2017/0055898 A1 3/2017 Bandyopadhyay et al.
2017/0055900 A1 3/2017 Jain et al.
2017/0055913 A1 3/2017 Bandyopadhyay et al.
2017/0056363 A1 3/2017 Goodenowe
2017/0056467 A1 3/2017 Deisseroth et al.
2017/0056642 A1 3/2017 Moffitt et al.
2017/0056655 A1 3/2017 Lineaweaver
2017/0056663 A1 3/2017 Kaemmerer et al.
2017/0060298 A1 3/2017 Hwang et al.
2017/0061034 A1 3/2017 Ritchey et al.
2017/0061589 A1 3/2017 Kuo et al.
2017/0061760 A1 3/2017 Lee et al.
2017/0065199 A1 3/2017 Meisel
2017/0065218 A1 3/2017 Leininger et al.
2017/0065229 A1 3/2017 Howard
2017/0065349 A1 3/2017 Ourselin et al.
2017/0065379 A1 3/2017 Cowburn et al.
2017/0065638 A1 3/2017 Fraser
2017/0065816 A1 3/2017 Wingeier et al.
2017/0066806 A1 3/2017 Deisseroth et al.
2017/0067323 A1 3/2017 Katterbauer et al.
2017/0069306 A1 3/2017 Asaei et al.
2017/0071495 A1 3/2017 Denison et al.
2017/0071521 A1 3/2017 Mestha et al.
2017/0071523 A1 3/2017 Jain et al.
2017/0071529 A1 3/2017 Haugland et al.
2017/0071532 A1 3/2017 Greco
2017/0071537 A1 3/2017 Jain et al.
2017/0071546 A1 3/2017 Jain et al.
2017/0071551 A1 3/2017 Jain et al.
2017/0071552 A1 3/2017 Harpe et al.
2017/0076452 A1 3/2017 Yui et al.
2017/0079538 A1 3/2017 Liang et al.
2017/0079543 A1 3/2017 Sadeghian-Motahar
2017/0079573 A1 3/2017 Osorio
2017/0079588 A1 3/2017 Ghaffari et al.
2017/0079589 A1 3/2017 Ghaffari et al.
2017/0079596 A1 3/2017 Teixeira
2017/0080050 A1 3/2017 Deisseroth et al.
2017/0080234 A1 3/2017 Gillespie et al.
2017/0080256 A1 3/2017 Kim et al.
2017/0080320 A1 3/2017 Smith
2017/0084175 A1 3/2017 Sedlik et al.
2017/0084187 A1 3/2017 Mollicone et al.
2017/0085547 A1 3/2017 De Aguiar et al.
2017/0085855 A1 3/2017 Roberts et al.
2017/0086672 A1 3/2017 Tran
2017/0086695 A1 3/2017 Mullins et al.
2017/0086727 A1 3/2017 Dagum
2017/0086729 A1 3/2017 Bruno
2017/0086763 A1 3/2017 Verma et al.
2017/0087302 A1 3/2017 Osorio
2017/0087330 A1 3/2017 Kahn et al.
2017/0087354 A1 3/2017 Stevenson et al.
2017/0087355 A1 3/2017 Stevenson et al.
2017/0087356 A1 3/2017 Stevenson et al.
2017/0087364 A1 3/2017 Cartledge et al.
2017/0087367 A1 3/2017 Weisend
2017/0090475 A1 3/2017 Choi et al.
2017/0091418 A1 3/2017 Chen et al.
2017/0091567 A1 3/2017 Wang et al.
2017/0094385 A1 3/2017 Lee et al.
2017/0095157 A1 4/2017 Tzvieli et al.
2017/0095174 A1 4/2017 Fokas et al.
2017/0095199 A1 4/2017 Kranck
2017/0095670 A1 4/2017 Ghaffari et al.

(56) References Cited

U.S. PATENT DOCUMENTS

2017/0095676 A1 4/2017 Caparso et al.
2017/0095721 A1 4/2017 Bleich et al.
2017/0099479 A1 4/2017 Browd et al.
2017/0099713 A1 4/2017 Perez et al.
2017/0100051 A1 4/2017 Honkura
2017/0100540 A1 4/2017 Hyde et al.
2017/0100591 A1 4/2017 Nudo et al.
2017/0103440 A1 4/2017 Xing et al.
2017/0105647 A1 4/2017 Duffy
2017/0106193 A1 4/2017 Carcieri
2017/0107575 A1 4/2017 Umansky et al.
2017/0108926 A1 4/2017 Moon et al.
2017/0112379 A1 4/2017 Swiston et al.
2017/0112403 A1 4/2017 Doidge et al.
2017/0112427 A1 4/2017 Simon et al.
2017/0112446 A1 4/2017 Dagum
2017/0112577 A1 4/2017 Bonutti et al.
2017/0112671 A1 4/2017 Goldstein
2017/0112947 A1 4/2017 Abebe
2017/0113042 A1 4/2017 Goodall et al.
2017/0113046 A1 4/2017 Fried et al.
2017/0113056 A1 4/2017 Stocco et al.
2017/0113057 A1 4/2017 Goodall et al.
2017/0117866 A1 4/2017 Stevenson et al.
2017/0119270 A1 5/2017 Juan et al.
2017/0119271 A1 5/2017 Leuthardt et al.
2017/0119994 A1 5/2017 Argaman
2017/0120041 A1 5/2017 Wenger et al.
2017/0120043 A1 5/2017 John
2017/0120052 A9 5/2017 Simon et al.
2017/0120054 A1 5/2017 Moffitt et al.
2017/0120066 A1 5/2017 Phillips et al.
2017/0127727 A1 5/2017 Davidson et al.
2017/0127946 A1 5/2017 Levinson et al.
2017/0128006 A1 5/2017 Seo et al.
2017/0128015 A1 5/2017 Rogers et al.
2017/0128032 A1 5/2017 Buchert et al.
2017/0131293 A1 5/2017 Haslett et al.
2017/0132816 A1 5/2017 Aston et al.
2017/0133576 A1 5/2017 Marcus et al.
2017/0133577 A1 5/2017 Cybart et al.
2017/0135594 A1 5/2017 Hartings et al.
2017/0135597 A1 5/2017 Mann
2017/0135604 A1 5/2017 Kent et al.
2017/0135626 A1 5/2017 Singer
2017/0135629 A1 5/2017 Kent et al.
2017/0135631 A1 5/2017 Zuckerman-Stark et al.
2017/0135633 A1 5/2017 Connor
2017/0135640 A1 5/2017 Gunasekar et al.
2017/0136238 A1 5/2017 Hartig et al.
2017/0136240 A1 5/2017 Mogul
2017/0136264 A1 5/2017 Hyde et al.
2017/0136265 A1 5/2017 Hyde et al.
2017/0138132 A1 5/2017 Wilson et al.
2017/0140124 A1 5/2017 Sehgal et al.
2017/0143231 A1 5/2017 Ostberg et al.
2017/0143249 A1 5/2017 Davis et al.
2017/0143255 A1 5/2017 Babaeizadeh et al.
2017/0143257 A1 5/2017 Kent et al.
2017/0143259 A1 5/2017 Kent et al.
2017/0143266 A1 5/2017 Kovacs et al.
2017/0143267 A1 5/2017 Kovacs et al.
2017/0143268 A1 5/2017 Kovacs et al.
2017/0143273 A1 5/2017 Osorio et al.
2017/0143280 A1 5/2017 Kent et al.
2017/0143282 A1 5/2017 Kovacs et al.
2017/0143442 A1 5/2017 Tesar et al.
2017/0143550 A1 5/2017 Kilgard et al.
2017/0143960 A1 5/2017 Kent et al.
2017/0143963 A1 5/2017 Osorio
2017/0143966 A1 5/2017 Reymers et al.
2017/0143986 A1 5/2017 Deisseroth et al.
2017/0146386 A1 5/2017 Wiard et al.
2017/0146387 A1 5/2017 Wiard et al.
2017/0146390 A1 5/2017 Kovacs
2017/0146391 A1 5/2017 Kovacs et al.
2017/0146615 A1 5/2017 Wolf et al.
2017/0146801 A1 5/2017 Stempora
2017/0147578 A1 5/2017 Hecht et al.
2017/0147754 A1 5/2017 Kovacs
2017/0148213 A1 5/2017 Thomas et al.
2017/0148240 A1 5/2017 Kovacs et al.
2017/0148340 A1 5/2017 Popa-Simil et al.
2017/0148592 A1 5/2017 Tabib-Azir
2017/0149945 A1 5/2017 Lee et al.
2017/0150896 A9 6/2017 Lu et al.
2017/0150916 A1 6/2017 Osorio
2017/0150921 A1 6/2017 Yun et al.
2017/0150925 A1 6/2017 Jung
2017/0151433 A1 6/2017 Simon et al.
2017/0151435 A1 6/2017 Deadwyler et al.
2017/0151436 A1 6/2017 Flaherty et al.
2017/0154167 A1 6/2017 Ovtchinnikov
2017/0156593 A1 6/2017 Ferber et al.
2017/0156606 A1 6/2017 Ferber et al.
2017/0156622 A1 6/2017 Mahoor et al.
2017/0156655 A1 6/2017 Austin et al.
2017/0156662 A1 6/2017 Goodall et al.
2017/0156674 A1 6/2017 Hochman
2017/0157343 A1 6/2017 Davidson et al.
2017/0157402 A1 6/2017 Osorio
2017/0157410 A1 6/2017 Moffitt et al.
2017/0160360 A1 6/2017 Deisseroth et al.
2017/0162072 A1 6/2017 Horseman et al.
2017/0164861 A1 6/2017 Cahan et al.
2017/0164862 A1 6/2017 Dolev et al.
2017/0164876 A1 6/2017 Hyde et al.
2017/0164878 A1 6/2017 Connor
2017/0164893 A1 6/2017 Narayan et al.
2017/0164894 A1 6/2017 Yoo et al.
2017/0164895 A1 6/2017 Howard
2017/0164901 A1 6/2017 Shusterman
2017/0165020 A1 6/2017 Martel
2017/0165481 A1 6/2017 Menon
2017/0165496 A1 6/2017 Pilla et al.
2017/0168121 A1 6/2017 Yu et al.
2017/0168566 A1 6/2017 Osterhout et al.
2017/0168568 A1 6/2017 Petrov
2017/0169714 A1 6/2017 Lin et al.
2017/0171441 A1 6/2017 Kearns et al.
2017/0172414 A1 6/2017 Nierenberg et al.
2017/0172446 A1 6/2017 Kuzum et al.
2017/0172499 A1 6/2017 Yoo
2017/0172501 A1 6/2017 Badower et al.
2017/0172520 A1 6/2017 Kannan et al.
2017/0172527 A1 6/2017 Uber
2017/0173262 A1 6/2017 Veltz
2017/0173326 A1 6/2017 Bloch et al.
2017/0173391 A1 6/2017 Wiebe et al.
2017/0177023 A1 6/2017 Simon et al.
2017/0178001 A1 6/2017 Anderson et al.
2017/0178340 A1 6/2017 Schadewaldt et al.
2017/0180558 A1 6/2017 Li et al.
2017/0181252 A1 6/2017 Wouhaybi et al.
2017/0181693 A1 6/2017 Kim et al.
2017/0182176 A1 6/2017 Satchi-Fainaro et al.
2017/0182285 A1 6/2017 Tyler et al.
2017/0182312 A1 6/2017 Durand et al.
2017/0185149 A1 6/2017 Oluwafemi et al.
2017/0185714 A1 6/2017 Halter et al.
2017/0185741 A1 6/2017 Moffitt et al.
2017/0188862 A1 7/2017 Kale et al.
2017/0188865 A1 7/2017 Nierenberg et al.
2017/0188866 A1 7/2017 Kale et al.
2017/0188868 A1 7/2017 Kale et al.
2017/0188869 A1 7/2017 Kale et al.
2017/0188870 A1 7/2017 Hilty
2017/0188872 A1 7/2017 Hughes et al.
2017/0188876 A1 7/2017 Marci et al.
2017/0188905 A1 7/2017 Lee et al.
2017/0188916 A1 7/2017 Wang et al.
2017/0188922 A1 7/2017 Lee et al.
2017/0188932 A1 7/2017 Singer et al.
2017/0188933 A1 7/2017 Huggins et al.

(56) References Cited

U.S. PATENT DOCUMENTS

2017/0188947 A1 7/2017 Connor
2017/0188992 A1 7/2017 O'Brien et al.
2017/0189685 A1 7/2017 Steinke et al.
2017/0189686 A1 7/2017 Steinke et al.
2017/0189687 A1 7/2017 Steinke et al.
2017/0189688 A1 7/2017 Steinke et al.
2017/0189689 A1 7/2017 Steinke et al.
2017/0189691 A1 7/2017 De Ridder
2017/0189700 A1 7/2017 Moffitt et al.
2017/0189707 A1 7/2017 Zabara
2017/0190765 A1 7/2017 El-Agnaf
2017/0193161 A1 7/2017 Sapiro et al.
2017/0193831 A1 7/2017 Walter et al.
2017/0196497 A1 7/2017 Ray et al.
2017/0196501 A1 7/2017 Watson et al.
2017/0196503 A1 7/2017 Narayan et al.
2017/0196519 A1 7/2017 Miller et al.
2017/0197080 A1 7/2017 Wagner et al.
2017/0197081 A1 7/2017 Charlesworth et al.
2017/0197086 A1 7/2017 Howard et al.
2017/0198017 A1 7/2017 Deisseroth et al.
2017/0198349 A1 7/2017 Rice
2017/0199251 A1 7/2017 Fujii et al.
2017/0202474 A1 7/2017 Banerjee et al.
2017/0202475 A1 7/2017 Leuthardt
2017/0202476 A1 7/2017 Desain et al.
2017/0202518 A1 7/2017 Furman et al.
2017/0202621 A1 7/2017 Taylor
2017/0202633 A1 7/2017 Liu
2017/0203154 A1 7/2017 Solinsky
2017/0205259 A1 7/2017 Jang et al.
2017/0206654 A1 7/2017 Shiroishi et al.
2017/0206691 A1 7/2017 Harrises et al.
2017/0206913 A1 7/2017 Nahman et al.
2017/0209043 A1 7/2017 Gross et al.
2017/0209044 A1 7/2017 Ito et al.
2017/0209053 A1 7/2017 Pantelopoulos et al.
2017/0209062 A1 7/2017 Iwasaki et al.
2017/0209083 A1 7/2017 Zarandi et al.
2017/0209094 A1 7/2017 Derchak et al.
2017/0209225 A1 7/2017 Wu
2017/0209389 A1 7/2017 Toth et al.
2017/0209737 A1 7/2017 Tadi et al.
2017/0212188 A1 7/2017 Kikitsu et al.
2017/0213339 A1 7/2017 Hibbard et al.
2017/0214786 A1 7/2017 Lee et al.
2017/0216595 A1 8/2017 Geva et al.
2017/0221206 A1 8/2017 Han et al.
2017/0224990 A1 8/2017 Goldwasser et al.
2017/0224994 A1 8/2017 Kilgard et al.
2017/0231560 A1 8/2017 Hyde et al.
2017/0239486 A1 8/2017 Suryavanshi
2017/0239489 A1 8/2017 Bourke, Jr. et al.
2017/0319817 A1* 11/2017 Morishima ........... A61B 5/486

* cited by examiner

SYSTEM AND METHOD OF IMPROVING SLEEP

CROSS-REFERENCE TO RELATED APPLICATIONS

This application is a Continuation of U.S. patent application Ser. No. 17/572,153, filed Sep. 16, 2019, now U.S. Pat. No. 11,452,839, issued Sep. 27, 2022, which claims benefit of priority from U.S. Patent Application No. 62/731,674, filed Sep. 14, 2018, the entirety of which are expressly incorporated herein by reference.

This application also incorporates by reference the entirety of U.S. Provisional Patent App. Nos. 62/560,502 filed Sep. 19, 2017; 62/568,610 filed Oct. 5, 2017; 62/594,452 filed Dec. 4, 2017; 62/612,565, filed Dec. 31, 2017; and 62/660,839 filed Apr. 20, 2018, and U.S. patent application Ser. No. 16/134,309, filed Sep. 18, 2018, Ser. No. 16/209,301, filed Dec. 4, 2018, PCT/US18/68220 filed Dec. 31, 2018, Ser. No. 16/237,497, filed Dec. 31, 2018, Ser. No. 16/237,483, filed Dec. 31, 2018, Ser. No. 16/237,180, filed Dec. 31, 2018, and Ser. No. 16/388,845, filed Apr. 18, 2019, each of which is expressly incorporated herein by reference in its entirety.

FIELD OF THE INVENTION

The present invention generally relates to the field of neuromodulation and neuroenhancement, and more specifically to systems and methods for improving sleep states in humans or animals.

BACKGROUND OF THE INVENTION

Each reference and document cited herein is expressly incorporated herein by reference in its entirety, for all purposes.

Time in a biological manner: Almost everything in biology is subject to change over time. These changes occur on many different time scales, which vary greatly. For example, there are evolutionary changes that affect entire populations over time rather than a single organism. Evolutionary changes are often slower than a human time scale that spans many years (usually a human lifetime). Faster variations of the timing and duration of biological activity in living organisms occur, for example, in many essential biological processes in everyday life: in humans and animals, these variations occur, for example, in eating, sleeping, mating, hibernating, migration, cellular regeneration, etc. Other fast changes may include the transmission of a neural signal, for example, through a synapse such as the calyx of held, a particularly large synapse in the auditory central nervous system of mammals that can reach transmission frequencies of up to 50 Hz. With recruitment modulation, the effective frequencies can be higher. A single nerve impulse can reach a speed as high as one hundred meters (0.06 mile) per second (Kraus, David. Concepts in Modern Biology. New York: Globe Book Company, 1969: 170.). Myelination of axons can increase the speed of transmission by segmenting the membrane depolarization process.

Many of these changes over time are repetitive or rhythmic and are described as some frequency or oscillation. The field of chronobiology, for example, examines such periodic (cyclic) phenomena in living organisms and their adaptation, for example, to solar and lunar-related rhythms [DeCoursey, et al. (2003).] These cycles are also known as biological rhythms. The related terms chronomics and chronome have been used in some cases to describe either the molecular mechanisms involved in chronobiological phenomena or the more quantitative aspects of chronobiology, particularly where comparison of cycles between organisms is required. Chronobiological studies include, but are not limited to, comparative anatomy, physiology, genetics, molecular biology and behavior of organisms within biological rhythms mechanics [DeCoursey et al. (2003).]. Other aspects include epigenetics, development, reproduction, ecology, and evolution.

The most important rhythms in chronobiology are the circadian rhythms, roughly 24-hour cycles shown by physiological processes in all these organisms. It is regulated by circadian clocks. The circadian rhythms can be further broken down into routine cycles during the 24-hour day [Nelson R J. 2005. An Introduction to Behavioral Endocrinology. Sinauer Associates, Inc.: Massachusetts. Pg. 587.] All animals can be classified according to their activity cycles: Diurnal, which describes organisms active during daytime; Nocturnal, which describes organisms active in the night; and Crepuscular, which describes animals primarily active during the dawn and dusk hours (ex: white-tailed deer, some bats).

While circadian rhythms are defined as regulated by endogenous processes, other biological cycles may be regulated by exogenous signals. In some cases, multi-trophic systems may exhibit rhythms driven by the circadian clock of one of the members (which may also be influenced or reset by external factors).

Many other important cycles are also studied, including: Infradian rhythms, which are cycles longer than a day. Examples include circannual or annual cycles that govern migration or reproduction cycles in many plants and animals, or the human menstrual cycle; Ultradian rhythms, which are cycles shorter than 24 hours, such as the 90-minute REM cycle, the 4-hour nasal cycle, or the 3-hour cycle of growth hormone production; Tidal rhythms, commonly observed in marine life, which follow the roughly 12.4-hour transition from high to low tide and back; Lunar rhythms, which follow the lunar month (29.5 days). They are relevant, for example, to marine life, as the level of the tides is modulated across the lunar cycle; and Gene oscillations—some genes are expressed more during certain hours of the day than during other hours.

Within each cycle, the time period during which the process is more active is called the acrophase [Refinetti, Roberto (2006). Circadian Physiology. CRC Press/Taylor & Francis Group. ISBN 0-8493-2233-2. Lay summary]. When the process is less active, the cycle is in its bathyphase, or trough phase. The particular moment of highest activity is the peak or maximum; the lowest point is the nadir. How high (or low) the process gets is measured by the amplitude.

The sleep cycle and the ultradian rhythms: The normal cycle of sleep and wakefulness implies that, at specific times, various neural systems are being activated while others are being turned off. A key to the neurobiology of sleep is therefore to understand the various stages of sleep. In 1953, Nathaniel Kleitman and Eugene Aserinksy showed, using electroencephalographic (EEG) recordings from normal human subjects, that sleep comprises different stages that occur in a characteristic sequence.

Humans descend into sleep in stages that succeed each other over the first hour or so after retiring. These characteristic stages are defined primarily by electroencephalographic criteria. Initially, during "drowsiness," the frequency spectrum of the electroencephalogram (EEG) is shifted toward lower values, and the amplitude of the cortical waves slightly increases. This drowsy period, called stage I sleep, eventually gives way to light or stage II sleep, which is characterized by a further decrease in the frequency of the EEG waves and an increase in their amplitude, together with intermittent high-frequency spike clusters called sleep spindles. Sleep spindles are periodic bursts of activity at about 10-12 Hz that generally last 1 or 2 seconds and arise as a result of interactions between thalamic and cortical neurons. In stage III sleep, which represents moderate to deep sleep, the number of spindles decreases, whereas the amplitude of low-frequency waves increases still more. In the deepest level of sleep, stage IV sleep, the predominant EEG activity consists of low-frequency (1-4 Hz), high-amplitude fluctuations called delta waves, the characteristic slow waves for which this phase of sleep is named. The entire sequence from drowsiness to deep stage IV sleep usually takes about an hour.

These four sleep stages are called non-rapid eye movement (non-REM) sleep, and its most prominent feature is the slow-wave (stage IV) sleep. It is most difficult to awaken people from slow-wave sleep; hence it is considered to be the deepest stage of sleep. Following a period of slow-wave sleep, however, EEG recordings show that the stages of sleep reverse to reach a quite different state called rapid eye movement, or REM, sleep. In REM sleep, the EEG recordings are remarkably similar to that of the awake state. This mode is bizarre: a dreamer's brain becomes highly active while the body's muscles are paralyzed, and breathing and heart rate become erratic. After about 10 minutes in REM sleep, the brain typically cycles back through the non-REM sleep stages. Slow-wave sleep usually occurs again in the second period of this continual cycling, but not during the rest of the night. On average, four additional periods of REM sleep occur, each having longer than the preceding cycle durations.

In summary, the typical 8 hours of sleep experienced each night actually comprise several cycles that alternate between non-REM and REM sleep, the brain being quite active during much of this supposedly dormant, restful time. For reasons that are not clear, the amount of REM sleep each day decreases from about 8 hours at birth to 2 hours at 20 years, to only about 45 minutes at 70 years of age.

Falling asleep: When falling asleep, a series of highly orchestrated events puts the brain to sleep in the above-mentioned stages. Technically sleep starts in the brain areas that produce slow-wave sleep (SWS). It has been shown that two groups of cells—the ventrolateral preoptic nucleus in the hypothalamus and the parafacial zone in the brain stem—are involved in prompting SWS. When these cells are activated, it triggers a loss of consciousness. After SWS, REM sleep begins. The purpose of REM sleep remains a biological mystery, despite our growing understanding of its biochemistry and neurobiology. It has been shown that a small group of cells in the brain stem, called the subcoeruleus nucleus, control REM sleep. When these cells become injured or diseased, people do not experience the muscle paralysis associated with REM sleep, which can lead to REM sleep behavior disorder—a serious condition in which the afflicted violently act out their dreams.

Neural Correlates: A neural correlate of a sleep state is an electro-neuro-biological state or the state assumed by some biophysical subsystem of the brain, whose presence necessarily and regularly correlates with such specific sleep states. All properties credited to the mind, including consciousness, emotion, and desires are thought to have direct neural correlates. For our purposes, neural correlates of a sleep state can be defined as the minimal set of neuronal oscillations that correspond to the given sleep stage. Neuroscientists use empirical approaches to discover neural correlates of sleep stages.

Mental State: A mental state is a state of mind that a subject is in. Some mental states are pure and unambiguous, while humans are capable of complex states that are a combination of mental representations, which may have in their pure state contradictory characteristics. There are several paradigmatic states of mind that a subject has: love, hate, pleasure, fear, and pain. Mental states can also include a waking state, a sleeping state, a flow (or being in the "zone"), and a mood (a mental state). A mental state is a hypothetical state that corresponds to thinking and feeling, and consists of a conglomeration of mental representations. A mental state is related to an emotion, though it can also relate to cognitive processes. Because the mental state itself is complex and potentially possess inconsistent attributes, clear interpretation of mental state through external analysis (other than self-reporting) is difficult or impossible. However, some studies report that certain attributes of mental state or thought processes may, in fact, be determined through passive monitoring, such as EEG, or fMRI with some degree of statistical reliability. In most studies, the characterization of mental state was an endpoint, and the raw signals, after statistical classification or semantic labeling, are superseded. The remaining signal energy treated as noise. Current technology does not permit a precise abstract encoding or characterization of the full range of mental states based on neural correlates of mental state.

Brain: The brain is a key part of the central nervous system, enclosed in the skull. In humans, and mammals more generally, the brain controls both autonomic processes, as well as cognitive processes. The brain (and to a lesser extent, the spinal cord) controls all volitional functions of the body and interprets information from the outside world. Intelligence, memory, emotions, speech, thoughts, movements and creativity are controlled by the brain. The central nervous system also controls autonomic functions and many homeostatic and reflex actions, such as breathing, heart rate, etc. The human brain consists of the cerebrum, cerebellum, and brainstem. The brainstem includes the midbrain, the pons, and the medulla oblongata. Sometimes the diencephalon, the caudal part of the forebrain, is included.

The brain is composed of neurons, neuroglia (a.k.a., glia), and other cell types in connected networks that integrate sensory inputs, control movements, facilitate learning and memory, activate and express emotions, and control all other behavioral and cognitive functions. Neurons communicate primarily through electrochemical pulses that transmit signals between connected cells within and between brain areas. Thus, the desire to noninvasively capture and replicate neural activity associated with cognitive states has been a subject of interest to behavioral and cognitive neuroscientists.

Technological advances now allow for non-invasive recording of large quantities of information from the brain at multiple spatial and temporal scales. Examples include electroencephalogram ("EEG") data using multi-channel electrode arrays placed on the scalp or inside the brain, magnetoencephalography ("MEG"), magnetic resonance imaging ("MRI"), functional data using functional magnetic resonance imaging ("fMRI"), positron emission tomography ("PET"), near-infrared spectroscopy ("NIRS"), single-photon emission computed tomography ("SPECT"), and others.

Noninvasive neuromodulation technologies have also been developed that can modulate the pattern of neural activity, and thereby cause altered behavior, cognitive states, perception, and motor output. Integration of noninvasive measurement and neuromodulation techniques for identifying and transplanting brain states from neural activity would be very valuable for clinical therapies, such as brain stimulation and related technologies often attempting to treat disorders of cognition.

The brainstem provides the main motor and sensory innervation to the face and neck via the cranial nerves. Of the twelve pairs of cranial nerves, ten pairs come from the brainstem. This is an extremely important part of the brain, as the nerve connections of the motor and sensory systems from the main part of the brain to the rest of the body pass through the brainstem. This includes the corticospinal tract (motor), the posterior column-medial lemniscus pathway (fine touch, vibration sensation, and proprioception), and the spinothalamic tract (pain, temperature, itch, and crude touch). The brainstem also plays an important role in the regulation of cardiac and respiratory function. It also regulates the central nervous system and is pivotal in maintaining consciousness and regulating the sleep cycle. The brainstem has many basic functions including controlling heart rate, breathing, sleeping, and eating.

The function of the skull is to protect delicate brain tissue from injury. The skull consists of eight fused bones: the frontal, two parietal, two temporal, sphenoid, occipital and ethmoid. The face is formed by 14 paired bones including the maxilla, zygoma, nasal, palatine, lacrimal, inferior nasal conchae, mandible, and vomer. The bony skull is separated from the brain by the dura, a membranous organ, which in turn contains cerebrospinal fluid. The cortical surface of the brain typically is not subject to localized pressure from the skull. The skull, therefore, imposes a barrier to electrical access to the brain functions, and in a healthy human, breaching the dura to access the brain is highly disfavored. The result is that electrical readings of brain activity are filtered by the dura, the cerebrospinal fluid, the skull, the scalp, skin appendages (e.g., hair), resulting in a loss of potential spatial resolution and amplitude of signals emanating from the brain. While magnetic fields resulting from brain electrical activity are accessible, the spatial resolution using feasible sensors is also limited.

The cerebrum is the largest part of the brain and is composed of right and left hemispheres. It performs higher functions, such as interpreting inputs from the senses, as well as speech, reasoning, emotions, learning, and fine control of movement. The surface of the cerebrum has a folded appearance called the cortex. The human cortex contains about 70% of the nerve cells (neurons) and gives an appearance of gray color (grey matter). Beneath the cortex are long connecting fibers between neurons, called axons, which make up the white matter.

The cerebellum is located behind the cerebrum and brainstem. It coordinates muscle movements, helps to maintain balance and posture. The cerebellum may also be involved in some cognitive functions such as attention and language, as well as in regulating fear and pleasure responses. There is considerable evidence that the cerebellum plays an essential role in some types of motor learning. The tasks where the cerebellum most clearly comes into play are those in which it is necessary to make fine adjustments to the way an action is performed. There is a dispute about whether learning takes place within the cerebellum itself, or whether it merely serves to provide signals that promote learning in other brain structures. Cerebellum also plays an important role in sleep and long-term memory formation.

The brain communicates with the body through the spinal cord and twelve pairs of cranial nerves. Ten of the twelve pairs of cranial nerves that control hearing, eye movement, facial sensations, taste, swallowing and movement of the face, neck, shoulder and tongue muscles originate in the brainstem. The cranial nerves for smell and vision originate in the cerebrum.

The right and left hemispheres of the brain are joined by a structure consisting of fibers called the corpus callosum. Each hemisphere controls the opposite side of the body. The right eye sends visual signals to the left hemisphere and vice versa. However, the right ear sends signals to the right hemisphere, and the left ear sends signals to the left hemisphere. Not all functions of the hemispheres are shared. For example, speech is processed exclusively in the left hemisphere.

The cerebral hemispheres have distinct structures, which divide the brain into lobes. Each hemisphere has four lobes: frontal, temporal, parietal, and occipital. There are very complex relationships between the lobes of the brain and between the right and left hemispheres:

Frontal lobes control judgment, planning, problem-solving, behavior, emotions, personality, speech, self-awareness, concentration, intelligence, body movements.

Temporal lobes control understanding of language, memory, organization, and hearing.

Parietal lobes control the interpretation of language; input from vision, hearing, sensory, and motor; temperature, pain, tactile signals, memory, spatial and visual perception.

Occipital lobes interpret visual input (movement, light, color).

A neuron is a fundamental unit of the nervous system, which comprises the autonomic nervous system and the central nervous system.

Brain structures and particular areas within brain structures include but are not limited to Hindbrain structures (e.g., Myelencephalon structures (e.g., Medulla oblongata, Medullary pyramids, Olivary body, Inferior olivary nucleus, Respiratory center, Cuneate nucleus, Gracile nucleus, Intercalated nucleus, Medullary cranial nerve nuclei, Inferior salivatory nucleus, Nucleus ambiguous, Dorsal nucleus of vagus nerve, Hypoglossal nucleus, Solitary nucleus, etc.), Metencephalon structures (e.g., Pons, Pontine cranial nerve nuclei, chief or pontine nucleus of the trigeminal nerve sensory nucleus (V), Motor nucleus for the trigeminal nerve (V), Abducens nucleus (VI), Facial nerve nucleus (VII), vestibulocochlear nuclei (vestibular nuclei and cochlear nuclei) (VIII), Superior salivatory nucleus, Pontine tegmentum, Respiratory centers, Pneumotaxic center, Apneustic center, Pontine micturition center (Barrington's nucleus), Locus coeruleus, Pedunculopontine nucleus, Laterodorsal tegmental nucleus, Tegmental pontine reticular nucleus, Superior olivary complex, Paramedian pontine reticular formation, Cerebellar peduncles, Superior cerebellar peduncle, Middle cerebellar peduncle, Inferior cerebellar peduncle, Fourth ventricle, Cerebellum, Cerebellar vermis, Cerebellar hemispheres, Anterior lobe, Posterior lobe, Flocculonodular lobe, Cerebellar nuclei, Fastigial nucleus, Interposed nucleus, Globose nucleus, Emboliform nucleus, Dentate nucleus, etc.)), Midbrain structures (e.g., Tectum, Corpora quadrigemina, inferior colliculi, superior colliculi, Pretectum, Tegmentum, Periaqueductal gray, Parabrachial area, Medial parabrachial nucleus, Lateral parabrachial nucleus, Subparabrachial nucleus (Kolliker-Fuse nucleus), Rostral interstitial nucleus of medial longitudinal fasciculus, Midbrain reticular formation, Dorsal raphe nucleus, Red nucleus, Ventral tegmental area, Substantia nigra, Pars compacta, Pars reticulata, Interpeduncular nucleus, Cerebral peduncle, Cms cerebri, Mesencephalic ranial nerve nuclei, Oculomotor nucleus (III), Trochlear nucleus (IV), Mesencephalic duct (cerebral aqueduct, aqueduct of Sylvius), etc.), Forebrain structures (e.g., Diencephalon, Epithalamus structures (e.g., Pineal body, Habenular nuclei, Stria medullares, Taenia thalami, etc.) Third ventricle, Thalamus structures (e.g., Anterior nuclear group, Anteroventral nucleus (aka ventral anterior nucleus), Anterodorsal nucleus, Anteromedial nucleus, Medial nuclear group, Medial dorsal nucleus, Midline nuclear group, Paratenial nucleus, Reuniens nucleus, Rhomboidal nucleus, Intralaminar nuclear group, Centromedial nucleus, Parafascicular nucleus, Paracentral nucleus, Central lateral nucleus, Central medial nucleus, Lateral nuclear group, Lateral dorsal nucleus, Lateral posterior nucleus, Pulvinar, Ventral nuclear group, Ventral anterior nucleus, Ventral lateral nucleus, Ventral posterior nucleus, Ventral posterior lateral nucleus, Ventral posterior medial nucleus, Metathalamus, Medial geniculate body, Lateral geniculate body, Thalamic reticular nucleus, etc.), Hypothalamus structures (e.g., Anterior, Medial area, Parts of preoptic area, Medial preoptic nucleus, Suprachiasmatic nucleus, Paraventricular nucleus, Supraoptic nucleus (mainly), Anterior hypothalamic nucleus, Lateral area, Parts of preoptic area, Lateral preoptic nucleus, Anterior part of Lateral nucleus, Part of supraoptic nucleus, Other nuclei of preoptic area, median preoptic nucleus, periventricular preoptic nucleus, Tuberal, Medial area, Dorsomedial hypothalamic nucleus, Ventromedial nucleus, Arcuate nucleus, Lateral area, Tuberal part of Lateral nucleus, Lateral tuberal nuclei, Posterior, Medial area, Mammillary nuclei (part of mammillary bodies), Posterior nucleus, Lateral area, Posterior part of Lateral nucleus, Optic chiasm, Subfornical organ, Periventricular nucleus, Pituitary stalk, Tuber cinereum, Tuberal nucleus, Tuberomammillary nucleus, Tuberal region, Mammillary bodies, Mammillary nucleus, etc.), Subthalamus structures (e.g., Thalamic nucleus, Zona incerta, etc.), Pituitary gland structures (e.g., neurohypophysis, Pars intermedia (Intermediate Lobe), adenohypophysis, etc.), Telencephalon structures, white matter structures (e.g., *Corona radiata*, Internal capsule, External capsule, Extreme capsule, Arcuate fasciculus, Uncinate fasciculus, Perforant Path, etc.), Subcortical structures (e.g., Hippocampus (Medial Temporal Lobe), Dentate gyrus, *Cornu ammonis* (CA fields), *Cornu ammonis* area 1, *Cornu ammonis* area 2, *Cornu ammonis* area 3, *Cornu ammonis* area 4, Amygdala (limbic system) (limbic lobe), Central nucleus (autonomic nervous system), Medial nucleus (accessory olfactory system), Cortical and basomedial nuclei (main olfactory system), Lateral[disambiguation needed] and basolateral nuclei (frontotemporal cortical system), Claustrum, Basal ganglia, Striatum, Dorsal striatum (aka neostriatum), Putamen, Caudate nucleus, Ventral striatum, Nucleus accumbens, Olfactory tubercle, Globus pallidus (forms nucleus *lentiformis* with putamen), Subthalamic nucleus, Basal forebrain, Anterior perforated substance, Substantia innominata, Nucleus basalis, Diagonal band of Broca, Medial septal nuclei, etc.), Rhinencephalon structures (e.g., Olfactory bulb, Piriform cortex, Anterior olfactory nucleus, Olfactory tract, Anterior commissure, Uncus, etc.), Cerebral cortex structures (e.g., Frontal lobe, Cortex, Primary motor cortex (Precentral gyrus, M1), Supplementary motor cortex, Premotor cortex, Prefrontal cortex, Gyri, Superior frontal gyrus, Middle frontal gyrus, Inferior frontal gyrus, Brodmann areas: 4, 6, 8, 9, 10, 11, 12, 24, 25, 32, 33, 44, 45, 46, 47, Parietal lobe, Cortex, Primary somatosensory cortex (S1), Secondary somatosensory cortex (S2), Posterior parietal cortex, Gyri, Postcentral gyrus (Primary somesthetic area), Other, Precuneus, Brodmann areas 1, 2, 3 (Primary somesthetic area); 5, 7, 23, 26, 29, 31, 39, 40, Occipital lobe, Cortex, Primary visual cortex (V1), V2, V3, V4, V5/MT, Gyri, Lateral occipital gyrus, Cuneus, Brodmann areas 17 (V1, primary visual cortex); 18, 19, Temporal lobe, Cortex, Primary auditory cortex (A1), secondary auditory cortex (A2), Inferior temporal cortex, Posterior inferior temporal cortex, Superior temporal gyrus, Middle temporal gyrus, Inferior temporal gyrus, Entorhinal Cortex, Perirhinal Cortex, Parahippocampal gyrus, Fusiform gyrus, Brodmann areas: 9, 20, 21, 22, 27, 34, 35, 36, 37, 38, 41, 42, Medial superior temporal area (MST), Insular cortex, Cingulate cortex, Anterior cingulate, Posterior cingulate, Retrosplenial cortex, Indusium *griseum*, Subgenual area 25, Brodmann areas 23, 24; 26, 29, 30 (retrosplenial areas); 31, 32, etc.)).

Neurons: Neurons are electrically excitable cells that receive, process, and transmit information, and based on that information sends a signal to other neurons, muscles, or glands through electrical and chemical signals. These signals between neurons occur via specialized connections called synapses. Neurons can connect to each other to form neural networks. The basic purpose of a neuron is to receive incoming information and, based upon that information send a signal to other neurons, muscles, or glands. Neurons are designed to rapidly send signals across physiologically long distances. They do this using electrical signals called nerve impulses or action potentials. When a nerve impulse reaches the end of a neuron, it triggers the release of a chemical, or neurotransmitter. The neurotransmitter travels rapidly across the short gap between cells (the synapse) and acts to signal the adjacent cell. See www.biologyreference.com/Mo-Nu/Neuron.html#ixzz5AVxCuM5a.

Neurons can receive thousands of inputs from other neurons through synapses. Synaptic integration is a mechanism whereby neurons integrate these inputs before the generation of a nerve impulse, or action potential. The ability of synaptic inputs to effect neuronal output is determined by a number of factors: Size, shape and relative timing of electrical potentials generated by synaptic inputs; the geometric structure of the target neuron; the physical location of synaptic inputs within that structure; and the expression of voltage-gated channels in different regions of the neuronal membrane.

Neurons within a neural network receive information from, and send information to, many other cells, at specialized junctions called synapses. Synaptic integration is the computational process by which an individual neuron processes its synaptic inputs and converts them into an output signal. Synaptic potentials occur when neurotransmitter binds to and opens ligand-operated channels in the dendritic membrane, allowing ions to move into or out of the cell according to their electrochemical gradient. Synaptic potentials can be either excitatory or inhibitory depending on the direction and charge of ion movement. Action potentials occur if the summed synaptic inputs to a neuron reach a threshold level of depolarisation and trigger regenerative opening of voltage-gated ion channels. Synaptic potentials are often brief and of small amplitude, therefore summation of inputs in time (temporal summation) or from multiple synaptic inputs (spatial summation) is usually required to reach action potential firing threshold.

There are two types of synapses: electrical synapses and chemical synapses. Electrical synapses are a direct electrical coupling between two cells mediated by gap junctions, which are pores constructed of connexin proteins—essentially result in the passing of a gradient potential (may be depolarizing or hyperpolarizing) between two cells. Electrical synapses are very rapid (no synaptic delay). It is a passive process where signal can degrade with distance and may not produce a large enough depolarization to initiate an action potential in the postsynaptic cell. Electrical synapses are bidirectional, i.e., postsynaptic ell can actually send messages to the presynaptic cell.

Chemical synapses are a coupling between two cells through neuro-transmitters, ligand or voltage gated channels, receptors. They are influenced by the concentration and types of ions on either side of the membrane. Among the neurotransmitters, Glutamate, sodium, potassium, and calcium are positively charged. GABA and chloride are negatively charged. Neurotransmitter junctions provide an opportunity for pharmacological intervention, and many different drugs, including illicit drugs, act at synapses.

An excitatory postsynaptic potential (EPSP) is a postsynaptic potential that makes the postsynaptic neuron more likely to fire an action potential. An electrical charge (hyperpolarization) in the membrane of a postsynaptic neuron is caused by the binding of an inhibitory neurotransmitter from a presynaptic ell to a postsynaptic receptor. It makes it more difficult for a postsynaptic neuron to generate an action potential. An electrical change (depolarization) in the membrane of a postsynaptic neuron caused by the binding of an excitatory neurotransmitter from a presynaptic ell to a postsynaptic receptor. It makes it more likely for a postsynaptic neuron to generate an action potential. In a neuronal synapse that uses glutamate as receptor, for example, receptors open ion channels that are non-selectively permeable to cations. When these glutamate receptors are activated, both Na+ and K+ flow across the postsynaptic membrane. The reversal potential (Erev) for the post-synaptic current is approximately 0 mV. The resting potential of neurons is approximately −60 mV. The resulting EPSP will depolarize the post synaptic membrane potential, bringing it toward 0 mV.

An inhibitory postsynaptic potential (IPSP) is a kind of synaptic potential that makes a postsynaptic neuron less likely to generate an action potential. An example of inhibitory post synaptic s action is a neuronal synapse that uses γ-Aminobutyric acid (GABA) as its transmitter. At such synapses, the GABA receptors typically open channels that are selectively permeable to Cl—. When these channels open, negatively charged chloride ions can flow across the membrane. The postsynaptic neuron has a resting potential of −60 mV and an action potential threshold of −40 mV. Transmitter release at this synapse will inhibit the postsynaptic cell. Since ECI is more negative than the action potential threshold, e.g., −70 mV, it reduces the probability that the postsynaptic cell will fire an action potential.

Some types of neurotransmitters, such as glutamate, consistently result in EPSPs. Others, such as GABA, consistently result in IPSPs. The action potential lasts about one millisecond (1 msec). In contrast, the EPSPs and IPSPs can last as long as 5 to 10 msec. This allows the effect of one postsynaptic potential to build upon the next and so on.

Membrane leakage, and to a lesser extent, potentials per se, can be influenced by external electrical and magnetic fields. These fields may be generated focally, such as through implanted electrodes, or less specifically, such as through transcranial stimulation. Transcranial stimulation may be subthreshold or superthreshold. In the former case, the external stimulation acts to modulate resting membrane potential, making nerves more or less excitable. Such stimulation may be direct current or alternating current. In the latter case, this will tend to synchronize neuron depolarization with the signals. Superthreshold stimulation can be painful (at least because the stimulus directly excites pain neurons) and must be pulsed. Since this has correspondence to electroconvulsive therapy, superthresold transcranial stimulation is sparingly used.

A number of neurotransmitters are known, as are pharmaceutical interventions and therapies that influence these compounds. Typically, the major neurotransmitters are small monoamine molecules, such as dopamine, epinephrine, norepinephrine, serotonin, GABA, histamine, etc., as well as acetylcholine. In addition, neurotransmitters also include amino acids, gas molecules such as nitric oxide, carbon monoxide, carbon dioxide, and hydrogen sulfide, as well as peptides. The presence, metabolism, and modulation of these molecules may influence learning and memory. Supply of neurotransmitter precursors, control of oxidative and mental stress conditions, and other influences on learning and memory-related brain chemistry, may be employed to facilitate memory, learning, and learning adaption transfer.

The neuropeptides, as well as their respective receptors, are widely distributed throughout the mammalian central nervous system. During learning and memory processes, besides structural synaptic remodeling, changes are observed at molecular and metabolic levels with the alterations in neurotransmitter and neuropeptide synthesis and release. While there is a consensus that brain cholinergic neurotransmission plays a critical role in the processes related to learning and memory, it is also well known that these functions are influenced by a tremendous number of neuropeptides and non-peptide molecules. Arginine vasopressin (AVP), oxytocin, angiotensin II, insulin, growth factors, serotonin (5-HT), melanin-concentrating hormone, histamine, bombesin and gastrin-releasing peptide (GRP), glucagon-like peptide-1 (GLP-1), cholecystokinin (CCK), dopamine, corticotropin-releasing factor (CRF) have modulatory effects on learning and memory. Among these peptides, CCK, 5-HT, and CRF play strategic roles in the modulation of memory processes under stressful conditions. CRF is accepted as the main neuropeptide involved in both physical and emotional stress, with a protective role during stress, possibly through the activation of the hypothalamo-pituitary (HPA) axis. The peptide CCK has been proposed to facilitate memory processing, and CCK-like immunoreactivity in the hypothalamus was observed upon stress exposure, suggesting that CCK may participate in the central control of stress response and stress-induced memory dysfunction. On the other hand, 5-HT appears to play a role in behaviors that involve a high cognitive demand and stress exposure activates serotonergic systems in a variety of brain regions. See:

Mehmetali Gülpinar, Berrak C Yeğen, "The Physiology of Learning and Memory: Role of Peptides and Stress", Current Protein and Peptide Science, 2004(5)

www.researchgate.net/publication/8147320_The_Physiology_of_Learning_and_Memory_Role_of_Peptides_and_Stress.Deep brain stimulation is described in NIH Research Matters, "A noninvasive deep brain stimulation technique", (2017), Brainworks, "QEEG Brain Mapping".

Carmon, A., Mor, J., & Goldberg, J. (1976). Evoked cerebral responses to noxious thermal stimuli in humans. Experimental Brain Research, 25(1), 103-107.

Mental State: A number of studies report that certain attributes of mental state or thought processes may in fact be determined through passive monitoring, such as EEG, with some degree of statistical reliability. In most studies, the characterization of mental state was an endpoint, and the raw signals, after statistically classification or semantic labelling, are superseded and the remaining signal energy treated as noise.

Neural Correlates: A neural correlate of a mental state is an electro-neuro-biological state or the state assumed by some biophysical subsystem of the brain, whose presence necessarily and regularly correlates with such specific mental state. All properties credited to the en.wikipedia.org/wiki/Mind, including consciousness, emotion, and desires are thought to have direct neural correlates. For our purposes, neural correlates of a mental state can be defined as the minimal set of neuronal oscillations that correspond to the given mental state. Neuroscientists use empirical approaches to discover neural correlates of subjective mental states.

Brainwaves: At the root of all our thoughts, emotions and behaviors is the communication between neurons within our brains, a rhythmic or repetitive neural activity in the central nervous system. The oscillation can be produced by a single neuron or by synchronized electrical pulses from ensembles of neurons communicating with each other. The interaction between neurons can give rise to oscillations at a different frequency than the firing frequency of individual neurons. The synchronized activity of large numbers of neurons produces macroscopic oscillations, which can be observed in an electroencephalogram. They are divided into bandwidths to describe their purported functions or functional relationships. Oscillatory activity in the brain is widely observed at different levels of organization and is thought to play a key role in processing neural information. Numerous experimental studies support a functional role of neural oscillations. A unified interpretation, however, is still not determined. Neural oscillations and synchronization have been linked to many cognitive functions such as information transfer, perception, motor control and memory. Electroencephalographic (EEG) signals are relatively easy and safe to acquire, have a long history of analysis, and can have high dimensionality, e.g., up to 128 or 256 separate recording electrodes. While the information represented in each electrode is not independent of the others, and the noise in the signals high, there is much information available through such signals that has not been fully characterized to date.

Brain waves have been widely studied in neural activity generated by large groups of neurons, mostly by EEG. In general, EEG signals reveal oscillatory activity (groups of neurons periodically firing in synchrony), in specific frequency bands: alpha (7.5-12.5 Hz) that can be detected from the occipital lobe during relaxed wakefulness and which increases when the eyes are closed; delta (1-4 Hz), theta (4-8 Hz), beta (13-30 Hz), low gamma (30-70 Hz), and high gamma (70-150 Hz) frequency bands, where faster rhythms such as gamma activity have been linked to cognitive processing. Higher frequencies imply multiple groups of neurons firing in coordination, either in parallel or in series, or both, since individual neurons do not fire at rates of 100 Hz. Neural oscillations of specific characteristics have been linked to cognitive states, such as awareness and consciousness and different sleep stages.

Nyquist Theorem states that the highest frequency that can be accurately represented is one-half of the sampling rate. Practically, the sampling rate should be ten times higher than the highest frequency of the signal. (See, www.slideshare.net/ertvk/eeg-examples). While EEG signals are largely band limited, the superimposed noise may not be. Further, the EEG signals themselves represent components from a large number of neurons, which fire independently. Therefore, large bandwidth signal acquisition may have utility.

It is a useful analogy to think of brainwaves as musical notes. Like in symphony, the higher and lower frequencies link and cohere with each other through harmonics, especially when one considers that neurons may be coordinated not only based on transitions, but also on phase delay. Oscillatory activity is observed throughout the central nervous system at all levels of organization. The dominant neuro oscillation frequency is associated with a respective mental state.

The functions of brain waves are wide-ranging and vary for different types of oscillatory activity. Neural oscillations also play an important role in many neurological disorders.

In standard EEG recording practice, 19 recording electrodes are placed uniformly on the scalp (the International 10-20 System). In addition, one or two reference electrodes (often placed on earlobes) and a ground electrode (often placed on the nose to provide amplifiers with reference voltages) are required. However, additional electrodes may add minimal useful information unless supplemented by computer algorithms to reduce raw EEG data to a manageable form. When large numbers of electrodes are employed, the potential at each location may be measured with respect to the average of all potentials (the common average reference), which often provides a good estimate of potential at infinity. The common average reference is not appropriate when electrode coverage is sparse (perhaps less than 64 electrodes). See, Paul L. Nunez and Ramesh Srinivasan (2007) Electroencephalogram. Scholarpedia, 2(2):1348, scholarpedia.org/article/Electroencephalogram. Dipole localization algorithms may be useful to determine spatial emission patterns in EEG.

Scalp potential may be expressed as a volume integral of dipole moment per unit volume over the entire brain provided P(r,t) is defined generally rather than in columnar terms. For the important case of dominant cortical sources, scalp potential may be approximated by the following integral over the cortical volume Θ, $VS(r,t)=\iiint_{\Theta} G(r,r')\cdot P(r',t)d\Theta(r')$. If the volume element dΘ(r') is defined in terms of cortical columns, the volume integral may be reduced to an integral over the folded cortical surface. The time-dependence of scalp potential is the weighted sum of all dipole time variations in the brain, although deep dipole volumes typically make negligible contributions. The vector Green's function G(r,r') contains all geometric and conductive information about the head volume conductor and weights the integral accordingly. Thus, each scalar component of the Green's function is essentially an inverse electrical distance between each source component and scalp location. For the idealized case of sources in an infinite medium of constant conductivity, the electrical distance equals the geometric distance. The Green's function accounts for the tissue's finite spatial extent and its inhomogeneity and anisotropy. The forward problem in EEG consists of choosing a head model to provide G(r,r') and carrying out the integral for some assumed source distribution. The inverse problem consists of using the recorded scalp potential distribution VS(r,t) plus some constraints (usual assumptions) on P(r,t) to find the best fit source distribution P(r,t). Since the inverse problem has no unique solution, any inverse solution depends critically on the chosen constraints, for example, only one or two isolated sources, distributed sources confined to the cortex, or spatial and temporal smoothness criteria. High-resolution EEG uses the experimental scalp potential VS(r,t) to predict the potential on the dura surface (the unfolded membrane surrounding the cerebral cortex) VD(r,t). This may be accomplished using a head model Green's function G(r,r') or by estimating the surface Laplacian with either spherical or 3D splines. These two approaches typically provide very similar dura potentials VD(r,t); the estimates of dura potential distribution are unique subject to head model, electrode density, and noise issues.

In an EEG recording system, each electrode is connected to one input of a differential amplifier (one amplifier per pair of electrodes); a common system reference electrode (or synthesized reference) is connected to the other input of each differential amplifier. These amplifiers amplify the voltage between the active electrode and the reference (typically 1,000-100,000 times, or 60-100 dB of voltage gain). The amplified signal is digitized via an analog-to-digital converter, after being passed through an anti-aliasing filter. Analog-to-digital sampling typically occurs at 256-512 Hz in clinical scalp EEG; sampling rates of up to 20 kHz are used in some research applications. The EEG signals can be captured with open-source hardware such as OpenBCI, and the signal can be processed by freely available EEG software such as EEGLAB or the Neurophysiological Biomarker Toolbox. A typical adult human EEG signal is about 10 μV to 100 μV in amplitude when measured from the scalp and is about 10-20 mV when measured from subdural electrodes.

Delta wave (en.wikipedia.org/wiki/Delta_wave) is the frequency range up to 4 Hz. It tends to be the highest in amplitude and the slowest waves. It is normally seen in adults in NREM (en.wikipedia.org/wiki/NREM). It is also seen normally in babies. It may occur focally with subcortical lesions and in general distribution with diffuse lesions, metabolic encephalopathy hydrocephalus or deep midline lesions. It is usually most prominent frontally in adults (e.g., FIRDA-frontal intermittent rhythmic delta) and posteriorly in children (e.g., OIRDA-occipital intermittent rhythmic delta).

Theta is the frequency range from 4 Hz to 7 Hz. Theta is normally seen in young children. It may be seen in drowsiness or arousal in older children and adults; it can also be seen in meditation. Excess theta for age represents abnormal activity. It can be seen as a focal disturbance in focal subcortical lesions; it can be seen in generalized distribution in diffuse disorder or metabolic encephalopathy or deep midline disorders or some instances of hydrocephalus. On the contrary, this range has been associated with reports of relaxed, meditative, and creative states.

Alpha is the frequency range from 7 Hz to 14 Hz. This was the "posterior basic rhythm" (also called the "posterior dominant rhythm" or the "posterior alpha rhythm"), seen in the posterior regions of the head on both sides, higher in amplitude on the dominant side. It emerges with the closing of the eyes and with relaxation and attenuates with eye opening or mental exertion. The posterior basic rhythm is actually slower than 8 Hz in young children (therefore technically in the theta range). In addition to the posterior basic rhythm, there are other normal alpha rhythms such as the sensorimotor, or mu rhythm (alpha activity in the contralateral sensory and motor cortical areas) that emerges when the hands and arms are idle; and the "third rhythm" (alpha activity in the temporal or frontal lobes). Alpha can be abnormal; for example, an EEG that has diffuse alpha occurring in coma and is not responsive to external stimuli is referred to as "alpha coma."

Beta is the frequency range from 15 Hz to about 30 Hz. It is usually seen on both sides in symmetrical distribution and is most evident frontally. Beta activity is closely linked to motor behavior and is generally attenuated during active movements. Low-amplitude beta with multiple and varying frequencies is often associated with active, busy or anxious thinking and active concentration. Rhythmic beta with a dominant set of frequencies is associated with various pathologies, such as Dup15q syndrome, and drug effects, especially benzodiazepines. It may be absent or reduced in areas of cortical damage. It is the dominant rhythm in patients who are alert or anxious or who have their eyes open.

Gamma is the frequency range approximately 30-100 Hz. Gamma rhythms are thought to represent binding of different populations of neurons together into a network to carry out a certain cognitive or motor function.

Mu range is 8-13 Hz and partly overlaps with other frequencies. It reflects the synchronous firing of motor neurons in a rest state. Mu suppression is thought to reflect motor mirror neuron systems, because when an action is observed, the pattern extinguishes, possibly because of the normal neuronal system and the mirror neuron system "go out of sync" and interfere with each other. (en.wikipedia.org/wiki/Electroencephalography). See:

Abeles M, Local Cortical Circuits (1982) New York: Springer-Verlag.

Braitenberg V and Schuz A (1991) Anatomy of the Cortex. Statistics and Geometry. New York: Springer-Verlag.

Ebersole J S (1997) Defining epileptogenic foci: past, present, future. J. Clin. Neurophysiology 14: 470-483.

Edelman G M and Tononi G (2000) A Universe of Consciousness, New York: Basic Books.

Freeman W J (1975) Mass Action in the Nervous System, New York: Academic Press.

Gevins A S and Cutillo B A (1995) Neuroelectric measures of mind. In: P L Nunez (Au), Neocortical Dynamics and Human EEG Rhythms. N Y: Oxford U. Press, pp. 304-338.

Gevins A S, Le J, Martin N, Brickett P, Desmond J, and Reutter B (1994) High resolution EEG: 124-channel recording, spatial enhancement, and MRI integration methods. Electroencephalography and Clin. Neurophysiology 90: 337-358.

Gevins A S, Smith M E, McEvoy L and Yu D (1997) High-resolution mapping of cortical activation related to working memory: effects of task difficulty, type of processing, and practice. Cerebral Cortex 7: 374-385.

Haken H (1983) Synergetics: An Introduction, 3rd Edition, Springer-Verlag.

Haken H (1999) What can synergetics contribute to the understanding of brain functioning? In: Analysis of Neurophysiological Brain Functioning, C Uhl (Ed), Berlin: Springer-Verlag, pp 7-40.

Ingber L (1995) Statistical mechanics of multiple scales of neocortical interactions. In: P L Nunez (Au), Neocortical Dynamics and Human EEG Rhythms. NY: Oxford U. Press, 628-681.

Izhikevich E M (1999) Weakly connected quasi-periodic oscillators, FM interactions, and multiplexing in the brain, SIAM J. Applied Mathematics 59: 2193-2223.

Jirsa V K and Haken H (1997) A derivation of a macroscopic field theory of the brain from the quasi-microscopic neural dynamics. Physica D 99: 503-526.

Jirsa V K and Kelso J A S (2000) Spatiotemporal pattern formation in continuous systems with heterogeneous connection topologies. Physical Review E 62: 8462-8465.

Katznelson R D (1981) Normal modes of the brain: Neuroanatomical basis and a physiological theoretical model. In PL Nunez (Au), Electric Fields of the Brain: The Neurophysics of EEG, 1st Edition, NY: Oxford U. Press, pp 401-442.

Klimesch W (1996) Memory processes, brain oscillations and EEG synchronization. International J. Psychophysiology 24: 61-100.

Law S K, Nunez P L and Wijesinghe R S (1993) High resolution EEG using spline generated surface Laplacians on spherical and ellipsoidal surfaces. IEEE Transactions on Biomedical Engineering 40: 145-153.

Liley D T J, Cadusch P J and Dafilis M P (2002) A spatially continuous mean field theory of electrocortical activity network. Computation in Neural Systems 13: 67-113.

Malmuvino J and Plonsey R (1995) Bioelectromagetism. N Y: Oxford U. Press.

Niedermeyer E and Lopes da Silva F H (Eds) (2005) Electroencephalography. Basic Principals, Clin. Applications, and Related Fields. Fifth Edition. London: Williams and Wilkins.

Nunez P L (1989) Generation of human EEG by a combination of long and short range neocortical interactions. Brain Topography 1: 199-215.

Nunez P L (1995) Neocortical Dynamics and Human EEG Rhythms. NY: Oxford U. Press.

Nunez P L (2000) Toward a large-scale quantitative description of neocortical dynamic function and EEG (Target article), Behavioral and Brain Sciences 23: 371-398.

Nunez P L (2000) Neocortical dynamic theory should be as simple as possible, but not simpler (Response to 18 commentaries on target article), Behavioral and Brain Sciences 23: 415-437.

Nunez P L (2002) EEG. In V S Ramachandran (Ed) Encyclopedia of the Human Brain, La Jolla: Academic Press, 169-179.

Nunez P L and Silberstein R B (2001) On the relationship of synaptic activity to macroscopic measurements: Does co-registration of EEG with fMRI make sense? Brain Topog. 13:79-96.

Nunez P L and Srinivasan R (2006) Electric Fields of the Brain: The Neurophysics of EEG, 2nd Edition, NY: Oxford U. Press.

Nunez P L and Srinivasan R (2006) A theoretical basis for standing and traveling brain waves measured with human EEG with implications for an integrated consciousness. Clin. Neurophysiology 117: 2424-2435.

Nunez P L, Srinivasan R, Westdorp A F, Wijesinghe R S, Tucker D M, Silberstein R B, and Cadusch P J (1997) EEG coherency I: Statistics, reference electrode, volume conduction, Laplacians, cortical imaging, and interpretation at multiple scales. Electroencephalography and Clin. Neurophysiology 103: 516-527.

Nunez P L. Wingeier B M and Silberstein R B (2001) Spatial-temporal structures of human alpha rhythms: theory, micro-current sources, multiscale measurements, and global binding of local networks, Human Brain Mapping 13: 125-164.

Nuwer M (1997) Assessment of digital EEG, quantitative EEG, and EEG brain mapping: report of the American Academy of Neurology and the American Clin. Neurophysiology Society. Neurology 49: 277-292.

Penfield W and Jasper H D (1954) Epilepsy and the Functional Anatomy of the Human Brain. London: Little, Brown and Co.

Robinson P A, Rennie C J, Rowe D L and O'Conner S C (2004) Estimation of multiscale neurophysiologic parameters by electroencephalographic means. Human Brain Mapping 23: 53-72.

Scott A C (1995) Stairway to the Mind. New York: Springer-Verlag.

Silberstein R B, Danieli F and Nunez P L (2003) Fronto-parietal evoked potential synchronization is increased during mental rotation, NeuroReport 14: 67-71.

Silberstein R B, Song J, Nunez P L and Park W (2004) Dynamic sculpting of brain functional connectivity is correlated with performance, Brain Topography 16: 240-254.

Srinivasan R and Petrovic S (2006) MEG phase follows conscious perception during binocular rivalry induced by visual stream segregation. Cerebral Cortex, 16: 597-608.

Srinivasan R, Nunez P L and Silberstein R B (1998) Spatial filtering and neocortical dynamics: estimates of EEG coherence. IEEE Trans. on Biomedical Engineering, 45: 814-825.

Srinivasan R, Russell D P, Edelman G M, and Tononi G (1999) Frequency tagging competing stimuli in binocular rivalry reveals increased synchronization of neuromagnetic responses during conscious perception. J. Neuroscience 19: 5435-5448.

Uhl C (Ed) (1999) Analysis of Neurophysiological Brain Functioning. Berlin: Springer-Verlag, Wingeier B M, Nunez P L and Silberstein R B (2001) Spherical harmonic decomposition applied to spatial-temporal analysis of human high-density electroencephalogram. Physical Review E 64: 051916-1 to 9.

TABLE 1

Comparison of EEG bands

| Band | Freq. (Hz) | Location | Normally | Pathologically |
|---|---|---|---|---|
| Delta | <4 | frontally in adults, posteriorly in children; high-amplitude waves | adult slow-wave sleep<br>in babies<br>Has been found during some continuous-attention tasks | subcortical lesions<br>diffuse lesions<br>metabolic encephalopathy<br>hydrocephalus<br>deep midline lesions |
| Theta | 4-7 | Found in locations not related to task at hand | higher in young children<br>drowsiness in adults and teens<br>idling<br>Associated with inhibition of elicited responses (has been found to spike in situations where a person is actively trying to repress a response or action). | focal subcortical lesions<br>metabolic encephalopathy<br>deep midline disorders<br>some instances of hydrocephalus |

TABLE 1-continued

Comparison of EEG bands

| Band | Freq. (Hz) | Location | Normally | Pathologically |
|---|---|---|---|---|
| Alpha | 8-15 | posterior regions of head, both sides, higher in amplitude on dominant side. Central sites (c3-c4) at rest | relaxed/reflecting closing the eyes Also associated with inhibition control, seemingly with the purpose of timing inhibitory activity in different locations across the brain. | Coma |
| Beta | 16-31 | both sides, symmetrical distribution, most evident frontally; low-amplitude waves | range span: active calm → intense → stressed → mild obsessive active thinking, focus, high alert, anxious | Benzodiazepines (en.wikipedia.org/wiki/ Benzodiazepines) Dup15q syndrome |
| Gamma | >32 | Somatosensory cortex | Displays during cross-modal sensory processing (perception that combines two different senses, such as sound and sight) Also is shown during short-term memory matching of recognized objects, sounds, or tactile sensations | A decrease in gamma-band activity may be associated with cognitive decline, especially when related to the theta band; however, this has not been proven for use as a clinical diagnostic measurement |
| Mu | 8-12 | Sensorimotor cortex | Shows rest-state motor neurons. | Mu suppression could indicate that motor mirror neurons are working. Deficits in Mu suppression, and thus in mirror neurons, might play a role in autism. |

EEG AND qEEG: An EEG electrode will mainly detect the neuronal activity in the brain region just beneath it. However, the electrodes receive the activity from thousands of neurons. One square millimeter of cortex surface, for example, has more than 100,000 neurons. It is only when the input to a region is synchronized with electrical activity occurring at the same time that simple periodic waveforms in the EEG become distinguishable. The temporal pattern associated with specific brainwaves can be digitized and encoded a non-transient memory, and embodied in or referenced by, computer software.

EEG (electroencephalography) and MEG (magnetoencephalography) are available technologies to monitor brain electrical activity. Each generally has sufficient temporal resolution to follow dynamic changes in brain electrical activity. Electroencephalography (EEG) and quantitative electroencephalography (qEEG) are electrophysiological monitoring methods that analyze the electrical activity of the brain to measure and display patterns that correspond to cognitive states and/or diagnostic information. It is typically noninvasive, with the electrodes placed on the scalp, although invasive electrodes are also used in some cases. EEG signals may be captured and analyzed by a mobile device, often referred as "brain wearables". There are a variety of "brain wearables" readily available on the market today. EEGs can be obtained with a non-invasive method where the aggregate oscillations of brain electric potentials are recorded with numerous electrodes attached to the scalp of a person. Most EEG signals originate in the brain's outer layer (the cerebral cortex), believed largely responsible for our thoughts, emotions, and behavior. Cortical synaptic action generates electrical signals that change in the 10 to 100-millisecond range. Transcutaneous EEG signals are limited by the relatively insulating nature of the skull surrounding the brain, the conductivity of the cerebrospinal fluid and brain tissue, relatively low amplitude of individual cellular electrical activity, and distances between the cellular current flows and the electrodes. EEG is characterized by: (1) Voltage; (2) Frequency; (3) Spatial location; (4) Inter-hemispheric symmetries; (5) Reactivity (reaction to state change); (6) Character of waveform occurrence (random, serial, continuous); and (7) Morphology of transient events. EEGs can be separated into two main categories. Spontaneous EEG which occur in the absence of specific sensory stimuli and evoked potentials (EPs) which are associated with sensory stimuli like repeated light flashes, auditory tones, finger pressure or mild electric shocks. The latter is recorded for example by time averaging to remove effects of spontaneous EEG. Non-sensory triggered potentials are also known. EP's typically are time synchronized with the trigger, and thus have an organization principle. Event-related potentials (ERPs) provide evidence of a direct link between cognitive events and brain electrical activity in a wide range of cognitive paradigms. It has generally been held that an ERP is the result of a set of discrete stimulus-evoked brain events. Event-related potentials (ERPs) are recorded in the same way as EPs, but occur at longer latencies from the stimuli and are more associated with an endogenous brain state.

Typically, a magnetic sensor with sufficient sensitivity to individual cell depolarization or small groups is a superconducting quantum interference device (SQIUD), which requires cryogenic temperature operation, either at liquid nitrogen temperatures (high temperature superconductors, HTS) or at liquid helium temperatures (low temperature superconductors, LTS). However, current research shows possible feasibility of room temperature superconductors (20 C). Magnetic sensing has an advantage, due to the dipole nature of sources, of having better potential volumetric localization; however, due to this added information, complexity of signal analysis is increased.

In general, the electromagnetic signals detected represent action potentials, an automatic response of a nerve cell to depolarization beyond a threshold, which briefly opens conduction channels. The cells have ion pumps which seek to maintain a depolarized state. Once triggered, the action potential propagates along the membrane in two-dimensions, causing a brief high level of depolarizing ion flow. There is a quiescent period after depolarization that generally prevents oscillation within a single cell. Since the exon extends from the body of the neuron, the action potential will typically proceed along the length of the axon, which terminates in a synapse with another cell. While direct electrical connections between cells occur, often the axon releases a neurotransmitter compound into the synapse, which causes a depolarization or hyperpolarization of the target cell. Indeed, the result may also be release of a hormone or peptide, which may have a local or more distant effect.

The electrical fields detectable externally tend to not include signals which low frequency signals, such as static levels of polarization, or cumulative depolarizing or hyperpolarizing effects between action potentials. In myelinated tracts, the current flows at the segments tend to be small, and therefore the signals from individual cells are small. Therefore, the largest signal components are from the synapses and cell bodies. In the cerebrum and cerebellum, these structures are mainly in the cortex, which is largely near the skull, making electroencephalography useful, since it provides spatial discrimination based on electrode location. However, deep signals are attenuated, and poorly localized. Magnetoencephalography detects dipoles, which derive from current flow, rather than voltage changes. In the case of a radially or spherically symmetric current flow within a short distance, the dipoles will tend to cancel, while net current flows long axons will reinforce. Therefore, an electroencephalogram reads a different signal than a magnetoencephalogram.

EEG-based studies of emotional specificity at the single-electrode level demonstrated that asymmetric activity at the frontal site, especially in the alpha (8-12 Hz) band, is associated with emotion. Voluntary facial expressions of smiles of enjoyment produce higher left frontal activation. Decreased left frontal activity is observed during the voluntary facial expressions of fear. In addition to alpha band activity, theta band power at the frontal midline (Fm) has also been found to relate to emotional states. Pleasant (as opposed to unpleasant) emotions are associated with an increase in frontal midline theta power. Many studies have sought to utilize pattern classification, such as neural networks, statistical classifiers, clustering algorithms, etc., to differentiate between various emotional states reflected in EEG.

EEG-based studies of emotional specificity at the single-electrode level demonstrated that asymmetric activity at the frontal site, especially in the alpha (8-12 Hz) band, is associated with emotion. Ekman and Davidson found that voluntary facial expressions of smiles of enjoyment produced higher left frontal activation (Ekman P, Davidson R J (1993) Voluntary Smiling Changes Regional Brain Activity. Psychol Sci 4: 342-345). Another study by Coan et al. found decreased left frontal activity during the voluntary facial expressions of fear (Coan J A, Allen J J, Harmon-Jones E (2001) Voluntary facial expression and hemispheric asymmetry over the frontal cortex. Psychophysiology 38: 912-925). In addition to alpha band activity, theta band power at the frontal midline (Fm) has also been found to relate to emotional states. Sammler and colleagues, for example, showed that pleasant (as opposed to unpleasant) emotion is associated with an increase in frontal midline theta power (Sammler D, Grigutsch M, Fritz T, Koelsch S (2007) Music and emotion: Electrophysiological correlates of the processing of pleasant and unpleasant music. Psychophysiology 44: 293-304). To further demonstrate whether these emotion-specific EEG characteristics are strong enough to differentiate between various emotional states, some studies have utilized a pattern classification analysis approach. See, for example:

Dan N, Xiao-Wei W, Li-Chen S, Bao-Liang L. EEG-based emotion recognition during watching movies; 2011 Apr. 27, 2011-May 1. 2011:667-670;

Lin Y P, Wang C H, Jung T P, Wu T L, Jeng S K, et al. (2010) EEG-Based Emotion Recognition in Music Listening. Ieee T Bio Med Eng 57: 1798-1806;

Murugappan M, Nagarajan R, Yaacob S (2010) Classification of human emotion from EEG using discrete wavelet transform. J Biomed Sci Eng 3: 390-396;

Murugappan M, Nagarajan R, Yaacob S (2011) Combining Spatial Filtering and Wavelet Transform for Classifying Human Emotions Using EEG Signals. J Med. Bio. Eng. 31: 45-51.

Detecting different emotional states by EEG may be more appropriate using EEG-based functional connectivity. There are various ways to estimate EEG-based functional brain connectivity: correlation, coherence and phase synchronization indices between each pair of EEG electrodes had been used. The assumption is that a higher correlation map indicates a stronger relationship between two signals. (Brazier M A, Casby J U (1952) Cross-correlation and autocorrelation studies of electroencephalographic potentials. Electroen clin neuro 4: 201-211). Coherence gives information similar to correlation, but also includes the covariation between two signals as a function of frequency. (Cantero J L, Atienza M, Salas R M, Gomez C M (1999) Alpha EEG coherence in different brain states: an electrophysiological index of the arousal level in human subjects. Neurosci lett 271: 167-70.) The assumption is that higher correlation indicates a stronger relationship between two signals. (Guevara M A, Corsi-Cabrera M (1996) EEG coherence or EEG correlation? Int J Psychophysiology 23: 145-153; Cantero J L, Atienza M, Salas R M, Gomez C M (1999) Alpha EEG coherence in different brain states: an electrophysiological index of the arousal level in human subjects. Neurosci lett 271: 167-70; Adler G, Brassen S, Jajcevic A (2003) EEG coherence in Alzheimer's dementia. J Neural Transm 110: 1051-1058; Deeny S P, Hillman C H, Janelle C M, Hatfield B D (2003) Cortico-cortical communication and superior performance in skilled marksmen: An EEG coherence analysis. J Sport Exercise Psy 25: 188-204.) Phase synchronization among the neuronal groups estimated based on the phase difference between two signals is another way to estimate the EEG-based functional connectivity among brain areas. It is. (Franaszczuk P J, Bergey G K (1999) An autoregressive method for the measurement of synchronization of interictal and ictal EEG signals. Biol Cybern 81: 3-9.)

A number of groups have examined emotional specificity using EEG-based functional brain connectivity. For example, Shin and Park showed that, when emotional states become more negative at high room temperatures, correlation coefficients between the channels in temporal and occipital sites increase (Shin J-H, Park D-H. (2011) Analysis for Characteristics of Electroencephalogram (EEG) and Influence of Environmental Factors According to Emotional Changes. In Lee G, Howard D, Ślęzak D, editors. Convergence and Hybrid Information Technology. Springer Berlin Heidelberg, 488-500.) Hinrichs and Machleidt demonstrated that coherence decreases in the alpha band during sadness, compared to happiness (Hinrichs H, Machleidt W (1992) Basic emotions reflected in EEG-coherences. Int J Psychophysiol 13: 225-232). Miskovic and Schmidt found that EEG coherence between the prefrontal cortex and the posterior cortex increased while viewing highly emotionally arousing (i.e., threatening) images, compared to viewing neutral images (Miskovic V, Schmidt L A (2010) Cross-regional cortical synchronization during affective image viewing. Brain Res 1362: 102-111). Costa and colleagues applied the synchronization index to detect interaction in different brain sites under different emotional states (Costa T, Rognoni E, Galati D (2006) EEG phase synchronization during emotional response to positive and negative film stimuli. Neurosci Lett 406: 159-164). Costa's results showed an overall increase in the synchronization index among frontal channels during emotional stimulation, particularly during negative emotion (i.e., sadness). Furthermore, phase synchronization patterns were found to differ between positive and negative emotions. Costa also found that sadness was more synchronized than happiness at each frequency band and was associated with a wider synchronization both between the right and left frontal sites and within the left hemisphere. In contrast, happiness was associated with a wider synchronization between the frontal and occipital sites.

Different connectivity indices are sensitive to different characteristics of EEG signals. Correlation is sensitive to phase and polarity, but is independent of amplitudes. Changes in both amplitude and phase lead to a change in coherence (Guevara M A, Corsi-Cabrera M (1996) EEG coherence or EEG correlation? Int J Psychophysiol 23: 145-153). The phase synchronization index is only sensitive to a change in phase (Lachaux J P, Rodriguez E, Martinerie J, Varela F J (1999) Measuring phase synchrony in brain signals. Hum Brain Mapp 8: 194-208).

A number of studies have tried to classify emotional states by means of recording and statistically analyzing EEG signals from the central nervous systems. See for example:

Lin Y P, Wang C H, Jung T P, Wu T L, Jeng S K, et al. (2010) EEG-Based Emotion Recognition in Music Listening. IEEE T Bio Med Eng 57:1798-1806

Murugappan M, Nagarajan R, Yaacob S (2010) Classification of human emotion from EEG using discrete wavelet transform. J Biomed Sci Eng 3: 390-396.

Murugappan M, Nagarajan R, Yaacob S (2011) Combining Spatial Filtering and Wavelet Transform for Classifying Human Emotions Using EEG Signals. J Med. Bio. Eng. 31: 45-51.

Berkman E, Wong D K, Guimaraes M P, Uy E T, Gross J J, et al. (2004) Brain wave recognition of emotions in EEG. Psychophysiology 41: S71-S71.

Chanel G, Kronegg J, Grandjean D, Pun T (2006) Emotion assessment: Arousal evaluation using EEG's and peripheral physiological signals. Multimedia Content Representation, Classification and Security 4105: 530-537.

Hagiwara KIaM (2003) A Feeling Estimation System Using a Simple Electroencephalograph. IEEE International Conference on Systems, Man and Cybernetics. 4204-4209.

You-Yun Lee and Shulan Hsieh studied different emotional states by means of EEG-based functional connectivity patterns. They used emotional film clips to elicit three different emotional states.

The dimensional theory of emotion, which asserts that there are neutral, positive, and negative emotional states, may be used to classify emotional states, because numerous studies have suggested that the responses of the central nervous system correlate with emotional valence and arousal. (See for example, Davidson R J (1993) Cerebral Asymmetry and Emotion—Conceptual and Methodological Conundrums. Cognition Emotion 7: 115-138; Jones N A, Fox N A (1992) Electroencephalogram asymmetry during emotionally evocative films and its relation to positive and negative affectivity. Brain Cogn 20: 280-299; Schmidt L A, Trainor L J (2001) Frontal brain electrical activity (EEG) distinguishes valence and intensity of musical emotions. Cognition Emotion 15: 487-500; Tomarken A J, Davidson R J, Henriques J B (1990) Resting frontal brain asymmetry predicts affective responses to films. J Pers Soc Psychol 59: 791-801.) As suggested by Mauss and Robins (2009), "measures of emotional responding appear to be structured along dimensions (e.g., valence, arousal) rather than discrete emotional states (e.g., sadness, fear, anger)".

EEG-based functional connectivity change was found to be significantly different among emotional states of neutral, positive, or negative. Lee Y-Y, Hsieh S (2014) Classifying Different Emotional States by Means of EEG-Based Functional Connectivity Patterns. PLoS ONE 9(4): e95415. doi.org/10.1371/journal.pone.0095415. A connectivity pattern may be detected by pattern classification analysis using Quadratic Discriminant Analysis. The results indicated that the classification rate was better than chance. They concluded that estimating EEG-based functional connectivity provides a useful tool for studying the relationship between brain activity and emotional states.

Emotions affects learning. Intelligent Tutoring Systems (ITS) learner model initially composed of a cognitive module was extended to include a psychological module and an emotional module. Alicia Heraz et al. introduced an emomental agent. It interacts with an ITS to communicate the emotional state of the learner based upon his mental state. The mental state was obtained from the learner's brainwaves. The agent learns to predict the learner's emotions by using machine learning techniques. (Alicia Heraz, Ryad Razaki; Claude Frasson, "Using machine learning to predict learner emotional state from brainwaves" Advanced Learning Technologies, 2007. ICALT 2007. Seventh IEEE International Conference on Advanced Learning Technologies (ICALT 2007)) See also:

Ella T. Mampusti, Jose S. Ng, Jarren James I. Quinto, Grizelda L. Teng, Merlin Teodosia C. Suarez, Rhia S. Trogo, "Measuring Academic Affective States of Students via Brainwave Signals", Knowledge and Systems Engineering (KSE) 2011 Third International Conference on, pp. 226-231, 2011

Judith J. Azcarraga, John Francis Ibanez Jr., Ianne Robert Lim, Nestor Lumanas Jr., "Use of Personality Profile in Predicting Academic Emotion Based on Brainwaves Signals and Mouse Behavior", Knowledge and Systems Engineering (KSE) 2011 Third International Conference on, pp. 239-244, 2011.

Yi-Hung Liu, Chien-Te Wu, Yung-Hwa Kao, Ya-Ting Chen, "Single-trial EEG-based emotion recognition using kernel Eigen-emotion pattern and adaptive support vector machine", Engineering in Medicine and Biology Society (EMBC) 2013 35th Annual International Conference of the IEEE, pp. 4306-4309, 2013, ISSN 1557-170X.

Thong Tri Vo, Nam Phuong Nguyen, Toi Vo Van, IFMBE Proceedings, vol. 63, pp. 621, 2018, ISSN 1680-0737, ISBN 978-981-10-4360-4.

Adrian Rodriguez Aguiñaga, Miguel Angel Lopez Ramirez, Lecture Notes in Computer Science, vol. 9456, pp. 177, 2015, ISSN 0302-9743, ISBN 978-3-319-26507-0.

Judith Azcarraga, Merlin Teodosia Suarez, "Recognizing Student Emotions using Brainwaves and Mouse Behavior Data", International Journal of Distance Education Technologies, vol. 11, pp. 1, 2013, ISSN 1539-3100.

Tri Thong Vo, Phuong Nam Nguyen, Van Toi Vo, IFMBE Proceedings, vol. 61, pp. 67, 2017, ISSN 1680-0737, ISBN 978-981-10-4219-5.

Alicia Heraz, Claude Frasson, Lecture Notes in Computer Science, vol. 5535, pp. 367, 2009, ISSN 0302-9743, ISBN 978-3-642-02246-3.

Hamwira Yaacob, Wahab Abdul, Norhaslinda Kamaruddin, "Classification of EEG signals using MLP based on categorical and dimensional perceptions of emotions", Information and Communication Technology for the Muslim World (ICT4M) 2013 5th International Conference on, pp. 1-6, 2013.

Yuan-Pin Lin, Chi-Hong Wang, Tzyy-Ping Jung, Tien-Lin Wu, Shyh-Kang Jeng, Jeng-Ren Duann, Jyh-Horng Chen, "EEG-Based Emotion Recognition in Music Listening", Biomedical Engineering IEEE Transactions on, vol. 57, pp. 1798-1806, 2010, ISSN 0018-9294.

Yi-Hung Liu, Wei-Teng Cheng, Yu-Tsung Hsiao, Chien-Te Wu, Mu-Der Jeng, "EEG-based emotion recognition based on kernel Fisher's discriminant analysis and spectral powers", Systems Man and Cybernetics (SMC) 2014 IEEE International Conference on, pp. 2221-2225, 2014.

Using EEG to assess the emotional state has numerous practical applications. One of the first such applications was the development of a travel guide based on emotions by measuring brainwaves by the Singapore tourism group. "By studying the brainwaves of a family on vacation, the researchers drew up the Singapore Emotion Travel Guide, which advises future visitors of the emotions they can expect to experience at different attractions." (www.lonelyplanet.com/news/2017/04/12/singapore-emotion-travel-guide) Joel Pearson at University of New South Wales and his group developed the protocol of measuring brainwaves of travelers using EEG and decoding specific emotional states.

Another recently released application pertains to virtual reality (VR) technology. On Sep. 18, 2017, Looxid Labs launched a technology that harnesses EEG from a subject waring a VR headset. Looxid Labs intention is to factor in brain waves into VR applications in order to accurately infer emotions. Other products such as MindMaze and even Samsung have tried creating similar applications through facial muscles recognition. (scottamyx.com/2017/10/13/looxid-labs-vr-brain-waves-human-emotions/). According to its website (looxidlabs.com/device-2/), the Looxid Labs Development Kit provides a VR headset embedded with miniaturized eye and brain sensors. It uses 6 EEG channels: Fp1, Fp2, AF7, AF8, AF3, AF4 in international 10-20 system.

To assess a user's state of mind, a computer may be used to analyze the EEG signals produced by the brain of the user. However, the emotional states of a brain are complex, and the brain waves associated with specific emotions seem to change over time. Wei-Long Zheng at Shanghai Jiao Tong University used machine learning to identify the emotional brain states and to repeat it reliably. The machine learning algorithm found a set of patterns that clearly distinguished positive, negative, and neutral emotions that worked for different subjects and for the same subjects over time with an accuracy of about 80 percent. (See Wei-Long Zheng, Jia-Yi Zhu, Bao-Liang Lu, Identifying Stable Patterns over Time for Emotion Recognition from EEG, arxiv.org/abs/1601.02197; see also How One Intelligent Machine Learned to Recognize Human Emotions, MIT Technology Review, Jan. 23, 2016.)

MEG: Magnetoencephalography (MEG) is a functional neuroimaging technique for mapping brain activity by recording magnetic fields produced by electrical currents occurring naturally in the brain, using very sensitive magnetometers. Arrays of SQUIDs (superconducting quantum interference devices) are currently the most common magnetometer, while the SERF (spin exchange relaxation-free) magnetometer is being investigated (Hämäläinen, Matti; Hari, Riitta; Ilmoniemi, Risto J; Knuutila, Jukka; Lounasmaa, Ollii V. (1993). "Magnetoencephalography-theory, instrumentation, and applications to noninvasive studies of the working human brain". Reviews of Modern Physics. 65 (2): 413-497. ISSN 0034-6861. doi:10.1103/RevModPhys.65.413.) It is known that "neuronal activity causes local changes in cerebral blood flow, blood volume, and blood oxygenation" (Dynamic magnetic resonance imaging of human brain activity during primary sensory stimulation. K. K. Kwong, J. W. Belliveau, D. A. Chesler, I. E. Goldberg, R. M. Weisskoff, B. P. Poncelet, D. N. Kennedy, B. E. Hoppel, M. S. Cohen, and R. Turner). Using "a 122-channel D.C. SQUID magnetometer with a helmet-shaped detector array covering the subject's head" it has been shown that the "system allows simultaneous recording of magnetic activity all over the head." (122-channel squid instrument for investigating the magnetic signals from the human brain.) A. I. Ahonen, M. S. Hämäläinen, M. J. Kajola, J. E. T. Knuutila, P. P. Laine, O. V. Lounasmaa, L. T. Parkkonen, J. T. Simola, and C. D. Tesche Physica Scripta, Volume 1993, T49A).

In some cases, magnetic fields cancel, and thus the detectable electrical activity may fundamentally differ from the detectable electrical activity obtained via EEG. However, the main types of brain rhythms are detectable by both methods.

See: U.S. Pat. Nos. 5,059,814; 5,118,606; 5,136,687; 5,224,203; 5,303,705; 5,325,862; 5,461,699; 5,522,863; 5,640,493; 5,715,821; 5,719,561; 5,722,418; 5,730,146; 5,736,543; 5,737,485; 5,747,492; 5,791,342; 5,816,247; 6,497,658; 6,510,340; 6,654,729; 6,893,407; 6,950,697; 8,135,957; 8,620,206; 8,644,754; 9,118,775; 9,179,875; 9,642,552; 20030018278; 20030171689; 20060293578; 20070156457; 20070259323; 20080015458; 20080154148; 20080229408; 20100010365; 20100076334; 20100090835; 20120046531; 20120052905; 20130041281; 20150081299; 20150262016. See EP1304073A2; EP1304073A3; WO2000025668A1; and WO2001087153A1.

MEGs seek to detect the magnetic dipole emission from an electrical discharge in cells, e.g., neural action potentials. Typical sensors for MEGs are superconducting quantum interference devices (SQUIDs). These currently require cooling to liquid nitrogen or liquid helium temperatures. However, the development of room temperature, or near room temperature superconductors, and miniature cryocoolers, may permit field deployments and portable or mobile detectors. Because MEGs are less influenced by medium conductivity and dielectric properties, and because they inherently detect the magnetic field vector, MEG technology permits volumetric mapping of brain activity and distinction of complementary activity that might suppress detectable EEG signals. MEG technology also supports vector mapping of fields, since magnetic emitters are inherently dipoles, and therefore a larger amount of information is inherently available.

See, U.S. Pat. Nos. 4,862,359; 5,027,817; 5,198,977; 5,230,346; 5,269,315; 5,309,923; 5,325,862; 5,331,970; 5,546,943; 5,568,816; 5,662,109; 5,724,987; 5,797,853; 5,840,040; 5,845,639; 6,042,548; 6,080,164; 6,088,611; 6,097,980; 6,144,872; 6,161,031; 6,171,239; 6,240,308; 6,241,686; 6,280,393; 6,309,361; 6,319,205; 6,322,515; 6,356,781; 6,370,414; 6,377,833; 6,385,479; 6,390,979; 6,402,689; 6,419,629; 6,466,816; 6,490,472; 6,526,297; 6,527,715; 6,530,884; 6,547,746; 6,551,243; 6,553,252; 6,622,036; 6,644,976; 6,648,880; 6,663,571; 6,684,098; 6,697,660; 6,728,564; 6,740,032; 6,743,167; 6,773,400; 6,907,280; 6,947,790; 6,950,698; 6,963,770; 6,963,771; 6,996,261; 7,010,340; 7,011,814; 7,022,083; 7,092,748; 7,104,947; 7,105,824; 7,120,486; 7,130,673; 7,171,252; 7,177,675; 7,231,245; 7,254,500; 7,283,861; 7,286,871; 7,338,455; 7,346,395; 7,378,056; 7,461,045; 7,489,964; 7,490,085; 7,499,745; 7,510,699; 7,539,528; 7,547,284; 7,565,193; 7,567,693; 7,577,472; 7,613,502; 7,627,370; 7,647,098; 7,653,433; 7,697,979; 7,729,755; 7,754,190; 7,756,568; 7,766,827; 7,769,431; 7,778,692; 7,787,937; 7,787,946; 7,794,403; 7,831,305; 7,840,250; 7,856,264; 7,860,552; 7,899,524; 7,904,139; 7,904,144; 7,933,645; 7,962,204; 7,983,740; 7,986,991; 8,000,773; 8,000,793; 8,002,553; 8,014,847; 8,036,434; 8,065,360; 8,069,125; 8,086,296; 8,121,694; 8,190,248; 8,190,264; 8,197,437; 8,224,433; 8,233,682; 8,233,965; 8,236,038; 8,262,714; 8,280,514; 8,295,914; 8,306,607; 8,306,610; 8,313,441; 8,326,433; 8,337,404; 8,346,331; 8,346,342; 8,356,004; 8,358,818; 8,364,271; 8,380,289; 8,380,290; 8,380,314; 8,391,942; 8,391,956; 8,423,125; 8,425,583; 8,429,225; 8,445,851; 8,457,746; 8,467,878; 8,473,024; 8,498,708; 8,509,879; 8,527,035; 8,532,756; 8,538,513; 8,543,189; 8,554,325; 8,562,951; 8,571,629; 8,586,932; 8,591,419; 8,606,349; 8,606,356; 8,615,479; 8,626,264; 8,626,301; 8,632,750; 8,644,910; 8,655,817; 8,657,756; 8,666,478; 8,679,009; 8,684,926; 8,690,748; 8,696,722; 8,706,205; 8,706,241; 8,706,518; 8,712,512; 8,717,430; 8,725,669; 8,738,395; 8,761,869; 8,761,889; 8,768,022; 8,805,516; 8,814,923; 8,831,731; 8,834,546; 8,838,227; 8,849,392; 8,849,632; 8,852,103; 8,855,773; 8,858,440; 8,868,174; 8,888,702; 8,915,741; 8,918,162; 8,938,289; 8,938,290; 8,951,189; 8,951,192; 8,956,277; 8,965,513; 8,977,362; 8,989,836; 8,998,828; 9,005,126; 9,020,576; 9,022,936; 9,026,217; 9,026,218; 9,028,412; 9,033,884; 9,037,224; 9,042,201; 9,050,470; 9,067,052; 9,072,905; 9,084,896; 9,089,400; 9,089,683; 9,092,556; 9,095,266; 9,101,276; 9,107,595; 9,116,835; 9,133,024; 9,144,392; 9,149,255; 9,155,521; 9,167,970; 9,167,976; 9,167,977; 9,167,978; 9,171,366; 9,173,609; 9,179,850; 9,179,854; 9,179,858; 9,179,875; 9,192,300; 9,198,637; 9,198,707; 9,204,835; 9,211,077; 9,211,212; 9,213,074; 9,242,067; 9,247,890; 9,247,924; 9,248,288; 9,254,097; 9,254,383; 9,268,014; 9,268,015; 9,271,651; 9,271,674; 9,282,930; 9,289,143; 9,302,110; 9,308,372; 9,320,449; 9,322,895; 9,326,742; 9,332,939; 9,336,611; 9,339,227; 9,357,941; 9,367,131; 9,370,309; 9,375,145; 9,375,564; 9,387,320; 9,395,425; 9,402,558; 9,403,038; 9,414,029; 9,436,989; 9,440,064; 9,463,327; 9,470,728; 9,471,978; 9,474,852; 9,486,632; 9,492,313; 9,560,967; 9,579,048; 9,592,409; 9,597,493; 9,597,494; 9,615,789; 9,616,166; 9,655,573; 9,655,669; 9,662,049; 9,662,492; 9,669,185; 9,675,292; 9,682,232; 9,687,187; 9,707,396; 9,713,433; 9,713,444; 20010020127; 20010021800; 20010051774; 20020005784; 20020016552; 20020017994; 20020042563; 20020058867; 20020099273; 20020099295; 20020103428; 20020103429; 20020128638; 20030001098; 20030009096; 20030013981; 20030032870; 20030040660; 20030068605; 20030074032; 20030093004; 20030093005; 20030120140; 20030128801; 20030135128; 20030153818; 20030163027; 20030163028; 20030181821; 20030187359; 20030204135; 20030225335; 20030236458; 20040030585; 20040059241; 20040072133; 20040077960; 20040092809; 20040096395; 20040097802; 20040116798; 20040122787; 20040122790; 20040144925; 20040204656; 20050004489; 20050007091; 20050027284; 20050033122; 20050033154; 20050033379; 20050079474; 20050079636; 20050106713; 20050107654; 20050119547; 20050131311; 20050136002; 20050159670; 20050159671; 20050182456; 20050192514; 20050222639; 20050283053; 20060004422; 20060015034; 20060018525; 20060036152; 20060036153; 20060051814; 20060052706; 20060058683; 20060074290; 20060074298; 20060078183; 20060084858; 20060100526; 20060111644; 20060116556; 20060122481; 20060129324; 20060173510; 20060189866; 20060241373; 20060241382; 20070005115; 20070007454; 20070008172; 20070015985; 20070032737; 20070055145; 20070100251; 20070138886; 20070179534; 20070184507; 20070191704; 20070191727; 20070203401; 20070239059; 20070250138; 20070255135; 20070293760; 20070299370; 20080001600; 20080021332; 20080021340; 20080033297; 20080039698; 20080039737; 20080042067; 20080058664; 20080091118; 20080097197; 20080123927; 20080125669; 20080128626; 20080154126; 20080167571; 20080221441; 20080230702; 20080230705; 20080249430; 20080255949; 20080275340; 20080306365; 20080311549; 20090012387; 20090018407; 20090018431; 20090018462; 20090024050; 20090048507; 20090054788; 20090054800; 20090054958; 20090062676; 20090078875; 20090082829; 20090099627; 20090112117; 20090112273; 20090112277; 20090112278; 20090112279; 20090112280; 20090118622; 20090131995; 20090137923; 20090156907; 20090156955; 20090157323; 20090157481; 20090157482; 20090157625; 20090157662; 20090157751; 20090157813; 20090163777; 20090164131; 20090164132; 20090171164; 20090172540; 20090177050; 20090179642; 20090191131; 20090209845; 20090216091; 20090220429; 20090221928; 20090221930; 20090246138; 20090264785; 20090267758; 20090270694; 20090287271; 20090287272; 20090287273; 20090287274; 20090287467; 20090292180; 20090292713; 20090292724; 20090299169; 20090304582; 20090306531; 20090306534; 20090318773; 20090318794; 20100021378; 20100030073; 20100036233; 20100036453; 20100041962; 20100042011; 20100049276; 20100069739; 20100069777; 20100076274; 20100082506; 20100087719; 20100094154; 20100094155; 20100099975; 20100106043; 20100113959; 20100114193; 20100114237; 20100130869; 20100143256; 20100163027; 20100163028; 20100163035; 20100168525; 20100168529; 20100168602; 20100189318; 20100191095; 20100191124; 20100204748; 20100248275; 20100249573; 20100261993; 20100298735; 20100324441; 20110004115; 20110004412; 20110009777; 20110015515; 20110015539; 20110028859; 20110034821; 20110046491; 20110054345; 20110054562; 20110077503; 20110092800; 20110092882; 20110112394; 20110112426; 20110119212; 20110125048; 20110125238; 20110129129; 20110144521; 20110160543; 20110160607; 20110160608; 20110161011; 20110178359; 20110178441; 20110178442; 20110207988; 20110208094; 20110213200; 20110218405; 20110230738; 20110257517; 20110263962; 20110263968; 20110270074; 20110270914; 20110275927; 20110295143; 20110295166; 20110301448; 20110306845; 20110306846; 20110307029; 20110313268; 20110313487; 20120004561; 20120021394; 20120022343;

20120022884; 20120035765; 20120046531; 20120046971; 20120053449; 20120053483; 20120078327; 20120083700; 20120108998; 20120130228; 20120130229; 20120149042; 20120150545; 20120163689; 20120165899; 20120165904; 20120197163; 20120215114; 20120219507; 20120226091; 20120226185; 20120232327; 20120232433; 20120245493; 20120253219; 20120253434; 20120265267; 20120271148; 20120271151; 20120271376; 20120283502; 20120283604; 20120296241; 20120296253; 20120296569; 20120302867; 20120310107; 20120310298; 20120316793; 20130012804; 20130063434; 20130066350; 20130066391; 20130066394; 20130072780; 20130079621; 20130085678; 20130096441; 20130096454; 20130102897; 20130109996; 20130110616; 20130116561; 20130131755; 20130138177; 20130172716; 20130178693; 20130184728; 20130188854; 20130204085; 20130211238; 20130226261; 20130231580; 20130238063; 20130245422; 20130245424; 20130245486; 20130261506; 20130274586; 20130281879; 20130281890; 20130289386; 20130304153; 20140000630; 20140005518; 20140031703; 20140057232; 20140058241; 20140058292; 20140066763; 20140081115; 20140088377; 20140094719; 20140094720; 20140111335; 20140114207; 20140119621; 20140128763; 20140135642; 20140148657; 20140151563; 20140155952; 20140163328; 20140163368; 20140163409; 20140171749; 20140171757; 20140171819; 20140180088; 20140180092; 20140180093; 20140180094; 20140180095; 20140180096; 20140180097; 20140180099; 20140180100; 20140180112; 20140180113; 20140180176; 20140180177; 20140193336; 20140194726; 20140200414; 20140211593; 20140228649; 20140228702; 20140243614; 20140243652; 20140243714; 20140249360; 20140249445; 20140257073; 20140270438; 20140275807; 20140275851; 20140275891; 20140276013; 20140276014; 20140276187; 20140276702; 20140279746; 20140296646; 20140296655; 20140303425; 20140303486; 20140316248; 20140323849; 20140330268; 20140330394; 20140335489; 20140336489; 20140340084; 20140343397; 20140357962; 20140364721; 20140371573; 20140378830; 20140378941; 20150011866; 20150011877; 20150018665; 20150018905; 20150024356; 20150025408; 20150025422; 20150025610; 20150029087; 20150033245; 20150033258; 20150033259; 20150033262; 20150033266; 20150035959; 20150038812; 20150038822; 20150038869; 20150039066; 20150073237; 20150080753; 20150088120; 20150119658; 20150119689; 20150119698; 20150140528; 20150141529; 20150141773; 20150150473; 20150151142; 20150157266; 20150165239; 20150174418; 20150182417; 20150196800; 20150201879; 20150208994; 20150219732; 20150223721; 20150227702; 20150230744; 20150246238; 20150247921; 20150257700; 20150290420; 20150297106; 20150297893; 20150305799; 20150305800; 20150305801; 20150306340; 20150313540; 20150317796; 20150320591; 20150327813; 20150335281; 20150335294; 20150339363; 20150343242; 20150359431; 20150360039; 20160001065; 20160001096; 20160001098; 20160008620; 20160008632; 20160015289; 20160022165; 20160022167; 20160022168; 20160022206; 20160027342; 20160029946; 20160029965; 20160038049; 20160038559; 20160048659; 20160051161; 20160051162; 20160058354; 20160058392; 20160066828; 20160066838; 20160081613; 20160100769; 20160120480; 20160128864; 20160143541; 20160143574; 20160151018; 20160151628; 20160157828; 20160158553; 20160166219; 20160184599; 20160196393; 20160199241; 20160203597; 20160206380; 20160206871; 20160206877; 20160213276; 20160235324; 20160235980; 20160235983; 20160239966; 20160239968; 20160245670; 20160245766; 20160270723; 20160278687; 20160287118; 20160287436; 20160296746; 20160302720; 20160303397; 20160303402; 20160320210; 20160339243; 20160341684; 20160361534; 20160366462; 20160371721; 20170021161; 20170027539; 20170032098; 20170039706; 20170042474; 20170043167; 20170065349; 20170079538; 20170080320; 20170085855; 20170086729; 20170086763; 20170087367; 20170091418; 20170112403; 20170112427; 20170112446; 20170112577; 20170147578; 20170151435; 20170160360; 20170164861; 20170164862; 20170164893; 20170164894; 20170172527; 20170173262; 20170185714; 20170188862; 20170188866; 20170188868; 20170188869; 20170188932; 20170189691; 20170196501; and 20170202633.

Allen, Philip B., et al. High-temperature superconductivity. Springer Science & Business Media, 2012;

Fausti, Daniele, et al. "Light-induced superconductivity in a stripe-ordered cuprate." Science 331.6014 (2011): 189-191;

Inoue, Mitsuteru, et al. "Investigating the use of magnonic crystals as extremely sensitive magnetic field sensors at room temperature." Applied Physics Letters 98.13 (2011): 132511;

Kaiser, Stefan, et al. "Optically induced coherent transport far above Tc in underdoped YBa2 Cu3O6+δ." Physical Review B 89.18 (2014):184516;

Malik, M. A., and B. A. Malik. "High Temperature Superconductivity: Materials, Mechanism and Applications." Bulgarian J. Physics 41.4 (2014).

Mankowsky, Roman, et al. "Nonlinear lattice dynamics as a basis for enhanced superconductivity in YBa2Cu3O6. 5." arXiv preprint arXiv:1405.2266 (2014);

Mcfetridge, Grant. "Room temperature superconductor." U.S. Pub. App. No. 20020006875.

Mitrano, Matteo, et al. "Possible light-induced superconductivity in K3C60 at high temperature." Nature 530.7591 (2016): 461-464;

Mourachkine, Andrei. Room-temperature superconductivity. Cambridge Int Science Publishing, 2004;

Narlikar, Anant V., ed. High Temperature Superconductivity 2. Springer Science & Business Media, 2013;

Pickett, Warren E. "Design for a room-temperature superconductor." J. superconductivity and novel magnetism 19.3 (2006): 291-297;

Sleight, Arthur W. "Room temperature superconductors." Accounts of chemical research 28.3 (1995): 103-108.

Hämäläinen, Matti; Hari, Riitta; Ilmoniemi, Risto J; Knuutila, Jukka; Lounasmaa, Olli V. (1993). "Magnetoencephalography-theory, instrumentation, and applications to noninvasive studies of the working human brain". Reviews of Modern Physics. 65 (2): 413-497. ISSN 0034-6861. doi:10.1103/RevModPhys.65.413.

EEGs and MEGs can monitor the state of consciousness. For example, states of deep sleep are associated with slower EEG oscillations of larger amplitude. Various signal analysis methods allow for robust identifications of distinct sleep stages, depth of anesthesia, epileptic seizures and connections to detailed cognitive events.

Positron Emission Tomography (PET) Scan: A PET scan is an imaging test that helps reveal how tissues and organs are functioning (Bailey, D. L; D. W. Townsend; P. E. Valk; M. N. Maisey (2005). Positron Emission Tomography: Basic Sciences. Secaucus, NJ: Springer-Verlag. ISBN 1-85233-798-2.). A PET scan uses a radioactive drug (positron-emitting tracer) to show this activity. It uses this radiation to produce 3-D, images colored for the different activity of the brain. See, e.g.:

Jarden, Jens O., Vijay Dhawan, Alexander Poltorak, Jerome B. Posner, and David A. Rottenberg. "Positron emission tomographic measurement of blood-to-brain and bloodto-tumor transport of 82Rb: The effect of dexamethasone and whole-brain radiation therapy." Annals of neurology 18, no. 6 (1985): 636-646.

Dhawan, V. I. J. A. Y., A. Poltorak, J. R. Moeller, J. O. Jarden, S. C. Strother, H. Thaler, and D. A. Rottenberg. "Positron emission tomographic measurement of blood-to-brain and blood-to-tumour transport of 82Rb. I: Error analysis and computer simulations." Physics in medicine and biology 34, no. 12 (1989): 1773.

U.S. Pat. Nos. 4,977,505; 5,331,970; 5,568,816; 5,724,987; 5,825,830; 5,840,040; 5,845,639; 6,053,739; 6,132,724; 6,161,031; 6,226,418; 6,240,308; 6,266,453; 6,364,845; 6,408,107; 6,490,472; 6,547,746; 6,615,158; 6,633,686; 6,644,976; 6,728,424; 6,775,405; 6,885,886; 6,947,790; 6,996,549; 7,117,026; 7,127,100; 7,150,717; 7,254,500; 7,309,315; 7,355,597; 7,367,807; 7,383,237; 7,483,747; 7,583,857; 7,627,370; 7,647,098; 7,678,047; 7,738,683; 7,778,490; 7,787,946; 7,876,938; 7,884,101; 7,890,155; 7,901,211; 7,904,144; 7,961,922; 7,983,762; 7,986,991; 8,002,553; 8,069,125; 8,090,164; 8,099,299; 8,121,361; 8,126,228; 8,126,243; 8,148,417; 8,148,418; 8,150,796; 8,160,317; 8,167,826; 8,170,315; 8,170,347; 8,175,359; 8,175,360; 8,175,686; 8,180,125; 8,180,148; 8,185,186; 8,195,593; 8,199,982; 8,199,985; 8,233,689; 8,233,965; 8,249,815; 8,303,636; 8,306,610; 8,311,747; 8,311,748; 8,311,750; 8,315,812; 8,315,813; 8,315,814; 8,321,150; 8,356,004; 8,358,818; 8,374,411; 8,379,947; 8,386,188; 8,388,529; 8,423,118; 8,430,816; 8,463,006; 8,473,024; 8,496,594; 8,520,974; 8,523,779; 8,538,108; 8,571,293; 8,574,279; 8,577,103; 8,588,486; 8,588,552; 8,594,950; 8,606,356; 8,606,361; 8,606,530; 8,606,592; 8,615,479; 8,630,812; 8,634,616; 8,657,756; 8,664,258; 8,675,936; 8,675,983; 8,680,119; 8,690,748; 8,706,518; 8,724,871; 8,725,669; 8,734,356; 8,734,357; 8,738,395; 8,754,238; 8,768,022; 8,768,431; 8,785,441; 8,787,637; 8,795,175; 8,812,245; 8,812,246; 8,838,201; 8,838,227; 8,861,819; 8,868,174; 8,871,797; 8,913,810; 8,915,741; 8,918,162; 8,934,685; 8,938,102; 8,980,891; 8,989,836; 9,025,845; 9,034,911; 9,037,224; 9,042,201; 9,053,534; 9,064,036; 9,076,212; 9,078,564; 9,081,882; 9,082,169; 9,087,147; 9,095,266; 9,138,175; 9,144,392; 9,149,197; 9,152,757; 9,167,974; 9,171,353; 9,171,366; 9,177,379; 9,177,416; 9,179,854; 9,186,510; 9,198,612; 9,198,624; 9,204,835; 9,208,430; 9,208,557; 9,211,077; 9,221,755; 9,226,672; 9,235,679; 9,256,982; 9,268,902; 9,271,657; 9,273,035; 9,275,451; 9,282,930; 9,292,858; 9,295,838; 9,305,376; 9,311,335; 9,320,449; 9,328,107; 9,339,200; 9,339,227; 9,367,131; 9,370,309; 9,390,233; 9,396,533; 9,401,021; 9,402,558; 9,412,076; 9,418,368; 9,434,692; 9,436,989; 9,449,147; 9,451,303; 9,471,978; 9,472,000; 9,483,613; 9,495,684; 9,556,149; 9,558,558; 9,560,967; 9,563,950; 9,567,327; 9,582,152; 9,585,723; 9,600,138; 9,600,778; 9,604,056; 9,607,377; 9,613,186; 9,652,871; 9,662,083; 9,697,330; 9,706,925; 9,717,461; 9,729,252; 9,732,039; 9,734,589; 9,734,601; 9,734,632; 9,740,710; 9,740,946; 9,741,114; 9,743,835; RE45336; RE45337; 20020032375; 20020183607; 20030013981; 20030028348; 20030031357; 20030032870; 20030068605; 20030128801; 20030233039; 20030233250; 20030234781; 20040049124; 20040072133; 20040116798; 20040151368; 20040184024; 20050007091; 20050065412; 20050080124; 20050096311; 20050118286; 20050144042; 20050215889; 20050244045; 20060015153; 20060074290; 20060084858; 20060129324; 20060188134; 20070019846; 20070032737; 20070036402; 20070072857; 20070078134; 20070081712; 20070100251; 20070127793; 20070280508; 20080021340; 20080069446; 20080123927; 20080167571; 20080219917; 20080221441; 20080241804; 20080247618; 20080249430; 20080279436; 20080281238; 20080286453; 20080287774; 20080287821; 20080298653; 20080298659; 20080310697; 20080317317; 20090018407; 20090024050; 20090036781; 20090048507; 20090054800; 20090074279; 20090099783; 20090143654; 20090148019; 20090156907; 20090156955; 20090157323; 20090157481; 20090157482; 20090157625; 20090157660; 20090157751; 20090157813; 20090163777; 20090164131; 20090164132; 20090164302; 20090164401; 20090164403; 20090164458; 20090164503; 20090164549; 20090171164; 20090172540; 20090221904; 20090246138; 20090264785; 20090267758; 20090270694; 20090271011; 20090271120; 20090271122; 20090271347; 20090290772; 20090292180; 20090292478; 20090292551; 20090299435; 20090312595; 20090312668; 20090316968; 20090316969; 20090318773; 20100004762; 20100010316; 20100010363; 20100014730; 20100014732; 20100015583; 20100017001; 20100022820; 20100030089; 20100036233; 20100041958; 20100041962; 20100041964; 20100042011; 20100042578; 20100063368; 20100069724; 20100069777; 20100076249; 20100080432; 20100081860; 20100081861; 20100094155; 20100100036; 20100125561; 20100130811; 20100130878; 20100135556; 20100142774; 20100163027; 20100163028; 20100163035; 20100168525; 20100168529; 20100168602; 20100172567; 20100179415; 20100189318; 20100191124; 20100219820; 20100241449; 20100249573; 20100260402; 20100268057; 20100268108; 20100274577; 20100274578; 20100280332; 20100293002; 20100305962; 20100305963; 20100312579; 20100322488; 20100322497; 20110028825; 20110035231; 20110038850; 20110046451; 20110077503; 20110125048; 20110152729; 20110160543; 20110229005; 20110230755; 20110263962; 20110293193; 20120035765; 20120041318; 20120041319; 20120041320; 20120041321; 20120041322; 20120041323; 20120041324; 20120041498; 20120041735; 20120041739; 20120053919; 20120053921; 20120059246; 20120070044; 20120080305; 20120128683; 20120150516; 20120207362; 20120226185; 20120263393; 20120283502; 20120288143; 20120302867; 20120316793; 20120321152; 20120321160; 20120323108; 20130018596; 20130028496; 20130054214; 20130058548; 20130063434; 20130064438; 20130066618; 20130085678; 20130102877; 20130102907; 20130116540; 20130144192; 20130151163; 20130188830; 20130197401; 20130211728; 20130226464; 20130231580; 20130237541; 20130243287; 20130245422; 20130274586; 20130318546; 20140003696; 20140005518; 20140018649; 20140029830; 20140058189; 20140063054; 20140063055; 20140067740; 20140081115; 20140107935; 20140119621; 20140133720; 20140133722; 20140148693; 20140155770; 20140163627; 20140171757; 20140194726; 20140207432; 20140211593; 20140222113; 20140222406; 20140226888; 20140236492; 20140243663; 20140247970; 20140249791; 20140249792; 20140257073; 20140270438; 20140343397; 20140348412; 20140350380; 20140355859; 20140371573; 20150010223; 20150012466; 20150019241; 20150029087; 20150033245; 20150033258; 20150033259; 20150033262; 20150033266; 20150073141; 20150073722; 20150080753; 20150088015; 20150088478; 20150150530; 20150150753; 20150157266; 20150161326; 20150161348; 20150174418; 20150196800; 20150199121; 20150201849; 20150216762; 20150227793; 20150257700; 20150272448; 20150287223; 20150294445; 20150297106; 20150306340; 20150317796; 20150324545; 20150327813; 20150332015; 20150335303; 20150339459; 20150343242; 20150363941; 20150379230; 20160004396; 20160004821; 20160004957; 20160007945; 20160019693; 20160027178; 20160027342; 20160035093; 20160038049; 20160038770; 20160048965; 20160067496; 20160070436; 20160073991; 20160082319; 20160110517;

20160110866; 20160110867; 20160113528; 20160113726; 20160117815; 20160117816; 20160117819; 20160128661; 20160133015; 20160140313; 20160140707; 20160151018; 20160155005; 20160166205; 20160180055; 20160203597; 20160213947; 20160217586; 20160217595; 20160232667; 20160235324; 20160239966; 20160239968; 20160246939; 20160263380; 20160284082; 20160296287; 20160300352; 20160302720; 20160364859; 20160364860; 20160364861; 20160366462; 20160367209; 20160371455; 20160374990; 20170024886; 20170027539; 20170032524; 20170032527; 20170032544; 20170039706; 20170053092; 20170061589; 20170076452; 20170085855; 20170091418; 20170112577; 20170128032; 20170147578; 20170148213; 20170168566; 20170178340; 20170193161; 20170198349; 20170202621; 20170213339; 20170216595; 20170221206; and 20170231560.

fMRI: Functional magnetic resonance imaging or functional MRI (fMRI) is a functional neuroimaging procedure using MRI technology that measures brain activity by detecting changes associated with blood flow ("Magnetic Resonance, a critical peer-reviewed introduction; functional MRI". European Magnetic Resonance Forum. Retrieved 17 Nov. 2014; Huettel, Song & McCarthy (2009)).

Yukiyasu Kamitani et al., Neuron (DOI: 10.1016/j.neuron.2008.11.004) used an image of brain activity taken in a functional MRI scanner to recreate a black-and-white image from scratch. See also 'Mind-reading' software could record your dreams" By Celeste Biever. New Scientist, 12 Dec. 2008. (www.newscientist.com/artide/dn16267-mind-reading-software-could-record-your-dreams/)

See, U.S. Pat. Nos. 6,622,036; 7,120,486; 7,177,675; 7,209,788; 7,489,964; 7,697,979; 7,754,190; 7,856,264; 7,873,411; 7,962,204; 8,060,181; 8,224,433; 8,315,962; 8,320,649; 8,326,433; 8,356,004; 8,380,314; 8,386,312; 8,392,253; 8,532,756; 8,562,951; 8,626,264; 8,632,750; 8,655,817; 8,679,009; 8,684,742; 8,684,926; 8,698,639; 8,706,241; 8,725,669; 8,831,731; 8,849,632; 8,855,773; 8,868,174; 8,915,871; 8,918,162; 8,939,903; 8,951,189; 8,951,192; 9,026,217; 9,037,224; 9,042,201; 9,050,470; 9,072,905; 9,084,896; 9,095,266; 9,101,276; 9,101,279; 9,135,221; 9,161,715; 9,192,300; 9,230,065; 9,248,286; 9,248,288; 9,265,458; 9,265,974; 9,292,471; 9,296,382; 9,302,110; 9,308,372; 9,345,412; 9,367,131; 9,420,970; 9,440,646; 9,451,899; 9,454,646; 9,463,327; 9,468,541; 9,474,481; 9,475,502; 9,489,854; 9,505,402; 9,538,948; 9,579,247; 9,579,457; 9,615,746; 9,693,724; 9,693,734; 9,694,155; 9,713,433; 9,713,444; 20030093129; 20030135128; 20040059241; 20050131311; 20050240253; 20060015034; 20060074822; 20060129324; 20060161218; 20060167564; 20060189899; 20060241718; 20070179534; 20070244387; 20080009772; 20080091118; 20080125669; 20080228239; 20090006001; 20090009284; 20090030930; 20090062676; 20090062679; 20090082829; 20090132275; 20090137923; 20090157662; 20090164132; 20090209845; 20090216091; 20090220429; 20090270754; 20090287271; 20090287272; 20090287273; 20090287467; 20090290767; 20090292713; 20090297000; 20090312808; 20090312817; 20090312998; 20090318773; 20090326604; 20090327068; 20100036233; 20100049276; 20100076274; 20100094154; 20100143256; 20100145215; 20100191124; 20100298735; 20110004412; 20110028827; 20110034821; 20110092882; 20110106750; 20110119212; 20110256520; 20110306845; 20110306846; 20110313268; 20110313487; 20120035428; 20120035765; 20120052469; 20120060851; 20120083668; 20120108909; 20120165696; 20120203725; 20120212353; 20120226185; 20120253219; 20120265267; 20120271376; 20120296569; 20130031038; 20130063550; 20130080127; 20130085678; 20130130799; 20130131755; 20130158883; 20130185145; 20130218053; 20130226261; 20130226408; 20130245886; 20130253363; 20130338803; 20140058528; 20140114889; 20140135642; 20140142654; 20140154650; 20140163328; 20140163409; 20140171757; 20140200414; 20140200432; 20140211593; 20140214335; 20140243652; 20140276549; 20140279746; 20140309881; 20140315169; 20140347265; 20140371984; 20150024356; 20150029087; 20150033245; 20150033258; 20150033259; 20150033262; 20150033266; 20150038812; 20150080753; 20150094962; 20150112899; 20150119658; 20150164431; 20150174362; 20150174418; 20150196800; 20150227702; 20150248470; 20150257700; 20150290453; 20150290454; 20150297893; 20150305685; 20150324692; 20150327813; 20150339363; 20150343242; 20150351655; 20150359431; 20150360039; 20150366482; 20160015307; 20160027342; 20160031479; 20160038049; 20160048659; 20160051161; 20160051162; 20160055304; 20160107653; 20160120437; 20160144175; 20160152233; 20160158553; 20160206380; 20160213276; 20160262680; 20160263318; 20160302711; 20160306942; 20160324457; 20160357256; 20160366462; 20170027812; 20170031440; 20170032098; 20170042474; 20170043160; 20170043167; 20170061034; 20170065349; 20170085547; 20170086727; 20170087302; 20170091418; 20170113046; 20170188876; 20170196501; 20170202476; 20170202518; and 20170206913.

Functional near infrared spectroscopy (fNIRS): fNIR is a non-invasive imaging method involving the quantification of chromophore concentration resolved from the measurement of near infrared (NIR) light attenuation or temporal or phasic changes. NIR spectrum light takes advantage of the optical window in which skin, tissue, and bone are mostly transparent to NIR light in the spectrum of 700-900 nm, while hemoglobin (Hb) and deoxygenated-hemoglobin (deoxy-Hb) are stronger absorbers of light. Differences in the absorption spectra of deoxy-Hb and oxy-Hb allow the measurement of relative changes in hemoglobin concentration through the use of light attenuation at multiple wavelengths. Two or more wavelengths are selected, with one wavelength above and one below the isosbestic point of 810 nm at which deoxy-Hb and oxy-Hb have identical absorption coefficients. Using the modified Beer-Lambert law (mBLL), relative concentration can be calculated as a function of total photon path length. Typically, the light emitter and detector are placed ipsilaterally on the subjects skull so recorded measurements are due to back-scattered (reflected) light following elliptical pathways. The use of fNIR as a functional imaging method relies on the principle of neuro-vascular coupling also known as the hemodynamic response or blood-oxygen-level dependent (BOLD) response. This principle also forms the core of fMRI techniques. Through neuro-vascular coupling, neuronal activity is linked to related changes in localized cerebral blood flow. fNIR and fMRI are sensitive to similar physiologic changes and are often comparative methods. Studies relating fMRI and fNIR show highly correlated results in cognitive tasks. fNIR has several advantages in cost and portability over fMRI, but cannot be used to measure cortical activity more than 4 cm deep due to limitations in light emitter power and has more limited spatial resolution. fNIR includes the use of diffuse optical tomography (DOT/NIRDOT) for functional purposes. Multiplexing fNIRS channels can allow 2D topographic functional maps of brain activity (e.g. with Hitachi ETG-4000 or Artinis Oxymon) while using multiple emitter spacings may be used to build 3D tomographic maps.

Beste Yuksel and Robert Jacob, Brain Automated Chorales (BACh), ACM CHI 2016, DOI: 10.1145/

2858036.2858388, provides a system that helps beginners learn to play Bach chorales on piano by measuring how hard their brains are working. This is accomplished by estimating the brain's workload using functional Near-Infrared Spectroscopy (fNIRS), a technique that measures oxygen levels in the brain—in this case in the prefrontal cortex. A brain that's working hard pulls in more oxygen. Sensors strapped to the player's forehead talk to a computer, which delivers the new music, one line at a time. See also "Mind-reading tech helps beginners quickly learn to play Bach." By Anna Nowogrodzki, New Scientist, 9 Feb. 2016 available online at www.newscientist.com/article/2076899-mind-reading-tech-helps-beginners-quickly-learn-to-play-bach/.

LORETA: Low-resolution brain electromagnetic tomography often referred as LORETA is a functional imaging technology usually using a linearly constrained minimum variance vector beamformer in the time-frequency domain as described in Gross et al., ""Dynamic imaging of coherent sources: Studying neural interactions in the human brain"", PNAS 98, 694-699, 2001. It allows to the image (mostly 3D) evoked and induced oscillatory activity in a variable time-frequency range, where time is taken relative to a triggered event. There are three categories of imaging related to the technique used for LORETA. See, wiki.besa.de/index.php?title=Source_Analysis_3D_Imaging#Multiple_Source_Beamformer_.28MSBF.29. The Multiple Source Beamformer (MSBF) is a tool for imaging brain activity. It is applied in the time-frequency domain and based on single-trial data. Therefore, it can image not only evoked, but also induced activity, which is not visible in time-domain averages of the data. Dynamic Imaging of Coherent Sources (DICS) can find coherence between any two pairs of voxels in the brain or between an external source and brain voxels. DICS requires time-frequency-transformed data and can find coherence for evoked and induced activity. The following imaging methods provides an image of brain activity based on a distributed multiple source model: CLARA is an iterative application of LORETA images, focusing the obtained 3D image in each iteration step. LAURA uses a spatial weighting function that has the form of a local autoregressive function. LORETA has the 3D Laplacian operator implemented as spatial weighting prior. sLORETA is an unweighted minimum norm that is standardized by the resolution matrix. swLORETA is equivalent to sLORETA, except for an additional depth weighting. SSLOFO is an iterative application of standardized minimum norm images with consecutive shrinkage of the source space. A User-defined volume image allows experimenting with the different imaging techniques. It is possible to specify user-defined parameters for the family of distributed source images to create a new imaging technique. If no individual MRI is available, the minimum norm image is displayed on a standard brain surface and computed for standard source locations. If available, an individual brain surface is used to construct the distributed source model and to image the brain activity. Unlike classical LORETA, cortical LORETA is not computed in a 3D volume, but on the cortical surface. Unlike classical CLARA, cortical CLARA is not computed in a 3D volume, but on the cortical surface. The Multiple Source Probe Scan (MSPS) is a tool for the validation of a discrete multiple source model. The Source Sensitivity image displays the sensitivity of a selected source in the current discrete source model and is, therefore, data independent.

See U.S. Pat. Nos. 4,562,540; 4,594,662; 5,650,726; 5,859,533; 6,026,173; 6,182,013; 6,294,917; 6,332,087; 6,393,363; 6,534,986; 6,703,838; 6,791,331; 6,856,830; 6,863,127; 7,030,617; 7,092,748; 7,119,553; 7,170,294; 7,239,731; 7,276,916; 7,286,871; 7,295,019; 7,353,065; 7,363,164; 7,454,243; 7,499,894; 7,648,498; 7,804,441; 7,809,434; 7,841,986; 7,852,087; 7,937,222; 8,000,795; 8,046,076; 8,131,526; 8,174,430; 8,188,749; 8,244,341; 8,263,574; 8,332,191; 8,346,365; 8,362,780; 8,456,166; 8,538,700; 8,565,883; 8,593,154; 8,600,513; 8,706,205; 8,711,655; 8,731,987; 8,756,017; 8,761,438; 8,812,237; 8,829,908; 8,958,882; 9,008,970; 9,035,657; 9,069,097; 9,072,449; 9,091,785; 9,092,895; 9,121,964; 9,133,709; 9,165,472; 9,179,854; 9,320,451; 9,367,738; 9,414,749; 9,414,763; 9,414,764; 9,442,088; 9,468,541; 9,513,398; 9,545,225; 9,557,439; 9,562,988; 9,568,635; 9,651,706; 9,675,254; 9,675,255; 9,675,292; 9,713,433; 9,715,032; 20020000808; 20020017905; 20030018277; 20030093004; 20040097802; 20040116798; 20040131998; 20040140811; 20040145370; 20050156602; 20060058856; 20060069059; 20060136135; 20060149160; 20060152227; 20060170424; 20060176062; 20060184058; 20060206108; 20070060974; 20070159185; 20070191727; 20080033513; 20080097235; 20080125830; 20080125831; 20080183072; 20080242976; 20080255816; 20080281667; 20090039889; 20090054801; 20090082688; 20090099783; 20090216146; 20090261832; 20090306534; 20090312663; 20100010366; 20100030097; 20100042011; 20100056276; 20100092934; 20100132448; 20100134113; 20100168053; 20100198519; 20100231221; 20100238763; 20110004115; 20110050232; 20110160607; 20110308789; 20120010493; 20120011927; 20120016430; 20120083690; 20120130641; 20120150257; 20120162002; 20120215448; 20120245474; 20120268272; 20120269385; 20120296569; 20130091941; 20130096408; 20130141103; 20130231709; 20130289385; 20130303934; 20140015852; 20140025133; 20140058528; 20140066739; 20140107519; 20140128763; 20140155740; 20140161352; 20140163328; 20140163893; 20140228702; 20140243714; 20140275944; 20140276012; 20140323899; 20150051663; 20150112409; 20150119689; 20150137817; 20150145519; 20150157235; 20150167459; 20150177413; 20150248615; 20150257648; 20150257649; 20150301218; 20150342472; 20160002523; 20160038049; 20160040514; 20160051161; 20160051162; 20160091448; 20160102500; 20160120436; 20160136427; 20160187524; 20160213276; 20160220821; 20160223703; 20160235983; 20160245952; 20160256109; 20160259085; 20160262623; 20160298449; 20160334534; 20160345856; 20160356911; 20160367812; 20170001016; 20170067323; 20170138132; and 20170151436.

Neurofeedback: Neurofeedback (NFB), also called neurotherapy or neurobiofeedback, is a type of biofeedback that uses real-time displays of brain activity-most commonly electroencephalography (EEG), to teach self-regulation of brain function. Typically, sensors are placed on the scalp to measure activity, with measurements displayed using video displays or sound. The feedback may be in various other forms as well. Typically, the feedback is sought to be presented through primary sensory inputs, but this is not a limitation on the technique.

The applications of neurofeedback to enhance performance extend to the arts in fields such as music, dance, and acting. A study with conservatoire musicians found that alpha-theta training benefitted the three music domains of musicality, communication, and technique. Historically, alpha-theta training, a form of neurofeedback, was created to assist creativity by inducing hypnagogia, a "borderline waking state associated with creative insights", through facilitation of neural connectivity. Alpha-theta training has also been shown to improve novice singing in children. Alpha-theta neurofeedback, in conjunction with heart rate variability training, a form of biofeedback, has also produced benefits in dance by enhancing performance in competitive ballroom dancing and increasing cognitive creativity in contemporary dancers. Additionally, neurofeedback has also been shown to instill a superior flow state in actors, possibly due to greater immersion while performing.

Several studies of brain wave activity in experts while performing a task related to their respective area of expertise revealed certain characteristic telltale signs of so-called "flow" associated with top-flight performance. Mihaly Csikszentmihalyi (University of Chicago) found that the most skilled chess players showed less EEG activity in the prefrontal cortex, which is typically associated with higher cognitive processes such as working memory and verbalization, during a game.

Chris Berka et al., Advanced Brain Monitoring, Carlsbad, California, The International J. Sport and Society, vol 1, p 87, looked at the brain waves of Olympic archers and professional golfers. A few seconds before the archers fired off an arrow or the golfers hit the ball, the team spotted a small increase in alpha band patterns. This may correspond to the contingent negative variation observed in evoked potential studies, and the Bereitschafts potential or BP (from German, "readiness potential"), also called the pre-motor potential or readiness potential (RP), a measure of activity in the motor cortex and supplementary motor area of the brain leading up to voluntary muscle movement. Berka also trained novice marksmen using neurofeedback. Each person was hooked up to electrodes that tease out and display specific brain waves, along with a monitor that measured their heartbeat. By controlling their breathing and learning to deliberately manipulate the waveforms on the screen in front of them, the novices managed to produce the alpha waves characteristic of the flow state. This, in turn, helped them improve their accuracy at hitting the targets.

Low Energy Neurofeedback System (LENS): The LENS, or Low Energy Neurofeedback System, uses a very low power electromagnetic field, to carry feedback to the person receiving it. The feedback travels down the same wires carrying the brain waves to the amplifier and computer. Although the feedback signal is weak, it produces a measurable change in the brainwaves without conscious effort from the individual receiving the feedback. The system is software controlled, to receive input from EEG electrodes, to control the stimulation. Through the scalp. Neurofeedback uses a feedback frequency that is different from, but correlates with, the dominant brainwave frequency. When exposed to this feedback frequency, the EEG amplitude distribution changes in power. Most of the time the brain waves reduce in power; but at times they also increase in power. In either case the result is a changed brainwave state, and much greater ability for the brain to regulate itself.

Content-Based Brainwave Analysis: Memories are not unique. Janice Chen, Nature Neuroscience, DOI: 10.1038/nn.4450, showed that when people describe the episode from Sherlock Holmes drama, their brain activity patterns were almost exactly the same as each other's, for each scene. Moreover, there's also evidence that, when a person tells someone else about it, they implant that same activity into their brain as well. Moreover, research in which people who have not seen a movie listen to someone else's description of it, Chen et al. have found that the listener's brain activity looks much like that of the person who has seen it. See also "Our brains record and remember things in exactly the same way" by Andy Coghlan, New Scientist, Dec. 5, 2016 (www.newscientist.com/artide/2115093-our-brains-record-and-remember-things-in-exactly-the-same-way/)

Brian Pasley, Frontiers in Neuroengineering, doi.org/whb, developed a technique for reading thoughts. The team hypothesized that hearing speech and thinking to oneself might spark some of the same neural signatures in the brain. They supposed that an algorithm trained to identify speech heard out loud might also be able to identify words that are thought. In the experiment, the decoder trained on speech was able to reconstruct which words several of the volunteers were thinking, using neural activity alone. See also "Hearing our inner voice" by Helen Thomson. New Scientist, Oct. 29, 2014 (www.newscientist.com/artide/mg22429934-000-brain-decoder-can-eavesdrop-on-your-inner-voice/)

Jack Gallant et al. were able to detect which of a set of images someone was looking at from a brain scan, using software that compared the subject's brain activity while looking at an image with that captured while they were looking at "training" photographs. The program then picked the most likely match from a set of previously unseen pictures.

Ann Graybiel and Mark Howe used electrodes to analyze brainwaves in the ventromedial striatum of rats while they were taught to navigate a maze. As rats were learning the task, their brain activity showed bursts of fast gamma waves. Once the rats mastered the task, their brainwaves slowed to almost a quarter of their initial frequency, becoming beta waves. Graybiel's team posited that this transition reflects when learning becomes a habit.

Bernard Balleine, Proceedings of the National Academy of Sciences, DOI: 10.1073/pnas.1113158108. See also "Habits form when brainwaves slow down" by Wendy Zukerman. New Scientist, Sep. 26, 2011 (www.newscientist.com/article/dn20964-habits-form-when-brain-waves-slow-down/) posits that the slower brainwaves may be the brain weeding out excess activity to refine behavior. He suggests it might be possible to boost the rate at which they learn a skill by enhancing such beta-wave activity.

U.S. Pat. No. 9,763,592 provides a system for instructing a user behavior change comprising: collecting and analyzing bioelectrical signal datasets; and providing a behavior change suggestion based upon the analysis. A stimulus may be provided to prompt an action by the user, which may be visual, auditory, or haptic. See also U.S. Pat. No. 9,622,660, 20170041699; 20130317384; 20130317382; 20130314243; 20070173733; and 20070066914.

The chess game is a good example of a cognitive task which needs a lot of training and experience. A number of EEG studies have been done on chess players. Pawel Stepien, Wlodzimierz Klonowski and Nikolay Suvorov, Nonlinear analysis of EEG in chess players, EPJ Nonlinear Biomedical Physics 20153:1, showed better applicability of Higuchi Fractal Dimension method for analysis of EEG signals related to chess tasks than that of Sliding Window Empirical Mode Decomposition. The paper shows that the EEG signal during the game is more complex, non-linear, and non-stationary even when there are no significant differences between the game and relaxed state in the contribution of different EEG bands to total power of the signal. There is the need of gathering more data from more chess experts and of comparing them with data from novice chess players. See also Junior, L. R. S., Cesar, F. H. G., Rocha, F. T., and Thomaz, C. E. EEG and Eye Movement Maps of Chess Players. Proceedings of the Sixth International Conference on Pattern Recognition Applications and Methods. (ICPRAM 2017) pp. 343-441. (fei.edu.br/~cet/icpram17_LaercioJunior.pdf).

Estimating EEG-based functional connectivity provides a useful tool for studying the relationship between brain activity and emotional states. See You-Yun Lee, Shulan Hsieh. Classifying Different Emotional States by Means of EEG-Based Functional Connectivity Patterns. Apr. 17, 2014, (doi.org/10.1371/journal.pone.0095415), which aimed to classify different emotional states by means of EEG-based functional connectivity patterns, and showed that the EEG-based functional connectivity change was significantly different among emotional states. Furthermore, the connectivity pattern was detected by pattern classification analysis using Quadratic Discriminant Analysis. The results indicated that the classification rate was better than chance. Estimating EEG-based functional connectivity provides a useful tool for studying the relationship between brain activity and emotional states.

Neuromodulation/Neuroenhancement: Neuromodulation is the alteration of nerve activity through targeted delivery of a stimulus, such as electrical stimulation or chemical agents, to specific neurological sites in the body. It is carried out to normalize—or modulate—nervous tissue function. Neuromodulation is an evolving therapy that can involve a range of electromagnetic stimuli such as a magnetic field (TMS, rTMS), an electric current (TES, e.g., tDCS, HD-tDCS, tACS, electrosleep), or a drug instilled directly in the subdural space (intrathecal drug delivery). Emerging applications involve targeted introduction of genes or gene regulators and light (optogenetics). The most clinical experience has been with electrical stimulation. Neuromodulation, whether electrical or magnetic, employs the body's natural biological response by stimulating nerve cell activity that can influence populations of nerves by releasing transmitters, such as dopamine, or other chemical messengers such as the peptide Substance P, that can modulate the excitability and firing patterns of neural circuits. There may also be more direct electrophysiological effects on neural membranes. According to some applications, the end effect is a "normalization" of a neural network function from its perturbed state. Presumed mechanisms of action for neurostimulation include depolarizing blockade, stochastic normalization of neural firing, axonal blockade, reduction of neural firing keratosis, and suppression of neural network oscillations. Although the exact mechanisms of neurostimulation are not known, the empirical effectiveness has led to considerable application clinically.

Neuroenhancement refers to the targeted enhancement and extension of cognitive and affective abilities based on an understanding of their underlying neurobiology in healthy persons who do not have any mental illness. As such, it can be thought of as an umbrella term that encompasses pharmacological and non-pharmacological methods of improving cognitive, affective, and motor functionality, as well as the overarching ethico-legal discourse that accompanies these aims. Critically, for any agent to qualify as a neuroenhancer, it must reliably engender substantial cognitive, affective, or motor benefits beyond normal functioning in healthy individuals (or in select groups of individuals having pathology), whilst causing few side effects: at most at the level of commonly used comparable legal substances or activities, such as caffeine, alcohol, and sleep-deprivation. Pharmacological neuroenhancement agents include the well-validated nootropics, such as racetam, vinpocetine, and phosphatidylserine, as well as other drugs used for treating patients suffering from neurological disorders. Non-pharmacological measures include non-invasive brain stimulation, which has been employed to improve various cognitive and affective functions, and brain-machine interfaces, which hold much potential to extend the repertoire of motor and cognitive actions available to humans.

Brain Stimulation: Non-invasive brain stimulation (NIBS) bypasses the correlative approaches of other imaging techniques, making it possible to establish a causal relationship between cognitive processes and the functioning of specific brain areas. NIBS can provide information about where a particular process occurs. NIBS offers the opportunity to study brain mechanisms beyond process localization, providing information about when activity in a given brain region is involved in a cognitive process, and even how it is involved. When using NIBS to explore cognitive processes, it is important to understand not only how NIBS functions but also the functioning of the neural structures themselves. Non-invasive brain stimulation (NIBS) methods, which include transcranial magnetic stimulation (TMS) and transcranial electric stimulation (TES), are used in cognitive neuroscience to induce transient changes in brain activity and thereby alter the behavior of the subject.

The application of NIBS aims at establishing the role of a given cortical area in an ongoing specific motor, perceptual or cognitive process. Physically, NIBS techniques affect neuronal states through different mechanisms. In TMS, a solenoid (coil) is used to deliver a strong and transient magnetic field, or "pulse," to induce a transitory electric current at the cortical surface beneath the coil. The pulse causes the rapid and above-threshold depolarization of cell membranes affected by the current, followed by the transynaptic depolarization or hyperpolarization of interconnected neurons. Therefore, strong TMS can induce a current that elicits action potentials in neurons, while weak (subthreshold) can modify susceptibility of cells to depolarization. A complex set of coils can deliver a complex 3D excitation field. By contrast, in TES techniques, the stimulation involves the application of weak electrical currents directly to the scalp through a pair of electrodes. As a result, TES induces a subthreshold polarization of cortical neurons that is too weak to generate an action potential. (Superthreshold tES corresponds to electroconvulsive therapy, which is a currently disfavored, but apparently effective treatment for depression). However, by changing the intrinsic neuronal excitability, TES can induce changes in the resting membrane potential and the postsynaptic activity of cortical neurons. This, in turn, can alter the spontaneous firing rate of neurons and modulate their response to afferent signals, leading to changes in synaptic efficacy. The typical application of NIBS involves different types of protocols: TMS can be delivered as a single pulse (spTMS) at a precise time, as pairs of pulses separated by a variable interval, or as a series of stimuli in conventional or patterned protocols of repetitive TMS (rTMS). In tES, different protocols are established by the electrical current used and by its polarity, which can be direct (anodal or cathodal transcranial direct current stimulation: tDCS), alternating at a fix frequency (transcranial alternating current stimulation: tACS), oscillating transcranial direct current stimulation (osc-tDCS), high-definition transcranial direct current stimulation (HD-tDCS), or at random frequencies (transcranial random noise stimulation: tRNS). (Nitsche et al., 2008; Paulus, 2011).

In general, the final effects of NIBS on the central nervous system depend on a lengthy list of parameters (e.g., frequency, temporal characteristics, intensity, geometric configuration of the coil/electrode, current direction), when it is delivered before (off-line) or during (on-line) the task as part of the experimental procedure. In addition, these factors interact with several variables related to the anatomy (e.g., properties of the brain tissue and its location), as well as physiological (e.g., gender and age) and cognitive states of the stimulated area/subject. The entrainment hypothesis, suggests the possibility of inducing a particular oscillation frequency in the brain using an external oscillatory force (e.g., rTMS, but also tACS). The physiological basis of oscillatory cortical activity lies in the timing of the interacting neurons; when groups of neurons synchronize their firing activities, brain rhythms emerge, network oscillations are generated, and the basis for interactions between brain areas may develop. Because of the variety of experimental protocols for brain stimulation, limits on descriptions of the actual protocols employed, and limited controls, consistency of reported studies is lacking, and extrapolability is limited. Thus, while there is some consensus in various aspects of the effects of extra cranial brain stimulation, the results achieved have a degree of uncertainty dependent on details of implementation. On the other hand, within a specific experimental protocol, it is possible to obtain statistically significant and repeatable results. This implies that feedback control might be effective to control implementation of the stimulation for a given purpose; however, prior studies that employ feedback control are lacking.

Changes in the neuronal threshold result from changes in membrane permeability (Liebetanz et al., 2002), which influence the response of the task-related network. The same mechanism of action may be responsible for both TES methods and TMS, i.e., the induction of noise in the system. However, the neural activity induced by TES will be highly influenced by the state of the system because it is a neuromodulatory method (Paulus, 2011), and its effect will depend on the activity of the stimulated area. Therefore, the final result will depend strongly on the task characteristics, the system state and the way in which TES will interact with such a state.

In TMS, the magnetic pulse causes a rapid increase in current flow, which can in some cases cause and above-threshold depolarization of cell membranes affected by the current, triggering an action potential, and leading to the trans-synaptic depolarization or hyperpolarization of connected cortical neurons, depending on their natural response to the firing of the stimulated neuron(s). Therefore, TMS activates a neural population that, depending on several factors, can be congruent (facilitate) or incongruent (inhibit) with task execution. TES induces a polarization of cortical neurons at a subthreshold level that is too weak to evoke an action potential. However, by inducing a polarity shift in the intrinsic neuronal excitability, TES can alter the spontaneous firing rate of neurons and modulate the response to afferent signals. In this sense, TES-induced effects are even more bound to the state of the stimulated area that is determined by the conditions. In short, NIBS leads to a stimulation-induced modulation of the state that can be substantially defined as noise induction. Induced noise will not be just random activity, but will depend on the interaction of many parameters, from the characteristics of the stimulation to the state.

The noise induced by NIBS will be influenced by the state of the neural population of the stimulated area. Although the types and number of neurons "triggered" by NIBS are theoretically random, the induced change in neuronal activity is likely to be correlated with ongoing activity, yet even if we are referring to a non-deterministic process, the noise introduced will not be a totally random element. Because it will be partially determined by the experimental variables, the level of noise that will be introduced by the stimulation and by the context can be estimated, as well as the interaction between the two levels of noise (stimulation and context). Known transcranial stimulation does not permit stimulation with a focused and highly targeted signal to a clearly defined area of the brain to establish a unique brain-behavior relationship; therefore, the known introduced stimulus activity in the brain stimulation is 'noise.'

Cosmetic neuroscience has emerged as a new field of research. Roy Hamilton, Samuel Messing, and Anjan Chatterjee, "Rethinking the thinking cap—Ethics of neural enhancement using noninvasive brain stimulation." Neurology, Jan. 11, 2011, vol. 76 no. 2 187-193. (www.neurology.org/content/76/2/187.) discuss the use noninvasive brain stimulation techniques such as transcranial magnetic stimulation and transcranial direct current stimulation to enhance neurologic function: cognitive skills, mood, and social cognition.

Electrical brain stimulation (EBS), or focal brain stimulation (FBS), is a form of clinical neurobiology electrotherapy used to stimulate a neuron or neural network in the brain through the direct or indirect excitation of cell membranes using an electric current. See, en.wikipedia.org/wiki/Electrical brain stimulation; U.S. Pat. Nos. 7,753,836; 7,94673; 8,545,378; 9,345,901; 9,610,456; 9,694,178; 20140330337; 20150112403; and 20150119689.

Motor skills can be affected by CNS stimulation.

See, U.S. Pat. Nos. 5,343,871; 5,742,748; 6,057,846; 6,390,979; 6,644,976; 6,656,137; 7,063,535; 7,558,622; 7,618,381; 7,733,224; 7,829,562; 7,863,272; 8,016,597; 8,065,240; 8,069,125; 8,108,036; 8,126,542; 8,150,796; 8,195,593; 8,356,004; 8,449,471; 8,461,988; 8,525,673; 8,525,687; 8,531,291; 8,591,419; 8,606,592; 8,615,479; 8,680,991; 8,682,449; 8,706,518; 8,747,336; 8,750,971; 8,764,651; 8,784,109; 8,858,440; 8,862,236; 8,938,289; 8,962,042; 9,005,649; 9,064,036; 9,107,586; 9,125,788; 9,138,579; 9,149,599; 9,173,582; 9,204,796; 9,211,077; 9,265,458; 9,351,640; 9,358,361; 9,380,976; 9,403,038; 9,418,368; 9,468,541; 9,495,684; 9,545,515; 9,549,691; 9,560,967; 9,577,992; 9,590,986; 20030068605; 20040072133; 20050020483; 20050032827; 20050059689; 20050153268; 20060014753; 20060052386; 20060106326; 20060191543; 20060229164; 20070031798; 20070138886; 20070276270; 20080001735; 20080004904; 20080243005; 20080287821; 20080294019; 20090005654; 20090018407; 20090024050; 20090118593; 20090119154; 20090132275; 20090156907; 20090156955; 20090157323; 20090157481; 20090157482; 20090157625; 20090157660; 20090157751; 20090157813; 20090163777; 20090164131; 20090164132; 20090164302; 20090164401; 20090164403; 20090164458; 20090164503; 20090164549; 20090171164; 20090172540; 20090221928; 20090267758; 20090271011; 20090271120; 20090271347; 20090312595; 20090312668; 20090318773; 20090318779; 20090319002; 20100004762; 20100015583; 20100017001; 20100022820; 20100041958; 20100042578; 20100063368; 20100069724; 20100076249; 20100081860; 20100081861; 20100100036; 20100125561; 20100130811; 20100145219; 20100163027; 20100163035; 20100168525; 20100168602; 20100280332; 20110015209; 20110015469; 20110082154; 20110105859; 20110115624; 20110152284; 20110178441; 20110181422; 20110288119; 20120092156; 20120092157; 20120130300; 20120143104; 20120164613; 20120177716; 20120316793; 20120330109; 20130009783; 20130018592; 20130034837; 20130053656; 20130054215; 20130085678; 20130121984; 20130132029; 20130137717; 20130144537; 20130184728; 20130184997; 20130211291; 20130231574; 20130281890; 20130289385; 20130330428; 20140039571; 20140058528; 20140077946; 20140094720; 20140104059; 20140148479; 20140155430; 20140163425;

20140207224; 20140235965; 20140249429; 20150025410; 20150025422; 20150068069; 20150071907; 20150141773; 20150208982; 20150265583; 20150290419; 20150294067; 20150294085; 20150294086; 20150359467; 20150379878; 20160001096; 20160007904; 20160007915; 20160030749; 20160030750; 20160067492; 20160074657; 20160120437; 20160140834; 20160198968; 20160206671; 20160220821; 20160303402; 20160351069; 20160360965; 20170046971; 20170065638; 20170080320; 20170084187; 20170086672; 20170112947; 20170127727; 20170131293; 20170143966; 20170151436; 20170157343; and 20170193831. See:

Abraham, W. C., 2008. Metaplasticity: tuning synapses and networks for plasticity. Nature Reviews Neuroscience 9, 387.

Abrahamyan, A., Clifford, C. W., Arabzadeh, E., Harris, J. A., 2011. Improving visual sensitivity with subthreshold transcranial magnetic stimulation. J. Neuroscience 31, 3290-3294.

Adrian, E. D., 1928. The Basis of Sensation. W. W. Norton, New York.

Amassian, V. E., Cracco, R. Q., Maccabee, P. J., Cracco, J. B., Rudell, A., Eberle, L., 1989. Suppression of visual perception by magnetic oil stimulation of human occipital cortex. Electroencephalography and Clin. Neurophysiology 74, 458-462.

Amassian, V. E., Eberle, L., Maccabee, P. J., Cracco, R. Q., 1992. Modelling magnetic oil excitation of human cerebral cortex with a peripheral nerve immersed in a brain-shaped volume conductor: the significance of fiber bending in excitation. Electroencephalography and Clin. Neurophysiology 85, 291-301.

Antal, A., Boros, K., Poreisz, C., Chaieb, L., Terney, D., Paulus, W., 2008. Comparatively weak after-effects of transcranial alternating current stimulation (tACS) on cortical excitability in humans. Brain Stimulation 1, 97-105.

Antal, A., Nitsche, M. A., Kruse, W., Kincses, T. Z., Hoffmann, K. P., Paulus, W., 2004. Direct current stimulation over V5 enhances visuomotor coordination by improving motion perception in humans. J. Cognitive Neuroscience 16, 521-527.

Ashbridge, E., Walsh, V., Cowey, A., 1997. Temporal aspects of visual search studied by transcranial magnetic stimulation. Neuropsychologia 35, 1121-1131.

Barker, A. T., Freeston, I. L., Jalinous, R., Jarratt, J. A., 1987. Magnetic stimulation of the human brain and peripheral nervous system: an introduction and the results of an initial clinical evaluation. Neurosurgery 20, 100-109.

Barker, A. T., Jalinous, R., Freeston, I. L., 1985. Non-invasive magnetic stimulation of human motor cortex. Lancet 1, 1106-1107.

Bi, G., Poo, M., 2001. Synaptic modification by correlated activity: Hebb's postulate revisited. Annual Review of Neuroscience 24, 139-166.

Bialek, W., Rieke, F., 1992. Reliability and information transmission in spiking neurons. Trends in Neurosciences 15, 428-434.

Bienenstock, E. L., Cooper, L. N., Munro, P. W., 1982. Theory for the development of neuron selectivity: orientation specificity and binocular interaction in visual cortex. J. Neuroscience 2, 32-48.

Bindman, L. J., Lippold, O. C., Milne, A. R., 1979. Prolonged changes in excitability of pyramidal tract neurones in the cat: a post-synaptic mechanism. J. Physiology 286, 457-477.

Bindman, L. J., Lippold, O. C., Redfearn, J. W., 1962. Long-lasting changes in the level of the electrical activity of the cerebral cortex produced by polarizing currents. Nature 196, 584-585.

Bindman, L. J., Lippold, O. C., Redfearn, J. W., 1964. The action of brief polarizing currents on the cerebral cortex of the rat (1) during current flow and (2) in the production of long-lasting after-effects. J. Physiology 172, 369-382.

Brignani, D., Ruzzoli, M., Mauri, P., Miniussi, C., 2013. Is transcranial alternating current stimulation effective in modulating brain oscillations? PLoS ONE 8, e56589. Buzsàki, G., 2006. Rhythms of the Brain. Oxford University Press, Oxford.

Canolty, R. T., Knight, R. T., 2010. The functional role of cross-frequency coupling. Trends in Cognitive Sciences 14, 506-515.

Carandini, M., Ferster, D., 1997. A tonic hyperpolarization underlying contrast adaptation in cat visual cortex. Science 276, 949-952.

Cattaneo, L., Sandrini, M., Schwarzbach, J., 2010. State-dependent TMS reveals a hierarchical representation of observed acts in the temporal, parietal, and premotor cortices. Cerebral Cortex 20, 2252-2258.

Cattaneo, Z., Rota, F., Vecchi, T., Silvanto, J., 2008. Using state-dependency of trans-cranial magnetic stimulation (TMS) to investigate letter selectivity in the left posterior parietal cortex: a comparison of TMS-priming and TMS-adaptation paradigms. Eur. J. Neuroscience 28, 1924-1929.

Chambers, C. D., Payne, J. M., Stokes, M. G., Mattingley, J. B., 2004. Fast and slow parietal pathways mediate spatial attention. Nature Neuroscience 7, 217-218.

Corthout, E., Uttl, B., Walsh, V., Hallett, M., Cowey, A., 1999. Timing of activity in early visual cortex as revealed by transcranial magnetic stimulation. Neuroreport 10, 2631-2634.

Creutzfeldt, O. D., Fromm, G. H., Kapp, H., 1962. Influence of transcortical d-c currents on cortical neuronal activity. Experimental Neurology 5, 436-452.

Deans, J. K., Powell, A. D., Jefferys, J. G., 2007. Sensitivity of coherent oscillations in rat hippocampus to AC electric fields. J. Physiology 583, 555-565.

Dockery, C. A., Hueckel-Weng, R., Birbaumer, N., Plewnia, C., 2009. Enhancement of planning ability by transcranial direct current stimulation. J. Neuroscience 29, 7271-7277.

Ermentrout, G. B., Galan, R. F., Urban, N. N., 2008. Reliability, synchrony and noise. Trends in Neurosciences 31, 428-434.

Epstein, C. M., Rothwell, J. C., 2003. Therapeutic uses of rTMS. Cambridge University Press, Cambridge, pp. 246-263.

Faisal, A. A., Selen, L. P., Wolpert, D. M., 2008. Noise in the nervous system. Nature Reviews Neuroscience 9, 292-303.

Ferbert, A., Caramia, D., Priori, A., Bertolasi, L., Rothwell, J. C., 1992. Cortical projection to erector spinae muscles in man as assessed by focal transcranial magnetic stimulation. Electroencephalography and Clin. Neurophysiology 85, 382-387.

Fertonani, A., Pirulli, C., Miniussi, C., 2011. Random noise stimulation improves neuroplasticity in perceptual learning. J. Neuroscience 31, 15416-15423. Feurra, M., Galli, G., Rossi, S., 2012. Transcranial alternating current stimulation affects decision making. Frontiers in Systems Neuroscience 6, 39.

Guyonneau, R., Vanrullen, R., Thorpe, S. J., 2004. Temporal codes and sparse representations: a key to understanding rapid processing in the visual system. J. Physiology, Paris 98, 487-497.

Hallett, M., 2000. Transcranial magnetic stimulation and the human brain. Nature 406, 147-150.

Harris, I. M., Miniussi, C., 2003. Parietal lobe contribution to mental rotation demonstrated with rTMS. J. Cognitive Neuroscience 15, 315-323.

Harris, J. A., Clifford, C. W., Miniussi, C., 2008. The functional effect of transcranial magnetic stimulation: signal suppression or neural noise generation. J. Cognitive Neuroscience 20, 734-740.

Hebb, D. O., 1949. The Organization of Behavior; A Neuropsychological Theory. Wiley, New York.

Hutcheon, B., Yarom, Y., 2000. Resonance, oscillation and the intrinsic frequency preferences of neurons. Trends in Neurosciences 23, 216-222.

Jacobson, L., Koslowsky, M., Lavidor, M., 2011. tDCS polarity effects in motor and cognitive domains: a meta-analytical review. Experimental Brain Research 216, 1-10.

Joundi, R. A., Jenkinson, N., Brittain, J. S., Aziz, T. Z., Brown, P., 2012. Driving oscillatory activity in the human cortex enhances motor performance. Current Biology 22, 403-407.

Kahn, I., Pascual-Leone, A., Theoret, H., Fregni, F., Clark, D., Wagner, A. D., 2005. Transient disruption of ventrolateral prefrontal cortex during verbal encoding affects subsequent memory performance. J. Neurophysiology 94, 688-698.

Kanai, R., Chaieb, L., Antal, A., Walsh, V., Paulus, W., 2008. Frequency-dependent electrical stimulation of the visual cortex. Current Biology 18, 1839-1843.

Kitajo, K., Doesburg, S. M., Yamanaka, K., Nozaki, D., Ward, L. M., Yamamoto, Y., 2007. Noise-induced large-scale phase synchronization of human-brain activity associated with behavioral stochastic resonance. EPL—Europhysics Letters, 80.

Kitajo, K., Nozaki, D., Ward, L. M., Yamamoto, Y., 2003. Behavioral stochastic resonance within the human brain. Physical Review Letters 90, 218103.

Landi, D., Rossini, P. M., 2010. Cerebral restorative plasticity from normal aging to brain diseases: a never-ending story. Restorative Neurology and Neuroscience 28, 349-366.

Lang, N., Rothkegel, H., Reiber, H., Hasan, A., Sueske, E., Tergau, F., Ehrenreich, H., Wuttke, W., Paulus, W., 2011. Circadian modulation of GABA-mediated cortical inhibition. Cerebral Cortex 21, 2299-2306.

Laycock, R., Crewther, D. P., Fitzgerald, P. B., Crewther, S. G., 2007. Evidence for fast signals and later processing in human V1/V2 and V5/MT+. A TMS study of motion perception. J. Neurophysiology 98, 1253-1262.

Liebetanz, D., Nitsche, M. A., Tergau, F., Paulus, W., 2002. Pharmacological approach to the mechanisms of transcranial DC-stimulation-induced after-effects of human motor cortex excitability. Brain 125, 2238-2247.

Longtin, A., 1997. Autonomous stochastic resonance in bursting neurons. Physical Review E 55, 868-876.

Manenti, R., Cappa, S. F., Rossini, P. M., Miniussi, C., 2008. The role of the prefrontal cortex in sentence comprehension: an rTMS study. Cortex 44, 337-344.

Marzi, C. A., Miniussi, C., Maravita, A., Bertolasi, L., Zanette, G., Rothwell, J. C., Sanes, J. N., 1998. Transcranial magnetic stimulation selectively impairs interhemispheric transfer of visuo-motor information in humans. Experimental Brain Research 118, 435-438.

Masquelier, T., Thorpe, S. J., 2007. Unsupervised learning of visual features through spike timing dependent plasticity. PLOS Computational Biology 3, e31.

Miniussi, C., Brignani, D., Pellicciari, M. C., 2012a. Combining transcranial electrical stimulation with electroencephalography: a multimodal approach. Clin. EEG and Neuroscience 43, 184-191.

Miniussi, C., Paulus, W., Rossini, P. M., 2012b. Transcranial Brain Stimulation. CRC Press, Boca Raton, FL.

Miniussi, C., Ruzzoli, M., Walsh, V., 2010. The mechanism of transcranial magnetic stimulation in cognition. Cortex 46, 128-130.

Moliadze, V., Zhao, Y., Eysel, U., Funke, K., 2003. Effect of transcranial magnetic stimulation on single-unit activity in the cat primary visual cortex. J. Physiology 553, 665-679.

Moss, F., Ward, L. M., Sannita, W. G., 2004. Stochastic resonance and sensory information processing: a tutorial and review of application. Clin. Neurophysiology 115, 267-281.

Mottaghy, F. M., Gangitano, M., Krause, B. J., Pascual-Leone, A., 2003. Chronometry of parietal and prefrontal activations in verbal working memory revealed by transcranial magnetic stimulation. Neuroimage 18, 565-575.

Nachmias, J., Sansbury, R. V., 1974. Grating contrast: discrimination may be better than detection. Vision Research 14, 1039-1042.

Nitsche, M. A., Cohen, L. G., Wassermann, E. M., Priori, A., Lang, N., Antal, A., Paulus, W., Hummel, F., Boggio, P. S., Fregni, F., Pascual-Leone, A., 2008. Transcranial direct current stimulation: state of the art 2008. Brain Stimulation 1, 206-223.

Nitsche, M. A., Liebetanz, D., Lang, N., Antal, A., Tergau, F., Paulus, W., 2003a. Safety criteria for transcranial direct current stimulation (tDCS) in humans. Clin. Neurophysiology 114, 2220-2222, author reply 2222-2223.

Nitsche, M. A., Niehaus, L., Hoffmann, K. T., Hengst, S., Liebetanz, D., Paulus, W., Meyer, B. U., 2004. MRI study of human brain exposed to weak direct current stimulation of the frontal cortex. Clin. Neurophysiology 115, 2419-2423.

Nitsche, M. A., Nitsche, M. S., Klein, C. C., Tergau, F., Rothwell, J. C., Paulus, W., 2003b. Level of action of cathodal DC polarisation induced inhibition of the human motor cortex. Clin. Neurophysiology 114, 600-604.

Nitsche, M. A., Paulus, W., 2000. Excitability changes induced in the human motor cortex by weak transcranial direct current stimulation. J. Physiology 527 (Pt 3), 633-639.

Nitsche, M. A., Paulus, W., 2011. Transcranial direct current stimulation—update 2011. Restorative Neurology and Neuroscience 29, 463-492.

Nitsche, M. A., Seeber, A., Frommann, K., Klein, C. C., Rochford, C., Nitsche, M. S., Fricke, K., Liebetanz, D., Lang, N., Antal, A., Paulus, W., Tergau, F., 2005. Modulating parameters of excitability during and after transcranial direct current stimulation of the human motor cortex. J. Physiology 568, 291-303.

Pascual-Leone, A., Walsh, V., Rothwell, J., 2000. Transcranial magnetic stimulation in cognitive neuroscience-virtual lesion, chronometry, and functional connectivity. Current Opinion in Neurobiology 10, 232-237.

Pasley, B. N., Allen, E. A., Freeman, R. D., 2009. State-dependent variability of neuronal responses to transcranial magnetic stimulation of the visual cortex. Neuron 62, 291-303.

Paulus, W., 2011. Transcranial electrical stimulation (tES-tDCS; tRNS, tACS) methods. Neuropsychological Rehabilitation 21, 602-617.

Plewnia, C., Rilk, A. J., Soekadar, S. R., Arfeller, C., Huber, H. S., Sauseng, P., Hummel, F., Gerloff, C., 2008. Enhancement of long-range EEG coherence by synchronous bifocal transcranial magnetic stimulation. European J. Neuroscience 27, 1577-1583.

Pogosyan, A., Gaynor, L. D., Eusebio, A., Brown, P., 2009. Boosting cortical activity at Beta-band frequencies slows movement in humans. Current Biology 19, 1637-1641.

Priori, A., Berardelli, A., Rona, S., Accornero, N., Manfredi, M., 1998. Polarization of the human motor cortex through the scalp. Neuroreport 9, 2257-2260.

Radman, T., Datta, A., Peterchev, A. V., 2007. In vitro modulation of endogenous rhythms by AC electric fields: syncing with clinical brain stimulation. J. Physiology 584, 369-370.

Rahnev, D. A., Maniscalco, B., Luber, B., Lau, H., Lisanby, S. H., 2012. Direct injection of noise to the visual cortex decreases accuracy but increases decision confidence. J. Neurophysiology 107, 1556-1563.

Reato, D., Rahman, A., Bikson, M., Parra, L. C., 2010. Low-intensity electrical stimulation affects network dynamics by modulating population rate and spike timing. J. Neuroscience 30, 15067-15079.

Ridding, M. C., Ziemann, U., 2010. Determinants of the induction of cortical plasticity by non-invasive brain stimulation in healthy subjects. J. Physiology 588, 2291-2304.

Rosanova, M., Casali, A., Bellina, V., Resta, F., Mariotti, M., Massimini, M., 2009. Natural frequencies of human corticothalamic circuits. J. Neuroscience 29, 7679-7685.

Rossi, S., Hallett, M., Rossini, P. M., Pascual-Leone, A., Safety of TMS Consensus Group, 2009. Safety, ethical considerations, and application guidelines for the use of transcranial magnetic stimulation in clinical practice and research. Clin. Neurophysiology 120, 2008-2039.

Roth, B. J., 1994. Mechanisms for electrical stimulation of excitable tissue. Critical Reviews in Biomedical Engineering 22, 253-305.

Rothwell, J. C., Day, B. L., Thompson, P. D., Dick, J. P., Marsden, C. D., 1987. Some experiences of techniques for stimulation of the human cerebral motor cortex through the scalp. Neurosurgery 20, 156-163.

Ruohonen, J., 2003. Background physics for magnetic stimulation. Supplements to Clin. Neurophysiology 56, 3-12.

Ruzzoli, M., Abrahamyan, A., Clifford, C. W., Marzi, C. A., Miniussi, C., Harris, J. A., 2011. The effect of TMS on visual motion sensitivity: an increase in neural noise or a decrease in signal strength. J. Neurophysiology 106, 138-143.

Ruzzoli, M., Marzi, C. A., Miniussi, C., 2010. The neural mechanisms of the effects of transcranial magnetic stimulation on perception. J. Neurophysiology 103, 2982-2989.

Sack, A. T., Linden, D. E., 2003. Combining transcranial magnetic stimulation and functional imaging in cognitive brain research: possibilities and limitations. Brain Research: Brain Research Reviews 43, 41-56.

Sandrini, M., Umilta, C., Rusconi, E., 2011. The use of transcranial magnetic stimulation in cognitive neuroscience: a new synthesis of methodological issues. Neuroscience and Biobehavioral Reviews 35, 516-536.

Schutter, D. J., Hortensius, R., 2010. Retinal origin of phosphenes to transcranial alternating current stimulation. Clin. Neurophysiology 121, 1080-1084.

Schwarzkopf, D. S., Silvanto, J., Rees, G., 2011. Stochastic resonance effects reveal the neural mechanisms of transcranial magnetic stimulation. J. Neuro-science 31, 3143-3147.

Schwiedrzik, C. M., 2009. Retina or visual cortex? The site of phosphene induction by transcranial alternating current stimulation. Frontiers in Integrative Neuro-science 3, 6.

Sclar, G., Lennie, P., DePriest, D. D., 1989. Contrast adaptation in striate cortex of macaque. Vision Research 29, 747-755.

Seyal, M., Masuoka, L. K., Browne, J. K., 1992. Suppression of cutaneous perception by magnetic pulse stimulation of the human brain. Electroencephalography and Clin. Neurophysiology 85, 397-401.

Siebner, H. R., Lang, N., Rizzo, V., Nitsche, M. A., Paulus, W., Lemon, R. N., Rothwell, J. C., 2004. Preconditioning of low-frequency repetitive transcranial magnetic stimulation with transcranial direct current stimulation: evidence for homeostatic plasticity in the human motor cortex. The J. Neuroscience 24, 3379-3385.

Silvanto, J., Muggleton, N., Walsh, V., 2008. State-dependency in brain stimulation studies of perception and cognition. Trends in Cognitive Sciences 12, 447-454.

Silvanto, J., Muggleton, N. G., Cowey, A., Walsh, V., 2007. Neural adaptation reveals state-dependent effects of transcranial magnetic stimulation. Eur. J. Neuroscience 25, 1874-1881.

Solomon, J. A., 2009. The history of dipper functions. Attention, Perception, and Psychophysics 71, 435-443.

Stein, R. B., Gossen, E. R., Jones, K. E., 2005. Neuronal variability: noise or part of the signal? Nature Reviews Neuroscience 6, 389-397.

Terney, D., Chaieb, L., Moliadze, V., Antal, A., Paulus, W., 2008. Increasing human brain excitability by transcranial high-frequency random noise stimulation. J. Neuroscience 28, 14147-14155.

Thut, G., Miniussi, C., 2009. New insights into rhythmic brain activity from TMS-EEG studies. Trends in Cognitive Sciences 13, 182-189.

Thut, G., Miniussi, C., Gross, J., 2012. The functional importance of rhythmic activity in the brain. Current Biology 22, R658 -Thut, G., Schyns, P. G., Gross, J., 2011a. Entrainment of perceptually relevant brain oscillations by non-invasive rhythmic stimulation of the human brain. Front. Psychology 2, 170.

Thut, G., Veniero, D., Romei, V., Miniussi, C., Schyns, P., Gross, J., 2011b. Rhythmic TMS causes local entrainment of natural oscillatory signatures. Current Biology 21, 1176-1185.

Vallar, G., Bolognini, N., 2011. Behavioural facilitation following brain stimula-tion: implications for neurorehabilitation. Neuropsychological Rehabilitation 21, 618-649.

Varela, F., Lachaux, J. P., Rodriguez, E., Martinerie, J., 2001. The brainweb: phase synchronization and large-scale integration. Nature Reviews Neuroscience 2, 229-239.

Veniero, D., Brignani, D., Thut, G., Miniussi, C., 2011. Alpha-generation as basic response-signature to transcranial magnetic stimulation (TMS) targeting the human resting motor cortex: a TMS/EEG co-registration study. Psychophysiology 48, 1381-1389.

Walsh, V., Cowey, A., 2000. Transcranial magnetic stimulation and cognitive neuroscience. Nature Reviews Neuroscience 1, 73-79.
Walsh, V., Ellison, A., Battelli, L., Cowey, A., 1998. Task-specific impairments and enhancements induced by magnetic stimulation of human visual area V5. Proceedings: Biological Sciences 265, 537-543.
Walsh, V., Pascual-Leone, A., 2003. Transcranial Magnetic Stimulation: A Neurochronometrics of Mind. MIT Press, Cambridge, MA.
Walsh, V., Rushworth, M., 1999. A primer of magnetic stimulation as a tool for neuropsychology. Neuropsychologia 37, 125-135.
Ward, L. M., Doesburg, S. M., Kitajo, K., MacLean, S. E., Roggeveen, A. B., 2006. Neural synchrony in stochastic resonance, attention, and consciousness. Canadian J. Experimental Psychology 60, 319-326.
Wassermann, E. M., Epstein, C., Ziemann, U., Walsh, V., Paus, T., Lisanby, S., 2008. Handbook of Transcranial Stimulation. Oxford University Press, Oxford, UK.
Waterston, M. L., Pack, C. C., 2010. Improved discrimination of visual stimuli following repetitive transcranial magnetic stimulation. PLoS ONE 5, e10354.
Wu, S., Amari, S., Nakahara, H., 2002. Population coding and decoding in a neural field: a computational study. Neural Computation 14, 999-1026.
Zaehle, T., Rach, S., Herrmann, C. S., 2010. Transcranial alternating current stimulation enhances individual alpha activity in human EEG. PLoS ONE 5, e13766.

Transcranial Electrical Stimulation (tES): tES (tDCS, tACS, and tRNS) is a set of noninvasive method of cortical stimulation, using weak direct currents to polarize target brain regions. The most used and best-known method is tDCS, as all considerations for the use of tDCS have been extended to the other tES methods. The hypotheses concerning the application of tDCS in cognition are very similar to those of TMS, with the exception that tDCS was never considered a virtual lesion method. tDCS can increase or decrease cortical excitability in the stimulated brain regions and facilitate or inhibit behavior accordingly. tES does not induce action potentials but instead modulates the neuronal response threshold so that it can be defined as subthreshold stimulation.

Michael A. Nitsche, and Armin Kibele. "Noninvasive brain stimulation and neural entrainment enhance athletic performance-a review." J. Cognitive Enhancement 1.1 (2017): 73-79, discusses that non-invasive brain stimulation (NIBS) bypasses the correlative approaches of other imaging techniques, making it possible to establish a causal relationship between cognitive processes and the functioning of specific brain areas. NIBS can provide information about where a particular process occurs. NIBS offers the opportunity to study brain mechanisms beyond process localization, providing information about when activity in a given brain region is involved in a cognitive process, and even how it is involved. When using NIBS to explore cognitive processes, it is important to understand not only how NIBS functions but also the functioning of the neural structures themselves. Non-invasive brain stimulation (NIBS) methods, which include transcranial magnetic stimulation (TMS) and transcranial electric stimulation (tES), are used in cognitive neuroscience to induce transient changes in brain activity and thereby alter the behavior of the subject. The application of NIBS aims at establishing the role of a given cortical area in an ongoing specific motor, perceptual or cognitive process (Hallett, 2000; Walsh and Cowey, 2000). Physically, NIBS techniques affect neuronal states through different mechanisms. In TMS, a solenoid (coil) is used to deliver a strong and transient magnetic field, or "pulse," to induce a transitory electric current at the cortical surface beneath the coil. (US 2004078056) The pulse causes the rapid and above-threshold depolarization of cell membranes affected by the current (Barker et al., 1985, 1987), followed by the transynaptic depolarization or hyperpolarization of interconnected neurons. Therefore, TMS induces a current that elicits action potentials in neurons. A complex set of coils can deliver a complex 3D excitation field. By contrast, in tES techniques, the stimulation involves the application of weak electrical currents directly to the scalp through a pair of electrodes (Nitsche and Paulus, 2000; Priori et al., 1998). As a result, tES induces a subthreshold polarization of cortical neurons that is too weak to generate an action potential. However, by changing the intrinsic neuronal excitability, tES can induce changes in the resting membrane potential and the postsynaptic activity of cortical neurons. This, in turn, can alter the spontaneous firing rate of neurons and modulate their response to afferent signals (Bindman et al., 1962, 1964, 1979; Creutzfeldt et al., 1962), leading to changes in synaptic efficacy. The typical application of NIBS involves different types of protocols: TMS can be delivered as a single pulse (spTMS) at a precise time, as pairs of pulses separated by a variable interval, or as a series of stimuli in conventional or patterned protocols of repetitive TMS (rTMS) (for a complete classification see Rossi et al., 2009). In general, the final effects of NIBS on the central nervous system depend on a lengthy list of parameters (e.g., frequency, temporal characteristics, intensity, geometric configuration of the coil/electrode, current direction), when it is delivered before (off-line) or during (on-line) the task as part of the experimental procedure (e.g., Jacobson et al., 2011; Nitsche and Paulus, 2011; Sandrini et al., 2011). In addition, these factors interact with several variables related to the anatomy (e.g., properties of the brain tissue and its location, Radman et al., 2007), as well as physiological (e.g., gender and age, Landi and Rossini, 2010; Lang et al., 2011; Ridding and Ziemann, 2010) and cognitive (e.g., Miniussi et al., 2010; Silvanto et al., 2008; Walsh et al., 1998) states of the stimulated area/subject.

Transcranial Direct Current Stimulation (tDCS): Cranial electrotherapy stimulation (CES) is a form of non-invasive brain stimulation that applies a small, pulsed electric current across a person's head to treat a variety of conditions such as anxiety, depression and insomnia. See, en.wikipedia.org/wiki/Cranial_electrotherapy_stimulation. Transcranial direct current stimulation (tDCS) is a form of neurostimulation that uses constant, low current delivered to the brain area of interest via electrodes on the scalp. It was originally developed to help patients with brain injuries or psychiatric conditions like major depressive disorder. tDCS appears to have some potential for treating depression. See, en.wikipedia.org/wiki/Transcranial_direct-current_stimulation.

tDCS is being studied for acceleration of learning. The mild electrical shock (usually, a 2-milliamp current) is used to depolarize the neuronal membranes, making the cells more excitable and responsive to inputs. Weisend, Experimental Brain Research, vol 213, p 9 (DARPA) showed that tDCS accelerates the formation of new neural pathways during the time that someone practices a skill. tDCS appears to bring about the flow state. The movements of the subjects become more automatic; they report calm, focused concentration, and their performance improves immediately. (See Adee, Sally, "Zap your brain into the zone: Fast track to pure focus", New Scientist, No. 2850, Feb. 1, 2012, www.newscientist.com/artide/mg21328501-600-zap-your-brain-into-the-zone-fast-track-to-pure-focus/).

U.S. Pat. Nos. 7,856,264; 8,706,241; 8,725,669; 9,037,224; 9,042,201; 9,095,266; 9,248,286; 9,349,178; 9,629,568; 9,693,725; 9,713,433; 20040195512; 20070179534; 20110092882; 20110311021; 20120165696; 20140142654; 20140200432; 20140211593; 20140316243; 20140347265; 20150099946; 20150174418; 20150257700; 20150327813; 20150343242; 20150351655; 20160000354; 20160038049; 20160113569; 20160144175; 20160148371; 20160148372; 20160180042; 20160213276; 20160228702; and 20160235323.

Reinhart, Robert M G. "Disruption and rescue of interareal theta phase coupling and adaptive behavior." Proceedings of the National Academy of Sciences (2017): provide evidence for a causal relation between interareal theta phase synchronization in frontal cortex and multiple components of adaptive human behavior. Reinhart's results support the idea that the precise timing of rhythmic population activity spatially distributed in frontal cortex conveys information to direct behavior. Given prior work showing that phase synchronization can change spike time-dependent plasticity, together with Reihart's findings showing stimulation effects on neural activity and behavior can outlast a 20-min period of electrical stimulation, it is reasonable to suppose that the externally modulated interareal coupling changed behavior by causing neuroplastic modifications in functional connectivity. Reinhart suggests that we may be able to noninvasively intervene in the temporal coupling of distant rhythmic activity in the human brain to optimize (or impede) the postsynaptic effect of spikes from one area on the other, improving (or impairing) the cross-area communication necessary for cognitive action control and learning. Moreover, these neuroplastic alterations in functional connectivity were induced with a 0° phase, suggesting that inducing synchronization does not require a meticulous accounting of the communication delay between regions such as MFC and IPFC to effectively modify behavior and learning. This conforms to work showing that despite long axonal conduction delays between distant brain areas, theta phase synchronizations at 0° phase lag can occur between these regions and underlie meaningful functions of cognition and action. It is also possible that a third subcortical or posterior region with a nonzero time lag interacted with these two frontal areas to drive changes in goal-directed behavior.

Alexander W H & Brown J W (2011) Medial prefrontal cortex as an action-outcome predictor. Nature Neuroscience 14(10):1338- 1344.

Alexander W H & Brown J W (2015) Hierarchical error representation: A computational model of anterior cingulate and dorsolateral prefrontal cortex. Neural Computation 27:2354-2410.

Anguera J A, et al. (2013) Video game training enhances cognitive control in older adults. Nature 501:97-101.

Aron A R, Fletcher P C, Bullmore E T, Sahakian B J, Robbins T W (2003) Stop-signal inhibition disrupted by damage to right inferior frontal gyrus in humans. Nat Neurosci 6:115-116.

Au J, et al. (2015) Improving fluid intelligence with training on working memory: a meta-analysis. Psychonomic Bulletin & Review 22:366-377.

Bellman R, Kalaba R (1959) A mathematical theory of adaptive control processes. Proc Natl Acad Sci USA 45:1288-1290.

Bibbig A, Traub R D, Whittington M A (2002) Long-range synchronization of gamma and beta oscillations and the plasticity of excitatory and inhibitory synapses: A network model. J Neurophysiol 88:1634-1654.

Botvinick M M (2012) Hierarchical reinforcement learning and decision making. Current Opinion in Neurobiology 22(6):956-962.

Botvinick M M, Braver T S, Barch D M, Carter C S, & Cohen J D (2001) Conflict monitoring and cognitive control. Psychological Review 108(3):624-652.

Bryck R L & Fisher P A (2012) Training the brain: practical applications of neural plasticity from the intersection of cognitive neuroscience, developmental psychology, and prevention science. American Psychologist 67:87-100.

Cavanagh J F, Cohen M X, & Allen J J (2009) Prelude to and resolution of an error: EEG phase synchrony reveals cognitive control dynamics during action monitoring. Journal of Neuroscience 29(1):98-105.

Cavanagh J F, Frank M J (2014) Frontal theta as a mechanism for cognitive control. Trends Cogn Sci 18:414-421.

Christie G J, Tata M S (2009) Right frontal cortex generates reward-related theta-band oscillatory activity. Neuroimage 48:415-422.

Cohen M X, Wilmes K, Vijver Iv (2011) Cortical electrophysiological network dynamics of feedback learning. Trends Cogn Sci 15:558-566.

Corbett A, et al. (2015) The effect of an online cognitive training package in healthy older adults: An online randomized controlled trial. J Am Med Dir Assoc 16:990-997.

Dale A M & Sereno M I (1993) Improved localization of cortical activity by combining EEG and MEG with MRI cortical surface reconstruction: A linear approach. Journal of Cognitive Neuroscience 5:162-176.

Dailey J W, Robbins T W (2017) Fractionating impulsivity: Neuropsychiatric implications. Nat Rev Neurosci 18:158-171.

Delorme A & Makeig S (2004) EEGLAB: An open source toolbox for analysis of singel-trial EEG dynamics including independent component analysis. Journal of Neuroscience Methods 134(1):9-21.

Diamond A & Lee K (2011) Interventions and programs demonstrated to aid executive function development in children 4-12 years of age. Science 333:959964.

Engel A K, Fries P, Singer W (2001) Dynamic predictions: Oscillations and synchrony in top-down processing. Nat Rev Neurosci 2:704-716.

Fairclough S H & Houston K (2004) A metabolic measure of mental effort. Biological Psychology 66:177-190.

Fell J, Axmacher N (2011) The role of phase synchronization in memory processes. Nat Rev Neurosci 12:105-118.

Fitzgerald K D, et al. (2005) Error-related hyperactivity of the anterior cingulate cortex in obsessive-compulsive disorder. Biol Psychiatry 57:287-294.

Foti D, Weinberg A, Dien J, Hajcak G (2011) Event-related potential activity in the basal ganglia differentiates rewards from nonrewards: Temporospatial principal components analysis and source localization of the feedback negativity. Hum Brain Mapp 32:2207-2216.

Fuchs M, Drenckhahn R, Wischmann H A, & Wagner M (1998) An improved boundary element method for realistic volume-conductor modeling. IEEE Trans Biomed Eng 45(8):980-997.

Gailliot M T & Baumeister R F (2007) The physiology of willpower: linking blood glucose to self-control. Personality and Social Psychology Review 11(4):303-327.

Gandiga P, Hummel F, & Cohen L (2006) Transcranial D C stimulation (tDCS): A tool for double-blind sham-controlled clinical studies in brain stimulation. Clinical Neurophysiology 117(4):845-850.

Gregoriou G G, Gotts S J, Zhou H, Desimone R (2009) High-frequency, long-range coupling between prefrontal and visual cortex during attention. Science 324: 1207-1210.

Hillman C H, Erickson K I, & Kramer A F (2008) Be smart, exercise your heart: exercise effects on brain and cognition. Nature Reviews Neuroscience 9(1):5865.

Holroyd C B & Yeung N (2012) Motivation of extended behaviors by anterior cingulate cortex. Trends in Cognitive Sciences 16:122-128.

Inzlicht M, Schmeichel B J, & Macrae C N (2014) Why self-control seems (but may not be) limited. Trends in Cognitive Sciences 18(3):127-133.

Jennings J R & Wood C C (1976) The e-adjustment procedure for repeated measures analyses of variance. Psychophysiology 13:277-278.

Kanai R, Chaieb L, Antal A, Walsh V, & Paulus W (2008) Frequency-dependent electrical stimulation of the visual cortex. Current Biology 18(23):1839-1843.

Kayser J & Tenke C E (2006) Principal components analysis of Laplacian waveforms as a generic method for identifying estimates: II. Adequacy of lowdensity estimates. Clinical Neurophysiology 117:369-380.

Kramer A F & Erickson K I (2007) Capitalizing on cortical plasticity: influence of physical activity on cognition and brain function. Trends in Cognitive Sciences 11:342-348.

Kurland J, Baldwin K, Tauer C (2010) Treatment-induced neuroplasticity following intensive naming therapy in a case of chronic wernicke's aphasia. Aphasiology 24: 737-751.

Lachaux J P, Rodriguez E, Martinerie J, & Varela F J (1999) Measuring phase synchrony in brain signals. Human Brain Mapping 8:194-208.

Lennie P (2003) The cost of cortical computation. Current Biology 13:493-497.

Luft C D B, Nolte G, & Bhattacharya J (2013) High-learners present larger midfrontal theta power and connectivity in response to incorrect performance feedback. Journal of Neuroscience 33(5):2029-2038.

Luft C D B, Nolte G, Bhattacharya J (2013) High-learners present larger mid-frontal theta power and connectivity in response to incorrect performance feedback. J Neurosci 33:2029-2038.

Marco-Pallares J, et al. (2008) Human oscillatory activity associated to reward processing in a gambling task. Neuropsychologia 46:241-248.

Marcora S M, Staiano W, & Manning V (2009) Mental fatigue impairs physical performance in humans. Journal of Applied Physiology 106:857-864.

Miltner W H R, Braun C H, & Coles M G H (1997) Event-related brain potentials following incorrect feedback in a time-estimation task: evidence for a "generic" neural system for error detection. Journal of Cognitive Neuroscience 9:788-798.

Noury N, Hipp J F, Siegel M (2016) Physiological processes non-linearly affect electrophysiological recordings during transcranial electric stimulation. Neuroimage 140: 99-109.

Oostenveld R, Fries P, Maris E, & Schoffelen J M (2011) FieldTrip: Open source software for advanced analysis of MEG, EEG, and invasive electrophysiological data. Computational Intelligence and Neuroscience 2011:1-9.

Owen A M, et al. (2010) Putting brain training to the test. Nature 465:775-778.

Pascual-Marqui R D (2002) Standardized low-resolution brain electromagnetic tomography (sLORETA): technical details. Methods & Findings in Experimental & Clinical Pharmacology 24:5-12.

Paulus W (2010) On the difficulties of separating retinal from cortical origins of phosphenes when using transcranial alternating current stimulation (tACS). Clinical Neurophysiology 121:987-991.

Poreisz C, Boros K, Antal A, & Paulus W (2007) Safety aspects of transcranial direct current stimulation concerning healthy subjects and patients. Brain Research Bulletin 72(4-6):208-214.

Raichle M E & Mintun M A (2006) Brain work and brain imaging. Annual Review of Neuroscience 29:449-476.

Reinhart R M G & Woodman G F (2014) Causal control of medial-frontal cortex governs electrophysiological and behavioral indices of performance monitoring and learning. Journal of Neuroscience 34(12):4214-4227.

Reinhart R M G & Woodman G F (2015) Enhancing long-term memory with stimulation tunes visual attention in one trial. Proceedings of the National Academy of Sciences of the USA 112(2):625-630.

Reinhart R M G, Cosman J D, Fukuda K, & Woodman G F (2017) Using transcranial direct-current stimulation (tDCS) to understand cognitive processing. Attention, Perception & Psychophysics 79(1):3-23.

Reinhart R M G, Woodman G F (2014) Oscillatory coupling reveals the dynamic reorganization of large-scale neural networks as cognitive demands change. J Cogn Neurosci 26:175-188.

Reinhart R M G, Xiao W, McClenahan L, & Woodman G F (2016) Electrical stimulation of visual cortex can immediately improve spatial vision. Current Biology 25(14): 1867-1872.

Reinhart R M G, Zhu J, Park S, & Woodman G F (2015) Medial-frontal stimulation enhances learning in schizophrenia by restoring prediction-error signaling. Journal of Neuroscience 35(35):12232-12240.

Reinhart R M G, Zhu J, Park S, & Woodman G F (2015) Synchronizing theta oscillations with direct-current stimulation strengthens adaptive control in the human brain. Proceedings of the National Academy of Sciences of the USA 112(30):9448-9453.

Ridderinkhof K R, Ullsperger M, Crone E A, & Nieuwenhuis S (2004) The role of the medial frontal cortex in cognitive control. Science 306:443-447.

Salinas E, Sejnowski T J (2001) Correlated neuronal activity and the flow of neural information. Nat Rev Neurosci 2:539-550.

Schnitzler A, Gross J (2005) Normal and pathological oscillatory communication in the brain. Nat Rev Neurosci 6:285-296.

Schutter D J & Hortensius R (2010) Retinal origin of phosphenes to transcranial alternating current stimulation. Clinical Neurophysiology 121(7):1080-1084.

Shallice T, Gazzaniga M S (2004) The fractionation of supervisory control. The Cognitive Neuroscience (MIT Press, Cambridge, MA), pp 943-956.

Shenhav A, Botvinick M M, & Cohen J D (2013) The expected value of control: An integrative theory of anterior cingulate cortex function. Neuron 79:217-240.

Shenhav A, Cohen J D, & Botvinick M M (2016) Dorsal anterior cingulate cortex and the value of control. Nature Neuroscience 19:1286-1291.

Siegel M, Donner T H, Engel A K (2012) Spectral fingerprints of large-scale neuronal interactions. Nat Rev Neurosci 13:121-134.

Srinivasan R, Winter W R, Ding J, & Nunez P L (2007) EEG and MEG coherence: measures of functional connectivity at distinct spatial scales of neocortical dynamics. Journal of Neuroscience Methods 166(1):41-52.

Tang Y, et al. (2010) Short term mental training induces white-matter changes in the anterior cingulate. Proceedings of the National Academy of Sciences 107:16649-16652.

Tang Y Y, et al. (2009) Central and autonomic nervous system interaction is altered by short term meditation. Proceedings of the National Academy of Sciences 106: 8865-8870.

Thrane G, Friborg O, Anke A, Indredavik B (2014) A meta-analysis of constraint-induced movement therapy after stroke. J Rehabil Med 46:833-842.

Uhlhaas P J, Singer W (2006) Neural synchrony in brain disorders: Relevance for cognitive dysfunctions and pathophysiology. Neuron 52:155-168.

Uhlhaas P J, Singer W (2010) Abnormal neural oscillations and synchrony in schizophrenia. Nat Rev Neurosci 11:100-113. van de Vijver I, Ridderinkhof K R, & Cohen M X (2011) Frontal oscillatory dynamics predict feedback learning and action adjustment. Journal of Cognitive Neuroscience 23:4106-4121.

van Driel J, Ridderinkhof K R, & Cohen M X (2012) Not all errors are alike: Theta and alpha EEG dynamics relate to differences in error-processing dynamics. Journal of Neuroscience 32(47):16795-16806.

van Meel C S, Heslenfeld D J, Oosterlaan J, Sergeant J A (2007) Adaptive control deficits in attention-deficit/hyperactivity disorder (ADHD): The role of error processing. Psychiatry Res 151:211-220.

Varela F, Lachaux J P, Rodriguez E, Martinerie 1(2001) The brainweb: Phase synchronization and large-scale integration. Nat Rev Neurosci 2:229-239.

Velligan D I, Ritch J L, *Sui* D, DiCocco M, Huntzinger C D (2002) Frontal systems behavior scale in schizophrenia: Relationships with psychiatric symptomatology, cognition and adaptive function. Psychiatry Res 113:227-236.

Vicente R, Gollo L L, Mirasso C R, Fischer I, Pipa G (2008) Dynamical relaying can yield zero time lag neuronal synchrony despite long conduction delays. Proc Natl Acad Sci USA 105:17157-17162.

Wagner M, Fuchs M, & Kastner J (2007) SWARM: sLORETA-weighted accurate minimum norm inverse solutions. International Congress Series 1300:185-188.

Wang X J (2010) Neurophysiological and computational principles of cortical rhythms in cognition. Physiol Rev 90:1195-1268.

Wolpert D M, Diedrichsen J, & Flanagan J R (2011) Principles of sensorimotor learning. Nature Reviews Neuroscience 12:739-751.

Xue S, Tang Y Y, Tang R, & Posner M I (2014) Short-term meditation induces changes in brain resting EEG theta networks. Brain & Cognition 87:1-6

Zatorre R J, Fields R D, & Johansen-Berg H (2012) Plasticity in gray and white: neuroimaging changes in brain structure during learning. Nature Neuroscience 15(4): 528-536. See, Daniel Stevenson. "Intro to Transcranial Direct Current Stimulation (tDCS)" (Mar. 26, 2017) (www.slideshare.net/DanielStevenson27/intro-to-transcranial-direct-curent-stimulation-tdcs).

High-Definition-tDCS: High-Definition transcranial Direct Current Stimulation (HD-tDCS) was invented at The City University of New York with the introduction of the 4×1 HD-tDCS montage. The 4×1 HD-tDCS montage allows precise targeting of cortical structures. The region of current flow is circumscribed by the area of the 4× ring, such that decreasing ring radius increases focality. 4×1 HD-tDCS allows for unifocal stimulation, meaning the polarity of the center 1× electrode will determine the direction of neuromodulation under the ring. This is in contrast to conventional tDCS where the need for one anode and one cathode always produces bidirectional modulation (even when an extra-cephalic electrode is used). 4×1 HD-tDCS thus provides the ability not only to select a cortical brain region to target, but to modulate the excitability of that brain region with a designed polarity without having to consider return counter-electrode flow.

Transcranial Alternative Current Stimulation (tACS): Transcranial alternating current stimulation (tACS) is a noninvasive means by which alternating electrical current applied through the skin and skull entrains in a frequency-specific fashion the neural oscillations of the underlying brain. See, en.wikipedia.org/wiki/Transcranial_alternating_current_stimulation U.S. Pub. App. No. 20170197081 discloses transdermal electrical stimulation of nerves to modify or induce a cognitive state using transdermal electrical stimulation (TES).

Transcranial alternating current stimulation (tACS) is a noninvasive means by which alternating electrical current applied through the skin and skull entrains in a frequency-specific fashion the neural oscillations of the underlying brain. See, en.wikipedia.org/wiki/Transcranial_alternating_current_stimulation;

U.S. Pat. Nos. 6,804,558; 7,149,773; 7,181,505; 7,278,966; 9,042,201; 9,629,568; 9,713,433; 20010051787; 20020013613; 20020052539; 20020082665; 20050171410; 20140211593; 20140316243; 20150174418; 20150343242; 20160000354; 20160038049; 20160106513; 20160213276; 20160228702; 20160232330; 20160235323; and 20170113056.

Transcranial Random Noise Stimulation (tRNS): Transcranial random noise stimulation (tRNS) is a non-invasive brain stimulation technique and a form of transcranial electrical stimulation (tES). See, en.wikipedia.org/wiki/Transcranial random noise stimulation; U.S. Pat. Nos. 9,198,733; 9,713,433; 20140316243; 20160038049; and 20160213276.

The stimulus may comprise transcranial pulsed current stimulation (tPCS). See:

Shapour Jaberzadeh, Andisheh Bastani, Maryam Zoghi, "Anodal transcranial pulsed current stimulation: A novel technique to enhance corticospinal excitability," Clin. Neurophysiology, Volume 125, Issue 2, February 2014, Pages 344-351, doi.org/10.1016/j.clinph.2013.08.025;

earthpulse.net/tpcs-transcranial-pulsed-current-stimulation/; help.focus/artide/16-tpcs-transcranial-pulsed-current-stimulation.

Transcranial Magnetic Stimulation: Transcranial magnetic stimulation (TMS) is a method in which a changing magnetic field is used to cause electric current to flow in a small region of the brain via electromagnetic induction. During a TMS procedure, a magnetic field generator, or "coil", is placed near the head of the person receiving the treatment. The coil is connected to a pulse generator, or stimulator, that delivers a changing electric current to the coil. TMS is used diagnostically to measure the connection between the central nervous system and skeletal muscle to evaluate damage in a wide variety of disease states, including stroke, multiple sclerosis, amyotrophic lateral sclerosis, movement disorders, and motor neuron diseases. Evidence is available suggesting that TMS is useful in treating neuropathic pain, major depressive disorder, and other conditions.

See, en.wikipedia.org/wiki/Transcranial magnetic stimulation,

See U.S. Pat. Nos. 4,296,756; 4,367,527; 5,069,218; 5,088,497; 5,359,363; 5,384,588; 5,459,536; 5,711,305; 5,877,801; 5,891,131; 5,954,662; 5,971,923; 6,188,924; 6,259,399; 6,487,441; 6,603,502; 7,714,936; 7,844,324; 7,856,264; 8,221,330; 8,655,817; 8,706,241; 8,725,669; 8,914,115; 9,037,224; 9,042,201; 9,095,266; 9,149,195; 9,248,286; 9,265,458; 9,414,776; 9,445,713; 9,713,433; 20020097332; 20040088732; 20070179534; 20070249949; 20080194981; 20090006001; 20110004412; 20110007129; 20110087127; 20110092882; 20110119212; 20110137371; 20120165696; 20120296569; 20130339043; 20140142654; 20140163328; 20140200432; 20140211593; 20140257047; 20140279746; 20140316243; 20140350369; 20150065803; 20150099946; 20150148617; 20150174418; 20150257700; 20150327813; 20150343242; 20150351655; 20160038049; 20160140306; 20160144175; 20160213276; 20160235323; 20160284082; 20160306942; 20160317077; 20170084175; and 20170113056.

PEMF: Pulsed electromagnetic field (PEMF) when applied to the brain is referred to as Transcranial magnetic stimulation, and has been FDA approved since 2008 for use in people who failed to respond to antidepressants. Weak magnetic stimulation of the brain is often called transcranial pulsed electromagnetic field (tPEMF) therapy. See, en.wikipedia.org/wiki/Pulsed_electromagnetic_field_therapy, See, U.S. Pat. Nos. 7,280,861; 8,343,027; 8,415,123; 8,430,805; 8,435,166; 8,571,642; 8,657,732; 8,775,340; 8,961,385; 8,968,172; 9,002,477; 9,005,102; 9,278,231; 9,320,913; 9,339,641; 9,387,338; 9,415,233; 9,427,598; 9,433,797; 9,440,089; 9,610,459; 9,630,004; 9,656,096; 20030181791; 20060129022; 20100057655; 20100197993; 20120101544; 20120116149; 20120143285; 20120253101; 20130013339; 20140213843; 20140213844; 20140221726; 20140228620; 20140303425; 20160235983; 20170087367; and 20170165496.

Deep Brain Stimulation (DBS): Deep brain stimulation (DBS) is a neurosurgical procedure involving the implantation of a medical device called a neurostimulator (sometimes referred to as a ‘brain pacemaker’), which sends electrical impulses, through implanted electrodes, to specific targets in the brain (brain nuclei) for the treatment of movement and neuropsychiatric disorders. See, en.wikipedia.org/wiki/Deep brain stimulation;

See, U.S. Pat. Nos. 6,539,263; 6,671,555; 6,959,215; 6,990,377; 7,006,872; 7,010,351; 7,024,247; 7,079,977; 7,146,211; 7,146,217; 7,149,572; 7,174,206; 7,184,837; 7,209,787; 7,221,981; 7,231,254; 7,236,830; 7,236,831; 7,239,926; 7,242,983; 7,242,984; 7,252,090; 7,257,439; 7,267,644; 7,277,758; 7,280,867; 7,282,030; 7,299,096; 7,302,298; 7,305,268; 7,313,442; 7,321,837; 7,324,851; 7,346,382; 7,353,064; 7,403,820; 7,437,196; 7,463,927; 7,483,747; 7,499,752; 7,565,199; 7,565,200; 7,577,481; 7,582,062; 7,594,889; 7,603,174; 7,606,405; 7,610,096; 7,617,002; 7,620,456; 7,623,928; 7,624,293; 7,629,889; 7,670,838; 7,672,730; 7,676,263; 7,680,526; 7,680,540; 7,684,866; 7,684,867; 7,715,919; 7,725,192; 7,729,773; 7,742,820; 7,747,325; 7,747,326; 7,756,584; 7,769,464; 7,775,993; 7,822,481; 7,831,305; 7,853,322; 7,853,323; 7,853,329; 7,856,264; 7,860,548; 7,894,903; 7,899,545; 7,904,134; 7,908,009; 7,917,206; 7,917,225; 7,930,035; 7,933,646; 7,945,330; 7,957,797; 7,957,809; 7,976,465; 7,983,762; 7,991,477; 8,000,794; 8,000,795; 8,005,534; 8,027,730; 8,031,076; 8,032,229; 8,050,768; 8,055,348; 8,065,012; 8,073,546; 8,082,033; 8,092,549; 8,121,694; 8,126,567; 8,126,568; 8,135,472; 8,145,295; 8,150,523; 8,150,524; 8,160,680; 8,180,436; 8,180,601; 8,187,181; 8,195,298; 8,195,300; 8,200,340; 8,223,023; 8,229,559; 8,233,990; 8,239,029; 8,244,347; 8,249,718; 8,262,714; 8,280,517; 8,290,596; 8,295,934; 8,295,935; 8,301,257; 8,303,636; 8,308,661; 8,315,703; 8,315,710; 8,326,420; 8,326,433; 8,332,038; 8,332,041; 8,346,365; 8,364,271; 8,364,272; 8,374,703; 8,379,952; 8,380,314; 8,388,555; 8,396,565; 8,398,692; 8,401,666; 8,412,335; 8,433,414; 8,437,861; 8,447,392; 8,447,411; 8,456,309; 8,463,374; 8,463,387; 8,467,877; 8,475,506; 8,504,150; 8,506,469; 8,512,219; 8,515,549; 8,515,550; 8,538,536; 8,538,543; 8,543,214; 8,554,325; 8,565,883; 8,565,886; 8,574,279; 8,579,786; 8,579,834; 8,583,238; 8,583,252; 8,588,899; 8,588,929; 8,588,933; 8,589,316; 8,594,798; 8,603,790; 8,606,360; 8,606,361; 8,644,945; 8,649,845; 8,655,817; 8,660,642; 8,675,945; 8,676,324; 8,676,330; 8,684,921; 8,690,748; 8,694,087; 8,694,092; 8,696,722; 8,700,174; 8,706,237; 8,706,241; 8,708,934; 8,716,447; 8,718,777; 8,725,243; 8,725,669; 8,729,040; 8,731,656; 8,734,498; 8,738,136; 8,738,140; 8,751,008; 8,751,011; 8,755,901; 8,758,274; 8,761,889; 8,762,065; 8,768,718; 8,774,923; 8,781,597; 8,788,033; 8,788,044; 8,788,055; 8,792,972; 8,792,991; 8,805,518; 8,815,582; 8,821,559; 8,825,166; 8,831,731; 8,834,392; 8,834,546; 8,843,201; 8,843,210; 8,849,407; 8,849,632; 8,855,773; 8,855,775; 8,868,172; 8,868,173; 8,868,201; 8,886,302; 8,892,207; 8,900,284; 8,903,486; 8,903,494; 8,906,360; 8,909,345; 8,910,638; 8,914,115; 8,914,119; 8,918,176; 8,918,178; 8,918,183; 8,926,959; 8,929,991; 8,932,562; 8,934,979; 8,936,629; 8,938,290; 8,942,817; 8,945,006; 8,951,203; 8,956,363; 8,958,870; 8,962,589; 8,965,513; 8,965,514; 8,974,365; 8,977,362; 8,983,155; 8,983,620; 8,983,628; 8,983,629; 8,989,871; 9,008,780; 9,011,329; 9,014,823; 9,020,598; 9,020,612; 9,020,789; 9,022,930; 9,026,217; 9,037,224; 9,037,254; 9,037,256; 9,042,201; 9,042,988; 9,043,001; 9,044,188; 9,050,470; 9,050,471; 9,061,153; 9,063,643; 9,072,832; 9,072,870; 9,072,905; 9,079,039; 9,079,940; 9,081,488; 9,084,885; 9,084,896; 9,084,900; 9,089,713; 9,095,266; 9,101,690; 9,101,759; 9,101,766; 9,113,801; 9,126,050; 9,135,400; 9,149,210; 9,167,976; 9,167,977; 9,167,978; 9,173,609; 9,174,055; 9,175,095; 9,179,850; 9,179,875; 9,186,510; 9,187,745; 9,198,563; 9,204,838; 9,211,411; 9,211,417; 9,215,298; 9,220,917; 9,227,056; 9,233,245; 9,233,246; 9,235,685; 9,238,142; 9,238,150; 9,248,280; 9,248,286; 9,248,288; 9,248,296; 9,249,200; 9,249,234; 9,254,383; 9,254,387; 9,259,591; 9,271,674; 9,272,091; 9,272,139; 9,272,153; 9,278,159; 9,284,353; 9,289,143; 9,289,595; 9,289,603; 9,289,609; 9,295,838; 9,302,103; 9,302,110; 9,302,114; 9,302,116; 9,308,372; 9,308,392; 9,309,296; 9,310,985; 9,314,190; 9,320,900; 9,320,914; 9,327,070; 9,333,350; 9,340,589; 9,348,974; 9,352,156; 9,357,949; 9,358,381; 9,358,398; 9,359,449; 9,360,472; 9,364,665; 9,364,679; 9,365,628; 9,375,564; 9,375,571; 9,375,573; 9,381,346; 9,387,320; 9,393,406; 9,393,418; 9,394,347; 9,399,134; 9,399,144; 9,403,001; 9,403,010; 9,408,530; 9,411,935; 9,414,776; 9,415,219; 9,415,222; 9,421,258; 9,421,373; 9,421,379; 9,427,581; 9,427,585; 9,439,150; 9,440,063; 9,440,064; 9,440,070; 9,440,084; 9,452,287; 9,453,215; 9,458,208; 9,463,327; 9,474,903; 9,480,841; 9,480,845; 9,486,632; 9,498,628; 9,501,829; 9,505,817; 9,517,020; 9,522,278; 9,522,288; 9,526,902; 9,526,913; 9,526,914; 9,533,148; 9,533,150; 9,538,951; 9,545,510; 9,561,380; 9,566,426; 9,579,247; 9,586,053; 9,592,004; 9,592,387; 9,592,389; 9,597,493;

9,597,494; 9,597,501; 9,597,504; 9,604,056; 9,604,067; 9,604,073; 9,613,184; 9,615,789; 9,622,675; 9,622,700; 9,623,240; 9,623,241; 9,629,548; 9,630,011; 9,636,185; 9,642,552; 9,643,015; 9,643,017; 9,643,019; 9,649,439; 9,649,494; 9,649,501; 9,656,069; 9,656,078; 9,662,502; 9,697,336; 9,706,957; 9,713,433; 9,717,920; 9,724,517; 9,729,252; 20020087201; 20020091419; 20020188330; 20030088274; 20030097159; 20030097161; 20030125786; 20030130706; 20030181955; 20040133118; 20040133119; 20040133120; 20040133248; 20040133390; 20040138516; 20040138517; 20040138518; 20040138536; 20040138580; 20040138581; 20040138647; 20040138711; 20040152958; 20040158119; 20040158298; 20050021105; 20050060001; 20050060007; 20050060008; 20050060009; 20050060010; 20050065427; 20050124848; 20050154425; 20050154426; 20050182389; 20050209512; 20050222522; 20050240253; 20050267011; 20060004422; 20060015153; 20060064138; 20060069415; 20060100671; 20060106274; 20060106430; 20060149337; 20060155348; 20060155495; 20060161218; 20060161384; 20060167370; 20060195155; 20060200206; 20060212090; 20060217781; 20060224421; 20060239482; 20060241718; 20070000372; 20070014454; 20070025608; 20070027486; 20070027498; 20070027499; 20070027500; 20070027501; 20070032834; 20070043401; 20070060974; 20070066915; 20070100278; 20070100389; 20070100392; 20070100398; 20070118197; 20070129769; 20070129774; 20070142874; 20070150026; 20070150029; 20070179534; 20070179558; 20070225774; 20070250119; 20070276441; 20080009772; 20080015459; 20080033503; 20080033508; 20080045775; 20080046012; 20080046035; 20080058773; 20080064934; 20080071150; 20080071326; 20080097553; 20080103547; 20080103548; 20080109050; 20080125829; 20080154331; 20080154332; 20080157980; 20080161700; 20080161879; 20080161880; 20080161881; 20080162182; 20080183097; 20080208285; 20080215112; 20080228239; 20080269812; 20080269843; 20080275526; 20080281381; 20080288018; 20090018462; 20090076567; 20090082829; 20090093862; 20090099627; 20090105785; 20090112273; 20090112277; 20090112278; 20090112279; 20090112280; 20090118786; 20090118787; 20090163982; 20090192556; 20090210018; 20090216288; 20090234419; 20090264789; 20090264954; 20090264955; 20090264956; 20090264957; 20090264958; 20090264967; 20090281594; 20090287035; 20090287271; 20090287272; 20090287273; 20090287274; 20090287467; 20090299126; 20090299435; 20090306491; 20090306741; 20090312808; 20090312817; 20090319000; 20090319001; 20090326604; 20100004500; 20100010383; 20100010388; 20100010391; 20100010392; 20100010571; 20100010572; 20100010573; 20100010574; 20100010575; 20100010576; 20100010577; 20100010578; 20100010579; 20100010580; 20100010584; 20100010585; 20100010587; 20100010588; 20100010589; 20100010590; 20100016783; 20100045467; 20100049276; 20100057159; 20100057160; 20100070001; 20100076525; 20100114237; 20100114272; 20100121415; 20100131030; 20100145427; 20100191305; 20100198090; 20100222845; 20100241020; 20100256592; 20100274106; 20100274141; 20100274147; 20100274305; 20100280334; 20100280335; 20100280500; 20100280571; 20100280574; 20100280579; 20100292602; 20110004270; 20110009928; 20110021970; 20110022981; 20110028798; 20110028799; 20110034812; 20110040356; 20110040546; 20110040547; 20110082522; 20110092882; 20110093033; 20110106206; 20110112590; 20110119212; 20110137371; 20110137381; 20110160796; 20110172554; 20110172562; 20110172564; 20110172567; 20110172738; 20110172743; 20110172927; 20110184487; 20110191275; 20110208012; 20110208264; 20110213222; 20110230701; 20110238130; 20110238136; 20110245734; 20110257501; 20110270348; 20110275927; 20110276107; 20110307030; 20110307079; 20110313268; 20110313487; 20110319726; 20110319975; 20120016430; 20120016432; 20120016435; 20120022340; 20120022611; 20120041498; 20120046531; 20120046715; 20120053508; 20120089205; 20120108998; 20120109020; 20120116244; 20120116475; 20120157963; 20120165696; 20120165898; 20120179071; 20120179228; 20120184801; 20120185020; 20120195860; 20120197322; 20120209346; 20120253421; 20120253429; 20120253442; 20120265267; 20120271148; 20120271183; 20120271189; 20120271374; 20120271375; 20120271376; 20120271380; 20120277833; 20120289869; 20120290058; 20120302912; 20120303087; 20120310050; 20120316630; 20130018435; 20130066392; 20130066394; 20130066395; 20130073022; 20130090706; 20130102919; 20130104066; 20130116578; 20130116748; 20130123568; 20130123684; 20130131746; 20130131753; 20130131755; 20130138176; 20130138177; 20130144353; 20130150921; 20130178913; 20130184781; 20130184792; 20130197401; 20130211183; 20130218232; 20130218819; 20130226261; 20130231709; 20130231716; 20130231721; 20130238049; 20130238050; 20130245466; 20130245486; 20130245711; 20130245712; 20130281758; 20130281811; 20130282075; 20130289385; 20130310909; 20130317474; 20130317568; 20130317580; 20130338526; 20130338738; 20140005743; 20140005744; 20140025133; 20140039577; 20140058289; 20140066796; 20140074060; 20140074179; 20140074180; 20140081071; 20140081347; 20140107397; 20140107398; 20140107728; 20140122379; 20140135642; 20140135886; 20140142654; 20140142669; 20140148872; 20140163627; 20140180194; 20140180358; 20140194720; 20140194726; 20140211593; 20140213842; 20140222113; 20140237073; 20140243613; 20140243926; 20140243934; 20140249396; 20140249445; 20140257047; 20140257437; 20140257438; 20140276185; 20140277282; 20140277286; 20140279746; 20140296646; 20140309614; 20140323924; 20140323946; 20140324118; 20140324138; 20140330334; 20140330335; 20140330345; 20140350634; 20140350636; 20140358024; 20140358199; 20140364721; 20140371515; 20150005680; 20150012057; 20150018699; 20150025408; 20150025421; 20150025610; 20150032178; 20150038822; 20150039066; 20150065831; 20150073505; 20150088224; 20150088228; 20150119689; 20150119898; 20150134031; 20150142082; 20150174406; 20150174418; 20150190636; 20150190637; 20150196246; 20150202447; 20150223721; 20150231395; 20150231397; 20150238693; 20150238765; 20150245781; 20150251016; 20150254413; 20150257700; 20150265207; 20150265830; 20150265836; 20150273211; 20150273223; 20150283379; 20150290453; 20150290454; 20150297893; 20150306391; 20150321000; 20150327813; 20150343215; 20150343242; 20150352363; 20150360026; 20150360039; 20150366482; 20150374983; 20160001065; 20160001096; 20160001098; 20160008600; 20160008632; 20160016014; 20160030666; 20160030749; 20160030750; 20160038049; 20160044841; 20160058359; 20160066789; 20160067494; 20160067496; 20160067526; 20160074661; 20160095546; 20160096025; 20160106997; 20160120437; 20160121114; 20160121116; 20160136429; 20160136430; 20160136443; 20160144175; 20160144186; 20160147964; 20160151628; 20160158553; 20160184596; 20160199662; 20160206380; 20160213276; 20160213314; 20160220821; 20160220850; 20160228204; 20160228640; 20160228702; 20160228705; 20160235323; 20160249846; 20160250473; 20160256690; 20160256691; 20160256693; 20160263380; 20160263393; 20160278870; 20160279410; 20160279417; 20160287436; 20160287869; 20160287889; 20160296746; 20160303322; 20160317077; 20160317824; 20160325111;

20160331970; 20160339243; 20160342762; 20160346542; 20160361540; 20160367808; 20160375259; 20170007820; 20170007828; 20170014625; 20170014630; 20170021161; 20170036024; 20170042474; 20170042713; 20170043167; 20170043178; 20170050046; 20170056642; 20170056663; 20170065349; 20170079573; 20170080234; 20170095670; 20170095676; 20170100591; 20170106193; 20170113046; 20170120043; 20170120052; 20170120054; 20170136238; 20170143966; 20170151433; 20170151435; 20170151436; 20170156622; 20170157410; 20170164895; 20170165481; 20170173326; 20170182285; 20170185741; 20170189685; 20170189686; 20170189687; 20170189688; 20170189689; 20170189700; 20170197080; 20170197086; 20170216595; 20170224990; 20170239486; and 20170239489.

Transcranial Pulse Ultrasound (TPU): Transcranial pulsed ultrasound (TPU) uses low intensity, low frequency ultrasound (LILFU) as a method to stimulate the brain. See, en.wikipedia.org/wiki/Transcranial pulsed ultrasound;

U.S. Pat. Nos. 8,591,419; 8,858,440; 8,903,494; 8,921,320; 9,002,458; 9,014,811; 9,036,844; 9,042,201; 9,061,133; 9,233,244; 9,333,334; 9,399,126; 9,403,038; 9,440,070; 9,630,029; 9,669,239; 20120259249; 20120283502; 20120289869; 20130079621; 20130144192; 20130184218; 20140058219; 20140211593; 20140228653; 20140249454; 20140316243; 20150080327; 20150133716; 20150343242; 20160143541; 20160176053; and 20160220850.

Sensory Stimulation: Light, sound or electromagnetic fields may be used to remotely convey a temporal pattern of brainwaves. See:

U.S. Pat. Nos. 5,293,187; 5,422,689; 5,447,166; 5,491,492; 5,546,943; 5,622,168; 5,649,061; 5,720,619; 5,740,812; 5,983,129; 6,050,962; 6,092,058; 6,149,586; 6,325,475; 6,377,833; 6,394,963; 6,428,490; 6,482,165; 6,503,085; 6,520,921; 6,522,906; 6,527,730; 6,556,695; 6,565,518; 6,652,458; 6,652,470; 6,701,173; 6,726,624; 6,743,182; 6,746,409; 6,758,813; 6,843,774; 6,896,655; 6,996,261; 7,037,260; 7,070,571; 7,107,090; 7,120,486; 7,212,851; 7,215,994; 7,260,430; 7,269,455; 7,280,870; 7,392,079; 7,407,485; 7,463,142; 7,478,108; 7,488,294; 7,515,054; 7,567,693; 7,647,097; 7,740,592; 7,751,877; 7,831,305; 7,856,264; 7,881,780; 7,970,734; 7,972,278; 7,974,787; 7,991,461; 8,012,107; 8,032,486; 8,033,996; 8,060,194; 8,095,209; 8,209,224; 8,239,030; 8,262,714; 8,320,649; 8,358,818; 8,376,965; 8,380,316; 8,386,312; 8,386,313; 8,392,250; 8,392,253; 8,392,254; 8,392,255; 8,437,844; 8,464,288; 8,475,371; 8,483,816; 8,494,905; 8,517,912; 8,533,042; 8,545,420; 8,560,041; 8,655,428; 8,672,852; 8,682,687; 8,684,742; 8,694,157; 8,706,241; 8,706,518; 8,738,395; 8,753,296; 8,762,202; 8,764,673; 8,768,022; 8,788,030; 8,790,255; 8,790,297; 8,821,376; 8,838,247; 8,864,310; 8,872,640; 8,888,723; 8,915,871; 8,938,289; 8,938,301; 8,942,813; 8,955,010; 8,955,974; 8,958,882; 8,964,298; 8,971,936; 8,989,835; 8,992,230; 8,998,828; 9,004,687; 9,060,671; 9,101,279; 9,135,221; 9,142,145; 9,165,472; 9,173,582; 9,179,855; 9,208,558; 9,215,978; 9,232,984; 9,241,665; 9,242,067; 9,254,099; 9,271,660; 9,275,191; 9,282,927; 9,292,858; 9,292,920; 9,320,450; 9,326,705; 9,330,206; 9,357,941; 9,396,669; 9,398,873; 9,414,780; 9,414,907; 9,424,761; 9,445,739; 9,445,763; 9,451,303; 9,451,899; 9,454,646; 9,462,977; 9,468,541; 9,483,117; 9,492,120; 9,504,420; 9,504,788; 9,526,419; 9,541,383; 9,545,221; 9,545,222; 9,545,225; 9,560,967; 9,560,984; 9,563,740; 9,582,072; 9,596,224; 9,615,746; 9,622,702; 9,622,703; 9,626,756; 9,629,568; 9,642,699; 9,649,030; 9,651,368; 9,655,573; 9,668,694; 9,672,302; 9,672,617; 9,682,232; 9,693,734; 9,694,155; 9,704,205; 9,706,910; 9,710,788; RE44408; RE45766; 20020024450; 20020103428; 20020103429; 20020112732; 20020128540; 20030028081; 20030028121; 20030070685; 20030083596; 20030100844; 20030120172; 20030149351; 20030158496; 20030158497; 20030171658; 20040019257; 20040024287; 20040068172; 20040092809; 20040101146; 20040116784; 20040143170; 20040267152; 20050010091; 20050019734; 20050025704; 20050038354; 20050113713; 20050124851; 20050148828; 20050228785; 20050240253; 20050245796; 20050267343; 20050267344; 20050283053; 20060020184; 20060061544; 20060078183; 20060087746; 20060102171; 20060129277; 20060161218; 20060189866; 20060200013; 20060241718; 20060252978; 20060252979; 20070050715; 20070179534; 20070191704; 20070238934; 20070273611; 20070282228; 20070299371; 20080004550; 20080009772; 20080058668; 20080081963; 20080119763; 20080123927; 20080132383; 20080228239; 20080234113; 20080234601; 20080242521; 20080255949; 20090018419; 20090058660; 20090062698; 20090076406; 20090099474; 20090112523; 20090221928; 20090267758; 20090270687; 20090270688; 20090270692; 20090270693; 20090270694; 20090270786; 20090281400; 20090287108; 20090297000; 20090299169; 20090311655; 20090312808; 20090312817; 20090318794; 20090326604; 20100004977; 20100010289; 20100010366; 20100041949; 20100069739; 20100069780; 20100163027; 20100163028; 20100163035; 20100165593; 20100168525; 20100168529; 20100168602; 20100268055; 20100293115; 20110004412; 20110009777; 20110015515; 20110015539; 20110043759; 20110054272; 20110077548; 20110092882; 20110105859; 20110130643; 20110172500; 20110218456; 20110256520; 20110270074; 20110301488; 20110307079; 20120004579; 20120021394; 20120036004; 20120071771; 20120108909; 20120108995; 20120136274; 20120150545; 20120203130; 20120262558; 20120271377; 20120310106; 20130012804; 20130046715; 20130063434; 20130063550; 20130080127; 20130120246; 20130127980; 20130185144; 20130189663; 20130204085; 20130211238; 20130226464; 20130242262; 20130245424; 20130281759; 20130289360; 20130293844; 20130308099; 20130318546; 20140058528; 20140155714; 20140171757; 20140200432; 20140214335; 20140221866; 20140243608; 20140243614; 20140243652; 20140276130; 20140276944; 20140288614; 20140296750; 20140300532; 20140303508; 20140304773; 20140313303; 20140315169; 20140316191; 20140316192; 20140316235; 20140316248; 20140323899; 20140335489; 20140343408; 20140347491; 20140350353; 20140350431; 20140364721; 20140378810; 20150002815; 20150003698; 20150003699; 20150005640; 20150005644; 20150006186; 20150012111; 20150038869; 20150045606; 20150051663; 20150099946; 20150112409; 20150120007; 20150124220; 20150126845; 20150126873; 20150133812; 20150141773; 20150145676; 20150154889; 20150174362; 20150196800; 20150213191; 20150223731; 20150234477; 20150235088; 20150235370; 20150235441; 20150235447; 20150241705; 20150241959; 20150242575; 20150242943; 20150243100; 20150243105; 20150243106; 20150247723; 20150247975; 20150247976; 20150248169; 20150248170; 20150248787; 20150248788; 20150248789; 20150248791; 20150248792; 20150248793; 20150290453; 20150290454; 20150305685; 20150306340; 20150309563; 20150313496; 20150313539; 20150324692; 20150325151; 20150335288; 20150339363; 20150351690; 20150366497; 20150366504; 20150366656; 20150366659; 20150369864; 20150370320; 20160000354; 20160004298; 20160005320; 20160007915; 20160008620; 20160012749; 20160015289; 20160022167; 20160022206; 20160029946; 20160029965; 20160038069; 20160051187; 20160051793; 20160066838; 20160073886; 20160077547; 20160078780; 20160106950; 20160112684; 20160120436;

20160143582; 20160166219; 20160167672; 20160176053; 20160180054; 20160198950; 20160199577; 20160202755; 20160216760; 20160220439; 20160228640; 20160232625; 20160232811; 20160235323; 20160239084; 20160248994; 20160249826; 20160256108; 20160267809; 20160270656; 20160287157; 20160302711; 20160306942; 20160313798; 20160317060; 20160317383; 20160324478; 20160324580; 20160334866; 20160338644; 20160338825; 20160339300; 20160345901; 20160357256; 20160360970; 20160363483; 20170000324; 20170000325; 20170000326; 20170000329; 20170000330; 20170000331; 20170000332; 20170000333; 20170000334; 20170000335; 20170000337; 20170000340; 20170000341; 20170000342; 20170000343; 20170000345; 20170000454; 20170000683; 20170001032; 20170006931; 20170007111; 20170007115; 20170007116; 20170007122; 20170007123; 20170007165; 20170007182; 20170007450; 20170007799; 20170007843; 20170010469; 20170010470; 20170017083; 20170020447; 20170020454; 20170020627; 20170027467; 20170027651; 20170027812; 20170031440; 20170032098; 20170035344; 20170043160; 20170055900; 20170060298; 20170061034; 20170071523; 20170071537; 20170071546; 20170071551; 20170080320; 20170086729; 20170095157; 20170099479; 20170100540; 20170103440; 20170112427; 20170112671; 20170113046; 20170113056; 20170119994; 20170135597; 20170135633; 20170136264; 20170136265; 20170143249; 20170143442; 20170148340; 20170156662; 20170162072; 20170164876; 20170164878; 20170168568; 20170173262; 20170173326; 20170177023; 20170188947; 20170202633; 20170209043; 20170209094; and 20170209737.

Light Stimulation: The functional relevance of brain oscillations in the alpha frequency range (8-13 Hz) has been repeatedly investigated through the use of rhythmic visual stimulation. There are two hypotheses on the origin of steady-state visual evoked potential (SSVEP) measured in EEG during rhythmic stimulation: entrainment of brain oscillations and superposition of event-related responses (ERPs). The entrainment but not the superposition hypothesis justifies rhythmic visual stimulation as a means to manipulate brain oscillations, because superposition assumes a linear summation of single responses, independent from ongoing brain oscillations. Participants stimulated with rhythmic flickering light of different frequencies and intensities, and entrainment was measured by comparing the phase coupling of brain oscillations stimulated by rhythmic visual flicker with the oscillations induced by arrhythmic littered stimulation, varying the time, stimulation frequency, and intensity conditions. Phase coupling was found to be more pronounced with increasing stimulation intensity as well as at stimulation frequencies closer to each participant's intrinsic frequency. Even in a single sequence of an SSVEP, non-linear features (intermittency of phase locking) was found that contradict the linear summation of single responses, as assumed by the superposition hypothesis. Thus, evidence suggests that visual rhythmic stimulation entrains brain oscillations, validating the approach of rhythmic stimulation as a manipulation of brain oscillations. See, Notbohm A, Kurths J, Herrmann C S, Modification of Brain Oscillations via Rhythmic Light Stimulation Provides Evidence for Entrainment but Not for Superposition of Event-Related Responses, Front Hum Neurosci. 2016 Feb. 3; 10:10. doi: 10.3389/fnhum.2016.00010. eCollection 2016.

It is also known that periodic visual stimulation can trigger epileptic seizures.

Cochlear Implant: A cochlear implant is a surgically implanted electronic device that provides a sense of sound to a person who is profoundly deaf or severely hard of hearing in both ears. See, en.wikipedia.org/wiki/Cochlear implant;

See, U.S. Pat. Nos. 5,999,856; 6,354,299; 6,427,086; 6,430,443; 6,665,562; 6,873,872; 7,359,837; 7,440,806; 7,493,171; 7,610,083; 7,610,100; 7,702,387; 7,747,318; 7,765,088; 7,853,321; 7,890,176; 7,917,199; 7,920,916; 7,957,806; 8,014,870; 8,024,029; 8,065,017; 8,108,033; 8,108,042; 8,140,152; 8,165,687; 8,175,700; 8,195,295; 8,209,018; 8,224,431; 8,315,704; 8,332,024; 8,401,654; 8,433,410; 8,478,417; 8,515,541; 8,538,543; 8,560,041; 8,565,864; 8,574,164; 8,577,464; 8,577,465; 8,577,466; 8,577,467; 8,577,468; 8,577,472; 8,577,478; 8,588,941; 8,594,800; 8,644,946; 8,644,957; 8,652,187; 8,676,325; 8,696,724; 8,700,183; 8,718,776; 8,768,446; 8,768,477; 8,788,057; 8,798,728; 8,798,773; 8,812,126; 8,864,806; 8,868,189; 8,929,999; 8,968,376; 8,989,868; 8,996,120; 9,002,471; 9,044,612; 9,061,132; 9,061,151; 9,095,713; 9,135,400; 9,186,503; 9,235,685; 9,242,067; 9,248,290; 9,248,291; 9,259,177; 9,302,093; 9,314,613; 9,327,069; 9,352,145; 9,352,152; 9,358,392; 9,358,393; 9,403,009; 9,409,013; 9,415,215; 9,415,216; 9,421,372; 9,432,777; 9,501,829; 9,526,902; 9,533,144; 9,545,510; 9,550,064; 9,561,380; 9,578,425; 9,592,389; 9,604,067; 9,616,227; 9,643,017; 9,649,493; 9,674,621; 9,682,232; 9,743,197; 9,744,358; 20010014818; 20010029391; 20020099412; 20030114886; 20040073273; 20050149157; 20050182389; 20050182450; 20050182467; 20050182468; 20050182469; 20050187600; 20050192647; 20050209664; 20050209665; 20050209666; 20050228451; 20050240229; 20060064140; 20060094970; 20060094971; 20060094972; 20060095091; 20060095092; 20060161217; 20060173259; 20060178709; 20060195039; 20060206165; 20060235484; 20060235489; 20060247728; 20060282123; 20060287691; 20070038264; 20070049988; 20070156180; 20070198063; 20070213785; 20070244407; 20070255155; 20070255531; 20080049376; 20080140149; 20080161886; 20080208280; 20080235469; 20080249589; 20090163980; 20090163981; 20090243756; 20090259277; 20090270944; 20090280153; 20100030287; 20100100164; 20100198282; 20100217341; 20100231327; 20100241195; 20100268055; 20100268288; 20100318160; 20110004283; 20110060382; 20110166471; 20110295344; 20110295345; 20110295346; 20110295347; 20120035698; 20120116179; 20120116741; 20120150255; 20120245655; 20120262250; 20120265270; 20130165996; 20130197944; 20130235550; 20140032512; 20140098981; 20140200623; 20140249608; 20140275847; 20140330357; 20140350634; 20150018699; 20150045607; 20150051668; 20150065831; 20150066124; 20150080674; 20150328455; 20150374986; 20150374987; 20160067485; 20160243362; 20160261962; 20170056655; 20170087354; 20170087355; 20170087356; 20170113046; 20170117866; 20170135633; and 20170182312.

Vagus Nerve Stimulation: Vagus nerve stimulation (VNS) is a medical treatment that involves delivering electrical impulses to the vagus nerve. It is used as an adjunctive treatment for certain types of intractable epilepsy and treatment-resistant depression. See, en.wikipedia.org/wiki/Vagus_nerve_stimulation;

See, U.S. Pat. Nos. 5,215,086; 5,231,988; 5,299,569; 5,335,657; 5,571,150; 5,928,272; 5,995,868; 6,104,956; 6,167,311; 6,205,359; 6,208,902; 6,248,126; 6,269,270; 6,339,725; 6,341,236; 6,356,788; 6,366,814; 6,418,344; 6,497,699; 6,549,804; 6,556,868; 6,560,486; 6,587,727; 6,591,137; 6,597,954; 6,609,030; 6,622,047; 6,665,562; 6,671,556; 6,684,105; 6,708,064; 6,735,475; 6,782,292; 6,788,975; 6,873,872; 6,879,859; 6,882,881; 6,920,357; 6,961,618; 7,003,352; 7,151,961; 7,155,279; 7,167,751;

7,177,678; 7,203,548; 7,209,787; 7,228,167; 7,231,254; 7,242,984; 7,277,758; 7,292,890; 7,313,442; 7,324,851; 7,346,395; 7,366,571; 7,386,347; 7,389,144; 7,403,820; 7,418,290; 7,422,555; 7,444,184; 7,454,245; 7,457,665; 7,463,927; 7,486,986; 7,493,172; 7,499,752; 7,561,918; 7,620,455; 7,623,927; 7,623,928; 7,630,757; 7,634,317; 7,643,881; 7,653,433; 7,657,316; 7,676,263; 7,680,526; 7,684,858; 7,706,871; 7,711,432; 7,734,355; 7,736,382; 7,747,325; 7,747,326; 7,769,461; 7,783,362; 7,801,601; 7,805,203; 7,840,280; 7,848,803; 7,853,321; 7,853,329; 7,860,548; 7,860,570; 7,865,244; 7,869,867; 7,869,884; 7,869,885; 7,890,185; 7,894,903; 7,899,539; 7,904,134; 7,904,151; 7,904,175; 7,908,008; 7,920,915; 7,925,353; 7,945,316; 7,957,796; 7,962,214; 7,962,219; 7,962,220; 7,974,688; 7,974,693; 7,974,697; 7,974,701; 7,996,079; 8,000,788; 8,027,730; 8,036,745; 8,041,418; 8,041,419; 8,046,076; 8,064,994; 8,068,911; 8,097,926; 8,108,038; 8,112,148; 8,112,153; 8,116,883; 8,150,508; 8,150,524; 8,160,696; 8,172,759; 8,180,601; 8,190,251; 8,190,264; 8,204,603; 8,209,009; 8,209,019; 8,214,035; 8,219,188; 8,224,444; 8,224,451; 8,229,559; 8,239,028; 8,260,426; 8,280,505; 8,306,627; 8,315,703; 8,315,704; 8,326,418; 8,337,404; 8,340,771; 8,346,354; 8,352,031; 8,374,696; 8,374,701; 8,379,952; 8,382,667; 8,401,634; 8,412,334; 8,412,338; 8,417,344; 8,423,155; 8,428,726; 8,452,387; 8,454,555; 8,457,747; 8,467,878; 8,478,428; 8,485,979; 8,489,185; 8,498,699; 8,515,538; 8,536,667; 8,538,523; 8,538,543; 8,548,583; 8,548,594; 8,548,604; 8,560,073; 8,562,536; 8,562,660; 8,565,867; 8,571,643; 8,571,653; 8,588,933; 8,591,419; 8,600,521; 8,603,790; 8,606,360; 8,615,309; 8,630,705; 8,634,922; 8,641,646; 8,644,954; 8,649,871; 8,652,187; 8,660,666; 8,666,501; 8,676,324; 8,676,330; 8,684,921; 8,694,118; 8,700,163; 8,712,547; 8,716,447; 8,718,779; 8,725,243; 8,738,126; 8,744,562; 8,761,868; 8,762,065; 8,768,471; 8,781,597; 8,815,582; 8,827,912; 8,831,732; 8,843,210; 8,849,409; 8,852,100; 8,855,775; 8,858,440; 8,864,806; 8,868,172; 8,868,177; 8,874,205; 8,874,218; 8,874,227; 8,888,702; 8,914,122; 8,918,178; 8,934,967; 8,942,817; 8,945,006; 8,948,855; 8,965,514; 8,968,376; 8,972,004; 8,972,013; 8,983,155; 8,983,628; 8,983,629; 8,985,119; 8,989,863; 8,989,867; 9,014,804; 9,014,823; 9,020,582; 9,020,598; 9,020,789; 9,026,218; 9,031,655; 9,042,201; 9,042,988; 9,043,001; 9,044,188; 9,050,469; 9,056,195; 9,067,054; 9,067,070; 9,079,940; 9,089,707; 9,089,719; 9,095,303; 9,095,314; 9,108,041; 9,113,801; 9,119,533; 9,135,400; 9,138,580; 9,162,051; 9,162,052; 9,174,045; 9,174,066; 9,186,060; 9,186,106; 9,204,838; 9,204,998; 9,220,910; 9,233,246; 9,233,258; 9,235,685; 9,238,150; 9,241,647; 9,242,067; 9,242,092; 9,248,286; 9,249,200; 9,249,234; 9,254,383; 9,259,591; 9,265,660; 9,265,661; 9,265,662; 9,265,663; 9,265,931; 9,265,946; 9,272,145; 9,283,394; 9,284,353; 9,289,599; 9,302,109; 9,309,296; 9,314,633; 9,314,635; 9,320,900; 9,326,720; 9,332,939; 9,333,347; 9,339,654; 9,345,886; 9,358,381; 9,359,449; 9,364,674; 9,365,628; 9,375,571; 9,375,573; 9,381,346; 9,394,347; 9,399,133; 9,399,134; 9,402,994; 9,403,000; 9,403,001; 9,403,038; 9,409,022; 9,409,028; 9,415,219; 9,415,222; 9,427,581; 9,440,063; 9,458,208; 9,468,761; 9,474,852; 9,480,845; 9,492,656; 9,492,678; 9,501,829; 9,504,390; 9,505,817; 9,522,085; 9,522,282; 9,526,902; 9,533,147; 9,533,151; 9,538,951; 9,545,226; 9,545,510; 9,561,380; 9,566,426; 9,579,506; 9,586,047; 9,592,003; 9,592,004; 9,592,409; 9,604,067; 9,604,073; 9,610,442; 9,622,675; 9,623,240; 9,643,017; 9,643,019; 9,656,075; 9,662,069; 9,662,490; 9,675,794; 9,675,809; 9,682,232; 9,682,241; 9,700,256; 9,700,716; 9,700,723; 9,707,390; 9,707,391; 9,717,904; 9,729,252; 9,737,230; 20010003799; 20010029391; 20020013612; 20020072776; 20020072782; 20020099417; 20020099418; 20020151939; 20030023282; 20030045914; 20030083716; 20030114886; 20030181954; 20030195574; 20030236557; 20030236558; 20040015204; 20040015205; 20040073273; 20040138721; 20040153129; 20040172089; 20040172091; 20040172094; 20040193220; 20040243182; 20040260356; 20050027284; 20050033379; 20050043774; 20050049651; 20050137645; 20050149123; 20050149157; 20050154419; 20050154426; 20050165458; 20050182288; 20050182450; 20050182453; 20050182467; 20050182468; 20050182469; 20050187600; 20050192644; 20050192647; 20050197590; 20050197675; 20050197678; 20050209654; 20050209664; 20050209665; 20050209666; 20050216070; 20050216071; 20050251220; 20050267542; 20060009815; 20060047325; 20060052657; 20060064138; 20060064139; 20060064140; 20060079936; 20060111644; 20060129202; 20060142802; 20060155348; 20060167497; 20060173493; 20060173494; 20060173495; 20060195154; 20060206155; 20060212090; 20060212091; 20060217781; 20060224216; 20060259077; 20060282123; 20060293721; 20060293723; 20070005115; 20070021800; 20070043401; 20070060954; 20070060984; 20070066997; 20070067003; 20070067004; 20070093870; 20070100377; 20070100378; 20070100392; 20070112404; 20070150024; 20070150025; 20070162085; 20070173902; 20070198063; 20070213786; 20070233192; 20070233193; 20070255320; 20070255379; 20080021341; 20080027347; 20080027348; 20080027515; 20080033502; 20080039904; 20080065183; 20080077191; 20080086182; 20080091240; 20080125829; 20080140141; 20080147137; 20080154332; 20080161894; 20080167571; 20080183097; 20080269542; 20080269833; 20080269834; 20080269840; 20090018462; 20090036950; 20090054946; 20090088680; 20090093403; 20090118780; 20090163982; 20090171405; 20090187230; 20090234419; 20090276011; 20090276012; 20090280153; 20090326605; 20100003656; 20100004705; 20100004717; 20100057159; 20100063563; 20100106217; 20100114190; 20100114192; 20100114193; 20100125219; 20100125304; 20100145428; 20100191304; 20100198098; 20100198296; 20100204749; 20100268288; 20100274303; 20100274308; 20100292602; 20110009920; 20110021899; 20110028799; 20110029038; 20110029044; 20110034912; 20110054569; 20110077721; 20110092800; 20110098778; 20110105998; 20110125203; 20110130615; 20110137381; 20110152967; 20110152988; 20110160795; 20110166430; 20110166546; 20110172554; 20110172725; 20110172732; 20110172739; 20110178441; 20110178442; 20110190569; 20110201944; 20110213222; 20110224602; 20110224749; 20110230701; 20110230938; 20110257517; 20110264182; 20110270095; 20110270096; 20110270346; 20110270347; 20110276107; 20110276112; 20110282225; 20110295344; 20110295345; 20110295346; 20110295347; 20110301529; 20110307030; 20110311489; 20110319975; 20120016336; 20120016432; 20120029591; 20120029601; 20120046711; 20120059431; 20120078323; 20120083700; 20120083701; 20120101326; 20120116741; 20120158092; 20120179228; 20120184801; 20120185020; 20120191158; 20120203079; 20120209346; 20120226130; 20120232327; 20120265262; 20120303080; 20120310050; 20120316622; 20120330369; 20130006332; 20130018438; 20130018439; 20130018440; 20130019325; 20130046358; 20130066350; 20130066392; 20130066395; 20130072996; 20130089503; 20130090454; 20130096441; 20130131753; 20130165846; 20130178913; 20130184639; 20130184792; 20130204144; 20130225953; 20130225992; 20130231721; 20130238049; 20130238050; 20130238053; 20130244323; 20130245464; 20130245486; 20130245711; 20130245712; 20130253612; 20130261703;

20130274625; 20130281890; 20130289653; 20130289669; 20130296406; 20130296637; 20130304159; 20130309278; 20130310909; 20130317580; 20130338450; 20140039290; 20140039336; 20140039578; 20140046203; 20140046407; 20140052213; 20140056815; 20140058189; 20140058292; 20140074188; 20140081071; 20140081353; 20140094720; 20140100633; 20140107397; 20140107398; 20140113367; 20140128938; 20140135680; 20140135886; 20140142653; 20140142654; 20140142669; 20140155772; 20140155952; 20140163643; 20140213842; 20140213961; 20140214135; 20140235826; 20140236272; 20140243613; 20140243714; 20140257118; 20140257132; 20140257430; 20140257437; 20140257438; 20140275716; 20140276194; 20140277255; 20140277256; 20140288620; 20140303452; 20140324118; 20140330334; 20140330335; 20140330336; 20140336514; 20140336730; 20140343463; 20140357936; 20140358067; 20140358193; 20140378851; 20150005592; 20150005839; 20150012054; 20150018893; 20150025422; 20150032044; 20150032178; 20150051655; 20150051656; 20150051657; 20150051658; 20150051659; 20150057715; 20150072394; 20150073237; 20150073505; 20150119689; 20150119794; 20150119956; 20150142082; 20150148878; 20150157859; 20150165226; 20150174398; 20150174405; 20150174407; 20150182753; 20150182756; 20150190636; 20150190637; 20150196246; 20150202428; 20150208978; 20150216469; 20150231330; 20150238761; 20150265830; 20150265836; 20150283265; 20150297719; 20150297889; 20150306392; 20150343222; 20150352362; 20150360030; 20150366482; 20150374973; 20150374993; 20160001096; 20160008620; 20160012749; 20160030666; 20160045162; 20160045731; 20160051818; 20160058359; 20160074660; 20160081610; 20160114165; 20160121114; 20160121116; 20160135727; 20160136423; 20160144175; 20160151628; 20160158554; 20160175607; 20160199656; 20160199662; 20160206236; 20160222073; 20160232811; 20160243381; 20160249846; 20160250465; 20160263376; 20160279021; 20160279022; 20160279023; 20160279024; 20160279025; 20160279267; 20160279410; 20160279435; 20160287869; 20160287895; 20160303396; 20160303402; 20160310070; 20160331952; 20160331974; 20160331982; 20160339237; 20160339238; 20160339239; 20160339242; 20160346542; 20160361540; 20160361546; 20160367808; 20160375245; 20170007820; 20170027812; 20170043160; 20170056467; 20170056642; 20170066806; 20170079573; 20170080050; 20170087364; 20170095199; 20170095670; 20170113042; 20170113057; 20170120043; 20170120052; 20170143550; 20170143963; 20170143986; 20170150916; 20170150921; 20170151433; 20170157402; 20170164894; 20170189707; 20170198017; and 20170224994.

Brain-To-Brain Interface: A brain-brain interface is a direct communication pathway between the brain of one animal and the brain of another animal. Brain to brain interfaces have been used to help rats collaborate with each other. When a second rat was unable to choose the correct lever, the first rat noticed (not getting a second reward), and produced a round of task-related neuron firing that made the second rat more likely to choose the correct lever. Human studies have also been conducted.

In 2013, researcher from the University of Washington were able to use electrical brain recordings and a form of magnetic stimulation to send a brain signal to a recipient, which caused the recipient to hit the fire button on a computer game. In 2015, researchers linked up multiple brains, of both monkeys and rats, to form an "organic computer." It is hypothesized that by using brain-to-brain interfaces (BTBIs) a biological computer, or brain-net, could be constructed using animal brains as its computational units. Initial exploratory work demonstrated collaboration between rats in distant cages linked by signals from cortical microelectrode arrays implanted in their brains. The rats were rewarded when actions were performed by the "decoding rat" which conformed to incoming signals and when signals were transmitted by the "encoding rat" which resulted in the desired action. In the initial experiment the rewarded action was pushing a lever in the remote location corresponding to the position of a lever near a lighted LED at the home location. About a month was required for the rats to acclimate themselves to incoming "brainwaves." When a decoding rat was unable to choose the correct lever, the encoding rat noticed (not getting an expected reward), and produced a round of task-related neuron firing that made the second rat more likely to choose the correct lever.

In another study, electrical brain readings were used to trigger a form of magnetic stimulation, to send a brain signal based on brain activity on a subject to a recipient, which caused the recipient to hit the fire button on a computer game.

Brain-To-Computer Interface: A brain-computer interface (BCI), sometimes called a neural-control interface (NCI), mind-machine interface (MMI), direct neural interface (DNI), or brain-machine interface (BMI), is a direct communication pathway between an enhanced or wired brain and an external device. BCI differs from neuromodulation in that it allows for bidirectional information flow. BC's are often directed at researching, mapping, assisting, augmenting, or repairing human cognitive or sensory-motor functions.

Synthetic telepathy, also known as techlepathy or psychotronics (geeldon.wordpress.com/2010/09/06/synthetic-telepathy-also-known-as-techlepathy-or-psychotronics/), describes the process of use of brain-computer interfaces by which human thought (as electromagnetic radiation) is intercepted, processed by computer and a return signal generated that is perceptible by the human brain. Dewan, E. M., "Occipital Alpha Rhythm Eye Position and Lens Accommodation." Nature 214, 975-977 (3 Jun. 1967), demonstrates the mental control of Alpha waves, turning them on and off, to produce Morse code representations of words and phrases by thought alone. U.S. Pat. No. 3,951,134 proposes remotely monitoring and altering brainwaves using radio, and references demodulating the waveform, displaying it to an operator for viewing and passing this to a computer for further analysis. In 1988, Farwell, L. A., & Donchin, E. (1988). Talking off the top of your head: toward a mental prosthesis utilizing event-related brain potentials. Electroencephalography and Clinical Neurophysiology, 70(6), 510-523 describes a method of transmitting linguistic information using the P300 response system, which combines matching observed information to what the subject was thinking of. In this case, being able to select a letter of the alphabet that the subject was thinking of. In theory, any input could be used and a lexicon constructed. U.S. Pat. No. 6,011,991 describes a method of monitoring an individual's brain waves remotely, for the purposes of communication, and outlines a system that monitors an individual's brainwaves via a sensor, then transmits this information, specifically by satellite, to a computer for analysis. This analysis would determine if the individual was attempting to communicate a "word, phrase, or thought corresponding to the matched stored normalized signal."

Approaches to synthetic telepathy can be categorized into two major groups, passive and active. Like sonar, the receiver can take part or passively listen. Passive reception is the ability to "read" a signal without first broadcasting a signal. This can be roughly equated to tuning into a radio station—the brain generates electromagnetic radiation which can be received at a distance. That distance is determined by the sensitivity of the receiver, the filters used and the bandwidth required. Most universities would have limited budgets, and receivers, such as EEG (and similar devices), would be used. A related military technology is the surveillance system TEMPEST. Robert G. Malech's approach requires a modulated signal to be broadcast at the target. The method uses an active signal, which is interfered with by the brain's modulation. Thus, the return signal can be used to infer the original brainwave.

Computer mediation falls into two basic categories, interpretative and interactive. Interpretative mediation is the passive analysis of signals coming from the human brain. A computer "reads" the signal then compares that signal against a database of signals and their meanings. Using statistical analysis and repetition, false-positives are reduced over time. Interactive mediation can be in a passive-active mode or active-active mode. In this case, passive and active denote the method of reading and writing to the brain and whether or not they make use of a broadcast signal. Interactive mediation can also be performed manually or via artificial intelligence. Manual interactive mediation involves a human operator producing return signals such as speech or images. A.I. mediation leverages the cognitive system of the subject to identify images, pre-speech, objects, sounds and other artifacts, rather than developing A.I. routines to perform such activities. A.I. based systems may incorporate natural language processing interfaces that produce sensations, mental impressions, humor and conversation to provide a mental picture of a computerized personality. Statistical analysis and machine learning techniques, such as neural networks can be used.

ITV News Service, in March 1991, produced a report of ultrasound piggybacked on a commercial radio broadcast (100 Mhz) aimed at entraining the brains of Iraqi troops and creating feelings of despair. U.S. Pat. No. 5,159,703 that refers to a "silent communications system in which nonaural carriers, in the very low or very high audio frequency range or in the adjacent ultrasonic frequency spectrum, are amplitude or frequency modulated with the desired intelligence and propagated acoustically or vibrationally, for inducement into the brain, typically through the use of loudspeakers, earphones or piezoelectric transducers." See:

Dr Nick Begich—Controlling the Human Mind, Earth Pulse Press Anchorage—isbn=1-890693-54-5 cbcg.org/gjcsl.htm %7C God's Judgment Cometh Soon cnslab.ss.uci.edu/muri/research.html, #Dewan, #Farwell-Donchin, #ImaginedSpeechProduction, #Overview, MURI: Synthetic Telepathy daprocess.com/01.welcome.html DaProcess of A Federal Investigation deepthought.newsvine.com/_news/2012/01/01/9865851-nsa-disinformation-watch-the-watchers-with-me deepthought.newsvine.com/_news/2012/01/09/10074589-nsa-disinformation-watch-the-watchers-with-me-part-2 deepthought.newsvine.com/_news/2012/01/16/10169491-the-nsa-behind-the-curtain genamason.wordpress.com/2009/10/18/more-on-synthetic-telepathy/ io9.com/5065304/tips-and-tricks-for-mind-control-from-the-us-military newdawnmagazine.com.au/Artide/Brain_Zapping_Part_One.html pinktentade.com/2008/12/scientists-extract-images-directly-from-brain/Scientists extract images directly from brain timesofindia.indiatimes.com/HealthSci/US_army_developing_synthetic_telepathy/ www.bibliotecapleyades.net/ciencia/ciencia_nonlethalweapons02.htm Eleanor White—New Devices That 'Talk' To The Human Mind Need Debate, Controls www.cbsnews.com/stories/2008/12/31/60 minutes/main4694713.shtml 60 Minutes: Incredible Research Lets Scientists Get A Glimpse At Your Thoughts www.cbsnews.com/video/watch/?id=5119805n&tag=related; photovideo 60 Minutes: Video—Mind Reading www.charlesrehn.com/charlesrehn/books/aconversationwithamerica/essays/myessays/The NSA.doc www.govtrack.us/congress/billtext.xpd?bill=h107-2977 Space Preservation Act of 2001 www.informaworld.com/smpp/content~db=all~content=a785359968 Partial Amnesia for a Narrative Following Application of Theta Frequency Electromagnetic Fields www.msnbc.msn.com/id/27162401/ www.psychology.nottingham.acuk/staff/Ipxdts/TMS info.html Transcranial Magnetic Stimulation www.raven1.net/silsoun2.htm Psy-Ops Weaponry Used In The Persian Gulf War www.scribd.com/doc/24531011/Operation-Mind-Control www.scribd.com/doc/6508206/synthetic-telepathy-and-the-early-mind-wars www.slavery.org.uk/Bioeffects_of_Selected_Non-Lethal_Weapons.pdf—Bioeffects of selected non-lethal weapons www.sst.ws/tempstandards.php?pab=1_1 TEMPEST measurement standards www.uwe.acuk/hIss/research/cpss/Journal_Psycho-Social_Studies/v2-2/SmithC.shtml Journal of Psycho-Social Studies—Vol 2 (2) 2003—On the Need for New Criteria of Diagnosis of Psychosis in the Light of Mind Invasive Technology by Dr. Carole Smith www.wired.com/dangerroom/2009/05/pentagon-preps-soldier-telepathy-push www.wired.com/wired/archive/7.11/persinger.html This Is Your Brain on God Noah, Shachtman—Pentagon's PCs Bend to Your Brain www.wired.com/dangerroom/2007/03/the_us_military Soldier-Telepathy" Drummond, Katie—Pentagon Preps Soldier Telepathy Push U.S. Pat. No. 3,951,134

U.S. Pat. No. 5,159,703 Silent subliminal presentation system

U.S. Pat. No. 6,011,991

U.S. Pat. No. 6,587,729 Apparatus for audibly communicating speech using the radio frequency hearing effect Wall, Judy, "Military Use of Mind Control Weapons", NEXUS, 5/06, October-November 1998

It is known to analyze EEG patterns to extract an indication of certain volitional activity (U.S. Pat. No. 6,011,991). This technique describes that an EEG recording can be matched against a stored normalized signal using a computer. This matched signal is then translated into the corresponding reference. The patent application describes a method "a system capable of identifying particular nodes in an individual's brain, the firings of which affect characteristics such as appetite, hunger, thirst, communication skills" and "devices mounted to the person (e.g. underneath the scalp) may be energized in a predetermined manner or sequence to remotely cause particular identified brain node(s) to be fired in order to cause a predetermined feeling or reaction in the individual" without technical description of implementation. This patent also describes, that "brain activity [is monitored] by way of electroencephalography (EEG) methods, magnetoencephalography (MEG) methods, and the like. For example, see U.S. Pat. Nos. 5,816,247 and 5,325,862.

See also, U.S. Pat. Nos. 3,951,134; 4,437,064; 4,591,787; 4,613,817; 4,689,559; 4,693,000; 4,700,135; 4,733,180; 4,736,751; 4,749,946; 4,753,246; 4,761,611; 4,771,239; 4,801,882; 4,862,359; 4,913,152; 4,937,525; 4,940,058; 4,947,480; 4,949,725; 4,951,674; 4,974,602; 4,982,157; 4,983,912; 4,996,479; 5,008,622; 5,012,190; 5,020,538; 5,061,680; 5,092,835; 5,095,270; 5,126,315; 5,158,932; 5,159,703; 5,159,928; 5,166,614; 5,187,327; 5,198,977; 5,213,338; 5,241,967; 5,243,281; 5,243,517; 5,263,488; 5,265,611; 5,269,325; 5,282,474; 5,283,523; 5,291,888; 5,303,705; 5,307,807; 5,309,095; 5,311,129; 5,323,777; 5,325,862; 5,326,745; 5,339,811; 5,417,211; 5,418,512; 5,442,289; 5,447,154; 5,458,142; 5,469,057; 5,476,438; 5,496,798; 5,513,649; 5,515,301; 5,552,375; 5,579,241; 5,594,849; 5,600,243; 5,601,081; 5,617,856; 5,626,145; 5,656,937; 5,671,740; 5,682,889; 5,701,909; 5,706,402; 5,706,811; 5,729,046; 5,743,854; 5,743,860; 5,752,514; 5,752,911; 5,755,227; 5,761,332; 5,762,611; 5,767,043; 5,771,261; 5,771,893; 5,771,894; 5,797,853; 5,813,993; 5,815,413; 5,842,986; 5,857,978; 5,885,976; 5,921,245; 5,938,598; 5,938,688; 5,970,499; 6,002,254; 6,011,991; 6,023,161; 6,066,084; 6,069,369; 6,080,164; 6,099,319; 6,144,872; 6,154,026; 6,155,966; 6,167,298; 6,167,311; 6,195,576; 6,230,037; 6,239,145; 6,263,189; 6,290,638; 6,354,087; 6,356,079; 6,370,414; 6,374,131; 6,385,479; 6,418,344; 6,442,948; 6,470,220; 6,488,617; 6,516,246; 6,526,415; 6,529,759; 6,538,436; 6,539,245; 6,539,263; 6,544,170; 6,547,746; 6,557,558; 6,587,729; 6,591,132; 6,609,030; 6,611,698; 6,648,822; 6,658,287; 6,665,552; 6,665,553; 6,665,562; 6,684,098; 6,687,525; 6,695,761; 6,697,660; 6,708,051; 6,708,064; 6,708,184; 6,725,080; 6,735,460; 6,774,929; 6,785,409; 6,795,724; 6,804,661; 6,815,949; 6,853,186; 6,856,830; 6,873,872; 6,876,196; 6,885,192; 6,907,280; 6,926,921; 6,947,790; 6,978,179; 6,980,863; 6,983,184; 6,983,264; 6,996,261; 7,022,083; 7,023,206; 7,024,247; 7,035,686; 7,038,450; 7,039,266; 7,039,547; 7,053,610; 7,062,391; 7,092,748; 7,105,824; 7,116,102; 7,120,486; 7,130,675; 7,145,333; 7,171,339; 7,176,680; 7,177,675; 7,183,381; 7,186,209; 7,187,169; 7,190,826; 7,193,413; 7,196,514; 7,197,352; 7,199,708; 7,209,787; 7,218,104; 7,222,964; 7,224,282; 7,228,178; 7,231,254; 7,242,984; 7,254,500; 7,258,659; 7,269,516; 7,277,758; 7,280,861; 7,286,871; 7,313,442; 7,324,851; 7,334,892; 7,338,171; 7,340,125; 7,340,289; 7,346,395; 7,353,064; 7,353,065; 7,369,896; 7,371,365; 7,376,459; 7,394,246; 7,400,984; 7,403,809; 7,403,820; 7,409,321; 7,418,290; 7,420,033; 7,437,196; 7,440,789; 7,453,263; 7,454,387; 7,457,653; 7,461,045; 7,462,155; 7,463,024; 7,466,132; 7,468,350; 7,482,298; 7,489,964; 7,502,720; 7,539,528; 7,539,543; 7,553,810; 7,565,200; 7,565,809; 7,567,693; 7,570,054; 7,573,264; 7,573,268; 7,580,798; 7,603,174; 7,608,579; 7,613,502; 7,613,519; 7,613,520; 7,620,456; 7,623,927; 7,623,928; 7,625,340; 7,627,370; 7,647,098; 7,649,351; 7,653,433; 7,672,707; 7,676,263; 7,678,767; 7,697,979; 7,706,871; 7,715,894; 7,720,519; 7,729,740; 7,729,773; 7,733,973; 7,734,340; 7,737,687; 7,742,820; 7,746,979; 7,747,325; 7,747,326; 7,747,551; 7,756,564; 7,763,588; 7,769,424; 7,771,341; 7,792,575; 7,800,493; 7,801,591; 7,801,686; 7,831,305; 7,834,627; 7,835,787; 7,840,039; 7,840,248; 7,840,250; 7,853,329; 7,856,264; 7,860,552; 7,873,411; 7,881,760; 7,881,770; 7,882,135; 7,891,814; 7,892,764; 7,894,903; 7,895,033; 7,904,139; 7,904,507; 7,908,009; 7,912,530; 7,917,221; 7,917,225; 7,929,693; 7,930,035; 7,932,225; 7,933,727; 7,937,152; 7,945,304; 7,962,204; 7,974,787; 7,986,991; 7,988,969; 8,000,767; 8,000,794; 8,001,179; 8,005,894; 8,010,178; 8,014,870; 8,027,730; 8,029,553; 8,032,209; 8,036,736; 8,055,591; 8,059,879; 8,065,360; 8,069,125; 8,073,631; 8,082,215; 8,083,786; 8,086,563; 8,116,874; 8,116,877; 8,121,694; 8,121,695; 8,150,523; 8,150,796; 8,155,726; 8,160,273; 8,185,382; 8,190,248; 8,190,264; 8,195,593; 8,209,224; 8,212,556; 8,222,378; 8,224,433; 8,229,540; 8,239,029; 8,244,552; 8,244,553; 8,248,069; 8,249,316; 8,270,814; 8,280,514; 8,285,351; 8,290,596; 8,295,934; 8,301,222; 8,301,257; 8,303,636; 8,304,246; 8,305,078; 8,308,646; 8,315,703; 8,334,690; 8,335,715; 8,335,716; 8,337,404; 8,343,066; 8,346,331; 8,350,804; 8,354,438; 8,356,004; 8,364,271; 8,374,412; 8,374,696; 8,380,314; 8,380,316; 8,380,658; 8,386,312; 8,386,313; 8,388,530; 8,392,250; 8,392,251; 8,392,253; 8,392,254; 8,392,255; 8,396,545; 8,396,546; 8,396,744; 8,401,655; 8,406,838; 8,406,848; 8,412,337; 8,423,144; 8,423,297; 8,429,225; 8,431,537; 8,433,388; 8,433,414; 8,433,418; 8,439,845; 8,444,571; 8,445,021; 8,447,407; 8,456,164; 8,457,730; 8,463,374; 8,463,378; 8,463,386; 8,463,387; 8,464,288; 8,467,878; 8,473,345; 8,483,795; 8,484,081; 8,487,760; 8,492,336; 8,494,610; 8,494,857; 8,494,905; 8,498,697; 8,509,904; 8,519,705; 8,527,029; 8,527,035; 8,529,463; 8,532,756; 8,532,757; 8,533,042; 8,538,513; 8,538,536; 8,543,199; 8,548,786; 8,548,852; 8,553,956; 8,554,325; 8,559,645; 8,562,540; 8,562,548; 8,565,606; 8,568,231; 8,571,629; 8,574,279; 8,586,019; 8,587,304; 8,588,933; 8,591,419; 8,593,141; 8,600,493; 8,600,696; 8,603,790; 8,606,592; 8,612,005; 8,613,695; 8,613,905; 8,614,254; 8,614,873; 8,615,293; 8,615,479; 8,615,664; 8,618,799; 8,626,264; 8,628,328; 8,635,105; 8,648,017; 8,652,189; 8,655,428; 8,655,437; 8,655,817; 8,658,149; 8,660,649; 8,666,099; 8,679,009; 8,682,441; 8,690,748; 8,693,765; 8,700,167; 8,703,114; 8,706,205; 8,706,206; 8,706,241; 8,706,518; 8,712,512; 8,716,447; 8,721,695; 8,725,243; 8,725,668; 8,725,669; 8,725,796; 8,731,650; 8,733,290; 8,738,395; 8,762,065; 8,762,202; 8,768,427; 8,768,447; 8,781,197; 8,781,597; 8,786,624; 8,798,717; 8,814,923; 8,815,582; 8,825,167; 8,838,225; 8,838,247; 8,845,545; 8,849,390; 8,849,392; 8,855,775; 8,858,440; 8,868,173; 8,874,439; 8,888,702; 8,893,120; 8,903,494; 8,907,668; 8,914,119; 8,918,176; 8,922,376; 8,933,696; 8,934,965; 8,938,289; 8,948,849; 8,951,189; 8,951,192; 8,954,293; 8,955,010; 8,961,187; 8,974,365; 8,977,024; 8,977,110; 8,977,362; 8,993,623; 9,002,458; 9,014,811; 9,015,087; 9,020,576; 9,026,194; 9,026,218; 9,026,372; 9,031,658; 9,034,055; 9,034,923; 9,037,224; 9,042,074; 9,042,201; 9,042,988; 9,044,188; 9,053,516; 9,063,183; 9,064,036; 9,069,031; 9,072,482; 9,074,976; 9,079,940; 9,081,890; 9,095,266; 9,095,303; 9,095,618; 9,101,263; 9,101,276; 9,102,717; 9,113,801; 9,113,803; 9,116,201; 9,125,581; 9,125,788; 9,138,156; 9,142,185; 9,155,373; 9,161,715; 9,167,979; 9,173,609; 9,179,854; 9,179,875; 9,183,351; 9,192,300; 9,198,621; 9,198,707; 9,204,835; 9,211,076; 9,211,077; 9,213,074; 9,229,080; 9,230,539; 9,233,244; 9,238,150; 9,241,665; 9,242,067; 9,247,890; 9,247,911; 9,248,003; 9,248,288; 9,249,200; 9,249,234; 9,251,566; 9,254,097; 9,254,383; 9,259,482; 9,259,591; 9,261,573; 9,265,943; 9,265,965; 9,271,679; 9,280,784; 9,283,279; 9,284,353; 9,285,249; 9,289,595; 9,302,069; 9,309,296; 9,320,900; 9,329,758; 9,331,841; 9,332,939;

9,333,334; 9,336,535; 9,336,611; 9,339,227; 9,345,609; 9,351,651; 9,357,240; 9,357,298; 9,357,970; 9,358,393; 9,359,449; 9,364,462; 9,365,628; 9,367,738; 9,368,018; 9,370,309; 9,370,667; 9,375,573; 9,377,348; 9,377,515; 9,381,352; 9,383,208; 9,392,955; 9,394,347; 9,395,425; 9,396,669; 9,401,033; 9,402,558; 9,403,038; 9,405,366; 9,410,885; 9,411,033; 9,412,233; 9,415,222; 9,418,368; 9,421,373; 9,427,474; 9,438,650; 9,440,070; 9,445,730; 9,446,238; 9,448,289; 9,451,734; 9,451,899; 9,458,208; 9,460,400; 9,462,733; 9,463,327; 9,468,541; 9,471,978; 9,474,852; 9,480,845; 9,480,854; 9,483,117; 9,486,381; 9,486,389; 9,486,618; 9,486,632; 9,492,114; 9,495,684; 9,497,017; 9,498,134; 9,498,634; 9,500,722; 9,505,817; 9,517,031; 9,517,222; 9,519,981; 9,521,958; 9,534,044; 9,538,635; 9,539,118; 9,556,487; 9,558,558; 9,560,458; 9,560,967; 9,560,984; 9,560,986; 9,563,950; 9,568,564; 9,572,996; 9,579,035; 9,579,048; 9,582,925; 9,584,928; 9,588,203; 9,588,490; 9,592,384; 9,600,138; 9,604,073; 9,612,295; 9,618,591; 9,622,660; 9,622,675; 9,630,008; 9,642,553; 9,642,554; 9,643,019; 9,646,248; 9,649,501; 9,655,573; 9,659,186; 9,664,856; 9,665,824; 9,665,987; 9,675,292; 9,681,814; 9,682,232; 9,684,051; 9,685,600; 9,687,562; 9,694,178; 9,694,197; 9,713,428; 9,713,433; 9,713,444; 9,713,712; D627476; RE44097; RE46209; 20010009975; 20020103428; 20020103429; 20020158631; 20020173714; 20030004429; 20030013981; 20030018277; 20030081818; 20030093004; 20030097159; 20030105408; 20030158495; 20030199749; 20040019370; 20040034299; 20040092809; 20040127803; 20040186542; 20040193037; 20040210127; 20040210156; 20040263162; 20050015205; 20050033154; 20050043774; 20050059874; 20050216071; 20050256378; 20050283053; 20060074822; 20060078183; 20060100526; 20060135880; 20060225437; 20070005391; 20070036355; 20070038067; 20070043392; 20070049844; 20070083128; 20070100251; 20070165915; 20070167723; 20070191704; 20070197930; 20070239059; 20080001600; 20080021340; 20080091118; 20080167571; 20080249430; 20080304731; 20090018432; 20090082688; 20090099783; 20090149736; 20090179642; 20090216288; 20090299169; 20090312624; 20090318794; 20090319001; 20090319004; 20100010366; 20100030097; 20100049482; 20100056276; 20100069739; 20100092934; 20100094155; 20100113959; 20100131034; 20100174533; 20100197610; 20100219820; 20110015515; 20110015539; 20110046491; 20110082360; 20110110868; 20110150253; 20110182501; 20110217240; 20110218453; 20110270074; 20110301448; 20120021394; 20120143104; 20120150262; 20120191542; 20120232376; 20120249274; 20120253168; 20120271148; 20130012804; 20130013667; 20130066394; 20130072780; 20130096453; 20130150702; 20130165766; 20130211238; 20130245424; 20130251641; 20130255586; 20130304472; 20140005518; 20140058241; 20140062472; 20140077612; 20140101084; 20140121565; 20140135873; 20140142448; 20140155730; 20140159862; 20140206981; 20140243647; 20140243652; 20140245191; 20140249445; 20140249447; 20140271483; 20140275891; 20140276013; 20140276014; 20140276187; 20140276702; 20140277582; 20140279746; 20140296733; 20140297397; 20140300532; 20140303424; 20140303425; 20140303511; 20140316248; 20140323899; 20140328487; 20140330093; 20140330394; 20140330580; 20140335489; 20140336489; 20140336547; 20140343397; 20140343882; 20140348183; 20140350380; 20140354278; 20140357507; 20140357932; 20140357935; 20140358067; 20140364721; 20140370479; 20140371573; 20140371611; 20140378815; 20140378830; 20150005840; 20150005841; 20150008916; 20150011877; 20150017115; 20150018665; 20150018702; 20150018705; 20150018706; 20150019266; 20150025422; 20150025917; 20150026446; 20150030220; 20150033363; 20150044138; 20150065838; 20150065845; 20150069846; 20150072394; 20150073237; 20150073249; 20150080695; 20150080703; 20150080753; 20150080985; 20150088024; 20150088224; 20150091730; 20150091791; 20150096564; 20150099962; 20150105844; 20150112403; 20150119658; 20150119689; 20150119698; 20150119745; 20150123653; 20150133811; 20150133812; 20150133830; 20150140528; 20150141529; 20150141773; 20150148619; 20150150473; 20150150475; 20150151142; 20150154721; 20150154764; 20150157271; 20150161738; 20150174403; 20150174418; 20150178631; 20150178978; 20150182417; 20150186923; 20150192532; 20150196800; 20150201879; 20150202330; 20150206051; 20150206174; 20150212168; 20150213012; 20150213019; 20150213020; 20150215412; 20150216762; 20150219729; 20150219732; 20150220830; 20150223721; 20150226813; 20150227702; 20150230719; 20150230744; 20150231330; 20150231395; 20150231405; 20150238104; 20150248615; 20150253391; 20150257700; 20150264492; 20150272461; 20150272465; 20150283393; 20150289813; 20150289929; 20150293004; 20150294074; 20150297108; 20150297139; 20150297444; 20150297719; 20150304048; 20150305799; 20150305800; 20150305801; 20150306057; 20150306390; 20150309582; 20150313496; 20150313971; 20150315554; 20150317447; 20150320591; 20150324544; 20150324692; 20150327813; 20150328330; 20150335281; 20150335294; 20150335876; 20150335877; 20150343242; 20150359431; 20150360039; 20150366503; 20150370325; 20150374250; 20160000383; 20160005235; 20160008489; 20160008598; 20160008620; 20160008632; 20160012011; 20160012583; 20160015673; 20160019434; 20160019693; 20160022165; 20160022168; 20160022207; 20160022981; 20160023016; 20160029958; 20160029959; 20160029998; 20160030666; 20160030834; 20160038049; 20160038559; 20160038770; 20160048659; 20160048948; 20160048965; 20160051161; 20160051162; 20160055236; 20160058322; 20160063207; 20160063883; 20160066838; 20160070436; 20160073916; 20160073947; 20160081577; 20160081793; 20160082180; 20160082319; 20160084925; 20160086622; 20160095838; 20160097824; 20160100769; 20160103487; 20160103963; 20160109851; 20160113587; 20160116472; 20160116553; 20160120432; 20160120436; 20160120480; 20160121074; 20160128589; 20160128632; 20160129249; 20160131723; 20160135748; 20160139215; 20160140975; 20160143540; 20160143541; 20160148077; 20160148400; 20160151628; 20160157742; 20160157777; 20160157828; 20160158553; 20160162652; 20160164813; 20160166207; 20160166219; 20160168137; 20160170996; 20160170998; 20160171514; 20160174862; 20160174867; 20160175557; 20160175607; 20160184599; 20160198968; 20160203726; 20160204937; 20160205450; 20160206581; 20160206871; 20160206877; 20160210872; 20160213276; 20160219345; 20160220163; 20160220821; 20160222073; 20160223622; 20160223627; 20160224803; 20160235324; 20160238673; 20160239966; 20160239968; 20160240212; 20160240765; 20160242665; 20160242670; 20160250473; 20160256130; 20160257957; 20160262680; 20160275536; 20160278653; 20160278662; 20160278687; 20160278736; 20160279267; 20160287117; 20160287308; 20160287334; 20160287895; 20160299568; 20160300252; 20160300352; 20160302711; 20160302720; 20160303396; 20160303402; 20160306844; 20160313408; 20160313417; 20160313418; 20160321742; 20160324677; 20160324942; 20160334475; 20160338608; 20160339300; 20160346530; 20160357003; 20160360970; 20160361532; 20160361534; 20160371387; 20170000422; 20170014080; 20170020454; 20170021158; 20170021161; 20170027517; 20170032527; 20170039591; 20170039706;

20170041699; 20170042474; 20170042476; 20170042827; 20170043166; 20170043167; 20170045601; 20170052170; 20170053082; 20170053088; 20170053461; 20170053665; 20170056363; 20170056467; 20170056655; 20170065199; 20170065349; 20170065379; 20170065816; 20170066806; 20170079538; 20170079543; 20170080050; 20170080256; 20170085547; 20170085855; 20170086729; 20170087367; 20170091418; 20170095174; 20170100051; 20170105647; 20170107575; 20170108926; 20170119270; 20170119271; 20170120043; 20170131293; 20170133576; 20170133577; 20170135640; 20170140124; 20170143986; 20170146615; 20170146801; 20170147578; 20170148213; 20170148592; 20170150925; 20170151435; 20170151436; 20170154167; 20170156674; 20170165481; 20170168121; 20170168568; 20170172446; 20170173391; 20170178001; 20170178340; 20170180558; 20170181252; 20170182176; 20170188932; 20170189691; 20170190765; 20170196519; 20170197081; 20170198017; 20170199251; 20170202476; 20170202518; 20170206654; 20170209044; 20170209062; 20170209225; 20170209389; and 20170212188.

Brain Entrainment: Brain entrainment, also referred to as brainwave synchronization and neural entrainment, refers to the capacity of the brain to naturally synchronize its brainwave frequencies with the rhythm of periodic external stimuli, most commonly auditory, visual, or tactile. Brainwave entrainment technologies are used to induce various brain states, such as relaxation or sleep, by creating stimuli that occur at regular, periodic intervals to mimic electrical cycles of the brain during the desired states, thereby "training" the brain to consciously alter states. Recurrent acoustic frequencies, flickering lights, or tactile vibrations are the most common examples of stimuli applied to generate different sensory responses. It is hypothesized that listening to these beats of certain frequencies one can induce a desired state of consciousness that corresponds with specific neural activity. Patterns of neural firing, measured in Hz, correspond with alertness states such as focused attention, deep sleep, etc.

Neural oscillations are rhythmic or repetitive electrochemical activity in the brain and central nervous system. Such oscillations can be characterized by their frequency, amplitude and phase. Neural tissue can generate oscillatory activity driven by mechanisms within individual neurons, as well as by interactions between them. They may also adjust frequency to synchronize with the periodic vibration of external acoustic or visual stimuli. The functional role of neural oscillations is still not fully understood; however, they have been shown to correlate with emotional responses, motor control, and a number of cognitive functions including information transfer, perception, and memory. Specifically, neural oscillations, in particular theta activity, are extensively linked to memory function, and coupling between theta and gamma activity is considered to be vital for memory functions, including episodic memory. Electroencephalography (EEG) has been most widely used in the study of neural activity generated by large groups of neurons, known as neural ensembles, including investigations of the changes that occur in electroencephalographic profiles during cycles of sleep and wakefulness. EEG signals change dramatically during sleep and show a transition from faster frequencies to increasingly slower frequencies, indicating a relationship between the frequency of neural oscillations and cognitive states including awareness and consciousness.

The term 'entrainment' has been used to describe a shared tendency of many physical and biological systems to synchronize their periodicity and rhythm through interaction. This tendency has been identified as specifically pertinent to the study of sound and music generally, and acoustic rhythms specifically. The most ubiquitous and familiar examples of neuromotor entrainment to acoustic stimuli is observable in spontaneous foot or finger tapping to the rhythmic beat of a song. Exogenous rhythmic entrainment, which occurs outside the body, has been identified and documented for a variety of human activities, which include the way people adjust the rhythm of their speech patterns to those of the subject with whom they communicate, and the rhythmic unison of an audience clapping. Even among groups of strangers, the rate of breathing, locomotive and subtle expressive motor movements, and rhythmic speech patterns have been observed to synchronize and entrain, in response to an auditory stimulus, such as a piece of music with a consistent rhythm. Furthermore, motor synchronization to repetitive tactile stimuli occurs in animals, including cats and monkeys as well as humans, with accompanying shifts in electroencephalogram (EEG) readings. Examples of endogenous entrainment, which occurs within the body, include the synchronizing of human circadian sleep-wake cycles to the 24-hour cycle of light and dark, and the frequency following response of humans to sounds and music.

Brainwaves, or neural oscillations, share the fundamental constituents with acoustic and optical waves, including frequency, amplitude and periodicity. The synchronous electrical activity of cortical neural ensembles can synchronize in response to external acoustic or optical stimuli and also entrain or synchronize their frequency and phase to that of a specific stimulus. Brainwave entrainment is a colloquialism for such 'neural entrainment', which is a term used to denote the way in which the aggregate frequency of oscillations produced by the synchronous electrical activity in ensembles of cortical neurons can adjust to synchronize with the periodic vibration of an external stimuli, such as a sustained acoustic frequency perceived as pitch, a regularly repeating pattern of intermittent sounds, perceived as rhythm, or of a regularly rhythmically intermittent flashing light.

Changes in neural oscillations, demonstrable through electroencephalogram (EEG) measurements, are precipitated by listening to music, which can modulate autonomic arousal ergotropically and trophotropically, increasing and decreasing arousal respectively. Musical auditory stimulation has also been demonstrated to improve immune function, facilitate relaxation, improve mood, and contribute to the alleviation of stress.

The Frequency following response (FFR), also referred to as Frequency Following Potential (FFP), is a specific response to hearing sound and music, by which neural oscillations adjust their frequency to match the rhythm of auditory stimuli. The use of sound with intent to influence cortical brainwave frequency is called auditory driving, by which frequency of neural oscillation is 'driven' to entrain with that of the rhythm of a sound source.

See, en.wikipedia.org/wiki/Brainwave_entrainment;

U.S. Pat. Nos. 5,070,399; 5,306,228; 5,409,445; 6,656,137; 7,749,155; 7,819,794; 7,988,613; 8,088,057; 8,167,784; 8,213,670; 8,267,851; 8,298,078; 8,517,909; 8,517,912; 8,579,793; 8,579,795; 8,597,171; 8,636,640; 8,638,950; 8,668,496; 8,852,073; 8,932,218; 8,968,176; 9,330,523; 9,357,941; 9,459,597; 9,480,812; 9,563,273; 9,609,453; 9,640,167; 9,707,372; 20050153268; 20050182287; 20060106434; 20060206174; 20060281543; 20070066403; 20080039677; 20080304691; 20100010289; 20100010844; 20100028841; 20100056854; 20100076253; 20100130812; 20100222640; 20100286747; 20100298624; 20110298706;

20110319482; 20120003615; 20120053394; 20120150545; 20130030241; 20130072292; 20130131537; 20130172663; 20130184516; 20130203019; 20130234823; 20130338738; 20140088341; 20140107401; 20140114242; 20140154647; 20140174277; 20140275741; 20140309484; 20140371516; 20150142082; 20150283019; 20150296288; 20150313496; 20150313949; 20160008568; 20160019434; 20160055842; 20160205489; 20160235980; 20160239084; 20160345901; 20170034638; 20170061760; 20170087330; 20170094385; 20170095157; 20170099713; 20170135597; and 20170149945.

Carter, J., and H. Russell. "A pilot investigation of auditory and visual entrainment of brain wave activity in learning disabled boys." Texas Researcher 4.1 (1993): 65-75;

Casciaro, Francesco, et al. "Alpha-rhythm stimulation using brain entrainment enhances heart rate variability in subjects with reduced HRV." World J. Neuroscience 3.04 (2013): 213; Helfrich, Randolph F., et al. "Entrainment of brain oscillations by transcranial alternating current stimulation." Current Biology 24.3 (2014): 333-339;

Huang, Tina L., and Christine Charyton. "A comprehensive review of the psychological effects of brainwave entrainment." Alternative therapies in health and medicine 14.5 (2008): 38;

Joyce, Michael, and Dave Siever. "Audio-visual entrainment program as a treatment for behavior disorders in a school setting." J. Neurotherapy 4.2 (2000): 9-25;

Keitel, Christian, Cliodhna Quigley, and Philipp Ruhnau. "Stimulus-driven brain oscillations in the alpha range: entrainment of intrinsic rhythms or frequency-following response?" J. Neuroscience 34.31 (2014): 10137-10140;

Lakatos, Peter, et al. "Entrainment of neuronal oscillations as a mechanism of attentional selection." Science 320.5872 (2008): 110-113;

Mori, Toshio, and Shoichi Kai. "Noise-induced entrainment and stochastic resonance in human brain waves." Physical review letters 88.21 (2002): 218101;

Padmanabhan, R., A. J. Hildreth, and D. Laws. "A prospective, randomised, controlled study examining binaural beat audio and pre-operative anxiety in patients undergoing general anaesthesia for day case surgery." Anaesthesia 60.9 (2005): 874-877;

Schalles, Matt D., and Jaime A. Pineda. "Musical sequence learning and EEG correlates of audiomotor processing." Behavioural neurology 2015 (2015). www.hindawi.com/journals/bn/2015/638202/

Thaut, Michael H., David A. Peterson, and Gerald C. McIntosh. "Temporal entrainment of cognitive functions." Annals of the New York Academy of Sciences 1060.1 (2005): 243-254.

Thut, Gregor, Philippe G. Schyns, and Joachim Gross. "Entrainment of perceptually relevant brain oscillations by non-invasive rhythmic stimulation of the human brain." Frontiers in Psychology 2 (2011);

Trost, Wiebke, et al. "Getting the beat: entrainment of brain activity by musical rhythm and pleasantness." NeuroImage 103 (2014): 55-64;

Will, Udo, and Eric Berg. "Brain wave synchronization and entrainment to periodic acoustic stimuli." Neuroscience letters 424.1 (2007): 55-60; and Zhuang, Tianbao, Hong Zhao, and Zheng Tang. "A study of brainwave entrainment based on EEG brain dynamics." Computer and information science 2.2 (2009): 80.

A baseline correction of event-related time-frequency measure may be made to take pre-event baseline activity into consideration. In general, a baseline period is defined by the average of the values within a time window preceding the time-locking event. There are at least four common methods for baseline correction in time-frequency analysis. The methods include various baseline value normalizations. See, Canolty R T, Edwards E, Dalal S S, et al. High gamma power is phase-locked to theta oscillations in human neocortex. Science. 2006; 313:1626-1628.

Hoogenboom N, Schoffelen J M, Oostenveld R, Parkes L M, Fries P. Localizing human visual gamma-band activity in frequency, time and space. Neuroimage. 2006; 29:764-773;

Lachaux J P, Rodriguez E, Martinerie J, Varela F J. Measuring phase synchrony in brain signals. Hum Brain Mapp. 1999; 8:194-208, Le Van Quyen M, Foucher J, Lachaux J, et al. Comparison of Hilbert transform and wavelet methods for the analysis of neuronal synchrony. J Neurosci Methods. 2001; 111: 83-98, Rodriguez E, George N, Lachaux J P, Martinerie J, Renault B, Varela F J. Perception's shadow: long-distance synchronization of human brain activity. Nature. 1999; 397: 430-433., Spencer K M, Nestor P G, Perlmutter R, et al. Neural synchrony indexes disordered perception and cognition in schizophrenia. Proc Natl Acad Sci USA. 2004; 101: 17288-17293;

The question of whether different emotional states are associated with specific patterns of physiological response has long being a subject of neuroscience research See, for example:

James W (1884.) What is an emotion? Mind 9: 188-205; Lacey J I, Bateman D E, Vanlehn R (1953) Autonomic response specificity; an experimental study. Psychosom Med 15: 8-21;

Levenson R W, Heider K, Ekman P, Friesen W V (1992) Emotion and Autonomic Nervous-System Activity in the Minangkabau of West Sumatra. J Pers Soc Psychol 62: 972-988.

Some studies have indicated that the physiological correlates of emotions are likely to be found in the central nervous system (CNS). See, for example:

Buck R (1999) The biological affects: A typology. Psychological Review 106: 301-336; Izard C E (2007) Basic Emotions, Natural Kinds, Emotion Schemas, and a New Paradigm. Perspect Psychol Sci 2: 260-280;

Panksepp J (2007) Neurologizing the Psychology of Affects How Appraisal-Based Constructivism and Basic Emotion Theory Can Coexist. Perspect Psychol Sci 2: 281-296.

Electroencephalograms (EEG) and functional Magnetic Resonance Imaging, fMRI have been used to study specific brain activity associated with different emotional states. Mauss and Robinson, in their review paper, have indicated that "emotional state is likely to involve circuits rather than any brain region considered in isolation" (Mauss I B, Robinson M D (2009) Measures of emotion: A review. Cogn Emot 23: 209-237.)

The amplitude, latency from the stimulus, and covariance (in the case of multiple electrode sites) of each component can be examined in connection with a cognitive task (ERP) or with no task (EP). Steady-state visually evoked potentials (SSVEPs) use a continuous sinusoidally-modulated flickering light, typically superimposed in front of a TV monitor displaying a cognitive task. The brain response in a narrow frequency band containing the stimulus frequency is measured. Magnitude, phase, and coherence (in the case of multiple electrode sites) may be related to different parts of the cognitive task. Brain entrainment may be detected through EEG or MEG activity. Brain entrainment may be detected through EEG or MEG activity. See:

Abeln, Vera, et al. "Brainwave entrainment for better sleep and post-sleep state of young elite soccer players-A pilot study." European J. Sport science 14.5 (2014): 393-402;

Acton, George. "Methods for independent entrainment of visual field zones." U.S. Pat. No. 9,629,976. 25 Apr. 2017;

Albouy, Philippe, et al. "Selective entrainment of theta oscillations in the dorsal stream causally enhances auditory working memory performance." Neuron 94.1 (2017): 193-206.

Amengual, J., et al. "P018 Local entrainment and distribution across cerebral networks of natural oscillations elicited in implanted epilepsy patients by intracranial stimulation: Paving the way to develop causal connectomics of the healthy human brain." Clin. Neurophysiology 128.3 (2017): e18;

Argento, Emanuele, et al. "Augmented Cognition via Brainwave Entrainment in Virtual Reality: An Open, Integrated Brain Augmentation in a Neuroscience System Approach." Augmented Human Research 2.1 (2017): 3;

Bello, Nicholas P. "Altering Cognitive and Brain States Through Cortical Entrainment." (2014); Costa-Faidella, Jordi, Elyse S. Sussman, and Caries Escera. "Selective entrainment of brain oscillations drives auditory perceptual organization." NeuroImage (2017);

Börgers, Christoph. "Entrainment by Excitatory Input Pulses." An Introduction to Modeling Neuronal Dynamics. Springer International Publishing, 2017. 183-192;

Calderone, Daniel J., et al. "Entrainment of neural oscillations as a modifiable substrate of attention." Trends in cognitive sciences 18.6 (2014): 300-309;

Casciaro, Francesco, et al. "Alpha-rhythm stimulation using brain entrainment enhances heart rate variability in subjects with reduced HRV." World J. Neuroscience 3.04 (2013): 213;

Chang, Daniel Wonchul. "Method and system for brain entertainment." U.S. Pat. No. 8,636,640. 28 Jan. 2014;

Colzato, Lorenza S., Amengual, Julià L., et al. "Local entrainment of oscillatory activity induced by direct brain stimulation in humans." Scientific Reports 7 (2017);

Conte, Elio, et al. "A Fast Fourier Transform analysis of time series data of heart rate variability during alfa-rhythm stimulation in brain entrainment." NeuroQuantology 11.3 (2013);

Dikker, Suzanne, et al. "Brain-to-brain synchrony tracks real-world dynamic group interactions in the classroom." Current Biology 27.9 (2017):1375-1380;

Ding, Nai, and Jonathan Z. Simon. "Cortical entrainment to continuous speech: functional roles and interpretations." Frontiers in human neuroscience 8 (2014);

Doherty, Cormac "A comparison of alpha brainwave entrainment, with and without musical accompaniment." (2014);

Falk, Simone, Cosima Lanzilotti, and Daniele Schön. "Tuning neural phase entrainment to speech." J. Cognitive Neuroscience (2017);

Gao, Junling, et al. "Entrainment of chaotic activities in brain and heart during MBSR mindfulness training." Neuroscience letters 616 (2016): 218-223;

Gooding-Williams, Gerard, Hongfang Wang, and Klaus Kessler. "THETA-Rhythm Makes the World Go Round: Dissociative Effects of TMS Theta Versus Alpha Entrainment of Right pTPJ on Embodied Perspective Transformations." Brain Topography (2017): 1-4;

Hanslmayr, Simon, Jonas Matuschek, and Marie-Christin Fellner. "Entrainment of prefrontal beta oscillations induces an endogenous echo and impairs memory formation." Current Biology 24.8 (2014): 904-909;

Heideman, Simone G., Erik S. to Woerd, and Peter Praamstra. "Rhythmic entrainment of slow brain activity preceding leg movements." Clin. Neurophysiology 126.2 (2015): 348-355;

Helfrich, Randolph F., et al. "Entrainment of brain oscillations by transcranial alternating current stimulation." Current Biology 24.3 (2014): 333-339;

Henry, Molly J., et al. "Aging affects the balance of neural entrainment and top-down neural modulation in the listening brain." Nature Communications 8 (2017): ncomms15801;

Horr, Ninja K., Maria Wimber, and Massimiliano Di Luca. "Perceived time and temporal structure: Neural entrainment to isochronous stimulation increases duration estimates." Neuroimage 132 (2016):148-156;

Irwin, Rosie. "Entraining Brain Oscillations to Influence Facial Perception." (2015);

Kalyan, Ritu, and Bipan Kaushal. "Binaural Entrainment and Its Effects on Memory." (2016);

Keitel, Anne, et al. "Auditory cortical delta-entrainment interacts with oscillatory power in multiple fronto-parietal networks." NeuroImage 147 (2017): 32-42;

Keitel, Christian, Cliodhna Quigley, and Philipp Ruhnau. "Stimulus-driven brain oscillations in the alpha range: entrainment of intrinsic rhythms or frequency-following response?" J. Neuroscience 34.31 (2014): 10137-10140;

Koelsch, Stefan. "Music-evoked emotions: principles, brain correlates, and implications for therapy." Annals of the New York Academy of Sciences1337.1 (2015): 193-201;

Kösem, Anne, et al. "Neural entrainment reflects temporal predictions guiding speech comprehension." the Eighth Annual Meeting of the Society for the Neurobiology of Language (SNL 2016). 2016;

Lee, Daniel Keewoong, Dongyeup Daniel Synn, and Daniel Chesong Lee. "Intelligent earplug system." U.S. patent application Ser. No. 15/106,989;

Lefournour, Joseph, Ramaswamy Palaniappan, and Ian V. McLoughlin. "Inter-hemispheric and spectral power analyses of binaural beat effects on the brain." Matters 2.9 (2016): e201607000001;

Mai, Guangting, James W. Minett, and William S-Y. Wang. "Delta, theta, beta, and gamma brain oscillations index levels of auditory sentence processing." Neuroimage 133 (2016):516-528;

Marconi, Pier Luigi, et al. "The phase amplitude coupling to assess brain network system integration." Medical Measurements and Applications (MeMeA), 2016 IEEE International Symposium on. IEEE, 2016;

McLaren, Elgin-Skye, and Alissa N. Antle. "Exploring and Evaluating Sound for Helping Children Self-Regulate with a Brain-Computer Application." Proceedings of the 2017 Conference on Interaction Design and Children. ACM, 2017;

Moisa, Marius, et al. "Brain network mechanisms underlying motor enhancement by transcranial entrainment of gamma oscillations." J. Neuroscience 36.47 (2016): 12053-12065;

Molinaro, Nicola, et al. "Out-of-synchrony speech entrainment in developmental dyslexia." Human brain mapping 37.8 (2016): 2767-2783;

Moseley, Ralph. "Immersive brain entrainment in virtual worlds: actualizing meditative states." Emerging Trends and Advanced Technologies for Computational Intelligence. Springer International Publishing, 2016. 315-346;

Neuling, Toralf, et al. "Friends, not foes: magnetoencephalography as a tool to uncover brain dynamics during transcranial alternating current stimulation." Neuroimage 118 (2015): 406-413;

Notbohm, Annika, Jürgen Kurths, and Christoph S. Herrmann. "Modification of brain oscillations via rhythmic light stimulation provides evidence for entrainment but not for superposition of event-related responses." Frontiers in human neuroscience 10 (2016);

Nozaradan, S., et al. "P943: Neural entrainment to musical rhythms in the human auditory cortex, as revealed by intracerebral recordings." Clin. Neurophysiology 125 (2014): 5299;

Palaniappan, Ramaswamy, et al. "Improving the feature stability and classification performance of bimodal brain and heart biometrics." Advances in Signal Processing and Intelligent Recognition Systems. Springer, Cham, 2016. 175-186;

Palaniappan, Ramaswamy, Somnuk Phon-Amnuaisuk, and Chikkannan Eswaran. "On the binaural brain entrainment indicating lower heart rate variability." Int. J. Cardiol 190 (2015): 262-263;

Papagiannakis, G., et al. A virtual reality brainwave entrainment method for human augmentation applications. Technical Report, FORTH-ICS/TR-458, 2015;

Park, Hyojin, et al. "Frontal top-down signals increase coupling of auditory low-frequency oscillations to continuous speech in human listeners." Current Biology 25.12 (2015): 1649-1653;

Pérez, Alejandro, Manuel Carreiras, and Jon Andoni Duñabeitia. "Brain-to-brain entrainment: EEG interbrain synchronization while speaking and listening." Scientific Reports 7 (2017);

Riecke, Lars, Alexander T. Sack, and Charles E. Schroeder. "Endogenous delta/theta sound-brain phase entrainment accelerates the buildup of auditory streaming." Current Biology 25.24 (2015): 3196-3201;

Spaak, Eelke, Floris P. de Lange, and Ole Jensen. "Local entrainment of alpha oscillations by visual stimuli causes cyclic modulation of perception." J. Neuroscience 34.10 (2014):3536-3544;

Thaut, Michael H. "The discovery of human auditory-motor entrainment and its role in the development of neurologic music therapy." Progress in brain research 217 (2015): 253-266;

Thaut, Michael H., Gerald C. McIntosh, and Volker Hoemberg. "Neurobiological foundations of neurologic music therapy: rhythmic entrainment and the motor system." Frontiers in psychology 5 (2014);

Thut, G. "T030 Guiding TMS by EEG/MEG to interact with oscillatory brain activity and associated functions." Clin. Neurophysiology 128.3 (2017): e9;

Treviño, Guadalupe Villarreal, et al. "The Effect of Audio Visual Entrainment on Pre-Attentive Dysfunctional Processing to Stressful Events in Anxious Individuals." Open J. Medical Psychology 3.05 (2014): 364;

Trost, Wiebke, et al. "Getting the beat: entrainment of brain activity by musical rhythm and pleasantness." NeuroImage 103 (2014): 55-64;

Tsai, Shu-Hui, and Yue-Der Lin. "Autonomie feedback with brain entrainment." Awareness Science and Technology and Ubi-Media Computing (iCAST-UMEDIA), 2013 International Joint Conference on. IEEE, 2013;

Vossen, Alexandra, Joachim Gross, and Gregor Thut. "Alpha power increase after transcranial alternating current stimulation at alpha frequency (α-tACS) reflects plastic changes rather than entrainment." Brain Stimulation 8.3 (2015): 499-508;

Witkowski, Matthias, et al. "Mapping entrained brain oscillations during transcranial alternating current stimulation (tACS)." Neuroimage 140 (2016): 89-98;

Zlotnik, Anatoly, Raphael Nagao, and István Z. Kiss Jr-Shin Li. "Phase-selective entrainment of nonlinear oscillator ensembles." Nature Communications 7 (2016).

The entrainment hypothesis (Thut and Miniussi, 2009; Thut et al., 2011a, 2012), suggests the possibility of inducing a particular oscillation frequency in the brain using an external oscillatory force (e.g., rTMS, but also tACS). The physiological basis of oscillatory cortical activity lies in the timing of the interacting neurons; when groups of neurons synchronize their firing activities, brain rhythms emerge, network oscillations are generated, and the basis for interactions between brain areas may develop (Buzsàki, 2006). Because of the variety of experimental protocols for brain stimulation, limits on descriptions of the actual protocols employed, and limited controls, consistency of reported studies is lacking, and extrapolability is limited. Thus, while there is various consensus in various aspects of the effects of extra cranial brain stimulation, the results achieved have a degree of uncertainty dependent on details of implementation. On the other hand, within a specific experimental protocol, it is possible to obtain statistically significant and repeatable results. This implies that feedback control might be effective to control implementation of the stimulation for a given purpose; however, studies that employ feedback control are lacking.

Different cognitive states are associated with different oscillatory patterns in the brain (Buzsàki, 2006; Canolty and Knight, 2010; Varela et al., 2001). Thut et al. (2011b) directly tested the entrainment hypothesis by means of a concurrent EEG-TMS experiment. They first determined the individual source of the parietal-occipital alpha modulation and the individual alpha frequency (magnetoencephalography study). They then applied rTMS at the individual alpha power while recording the EEG activity at rest. The results confirmed the three predictions of the entrainment hypothesis: the induction of a specific frequency after TMS, the enhancement of oscillation during TMS stimulation due to synchronization, and a phase alignment of the induced frequency and the ongoing activity (Thut et al., 2011b).

If associative stimulation is a general principle for human neural plasticity in which the timing and strength of activation are critical factors, it is possible that synchronization within or between areas using an external force to phase/align oscillations can also favor efficient communication and associative plasticity (or alter communication). In this respect associative, cortico-cortical stimulation has been shown to enhance coherence of oscillatory activity between the stimulated areas (Plewnia et al., 2008).

In coherence resonance (Longtin, 1997), the addition of a certain amount of noise in an excitable system results in the most coherent and proficient oscillatory responses. The brain's response to external timing-embedded stimulation can result in a decrease in phase variance and an enhanced alignment (clustering) of the phase components of the ongoing EEG activity (entraining, phase resetting) that can change the signal-to-noise ratio and increase (or decrease) signal efficacy.

If one considers neuron activity within the brain as a set of loosely coupled oscillators, then the various parameters that might be controlled include the size of the region of neurons, frequency of oscillation, resonant frequency or time-constant, oscillator damping, noise, amplitude, coupling to other oscillators, and of course, external influences that may include stimulation and/or power loss. In a human brain, pharmacological intervention may be significant. For example, drugs that alter excitability, such as caffeine, neurotransmitter release and reuptake, nerve conductance, etc. can all influence operation of the neural oscillators. Likewise, sub-threshold external stimulation effects, including DC, AC and magnetic electromagnetic effects, can also influence operation of the neural oscillators.

Phase resetting or shifting can synchronize inputs and favor communication and, eventually, Hebbian plasticity (Hebb, 1949). Thus, rhythmic stimulation may induce a statistically higher degree of coherence in spiking neurons, which facilitates the induction of a specific cognitive process (or hinders that process). Here, the perspective is slightly different (coherence resonance), but the underlining mechanisms are similar to the ones described so far (stochastic resonance), and the additional key factor is the repetition at a specific rhythm of the stimulation.

In the 1970's, the British biophysicist and psychobiologist, C. Maxwell Cade, monitored the brainwave patterns of advanced meditators and 300 of his students. Here he found that the most advanced meditators have a specific brainwave pattern that was different from the rest of his students. He noted that these meditators showed high activity of alpha brainwaves accompanied by beta, theta and even delta waves that were about half the amplitude of the alpha waves. See, Cade "The Awakened Mind: Biofeedback and the Development of Higher States of Awareness" (Dell, 1979). Anna Wise extended Cade's studies, and found that extraordinary achievers which included composers, inventors, artists, athletes, dancers, scientists, mathematicians, CEO's and presidents of large corporations have brainwave patterns differ from average performers, with a specific balance between Beta, Alpha, Theta and Delta brainwaves where Alpha had the strongest amplitude. See, Anna Wise, "The High-Performance Mind: Mastering Brainwaves for Insight, Healing, and Creativity".

Entrainment is plausible because of the characteristics of the demonstrated EEG responses to a single TMS pulse, which have a spectral composition which resemble the spontaneous oscillations of the stimulated cortex. For example, TMS of the "resting" visual (Rosanova et al., 2009) or motor cortices (Veniero et al., 2011) triggers alpha-waves, the natural frequency at the resting state of both types of cortices. With the entrainment hypothesis, the noise generation framework moves to a more complex and extended level in which noise is synchronized with on-going activity. Nevertheless, the model to explain the outcome will not change, stimulation will interact with the system, and the final result will depend on introducing or modifying the noise level. The entrainment hypothesis makes clear predictions with respect to online repetitive TMS paradigms' frequency engagement as well as the possibility of inducing phase alignment, i.e., a reset of ongoing brain oscillations via external spTMS (Thut et al., 2011a, 2012; Veniero et al., 2011). The entrainment hypothesis is superior to the localization approach in gaining knowledge about how the brain works, rather than where or when a single process occurs. TMS pulses may phase-align the natural, ongoing oscillation of the target cortex. When additional TMS pulses are delivered in synchrony with the phase-aligned oscillation (i.e., at the same frequency), further synchronized phase-alignment will occur, which will bring the oscillation of the target area in resonance with the TMS train. Thus, entrainment may be expected when TMS is frequency-tuned to the underlying brain oscillations (Veniero et al., 2011).

Binaural Beats: Binaural beats are auditory brainstem responses which originate in the superior olivary nucleus of each hemisphere. They result from the interaction of two different auditory impulses, originating in opposite ears, below 1000 Hz and which differ in frequency between one and 30 Hz. For example, if a pure tone of 400 Hz is presented to the right ear and a pure tone of 410 Hz is presented simultaneously to the left ear, an amplitude modulated standing wave of 10 Hz, the difference between the two tones, is experienced as the two wave forms mesh in and out of phase within the superior olivary nuclei. This binaural beat is not heard in the ordinary sense of the word (the human range of hearing is from 20-20,000 Hz). It is perceived as an auditory beat and theoretically can be used to entrain specific neural rhythms through the frequency-following response (FFR)—the tendency for cortical potentials to entrain to or resonate at the frequency of an external stimulus. Thus, it is theoretically possible to utilize a specific binaural-beat frequency as a consciousness management technique to entrain a specific cortical rhythm. The binaural-beat appears to be associated with an electroencephalographic (EEG) frequency-following response in the brain.

Uses of audio with embedded binaural beats that are mixed with music or various pink or background sound are diverse. They range from relaxation, meditation, stress reduction, pain management, improved sleep quality, decrease in sleep requirements, super learning, enhanced creativity and intuition, remote viewing, telepathy, and out-of-body experience and lucid dreaming. Audio embedded with binaural beats is often combined with various meditation techniques, as well as positive affirmations and visualization.

When signals of two different frequencies are presented, one to each ear, the brain detects phase differences between these signals. "Under natural circumstances a detected phase difference would provide directional information. The brain processes this anomalous information differently when these phase differences are heard with stereo headphones or speakers. A perceptual integration of the two signals takes place, producing the sensation of a third "beat" frequency. The difference between the signals waxes and wanes as the two different input frequencies mesh in and out of phase. As a result of these constantly increasing and decreasing differences, an amplitude-modulated standing wave—the binaural beat—is heard. The binaural beat is perceived as a fluctuating rhythm at the frequency of the difference between the two auditory inputs. Evidence suggests that the binaural beats are generated in the brainstem's superior olivary nucleus, the first site of contralateral integration in the auditory system. Studies also suggest that the frequency-following response originates from the inferior colliculus. This activity is conducted to the cortex where it can be recorded by scalp electrodes. Binaural beats can easily be heard at the low frequencies (<30 Hz) that are characteristic of the EEG spectrum.

Synchronized brain waves have long been associated with meditative and hypnogogic states, and audio with embedded binaural beats has the ability to induce and improve such states of consciousness. The reason for this is physiological. Each ear is "hardwired" (so to speak) to both hemispheres of the brain. Each hemisphere has its own olivary nucleus (sound-processing center) which receives signals from each ear. In keeping with this physiological structure, when a binaural beat is perceived there are actually two standing waves of equal amplitude and frequency present, one in each hemisphere. So, there are two separate standing waves entraining portions of each hemisphere to the same frequency. The binaural beats appear to contribute to the hemispheric synchronization evidenced in meditative and hypnogogic states of consciousness. Brain function is also enhanced through the increase of cross-collosal communication between the left and right hemispheres of the brain. en.wikipedia.org/wiki/Beat_(acoustics)#Binaural_beats.

Atwater, F. H. (2001). Binaural beats and the regulation of arousal levels. Proceedings of the TANS, 11;

Colzato, L. S., Barone, H., Sellaro, R., & Hommel, B. (2017). More attentional focusing through binaural beats: evidence from the global—local task. Psychological research, 81(1), 271-277;

Foster, D. S. (1990). EEG and subjective correlates of alpha frequency binaural beats stimulation combined with alpha biofeedback (Doctoral dissertation, Memphis State University);

Gao, X., Cao, H., Ming, D., Qi, H., Wang, X., Wang, X., & Zhou, P. (2014). Analysis of EEG activity in response to binaural beats with different frequencies. International Journal of Psychophysiology, 94(3), 399-406;

Hink, R. F., Kodera, K., Yamada, O., Kaga, K., & Suzuki, J. (1980). Binaural interaction of a beating frequency-following response. Audiology, 19(1), 36-43;

Kasprzak, C. (2011). Influence of binaural beats on EEG signal. Acta Physica Polonica A, 119(6A), 986-990;

Lane, J. D., Kasian, S. J., Owens, J. E., & Marsh, G. R. (1998). Binaural auditory beats affect vigilance performance and mood. Physiology & behavior, 63(2), 249-252;

Mortazavi, S. M. J., Zahraei-Moghadam, S. M., Masoumi, S., Rafati, A., Haghani, M., Mortazavi, S. A. R., & Zehtabian, M. (2017). Short Term Exposure to Binaural Beats Adversely Affects Learning and Memory in Rats. Journal of Biomedical Physics and Engineering.

Oster, G (October 1973). "Auditory beats in the brain". Scientific American. 229 (4): 94-102. See:

Padmanabhan, R., Hildreth, A. J., & Laws, D. (2005). A prospective, randomised, controlled study examining binaural beat audio and pre-operative anxiety in patients undergoing general anaesthesia for day case surgery. Anaesthesia, 60(9), 874-877;

Pratt, H., Starr, A., Michalewski, H. J., Dimitrijevic, A., Bleich, N., & Mittelman, N. (2009). Cortical evoked potentials to an auditory illusion: binaural beats. Clinical Neurophysiology, 120(8), 1514-1524;

Pratt, H., Starr, A., Michalewski, H. J., Dimitrijevic, A., Bleich, N., & Mittelman, N. (2010). A comparison of auditory evoked potentials to acoustic beats and to binaural beats. Hearing research, 262(1), 34-44;

Reedijk, S. A., Bolders, A., & Hommel, B. (2013). The impact of binaural beats on creativity. Frontiers in human neuroscience, 7;

Sung, H. C., Lee, W. L., Li, H. M., Lin, C. Y., Wu, Y. Z., Wang, J. J., & Li, T. L. (2017). Familiar Music Listening with Binaural Beats for Older People with Depressive Symptoms in Retirement Homes. Neuropsychiatry, 7(4);

Brain Entrainment Frequency Following Response (or FFR). See, "Stimulating the Brain with Light and Sound," Transparent Corporation, Neuroprogrammer™ 3, www.transparentcorp.com/products/np/entrainment.php.

Isochronic Tones: Isochronic tones are regular beats of a single tone that are used alongside monaural beats and binaural beats in the process called brainwave entrainment. At its simplest level, an isochronic tone is a tone that is being turned on and off rapidly. They create sharp, distinctive pulses of sound. www.livingflow.net/isochronic-tones-work/;

Casciaro, F., Laterza, V., Conte, S., Pieralice, M., Federici, A., Todarello, O., . . . & Conte, E. (2013). Alpha-rhythm stimulation using brain entrainment enhances heart rate variability in subjects with reduced HRV. World Journal of Neuroscience, 3(04), 213;

Conte, E., Conte, S., Santacroce, N., Federici, A., Todarello, O., Orsucci, F., . . . & Laterza, V. (2013). A Fast Fourier Transform analysis of time series data of heart rate variability during alfa-rhythm stimulation in brain entrainment. NeuroQuantology, 11(3);

Doherty, C. (2014). A comparison of alpha brainwave entrainment, with and without musical accompaniment;

Huang, T. L., & Charyton, C. (2008). A comprehensive review of the psychological effects of brainwave entrainment. Alternative therapies in health and medicine, 14(5), 38;

Moseley, R. (2015, July). Inducing targeted brain states utilizing merged reality systems. In Science and Information Conference (SAI), 2015 (pp. 657-663). IEEE.

Oster, G. (1973). Auditory beats in the brain. Scientific American, 229(4), 94-102;

Schulze, H. H. (1989). The perception of temporal deviations in isochronic patterns. Attention, Perception, & Psychophysics, 45(4), 291-296;

Trost, W., Frühholz, S., Schön, D., Labbé, C., Pichon, S., Grandjean, D., & Vuilleumier, P.(2014). Getting the beat: entrainment of brain activity by musical rhythm and pleasantness. NeuroImage, 103, 55-64;

Time-Frequency Analysis: Brian J. Roach and Daniel H. Mathalon, "Event-related EEG time-frequency analysis: an overview of measures and analysis of early gamma band phase locking in schizophrenia. Schizophrenia Bull. USA. 2008; 34:5:907-926., describes a mechanism for EEG time-frequency analysis. Fourier and wavelet transforms (and their inverse) may be performed on EEG signals.

See, U.S. Pat. Nos. 4,407,299; 4,408,616; 4,421,122; 4,493,327; 4,550,736; 4,557,270; 4,579,125; 4,583,190; 4,585,011; 4,610,259; 4,649,482; 4,705,049; 4,736,307; 4,744,029; 4,776,345; 4,792,145; 4,794,533; 4,846,190; 4,862,359; 4,883,067; 4,907,597; 4,924,875; 4,940,058; 5,010,891; 5,020,540; 5,029,082; 5,083,571; 5,092,341; 5,105,354; 5,109,862; 5,218,530; 5,230,344; 5,230,346; 5,233,517; 5,241,967; 5,243,517; 5,269,315; 5,280,791; 5,287,859; 5,309,917; 5,309,923; 5,320,109; 5,339,811; 5,339,826; 5,377,100; 5,406,956; 5,406,957; 5,443,073; 5,447,166; 5,458,117; 5,474,082; 5,555,889; 5,611,350; 5,619,995; 5,632,272; 5,643,325; 5,678,561; 5,685,313; 5,692,517; 5,694,939; 5,699,808; 5,752,521; 5,755,739; 5,771,261; 5,771,897; 5,794,623; 5,795,304; 5,797,840; 5,810,737; 5,813,993; 5,827,195; 5,840,040; 5,846,189; 5,846,208; 5,853,005; 5,871,517; 5,884,626; 5,899,867; 5,916,171; 5,995,868; 6,002,952; 6,011,990; 6,016,444; 6,021,345; 6,032,072; 6,044,292; 6,050,940; 6,052,619; 6,067,462; 6,067,467; 6,070,098; 6,071,246; 6,081,735; 6,097,980; 6,097,981; 6,115,631; 6,117,075; 6,129,681; 6,155,993; 6,157,850; 6,157,857; 6,171,258; 6,195,576; 6,196,972; 6,224,549; 6,236,872; 6,287,328; 6,292,688; 6,293,904; 6,305,943; 6,306,077; 6,309,342; 6,315,736; 6,317,627; 6,325,761; 6,331,164; 6,338,713; 6,343,229; 6,358,201; 6,366,813; 6,370,423; 6,375,614; 6,377,833; 6,385,486; 6,394,963; 6,402,520; 6,475,163; 6,482,165; 6,493,577; 6,496,724; 6,511,424; 6,520,905; 6,520,921; 6,524,249; 6,527,730; 6,529,773; 6,544,170; 6,546,378; 6,547,736; 6,547,746; 6,549,804; 6,556,861; 6,565,518; 6,574,573; 6,594,524; 6,602,202; 6,616,611; 6,622,036; 6,625,485; 6,626,676; 6,650,917; 6,652,470; 6,654,632;

6,658,287; 6,678,548; 6,687,525; 6,699,194; 6,709,399; 6,726,624; 6,731,975; 6,735,467; 6,743,182; 6,745,060; 6,745,156; 6,746,409; 6,751,499; 6,768,920; 6,798,898; 6,801,803; 6,804,661; 6,816,744; 6,819,956; 6,826,426; 6,843,774; 6,865,494; 6,875,174; 6,882,881; 6,886,964; 6,915,241; 6,928,354; 6,931,274; 6,931,275; 6,981,947; 6,985,769; 6,988,056; 6,993,380; 7,011,410; 7,014,613; 7,016,722; 7,037,260; 7,043,293; 7,054,454; 7,089,927; 7,092,748; 7,099,714; 7,104,963; 7,105,824; 7,123,955; 7,128,713; 7,130,691; 7,146,218; 7,150,710; 7,150,715; 7,150,718; 7,163,512; 7,164,941; 7,177,675; 7,190,995; 7,207,948; 7,209,788; 7,215,986; 7,225,013; 7,228,169; 7,228,171; 7,231,245; 7,254,433; 7,254,439; 7,254,500; 7,267,652; 7,269,456; 7,286,871; 7,288,066; 7,297,110; 7,299,088; 7,324,845; 7,328,053; 7,333,619; 7,333,851; 7,343,198; 7,367,949; 7,373,198; 7,376,453; 7,381,185; 7,383,070; 7,392,079; 7,395,292; 7,396,333; 7,399,282; 7,403,814; 7,403,815; 7,418,290; 7,429,247; 7,450,986; 7,454,240; 7,462,151; 7,468,040; 7,469,697; 7,471,971; 7,471,978; 7,489,958; 7,489,964; 7,491,173; 7,496,393; 7,499,741; 7,499,745; 7,509,154; 7,509,161; 7,509,163; 7,510,531; 7,530,955; 7,537,568; 7,539,532; 7,539,533; 7,547,284; 7,558,622; 7,559,903; 7,570,991; 7,572,225; 7,574,007; 7,574,254; 7,593,767; 7,594,122; 7,596,535; 7,603,168; 7,604,603; 7,610,094; 7,623,912; 7,623,928; 7,625,340; 7,630,757; 7,640,055; 7,643,655; 7,647,098; 7,654,948; 7,668,579; 7,668,591; 7,672,717; 7,676,263; 7,678,061; 7,684,856; 7,697,979; 7,702,502; 7,706,871; 7,706,992; 7,711,417; 7,715,910; 7,720,530; 7,727,161; 7,729,753; 7,733,224; 7,734,334; 7,747,325; 7,751,878; 7,754,190; 7,757,690; 7,758,503; 7,764,987; 7,771,364; 7,774,052; 7,774,064; 7,778,693; 7,787,946; 7,794,406; 7,801,592; 7,801,593; 7,803,118; 7,803,119; 7,809,433; 7,811,279; 7,819,812; 7,831,302; 7,853,329; 7,860,561; 7,865,234; 7,865,235; 7,878,965; 7,879,043; 7,887,493; 7,894,890; 7,896,807; 7,899,525; 7,904,144; 7,907,994; 7,909,771; 7,918,779; 7,920,914; 7,930,035; 7,938,782; 7,938,785; 7,941,209; 7,942,824; 7,944,551; 7,962,204; 7,974,696; 7,983,741; 7,983,757; 7,986,991; 7,993,279; 7,996,075; 8,002,553; 8,005,534; 8,005,624; 8,010,347; 8,019,400; 8,019,410; 8,024,032; 8,025,404; 8,032,209; 8,033,996; 8,036,728; 8,036,736; 8,041,136; 8,046,041; 8,046,042; 8,065,011; 8,066,637; 8,066,647; 8,068,904; 8,073,534; 8,075,499; 8,079,953; 8,082,031; 8,086,294; 8,089,283; 8,095,210; 8,103,333; 8,108,036; 8,108,039; 8,114,021; 8,121,673; 8,126,528; 8,128,572; 8,131,354; 8,133,172; 8,137,269; 8,137,270; 8,145,310; 8,152,732; 8,155,736; 8,160,689; 8,172,766; 8,177,726; 8,177,727; 8,180,420; 8,180,601; 8,185,207; 8,187,201; 8,190,227; 8,190,249; 8,190,251; 8,197,395; 8,197,437; 8,200,319; 8,204,583; 8,211,035; 8,214,007; 8,224,433; 8,236,005; 8,239,014; 8,241,213; 8,244,340; 8,244,475; 8,249,698; 8,271,077; 8,280,502; 8,280,503; 8,280,514; 8,285,368; 8,290,575; 8,295,914; 8,296,108; 8,298,140; 8,301,232; 8,301,233; 8,306,610; 8,311,622; 8,314,707; 8,315,970; 8,320,649; 8,323,188; 8,323,189; 8,323,204; 8,328,718; 8,332,017; 8,332,024; 8,335,561; 8,337,404; 8,340,752; 8,340,753; 8,343,026; 8,346,342; 8,346,349; 8,352,023; 8,353,837; 8,354,881; 8,356,594; 8,359,080; 8,364,226; 8,364,254; 8,364,255; 8,369,940; 8,374,690; 8,374,703; 8,380,296; 8,382,667; 8,386,244; 8,391,966; 8,396,546; 8,396,557; 8,401,624; 8,401,626; 8,403,848; 8,425,415; 8,425,583; 8,428,696; 8,437,843; 8,437,844; 8,442,626; 8,449,471; 8,452,544; 8,454,555; 8,461,988; 8,463,007; 8,463,349; 8,463,370; 8,465,408; 8,467,877; 8,473,024; 8,473,044; 8,473,306; 8,475,354; 8,475,368; 8,475,387; 8,478,389; 8,478,394; 8,478,402; 8,480,554; 8,484,270; 8,494,829; 8,498,697; 8,500,282; 8,500,636; 8,509,885; 8,509,904; 8,512,221; 8,512,240; 8,515,535; 8,519,853; 8,521,284; 8,525,673; 8,525,687; 8,527,435; 8,531,291; 8,538,512; 8,538,514; 8,538,705; 8,542,900; 8,543,199; 8,543,219; 8,545,416; 8,545,436; 8,554,311; 8,554,325; 8,560,034; 8,560,073; 8,562,525; 8,562,526; 8,562,527; 8,562,951; 8,568,329; 8,571,642; 8,585,568; 8,588,933; 8,591,419; 8,591,498; 8,597,193; 8,600,502; 8,606,351; 8,606,356; 8,606,360; 8,620,419; 8,628,480; 8,630,699; 8,632,465; 8,632,750; 8,641,632; 8,644,914; 8,644,921; 8,647,278; 8,649,866; 8,652,038; 8,655,817; 8,657,756; 8,660,799; 8,666,467; 8,670,603; 8,672,852; 8,680,991; 8,684,900; 8,684,922; 8,684,926; 8,688,209; 8,690,748; 8,693,756; 8,694,087; 8,694,089; 8,694,107; 8,700,137; 8,700,141; 8,700,142; 8,706,205; 8,706,206; 8,706,207; 8,708,903; 8,712,507; 8,712,513; 8,725,238; 8,725,243; 8,725,311; 8,725,669; 8,727,978; 8,728,001; 8,738,121; 8,744,563; 8,747,313; 8,747,336; 8,750,971; 8,750,974; 8,750,992; 8,755,854; 8,755,856; 8,755,868; 8,755,869; 8,755,871; 8,761,866; 8,761,869; 8,764,651; 8,764,652; 8,764,653; 8,768,447; 8,771,194; 8,775,340; 8,781,193; 8,781,563; 8,781,595; 8,781,597; 8,784,322; 8,786,624; 8,790,255; 8,790,272; 8,792,974; 8,798,735; 8,798,736; 8,801,620; 8,821,408; 8,825,149; 8,825,428; 8,827,917; 8,831,705; 8,838,226; 8,838,227; 8,843,199; 8,843,210; 8,849,390; 8,849,392; 8,849,681; 8,852,100; 8,852,103; 8,855,758; 8,858,440; 8,858,449; 8,862,196; 8,862,210; 8,862,581; 8,868,148; 8,868,163; 8,868,172; 8,868,174; 8,868,175; 8,870,737; 8,880,207; 8,880,576; 8,886,299; 8,888,672; 8,888,673; 8,888,702; 8,888,708; 8,898,037; 8,902,070; 8,903,483; 8,914,100; 8,915,741; 8,915,871; 8,918,162; 8,918,178; 8,922,788; 8,923,958; 8,924,235; 8,932,227; 8,938,301; 8,942,777; 8,948,834; 8,948,860; 8,954,146; 8,958,882; 8,961,386; 8,965,492; 8,968,195; 8,977,362; 8,983,591; 8,983,628; 8,983,629; 8,986,207; 8,989,835; 8,989,836; 8,996,112; 9,008,367; 9,008,754; 9,008,771; 9,014,216; 9,014,453; 9,014,819; 9,015,057; 9,020,576; 9,020,585; 9,020,789; 9,022,936; 9,026,202; 9,028,405; 9,028,412; 9,033,884; 9,037,224; 9,037,225; 9,037,530; 9,042,952; 9,042,958; 9,044,188; 9,055,871; 9,058,473; 9,060,671; 9,060,683; 9,060,695; 9,060,722; 9,060,746; 9,072,482; 9,078,577; 9,084,584; 9,089,310; 9,089,400; 9,095,266; 9,095,268; 9,100,758; 9,107,586; 9,107,595; 9,113,777; 9,113,801; 9,113,830; 9,116,835; 9,119,551; 9,119,583; 9,119,597; 9,119,598; 9,125,574; 9,131,864; 9,135,221; 9,138,183; 9,149,214; 9,149,226; 9,149,255; 9,149,577; 9,155,484; 9,155,487; 9,155,521; 9,165,472; 9,173,582; 9,173,610; 9,179,854; 9,179,876; 9,183,351 RE34015; RE38476; RE38749; RE46189; 20010049480; 20010051774; 20020035338; 20020055675; 20020059159; 20020077536; 20020082513; 20020085174; 20020091319; 20020091335; 20020099295; 20020099306; 20020103512; 20020107454; 20020112732; 20020117176; 20020128544; 20020138013; 20020151771; 20020177882; 20020182574; 20020183644; 20020193670; 20030001098; 20030009078; 20030023183; 20030028121; 20030032888; 20030035301; 20030036689; 20030046018; 20030055355; 20030070685; 20030093004; 20030093129; 20030100844; 20030120172; 20030130709; 20030135128; 20030139681; 20030144601; 20030149678; 20030158466; 20030158496; 20030158587; 20030160622; 20030167019; 20030171658; 20030171685; 20030176804; 20030181821; 20030185408; 20030195429; 20030216654; 20030225340; 20030229291; 20030236458; 20040002635; 20040006265; 20040006376; 20040010203; 20040039268; 20040059203; 20040059241; 20040064020; 20040064066; 20040068164; 20040068199; 20040073098; 20040073129; 20040077967; 20040079372;

20040082862; 20040082876; 20040097802; 20040116784; 20040116791; 20040116798; 20040116825; 20040117098; 20040143170; 20040144925; 20040152995; 20040158300; 20040167418; 20040181162; 20040193068; 20040199482; 20040204636; 20040204637; 20040204659; 20040210146; 20040220494; 20040220782; 20040225179; 20040230105; 20040243017; 20040254493; 20040260169; 20050007091; 20050010116; 20050018858; 20050025704; 20050033154; 20050033174; 20050038354; 20050043774; 20050075568; 20050080349; 20050080828; 20050085744; 20050096517; 20050113713; 20050119586; 20050124848; 20050124863; 20050135102; 20050137494; 20050148893; 20050148894; 20050148895; 20050149123; 20050182456; 20050197590; 20050209517; 20050216071; 20050251055; 20050256385; 20050256418; 20050267362; 20050273017; 20050277813; 20050277912; 20060004298; 20060009704; 20060015034; 20060041201; 20060047187; 20060047216; 20060047324; 20060058590; 20060074334; 20060082727; 20060084877; 20060089541; 20060089549; 20060094968; 20060100530; 20060102171; 20060111644; 20060116556; 20060135880; 20060149144; 20060153396; 20060155206; 20060155207; 20060161071; 20060161075; 20060161218; 20060167370; 20060167722; 20060173364; 20060184059; 20060189880; 20060189882; 20060200016; 20060200034; 20060200035; 20060204532; 20060206033; 20060217609; 20060233390; 20060235315; 20060235324; 20060241562; 20060241718; 20060251303; 20060258896; 20060258950; 20060265022; 20060276695; 20070007454; 20070016095; 20070016264; 20070021673; 20070021675; 20070032733; 20070032737; 20070038382; 20070060830; 20070060831; 20070066914; 20070083128; 20070093721; 20070100246; 20070100251; 20070100666; 20070129647; 20070135724; 20070135728; 20070142862; 20070142873; 20070149860; 20070161919; 20070162086; 20070167694; 20070167853; 20070167858; 20070167991; 20070173733; 20070179396; 20070191688; 20070191691; 20070191697; 20070197930; 20070203448; 20070208212; 20070208269; 20070213786; 20070225581; 20070225674; 20070225932; 20070249918; 20070249952; 20070255135; 20070260151; 20070265508; 20070265533; 20070273504; 20070276270; 20070276278; 20070276279; 20070276609; 20070291832; 20080001600; 20080001735; 20080004514; 20080004904; 20080009685; 20080009772; 20080013747; 20080021332; 20080021336; 20080021340; 20080021342; 20080033266; 20080036752; 20080045823; 20080045844; 20080051669; 20080051858; 20080058668; 20080074307; 20080077010; 20080077015; 20080082018; 20080097197; 20080119716; 20080119747; 20080119900; 20080125669; 20080139953; 20080140403; 20080154111; 20080167535; 20080167540; 20080167569; 20080177195; 20080177196; 20080177197; 20080188765; 20080195166; 20080200831; 20080208072; 20080208073; 20080214902; 20080221400; 20080221472; 20080221969; 20080228100; 20080242521; 20080243014; 20080243017; 20080243021; 20080249430; 20080255469; 20080257349; 20080260212; 20080262367; 20080262371; 20080275327; 20080294019; 20080294063; 20080319326; 20080319505; 20090005675; 20090009284; 20090018429; 20090024007; 20090030476; 20090043221; 20090048530; 20090054788; 20090062660; 20090062670; 20090062676; 20090062679; 20090062680; 20090062696; 20090076339; 20090076399; 20090076400; 20090076407; 20090082689; 20090082690; 20090083071; 20090088658; 20090094305; 20090112281; 20090118636; 20090124869; 20090124921; 20090124922; 20090124923; 20090137915; 20090137923; 20090149148; 20090156954; 20090156956; 20090157662; 20090171232; 20090171240; 20090177090; 20090177108; 20090179642; 20090182211; 20090192394; 20090198144; 20090198145; 20090204015; 20090209835; 20090216091; 20090216146; 20090227876; 20090227877; 20090227882; 20090227889; 20090240119; 20090247893; 20090247894; 20090264785; 20090264952; 20090275853; 20090287107; 20090292180; 20090297000; 20090306534; 20090312663; 20090312664; 20090312808; 20090312817; 20090316925; 20090318779; 20090323049; 20090326353; 20100010364; 20100023089; 20100030073; 20100036211; 20100036276; 20100041962; 20100042011; 20100043795; 20100049069; 20100049075; 20100049482; 20100056939; 20100069762; 20100069775; 20100076333; 20100076338; 20100079292; 20100087900; 20100094103; 20100094152; 20100094155; 20100099954; 20100106044; 20100114813; 20100130869; 20100137728; 20100137937; 20100143256; 20100152621; 20100160737; 20100174161; 20100179447; 20100185113; 20100191124; 20100191139; 20100191305; 20100195770; 20100198098; 20100198101; 20100204614; 20100204748; 20100204750; 20100217100; 20100217146; 20100217348; 20100222694; 20100224188; 20100234705; 20100234752; 20100234753; 20100245093; 20100249627; 20100249635; 20100258126; 20100261977; 20100262377; 20100268055; 20100280403; 20100286549; 20100286747; 20100292752; 20100293115; 20100298735; 20100303101; 20100312188; 20100318025; 20100324441; 20100331649; 20100331715; 20110004115; 20110009715; 20110009729; 20110009752; 20110015501; 20110015536; 20110028802; 20110028859; 20110034822; 20110038515; 20110040202; 20110046473; 20110054279; 20110054345; 20110066005; 20110066041; 20110066042; 20110066053; 20110077538; 20110082381; 20110087125; 20110092834; 20110092839; 20110098583; 20110105859; 20110105915; 20110105938; 20110106206; 20110112379; 20110112381; 20110112426; 20110112427; 20110115624; 20110118536; 20110118618; 20110118619; 20110119212; 20110125046; 20110125048; 20110125238; 20110130675; 20110144520; 20110152710; 20110160607; 20110160608; 20110160795; 20110162645; 20110178441; 20110178581; 20110181422; 20110184650; 20110190600; 20110196693; 20110208539; 20110218453; 20110218950; 20110224569; 20110224570; 20110224602; 20110245709; 20110251583; 20110251985; 20110257517; 20110263995; 20110270117; 20110270579; 20110282234; 20110288424; 20110288431; 20110295142; 20110295143; 20110295338; 20110301436; 20110301439; 20110301441; 20110301448; 20110301486; 20110301487; 20110307029; 20110307079; 20110313308; 20110313760; 20110319724; 20120004561; 20120004564; 20120004749; 20120010536; 20120016218; 20120016252; 20120022336; 20120022350; 20120022351; 20120022365; 20120022384; 20120022392; 20120022844; 20120029320; 20120029378; 20120029379; 20120035431; 20120035433; 20120035765; 20120041330; 20120046711; 20120053433; 20120053491; 20120059273; 20120065536; 20120078115; 20120083700; 20120083701; 20120088987; 20120088992; 20120089004; 20120092156; 20120092157; 20120095352; 20120095357; 20120100514; 20120101387; 20120101401; 20120101402; 20120101430; 20120108999; 20120116235; 20120123232; 20120123290; 20120125337; 20120136242; 20120136605; 20120143074; 20120143075; 20120149997; 20120150545; 20120157963; 20120159656; 20120165624; 20120165631; 20120172682; 20120172689; 20120172743; 20120191000; 20120197092; 20120197153; 20120203087; 20120203130; 20120203131; 20120203133; 20120203725; 20120209126; 20120209136; 20120209139; 20120220843; 20120220889; 20120221310; 20120226334; 20120238890; 20120242501; 20120245464; 20120245481; 20120253141; 20120253219; 20120253249; 20120265080; 20120271190; 20120277545; 20120277548; 20120277816; 20120296182; 20120296569; 20120302842; 20120302845; 20120302856; 20120302894;

20120310100; 20120310105; 20120321759; 20120323132; 20120330109; 20130006124; 20130009783; 20130011819; 20130012786; 20130012787; 20130012788; 20130012789; 20130012790; 20130012802; 20130012830; 20130013327; 20130023783; 20130030257; 20130035579; 20130039498; 20130041235; 20130046151; 20130046193; 20130046715; 20130060110; 20130060125; 20130066392; 20130066394; 20130066395; 20130069780; 20130070929; 20130072807; 20130076885; 20130079606; 20130079621; 20130079647; 20130079656; 20130079657; 20130080127; 20130080489; 20130095459; 20130096391; 20130096393; 20130096394; 20130096408; 20130096441; 20130096839; 20130096840; 20130102833; 20130102897; 20130109995; 20130109996; 20130116520; 20130116561; 20130116588; 20130118494; 20130123584; 20130127708; 20130130799; 20130137936; 20130137938; 20130138002; 20130144106; 20130144107; 20130144108; 20130144183; 20130150650; 20130150651; 20130150659; 20130159041; 20130165812; 20130172686; 20130172691; 20130172716; 20130172763; 20130172767; 20130172772; 20130172774; 20130178718; 20130182860; 20130184552; 20130184558; 20130184603; 20130188854; 20130190577; 20130190642; 20130197321; 20130197322; 20130197328; 20130197339; 20130204150; 20130211224; 20130211276; 20130211291; 20130217982; 20130218043; 20130218053; 20130218233; 20130221961; 20130225940; 20130225992; 20130231574; 20130231580; 20130231947; 20130238049; 20130238050; 20130238063; 20130245422; 20130245486; 20130245711; 20130245712; 20130266163; 20130267760; 20130267866; 20130267928; 20130274580; 20130274625; 20130275159; 20130281811; 20130282339; 20130289401; 20130289413; 20130289417; 20130289424; 20130289433; 20130295016; 20130300573; 20130303828; 20130303934; 20130304153; 20130310660; 20130310909; 20130324880; 20130338449; 20130338459; 20130344465; 20130345522; 20130345523; 20140005988; 20140012061; 20140012110; 20140012133; 20140012153; 20140018792; 20140019165; 20140023999; 20140025396; 20140025397; 20140038147; 20140046208; 20140051044; 20140051960; 20140051961; 20140052213; 20140055284; 20140058241; 20140066739; 20140066763; 20140070958; 20140072127; 20140072130; 20140073863; 20140073864; 20140073866; 20140073870; 20140073875; 20140073876; 20140073877; 20140073878; 20140073898; 20140073948; 20140073949; 20140073951; 20140073953; 20140073954; 20140073955; 20140073956; 20140073960; 20140073961; 20140073963; 20140073965; 20140073966; 20140073967; 20140073968; 20140073974; 20140073975; 20140074060; 20140074179; 20140074180; 20140077946; 20140081114; 20140081115; 20140094720; 20140098981; 20140100467; 20140104059; 20140105436; 20140107464; 20140107519; 20140107525; 20140114165; 20140114205; 20140121446; 20140121476; 20140121554; 20140128762; 20140128764; 20140135879; 20140136585; 20140140567; 20140143064; 20140148723; 20140152673; 20140155706; 20140155714; 20140155730; 20140156000; 20140163328; 20140163330; 20140163331; 20140163332; 20140163333; 20140163335; 20140163336; 20140163337; 20140163385; 20140163409; 20140163425; 20140163897; 20140171820; 20140175261; 20140176944; 20140179980; 20140180088; 20140180092; 20140180093; 20140180094; 20140180095; 20140180096; 20140180097; 20140180099; 20140180100; 20140180112; 20140180113; 20140180145; 20140180153; 20140180160; 20140180161; 20140180176; 20140180177; 20140180597; 20140187994; 20140188006; 20140188770; 20140194702; 20140194758; 20140194759; 20140194768; 20140194769; 20140194780; 20140194793; 20140203797; 20140213937; 20140214330; 20140228651; 20140228702; 20140232516; 20140235965; 20140236039; 20140236077; 20140237073; 20140243614; 20140243621; 20140243628; 20140243694; 20140249429; 20140257073; 20140257147; 20140266696; 20140266787; 20140275886; 20140275889; 20140275891; 20140276013; 20140276014; 20140276090; 20140276123; 20140276130; 20140276181; 20140276183; 20140279746; 20140288381; 20140288614; 20140288953; 20140289172; 20140296724; 20140303453; 20140303454; 20140303508; 20140309943; 20140313303; 20140316217; 20140316221; 20140316230; 20140316235; 20140316278; 20140323900; 20140324118; 20140330102; 20140330157; 20140330159; 20140330334; 20140330404; 20140336473; 20140347491; 20140350431; 20140350436; 20140358025; 20140364721; 20140364746; 20140369537; 20140371544; 20140371599; 20140378809; 20140378810; 20140379620; 20150003698; 20150003699; 20150005592; 20150005594; 20150005640; 20150005644; 20150005660; 20150005680; 20150006186; 20150016618; 20150018758; 20150025351; 20150025422; 20150032017; 20150038804; 20150038869; 20150039110; 20150042477; 20150045686; 20150051663; 20150057512; 20150065839; 20150073237; 20150073306; 20150080671; 20150080746; 20150087931; 20150088024; 20150092949; 20150093729; 20150099941; 20150099962; 20150103360; 20150105631; 20150105641; 20150105837; 20150112222; 20150112409; 20150119652; 20150119743; 20150119746; 20150126821; 20150126845; 20150126848; 20150126873; 20150134264; 20150137988; 20150141529; 20150141789; 20150141794; 20150153477; 20150157235; 20150157266; 20150164349; 20150164362; 20150164375; 20150164404; 20150181840; 20150182417; 20150190070; 20150190085; 20150190636; 20150190637; 20150196213; 20150199010; 20150201879; 20150202447; 20150203822; 20150208940; 20150208975; 20150213191; 20150216436; 20150216468; 20150217082; 20150220486; 20150223743; 20150227702; 20150230750; 20150231408; 20150238106; 20150238112; 20150238137; 20150245800; 20150247921; 20150250393; 20150250401; 20150250415; 20150257645; 20150257673; 20150257674; 20150257700; 20150257712; 20150265164; 20150269825; 20150272465; 20150282730; 20150282755; 20150282760; 20150290420; 20150290453; 20150290454; 20150297106; 20150297141; 20150304101; 20150305685; 20150309563; 20150313496; 20150313535; 20150327813; 20150327837; 20150335292; 20150342478; 20150342493; 20150351655; 20150351701; 20150359441; 20150359450; 20150359452; 20150359467; 20150359486; 20150359492; 20150366497; 20150366504; 20150366516; 20150366518; 20150374285; 20150374292; 20150374300; 20150380009; 20160000348; 20160000354; 20160007915; 20160007918; 20160012749; 20160015281; 20160015289; 20160022141; 20160022156; 20160022164; 20160022167; 20160022206; 20160027293; 20160029917; 20160029918; 20160029946; 20160029950; 20160029965; 20160030702; 20160038037; 20160038038; 20160038049; 20160038091; 20160045150; 20160045756; 20160051161; 20160051162; 20160051187; 20160051195; 20160055415; 20160058301; 20160066788; 20160067494; 20160073886; 20160074661; 20160081577; 20160081616; 20160087603; 20160089031; 20160100769; 20160101260; 20160106331; 20160106344; 20160112022; 20160112684; 20160113539; 20160113545; 20160113567; 20160113587; 20160119726; 20160120433; 20160120434; 20160120464; 20160120480; 20160128596; 20160132654; 20160135691; 20160135727; 20160135754; 20160140834; 20160143554; 20160143560; 20160143594; 20160148531; 20160150988; 20160151014; 20160151018; 20160151628; 20160157742; 20160157828; 20160162652; 20160165852; 20160165853; 20160166169; 20160166197; 20160166199; 20160166208; 20160174099; 20160174863; 20160178392; 20160183828;

20160183861; 20160191517; 20160192841; 20160192842; 20160192847; 20160192879; 20160196758; 20160198963; 20160198966; 20160202755; 20160206877; 20160206880; 20160213276; 20160213314; 20160220133; 20160220134; 20160220136; 20160220166; 20160220836; 20160220837; 20160224757; 20160228019; 20160228029; 20160228059; 20160228705; 20160232811; 20160235324; 20160235351; 20160235352; 20160239084; 20160242659; 20160242690; 20160242699; 20160248434; 20160249841; 20160256063; 20160256112; 20160256118; 20160259905; 20160262664; 20160262685; 20160262695; 20160262703; 20160278651; 20160278697; 20160278713; 20160282941; 20160287120; 20160287157; 20160287162; 20160287166; 20160287871; 20160296157; 20160302683; 20160302704; 20160302709; 20160302720; 20160302737; 20160303402; 20160310031; 20160310070; 20160317056; 20160324465; 20160331264; 20160338634; 20160338644; 20160338798; 20160346542; 20160354003; 20160354027; 20160360965; 20160360970; 20160361021; 20160361041; 20160367204; 20160374581; 20160374618; 20170000404; 20170001016; 20170007165; 20170007173; 20170014037; 20170014083; 20170020434; 20170020447; 20170027467; 20170032098; 20170035392; 20170042430; 20170042469; 20170042475; 20170053513; 20170055839; 20170055898; 20170055913; 20170065199; 20170065218; 20170065229; 20170071495; 20170071523; 20170071529; 20170071532; 20170071537; 20170071546; 20170071551; 20170071552; 20170079538; 20170079596; 20170086672; 20170086695; 20170091567; 20170095721; 20170105647; 20170112379; 20170112427; 20170120066; 20170127946; 20170132816; 20170135597; 20170135604; 20170135626; 20170135629; 20170135631; 20170135633; 20170143231; 20170143249; 20170143255; 20170143257; 20170143259; 20170143266; 20170143267; 20170143268; 20170143273; 20170143280; 20170143282; 20170143960; 20170143963; 20170146386; 20170146387; 20170146390; 20170146391; 20170147754; 20170148240; 20170150896; 20170150916; 20170156593; 20170156606; 20170156655; 20170164878; 20170164901; 20170172414; 20170172501; 20170172520; 20170173262; 20170177023; 20170181693; 20170185149; 20170188865; 20170188872; 20170188947; 20170188992; 20170189691; 20170196497; 20170202474; 20170202518; 20170203154; 20170209053; and 20170209083.

There are many approaches to time-frequency decomposition of EEG data, including the short-term Fourier transform (SIFT), (Gabor D. Theory of Communication. J. Inst. Electr. Engrs. 1946; 93:429-457) continuous (Daubechies I. Ten Lectures on Wavelets. Philadelphia, Pa: Society for Industrial and Applied Mathematics; 1992:357. 21. Combes J M, Grossmann A, Tchamitchian P. Wavelets: Time-Frequency Methods and Phase Space-Proceedings of the International Conference; Dec. 14-18, 1987; Marseille, France) or discrete (Mallat S G. A theory for multiresolution signal decomposition: the wavelet representation. IEEE Trans Pattern Anal Mach Intell. 1989; 11:674-693) wavelet transforms, Hilbert transform (Lyons R G. Understanding Digital Signal Processing. 2nd ed. Upper Saddle River, NJ: Prentice Hall PTR; 2004:688), and matching pursuits (Mallat S, Zhang Z. Matching pursuits with time-frequency dictionaries. IEEE Trans. Signal Proc. 1993; 41(12):3397-3415). Prototype analysis systems may be implemented using, for example, MatLab with the Wavelet Toolbox, www.mathworks.com/products/wavelet.html.

See, U.S. Pat. Nos. 6,196,972; 6,338,713; 6,442,421; 6,507,754; 6,524,249; 6,547,736; 6,616,611; 6,816,744; 6,865,494; 6,915,241; 6,936,012; 6,996,261; 7,043,293; 7,054,454; 7,079,977; 7,128,713; 7,146,211; 7,149,572; 7,164,941; 7,209,788; 7,254,439; 7,280,867; 7,282,030; 7,321,837; 7,330,032; 7,333,619; 7,381,185; 7,537,568; 7,559,903; 7,565,193; 7,567,693; 7,604,603; 7,624,293; 7,640,055; 7,715,919; 7,725,174; 7,729,755; 7,751,878; 7,778,693; 7,794,406; 7,797,040; 7,801,592; 7,803,118; 7,803,119; 7,879,043; 7,896,807; 7,899,524; 7,917,206; 7,933,646; 7,937,138; 7,976,465; 8,014,847; 8,033,996; 8,073,534; 8,095,210; 8,137,269; 8,137,270; 8,175,696; 8,177,724; 8,177,726; 8,180,601; 8,187,181; 8,197,437; 8,233,965; 8,236,005; 8,244,341; 8,248,069; 8,249,698; 8,280,514; 8,295,914; 8,326,433; 8,335,664; 8,346,342; 8,355,768; 8,386,312; 8,386,313; 8,392,250; 8,392,253; 8,392,254; 8,392,255; 8,396,542; 8,406,841; 8,406,862; 8,412,655; 8,428,703; 8,428,704; 8,463,374; 8,464,288; 8,475,387; 8,483,815; 8,494,610; 8,494,829; 8,494,905; 8,498,699; 8,509,881; 8,533,042; 8,548,786; 8,571,629; 8,579,786; 8,591,419; 8,606,360; 8,628,480; 8,655,428; 8,666,478; 8,682,422; 8,706,183; 8,706,205; 8,718,747; 8,725,238; 8,738,136; 8,747,382; 8,755,877; 8,761,869; 8,762,202; 8,768,449; 8,781,796; 8,790,255; 8,790,272; 8,821,408; 8,825,149; 8,831,731; 8,843,210; 8,849,392; 8,849,632; 8,855,773; 8,858,440; 8,862,210; 8,862,581; 8,903,479; 8,918,178; 8,934,965; 8,951,190; 8,954,139; 8,955,010; 8,958,868; 8,983,628; 8,983,629; 8,989,835; 9,020,789; 9,026,217; 9,031,644; 9,050,470; 9,060,671; 9,070,492; 9,072,832; 9,072,905; 9,078,584; 9,084,896; 9,095,295; 9,101,276; 9,107,595; 9,116,835; 9,125,574; 9,149,719; 9,155,487; 9,192,309; 9,198,621; 9,204,835; 9,211,417; 9,215,978; 9,232,910; 9,232,984; 9,238,142; 9,242,067; 9,247,911; 9,248,286; 9,254,383; 9,277,871; 9,277,873; 9,282,934; 9,289,603; 9,302,110; 9,307,944; 9,308,372; 9,320,450; 9,336,535; 9,357,941; 9,375,151; 9,375,171; 9,375,571; 9,403,038; 9,415,219; 9,427,581; 9,443,141; 9,451,886; 9,454,646; 9,462,956; 9,462,975; 9,468,541; 9,471,978; 9,480,402; 9,492,084; 9,504,410; 9,522,278; 9,533,113; 9,545,285; 9,560,984; 9,563,740; 9,615,749; 9,616,166; 9,622,672; 9,622,676; 9,622,702; 9,622,703; 9,623,240; 9,636,019; 9,649,036; 9,659,229; 9,668,694; 9,681,814; 9,681,820; 9,682,232; 9,713,428; 20020035338; 20020091319; 20020095099; 20020103428; 20020103429; 20020193670; 20030032889; 20030046018; 20030093129; 20030160622; 20030185408; 20030216654; 20040039268; 20040049484; 20040092809; 20040133119; 20040133120; 20040133390; 20040138536; 20040138580; 20040138711; 20040152958; 20040158119; 20050010091; 20050018858; 20050033174; 20050075568; 20050085744; 20050119547; 20050148893; 20050148894; 20050148895; 20050154290; 20050167588; 20050240087; 20050245796; 20050267343; 20050267344; 20050283053; 20050283090; 20060020184; 20060036152; 20060036153; 20060074290; 20060078183; 20060135879; 20060153396; 20060155495; 20060161384; 20060173364; 20060200013; 20060217816; 20060233390; 20060281980; 20070016095; 20070066915; 20070100278; 20070179395; 20070179734; 20070191704; 20070209669; 20070225932; 20070255122; 20070255135; 20070260151; 20070265508; 20070287896; 20080021345; 20080033508; 20080064934; 20080074307; 20080077015; 20080091118; 20080097197; 20080119716; 20080177196; 20080221401; 20080221441; 20080243014; 20080243017; 20080255949; 20080262367; 20090005667; 20090033333; 20090036791; 20090054801; 20090062676; 20090177144; 20090220425; 20090221930; 20090270758; 20090281448; 20090287271; 20090287272; 20090287273; 20090287467; 20090299169; 20090306534; 20090312646; 20090318794; 20090322331; 20100030073; 20100036211; 20100049276; 20100068751; 20100069739; 20100094152; 20100099975; 20100106041; 20100198090; 20100204604; 20100204748;

20100249638; 20100280372; 20100331976; 20110004115; 20110015515; 20110015539; 20110040713; 20110066041; 20110066042; 20110074396; 20110077538; 20110092834; 20110092839; 20110098583; 20110160543; 20110172725; 20110178441; 20110184305; 20110191350; 20110218950; 20110257519; 20110270074; 20110282230; 20110288431; 20110295143; 20110301441; 20110313268; 20110313487; 20120004518; 20120004561; 20120021394; 20120022343; 20120029378; 20120041279; 20120046535; 20120053473; 20120053476; 20120053478; 20120053479; 20120083708; 20120108918; 20120108997; 20120143038; 20120145152; 20120150545; 20120157804; 20120159656; 20120172682; 20120184826; 20120197153; 20120209139; 20120253261; 20120265267; 20120271151; 20120271376; 20120289869; 20120310105; 20120321759; 20130012804; 20130041235; 20130060125; 20130066392; 20130066395; 20130072775; 20130079621; 20130102897; 20130116520; 20130123607; 20130127708; 20130131438; 20130131461; 20130165804; 20130167360; 20130172716; 20130172772; 20130178733; 20130184597; 20130204122; 20130211238; 20130223709; 20130226261; 20130237874; 20130238049; 20130238050; 20130245416; 20130245424; 20130245485; 20130245486; 20130245711; 20130245712; 20130261490; 20130274562; 20130289364; 20130295016; 20130310422; 20130310909; 20130317380; 20130338518; 20130338803; 20140039279; 20140057232; 20140058218; 20140058528; 20140074179; 20140074180; 20140094710; 20140094720; 20140107521; 20140142654; 20140148657; 20140148716; 20140148726; 20140180153; 20140180160; 20140187901; 20140228702; 20140243647; 20140243714; 20140257128; 20140275807; 20140276130; 20140276187; 20140303454; 20140303508; 20140309614; 20140316217; 20140316248; 20140324118; 20140330334; 20140330335; 20140330336; 20140330404; 20140335489; 20140350634; 20140350864; 20150005646; 20150005660; 20150011907; 20150018665; 20150018699; 20150018702; 20150025422; 20150038869; 20150073294; 20150073306; 20150073505; 20150080671; 20150080695; 20150099962; 20150126821; 20150151142; 20150164431; 20150190070; 20150190636; 20150190637; 20150196213; 20150196249; 20150213191; 20150216439; 20150245800; 20150248470; 20150248615; 20150272652; 20150297106; 20150297893; 20150305686; 20150313498; 20150366482; 20150379370; 20160000348; 20160007899; 20160022167; 20160022168; 20160022207; 20160027423; 20160029965; 20160038042; 20160038043; 20160045128; 20160051812; 20160058304; 20160066838; 20160107309; 20160113587; 20160120428; 20160120432; 20160120437; 20160120457; 20160128596; 20160128597; 20160135754; 20160143594; 20160144175; 20160151628; 20160157742; 20160157828; 20160174863; 20160174907; 20160176053; 20160183881; 20160184029; 20160198973; 20160206380; 20160213261; 20160213317; 20160220850; 20160228028; 20160228702; 20160235324; 20160239966; 20160239968; 20160242645; 20160242665; 20160242669; 20160242690; 20160249841; 20160250355; 20160256063; 20160256105; 20160262664; 20160278653; 20160278713; 20160287117; 20160287162; 20160287169; 20160287869; 20160303402; 20160331264; 20160331307; 20160345895; 20160345911; 20160346542; 20160361041; 20160361546; 20160367186; 20160367198; 20170031440; 20170031441; 20170039706; 20170042444; 20170045601; 20170071521; 20170079588; 20170079589; 20170091418; 20170113046; 20170120041; 20170128015; 20170135594; 20170135626; 20170136240; 20170165020; 20170172446; 20170173326; 20170188870; 20170188905; 20170188916; 20170188922; and 20170196519.

Single instruction, multiple data processors, such as graphic processing units including the nVidia CUDA environment or AMD Firepro high-performance computing environment are known, and may be employed for general purpose computing, finding particular application in data matrix transformations.

See, U.S. Pat. Nos. 5,273,038; 5,503,149; 6,240,308; 6,272,370; 6,298,259; 6,370,414; 6,385,479; 6,490,472; 6,556,695; 6,697,660; 6,801,648; 6,907,280; 6,996,261; 7,092,748; 7,254,500; 7,338,455; 7,346,382; 7,490,085; 7,497,828; 7,539,528; 7,565,193; 7,567,693; 7,577,472; 7,597,665; 7,627,370; 7,680,526; 7,729,755; 7,809,434; 7,840,257; 7,860,548; 7,872,235; 7,899,524; 7,904,134; 7,904,139; 7,907,998; 7,983,740; 7,983,741; 8,000,773; 8,014,847; 8,069,125; 8,233,682; 8,233,965; 8,235,907; 8,248,069; 8,356,004; 8,379,952; 8,406,838; 8,423,125; 8,445,851; 8,553,956; 8,586,932; 8,606,349; 8,615,479; 8,644,910; 8,679,009; 8,696,722; 8,712,512; 8,718,747; 8,761,866; 8,781,557; 8,814,923; 8,821,376; 8,834,546; 8,852,103; 8,870,737; 8,936,630; 8,951,189; 8,951,192; 8,958,882; 8,983,155; 9,005,126; 9,020,586; 9,022,936; 9,028,412; 9,033,884; 9,042,958; 9,078,584; 9,101,279; 9,135,400; 9,144,392; 9,149,255; 9,155,521; 9,167,970; 9,179,854; 9,179,858; 9,198,637; 9,204,835; 9,208,558; 9,211,077; 9,213,076; 9,235,685; 9,242,067; 9,247,924; 9,268,014; 9,268,015; 9,271,651; 9,271,674; 9,275,191; 9,292,920; 9,307,925; 9,322,895; 9,326,742; 9,330,206; 9,368,265; 9,395,425; 9,402,558; 9,414,776; 9,436,989; 9,451,883; 9,451,899; 9,468,541; 9,471,978; 9,480,402; 9,480,425; 9,486,168; 9,592,389; 9,615,789; 9,626,756; 9,672,302; 9,672,617; 9,682,232; 20020033454; 20020035317; 20020037095; 20020042563; 20020058867; 20020103428; 20020103429; 20030018277; 20030093004; 20030128801; 20040082862; 20040092809; 20040096395; 20040116791; 20040116798; 20040122787; 20040122790; 20040166536; 20040215082; 20050007091; 20050020918; 20050033154; 20050079636; 20050119547; 20050154290; 20050222639; 20050240253; 20050283053; 20060036152; 20060036153; 20060052706; 20060058683; 20060074290; 20060078183; 20060084858; 20060149160; 20060161218; 20060241382; 20060241718; 20070191704; 20070239059; 20080001600; 20080009772; 20080033291; 20080039737; 20080042067; 20080097235; 20080097785; 20080128626; 20080154126; 20080221441; 20080228077; 20080228239; 20080230702; 20080230705; 20080249430; 20080262327; 20080275340; 20090012387; 20090018407; 20090022825; 20090024050; 20090062660; 20090078875; 20090118610; 20090156907; 20090156955; 20090157323; 20090157481; 20090157482; 20090157625; 20090157751; 20090157813; 20090163777; 20090164131; 20090164132; 20090171164; 20090172540; 20090179642; 20090209831; 20090221930; 20090246138; 20090299169; 20090304582; 20090306532; 20090306534; 20090312808; 20090312817; 20090318773; 20090318794; 20090322331; 20090326604; 20100021378; 20100036233; 20100041949; 20100042011; 20100049482; 20100069739; 20100069777; 20100082506; 20100113959; 20100249573; 20110015515; 20110015539; 20110028827; 20110077503; 20110118536; 20110125077; 20110125078; 20110129129; 20110160543; 20110161011; 20110172509; 20110172553; 20110178359; 20110190846; 20110218405; 20110224571; 20110230738; 20110257519; 20110263962; 20110263968; 20110270074; 20110288400; 20110301448; 20110306845; 20110306846; 20110313274; 20120021394; 20120022343; 20120035433; 20120053483; 20120163689; 20120165904; 20120215114; 20120219195; 20120219507; 20120245474; 20120253261; 20120253434; 20120289854; 20120310107; 20120316793; 20130012804; 20130060125; 20130063550; 20130085678; 20130096408; 20130110616; 20130116561; 20130123607; 20130131438; 20130131461;

20130178693; 20130178733; 20130184558; 20130211238; 20130221961; 20130245424; 20130274586; 20130289385; 20130289386; 20130303934; 20140058528; 20140066763; 20140119621; 20140151563; 20140155730; 20140163368; 20140171757; 20140180088; 20140180092; 20140180093; 20140180094; 20140180095; 20140180096; 20140180097; 20140180099; 20140180100; 20140180112; 20140180113; 20140180176; 20140180177; 20140184550; 20140193336; 20140200414; 20140243614; 20140257047; 20140275807; 20140303486; 20140315169; 20140316248; 20140323849; 20140335489; 20140343397; 20140343399; 20140343408; 20140364721; 20140378830; 20150011866; 20150038812; 20150051663; 20150099959; 20150112409; 20150119658; 20150119689; 20150148700; 20150150473; 20150196800; 20150200046; 20150219732; 20150223905; 20150227702; 20150247921; 20150248615; 20150253410; 20150289779; 20150290453; 20150290454; 20150313540; 20150317796; 20150324692; 20150366482; 20150375006; 20160005320; 20160027342; 20160029965; 20160051161; 20160051162; 20160055304; 20160058304; 20160058392; 20160066838; 20160103487; 20160120437; 20160120457; 20160143541; 20160157742; 20160184029; 20160196393; 20160228702; 20160231401; 20160239966; 20160239968; 20160260216; 20160267809; 20160270723; 20160302720; 20160303397; 20160317077; 20160345911; 20170027539; 20170039706; 20170045601; 20170061034; 20170085855; 20170091418; 20170112403; 20170113046; 20170120041; 20170160360; 20170164861; 20170169714; 20170172527; and 20170202475.

Statistical analysis may be presented in a form that permits parallelization, which can be efficiently implemented using various parallel processors, a common form of which is a SIMD (single instruction, multiple data) processor, found in typical graphics processors (GPUs).

See, U.S. Pat. Nos. 8,406,890; 8,509,879; 8,542,916; 8,852,103; 8,934,986; 9,022,936; 9,028,412; 9,031,653; 9,033,884; 9,037,530; 9,055,974; 9,149,255; 9,155,521; 9,198,637; 9,247,924; 9,268,014; 9,268,015; 9,367,131; 9,4147,80; 9,420,970; 9,430,615; 9,442,525; 9,444,998; 9,445,763; 9,462,956; 9,474,481; 9,489,854; 9,504,420; 9,510,790; 9,519,981; 9,526,906; 9,538,948; 9,585,581; 9,622,672; 9,641,665; 9,652,626; 9,684,335; 9,687,187; 9,693,684; 9,693,724; 9,706,963; 9,712,736; 20090118622; 20100098289; 20110066041; 20110066042; 20110098583; 20110301441; 20120130204; 20120265271; 20120321759; 20130060158; 20130113816; 20130131438; 20130184786; 20140031889; 20140031903; 20140039975; 20140114889; 20140226131; 20140279341; 20140296733; 20140303424; 20140313303; 20140315169; 20140316235; 20140364721; 20140378810; 20150003698; 20150003699; 20150005640; 20150005644; 20150006186; 20150029087; 20150033245; 20150033258; 20150033259; 20150033262; 20150033266; 20150081226; 20150088093; 20150093729; 20150105701; 20150112899; 20150126845; 20150150122; 20150190062; 20150190070; 20150190077; 20150190094; 20150192776; 20150196213; 20150196800; 20150199010; 20150241916; 20150242608; 20150272496; 20150272510; 20150282705; 20150282749; 20150289217; 20150297109; 20150305689; 20150335295; 20150351655; 20150366482; 20160027342; 20160029896; 20160058366; 20160058376; 20160058673; 20160060926; 20160065724; 20160065840; 20160077547; 20160081625; 20160103487; 20160104006; 20160109959; 20160113517; 20160120048; 20160120428; 20160120457; 20160125228; 20160157773; 20160157828; 20160183812; 20160191517; 20160193499; 20160196185; 20160196635; 20160206241; 20160213317; 20160228064; 20160235341; 20160235359; 20160249857; 20160249864; 20160256086; 20160262680; 20160262685; 20160270656; 20160278672; 20160282113; 20160287142; 20160306942; 20160310071; 20160317056; 20160324445; 20160324457; 20160342241; 20160360100; 20160361027; 20160366462; 20160367138; 20160367195; 20160374616; 20160378608; 20160378965; 20170000324; 20170000325; 20170000326; 20170000329; 20170000330; 20170000331; 20170000332; 20170000333; 20170000334; 20170000335; 20170000337; 20170000340; 20170000341; 20170000342; 20170000343; 20170000345; 20170000454; 20170000683; 20170001032; 20170007111; 20170007115; 20170007116; 20170007122; 20170007123; 20170007182; 20170007450; 20170007799; 20170007843; 20170010469; 20170010470; 20170013562; 20170017083; 20170020627; 20170027521; 20170028563; 20170031440; 20170032221; 20170035309; 20170035317; 20170041699; 20170042485; 20170046052; 20170065349; 20170086695; 20170086727; 20170090475; 20170103440; 20170112446; 20170113056; 20170128006; 20170143249; 20170143442; 20170156593; 20170156606; 20170164893; 20170171441; 20170172499; 20170173262; 20170185714; 20170188933; 20170196503; 20170205259; 20170206913; and 20170214786.

Artificial neural networks have been employed to analyze EEG signals.

See, U.S. Pat. Nos. 9,443,141; 20110218950; 20150248167; 20150248764; 20150248765; 20150310862; 20150331929; 20150338915; 20160026913; 20160062459; 20160085302; 20160125572; 20160247064; 20160274660; 20170053665; 20170069306; 20170173262; and 20170206691.

See also:

Amari, S., Natural gradient works efficiently in learning, Neural Computation 10:251-276, 1998.

Amari S., Cichocki, A. & Yang, H. H., A new learning algorithm for blind signal separation. In: Advances in Neural Information Processing Systems 8, MIT Press, 1996.

Bandettini P A, Wong E C, Hinks R S, Tikofsky R S, Hyde J S, Time course E H of human brain function during task activation. Magn Reson Med 25:390-7,1992.

Bell A. J. & Sejnowski T. J. An information-maximization approach to blind separation and blind deconvolution. Neural Comput 7:1129-59, 1995.

Bell, A. J. & Sejnowski, T. J., Learning the higher-order structure of a natural sound, Network: Computation in Neural Systems 7, 1996b.

Bench C J, Frith C D, Grasby P M, Friston K J, Paulesu E, Frackowiak R S, Dolan R J, Investigations of the functional anatomy of attention using the Stroop test. Neuropsychologia 31:907-22, 1993.

Boynton G M, Engel S A, Glover G H, Heeger D J, Linear systems analysis of functional magnetic resonance imaging in human V I. J Neurosci 16:4207-21., 1996.

Bringer, Julien, Hervé Chabanne, and Bruno Kindarji. "Error-tolerant searchable encryption." In Communications, 2009. ICC'09. IEEE International Conference on, pp. 1-6. IEEE, 2009.

Buckner, R. L., Bandettini, P. A., O'Craven, K M, Savoy, R. L., Petersen, S. E., Raichle, M. E. & Rosen, B. R., Proc Natl Acad Sci USA 93, 14878-83, 1996.

Cardoso, J-F. & Laheld, B., Equivalent adaptive source separation, IEEE Trans. Signal Proc., in press.

Chapman, R. M. & McCrary, J. W., E P component identification and measurement by principal components analysis. Brain Lang. 27, 288-301, 1995.

Cichocki A., Unbehauen R., & Rummert E., Robust learning algorithm for blind separation of signals, Electronics Letters 30, 1386-1387, 1994.

Comon P, Independent component analysis, A new concept? Signal Processing 36:11-20, 1994.

Cover, T. M. & Thomas, J. A., Elements of Information Theory John Wiley, 1991.

Cox, R. W., AFNI: software for analysis and visualization of functional magnetic resonance neuroimages. Comput Biomed Res 29:162-73, 1996.

Cox, R. W. & Hyde J. S. Software tools for analysis and visualization of fMRI data, NMR in Biomedicine, in press.

Dale, A. M. & Sereno, M. I., Improved localization of cortical activity by combining EEG and MEG with MRI cortical surface reconstruction—a linear approach. J. Cogn. Neurosci. 5:162-176, 1993.

Friston K. J., Modes or models: A critique on independent component analysis for fMRI. Trends in Cognitive Sciences, in press.

Friston K. J., Commentary and opinion: II. Statistical parametric mapping: ontology and current issues. J Cereb Blood Flow Metab 15:361-70, 1995.

Friston K. J., Statistical Parametric Mapping and Other Analyses of Functional Imaging Data. In: A. W. Toga, J. C. Mazziotta eds., Brain Mapping, The Methods. San Diego: Academic Press, 1996:363-396, 1995.

Friston K J, Frith C D, Liddle P F, Frackowiak R S, Functional connectivity: the principal-component analysis of large (PET) data sets. J Cereb Blood Flow Metab 13:5-14, 1993.

Friston K J, Holmes A P, Worsley K J, Poline J P, Frith C D, and Frackowiak R. S. J., Statistical Parametric Maps in Functional Imaging: A General Linear Approach, Human Brain Mapping 2:189-210, 1995.

Friston K J, Williams S, Howard R, Frackowiak R S and Turner R, Movement-related effects in fMRI time-series. Magn Reson Med 35:346-55, 1996.

Galambos, R. and S. Makeig, "Dynamic changes in steady-state potentials," in: Dynamics of Sensory and Cognitive Processing of the Brain, ed. E. Basar Springer, pp. 178-199, 1987.

Galambos, R., S. Makeig, and P. Talmachoff, A 40 Hz auditory potential recorded from the human scalp, Proc Natl Acad Sci USA 78(4):2643-2647, 1981.

Galil, Zvi, Stuart Haber, and Moti Yung. "Cryptographic computation: Secure fault-tolerant protocols and the public-key model." In Conference on the Theory and Application of Cryptographic Techniques, pp. 135-155. Springer, Berlin, Heidelberg, 1987.

George J S, Aine C J, Mosher J C, Schmidt D M, Ranken D M, Schlitt H A, Wood C C, Lewine J D, Sanders J A, Belliveau J W. Mapping function in the human brain with magnetoencephalography, anatomical magnetic resonance imaging, and functional magnetic resonance imaging. J Clin Neurophysiol 12:406-31, 1995.

Ives, J. R., Warach S, Schmitt F, Edelman R R and Schomer D L. Monitoring the patient's EEG during echo planar MRI, Electroencephalogr Clin Neurophysiol, 87: 417-420, 1993.

Jackson, J. E., A User's Guide to Principal Components. New York: John Wiley & Sons, Inc., 1991.

Jokeit, H. and Makeig, S., Different event-related patterns of gamma-band power in brain waves of fast- and slow-reacting subjects, Proc. Nat. Acad. Sci USA 91:6339-6343, 1994.

Juels, Ari, and Madhu Sudan. "A fuzzy vault scheme." Designs, Codes and Cryptography 38, no. 2 (2006): 237-257.

Jueptner, M., K. M. Stephan, C. D. Frith, D. J. Brooks, R. S J. Frackowiak & R. E. Passingham, Anatomy of Motor Learning. I.

Frontal Cortex and Attention. J. Neurophysiology 77:1313-1324, 1977.

Jung, T-P., Humphries, C., Lee, T-W., Makeig, S., McKeown, M., Iragui, V. and Sejnowski, T. J., "Extended ICA removes artifacts from electroencephalographic recordings," In: Advances in Neural Information Processing Systems 10: MIT Press, Cambridge, MA, in press.

Jung, T-P., Humphries, C., Lee, T-W., McKeown, M. J., Iragui, V., Makeig, S. & Sejnowski, T. J., Removing electroencephalographic artifacts by blind source separation, submitted-a.

Jung, T-P., S. Makeig, M. Stensmo & T. Sejnowski, Estimating Alertness from the EEG Power Spectrum, IEEE Transactions on Biomedical Engineering, 44(1), 60-69, 1997.

Jung, T-P., Makeig, S., Westerfield, M., Townsend, J., Courchesne, E. and Sejnowski, T. J., Analysis and visualization of single-trial event-related potentials, submitted-b.

Jutten, C. & Herault, J., Blind separation of sources, part I: an adaptive algorithm based on neuromimetic architecture. Signal Processing 24, 1-10, 1991.

Karhumen, J., Oja, E., Wang, L., Vigario, R. & Joutsenalo, J., A class of neural networks for independent component analysis, IEEE Trans. Neural Networks, in press.

Kwong K. K., Functional magnetic resonance imaging with echo planar imaging. Magn Reson Q 11:1-20,1995.

Kwong K. K., Belliveau J W, Chesler D A, Goldberg I E, Weisskoff R M, Poncelet B P, Kennedy D N, Hoppel B E, Cohen M S, Turner R, et al., Dynamic magnetic resonance imaging of human brain activity during primary sensory stimulation. Proc Natl Acad Sci USA 89:5675-9, 1992.

Lee, T.-W., Girolami, M., and Sejnowski, T. J., Independent component analysis using an extended infomax algorithm for mixed Sub-gaussian and Super-gaussian sources, Neural Computation, submitted for publication.

Lewicki, Michael S., and Sejnowski, Terence J., Learning nonlinear overcomplete representations for efficient coding, Eds. M. Kearns, M. Jordan, and S. Solla, Advances in Neural Information Processing Systems 10, in press.

Linsker, R., Local synaptic learning rules suffice to maximise mutual information in a linear network. Neural Computation 4, 691-702, 1992.

Liu A K, Belliveau J W, Dale A M. Spatiotemporal imaging of human brain activity using functional MRI-constrained magnetoencephalography data: Monte Carlo simulations. Proc Natl Acad Sci USA 95:8945-50, 1998

Manoach D S, Schlaug G, Siewert B, Darby D G, Bly B M, Benfield A, Edelman R R, Warach S, Prefrontal cortex fMRI signal changes are correlated with working memory load. Neuroreport 8:545-9, 1997.

McCarthy, G., Luby, M., Gore, J. and Goldman-Rakic, P., Infrequent events transiently activate human prefrontal and parietal cortex as measured by functional MRI. J. Neurophysiology 77: 1630-1634, 1997.

McKeown, M., Makeig, S., Brown, G., Jung, T-P., Kindermann, S., Bell, Iragui, V. and Sejnowski, T. J., Blind separation of functional magnetic resonance imaging (fMRI) data, Human Brain Mapping, 6:160,18, 1998a.

McKeown, M. J., Humphries, C., Achermann, P., Borbely, A. A. and Sejnowski, T. J., A new method for detecting state changes in the EEG: exploratory application to sleep data. J. Sleep Res. 7 suppl. 1: 48-56, 1998b.

McKeown, M. J., Tzyy-Ping Jung, Scott Makeig, Greg Brown, Sandra S. Kindermann, Te-Won Lee and Terrence J. Sejnowski, Spatially independent activity patterns in functional magnetic resonance imaging data during the Stroop color-naming task, Proc. Natl. Acad. Sci USA, 95:803-810, 1998c.

McKeown, M. J. and Sejnowski, T. J., Independent component analysis of fMRI data: examining the assumptions. Human Brain Mapping 6:368-372, 1998d.

Makeig, S. Auditory event-related dynamics of the EEG spectrum and effects of exposure to tones, Electroencephalogr Clin Neurophysiol, 86:283-293, 1993.

Makeig, S. Toolbox for independent component analysis of psychophysiological data, [World Wide Web publication] www.cnl.salk.edu/~scott/ica.html, 1997.

Makeig, S. and Galambos, R., The CERP: Event-related perturbations in steady-state responses, in: Brain Dynamics Progress and Perspectives, (pp. 375-400), ed. E. Basar and T. H. Bullock, 1989.

Makeig, S. and Inlow, M., Lapses in alertness: coherence of fluctuations in performance and the EEG spectrum, Electroencephalogr din Neurophysiol, 86:23-35, 1993.

Makeig, S. and Jung, T-P., Changes in alertness are a principal component of variance in the EEG spectrum, NeuroReport 7:213-216, 1995.

Makeig, S. and T-P. Jung, Tonic, phasic, and transient EEG correlates of auditory awareness during drowsiness, Cognitive Brain Research 4:15-25, 1996.

Makeig, S., Bell, A. J., Jung, T-P. and Sejnowski, T. J., "Independent component analysis of electroencephalographic data," In: D. Touretzky, M. Mozer and M. Hasselmo (Eds). Advances in Neural Information Processing Systems 8:145-151 MIT Press, Cambridge, MA, 1996.

Makeig, S., Jung, T-P, and Sejnowski, T. J., "Using feedforward neural networks to monitor alertness from changes in EEG correlation and coherence," In: D. Touretzky, M. Mozer & M. Hasselmo(Eds). Advances in Neural Information Processing Systems 8:931-937 MIT Press, Cambridge, MA, 1996.

Makeig, S., T-P. Jung, D. Ghahremani, A. J. Bell & T. J. Sejnowski, Blind separation of auditory event-related brain responses into independent components. Proc. Natl. Acad. Sci. USA, 94:10979-10984, 1997.

Makeig, S., Westerfield, M., Jung, T-P., Covington, J., Townsend, J., Sejnowski, T. J. and Courchesne, E., Independent components of the late positive event-related potential in a visual spatial attention task, submitted.

Mitra P P, Ogawa S, Hu X, Ugurbil K, The nature of spatiotemporal changes in cerebral hemodynamics as manifested in functional magnetic resonance imaging. Magn Reson Med.37:511-8, 1997.

Nobre A C, Sebestyen G N, Gitelman D R, Mesulam M M, Frackowiak R S, Frith C D, Functional localization of the system for visuospatial attention using positron emission tomography. Brain 120:515-33, 1997.

Nunez, P. L., Electric Fields of the Brain. New York: Oxford, 1981.

Ogawa S, Tank D W, Menon R, Ellermann J M, Kim S G, Merkle H, Ugurbil K, Intrinsic signal changes accompanying sensory stimulation: functional brain mapping with magnetic resonance imaging. Proc Natl Acad Sci USA 89:5951-5, 1992.

Pearlmutter, B. and Parra, L. C. Maximum likelihood blind source separation: a context-sensitive generalization of ICA. In: M. C. Mozer, M. I. Jordan and T. Petsche (Eds.), Advances in Neural Information Processing Systems 9:613-619 MIT Press, Cambridge, MA, 1996.

Sakai K, Hikosaka O, Miyauchi S, Takino R, Sasaki Y, Putz B. Transition of brain activation from frontal to parietal areas in visuomotor sequence learning. J Neurosci 18:1827-40, 1998.

Sahai, Amit, and Brent Waters. "Fuzzy identity-based encryption." In Annual International Conference on the Theory and Applications of Cryptographic Techniques, pp. 457-473. Springer, Berlin, Heidelberg, 2005.

Scherg, M. & Von Cramon, D., Evoked dipole source potentials of the human auditory cortex. Electroencephalogr. Clin. Neurophysiol. 65:344-601, 1986.

Tallon-Baudry, C., Bertrand, O., Delpuech, C., & Pernier, J., Stimulus Specificity of Phase-Locked and Non-Phase-Locked 40 Hz Visual Responses in Human. J. Neurosci. 16: 4240-4249, 1996.

Thaker, Darshan D., Diana Franklin, John Oliver, Susmit Biswas, Derek Lockhart, Tzvetan Metodi, and Frederic T. Chong. "Characterization of error-tolerant applications when protecting control data." In Workload Characterization, 2006 IEEE International Symposium on, pp. 142-149. IEEE, 2006.

Tulving E, Markowitsch H J, Craik F E, Habib R, Houle S, Novelty and familiarity activations in PET studies of memory encoding and retrieval. Cereb Cortex 6:71-9, 1996.

Warach, S., J. R. Ives, G. Schaug, M. R. Patel, D. G. Darby, V. Thangaraj, R. R. Edelman and D. L. Schomer, EEG-triggered echo-planar functional MRI in epilepsy, Neurology 47: 89-93, 1996.

Principal Component Analysis: Principal component analysis (PCA) is a statistical procedure that uses an orthogonal transformation to convert a set of observations of possibly correlated variables into a set of values of linearly uncorrelated variables called principal components. If there are n observations with p variables, then the number of distinct principal components is $\min(n-1,p)$. This transformation is defined in such a way that the first principal component has the largest possible variance (that is, accounts for as much of the variability in the data as possible), and each succeeding component in turn has the highest variance possible under the constraint that it is orthogonal to the preceding components. The resulting vectors are an uncorrelated orthogonal basis set. PCA is sensitive to the relative scaling of the original variables. PCA is the simplest of the true eigenvector-based multivariate analyses. Often, its operation can be thought of as revealing the internal structure of the data in a way that best explains the variance in the data. If a multivariate dataset is visualized as a set of coordinates in a high-dimensional data space (1 axis per variable), PCA can supply the user with a lower-dimensional picture, a projection of this object when viewed from its most informative viewpoint. This is done by using only the first few principal components so that the dimensionality of the transformed data is reduced. PCA is closely related to factor analysis. Factor analysis typically incorporates more domain specific assumptions about the underlying structure and solves eigenvectors of a slightly different matrix. PCA is also related to canonical correlation analysis (CCA). CCA defines coordinate systems that optimally describe the cross-covariance between two datasets while PCA defines a new orthogonal coordinate system that optimally describes variance in a single dataset. See, en.wikipedia.org/wiki/Principal_component_analysis.

A general model for confirmatory factor analysis is expressed as $x=\alpha+\Lambda\xi+\varepsilon$. The covariance matrix is expressed as $E[(x-\mu)(x-\mu)']=\Lambda\Phi\Lambda'+\Theta$. If residual covariance matrix $\Theta=0$ and correlation matrix among latent factors $\Phi=I$, then factor analysis is equivalent to principal component analysis and the resulting covariance matrix is simplified to $\Sigma=\Lambda\Lambda'$. When there are p number of variables and all p components (or factors) are extracted, this covariance matrix can alternatively be expressed into $\Sigma=D\Lambda D'$, or $\Sigma=\lambda DAD'$, where $D=n\times p$ orthogonal matrix of eigenvectors, and $\Lambda=\lambda\Lambda$, $p\times p$ matrix of eigenvalues, where $\lambda$ is a scalar and A is a diagonal matrix whose elements are proportional to the eigenvalues of $\Sigma$. The following three components determine the geometric features of the observed data: $\lambda$ parameterizes the volume of the observation, D indicates the orientation, and A represents the shape of the observation.

When population heterogeneity is explicitly hypothesized as in model-based cluster analysis, the observed covariance matrix is decomposed into the following general form $$\sum_k = \lambda_k D_k A_k D_k^T,$$

where $\lambda_k$ parameterizes the volume of the $k^{th}$ cluster, $D_k$ indicates the orientation of that cluster, and $A_k$ represents the shape of that cluster. The subscript k indicates that each component (or cluster) can have different volume, shape, and orientation.

Assume a random vector X, taking values in $\Re^m$, has a mean and covariance matrix of $\mu_X$ and $\Sigma_X$, respectively. $\lambda_1>\lambda_2> \ldots >\lambda_m>0$ are ordered eigenvalues of $\Sigma_X$, such that the i-th eigenvalue of $\Sigma_X$ means the i-th largest of them. Similarly, a vector $\alpha_i$ is the i-th eigenvector of $\Sigma_X$ when it corresponds to the i-th eigenvalue of $\Sigma_X$. To derive the form of principal components (PCs), consider the optimization problem of maximizing $$\mathrm{var}[\alpha_1^T X] = \alpha_1^T \sum_X \alpha_1,$$

subject to $$\alpha_1^T \alpha_1 = 1.$$

The Lagrange multiplier method is used to solve this question.

$$L(\alpha_1, \phi_1) = \alpha_1^T \sum_X \alpha_1 + \phi_1(\alpha_1^T\alpha_1 - 1)$$

$$\frac{\partial L}{\partial \alpha_1} =$$

$$2\sum_X \alpha_1 + 2\phi_1\alpha_1 = 0 \Rightarrow \sum_X \alpha_1 = -\phi_1\alpha_1 \Rightarrow \mathrm{var}\,[\alpha_1^T X] = -\phi_1\alpha_1^T\alpha_1 = -\phi_1.$$

Because $-\phi_1$ is the eigenvalue of $\Sigma_X$, with $\alpha_1$ being the corresponding normalized eigenvector, $$\mathrm{var}[\alpha_1^T X]$$

maximized by choosing $\alpha_1$ to be the first eigenvector of $\Sigma_X$. In this case, $$z_1 = \alpha_1^T X$$

is named the first PC of X, $\alpha_1$ is the vector of coefficients for $z_1$, and $\mathrm{var}(z_1)=\lambda_1$.

To find the second PC, $$z_2 = \alpha_2^T X,$$

we need to maximize $$\mathrm{var}[\alpha_2^T X] = \alpha_2^T \sum_X \alpha_2$$

subject to $z_2$ being uncorrelated with $z_1$. Because $$\mathrm{cov}(\alpha_1^T X, \alpha_2^T X) = 0 \Rightarrow \alpha_1^T \sum_X \alpha_2 = 0 \Rightarrow \alpha_1^T\alpha_2 = 0,$$

this problem is equivalently set as maximizing $$\alpha_2^T \sum_X \alpha_2,$$

subject to $$\alpha_1^T\alpha_2 = 0,$$

and $$\alpha_2^T\alpha_2 = 1.$$

We still make use of the Lagrange multiplier method.

$$L(\alpha_2, \phi_1, \phi_2) = \alpha_2^T \sum_X \alpha_2 + \phi_1\alpha_1^T\alpha_2 + \phi_2(\alpha_2^T\alpha_2 - 1)$$

$$\frac{\partial L}{\partial \alpha_2} = 2\sum_X \alpha_2 + \phi_1\alpha_1 + 2\phi_2\alpha_2 = 0 \Rightarrow$$

$$\alpha_1^T\left(2\sum_X \alpha_2 + \phi_1\alpha_1 + 2\phi_2\alpha_2\right) = 0 \Rightarrow \phi_1 = 0 \Rightarrow$$

$$\sum_X \alpha_2 = -\phi_2\alpha_2 \Rightarrow \alpha_2^T \sum_X \alpha_2 = -\phi_2.$$

Because $-\phi_2$ is the eigenvalue of $\Sigma_X$, with $\alpha_2$ being the corresponding normalized eigenvector, $$\mathrm{var}[\alpha_2^T X]$$

is maximized by choosing $\alpha_2$ to be the second eigenvector of $\Sigma_X$. In this case, $$z_2 = \alpha_2^T X$$

is named the second PC of X, $\alpha_2$ is the vector of coefficients for $z_2$, and $\text{var}(z_2)=\lambda_2$. Continuing in this way, it can be shown that the i-th PC $$z_i = \alpha_i^T X$$

is constructed by selecting $\alpha_i$ to be the i-th eigenvector of $\Sigma_X$, and has variance of $\lambda_i$. The key result in regards to PCA is that the principal components are the only set of linear functions of original data that are uncorrelated and have orthogonal vectors of coefficients.

For any positive integer p≤m, let $B=[\beta_1, \beta_2, \ldots, \beta_p]$ be an real m×p matrix with orthonormal columns, i.e., $$\beta_i^T \beta_j = \delta_{ij},$$

and $Y=B^T X$. Then the trace of covariance matrix of Y is maximized by taking $B=[\alpha_1, \alpha_2, \ldots, \alpha_p]$, where $\alpha_i$ is the i-th eigenvector of $\Sigma_X$. Because $\Sigma_X$ is symmetric with all distinct eigenvalues, so $\{\alpha_1, \alpha_2, \ldots, \alpha_m\}$ is an orthonormal basis with $\alpha_i$ being the i-th eigenvector of $\Sigma_X$, and we can represent the columns of B as $$\beta_i = \sum_{j=1}^{m} c_{ji} \alpha_j,$$

i=1, . . . , p, So we have B=PC, where $P=[\alpha_1, \ldots, \alpha_m]$C=$\{c_{ij}\}$ is an m×P matrix. Then, $$P^T \sum_X p = \Lambda,$$

with $\Lambda$ being a diagonal matrix whose k-th diagonal element is $\lambda_k$, and the covariance matrix of Y is, $$\sum_Y = B^T \sum_X B = C^T P^T \sum_X PC = C^T \Lambda C = \lambda_1 c_1 c_1^T + \cdots + \lambda_m c_m c_m^T$$

where $$c_i^T$$

is the i-th row of C. So, $$\begin{aligned} \text{trace}\left(\sum_Y\right) &= \sum_{i=1}^{m} \lambda_i \,\text{trace}\left(c_i c_i^T\right) \\ &= \sum_{i=1}^{m} \lambda_i \,\text{trace}\left(c_i^T c_i\right) \\ &= \sum_{i=1}^{m} \lambda_i c_i^T c_i \\ &= \sum_{i=1}^{m} \left(\sum_{j=1}^{p} c_{ij}^2\right) \lambda_i \end{aligned}$$

Because $C^T C = B^T P P^T B = B^T B = I$, so $$\text{trace}\left(C^T C\right) = \sum_{i=1}^{m} \sum_{j=1}^{p} c_{ij}^2 = p,$$

and the columns of C are orthonormal. By the Gram-Schmidt method, C can expand to D, such that D has its columns as an orthonormal basis of $\Re^m$ and contains C as its first p columns. D is square shape, thus being an orthogonal matrix and having its rows as another orthonormal basis of $\Re$. One row of C is a part of one row of D, so $$\sum_{j=1}^{p} c_{ij}^2 \le 1,$$

i=1, . . . m. Considering the constraints $$\sum_{j=1}^{p} c_{ij}^2 \le 1, \quad \sum_{i=1}^{m} \sum_{j=1}^{p} c_{ij}^2 = p$$

and the objective $$\sum_{i=1}^{m} \left(\sum_{j=1}^{p} c_{ij}^2\right) \lambda_i.$$

We derive that trace $(\Sigma_Y)$ is maximized if $$\sum_{j=1}^{p} c_{ij}^2 = 1$$

for i=1 . . . p, and $$\sum_{j=1}^{p} c_{ij}^2 = 0$$

for i=p+1, . . . , m. When $B=[\alpha_1, \alpha_2, \ldots, \alpha_p]$, straightforward calculation yields that C is an all-zero matrix except $c_{ii}=1$, i=1, . . . , p. This fulfills the maximization condition. Actually, by taking $B=[\gamma_1, \gamma_2, \ldots, \gamma_p]$, where $\{\gamma_1, \gamma_2, \ldots, \gamma_p\}$ any orthonormal basis of the subspace of span$\{\alpha_1, \alpha_2, \ldots \alpha_p\}$, the maximization condition is also satisfied, yielding the same trace of covariance matrix of Y.

Suppose that we wish to approximate the random vector X by its projection onto a subspace spanned by columns of B, where $B=[\beta_1, \beta_2, \ldots, \beta_p]$ is a real m×p matrix with orthonormal columns, i.e., $$\beta_i^T\beta_j = \delta_{ij}.\text{ If } \sigma_i^2$$

is the residual variance for each component of X, then $$\sum_{i=1}^{m}\sigma_i^2$$

is minimized if $B=[\alpha_1, \alpha_2, \ldots, \alpha_p]$, where $\{\alpha_1, \alpha_2, \ldots, \alpha_p\}$ are the first p eigenvectors of $\Sigma_X$. In other words, the trace of covariance matrix of $X-BB^TX$ is minimized if $B=[\alpha_1, \alpha_2, \ldots, \alpha_p]$, When E(X)=0, which is a commonly applied preprocessing step in data analysis methods, this property is saying that $E\|X-BB^TX\|^2$ is minimized if B== $[\alpha_1, \alpha_2, \ldots, \alpha_p]$.

The projection of a random vector X onto a subspace spanned by columns of B is $\hat{X}=BB^TX$. Then the residual vector is $\varepsilon=X-BB^TX$, which has a covariance matrix $\Sigma_\varepsilon=(I-BB^T)\Sigma_X(I-BB^T)$. Then, $$\sum_{i=1}^{m}\sigma_i^2 = \text{trace }(\Sigma_\varepsilon) = \text{trace }\left(\Sigma_X - \Sigma_X BB^T - BB^T\Sigma_X + BB^T\Sigma_X BB^T\right).$$

Also, we know:

$$\text{trace}\left(\sum\nolimits_X BB^T\right) = \text{trace}\left(BB^T \sum\nolimits_X\right) = \text{trace}\left(B^T \sum\nolimits_X B\right)$$
$$\text{trace}\left(BB^T \sum\nolimits_X BB^T\right) = \text{trace}\left(B^T \sum\nolimits_X BB^TB\right) = \text{trace}\left(B^T \sum\nolimits_X B\right).$$

The last equation comes from the fact that B has orthonormal columns. So, $$\sum_{i=1}^{m}\sigma_i^2 = \text{trace }\left(\sum\nolimits_X\right) - \text{trace }\left(B^T\sum\nolimits_X B\right).$$

To minimize $$\sum_{i=1}^{m}\sigma_i^2,$$

it suffices to maximize $\text{trace}(B^T\Sigma_XB)$. This can be done by choosing $B=[\alpha_1, \alpha_2, \ldots, \alpha_p]$, where $\{\alpha_1, \alpha_2, \ldots, \alpha_p\}$ are the first p eigenvectors of $\Sigma_X$, as above.

See, Pietro Amenta, Luigi D'Ambra, "Generalized Constrained Principal Component Analysis with External Information," (2000). We assume that data on K sets of explanatory variables and S criterion variables of n statistical units are collected in matrices $X_k$(k=1, . . . , K) and $Y_s$ (s=1, . . . , S) of orders ($n\times p_1$), . . . , ($n\times p_K$) and ($n\times q_1$), . . . , ($n\times q_s$) respectively. We suppose, without loss of generality, identity matrices for the metrics of the spaces of variables of $X_k$ and $Y_s$ with $D_n$=diag(1/n), weight matrix of statistical units. We assume, moreover, that $X_k$'s and $Y_s$'s are centered as to the weights $D_n$.

Let $X=[X_1| \ldots |X_K]$ and $Y=[Y_1| \ldots |Y_S]$, respectively, be K and S matrices column linked of orders ($n\times\Sigma_k p_k$) and ($n\times\Sigma_s q_s$). Let be, also, $W_Y=YY'$ while we denote $v_k$ the coefficients vector ($p_k$, 1) of the linear combination for each $X_k$ such that $z_k=X_kv_k$. Let $C_k$ be the matrix of dimension $P_k\times m(m\leq p_k)$, associated to the external information explanatory variables of set k.

Generalized CPCA (GCPCA) (Amenta, D'Ambra, 1999) with external information consists in seeking for K coefficients vectors $v_k$ (or, in same way, K linear combinations $Z_k$) subject to the restriction $$C_k'v_k = 0$$

simultaneously, such that:

$$\begin{cases} \max\sum_{i=1}^{K}\sum_{j=1}^{K}\langle Y'X_iv_i,\ Y'X_jv_j\rangle \\ \text{with the constraints} \begin{array}{l} \sum_{k=1}^{K}\|X_kv_k\|^2 = 1 \\ \sum_{k=1}^{K}C_k'v_k = 0 \end{array} \end{cases} \quad (1)$$

or, in equivalent way, $$\begin{cases} \max v'(A'A)v \\ \text{with the constraints } \begin{array}{l} v'Bv = 1 \\ C'v = 0 \end{array} \end{cases} \text{ or}$$

$$\begin{cases} \max f'B^{-0.5}A'AB^{-0.5}f \\ \text{with the constraints } \begin{array}{l} f'f = 1 \\ C'v = 0 \end{array} \end{cases}$$

where $$A = Y'X,\ B = \text{diag}(X_1'X_1, \cdots, X_K'X_K),\ C' = [C_1'|\ldots|C_k'],\ v' = (v_1'|\ldots|v_k')$$

and $f=B^{0.5}v$, with $$A'A = \begin{bmatrix} X_1'YY'X_1 & \ldots & X_1'YY'X_K \\ \vdots & \ddots & \vdots \\ X_K'YY'X_1 & \ldots & X_k'YY'X_k \end{bmatrix}.$$

The constrained maximum problem turns out to be an extension of criterion $$sup_{\sum_k\|z_k\|^2=1}\sum\nolimits_i\sum\nolimits_k\langle z_i, z_k\rangle$$

(Sabatier, 1993) with more sets of criterion variables with external information. The solution of this constrained maximum problem leads to solve the eigen-equation $$(P_X - P_{XB^{-1}C})W_Y g = \lambda g$$

where $$g = Xv,\ P_X - P_{XB^{-1}C} = \sum_{k=1}^{K}\left(P_{X_k} - P_{X_k(X_k'X_k)^{-1}C_k}\right)$$

is the oblique projector operator associated to the direct sum decomposition of $\Re^n$ $$\Re^n = \mathrm{Im}(P_X - P_{XB^{-1}C}) \oplus \mathrm{Im}(P_C) \oplus \mathrm{Ker}(P_X)$$

with $$P_{X_k} = X_k(X_k'X_k)^{-1}X_k'$$

and $P_C = C(C'B^{-1}C)^{-1}C'B^{-1}$, respectively, /and $B^{-1}$ orthogonal projector operators onto the subspaces spanned by the columns of matrices $X_k$ and C. Furthermore, $$P_{XB^{-1}C} = XB^{-1}C(C'B^{-1}C)^{-1}C'B^{-1}X'$$

is the orthogonal projector operator onto the subspace spanned the columns of the matrix $XB^{-1}C$. Starting from the relation $$\left(P_{X_k} - P_{X_k(X_k'X_k)^{-1}C_k}\right)W_Y g = \lambda X_k v_k$$

(which is obtained from the expression $$(I - P_C)X'W_Y g = \lambda B v)$$

the coefficients vectors $v_k$ and the linear combinations $z_k = X_k v_k$ maximizing (1) can be given by the relations $$v_k = \frac{1}{\lambda}(X_k'X_k)^{-1}(I - P_{C_k})X_k'W_Y X v \text{ and}$$

$$z_k = \frac{1}{\lambda}(P_{X_k} - P_{X_k(X_k'X_k)^{-1}C_k})W_Y X v,$$

respectively.

The solution eigenvector g can be written, as sum of the linear combinations $z_k$: $g = \Sigma_k X_k v_k$. Notice that the eigenvalues associated to the eigen-system are, according to the Sturm theorem, lower or equal than those of GCPCA eigen-system:

$$\sum_{k=1}^{K} P_{X_k} W_Y g = \lambda g.$$

Amenta P., D'Ambra L. (1994) Analisi non Simmetrica delle Corrispondenze Multiple con Vincoli Lineari. *Atti. S.I.S. XXXVII Sanremo, Aprile* 1994

Amenta P., D'Ambra L. (1996) L'Analisi in Componenti Principali in rapporto ad un sottospazio di riferimento con informazioni esterne, *Quaderni del D.M.Q.T.E., University di Pescara*, n. 18.

Amenta P., D'Ambra L. (1999) Generalized Constrained Principal Component Analysis. *Atti Riunione Scientihth del Gruppo di Classificazione dell'FCS su "Classificazione e Analisi dei Dati", Roma.*

D'Ambra L., Lauro N. C. (1982) Analisi in componenti principali in rapporto ad un sottospazio di riferimento, *Rivista di Statistica Applicata*, n.1, vol. 15.

D'Ambra L., Sabatier R., Amenta P. (1998) Analisi fattoriale delle matrici a tre vie: sintesi e nuovi approcci, (invited lecture) *Atti XXXIX Riunione SIS.*

Huon de Kermadec F., Durand J. F., Sabatier R. (1996) Comparaison de méthodes de régression pour l'étude des liens entre données hédoniques, in Third Sensometrics Meeting, E.N.T.I.A.A., Nantes.

Huon de Kermadec F., Durand J. F., Sabatier R. (1997) Comparison between linear and nonlinear PLS methods to explain overall liking from sensory characteristics, *Food Quality and Preference,* 8, n. 5/6.

Kiers H. A. L. (1991) Hierarchical relations among three way methods *Psychometrika,* 56.

Kvalheim O. M. (1988) A partial least squares approach to interpretative analysis of multivariate analysis, *Chemometrics and Intelligent Laboratory System,* 3.

MacFie H. J. H, Thomson D. M. H. (1988) Preference mapping and multidimensional scaling methods, in: *Sensory Analysis of Foods*. Elsevier Applied Science, London.

Sabatier R. (1993) Critéres et contraintes pour l'ordination simultanée de K tableaux, *Biométrie et Environement*, Masson, 332.

Schlich P. (1995) Preference mapping: relating consumer preferences to sensory or instrumental measurements, in: *Bioflavour*, INRA, Dijon.

Wold S., Geladi P., Esbensen K., Ohman J. (1987) Multi-way principal components and PLS-analysis, *J. of Chemometrics*, vol. 1.

Spatial Principal Component Analysis

Let J(t, i; α, s) be the current density in voxel i, as estimated by LORETA, in condition α at t time-frames after stimulus onset for subject s. Let area:Voxel→fBA be a function, which assigns to each voxel i E Voxel the corresponding fBA b∈fBA. In a first pre-processing step, we calculate for each subject s the value of the current density averaged over each Fba $$x(t, b; \alpha, s) = \frac{1}{N_b}\sum_{i \in b} J(t, i; \alpha, s) \tag{4}$$

where $N_b$ is the number of voxels in the fBA b, in condition α for subject s.

In the second analysis stage, the mean current density x(t,b;α, s) from each fBA b, for every subject s and conditions α, was subjected to spatial PCA analysis of the correlation matrix and varimax rotation In the present study the spatial PCA uses the above-defined fBAs as variables sampled along the time epoch for which EEG has been sampled (0-1000 ms; 512 time-frames), and the inverse solution was estimated. Spatial matrices (each matrix was sized b×t=36×512 elements) for every subject and condition were collected, and subjected to PCA analyses, including the calculation of the covariance matrix; eigenvalue decomposition and varimax rotation, in order to maximize factor loadings. In other words, in the spatial PCA analysis we approximate the mean current density for each subject in each condition as $$x(t;\alpha,s)\approx x_0(\alpha,s)+\sum_k c_k(t)x_k(\alpha,s), \tag{5}$$

where here $x(t;\alpha,x)\in R^{36}$ is a vector, which denotes the time-dependent activation of the fBAs, $x_0(\alpha,s)$ is their mean activation, and $x_k(\alpha,s)$ and $c_k$ are the principal components and their corresponding coefficients (factor loadings) as computed using the principal component analysis.

See, download.lww.com/wolterskluwer.com/WNR_1_1_2010_03_22_ARZY_1_SDC1.doc.

Nonlinear Dimensionality Reduction: High-dimensional data, meaning data that requires more than two or three dimensions to represent, can be difficult to interpret. One approach to simplification is to assume that the data of interest lie on an embedded non-linear manifold within the higher-dimensional space. If the manifold is of low enough dimension, the data can be visualized in the low-dimensional space. Non-linear methods can be broadly classified into two groups: those that provide a mapping (either from the high-dimensional space to the low-dimensional embedding or vice versa), and those that just give a visualization. In the context of machine learning, mapping methods may be viewed as a preliminary feature extraction step, after which pattern recognition algorithms are applied. Typically, those that just give a visualization are based on proximity data—that is, distance measurements. Related Linear Decomposition Methods include Independent component analysis (ICA), Principal component analysis (PCA) (also called Karhunen—Loève transform—KLT), Singular value decomposition (SVD), and Factor analysis.

The self-organizing map (SOM, also called Kohonen map) and its probabilistic variant generative topographic mapping (GTM) use a point representation in the embedded space to form a latent variable model based on a non-linear mapping from the embedded space to the high-dimensional space. These techniques are related to work on density networks, which also are based around the same probabilistic model.

Principal curves and manifolds give the natural geometric framework for nonlinear dimensionality reduction and extend the geometric interpretation of PCA by explicitly constructing an embedded manifold, and by encoding using standard geometric projection onto the manifold. How to define the "simplicity" of the manifold is problem-dependent, however, it is commonly measured by the intrinsic dimensionality and/or the smoothness of the manifold. Usually, the principal manifold is defined as a solution to an optimization problem. The objective function includes a quality of data approximation and some penalty terms for the bending of the manifold. The popular initial approximations are generated by linear PCA, Kohonen's SOM or autoencoders. The elastic map method provides the expectation-maximization algorithm for principal manifold learning with minimization of quadratic energy functional at the "maximization" step.

An autoencoder is a feed-forward neural network which is trained to approximate the identity function. That is, it is trained to map from a vector of values to the same vector. When used for dimensionality reduction purposes, one of the hidden layers in the network is limited to contain only a small number of network units. Thus, the network must learn to encode the vector into a small number of dimensions and then decode it back into the original space. Thus, the first half of the network is a model which maps from high to low-dimensional space, and the second half maps from low to high-dimensional space. Although the idea of autoencoders is quite old, training of deep autoencoders has only recently become possible through the use of restricted Boltzmann machines and stacked denoising autoencoders. Related to autoencoders is the NeuroScale algorithm, which uses stress functions inspired by multidimensional scaling and Sammon mappings (see below) to learn a non-linear mapping from the high-dimensional to the embedded space. The mappings in NeuroScale are based on radial basis function networks.

Gaussian process latent variable models (GPLVM) are probabilistic dimensionality reduction methods that use Gaussian Processes (GPs) to find a lower dimensional non-linear embedding of high dimensional data. They are an extension of the Probabilistic formulation of PCA. The model is defined probabilistically and the latent variables are then marginalized and parameters are obtained by maximizing the likelihood. Like kernel PCA they use a kernel function to form a nonlinear mapping (in the form of a Gaussian process). However, in the GPLVM the mapping is from the embedded(latent) space to the data space (like density networks and GTM) whereas in kernel PCA it is in the opposite direction. It was originally proposed for visualization of high dimensional data but has been extended to construct a shared manifold model between two observation spaces. GPLVM and its many variants have been proposed specially for human motion modeling, e.g., back constrained GPLVM, GP dynamic model (GPDM), balanced GPDM (B-GPDM) and topologically constrained GPDM. To capture the coupling effect of the pose and gait manifolds in the gait analysis, a multi-layer joint gait-pose manifolds was proposed.

Curvilinear component analysis (CCA) looks for the configuration of points in the output space that preserves original distances as much as possible while focusing on small distances in the output space (conversely to Sammon's mapping which focus on small distances in original space). It should be noticed that CCA, as an iterative learning algorithm, actually starts with focus on large distances (like the Sammon algorithm), then gradually change focus to small distances. The small distance information will overwrite the large distance information, if compromises between the two have to be made. The stress function of CCA is related to a sum of right Bregman divergences. Curvilinear distance analysis (CDA) trains a self-organizing neural network to fit the manifold and seeks to preserve geodesic distances in its embedding. It is based on Curvilinear Component Analysis (which extended Sammon's mapping), but uses geodesic distances instead. Diffeomorphic Dimensionality Reduction or Diffeomap learns a smooth diffeomorphic mapping which transports the data onto a lower-dimensional linear subspace. The method solves for a smooth time indexed vector field such that flows along the field which start at the data points will end at a lower-dimensional linear subspace, thereby attempting to preserve pairwise differences under both the forward and inverse mapping.

Perhaps the most widely used algorithm for manifold learning is Kernel principal component analysis (kernel PCA). It is a combination of Principal component analysis and the kernel trick. PCA begins by computing the covariance matrix of the M×n Matrix X. It then projects the data onto the first k eigenvectors of that matrix. By comparison, KPCA begins by computing the covariance matrix of the data after being transformed into a higher-dimensional space. It then projects the transformed data onto the first k eigenvectors of that matrix, just like PCA. It uses the kernel trick to factor away much of the computation, such that the entire process can be performed without actually computing $\phi(x)$. Of course $\phi$ must be chosen such that it has a known corresponding kernel.

Laplacian Eigenmaps, (also known as Local Linear Eigenmaps, LLE) are special cases of kernel PCA, performed by constructing a data-dependent kernel matrix. KPCA has an internal model, so it can be used to map points onto its embedding that were not available at training time. Laplacian Eigenmaps uses spectral techniques to perform dimensionality reduction. This technique relies on the basic assumption that the data lies in a low-dimensional manifold in a high-dimensional space. This algorithm cannot embed out of sample points, but techniques based on Reproducing kernel Hilbert space regularization exist for adding this capability. Such techniques can be applied to other nonlinear dimensionality reduction algorithms as well. Traditional techniques like principal component analysis do not consider the intrinsic geometry of the data. Laplacian eigenmaps builds a graph from neighborhood information of the data set. Each data point serves as a node on the graph and connectivity between nodes is governed by the proximity of neighboring points (using e.g., the k-nearest neighbor algorithm). The graph thus generated can be considered as a discrete approximation of the low-dimensional manifold in the high-dimensional space. Minimization of a cost function based on the graph ensures that points close to each other on the manifold are mapped close to each other in the low-dimensional space, preserving local distances. The eigenfunctions of the Laplace—Beltrami operator on the manifold serve as the embedding dimensions, since under mild conditions this operator has a countable spectrum that is a basis for square integrable functions on the manifold (compare to Fourier series on the unit circle manifold). Attempts to place Laplacian eigenmaps on solid theoretical ground have met with some success, as under certain nonrestrictive assumptions, the graph Laplacian matrix has been shown to converge to the Laplace—Beltrami operator as the number of points goes to infinity. In classification applications, low dimension manifolds can be used to model data classes which can be defined from sets of observed instances. Each observed instance can be described by two independent factors termed 'content' and 'style', where 'content' is the invariant factor related to the essence of the class and 'style' expresses variations in that class between instances. Unfortunately, Laplacian Eigenmaps may fail to produce a coherent representation of a class of interest when training data consist of instances varying significantly in terms of style. In the case of classes which are represented by multivariate sequences, Structural Laplacian Eigenmaps has been proposed to overcome this issue by adding additional constraints within the Laplacian Eigenmaps neighborhood information graph to better reflect the intrinsic structure of the class. More specifically, the graph is used to encode both the sequential structure of the multivariate sequences and, to minimize stylistic variations, proximity between data points of different sequences or even within a sequence, if it contains repetitions. Using dynamic time warping, proximity is detected by finding correspondences between and within sections of the multivariate sequences that exhibit high similarity.

Like LLE, Hessian LLE is also based on sparse matrix techniques. It tends to yield results of a much higher quality than LLE. Unfortunately, it has a very costly computational complexity, so it is not well-suited for heavily sampled manifolds. It has no internal model. Modified LLE (MLLE) is another LLE variant which uses multiple weights in each neighborhood to address the local weight matrix conditioning problem which leads to distortions in LLE maps. MLLE produces robust projections similar to Hessian LLE, but without the significant additional computational cost.

Manifold alignment takes advantage of the assumption that disparate data sets produced by similar generating processes will share a similar underlying manifold representation. By learning projections from each original space to the shared manifold, correspondences are recovered and knowledge from one domain can be transferred to another. Most manifold alignment techniques consider only two data sets, but the concept extends to arbitrarily many initial data sets. Diffusion maps leverages the relationship between heat diffusion and a random walk (Markov Chain); an analogy is drawn between the diffusion operator on a manifold and a Markov transition matrix operating on functions defined on the graph whose nodes were sampled from the manifold. Relational perspective map is a multidimensional scaling algorithm. The algorithm finds a configuration of data points on a manifold by simulating a multi-particle dynamic system on a closed manifold, where data points are mapped to particles and distances (or dissimilarity) between data points represent a repulsive force. As the manifold gradually grows in size the multi-particle system cools down gradually and converges to a configuration that reflects the distance information of the data points. Local tangent space alignment (LISA) is based on the intuition that when a manifold is correctly unfolded, all of the tangent hyperplanes to the manifold will become aligned. It begins by computing the k-nearest neighbors of every point. It computes the tangent space at every point by computing the d-first principal components in each local neighborhood. It then optimizes to find an embedding that aligns the tangent spaces. Local Multidimensional Scaling performs multidimensional scaling in local regions, and then uses convex optimization to fit all the pieces together.

Maximum Variance Unfolding was formerly known as Semidefinite Embedding. The intuition for this algorithm is that when a manifold is properly unfolded, the variance over the points is maximized. This algorithm also begins by finding the k-nearest neighbors of every point. It then seeks to solve the problem of maximizing the distance between all non-neighboring points, constrained such that the distances between neighboring points are preserved. Nonlinear PCA (NLPCA) uses backpropagation to train a multi-layer perceptron (MLP) to fit to a manifold. Unlike typical MLP training, which only updates the weights, NLPCA updates both the weights and the inputs. That is, both the weights and inputs are treated as latent values. After training, the latent inputs are a low-dimensional representation of the observed vectors, and the MLP maps from that low-dimensional representation to the high-dimensional observation space. Manifold Sculpting uses graduated optimization to find an embedding. Like other algorithms, it computes the k-nearest neighbors and tries to seek an embedding that preserves relationships in local neighborhoods. It slowly scales variance out of higher dimensions, while simultaneously adjusting points in lower dimensions to preserve those relationships.

Ruffini (2015) discusses Multichannel transcranial current stimulation (tCS) systems that offer the possibility of EEG-guided optimized, non-invasive brain stimulation. A tCS electric field realistic brain model is used to create a forward "lead-field" matrix and, from that, an EEG inverter is employed for cortical mapping. Starting from EEG, 2D cortical surface dipole fields are defined that could produce the observed EEG electrode voltages.

Schestatsky et al. (2017) discuss transcranial direct current stimulation (tDCS), which stimulates through the scalp with a constant electric current that induces shifts in neuronal membrane excitability, resulting in secondary changes in cortical activity. Although tDCS has most of its neuromodulatory effects on the underlying cortex, tDCS effects can also be observed in distant neural networks. Concomitant EEG monitoring of the effects of tDCS can provide valuable information on the mechanisms of tDCS. EEG findings can be an important surrogate marker for the effects of tDCS and thus can be used to optimize its parameters. This combined EEG-tDCS system can also be used for preventive treatment of neurological conditions characterized by abnormal peaks of cortical excitability, such as seizures. Such a system would be the basis of a non-invasive closed-loop device. tDCS and EEG can be used concurrently.

Albert, Jacobo, Sara López-Martin, José Antonio Hinojosa, and Luis Carretié. "Spatiotemporal characterization of response inhibition." Neuroimage 76 (2013): 272-281.

Arzouan Y, Goldstein A, Faust M. Brainwaves are stethoscopes: ERP correlates of novel metaphor comprehension. Brain Res 2007; 1160: 69-81.

Arzouan Y, Goldstein A, Faust M. Dynamics of hemispheric activity during metaphor comprehension: electrophysiological measures. NeuroImage 2007; 36: 222-231.

Arzy, Shahar, Yossi Arzouan, Esther Adi-Japha, Sorin Solomon, and Olaf Blanke. "The 'intrinsic' system in the human cortex and self-projection: a data driven analysis." Neuroreport 21, no. 8 (2010): 569-574.

Bao, Xuecai, Jinli Wang, and Jianfeng Hu. "Method of individual identification based on electroencephalogram analysis." In New Trends in Information and Service Science, 2009. NISS'09. International Conference on, pp. 390-393. IEEE, 2009.

Bhattacharya, Joydeep. "Complexity analysis of spontaneous EEG." Acta neurobiologiae experimentalis 60, no. 4 (2000): 495-502.

Chapman R M, McCrary J W. EP component identification and measurement by principal components analysis. Brain and cognition 1995; 27: 288-310.

Clementz, Brett A., Stefanie K. Barber, and Jacqueline R. Dzau. "Knowledge of stimulus repetition affects the magnitude and spatial distribution of low-frequency event-related brain potentials." Audiology and Neurotology 7, no. 5 (2002): 303-314.

Dien J, Frishkoff G A, Cerbone A, Tucker D M. Parametric analysis of event-related potentials in semantic comprehension: evidence for parallel brain mechanisms. Brain research 2003; 15: 137-153.

Dien J, Frishkoff G A. Principal components analysis of event-related potential datasets. In: Handy T (ed). Event-Related Potentials: A Methods Handbook. Cambridge, Mass. MIT Press; 2004.

Elbert, T. "IIIrd Congress of the Spanish Society of Psychophysiology." Journal of Psychophysiology 17 (2003): 39-53.

Groppe, David M., Scott Makeig, Marta Kutas, and S. Diego. "Independent component analysis of event-related potentials." Cognitive science online 6, no. 1 (2008):1-44.

Have, Mid-Ventrolateral Prefrontal Cortex. "Heschl's Gyrus, Posterior Superior Temporal Gyrus." J Neurophysiol 97 (2007): 2075-2082.

Hinojosa, J. A., J. Albert, S. López-Martin, and L. Carretié. "Temporospatial analysis of explicit and implicit processing of negative content during word comprehension." Brain and cognition 87 (2014): 109-121.

Jarchi, Delaram, Saeid Sanei, Jose C. Principe, and Bahador Makkiabadi. "A new spatiotemporal filtering method for single-trial estimation of correlated ERP subcomponents." IEEE Transactions on Biomedical Engineering 58, no. 1 (2011): 132-143.

John, Erwin Roy. "A field theory of consciousness." Consciousness and cognition 10, no. 2 (2001):184-213.

Johnson, Mark H., Michelle de Haan, Andrew Oliver, Warwick Smith, Haralambos Hatzakis, Leslie A. Tucker, and Gergely Csibra. "Recording and analyzing high-density event-related potentials with infants using the Geodesic Sensor Net." Developmental Neuropsychology 19, no. 3 (2001): 295-323.

Jung, Tzyy-Ping, and Scott Makeig. "Mining Electroencephalographic Data Using Independent Component Analysis." EEG Journal (2003).

Kashyap, Rajan. "Improved localization of neural sources and dynamical causal modelling of latency-corrected event related brain potentials and applications to face recognition and priming." (2015).

Klawohn, Julia, Anja Riesel, Rosa Grützmann, Norbert Kathmann, and Tanja Endrass. "Performance monitoring in obsessive—compulsive disorder: A temporo-spatial principal component analysis." Cognitive, Affective, & Behavioral Neuroscience 14, no. 3 (2014): 983-995.

Lister, Jennifer J., Nathan D. Maxfield, and Gabriel J. Pitt. "Cortical evoked response to gaps in noise: within-channel and across-channel conditions." Ear and hearing 28, no. 6 (2007): 862.

Maess, Burkhard, Angela D. Friederici, Markus Damian, Antje S. Meyer, and Willem J M Levelt. "Semantic category interference in overt picture naming: Sharpening current density localization by PCA." Journal of cognitive neuroscience 14, no. 3 (2002): 455- 462.

Makeig, Scott, Marissa Westerfield, Jeanne Townsend, Tzyy-Ping Jung, Eric Courchesne, and Terrence J. Sejnowski. "Functionally independent components of early event-related potentials in a visual spatial attention task." Philosophical Transactions of the Royal Society B: Biological Sciences 354, no. 1387 (1999): 1135-1144.

Matsuda, Izumi, Hiroshi Nittono, Akihisa Hirota, Tokihiro Ogawa, and Noriyoshi Takasawa. "Event-related brain potentials during the standard autonomic-based concealed information test." International Journal of Psychophysiology 74, no. 1 (2009): 58-68.

Mazaheri, Ali, and Terence W. Picton. "EEG spectral dynamics during discrimination of auditory and visual targets." Cognitive Brain Research 24, no. 1 (2005): 81-96.

Pirmoradi, Mona, Boutheina Jemel, Anne Gallagher, Julie Tremblay, Fabien D'Hondt, Dang Khoa Nguyen, Renée Béland, and Maryse Lassonde. "Verbal memory and verbal fluency tasks used for language localization and lateralization during magnetoencephalography." Epilepsy research 119 (2016): 1-9.

Potts G F, Dien J, Hartry-Speiser A L, McDougal L M, Tucker D M. Dense sensor array topography of the event-related potential to task-relevant auditory stimuli. Electroencephalography and clinical neurophysiology 1998; 106: 444-456.

Rosier F, Manzey D. Principal components and varimax-rotated components in event-related potential research: some remarks on their interpretation. Biological psychology 1981; 13: 3-26.

Ruchkin D S, Malley M G, Glaser E M. Event related potentials and time estimation. Psychophysiology 1977; 14: 451-455.

Schroder, Hans S., James E. Glazer, Ken P. Bennett, Tim P. Moran, and Jason S. Moser. "Suppression of error-preceding brain activity explains exaggerated error monitoring in females with worry." Biological psychology 122 (2017): 33-41.

Spencer K M, Dien J, Donchin E. Spatiotemporal analysis of the late ERP responses to deviant stimuli. Psychophysiology 2001; 38: 343-358.

Squires K C, Squires N K, Hillyard S A. Decision-related cortical potentials during an auditory signal detection task with cued observation intervals. Journal of experimental psychology 1975; 1: 268-279.

van Boxtel A, Boelhouwer A J, Bos A R. Optimal EMG signal bandwidth and interelectrode distance for the recording of acoustic, electrocutaneous, and photic blink reflexes. Psychophysiology 1998; 35: 690-697.

Veen, Vincent van, and Cameron S. Carter. "The timing of action-monitoring processes in the anterior cingulate cortex." Journal of cognitive neuroscience 14, no. 4 (2002): 593-602.

Wackermann, Jiri. "Towards a quantitative characterisation of functional states of the brain: from the non-linear methodology to the global linear description." International Journal of Psychophysiology 34, no. 1 (1999): 65-80.

EEG analysis approaches have emerged, in which event-related changes in EEG dynamics in single event-related data records are analyzed. See Allen D. Malony et al., Computational Neuroinformatics for Integrated Electromagnetic Neuroimaging and Analysis, PAR-99-138. Pfurtscheller, reported a method for quantifying the average transient suppression of alpha band (circa 10-Hz) activity following stimulation. Event-related desynchronization (ERD, spectral amplitude decreases), and event-related synchronization (ERS, spectral amplitude increases) are observed in a variety of narrow frequency bands (4-40 Hz) which are systematically dependent on task and cognitive state variables as well as on stimulus parameters. Makeig (1993) reported event-related changes in the full EEG spectrum, yielding a 2-D time/frequency measure he called the event-related spectral perturbation (ERSP). This method avoided problems associated with analysis of a priori narrow frequency bands, since bands of interest for the analysis could be based on significant features of the complete time/frequency transform. Rappelsburger et al. introduced event-related coherence (ERCOH). A wide variety of other signal processing measures have been tested for use on EEG and/or MEG data, including dimensionality measures based on chaos theory and the bispectrum. Use of neural networks has also been proposed for EEG pattern recognition applied to clinical and practical problems, though usually these methods have not been employed with an aim of explicitly modeling the neurodynamics involved. Neurodynamics is the mobilization of the nervous system as an approach to physical treatment. The method relies on influencing pain and other neural physiology via mechanical treatment of neural tissues and the non-neural structures surrounding the nervous system. The body presents the nervous system with a mechanical interface via the musculoskeletal system. With movement, the musculoskeletal system exerts non-uniform stresses and movement in neural tissues, depending on the local anatomical and mechanical characteristics and the pattern of body movement. This activates an array of mechanical and physiological responses in neural tissues. These responses include neural sliding, pressurization, elongation, tension and changes in intraneural microcirculation, axonal transport and impulse traffic.

The availability of and interest in larger and larger numbers of EEG (and MEG) channels led immediately to the question of how to combine data from different channels. Donchin advocated the use of linear factor analysis methods based on principal component analysis (PCA) for this purpose. Temporal PCA assumes that the time course of activation of each derived component is the same in all data conditions. Because this is unreasonable for many data sets, spatial PCA (usually followed by a component rotation procedure such as Varimax or Promax) is of potentially greater interest. To this end, several variants of PCA have been proposed for ERP decomposition.

Bell and Sejnowski published an iterative algorithm based on information theory for decomposing linearly mixed signals into temporally independent by minimizing their mutual information. First approaches to blind source separation minimized third and fourth-order correlations among the observed variables and achieved limited success in simulations. A generalized approach uses a simple neural network algorithm that used joint information maximization or 'infomax' as a training criterion. By using a compressive nonlinearity to transform the data and then following the entropy gradient of the resulting mixtures, ten recorded voice and music sound sources were unmixed. A similar approach was used for performing blind deconvolution, and the 'infomax' method was used for decomposition of visual scenes.

The first applications of blind decomposition to biomedical time series analysis applied the infomax independent component analysis (ICA) algorithm to decomposition of EEG and event-related potential (ERP) data and reported the use of ICA to monitor alertness. This separated artifacts, and EEG data into constituent components defined by spatial stability and temporal independence. ICA can also be used to remove artifacts from continuous or event-related (single-trial) EEG data prior to averaging. Vigario et al. (1997), using a different ICA algorithm, supported the use of ICA for identifying artifacts in MEG data. Meanwhile, widespread interest in ICA has led to multiple applications to biomedical data as well as to other fields (Jung et al., 2000b). Most relevant to EEG/MEG analysis, ICA is effective in separating functionally independent components of functional magnetic resonance imaging (fMRI) data Since the publication of the original infomax ICA algorithm, several extensions have been proposed. Incorporation of a 'natural gradient' term avoided matrix inversions, greatly speeding the convergence of the algorithm and making it practical for use with personal computers on large data EEG and fMRI data sets. An initial 'sphering' step further increased the reliability of convergence of the algorithm. The original algorithm assumed that sources have 'sparse' (super-Gaussian) distributions of activation values.

This restriction has recently been relaxed in an 'extended-ICA' algorithm that allows both super-Gaussian and sub-Gaussian sources to be identified. A number of variant ICA algorithms have appeared in the signal processing literature. In general, these make more specific assumptions about the temporal or spatial structure of the components to be separated, and typically are more computationally intensive than the infomax algorithm.

Since individual electrodes (or magnetic sensors) each record a mixture of brain and non-brain sources, spectral measures are difficult to interpret and compare across scalp channels. For example, an increase in coherence between two electrode signals may reflect the activation of a strong brain source projecting to both electrodes, or the deactivation of a brain generator projecting mainly to one of the electrodes. If independent components of the EEG (or MEG) data can be considered to measure activity within functionally distinct brain networks, however, event-related coherence between independent components may reveal transient, event-related changes in their coupling and decoupling (at one or more EEG/MEG frequencies). ERCOH analysis has been applied to independent EEG components in a selective attention task.

SUMMARY OF THE INVENTION

Sleep disorders affect a significant portion of the adult population. Between 50 and 70 million adults in the U.S. have a sleep disorder1. Insomnia is the most common specific sleep disorder, with short-term issues reported by about 30% of adults and chronic insomnia by 10% 2,3. Chronic insomnia is associated with deterioration of memory, adverse effects on endocrine functions and immune responses, and an increase in the risk of obesity and diabetes3,4. While at any age, managing insomnia is a challenge, it is especially a critical condition in the elderly due to age-related increases in comorbid medical conditions and medication use, as well as age-related changes in sleep structure, which shorten sleep time and impair sleep quality 5,6. As a result, decreased sleep quality is one of the most common health complaints of older adults. Medications are widely prescribed for relief from insomnia. However, sleep-promoting agents, such as hypnotic drugs, can produce adverse effects, particularly in the elderly 7. Even natural supplements, such as melatonin, can cause some side effects including headache, depression, daytime sleepiness, dizziness, stomach cramps, and irritability 8.

Aside from the general deterioration of sleep quality with age in adult population, the deterioration in quantity and quality of the slow-wave sleep (SWS), which is non-REM deep sleep, is particularly troubling 9. SWS plays an important role in cerebral restoration and recovery in humans. Studies have shown that a 15% reduction in the amounts of SWS and increased number and duration of awakenings are associated with normal aging 10. Experimental disruption of SWS have been shown to increase shallow sleep, sleep fragmentation, daytime sleep propensity, and impair daytime function 11,12. Given that SWS contributes to sleep continuity, enhancement of SWS may lead to improvements in sleep quality and daytime function in patients with insomnia and in the elderly. Furthermore, accumulating evidence point to the SWS is the time when short-term memory is consolidated into long-term memory 13. Recent research connects the deterioration of the SWS with early onset of Alzheimer's disease and other forms of dementia 14,15. It is also suggested that the loss of SWS stage may play a role in these debilitating age-related diseases 16. Unfortunately, most standard sleeping pills, while alleviating insomnia, do little to improve the SWS 17. Some evidence suggests that some hypnotic drugs change the structure of sleep adversely affecting the SWS 7,17. Hence, there is an unmet need for non-pharmacological techniques for promoting sleep, particularly, the deep non-REM sleep stage (SWS) lacking in the elderly population.

One of the promising non-pharmacological approaches to promoting sleep is neuromodulation via light, sound and/or transcranial electric stimulation (TES). Limited human trials conducted by Neuroenhancement Lab in collaboration with the Neuromodulation Laboratory at The City College of New York (CUNY) showed promise in replicating the desired sleep stage of a healthy donor in other subjects (recipients). Electroencephalogram (EEG) of healthy volunteers were recorded as they dozed off entering the stage 1 of sleep, as evidenced by the predominance of alpha waves. These EEG recordings were subsequently filtered from noise, inverted, and used for transcranial Endogenous Sleep-Derived stimulation (tESD). Volunteer subjects stimulated with tESD modulated with the indigenous brainwaves recorded in a sleeping donor, quickly dozed off and entered stage 1 of sleep, as evidenced by EEG, heart rate, respiration rate, and post-sleep cognitive test. These results were better as compared to the control arms of the study that included sham stimulation, tDCS, and tACS (10 Hz). These results suggest that tACS modulated with indigenous brainwaves recorded from a healthy sleeping donor can be used to replicated a desired sleep stage of a healthy donor in another subject.

There is significant research to identify markers of different phases of healthy or pathological sleep; the markers allow classification of observed EEG to one of the phases of sleep/wake categories. The applicants are not aware of any research that aimed at comprehensive identification of all independent components of EEG signals during sleep; and comprehensive analysis of statistically significant inter-dependence of a presence of an independent component with the particular stage of sleep. Comprehensive identification and analysis of independent components associated with sleep would allow to use those components and/or derived signals for a tACS protocol.

EEG recordings of brainwaves are obtained and pre-processed from healthy human subjects during various stages of sleep. EEG recordings of three stages of sleep, and while being awake from at least 10 healthy subjects (e.g., through public EEG database), which are then smoothed and filtered. The EEG recordings are analyzed to identify statistically significant waveform components correlated with specific sleep stages. A model (e.g., a linear multivariate model) is developed for the coefficients of the components of the EEG, based on sleep stage/wakefulness status; and the statistical significance of the model is measured. Stimulation protocols are developed that can provide safe and effective neurostimulation to induce desired sleep stage.

Great economic burden and societal cost incurred due to sleeping disorder, particularly insomnia. Sleep disturbances are common symptoms in adults and are related to various factors, including the use of caffeine, tobacco, and alcohol; sleep habits; and comorbid diseases 1. Epidemiologic studies indicate sleep disorders are affecting a significant portion of adult population. Between 50 and 70 million adults in the U.S. have a sleep disorder. Insomnia is the most common specific sleep disorder, with short-term issues reported by about 30% of adults and chronic insomnia by 10%2,3,5,18. Chronic insomnia is associated with deterioration of memory, adverse effects on endocrine functions and immune responses, and an increase in the risk of obesity and diabetes3. In addition, there is a significant economic burden and societal cost associated with insomnia due to the impact on health care utilization, impact in the work domain, and quality of life. Recent estimates of direct and indirect costs are upwards of 100 billion dollars annually in the United States 19. While at any age, managing insomnia is a challenge, it is especially a critical condition in the elderly due to age-related increases in comorbid medical conditions and medication use, as well as age-related changes in sleep structure, which shorten sleep time and impair sleep quality 5. As a result, decreased subjective sleep quality is one of the most common health complaints of older adults.

There is a deterioration of the slow-wave sleep (SWS) in the elderly. Aside from the general deterioration of sleep quality with age in the adult population, the deterioration in quantity and quality of the slow-wave sleep (SWS), which is the deep non-REM sleep, is particularly troubling 9. SWS plays an important role in cerebral restoration and recovery in humans. It is the most prominent EEG event during sleep and appears as spontaneous large oscillations of the EEG signal occurring approximately once every second in the deepest stage of non-REM sleep 20. Studies have shown that a significant decrease (~15% reduction) in the amounts of SWS and increased number and duration of awakenings are associated with normal aging 10. Given that SWS contributes to sleep continuity and experimental disruption of SWS increases shallow sleep and sleep fragmentation, enhances daytime sleep propensity, and impairs daytime function 11,12, enhancement of SWS may lead to improvements in sleep maintenance and daytime function in patients with insomnia and in the elderly. Furthermore, accumulating evidence point to the SWS as the time when short-term memory is consolidated into long-term memory 13. Recent research connects the deterioration of the SWS with early onset of Alzheimer's disease and other forms of dementia 14,15. It is also suggested that the loss of SWS stage may be the culprit for these debilitating age-related diseases 16.

SWS enhancement is a potential non-pharmacological therapy for the elderly. Given the pivotal role of slow waves during sleep, it is not surprising that several efforts have been made to increase sleep efficacy by potentiating SWS. Recently, a number of drugs have been shown to increase SWS. Although acting on different synaptic sites, overall the slow wave enhancing the effect of these drugs is mediated by enhancing GABAergic transmission. Specifically, clinical investigations showed that both tiagabine and gaboxadol increased the duration of SWS after sleep restriction 17,21-23. Tiagabine also improved performance on cognitive tasks evaluating executive functions and reduced the negative effects of sleep restriction on alertness 24. Although these results are positive, pharmacological approaches to sleep enhancement often raise issues related to dependence and tolerance and are commonly associated with residual daytime side effects. Some evidence suggests that some hypnotic drugs, while alleviating insomnia, change the structure of sleep adversely affecting the SWS 7,17. Even natural supplements, such as melatonin, can cause some side effects including headache, short-term feelings of depression, daytime sleepiness, dizziness, stomach cramps, and irritability 8. Hence, there is an unmet need for non-pharmacological technique for promoting sleep, particularly in the deep non-REM sleep stage lacking in the elderly population.

The brain activity of a first subject (a "donor" who is in the desired sleeping state) may be captured by recording neural correlates of the sleep, as expressed by brain activity patterns, such as EEG signals. The representations of the neural correlates of the first subject are used to control stimulation of a second subject (a "recipient"), seeking to induce the same brain activity patterns of the donor in the recipient to assist the recipient to attain the desired sleep state that had been attained by the donor.

One strategy to enhance deep sleep non-pharmacologically is to stimulate the brain with light, sound, electrical currents, or magnetic fields based on artificial and synthetic stimulation paradigms. Intermittent transcranial direct-current stimulation (tDCS) applied at 0.75 Hz for 5-min intervals separated by 1-min off periods after SWS onset can increase the EEG power in the slow oscillation band (<1 Hz) during the stimulation-free intervals 26. Similarly, stimulated by tDCS at the beginning of SWS accelerate the SWA homeostatic decay in subjects 27. Furthermore, slow waves can be triggered by directly perturbing the cortex during non-REM sleep using transcranial magnetic stimulation (TMS) 28. Other research has focused on the possibility of inducing slow waves in a more physiological natural manner. In a larger study in healthy adults, bilateral electrical stimulation of the vestibular apparatus shortened sleep onset latency in comparison to sham nights where no stimulation was provided 29. The effect of somatosensory and auditory stimulation was also assessed 29,30. While the change observed with somatosensory stimulation was minor, acoustic stimulation was particularly efficacious in enhancing sleep slow waves. Specifically, using an intermittent stimulation, in which tones were played in blocks of 15 s spaced out by stimulation-free intervals, slow waves appeared remarkably large and numerous during the stimulation blocks 31,32. In addition, high-density EEG studies (hdEEG, 256 channels) showed that the morphology, topography, and traveling patterns of induced slow waves were indistinguishable from those of spontaneous slow waves observed during natural sleep. A recent study found that EEG SWA increased following tone presentation during non-REM sleep 33, and slow oscillation activity (0.5-1 Hz) was increased in response to continuous acoustic stimulation at 0.8 Hz starting 2 min before lights were turned off and lasting for 90 min 34. Unlike the previous neurostimulation methods with artificial and synthetic stimulation paradigms, the present stimulation protocol uses source-derived waveforms, extracted from the indigenous brain activity EEG recordings of the healthy subjects, processed by statistical methods (e.g., principal component analysis, or spatial principal component analysis, autocorrelation, etc.), which separates components of brain activity. These separated brain EEG activities are then modified or modulated and subsequently inverted and used for transcranial Endogenous Sleep-Derived stimulation (tESD). The application of endogenous brain waveform should not only retain the efficacy in triggering SWS but also alleviate the safety concerns that are associated with long-term brain stimulation using synthetic paradigms.

1. Ohayon M M. Epidemiology of insomnia: what we know and what we still need to learn. Sleep medicine reviews. 2002; 6(2):97-111.
2. Kessler R C, Berglund P A, Coulouvrat C, et al. Insomnia and the performance of US workers: results from the America insomnia survey. Sleep. 2011; 34(9):1161-1171.
3. Sateia M J, Doghramji K, Hauri P J, Morin C M. Evaluation of chronic insomnia. An American Academy of Sleep Medicine review. Sleep. 2000; 23(2):243-308.
4. Taylor D J, Mallory L J, Lichstein K L, Durrence H H, Riedel B W, Bush A J. Comorbidity of chronic insomnia with medical problems. Sleep. 2007; 30(2):213-218.

5. Ancoli-Israel S. Insomnia in the elderly: a review for the primary care practitioner. Sleep. 2000; 23:523-30; discussion S36-28.
6. Buysse D J. Insomnia, depression and aging. Assessing sleep and mood interactions in older adults. Geriatrics (Basel,
Switzerland). 2004; 59(2):47-51; quiz 52.
7. Sateia M J, Buysse D J, Krystal A D, Neubauer D N. Adverse Effects of Hypnotic Medications. J Clin Sleep Med. Jun. 15, 2017; 13(6):839.
8. Buscemi N, Vandermeer B, Hooton N, et al. The efficacy and safety of exogenous melatonin for primary sleep disorders a meta-analysis. Journal of general internal medicine. 2005; 20(12):1151-1158.
9. Roth T. Slow wave sleep: does it matter? Journal of clinical sleep medicine: JCSM: official publication of the American Academy of Sleep Medicine. 2009; 5(2 Suppl): 54.
10. Chinoy E D, Frey D J, Kaslovsky D N, Meyer F G, Wright Jr K P. Age-related changes in slow wave activity rise time and NREM sleep EEG with and without zolpidem in healthy young and older adults. Sleep medicine. 2014; 15(9):1037-1045.
11. Dijk D J. Regulation and functional correlates of slow wave sleep. J Clin Sleep Med. Apr. 15, 2009; 5(2 Suppl): 56-15.
12. Sleep R. Restoring Deep, Slow Wave Sleep to Enhance Health and Increase Lifespan.
13. Born J. Slow-wave sleep and the consolidation of long-term memory. The World Journal of Biological Psychiatry. 2010; 11(sup1):16-21.
14. Petit D, Gagnon J-F, Fantini M L, Ferini-Strambi L, Montplaisir J. Sleep and quantitative EEG in neurodegenerative disorders. Journal of psychosomatic research. 2004; 56(5):487-496.
15. McCurry S M, Ancoli-Israel S. Sleep dysfunction in Alzheimer's disease and other dementias. Current treatment options in neurology. 2003; 5(3):261-272.
16. Mattis J, Sehgal A. Circadian rhythms, sleep, and disorders of aging. Trends in Endocrinology & Metabolism. 2016; 27(4):192-203.
17. Walsh J K. Enhancement of slow wave sleep: implications for insomnia. Journal of clinical sleep medicine: JCSM: official publication of the American Academy of Sleep Medicine. 2009; 5(2 Suppl):527.
18. Ancoli-Israel S, Roth T. Characteristics of insomnia in the United States: results of the 1991 National Sleep Foundation Survey. I. Sleep. 1999; 22:5347-353.
19. Fullerton D S. The economic impact of insomnia in managed care: a clearer picture emerges. Am J Manag Care. May 2006; 12(8 Suppl):5246-252.
20. Achermann P, Dijk D-J, Brunner D P, Borbély A A. A model of human sleep homeostasis based on EEG slow-wave activity: quantitative comparison of data and simulations. Brain research bulletin. 1993; 31(1-2):97-113.
21. Mathias S, Wetter T C, Steiger A, Lancel M. The GABA uptake inhibitor tiagabine promotes slow wave sleep in normal elderly subjects. Neurobiology of aging. 2001; 22(2):247-253.
22. Walsh J K, Snyder E, Hall J, et al. Slow wave sleep enhancement with gaboxadol reduces daytime sleepiness during sleep restriction. Sleep. May 2008; 31(5):659-672.
23. Feld G B, Wilhelm I, Ma Y, et al. Slow wave sleep induced by GABA agonist tiagabine fails to benefit memory consolidation. Sleep. Sep. 1, 2013; 36(9):1317-1326.
24. Walsh J K, Randazzo A C, Stone K, et al. Tiagabine is associated with sustained attention during sleep restriction: evidence for the value of slow-wave sleep enhancement? Sleep-New York Then Westchester-. 2006; 29(4): 433.
25. Lang N, Siebner H R, Ward N S, et al. How does transcranial D C stimulation of the primary motor cortex alter regional neuronal activity in the human brain? European Journal of Neuroscience. 2005; 22(2):495-504.
26. Marshall L, Helgadottir H, Molle M, Born J. Boosting slow oscillations during sleep potentiates memory. Nature. Nov. 30, 2006; 444(7119):610-613.
27. Reato D, Gasca F, Datta A, Bikson M, Marshall L, Parra L C. Transcranial electrical stimulation accelerates human sleep homeostasis. PLoS Comput Biol. 2013; 9(2): e1002898.
28. Massimini M, Ferrarelli F, Esser S K, et al. Triggering sleep slow waves by transcranial magnetic stimulation. Proc Natl Acad Sci USA. May 15, 2007; 104(20):8496-8501.
29. Krystal A D, Zammit G K, Wyatt J K, et al. The effect of vestibular stimulation in a four-hour sleep phase advance model of transient insomnia. J Clin Sleep Med. Aug. 15, 2010; 6(4):315-321.
30. Ngo H V, Martinetz T, Born J, Molle M. Auditory closed-loop stimulation of the sleep slow oscillation enhances memory. Neuron. May 8, 2013; 78(3):545-553.
31. Tononi G, Riedner B, Hulse B, Ferrarelli F, Sarasso S. Enhancing sleep slow waves with natural stimuli. Medicamundi.
32. Bellesi M, Riedner B A, Garcia-Molina G N, Cirelli C, Tononi G. Enhancement of sleep slow waves: underlying mechanisms and practical consequences. Frontiers in systems neuroscience. 2014; 8:208.
33. Arzi A, Shedlesky L, Ben-Shaul M, et al. Humans can learn new information during sleep. Nature neuroscience. 2012; 15(10):1460.
34. Ngo H V, Claussen J C, Born J, Molle M. Induction of slow oscillations by rhythmic acoustic stimulation. J Sleep Res. February 2013; 22(422-31.
35. Ungureanu M, Bigan C, Strungaru R, Lazarescu V. Independent component analysis applied in biomedical signal processing. Measurement Science Review. 2004; 4(2):18.

The present technology provides a method of improving sleep by transplanting sleep states—one desired sleep stage, or the sequences of sleep stages—from the first subject (donor) (or from plurality of donors) to a second subject (recipient). (In some embodiments, the first and the second subject may be the same subject at different points in time, or based on a protocol or algorithm.)

The process seeks to achieve, in the subject, a brainwave pattern, which is derived from a human. The brainwave pattern is complex, representing a superposition of modulated waveforms. The modulation preferably is determined based on brain wave patterns of another subject or plurality of subjects.

Sleep is a natural periodic suspension of consciousness, basically a process that can hardly be influenced in its individual stages by the person sleeping., It is a subconscious (in a technical sense) mental state, representing a resting state, activity pattern, activity rhythm, readiness, receptivity, or other state, often independent of particular inputs. In essence, a sleep state in a particular sleep stage or a sequence of different sleep stages of the first subject (a "donor" who is in a desired sleep stage or goes through a sequence with its individual stages) is captured by recording neural correlates of the sleep state, e.g., as expressed by brain activity patterns, such as EEG or MEG signals. The neural correlates of the first subject, either as direct or recorded representations, may then be used to control a stimulation of the second subject (a "recipient"), seeking to induce the same brain activity patterns in the second subject (recipient) as were present in the first subject (donor), thereby transplanting the sleep state of the first subject (donor), to assist the second subject (recipient) to attain the desired sleep stage that had been attained by the donor. In an alternative embodiment, the signals from the first subject (donor) being in a first sleep stage are employed to prevent the second subject (recipient) from achieving a second sleep stage, wherein the second sleep stage is an undesirable one. Furthermore, the duration and timing of different sleep stages can be controlled in the second subject. This could enable the change of the individual duration or intensity of each sleep stage and the order in which they appear. In some embodiments the signals from the first subject can be used to trigger sleep in the second subject or to prevent sleep or sleepiness and associated symptoms such as fatigue, lack of concentration, etc.

In some embodiments, the acquiring of the sleep state information is preceded by or followed by identifying the sleep stage, by direct reporting by the first subject (donor) or an observer, or by automated analysis of the physiological parameters (e.g., brain activity patterns, heartbeat, breathing pattern, oxygen saturation in blood, temperature, eye movement, skin impedance, etc.) or both.

In other embodiments, the processing of the brain activity patterns does not seek to classify or characterize it, but rather to filter and transform the information to a form suitable for control of the stimulation of the second subject. In particular, according to this embodiment, the subtleties that are not yet reliably classified in traditional brain activity pattern analysis are respected. For example, it is understood that all brain activity is reflected in synaptic currents and other neural modulation and, therefore, theoretically, conscious and subconscious information is, in theory, accessible through brain activity pattern analysis. Since the available processing technology generally fails to distinguish a large number of different brain activity patterns, that available processing technology, is necessarily deficient, but improving. However, just because a computational algorithm is unavailable to extract the information, does not mean that the information is absent. Therefore, this embodiment employs relatively raw brain activity pattern data, such as filtered or unfiltered EEGs, to control the stimulation of the second subject, without a full comprehension or understanding of exactly what information of significance is present. In one embodiment, brainwaves are recorded and "played back" to another subject, similar to recoding and playing back music. Such recording-playback may be digital or analog. Typically, the stimulation may include a low dimensionality stimulus, such as stereo-optic, binaural, isotonic tones, tactile, or other sensory stimulation, operating bilaterally, and with control over frequency and phase and/or waveform and/or transcranial stimulation such as TES, tDCS, HD-tDCS, tACS, or TMS. A plurality of different types of stimulation may be applied concurrently, e.g., visual, auditory, other sensory, magnetic, electrical.

Likewise, a present lack of understanding of the essential characteristics of the signal components in the brain activity patterns does not prevent their acquisition, storage, communication, and processing (to some extent). The stimulation may be direct, i.e., a visual, auditory, or tactile stimulus corresponding to the brain activity pattern, or a derivative or feedback control based on the second subject's brain activity pattern.

To address the foregoing problems, in whole or in part, and/or other problems that may have been observed by persons skilled in the art, the present disclosure provides methods, processes, systems, apparatus, instruments, and/or devices, as described by way of example in implementations set forth below.

While mental states are typically considered internal to the individual, and subjective, in fact, such states are common across individuals and have determinable physiological and electrophysiological population characteristics. Further, mental states may be externally changed or induced in a manner that bypasses the normal cognitive processes. In some cases, the triggers for the mental state are subjective, and therefore the particular subject-dependent sensory or excitation scheme required to induce a particular state will differ. For example, olfactory stimulation can have different effects on different people, based on differences in history of exposure, social and cultural norms, and the like. On the other hand, some mental state response triggers are normative, for example "tear jerker" media.

Mental states are represented in brainwave patterns, and in normal humans, the brainwave patterns and metabolic (e.g. blood flow, oxygen consumption, etc.) follow prototypical patterns. Therefore, by monitoring brainwave patterns in an individual, a state or series of mental states in that person may be determined or estimated. However, the brainwave patterns may be interrelated with context, other activity, and past history. Further, while prototypical patterns may be observed, there are also individual variations in the patterns. The brainwave patterns may include characteristic spatial and temporal patterns indicative of mental state. The brainwave signals of a person may be processed to extract these patterns, which, for example, may be represented as hemispheric signals within a frequency range of 3-100 Hz. These signals may then be synthesized or modulated into one or more stimulation signals, which are then employed to induce a corresponding mental state into a recipient, in a manner seeking to achieve a similar brainwave pattern from the source. The brainwave pattern to be introduced need not be newly acquired for each case. Rather, signals may be acquired from one or more individuals, to obtain an exemplar for various respective mental state. Once determined, the processed signal representation may be stored in a non-volatile memory for later use. However, in cases of complex interaction between a mental state and a context or content or activity, it may be appropriate to derived the signals from a single individual whose context or content-environment or activity is appropriate for the circumstances. Further, in some cases, a single mental state, emotion or mood is not described or fully characterized, and therefore acquiring signals from a source is an efficient exercise.

With a library of target brainwave patterns, a system and method is provided in which a target subject may be immersed in a presentation, which includes not only multimedia content, but also a series of defined mental states, emotional states or moods that accompany the multimedia content. In this way, the multimedia presentation becomes fully immersive. The stimulus in this case may be provided through a headset, such as a virtual reality or augmented reality headset. This headset is provided with a stereoscopic display, binaural audio, and a set of EEG and transcranial stimulatory electrodes. These electrodes (if provided) typically deliver a subthreshold signal, which is not painful, which is typically an AC signal which corresponds to the desired frequency, phase, and spatial location of the desired target pattern. The electrodes may also be used to counteract undesired signals, by destructively interfering with them while concurrently imposing the desired patterns. The headset may also generate visual and/or auditory signals which correspond to the desired state. For example, the auditory signals may induce binaural beats, which cause brainwave entrainment. The visual signals may include intensity fluctuations or other modulation patterns, especially those which are subliminal, that are also adapted to cause brainwave entrainment or induction of a desired brainwave pattern.

The headset preferably includes EEG electrodes for receiving feedback from the user. That is, the stimulatory system seeks to achieve a mental state, emotion or mood response from the user. The EEG electrodes permit determination of whether that state is achieved, and if not, what the current state is. It may be that achieving a desired brainwave pattern is state dependent, and therefore that characteristics of the stimulus to achieve a desired state depend on the starting state of the subject. Other ways of determining mental state, emotion, or mood include analysis of facial expression, electromyography (EMG) analysis of facial muscles, explicit user feedback, etc.

An authoring system is provided which permits a content designer to determine what mental states are desired, and then encode those states into media, which is then interpreted by a media reproduction system in order to generate appropriate stimuli. As noted above, the stimuli may be audio, visual, multimedia, other senses, or electrical or magnetic brain stimulation, and therefore a VR headset with transcranial electrical or magnetic stimulation is not required. Further, in some embodiments, the patterns may be directly encoded into the audiovisual content, subliminally encoded.

In some cases, the target mental state may be derived from an expert, actor or professional exemplar. The states may be read based on facial expressions, EMG, EEG, or other means, from the actor or exemplar. For example, a prototype exemplar engages in an activity that triggers a response, such as viewing the Grand Canyon or artworks within the Louvre. The responses of the exemplar are then recorded or represented, and preferably brainwave patterns recorded that represent the responses. A representation of the same experience is then presented to the target, with a goal of the target also experiencing the same experience as the exemplar. This is typically a voluntary and disclosed process, so the target will seek to willingly comply with the desired experiences. In some cases, the use of the technology is not disclosed to the target, for example in advertising presentations or billboards. In order for an actor to serve as the exemplar, the emotions achieved by that person must be authentic. However, so-called "method actors" do authentically achieve the emotions they convey. However, in some cases, for example where facial expressions are used as the indicator of mental state, an actor can present desired facial expressions with inauthentic mental states. The act of making a face corresponding to an emotion often achieves the targeted mental state.

In order to calibrate the system, the brain pattern of a person may be measured while in the desired state. The brain patterns acquired for calibration or feedback need not be of the same quality, or precision, or data depth, and indeed may represent responses rather than primary indicia. That is, there may be some asymmetry in the system, between the brainwave patterns representative of a mental state, and the stimulus patterns appropriate for inducing the brain state.

The present invention generally relates to achieving a mental state in a subject by conveying to the brain of the subject patterns of brainwaves. These brainwaves may be artificial or synthetic, or derived from the brain of a second subject (e.g., a person experiencing an authentic experience or engaged in an activity). Typically, the wave patterns of the second subject are derived while the second subject is experiencing an authentic experience.

A special case is where the first and second subjects are the same individual. For example, brainwave patterns are recorded while a subject is in a particular mental state. That same pattern may assist in achieving the same mental state at another time. Thus, there may be a time delay between acquisition of the brainwave information from the second subject, and exposing the first subject to corresponding stimulation. The signals may be recorded and transmitted.

The temporal pattern may be conveyed or induced non-invasively via light (visible or infrared), sound (or ultrasound), transcranial direct or alternating current stimulation (tDCS or tACS), transcranial magnetic stimulation (TMS), Deep transcranial magnetic stimulation (Deep TMS, or dTMS), Repetitive Transcranial Magnetic Stimulation (rTMS) olfactory stimulation, tactile stimulation, or any other means capable of conveying frequency patterns. In a preferred embodiment, normal human senses are employed to stimulate the subject, such as light, sound, smell and touch. Combinations of stimuli may be employed. In some cases, the stimulus or combination is innate, and therefore largely pan-subject. In other cases, response to a context is learned, and therefore subject-specific. Therefore, feedback from the subject may be appropriate to determine the triggers and stimuli appropriate to achieve a mental state.

This technology may be advantageously used to enhance mental response to a stimulus or context. Still another aspect provides for a change in the mental state. The technology may be used in humans or animals.

The present technology may employ an event-correlated EEG time and/or frequency analysis performed on neuronal activity patterns. In a time-analysis, the signal is analyzed temporally and spatially, generally looking for changes with respect to time and space. In a frequency analysis, over an epoch of analysis, the data, which is typically a time-sequence of samples, is transformed, using e.g., a Fourier transform (FT, or one implementation, the Fast Fourier Transform, FFT), into a frequency domain representation, and the frequencies present during the epoch are analyzed. The window of analysis may be rolling, and so the frequency analysis may be continuous. In a hybrid time-frequency analysis, for example, a wavelet analysis, the data during the epoch is transformed using a "wavelet transform", e.g., the Discrete Wavelet Transform (DWT) or continuous wavelet transform (CWT), which has the ability to construct a time-frequency representation of a signal that offers very good time and frequency localization. Changes in transformed data over time and space may be analyzed. In general, the spatial aspect of the brainwave analysis is anatomically modelled. In most cases, anatomy is considered universal, but in some cases, there are significant differences. For example, brain injury, psychiatric disease, age, race, native language, training, sex, handedness, and other factors may lead to distinct spatial arrangement of brain function, and therefore when transferring mood from one individual to another, it is preferred to normalize the brain anatomy of both individuals by experiencing roughly the same experiences, and measuring spatial parameters of the EEG or MEG. Note that spatial organization of the brain is highly persistent, absent injury or disease, and therefore this need only be performed infrequently. However, since electrode placement may be inexact, a spatial calibration may be performed after electrode placement.

Different aspects of EEG magnitude and phase relationships may be captured, to reveal details of the neuronal activity. The "time-frequency analysis" reveals the brain's parallel processing of information, with oscillations at various frequencies within various regions of the brain reflecting multiple neural processes co-occurring and interacting. See, Lisman J, Buzsaki G. A neural coding scheme formed by the combined function of gamma and theta oscillations. Schizophr Bull. Jun. 16, 2008; doid 0.1093/schbul/sbn060. Such a time-frequency analysis may take the form of a wavelet transform analysis. This may be used to assist in integrative and dynamically adaptive information processing. Of course, the transform may be essentially lossless and may be performed in any convenient information domain representation. These EEG-based data analyses reveal the frequency-specific neuronal oscillations and their synchronization in brain functions ranging from sensory processing to higher-order cognition. Therefore, these patterns may be selectively analyzed, for transfer to or induction in, a subject.

A statistical clustering analysis may be performed in high dimension space to isolate or segment regions which act as signal sources, and to characterize the coupling between various regions. This analysis may also be used to establish signal types within each brain region, and decision boundaries characterizing transitions between different signal types. These transitions may be state dependent, and therefore the transitions may be detected based on a temporal analysis, rather than merely a concurrent oscillator state.

The various measures make use of the magnitude and/or phase angle information derived from the complex data extracted from the EEG during spectral decomposition and/or temporal/spatial/spectral analysis. Some measures estimate the magnitude or phase consistency of the EEG within one channel across trials, whereas others estimate the consistency of the magnitude or phase differences between channels across trials. Beyond these two families of calculations, there are also measures that examine the coupling between frequencies, within trials and recording sites. Of course, in the realm of time-frequency analysis, many types of relationships can be examined beyond those already mentioned.

These sensory processing specific neuronal oscillations, e.g., brainwave patterns, e.g., of a subject (a "source") or to a person trained (for example, an actor trained in "the method") to create a desired state, and can be stored on a tangible medium and/or can be simultaneously conveyed to a recipient making use of the brain's frequency following response nature. See, Galbraith, Gary C., Darlene M. Olfman, and Todd M. Huffman. "Selective attention affects human brain stem frequency-following response." Neuroreport 14, no. 5 (2003): 735-738, journals.lww.com/neuroreport/Abstract/2003/04150/Selective_attention_affects_human_brain_stem.15.aspx.

According to one embodiment, the stimulation of the second subject is combined with a feedback process, to verify that the second subject has appropriately responded to the stimulation, e.g., has a predefined similarity to the sleep stage as the first subject, has a sleep stage with a predefined difference from the first subject, or has a desired change from a baseline sleep stage, not based on brain activity per se, or neural correlates of sleep stage, but rather physical, psychological, or behavioral effects that may be measured, reported or observed.

The feedback typically is provided to a controller with at least partial model basis, for the stimulator, which alters stimulation parameters to optimize the stimulation.

As discussed above, the model is typically difficult to define. Therefore, the model-based controller is incompletely defined, and the existence of errors and artifacts is to be expected. However, by employing a model-based controller, those parameters that are defined may be used to improve response over the corresponding controller, which lacks the model.

For example, it is believed that brainwaves represent a form of resonance, where ensembles of neurons interact in a coordinated fashion. The frequency of the wave is related to neural responsiveness to neurotransmitters, distances along neural pathways, diffusion limitations, etc. That is, the same sleep stage may be represented by slightly different frequencies in two different individuals, based on differences in the size of their brains, neuromodulators present, other anatomical, morphological and physiological differences, etc. These differences may be measured in microseconds or less, resulting in small changes in frequency. Therefore, the model component of the controller can determine the parameters of neural transmission and ensemble characteristics, vis-à-vis stimulation, and resynthesize the stimulus signal to match the correct frequency and phase of the subject's brainwave, with the optimization of the waveform adaptively determined. This may not be as simple as speeding up or slowing down playback of the signal, as different elements of the various brainwaves representing neural correlates of a sleep stage may have different relative differences between subjects.

Of course, in some cases, one or more components of the stimulation of the target subject (recipient) may be represented as abstract or semantically defined signals, and, more generally, the processing of the signals to define the stimulation will involve high level modulation or transformation between the source signal received from the first subject (donor) or plurality of donors, to define the target signal for stimulation of the second subject (recipient).

Preferably, each component represents a subset of the neural correlates reflecting brain activity that have a high autocorrelation in space and time, or in a hybrid representation such as wavelet. These may be separated by optimal filtering (e.g., spatial PCA), once the characteristics of the signal are known, and bearing in mind that the signal is accompanied by a modulation pattern, and that the two components themselves may have some weak coupling and interaction.

For example, if the first subject (donor) is listening to music, there will be significant components of the neural correlates that are synchronized with the particular music. On the other hand, the music per se may not be part of the desired stimulation of the target subject (recipient).Further, the target subject (recipient) may be in a different acoustic environment, and it may be appropriate to modify the residual signal dependent on the acoustic environment of the recipient, so that the stimulation is appropriate for achieving the desired effect, and does not represent phantoms, distractions, or irrelevant or inappropriate content. In order to perform signal processing, it is convenient to store the signals or a partially processed representation, though a complete real-time signal processing chain may be implemented. According to another embodiment, a particular stage of the sleep state of at least one first subject (donor) is identified, and the neural correlates of brain activity are captured, and the second subject (recipient) is subject to stimulation based on the captured neural correlates and the identified sleep stage. The sleep stage is typically represented as a semantic variable within a limited classification space. The sleep stage identification need not be through analysis of the neural correlates signal and may be a volitional self-identification by the first subject, e.g., on the basis of other body signals or by an observer, or a manual classification by third parties using, for example, observation, fMRI or psychological assessment. The identified sleep stage is useful, for example, because it represents a target toward (or, in some cases, against) which the second subject (recipient) can be steered.

The stimulation may be one or more stimulus applied to the second subject (trainee or recipient), which may be an electrical or magnetic transcranial stimulation (tDCS, HD-tDCS, tACS, osc-tDCS, or TMS), sensory stimulation (e.g., visual, auditory, or tactile), mechanical stimulation, ultrasonic stimulation, etc., and controlled with respect to waveform, frequency, phase, intensity/amplitude, duration, or controlled via feedback, self-reported effect by the second subject, manual classification by third parties, automated analysis of brain activity, behavior, physiological parameters, etc. of the second subject (recipient).

Typically, the goal of the process is to improve sleep in a recipient by transplanting the desired sleep stages, or a sequence of stages, of at least one first subject (donor) to the second subject (recipient) by inducing in the second subject (recipient) neural correlates of the sleep stage (or a sequence of stages) of at least one first subject (donor) corresponding to the sleep stage of the first subject, through the use of stimulation parameters comprising a waveform over a period of time derived from the neural correlates of the sleep stage of the first subject.

Typically, the first and the second subjects are spatially remote from each other and may be temporally remote as well. In some cases, the first and second subject are the same subject (human or animal), temporally displaced. In other cases, the first and the second subject are spatially proximate to each other. These different embodiments differ principally in the transfer of the signal from at least one first subject (donor) to the second subject (recipient). However, when the first and the second subjects share a common environment, the signal processing of the neural correlates and, especially of real-time feedback of neural correlates from the second subject, may involve interactive algorithms with the neural correlates of the first subject.

According to another embodiment, the first and second subjects are each subject to stimulation. In one particularly interesting embodiment, the first subject and the second subject communicate with each other in real-time, with the first subject receiving stimulation based on the second subject, and the second subject receiving feedback based on the first subject. This can lead to synchronization of neural correlates (e.g., neuronal oscillations, or brainwaves) and, consequently, of sleep stage between the two subjects. The neural correlates may be neuronal oscillations resulting in brainwaves that are detectable as, for example, EEG, qEEG, or MEG signals. Traditionally, these signals are found to have dominant frequencies, which may be determined by various analyses, such as spectral analysis, wavelet analysis, or principal component analysis (PCA), for example. One embodiment provides that the modulation pattern of a brainwave of at least one first subject (donor) is determined independent of the dominant frequency of the brainwave (though, typically, within the same class of brainwaves), and this modulation imposed on a brainwave corresponding to the dominant frequency of the second subject (recipient). That is, once the second subject achieves that same brainwave pattern as the first subject (which may be achieved by means other than electromagnetic, mechanical, or sensory stimulation), the modulation pattern of the first subject is imposed as a way of guiding the sleep stage of the second subject.

According to another embodiment, the second subject (recipient) is stimulated with a stimulation signal, which faithfully represents the frequency composition of a defined component of the neural correlates of at least one first subject (donor). The defined component may be determined based on a principal component analysis, independent component analysis (ICI), eigenvector-based multivariable analysis, factor analysis, canonical correlation analysis (CCA), nonlinear dimensionality reduction (NLDR), or related technique.

The stimulation may be performed, for example, by using a TES device, such as a tDCS device, a high-definition tDCS device, an osc-tDCS device, a pulse-tDCS ("electrosleep") device, an osc-tDCS, a tACS device, a CES device, a TMS device, rTMS device, a deep TMS device, a light source, or a sound source configured to modulate the dominant frequency on respectively the light signal or the sound signal. The stimulus may be a light signal, a sonic signal (sound), an electric signal, a magnetic field, olfactory or a tactile stimulation. The current signal may be a pulse signal or an oscillating signal. The stimulus may be applied via a cranial electric stimulation (CES), a transcranial electric stimulation (TES), a deep electric stimulation, a transcranial magnetic stimulation (TMS), a deep magnetic stimulation, a light stimulation, a sound stimulation, a tactile stimulation, or an olfactory stimulation. An auditory stimulus may be, for example, binaural beats or isochronic tones.

The technology also provides a processor configured to process the neural correlates of sleep stage from the first subject (donor), and to produce or define a stimulation pattern for the second subject (recipient) selectively dependent on a waveform pattern of the neural correlates from the first subject. The processor may also perform a PCA, a spatial PCA, an independent component analysis (ICA), eigenvalue decomposition, eigenvector-based multivariate analyses, factor analysis, an autoencoder neural network with a linear hidden layer, linear discriminant analysis, network component analysis, nonlinear dimensionality reduction (NLDR), or another statistical method of data analysis.

A signal is presented to a second apparatus, configured to stimulate the second subject (recipient), which may be an open loop stimulation dependent on a non-feedback-controlled algorithm, or a closed loop feedback dependent algorithm. The second apparatus produces a stimulation intended to induce in the second subject (recipient) the desired sleep stage, e.g., representing the same sleep stage as was present in the first subject (donor).

A typically process performed on the neural correlates is a filtering to remove noise. In some embodiments, noise filters may be provided, for example, at 50 Hz, 60 Hz, 100 Hz, 120 Hz, and additional overtones (e.g., tertiary and higher harmonics). The stimulator associated with the second subject (recipient) would typically perform decoding, decompression, decryption, inverse transformation, modulation, etc.

Alternately, an authentic wave or hash thereof may be authenticated via a blockchain, and thus authenticatable by an immutable record. In some cases, it is possible to use the stored encrypted signal in its encrypted form, without decryption.

Due to different brain sizes, and other anatomical, morphological, and/or physiological differences, dominant frequencies associated with the same sleep stage may be different in different subjects. Consequently, it may not be optimal to forcefully impose on the recipient the frequency of the donor that may or may not precisely correspond to the recipient's frequency associated with the same sleep stage. Accordingly, in some embodiments, the donor's frequency may be used to start the process of inducing the desired sleep stage in a recipient. As some point, when the recipient is closed to achieving the desired sleep state, the stimulation is either stopped or replaced with neurofeedback allowing the brain of the recipient to find its own optimal frequency associated with the desired sleep stage.

In one embodiment, the feedback signal from the second subject may be correspondingly encoded as per the source signal, and the error between the two minimized. According to one embodiment, the processor may perform a noise reduction distinct from a frequency-band filtering. According to one embodiment, the neural correlates are transformed into a sparse matrix, and in the transform domain, components having a high probability of representing noise are masked, while components having a high probability of representing signal are preserved. That is, in some cases, the components that represent modulation that are important may not be known a priori. However, dependent on their effect in inducing the desired response in the second subject (recipient), the "important" components may be identified, and the remainder filtered or suppressed. The transformed signal may then be inverse-transformed and used as a basis for a stimulation signal.

According to another embodiment, a method of sleep stage modification, e.g., brain entrainment, is provided, comprising: ascertaining a sleep stage in a plurality of first subjects (donors); acquiring brain waves of the plurality of first subjects (donors), e.g., using one of EEG and MEG, to create a dataset containing brain waves corresponding to different sleep stages. The database may be encoded with a classification of sleep stages, activities, environment, or stimulus patterns, applied to the plurality of first subjects, and the database may include acquired brainwaves across a large number of sleep stages, activities, environment, or stimulus patterns, for example. In many cases, the database records will reflect a characteristic or dominate frequency of the respective brainwaves.

The database may be accessed according to sleep stages, activities, environment, or stimulus patterns, for example, and a stimulation pattern for a second subject (recipient) defined based on the database records of one or more subjects (donors).

The record(s) thus retrieved are used to define a stimulation pattern for the second subject (recipient). As a relatively trivial example, a female recipient could be stimulated principally based on records from female donors. Similarly, a child recipient of a certain age could be stimulated principally based on the records from children donors of a similar age. Likewise, various demographic, personality, and/or physiological parameters may be matched to ensure a high degree of correspondence to between the source and target subjects. In the target subject, a guided or genetic algorithm may be employed to select modification parameters from the various components of the signal, which best achieve the desired target state based on feedback from the target subject.

Of course, a more nuanced approach is to process the entirety of the database and stimulate the second subject based on a global brainwave-stimulus model, though this is not required, and also, the underlying basis for the model may prove unreliable or inaccurate. In fact, it may be preferred to derive a stimulus waveform from only a single first subject (donor), in order to preserve micro-modulation aspects of the signal, which, as discussed above, have not been fully characterized. However, the selection of the donor(s) need not be static and can change frequently. The selection of donor records may be based on population statistics of other users of the records, i.e., whether or not the record had the expected effect, filtering donors whose response pattern correlates highest with a given recipient, etc. The selection of donor records may also be based on feedback patterns from the recipient.

The process of stimulation typically seeks to target a desired sleep stage in the recipient, which is automatically or semi-automatically determined or manually entered. In one embodiment, the records are used to define a modulation waveform of a synthesized carrier or set of carriers, and the process may include a frequency domain multiplexed multi-subcarrier signal (which is not necessarily orthogonal). A plurality of stimuli may be applied concurrently, through the different subchannels and/or though different stimulator electrodes, electric current stimulators, magnetic field generators, mechanical stimulators, sensory stimulators, etc. The stimulus may be applied to achieve brain entrainment (i.e., synchronization) of the second subject (recipient) with one or more first subjects (donors). If the plurality of donors are mutually entrained, then each will have a corresponding brainwave pattern dependent on the basis of brainwave entrainment. This link between donors may be helpful in determining compatibility between a respective donor and the recipient. For example, characteristic patterns in the entrained brainwaves may be determined, even for different target sleep stages, and the characteristic patterns may be correlated to find relatively close matches and to exclude relatively poor matches.

This technology may also provide a basis for a social network, dating site, employment, mission (e.g., space or military), or vocational testing, or other interpersonal environments, wherein people may be matched with each other based on entrainment characteristics. For example, people who efficiently entrain with each other may have better compatibility and, therefore, better marriage, work, or social relationships than those who do not. The entrainment effect need not be limited to sleep stages, and may arise across any context.

As discussed above, the plurality of first subjects (donors) may have their respective brainwave patterns stored in separate database records. Data from a plurality of first subjects (donors) is used to train the neural network, which is then accessed by inputting the target stage and/or feedback information, and which outputs a stimulation pattern or parameters for controlling a stimulator(s). When multiple first subject (donors) form the basis for the stimulation pattern, it is preferred that the neural network output parameters of the stimulation, derived from and comprising features of the brainwave patterns or other neural correlates of sleep stage from the plurality of first subject (donors), which are then used to control a stimulator which, for example, generates its own carrier wave(s) which are then modulated based on the output of the neural network. A trained neural network need not periodically retrieve records, and therefore may operate in a more time-continuous manner, rather than the more segmented scheme of record-based control.

In any of the feedback dependent methods, the brainwave patterns or other neural correlates of sleep stages may be processed by a neural network, to produce an output that guides or controls the stimulation. The stimulation, is, for example, at least one of a light signal, a sound signal, an electric signal, a magnetic field, an olfactory signal, a chemical signal, and a vibration or mechanical stimulus. The process may employ a relational database of sleep stages and brainwave patterns, e.g., frequencies/neural correlate waveform patterns associated with the respective sleep stages. The relational database may comprise a first table, the first table further comprising a plurality of data records of brainwave patterns, and a second table, the second table comprising a plurality of sleep stages, each of the sleep stages being linked to at least one brainwave pattern. Data related to sleep stages and brainwave patterns associated with the sleep stages are stored in the relational database and maintained. The relational database is accessed by receiving queries for selected (existing or desired) sleep stages, and data records are returned representing the associated brainwave pattern. The brainwave pattern retrieved from the relational database may then be used for modulating a stimulator seeking to produce an effect selectively dependent on the desired sleep stage.

A further aspect of the technology provides a computer apparatus for creating and maintaining a relational database of sleep stages and frequencies associated with the sleep stage. The computer apparatus may comprise a non-volatile memory for storing a relational database of sleep stages and neural correlates of brain activity associated with the sleep stages, the database comprising a first table comprising a plurality of data records of neural correlates of brain activity associated with the sleep stages, and a second table comprising a plurality of sleep stages, each of the sleep stages being linked to one or more records in the first table; a processor coupled with the non-volatile memory, and being configured to process relational database queries, which are then used for searching the database; RAM coupled with the processor and the non-volatile memory for temporary holding database queries and data records retrieved from the relational database; and an 10 interface configured to receive database queries and deliver data records retrieved from the relational database. A structured query language (SQL) or alternate to SQL (e.g., noSQL) database may also be used to store and retrieve records. A relational database described above maintained and operated by a general-purpose computer, improves the operations of the general-purpose computer by making searches of specific sleep stages and brainwaves associated therewith more efficient thereby, inter alia, reducing the demand on computing power.

A further aspect of the technology provides a method of brain entrainment comprising: ascertaining a sleep stage in at least one first subject (donor), recording brainwaves of said at least one first subject (donor) using at least one channel of EEG and/or MEG; storing the recorded brainwaves in a physical memory device, retrieving the brain waves from the memory device, applying a stimulus signal comprising a brainwave pattern derived from at least one-channel of the EEG and/or MEG to a second subject (recipient) via transcranial electrical and/or magnetic stimulation, whereby the sleep stage desired by the second subject (recipient) is achieved. The stimulation may be of the same dimension (number of channels) as the EEG or MEG, or a different number of channels, typically reduced. For example, the EEG or MEG may comprise 64, 128 or 256 channels, while the transcranial stimulator may have 32 or fewer channels. The placement of electrodes used for transcranial stimulation may be approximately the same as the placement of electrodes used in recording of EEG or MEG to preserve the topology of the recorded signals and, possibly, use these signals for spatial modulation.

One of the advantages of transforming the data is the ability to select a transform that separates the information of interest represented in the raw data, from noise or other information. Some transforms preserve the spatial and state transition history, and may be used for a more global analysis. Another advantage of a transform is that it can present the information of interest in a form where relatively simple linear or statistical functions of low order may be applied. In some cases, it is desired to perform an inverse transform on the data. For example, if the raw data includes noise, such as 50 or 60 Hz interference, a frequency transform may be performed, followed by a narrow band filtering of the interference and its higher order intermodulation products. An inverse transform may be performed to return the data to its time-domain representation for further processing. (In the case of simple filtering, a finite impulse response (FIR) or infinite impulse response (IIR) filter could be employed). In other cases, the analysis is continued in the transformed domain.

Transforms may be part of an efficient algorithm to compress data for storage or analysis, by making the representation of the information of interest consume fewer bits of information (if in digital form) and/or allow it to be communication using lower bandwidth. Typically, compression algorithms will not be lossless, and as a result, the compression is irreversible with respect to truncated information.

Typically, the transformation(s) and filtering of the signal are conducted using traditional computer logic, according to defined algorithms. The intermediate stages may be stored and analyzed. However, in some cases, neural networks or deep neural networks may be used, convolutional neural network architectures, or even analog signal processing. According to one set of embodiments, the transforms (if any) and analysis are implemented in a parallel processing environment. Such as using an SIMD processor such as a GPU (or GPGPU). Algorithms implemented in such systems are characterized by an avoidance of data-dependent branch instructions, with many threads concurrently executing the same instructions.

EEG signals are analyzed to determine the location (e.g., voxel or brain region) from which an electrical activity pattern is emitted, and the wave pattern characterized. The spatial processing of the EEG signals will typically precede the content analysis, since noise and artifacts may be useful for spatial resolution. Further, the signal from one brain region will typically be noise or interference in the signal analysis from another brain region; so the spatial analysis may represent part of the comprehension analysis. The spatial analysis is typically in the form of a geometrically and/or anatomically-constrained statistical model, employing all of the raw inputs in parallel. For example, where the input data is transcutaneous electroencephalogram information, from 32 EEG electrodes, the 32 input channels, sampled at e.g., 500 sps, 1 ksps or 2 ksps, are processed in a four or higher dimensional matrix, to permit mapping of locations and communication of impulses over time, space and state.

The matrix processing may be performed in a standard computing environment, e.g., an i7-7920HQ, i7-8700K, or i9-7980XE processor, under the Windows 10 operating system, executing Matlab (Mathworks, Woburn MA) software platform. Alternately, the matrix processing may be performed in a computer cluster or grid or cloud computing environment. The processing may also employ parallel processing, in either a distributed and loosely coupled environment, or asynchronous environment. One preferred embodiment employs a single instruction, multiple data processors, such as a graphics processing unit such as the nVidia CUDA environment or AMD Firepro high-performance computing environment.

Artificial intelligence (AI) and machine learning methods, such as artificial neural networks, deep neural networks, etc., may be implemented to extract the signals of interest. Neural networks act as an optimized statistical classifier and may have arbitrary complexity. A so-called deep neural network having multiple hidden layers may be employed. The processing is typically dependent on labeled training data, such as EEG data, or various processed, transformed, or classified representations of the EEG data. The label represents the emotion, mood, context, or state of the subject during acquisition. In order to handle the continuous stream of data represented by the EEG, a recurrent neural network architecture may be implemented. Depending preprocessing before the neural network, formal implementations of recurrence may be avoided. A four or more dimensional data matrix may be derived from the traditional spatial-temporal processing of the EEG and fed to a neural network. Since the time parameter is represented in the input data, a neural network temporal memory is not required, though this architecture may require a larger number of inputs. Principal component analysis (PCA, en.wikipedia.org/wiki/Principal_component_analysis), spatial PCA (arxiv.org/pdf/1501.03221v3.pdf, adegenet.r-forge.r-project.org/files/tutorial-spca.pdf, www.ncbi.nlm.nih.gov/pubmed/1510870); and clustering analysis may also be employed (en.wikipedia.org/wiki/Cluster_analysis, see U.S. Pat. Nos. 9,336,302, 9,607,023 and cited references).

In general, a neural network of this type of implementation will, in operation, be able to receive unlabeled EEG data, and produce the output signals representative of the predicted or estimated task, performance, context, or state of the subject during acquisition of the unclassified EEG. Of course, statistical classifiers may be used rather than neural networks.

The analyzed EEG, either by conventional processing, neural network processing, or both, serves two purposes. First, it permits one to deduce which areas of the brain are subject to which kinds of electrical activity under which conditions. Second, it permits feedback during training of a trainee (assuming proper spatial and anatomical correlates between the trainer and trainee), to help the system achieve the desired state, or as may be appropriate, desired series of states and/or state transitions. According to one aspect of the technology, the applied stimulation is dependent on a measured starting state or status (which may represent a complex context and history dependent matrix of parameters), and therefore the target represents a desired complex vector change. Therefore, this aspect of the technology seeks to understand a complex time-space-brain activity associated with an activity or task in a trainer, and to seek a corresponding complex time-space-brain activity associated with the same activity or task in a trainee, such that the complex time-space-brain activity state in the trainor is distinct from the corresponding state sought to be achieved in the trainee. This permits transfer of training paradigms from qualitatively different persons, in different contexts, and, to some extent, to achieve a different result.

The conditions of data acquisition from the trainer will include both task data, and sensory-stimulation data. That is, a preferred application of the system is to acquire EEG data from a trainer or skilled individual, which will then be used to transfer learning, or more likely, learning readiness states, to a naïve trainee. The goal for the trainee is to produce a set of stimulation parameters that will achieve, in the trainee, the corresponding neural activity resulting in the EEG state of the trainer at the time of or preceding the learning of a skill or a task, or performance of the task.

It is noted that EEG is not the only neural or brain activity or state data that may be acquired, and of course any and all such data may be included within the scope of the technology, and therefore EEG is a representative example only of the types of data that may be used. Other types include fMRI, magnetoencephalogram, motor neuron activity, PET, etc.

While mapping the stimulus-response patterns distinct from the task is not required in the trainer, it is advantageous to do so, because the trainer may be available for an extended period, the stimulus of the trainee may influence the neural activity patterns, and it is likely that the trainer will have correlated stimulus-response neural activity patterns with the trainee(s). It should be noted that the foregoing has suggested that the trainer is a single individual, while in practice, the trainer may be a population of trainers or skilled individuals. The analysis and processing of brain activity data may, therefore, be adaptive, both for each respective individual and for the population as a whole.

For example, the system may determine that not all human subjects have common stimulus-response brain activity correlates, and therefore that the population needs to be segregated and clustered. If the differences may be normalized, then a normalization matrix or other correction may be employed. On the other hand, if the differences do not permit feasible normalization, the population(s) may be segmented, with different trainers for the different segments. For example, in some tasks, male brains have different activity patterns and capabilities than female brains. This, coupled with anatomical differences between the sexes, implies that the system may provide gender-specific implementations. Similarly, age differences may provide a rational and scientific basis for segmentation of the population. However, depending on the size of the information base and matrices required, and some other factors, each system may be provided with substantially all parameters required for the whole population, with a user-specific implementation based on a user profile or initial setup, calibration, and system training session.

According to one aspect of the present invention, a source subject is instrumented with sensors to determine localized brain activity during experiencing an event. The objective is to identify regions of the brain involved in processing this response.

The sensors will typically seek to determine neuron firing patterns and brain region excitation patterns, which can be detected by implanted electrodes, transcutaneous electroencephalograms, magnetoencephalograms, fMRI, and other technologies. Where appropriate, transcutaneous EEG is preferred, since this is non-invasive and relatively simple.

The source is observed with the sensors in a quiet state, a state in which he or she is experiencing an event, and various control states in which the source is at rest or engaged in different activities resulting in different states. The data may be obtained for a sufficiently long period of time and over repeated trials to determine the effect of duration. The data may also be a population statistical result, and need not be derived from only a single individual at a single time.

The sensor data is then processed using a 4D (or higher) model to determine the characteristic location-dependent pattern of brain activity over time associated with the state of interest. Where the data is derived from a population with various degrees of arousal, the model maintains this arousal state variable dimension.

A recipient is then prepared for receipt of the mental state. The mental state of the recipient may be assessed. This can include responses to a questionnaire, sell-assessment, or other psychological assessment method. Further, the transcutaneous EEG (or other brain activity data) of the recipient may be obtained, to determine the starting state for the recipient, as well as activity during experiencing the desired mental state.

In addition, a set of stimuli, such as visual patterns, acoustic patterns, vestibular, smell, taste, touch (light touch, deep touch, proprioception, stretch, hot, cold, pain, pleasure, electric stimulation, acupuncture, etc.), vagus nerve (e.g., parasympathetic), are imposed on the subject, optionally over a range of baseline brain states, to acquire data defining the effect of individual and various combinations of sensory stimulation on the brain state of the recipient. Population data may also be used for this aspect.

The data from the source or population of sources (see above) may then be processed in conjunction with the recipient or population of recipient data, to extract information defining the optimal sensory stimulation over time of the recipient to achieve the desired brain state resulting in the desired mental state.

In general, for populations of sources and recipients, the data processing task is immense. However, the statistical analysis will generally be of a form that permits parallelization of mathematical transforms for processing the data, which can be efficiently implemented using various parallel processors, a common form of which is a SIMD (single instruction, multiple data) processor, found in typical graphics processors (GPUs). Because of the cost-efficiency of GPUs, it is referred to implement the analysis using efficient parallelizable algorithms, even if the computational complexity is nominally greater than a CISC-type processor implementation.

During stimulation of the recipient, the EEG pattern may be monitored to determine if the desired state is achieved through the sensory stimulation. A closed loop feedback control system may be implemented to modify the stimulation seeking to achieve the target. An evolving genetic algorithm may be used to develop a user model, which relates the mental state, arousal and valence, sensory stimulation, and brain activity patterns, both to optimize the current session of stimulation and learning, as well as to facilitate future sessions, where the mental states of the recipient have further enhanced, and to permit use of the system for a range of mental states.

The stimulus may comprise a chemical messenger or stimulus to alter the subject's level of consciousness or otherwise alter brain chemistry or functioning. The chemical may comprise a hormone or endocrine analog molecule, (such as adrenocorticotropic hormone [ACTH] (4-11)), a stimulant (such as cocaine, caffeine, nicotine, phenethylamines), a psychoactive drug, psychotropic or hallucinogenic substance (a chemical substance that alters brain function, resulting in temporary changes in perception, mood, consciousness and behavior such as pleasantness (e.g. euphoria) or advantageousness (e.g., increased alertness).

While typically, controlled or "illegal" substances are to be avoided, in some cases, these may be appropriate for use. For example, various drugs may alter the state of the brain to enhance or selectively enhance the effect of the stimulation. Such drugs include stimulants (e.g., cocaine, methylphenidate (Ritalin), ephedrine, phenylpropanolamine, amphetamines), narcotics/opiates (opium, morphine, heroin, methadone, oxymorphine, oxycodone, codeine, fentanyl), hallucinogens (lysergic acid diethylamide (LSD), PCP, MDMA (ecstasy), mescaline, psilocybin, magic mushroom (*Psilocybe cubensis*), *Amanita muscaria* mushroom, marijuana/*cannabis*), *Salvia divinorum*, diphenhydramine (Benadryl), flexeril, tobacco, nicotine, bupropion (Zyban), opiate antagonists, depressants, gamma aminobutyric acid (GABA) agonists or antagonists, NMDA receptor agonists or antagonists, depressants (e.g., alcohol, Xanax; Valium; Halcion; Librium; other benzodiazepines, Ativan; Klonopin; Amytal; Nembutal; Seconal; Phenobarbital, other barbiturates), psychedelics, disassociatives, and deliriants (e.g., a special class of acetylcholine-inhibitor hallucinogen). For example, Carhart-Harris showed using fMRI that LSD and psilocybin caused synchronization of different parts of the brain that normally work separately by making neurons fire simultaneously. This effect can be used to induce synchronization of various regions of the brain to heighten the mental state.

It is noted that a large number of substances, natural and artificial, can alter mood or arousal and, as a result, may impact emotions or non-target mental states. Typically, such substances will cross the blood-brain barrier, and exert a psychotropic effect. Often, however, this may not be necessary or appropriate. For example, a painful stimulus can alter mood, without acting as a psychotropic drug; on the other hand, a narcotic an also alter mood by dulling emotions. Further, sensory stimulation can induce mood and/or emotional changes, such as smells, sights, sounds, various types of touch and proprioception sensation, balance and vestibular stimulation, etc. Therefore, peripherally acting substances that alter sensory perception or stimulation may be relevant to mood. Likewise, pharmacopsychotropic drugs may alter alertness, perceptiveness, memory, and attention, which may be relevant to task-specific mental state control.

The mental state may be associated with a learning or performing a skill. The skill may comprise a mental skill, e.g., cognitive, alertness, concentration, attention, focusing, memorization, visualization, relaxation, meditation, speedreading, creative skill, "whole-brain-thinking", analytical, reasoning, problem-solving, critical thinking, intuitive, leadership, learning, speedreading, patience, balancing, perception, linguistic or language, language comprehension, quantitative, "fluid intelligence", pain management, skill of maintaining positive attitude, a foreign language, musical, musical composition, writing, poetry composition, mathematical, science, art, visual art, rhetorical, emotional control, empathy, compassion, motivational skill, people, computational, science skill, or an inventorship skill. See, U.S. Pat. Nos. 6,435,878, 5,911,581, and 20090069707. The skill may comprise a motor skill, e.g., fine motor, muscular coordination, walking, running, jumping, swimming, dancing, gymnastics, yoga; an athletic or sports, massage skill, martial arts or fighting, shooting, self-defense; speech, singing, playing a musical instrument, penmanship, calligraphy, drawing, painting, visual, auditory, olfactory, game-playing, gambling, sculptor's, craftsman, massage, or assembly skill. Where a skill is to be enhanced, and an emotion to be achieved (or suppressed), concurrently, the stimulus to the recipient may be combined in such a way as to achieve the result. In some cases, the component is universal, while in others, it is subjective. Therefore, the combination any require adaptation based on the recipient characteristics.

The technology may be embodied in apparatuses for acquiring the brain activity information from the source, processing the brain activity information to reveal a target brain activity state and a set of stimuli, which seek to achieve that state in a recipient, and generating stimuli for the recipient to achieve and maintain the target brain activity state over a period of time and potential state transitions. The generated stimuli may be feedback controlled. A general-purpose computer may be used for the processing of the information, a microprocessor, a FPGA, an ASIC, a system-on-a-chip, or a specialized system, which employs a customized configuration to efficiently achieve the information transformations required. Typically, the source and recipient act asynchronously, with the brain activity of the source recorded and later processed. However, real-time processing and brain activity transfer are also possible. In the case of a general-purpose programmable processor implementation or portions of the technology, computer instructions may be stored on a nontransient computer readable medium. Typically, the system will have special-purpose components, such as a transcranial stimulator, or a modified audio and/or display system, and therefore the system will not be a general-purpose system. Further, even in a general-purpose system the operation per se is enhanced according to the present technology.

Mental states may be induced in a subject non-invasively via light, sound, transcranial direct current stimulation (tDCS), transcranial alternating current stimulation (tDAS) or HD-tACS, transcranial magnetic stimulation (TMS) or other means capable of conveying frequency patterns.

The transmission of the brain waves can be accomplished through direct electrical contact with the electrodes implanted in the brain or remotely employing light, sound, electromagnetic waves and other non-invasive techniques. Light, sound, or electromagnetic fields may be used to remotely convey the temporal pattern of prerecorded brainwaves to a subject by modulating the encoded temporal frequency on the light, sound or electromagnetic filed signal to which the subject is exposed.

Every activity, mental or motor, and emotion is associated with unique brainwaves having specific spatial and temporal patterns, i.e., a characteristic frequency or a characteristic distribution of frequencies over time and space. Such waves can be read and recorded by several known techniques, including electroencephalography (EEG), magnetoencephalography (MEG), exact low-resolution brain electromagnetic tomography (eLORETA), sensory evoked potentials (SEP), fMRI, functional near-infrared spectroscopy (fNIRS), etc. The cerebral cortex is composed of neurons that are interconnected in networks. Cortical neurons constantly send and receive nerve impulses-electrical activity-even during sleep. The electrical or magnetic activity measured by an EEG or MEG (or another device) device reflects the intrinsic activity of neurons in the cerebral cortex and the information sent to it by subcortical structures and the sense receptors.

It has been observed that "playing back the brainwaves" to another animal or person by providing decoded temporal pattern through transcranial direct current stimulation (tDCS), transcranial alternating current stimulation (tACS), high definition transcranial alternating current stimulation (HD-tDCS), transcranial magnetic stimulation (TMS), or through electrodes implanted in the brain allows the recipient to achieve the mental state at hand or to increase a speed of achievement. For example, if the brain waves of a mouse navigated a familiar maze are decoded (by EEG or via implanted electrodes), playing this temporal pattern to another mouse unfamiliar with this maze will allow it to learn to navigate this maze faster.

Similarly, recording brainwaves associated with a specific response of one subject and later "playing back" this response to another subject will induce a similar response in the second subject. More generally, when one animal assumes a mental state, parts of the brain will have characteristic activity patterns. Further, by "artificially" inducing the same pattern in another animal, the other animal will have the same mental state, or more easily be induced into that state. The pattern of interest may reside deep in the brain, and thus be overwhelmed in an EEG signal by cortical potentials and patterns. However, techniques other than surface electrode EEG may be used to determine and spatially discriminate deep brain activity, e.g., from the limbic system. For example, various types of magnetic sensors may sense deep brain activity. See, e.g., 9,618,591; 9,261,573; 8,618,799; and 8,593,141.

In some cases, EEGs dominated by cortical excitation patterns may be employed to sense the mental state, since the cortical patterns may correlate with lower-level brain activity. Note that the determination of a state representation of a mental state need not be performed each time the system is used; rather, once the brain spatial and temporal activity patterns and synchronization states associated with a particular mental states are determined, those patterns may be used for multiple targets and over time.

Similarly, while the goal is, for example, to trigger the target to assume the same brain activity patterns are the exemplar, this can be achieved in various ways, and these methods of inducing the desired patterns need not be invasive. Further, user feedback, especially in the case of a human transferee, may be used to tune the process. Finally, using the various senses, especially sight, sound, vestibular, touch, proprioception, taste, smell, vagus afferent, other cranial nerve afferent, etc. can be used to trigger high level mental activity, that in a particular subject achieves the desired metal state, emotion or mood.

Thus, in an experimental subject, which may include laboratory scale and/or invasive monitoring, a set of brain electrical activity patterns that correspond to particular emotions or mental states is determined. Preferably, these are also correlated with surface EEG findings. For the transferee, a stimulation system is provided that is non-hazardous and non-invasive. For example, audiovisual stimulation may be exclusively used. A set of EEG electrodes is provided to measure brain activity, and an adaptive or genetic algorithm scheme is provided to optimize the audiovisual presentation, seeking to induce in the transferee the target pattern found in the experimental subject. After the stimulation patterns, which may be path dependent, are determined, it is likely that these patterns will be persistent, though over longer time periods, there may be some desensitization to the stimulation pattern(s). In some cases, audiovisual stimulation is insufficient, and TMS or other electromagnetic stimulation (superthreshold, or preferably subthreshold) is employed to assist in achieving the desired state and maintaining it for the desired period.

The transmission of the brain waves can be accomplished through direct electrical contact with the electrodes implanted in the brain or remotely employing light, sound, electromagnetic waves and other non-invasive techniques.

Light, sound or invisible electromagnetic fields may be used to remotely convey the temporal pattern of prerecorded brainwaves to a subject, by modulating the encoded temporal frequency on the light, sound or electromagnetic filed signal to which the subject is exposed.

Employing light, sound or electromagnetic field to remotely convey the temporal pattern of brainwaves (which may be prerecorded) to a subject by modulating the encoded temporal frequency on the light, sound or electromagnetic filed signal to which the subject is exposed.

When a group of neurons fires simultaneously, the activity appears as a brainwave. Different brainwave-frequencies are linked to different mental states in the brain.

A desired metal state may be induced in a target individual (e.g., human, animal), by providing selective stimulation according to a temporal pattern, wherein the temporal pattern is correlated with an EEG pattern of the target when in the desired mental state, or represents a transition which represents an intermediate toward achieving the desired mental state. The temporal pattern may be targeted to a discrete spatial region within the brain, either by a physical arrangement of a stimulator, or natural neural pathways through which the stimulation (or its result) passes.

The EEG pattern may be derived from another individual or individuals, the same individual at a different time, or an in vivo animal model of the desired metal state. The method may therefore replicate a mental state of a first subject in a second subject. The mental state typically is not a state of consciousness or an idea, but rather a subconscious (in a technical sense) state, representing an emotion, readiness, receptivity, or other state, often independent of particular thoughts or ideas. In essence, a mental state of the first subject (a "trainer" or "donor" who is in a desired mental state) is captured by recording neural correlates of the mental state, e.g., as expressed by brain activity patterns, such as EEG or MEG signals. The neural correlates of the first subject, either as direct or recorded representations, may then be used to control a stimulation of the second subject (a "trainee" or "recipient"), seeking to induce the same brain activity patterns in the second subject (recipient/trainee) as were present in the first subject (donor/trainer) to assist the second subject (recipient/trainee) to attain the desired mental state that had been attained by the donor/trainer. In an alternative embodiment, the signals from the first subject (donor/trainer) being in the first mental state are employed to prevent the second subject (recipient/trainee) from achieving a second mental state, wherein the second mental state is an undesirable one.

The source brain wave pattern may be acquired through multichannel EEG or MEG, from a human in the desired brain state. A computational model of the brain state is difficult to create. However, such a model is not required according to the present technology. Rather, the signals may be processed by a statistical process (e.g., PCA or a related technology), or a statistically trained process (e.g., a neural network). The processed signals preferably retain information regarding signal source special location, frequency, and phase. In stimulating the recipient's brain, the source may be modified to account for brain size differences, electrode locations, etc. Therefore, the preserved characteristics are normalized spatial characteristics, frequency, phase, and modulation patterns.

The normalization may be based on feedback from the target subject, for example based on a comparison of a present state of the target subject and a corresponding state of the source subject, or other comparison of known states between the target and source. Typically, the excitation electrodes in the target subject do not correspond to the feedback electrodes or the electrodes on the source subject. Therefore, an additional type of normalization is required, which may also be based on a statistical or statistically trained algorithm.

According to one embodiment, the stimulation of the second subject is associated with a feedback process, to verify that the second subject has appropriately responded to the stimulation, e.g., has a predefined similarity to the mental state as the first subject, has a mental state with a predefined difference from the first subject, or has a desire change from a baseline mental state. Advantageously, the stimulation may be adaptive to the feedback. In some cases, the feedback may be functional, i.e., not based on brain activity per se, or neural correlates of mental state, but rather physical, psychological, or behavioral effects that may be reported or observed.

The feedback typically is provided to a computational model-based controller for the stimulator, which alters stimulation parameters to optimize the stimulation in dependence on a brain and brain state model applicable to the target.

For example, it is believed that brainwaves represent a form of resonance, where ensembles of neurons interact in a coordinated fashion as a set of coupled or interacting oscillators. The frequency of the wave is related to neural responsivity to neurotransmitters, distances along neural pathways, diffusion limitations, etc., and perhaps pacemaker neurons or neural pathways. That is, the same mental state may be represented by different frequencies in two different individuals, based on differences in the size of their brains, neuromodulators present, physiological differences, etc. These differences may be measured in microseconds or less, resulting in fractional changes in frequency. However, if the stimulus is different from the natural or resonant frequency of the target process, the result may be different from that expected. Therefore, the model-based controller can determine the parameters of neural transmission and ensemble characteristics, vis-à-vis stimulation, and resynthesize the stimulus wave to match the correct waveform, with the optimization of the waveform adaptively determined. This may not be as simple as speeding up or slowing down playback of the signal, as different elements of the various waveforms representing neural correlates of mental state may have different relative differences between subjects. Therefore, according to one set of embodiments, the stimulator autocalibrates for the target, based on a correspondence (error) of a measured response to the stimulation and the desired mental state sought by the stimulation. In cases where the results are chaotic or unpredictable based on existing data, a genetic algorithm may be employed to explore the range of stimulation parameters, and determine the response of the target. In some cases, the target has an abnormal or unexpected response to stimulation based on a model maintained within the system. In this case, when the deviance from the expected response is identified, the system may seek to new model, such as from a model repository that may be on-line, such as through the Internet. If the models are predictable, a translation may be provided between an applicable model of a source or trainer, and the applicable model of the target, to account for differences. In some cases, the desired mental state is relatively universal, such as sleep and awake. In this case, the brain response model may be a statistical model, rather than a neural network or deep neural network type implementation.

Thus, in one embodiment, a hybrid approach is provided, with use of donor-derived brainwaves, on one hand, which may be extracted from the brain activity readings (e.g., EEG or MEG) of the first at least one subject (donor), preferably processed by principal component analysis, or spatial principal component analysis, autocorrelation, or other statistical processing technique (clustering, PCA, etc.) or statistically trained technique (backpropagation of errors, etc.) that separates components of brain activity, which can then be modified or modulated based on high-level parameters, e.g., abstractions. See, ml4a.githubio/ml4a/how_neural_networks_are_trained/. Thus, the stimulator may be programmed to induce a series of brain states defined by name (e.g., sleep stage 1, sleep stage 2, etc.) or as a sequence of "abstract" semantic labels, icons, or other representations, each corresponding to a technical brain state or sequence of sub-states. The sequence may be automatically defined, based on biology and the system training, and thus relieve the programmer of low-level tasks. However, in a general case, the present technology maintains use of components or subcomponents of the donor's brain activity readings, e.g., EEG or MEG, and does not seek to characterize or abstract them to a semantic level.

According to the present technology, a neural network system or statistical classifier may be employed to characterize the brain wave activity and/or other data from a subject. In addition to the classification or abstraction, a reliability parameter is presented, which predicts the accuracy of the output. Where the accuracy is high, a model-based stimulator may be provided to select and/or parameterize the model, and generate a stimulus for a target subject. Where the accuracy is low, a filtered representation of the signal may be used to control the stimulator, bypassing the model(s). The advantage of this hybrid scheme is that when the model-based stimulator is employed, many different parameters may be explicitly controlled independent of the source subject. On the other hand, where the data processing fails to yield a highly useful prediction of the correct model-based stimulator parameters, the model itself may be avoided, in favor of a direct stimulation type system.

Of course, in some cases, one or more components of the stimulation of the target subject may be represented as abstract or semantically defined signals, and more generally the processing of the signals to define the stimulation will involve high level modulation or transformation between the source signal received from the first subject, to define the target signal for stimulation of the second subject.

Preferably, each component represents a subset of the neural correlates reflecting brain activity that have a high spatial autocorrelation in space and time, or in a hybrid representation such as wavelet. For example, one signal may represent a modulated 10.2 Hz signal, while another signal represents a superposed modulated 15.7 Hz signal, with respectively different spatial origins. These may be separated by optimal filtering, once the spatial and temporal characteristics of the signal are known, and bearing in mind that the signal is accompanied by a modulation pattern, and that the two components themselves may have some weak coupling and interaction.

In some cases, the base frequency, modulation, coupling, noise, phase jitter, or other characteristic of the signal may be substituted. For example, if the first subject is listening to music, there will be significant components of the neural correlates that are synchronized with the particular music. On the other hand, the music per se may not be part of the desired stimulation of the target subject. Therefore, through signal analysis and decomposition, the components of the signal from the first subject, which have a high temporal correlation with the music, may be extracted or suppressed from the resulting signal. Further, the target subject may be in a different acoustic environment, and it may be appropriate to modify the residual signal dependent on the acoustic environment of the target subject, so that the stimulation is appropriate for achieving the desired effect, and does not represent phantoms, distractions, or irrelevant or inappropriate content. In order to perform processing, it is convenient to store the signals or a partially processed representation, though a complete real-time signal processing chain may be implemented. Such a real-time signal processing chain is generally characterized in that the average size of a buffer remains constant, i.e., the lag between output and input is relatively constant, bearing in mind that there may be periodicity to the processing.

The mental state of the first subject may be identified, and the neural correlates of brain activity captured. The second subject is subject to stimulation based on the captured neural correlates and the identified mental state. The mental state may be represented as a semantic variable, within a limited classification space. The mental state identification need not be through analysis of the neural correlates signal, and may be a volitional self-identification by the first subject, a manual classification by third parties, or an automated determination. The identified mental state is useful, for example, because it represents a target toward (or against) which the second subject can be steered.

The stimulation may be one or more inputs to the second subject, which may be an electrical or magnetic transcranial stimulation, sensors stimulation, mechanical stimulation, ultrasonic stimulation, etc., and controlled with respect to waveform, intensity/amplitude, duration, feedback, self-reported effect by the second subject, manual classification by third parties, automated analysis of brain activity, behavior, physiological parameters, etc. of the second subject.

The process may be used to induce in the target subject neural correlates of the desired mental state, which are derived from a different time for the same person, or a different person at the same or a different time. For example, one seeks to induce the neural correlates of the first subject in a desired mental state in a second subject, through the use of stimulation parameters comprising a waveform over a period of time derived from the neural correlates of mental state of the first subject.

The first and second subjects may be spatially remote from each other, and may be temporally remote as well. In some cases, the first and second subject are the same animal (e.g., human), temporally displaced. In other cases, the first and second subject are spatially proximate to each other. In some cases, neural correlates of a desired mental state are derived from a mammal having a simpler brain, which are then extrapolated to a human brain. (Animal brain stimulation is also possible, for example to enhance training and performance). When the first and second subjects share a common environment, the signal processing of the neural correlates, and especially of real-time feedback of neural correlates from the second subject may involve interactive algorithms with the neural correlates of the first subject.

The first and second subjects may each be subject to stimulators. The first subject and the second subject may communicate with each other in real-time, with the first subject receiving stimulation based on the second subject, and the second subject receiving feedback based on the first subject. This can lead to synchronization of mental state between the two subjects. However, the first subject need not receive stimulation based on real-time signals from the second subject, as the stimulation may derive from a third subject, or the first or second subjects at different points in time.

The neural correlates may be, for example, EEG, qEEG, or MEG signals. Traditionally, these signals are found to have dominant frequencies, which may be determined by various analyses. One embodiment provides that the modulation pattern of a brainwave of the first subject is determined independent of the dominant frequency of the brainwave (though typically within the same class of brainwaves), and this modulation imposed on a wave corresponding to the dominant frequency of the second subject. That is, once the second subject achieves that same brainwave pattern as the first subject (which may be achieved by means other than electromagnetic, mechanical, or sensors stimulation), the modulation pattern of the first subject is imposed as a way of guiding the mental state of the second subject.

The second subject may be stimulated with a stimulation signal which faithfully represents the frequency composition of a defined component of the neural correlates of the first subject.

The stimulation may be performed, for example, by using a tDCS device, a high-definition tDCS device, a tACS device, a TMS device, a deep TMS device, and a source of one of a light signal and a sound signal configured to modulate the dominant frequency on the one of a light signal and a sound signal. The stimulus may be at least one of a light signal, a sound signal, an electric signal, and a magnetic field. The electric signal may be a direct current signal or an alternating current signal. The stimulus may be a transcranial electric stimulation, a transcranial magnetic stimulation, a deep magnetic stimulation, a light stimulation, or a sound stimulation. A visual stimulus may be ambient light or a direct light. An auditory stimulus may be binaural beats or isochronic tones.

The technology may also provide a processor configured to process the neural correlates of mental state from the first subject, and to produce or define a stimulation pattern for the second subject selectively dependent on a waveform pattern of the neural correlates from the first subject. Typically, the processor performs signal analysis and calculates at least a dominant frequency of the brainwaves of the first subject, and preferably also spatial and phase patterns within the brain of the first subject.

A signal is presented to a second apparatus, configured to stimulate the second subject, which may be an open loop stimulation dependent on a non-feedback controlled algorithm, or a closed loop feedback dependent algorithm. In other cases, analog processing is employed in part or in whole, wherein the algorithm comprises an analog signal processing chain. The second apparatus receives information from the processor (first apparatus), typically comprising a representation of a portion of a waveform represented in the neural correlates. The second apparatus produces a stimulation intended to induce in the second subject the desired mental state, e.g., representing the same mental state as was present in the first subject.

A typical process performed on the neural correlates is a filtering to remove noise. For example, notch filters may be provided at 50 Hz, 60 Hz, 100 Hz, 120 Hz, and additional overtones. Other environmental signals may also be filtered in a frequency-selective or waveform-selective (temporal) manner. Higher level filtering may also be employed, as is known in the art. The neural correlates, after noise filtering, may be encoded, compressed (lossy or losslessly), encrypted, or otherwise processed or transformed. The stimulator associated with the second subject would typically perform decoding, decompression, decryption, inverse transformation, etc.

Information security and copy protection technology, similar to that employed for audio signals, may be employed to protect the neural correlate signals from copying or content analysis before use. In some cases, it is possible to use the stored encrypted signal in its encrypted for, without decryption. For example, with an asymmetric encryption scheme, which supports distance determination. See U.S. Pat. No. 7,269,277; Sahai and Waters (2005) Annual International Conference on the Theory and Applications of Cryptographic Techniques, pp. 457-473. Springer, Berlin, Heidelberg; Bringer et al. (2009) IEEE International Conference on Communications, pp. 1-6; Juels and Sudan (2006) Designs, Codes and Cryptography 2:237-257; Thaker et al. (2006) IEEE International Conference on Workload Characterization, pp. 142-149; Galil et al. (1987) Conference on the Theory and Application of Cryptographic Techniques, pp. 135-155.

Because the system may act intrusively, it may be desirable to authenticate the stimulator or parameters employed by the stimulator before use. For example, the stimulator and parameters it employs may be authenticated by a distributed ledger, e.g., a blockchain. On the other hand, in a closed system, digital signatures and other hierarchical authentication schemes may be employed. Permissions to perform certain processes may be defined according to smart contracts, which automated permissions (i.e., cryptographic authorization) provided from a blockchain or distributed ledger system. Of course, centralized management may also be employed.

In practice, the feedback signal from the second subject may be correspondingly encoded as per the source signal, and the error between the two minimized. In such an algorithm, the signal sought to be authenticated is typically brought within an error tolerance of the encrypted signal before usable feedback is available. One way to accomplish this is to provide a predetermined range of acceptable authenticatable signals which are then encoded, such that an authentication occurs when the putative signal matches any of the predetermined range. In the case of the neural correlates, a large set of digital hash patterns may be provided representing different signals as hash patterns. The net result is relatively weakened encryption, but the cryptographic strength may still be sufficiently high to abate the risks.

The processor may perform a noise reduction distinct from a frequency-band filtering. The neural correlates may be transformed into a sparse matrix, and in the transform domain, components representing high probability noise are masked, while components representing high probability signal are preserved. The distinction may be optimized or adaptive. That is, in some cases, the components which represent modulation that are important may not be known a priori. However, dependent on their effect in inducing the desired response in the second subject, the "important" components may be identified, and the remainder filtered or suppressed. The transformed signal may then be inverse-transformed, and used as a basis for a stimulation signal.

A mental state modification, e.g., brain entrainment, may be provided, which ascertains a mental state in a plurality of first subjects; acquires brain waves of the plurality of first subjects, e.g., using one of EEG and MEG, to create a dataset containing representing brain waves of the plurality of first subjects. The database may be encoded with a classification of mental state, activities, environment, or stimulus patterns, applied to the plurality of first subjects, and the database may include acquired brain waves across a large number of mental states, activities, environment, or stimulus patterns, for example. In many cases, the database records will reflect a characteristic or dominate frequency of the respective brain waves. As discussed above, the trainer or first subject is a convenient source of the stimulation parameters, but is not the sole available source. The database may be accessed according to its indexing, e.g., mental states, activities, environment, or stimulus patterns, for example, and a stimulation pattern for a second subject defined based on the database records of one or more subjects.

The record(s) thus retrieved are used to define a stimulation pattern for the second subject. The selection of records, and their use, may be dependent on the second subject and/or feedback from the second subject. As a relatively trivial example, a female second subject could be stimulated principally dependent on records from female first subjects. Of course, a more nuanced approach is to process the entirety of the database and stimulate the second subject based on a global brain wave-stimulus model, though this is not required, and also, the underlying basis for the model may prove unreliable or inaccurate. In fact, it may be preferred to derive a stimulus waveform from only a single first subject, in order to preserve micro-modulation aspects of the signal, which as discussed above have not been fully characterized. However, the selection of the first subject(s) need not be static, and can change frequently. The selection of first subject records may be based on population statistics of other users of the records (i.e., collaborative filtering, i.e., whose response pattern do I correlate highest with? etc.). The selection of first subject records may also be based on feedback patterns from the second user.

The process of stimulation may seek to target a desired mental state in the second subject, which is automatically or semi-automatically determined of manually entered. That target then represents a part of the query against the database to select the desired record(s). The selection of records may be a dynamic process, and reselection of records may be feedback dependent.

The records may be used to define a modulation waveform of a synthesized carrier or set of carriers, and the process may include a frequency domain multiplexed multi-subcarrier signal (which is not necessarily orthogonal). A plurality of stimuli may be applied concurrently, through the suffered subchannels and/or though different stimulator electrodes, magnetic field generators, mechanical stimulators, sensory stimulators, etc. The stimuli for the different sub-channels or modalities need not be derived from the same records.

The stimulus may be applied to achieve the desired mental state, e.g., brain entrainment of the second subject with one or more first subjects. Brain entrainment is not the only possible outcome of this process. If the plurality of first subjects are mutually entrained, then each will have a corresponding brain wave pattern dependent on the basis of brainwave entrainment. This link between first subject may be helpful in determining compatibility between a respective first subject and the second subject. For example, characteristic patterns in the entrained brainwaves may be determined, even for different target mental states, and the characteristic patterns correlated to find relatively close matches and to exclude relatively poor matches.

This technology may also provide a basis for a social network, dating site, employment or vocational testing, or other interpersonal environments, wherein people may be matched with each other based on entrainment characteristics. For example, people who efficiently entrain with each other may have better social relationships than those who do not. Thus, rather than seeking to match people based on personality profiles, the match could be made based on an ability of each party to efficiently entrain the brainwave pattern of the other party. This enhances non-verbal communication, and assists in achieving corresponding states during activities. This can be assessed by monitoring neural responses of each individual to video, and also by providing a test stimulation based on the other party's brainwave correlates of mental state, to see whether coupling is efficiently achieved. On the other hand, the technology could be used to assist in entrainment when natural coupling is inefficient, or to block coupling where the coupling is undesirable. An example of the latter is hostility; when two people are entrained in a hostile environment, emotional escalation ensures. However, if the entrainment is attenuated, undesired escalation may be impeded.

As discussed above, the plurality of first subjects may have their respective brain wave patterns stored in association with separate database records. However, they may also be combined into a more global model. One such model is a neural network or deep neural network. Typically, such a network would have recurrent features. Data from a plurality of first subjects is used to train the neural network, which is then accessed by inputting the target state and/or feedback information, and which outputs a stimulation pattern or parameters for controlling a stimulator. When multiple first subjects form the basis for the stimulation pattern, it is preferred that the neural network output parameters of the stimulation, derived from and comprising features of the brain wave patterns or other neural correlates of mental state from the plurality of first subjects, which are then used to control a stimulator which, for example, generates its own carrier wave(s) which are then modulated based on the output of the neural network. The neural network need not periodically retrieve records, and therefore may operate in a more time-continuous manner, rather than the more segmented scheme of record-based control.

In any of the feedback dependent methods, the brainwave patterns or other neural correlates of mental state may be processed by a neural network, to produce an output that guides or controls the stimulation. The stimulation, is, for example, at least one of a light (visual) signal, a sound signal, an electric signal, a magnetic field, and a vibration or mechanical stimulus, or other sensory input. The fields may be static or dynamically varying.

The process may employ a relational database of mental states and brainwave patterns, e.g., frequencies/neural correlate waveform patterns associated with the respective mental states. The relational database may comprise a first table, the first table further comprising a plurality of data records of brainwave patterns, and a second table, the second table comprising a plurality of mental states, each of the mental states being linked to at least one brainwave pattern. Data related to mental states and brainwave patterns associated with the mental states are stored in the relational database and maintained. The relational database is accessed by receiving queries for selected mental states, and data records are returned representing the associated brainwave pattern. The brainwave pattern retrieved from the relational database may then be used for modulating a stimulator seeking to produce an effect selectively dependent on the mental state at issue.

A computer apparatus may be provided for creating and maintaining a relational database of mental states and frequencies associated with the mental states, the computer apparatus comprising: a non-volatile memory for storing a relational database of mental states and neural correlates of brain activity associated with the mental states, the database comprising a first table, the first table further comprising a plurality of data records of neural correlates of brain activity associated with the mental states, and a second table, the second table comprising a plurality of mental states, each of the mental states being linked to one or more records in the first table; a processor coupled with the non-volatile memory, configured to process relational database queries, which are then used for searching the database; RAM coupled with the processor and the non-volatile memory for temporary holding database queries and data records retrieved from the relational database; and an I/O interface configured to receive database queries and deliver data records retrieved from the relational database. A SQL or noSQL database may also be used to store and retrieve records.

A further aspect of the technology provides a method of brain entrainment comprising: ascertaining a mental state in a first subject; recording brain waves of the plurality of subjects using at least one channel one of EEG and MEG; storing the recorded brain waves in a physical memory device; retrieving the brain waves from the memory device; applying a stimulus signal comprising a brainwave pattern derived from at least one-channel one of the EEG and MEG to a second subject via transcranial stimulation, whereby the mental state desired by the second subject is achieved. The stimulation may be of the same order (number of channels) as the EEG or MEG, or a different number of channels, typically reduced. For example, the EEG or MEG may comprise 128 or 256 channels, while the transcranial stimulator may have 8 or fewer channels. Sensory stimulation of various modalities and patterns may accompany the transcranial stimulation.

The at least one channel may be less than six channels and the placement of electrodes used for transcranial stimulation may be approximately the same as the placement of electrodes used in recording of said one of EEG and MEG.

The present technology may be responsive to chronobiology, and in particular to the subjective sense of time. For a subject, this may be determined volitionally subjectively, but also automatically, for example by judging attention span, using e.g., eye movements, and analyzing persistence of brainwave patterns or other physiological parameters after a discrete stimulus. Further, time-constants of the brain, reflected by delays and phase may also be analyzed. Further, the contingent negative variation (CNV) preceding a volitional act may be used, both to determine (or measure) conscious action timing, and also the time relationships between thought and action more generally.

Typically, brainwave activity is measured with a large number of EEG electrodes, which each receive signals from a small area on the scalp, or in the case of a MEG, by a number of sensitive magnetic field detectors, which are responsive to local field differences. Typically, the brainwave capture is performed in a relatively high number of spatial dimensions, e.g., corresponding to the number of sensors. It is often unfeasible to process the brainwave signals to create a source model, given that the brainwaves are created by billions of neurons, connected through axons, which have long distances. Further, the neurons are generally non-linear, and interconnected. However, a source model is not required.

Various types of artificial intelligence techniques may be exploited to analyze the neural correlates of a sleep stage represented in the brain activity data of both the first subject (donor) (or plurality of donors) and the second subject (recipient). The algorithm or implementation need not be the same, though in some cases, it is useful to conform the approach of the source processing and feedback processing so that the feedback does not achieve or seek a suboptimal target sleep stage. However, given the possible differences in conditions, resources, equipment, and purpose, there is no necessary coordination of these processes. The artificial intelligence may take the form of neural networks or deep neural networks, though rule/expert-based systems, hybrids, and more classical statistical analysis may be used. In a typical case, an artificial intelligence process will have at least one aspect, which is non-linear in its output response to an input signal, and thus at least the principle of linear superposition is violated. Such systems tend to permit discrimination, since a decision and the process of decision-making are, ultimately, non-linear. An artificially intelligent system requires a base of experience or information upon which to train. This can be a supervised (external labels applied to data), unsupervised (self-discrimination of classes), or semi-supervised (a portion of the data is externally labelled).

A self-learning or genetic algorithm may be used to tune the system, including both or either the signal processing at the donor system and the recipient system. In a genetic algorithm feedback-dependent self-learning system, the responsivity of a subject, e.g., the target, to various kinds of stimuli may be determined over a stimulus space. This stimulation may be in the context of use, with a specific target sleep stage provided, or unconstrained. The stimulator may operate using a library of stimulus patterns, or seek to generate synthetic patterns or modifications of patterns. Over a period of time, the system will learn to map a desired sleep stage to optimal context-dependent parameters of the stimulus pattern.

The technology may be used for both the creation of a desired sleep stages in the recipient, elimination of existing sleep stages in the recipient. In the latter case, a decision of what end state is to be achieved is less constrained, and therefore the optimization is distinct. For example, in the former case, it may be hard to achieve a particular sleep stage that is desired, requiring a set of transitions to cause the brain of the recipient to be enabled/prepared to enter the target state. In the case of a system seeking to eliminate an undesired sleep stage, the issue is principally what path to take to most efficiently leave the current state, bearing in mind the various costs, such as the comfort/discomfort of the stimulation, the time value cost, etc. Therefore, the series of states may differ in the implementation of these distinct goals, even if the endpoints are identical, i.e., the optimal algorithm to achieve state B from state A, may be different from the optimal algorithm to exist state A, and end up at state B.

The technology may be used to address sleep stages or sections of them associated with dreaming. Typically, dreaming is associated with many different brain regions. As such, the biology of dreaming is different. Often, dreams have a biochemical or hormonal component and, perhaps, a physiological component, that may be attenuated or absent from cognitive states. Dreaming had long been thought to occur largely during rapid eye-movement (REM) sleep, but dreams have also been reported to occur during non-REM sleep. However, dreams are typically remembered, if the dreamer wakes us during the REM phase of the sleep. In addition, it has been shown that dreaming, for example, about faces was linked to increased high-frequency activity in the specific region of the brain involved in face recognition, with dreams involving spatial perception, movement and thinking similarly linked to regions of the brain that handle such tasks when awake. Therefore, while the general brainwave or other neural correlates acquisition from a donor may be similar or identical, the stimulus used on the second subject (recipient) may be distinct in modality, spatial location, intensity/waveform, other stimulation parameters, and the types and application of feedback employed.

It is known that people who have more REM sleep and more intense theta (4 Hz-7 Hz) activity during REM are better able to consolidate emotional memories. It was suggested (Blagrove) that if we attempt to hack our dreams by artificially increasing theta waves, it might lead to the incorporation of more waking experiences into our dreams. (See "Dreams act as overnight therapy" New Scientist magazine on 5 May 2018). Transplanting theta frequency brainwaves from a vivid dreamer may also help achieve the same effect. Moreover, instead of stimulating the subject's brain with a synthetic theta frequency (e.g., isotonic tones or ambient sound beats), stimulating the recipient's brain using donor's brainwaves carrying secondary (and higher) harmonics, in addition to the dominant theta frequency, may induce the same category of dreams, i.e., if the donor dreamed of people, the recipient will be more likely to dream of people, albeit different people, because the donor's brainwaves will stimulate the visual cortex of the recipient. This may be helpful in treatment of PTSD, stress management, phobias and some psychiatric diseases.

In a medical treatment implementation, in some cases it may be appropriate to administer a drug or pharmacological agent, such as melatonin, hypnotic or soporific drug, a sedative (e.g., barbiturates, benzodiazepines, nonbenzodiazepine hypnotics, orexin antagonists, antihistamines, general anesthetics, *cannabis* and other herbal sedatives, methaqualone and analogues, muscle relaxants, opioids) that assists in achieving the target sleep stage, and for emotional states and/or dreams, this may include certain psychotropic drugs, such as epinephrine, norepinephrine reuptake inhibitors, serotonin reuptake inhibitors, peptide endocrine hormones, such as oxytocin, ACTH fragments, insulin, etc. Combining a drug with stimulation may reduce the required dose of the drug and the associated side effects of the drug.

It is therefore an object to provide a method of inducing sleep in a second subject comprising: recording brain activity patterns of a first subject (donor) who is asleep; and inducing sleep in the second subject (recipient) by replicating the brain activity patterns of the donor in the recipient.

It is also an object to provide a method of preventing sleep in a second subject (recipient) comprising: recording brain activity patterns of a first subject (donor) who is awake; and preventing sleep in the second subject (recipient) by replicating the brain activity patterns of the donor in the recipient.

It is further an object to provide a method of inducing sleep in a second subject (recipient) comprising: identifying the mental state of a first subject (donor); if the donor is asleep, recording brain activity patterns of the donor; and inducing sleep in the recipient by replicating the brain activity patterns of the donor in the recipient. The method may further comprise verifying that the recipient is asleep.

It is still a further object to provide a method of preventing sleep in a second subject (recipient) comprising: identifying a mental state of a first subject (donor); if the donor is awake, recording brain activity patterns of the first subject; and preventing sleep in the second subject by replicating the brain activity patterns of the second subject. The method may further comprise verifying that the second subject is awake.

Another object is a method of transplanting a desired mental state from a first subject (donor) to a second subject (recipient) comprising: identifying a mental state of the donor; capturing a mental state of the donor by recording brain activity patterns; saving the brain activity patterns in a non-volatile memory; retrieving the brain activity patterns from the non-volatile memory; and transplanting the desired mental state of the donor to the recipient by inducing the brain activity patterns in the recipient, wherein the desired mental state is one a sleeping state and a waking state.

Another object is a method of transplanting a desired sleep stage from a first subject (donor) to a second subject (recipient) comprising: identifying a sleep stage of the donor; capturing a sleep stage of the donor by recording brain activity patterns; saving the brain activity patterns in a non-volatile memory; retrieving the brain activity patterns from the non-volatile memory; and transplanting the desired sleep stage of the donor to the recipient by inducing the brain activity patterns in the recipient, wherein the desired sleep stage is one a sleep stage 1, sleep stage 2, and sleep stage 3.

Another object is a method of transplanting a desired sleep stage from a first subject (donor) to a second subject (recipient) comprising: identifying a sleep stage of the donor; capturing a sleep stage of the donor by recording brain activity patterns; saving the brain activity patterns in a non-volatile memory; retrieving the brain activity patterns from the non-volatile memory; and transplanting the desired sleep stage of the donor to the recipient by inducing the brain activity patterns in the recipient, wherein the desired sleep stage is one of a REM sleep stage and non-REM sleep stage.

Another object is a method of transplanting a desired sleep stage from a first subject (donor) to a second subject (recipient) comprising: identifying a sleep stage of the donor; capturing a sleep stage of the donor by recording brain activity patterns; saving the brain activity patterns in a non-volatile memory; retrieving the brain activity patterns from the non-volatile memory; and transplanting the desired sleep stage of the donor to the recipient by inducing the brain activity patterns in the recipient, wherein the desired sleep stage is a slow-wave deep non-REM sleep.

A further object is a method of improving sleep in a recipient by transplanting a mental state of a donor to the recipient comprising: recording brainwaves of the donor; and transplanting the mental state of the donor to the recipient by inducing the recorded brainwaves of the donor in the recipient, wherein the mental state is one of a waking state and a sleeping state.

A still further object is a method of transplanting a desired mental state of a first subject (donor) to a second subject comprising: identifying a mental state of the donor; recording brainwaves of the donor in a desired mental state; and transplanting the desired mental state of the donor to the recipient by inducing the brainwaves of the first subject in the second subject, wherein the desired mental state is one of a sleeping state and a waking state.

Another object is a method of improving sleep in a recipient by transplanting a desired state of a healthy sleep to the recipient comprising: identifying a mental state of the plurality of healthy donors; recording brainwaves of the plurality of healthy donor in a state of sleep; saving the brainwaves in a non-volatile memory; retrieving the brainwaves from the non-volatile memory; and transplanting the state of healthy sleep from the plurality of healthy donors to the recipient by inducing the brainwaves of the donor in the recipient. The method may comprise identifying a mental state of the recipient to verify that the recipient has the desired mental state. The brainwaves may be recorded using EEG, qEEG, or MEG. The method may further comprise filtering the recorded brainwaves from noise and/or performing PCA to determine dominant frequencies and secondary (and, possibly, higher) harmonics.

A further object is a system for transplanting a desired mental state from a first subject (donor) to a second subject (recipient) comprising: a first apparatus for recording brainwaves of the donor in a desired mental state; a non-volatile memory coupled with the first apparatus for storing the recording of the brainwaves; and a second apparatus for inducing the brainwaves in the recipient to transplant to the recipient the desired mental state of the donor, the second apparatus configured to receive the recording of the brainwaves of the donor from the non-volatile memory, wherein the desired mental state is one of a sleeping state and a waking state. The first apparatus may be one of an electroencephalograph and a magnetoencephalograph. The second apparatus may be one of a tDCS device, a tACS device, a HD tDCS device, a TMS device, a deep TMS device, an osc-tDCS, a source of light signal or sound signal configured to modulate donor's brainwave frequencies on the light signal or the sound signal.

Another object is a method of transplanting a desired mental state of a first subject (donor) to a second subject (recipient) comprising: identifying a mental state of the donor; recording at least one of EEG and MEG of the donor, said donor being in a desired mental state; processing the EEG or MEG signal; saving the processed signal in a nonvolatile memory; retrieving the processed signal from the nonvolatile memory; modulating the processed signal on at least one stimulus; and transplanting the desired mental state of the first subject to the second subject by stimulating the second subject with said at least one stimulus, wherein the desired mental state is a sleeping state or a waking state. The processing may comprise removing noise from the EEG or MEG signal; and/or compressing the EEG or MEG signal. The EEG or MEG signal retrieved from the nonvolatile memory may be decompressed. The stimulus may be a light signal, a sound signal, an electric signal, a magnetic field, or a combination thereof. The electric signal may be a direct current signal or an alternating current signal. The transcranial electric stimulation may be a tDCS, a high-definition tDCS, or a tACS. The transcranial magnetic stimulation may be a deep magnetic stimulation. The light stimulation may be an ambient light or a direct light. The sound stimulation may be binaural bits or isochronic tones.

A still another object is a system for transplanting a desired mental state of a first subject (donor) to a second subject (recipient) comprising: an electroencephalograph or a magnetoencephalograph for recoding brainwaves of the donor, the donor being in a desired mental state; a processor coupled with an electroencephalograph or a magnetoencephalograph, the processor configured to perform signal analysis and calculate at least one dominant frequency of the brainwaves of the donor; a nonvolatile memory coupled with the first processor for storing the at least one frequency of the brainwaves of the donor; a second apparatus for inducing the brainwaves in the recipient to transplant to the recipient the desired mental state of the donor, the second apparatus configured to receive said at least one dominant frequency of the brainwaves of the donor from the non-volatile memory, wherein the desired mental state is one of a sleeping state and a waking state.

The second apparatus may be a tDCS device, a high-definition tDCS device, a tACS device, a TMS device, a deep TMS device, an osc-tDCS, a light source capable of modulating said at least one dominant frequency on the light, a sound source capable of modulating said at least one dominant frequency on the sound, or a combination thereof. The sound source may be binaural beats source or isochronic tones source.

A further object is a method of transplanting a circadian rhythm of a first subject (donor) to a second subject (recipient) comprising: recording EEG or MEG of the donor, the donor having a desirable phase of the circadian rhythm; processing the recorded EEG or MEG to remove noise; saving the processed EEG or MEG in a nonvolatile memory; retrieving the processed EEG or MEG from the nonvolatile memory; and transplanting the desired phase of the circadian rhythm of the donor to the recipient by "playing back" the processed EEG or MEG of the donor to the recipient via transcranial stimulation or other one or more stimulus on which the donor's EEG or MEG is modulated. The method may further comprise compressing the recorded EEG or MEG, before saving it in the non-volatile memory; and decompressing the recorded EEG or MEG after retrieving compressed EEG or MEG from the non-volatile memory. The transcranial stimulation may be a tDCS, a HD-tDCS, a TMS, a deep-TMS and osc-tDCS.

Yet another object is a system for transplanting a circadian rhythm of a first subject (donor) to a second subject (recipient) comprising: an electroencephalograph or a magnetoencephalograph for recording EEG or MEG respectively; a first processor coupled to the electroencephalograph or the magnetoencephalograph and configured for digital signal processing for removing noise from the recorded EEG or MEG; a non-volatile memory coupled with the processor for storing the processed EEG or MEG; and a stimulation device coupled to the non-volatile memory for playing back the processed EEG or MEG to the recipient to induce the circadian rhythm of the donor to the recipient. The stimulation device may be a transcranial stimulation device, a source of light or a source of sound, each capable of modulating recorded EEG or MEG on a light signal or a sound signal respectively. The transcranial stimulation device may be one of a tDCS, a HD-tDCS, a TMS, a deep-TMS, and osc-tDCS. The first processor may be further configured to compress the processed EEG or MEG. A second processor configured to decompress compressed EEG or MEG may be coupled to the non-volatile memory and to the transcranial stimulation device or another stimulation device.

It is another object to provide a computer-readable medium for controlling a brain stimulator having a programmable processor, comprising: instructions for analyzing brain activity data from a subject to determine a sleep-awake state represented in the brain activity data; instructions for classifying the brain activity data with respect to the sleep-awake state; instructions for determining a desired change in the sleep-awake state represented in the brain activity data based on at least a cyclic model of sleep-awake states; instructions for controlling a brain stimulation pattern of the brain stimulator, to achieve the desired change in the sleep-awake state, substantially without directly awakening the subject through the stimulation. The brain stimulator may comprise at least one of an aural and visual stimulator which presents signals to the subject substantially devoid of semantic, music, or object content. The brain stimulation pattern may be adapted to synchronize a brainwave pattern with a modulated waveform. The desired change in sleep-awake state may be brain hemisphere specific. The computer-readable medium may further comprise instructions for modelling a response of the brain activity data to the brain stimulation pattern, and adapting the brain stimulation pattern to optimally achieve the desired change in the sleep-awake state. The computer-readable medium may further comprise instructions for normalizing the brain activity data with respect to a population norm, and accessing a database of stimulation patterns dependent on the population norm. The computer-readable medium may further comprise instructions for denormalizing a stimulation pattern accessed from the database of stimulation patterns, dependent on differences between the brain activity data of the subject and the population norm. The computer-readable instructions may further comprise instructions for introducing a noise pattern having a random component into the brain stimulation pattern.

It is a further object to provide a method of inducing mental states in a subject, corresponding to a predetermined sequence, comprising: determining the predetermined sequence of mental states and a current mental state of the subject; processing at least one record from a database to generate an optimal brain stimulation pattern for achieving a target mental state of the subject based on the predetermined sequence of mental states and a past history of mental states of the subject; and stimulating the subject with at least one of a direct brain stimulator and an indirect sensory-input brain stimulator, selectively dependent on the optimal brain stimulation pattern.

The technology may be used to modify or alter a mental state (e.g., from sleep to waking and vice versa) in a subject. Typically, the starting mental state, brain state, or brainwave pattern is assessed, such as by EEG, MEG, observation, stimulus-response amplitude and/or delay, or the like. Of particular interest in uncontrolled environments are automated mental state assessments, which do not rely on human observation or EEG signals, and rather may be acquired through MEG (e.g., SQID, optically-pumped magnetometer), EMG, MMG (magnetomyogram), mechanical (e.g., accelerometer, gyroscope, etc.), data from physiological sensors (e.g., AKG, heartrate, respiration rate, temperature, galvanic skim potential, etc.), or automated camera sensors.

For example, cortical stimulus-response pathways and reflexes may be exercised automatically, to determine their characteristics on a generally continuous basis. These characteristics may include, for example, a delay between stimulus and the observed central (e.g., EEG) or peripheral response (e.g., EMG, limb accelerometer, video). Typically, the same modality will be used to assess the pre-stimulation state, stimulus response, and post-stimulation state, though this is not a limitation.

In order to change the mental state, a stimulus is applied in a way designed to alter the mental state in a desired manner. A state transition table, or algorithm, may be employed to optimize the transition from a starting mental state to a desired mental state. The stimulus may be provided in an open loop (predetermined stimulus protocol) or closed loop (feedback adapted stimulus protocol), based on observed changes in a monitored variable.

Advantageously, a characteristic delay between application of stimulus and determination of response varies with the brain or mental state. For example, some mental states may lead to increased delay or greater variability in delay, while others may lead to decreased or lower variability. Further, some states may lead to attenuation of response, while others may lead to exaggerated response. In addition, different mental states can be associated with qualitatively different responses. Typically, the mere assessment of the brain or mental state should not itself alter the state, though in some cases the assessment and transition influence may be combined. For example, in seeking to assist in achieving a deep sleep state, excitation that disturbs sleep is contraindicated.

In cases where a brainwave pattern is itself determined by EEG (which may be limited to relatively controlled environments), brainwaves representing that pattern represent coherent firing of an ensemble of neurons, defining a phase. One way to change the state is to advance or retard the triggering of the neuronal excitation, which can be a direct or indirect excitation or inhibition, caused, for example, by electrical, magnetic, mechanical, or sensory stimulation. This stimulation may be time-synchronized with the detected (e.g., by EEG) brainwaves, for example with a phase lead or lag with respect to the detected pattern. Further, the excitation can steer the brainwave signal by continually advancing to a desired state, which through the continual phase rotation represents a different frequency. After the desired new state is achieved, the stimulus may cease, or be maintained in a phase-locked manner to hold the desired state.

A predictive model may be used to determine the current mental state, optimal transition to a desired mental state, when the subject has achieved the desired mental state, and how to maintain the desired mental state. The desired mental state itself may represent a dynamic sequence (e.g., stage 1 ⇒stage 2 ⇒stage 3, etc.), such that the subject's mental state is held for a desired period in a defined condition. Accordingly, the stimulus may be time-synchronized with respect to the measured brainwave pattern.

Direct measurement or determination of brainwaves or their phase relationships is not necessarily required. Rather, the system may determine tremor or reflex patterns. Typically, the reflex patterns of interest involve central pathways, and more preferably brain reflex pathways, and not spinal cord mediated reflexes, which are less dependent on instantaneous brain state. The central reflex patterns can reflect a time delay between stimulation and motor response, an amplitude of motor response, a distribution of response through various afferent pathways, variability of response, tremor or other modulation of motor activity, etc. Combinations of these characteristics may be employed, and different subsets may be employed at different times or to reflect different states. Similar to evoked potentials, the stimulus may be any sense, especially sight, sound, touch/proprioception/pain/etc., though the other senses, such as taste, smell, balance, etc., may also be exercised. A direct electrical or magnetic excitation is also possible. As discussed, the response may be determined through EEG, MEG, or peripheral afferent pathways.

A further object provides a system and method for enhancing deep non-REM sleep, comprising statistically separating slow-wave sleep components from acquired brainwave patterns; defining a stimulation pattern based on the statistically separating slow-wave sleep components; and stimulating a subject with the defined stimulation pattern. The neurological stimulator comprises a memory configured to store acquired brainwave patterns; at least one processor configured to: statistically separate slow-wave non-REM sleep components from the acquired brainwave patterns; and define a brain stimulation pattern based on the statistically separating slow-wave non-REM deep sleep components; and an output signal generator configured to defined brain stimulation pattern.

A still further object provides a system and method for enhancing deep sleep, comprising: extracting brainwave patterns representing a deep sleep state comprising slow wave sleep, from indigenous brain activity EEG recordings of at least one subject; processing the extracted brainwave patterns using a statistical processing algorithm to separate slow wave sleep components from the indigenous brain activity EEG recordings of the at least one subject; inverting the processed extracted brainwave patterns; and stimulating a subject with the inverted processed extracted brainwave patterns. The corresponding system for enhancing deep sleep comprises a memory configured to store brainwave patterns representing a deep sleep state comprising slow wave sleep, from indigenous brain activity EEG recordings of at least one subject; at least one processor configured to process the extracted brainwave patterns using a statistical processing algorithm to separate slow wave sleep components from the indigenous brain activity EEG recordings of the at least one subject; and a stimulator, configured to generate a stimulation signal based on the processed extracted brainwave patterns. The stimulator may comprise a transcranial alternating current electrical stimulator. In order to format the signal for stimulating the brain, it may be inverted.

Another object provides a method of inducing a desired mental arousal state in a second subject comprising: determining brain activity patterns of a first subject who has a respective mental arousal state; and inducing a corresponding mental arousal state in the second subject by stimulation of the second subject with the determined brain activity patterns of the first subject. The desired mental arousal state may be, e.g., sleep or awake. The determining may comprise determining at least one of a magetoencephalographic activity and an encephalographic activity. The stimulation of the second subject with the determined brain activity may comprise at least one of visual and auditory stimulation of the second subject according to a frequency-dependent brainwave pattern of the first subject. The desired mental arousal state may comprise a sequence of mental states comprising at least one sleep cycle. The stimulation may be selectively responsive to a determined mental state of the second subject prior to or during the stimulating. The stimulation may be provided to the second subject contingent on a predicate mental state of the second subject.

A further object provides a method of replicating a desired mental state of a first subject in a second subject comprising: identifying a mental state of the first subject; capturing a mental state of the first subject by recording brain activity patterns; saving the brain activity patterns in a non-volatile memory; retrieving the brain activity patterns from the non-volatile memory; and replicating the desired mental state of the first subject in the second subject by inducing the brain activity patterns in the second subject. The desired mental state may be one of a sleeping state and a waking state. The mental state of the first subject may be identified by automated brain activity classification, and the brain activity patterns are recorded as at least one of a magetoencephalographic activity and an encephalographic activity. The brain activity patterns may be recorded in the non-volatile memory as a set of compressed waveforms which retain frequency and phase relationship features of a plurality of signal acquisition channels. The replicating of the desired mental state of the first subject in the second subject by inducing the brain activity patterns in the second subject may comprise at least one of visual and aural stimulation of the second subject, selectively dependent on a determined brain activity patterns of the second subject prior to or contemporaneously with the at least one of visual and aural stimulation.

It is a still further object of provide a system for replicating a desired mental state of a first subject in a second subject comprising: a non-volatile digital data storage medium configured to store data representing a frequency and phase pattern of a plurality of channels of brainwaves of the first subject; a stimulator configured to induce a brainwave pattern in the second subject which emulates a mental state of the first subject when the brainwaves of the first subject were acquired; a sensor configured to determine a brainwave pattern of the second subject concurrently with stimulation by the stimulator; and a control, configured to read the non-volatile memory, and control the stimulator selectively dependent on the stored data and the determined brainwave pattern of the second subject. The mental state may be a mental arousal state, having a range comprising sleep and awake. The stored data may be derived from at least one of a magetoencephalographic sensor and an encephalographic sensor. The stimulator may be configured to provide at least one of visual and auditory stimulation of the second subject according to a frequency-dependent brainwave pattern of the brainwaves of the first subject. The sensor may be configured to determine a mental state of the second subject during stimulation. The control may be configured to control the stimulator to induce in the second subject a sequence of mental states comprising at least one sleep cycle. The stimulation may be provided to the second subject contingent on a predicate mental state of the second subject. Normalization of brain activity information may be spatial and/or temporal.

BRIEF DESCRIPTION OF THE DRAWINGS

The detailed description is described with reference to the accompanying figures. In the figures, the left-most digit(s) of a reference number identifies the figure in which the reference number first appears. The use of the same reference number in different figures indicates similar or identical items.

DETAILED DESCRIPTION OF THE PREFERRED EMBODIMENTS

Hereinafter, embodiments of the present disclosure will be described in detail with reference to the accompanying drawings so that the present disclosure may be readily implemented by those skilled in the art. However, it is to be noted that the present disclosure is not limited to the embodiments but can be embodied in various other ways.

Figure 1:
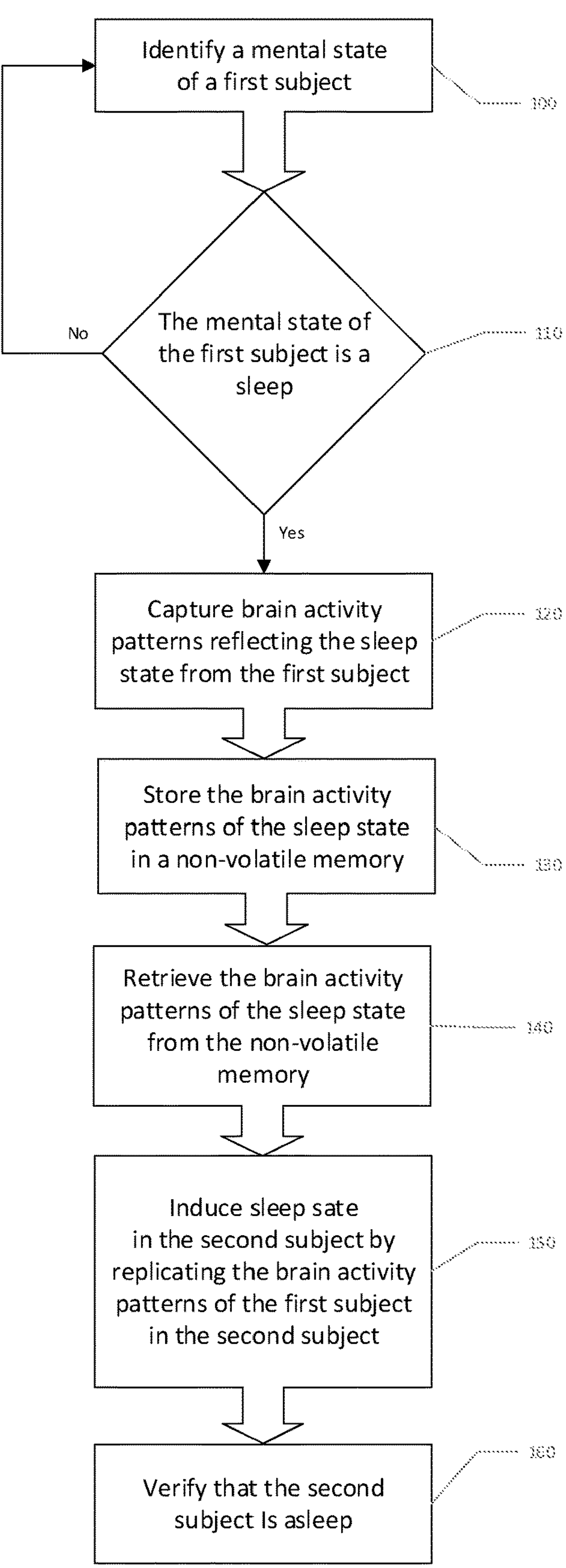
FIG. 1 shows a flowchart according to one embodiment of the invention illustrating a process of replicating a sleep state from one subject to another subject.

FIG. 1 shows a flowchart of a first embodiment according to the present invention. A first subject (donor), having a mental state, is interrogated, observed or sensed, to determine or identify his or her mental state 100. The first subject is typically human, though this is not a limit of the technology and the subject may be an animal. In this embodiment the process seeks to identify a characteristic sleep pattern, and therefore the mental state of the first subject is monitored until a sleep state occurs 110. When the first subject (donor) is asleep, brain activity patterns reflecting or characterizing the sleep state are captured 120. This step may be done by recording EEG or MEG of the first subject (donor), and the brain activity patterns are stored in a non-volatile memory 130. These stored patterns may be optionally processed, statistically aggregated, analyzed for perturbations or anomalies, filtered, compressed, etc. Stages of sleep may be determined. It is noted that the brain activity patterns change over time during sleep from stage to stage, and therefore the stored patterns may encompass one or more stages of sleep.

The stored data from the first subject (donor) is then used to induce sleep in a second subject (a recipient—also typically a human, but may be an animal) by replicating the brain activity patterns (or sequences of brain activity patterns) of the first subject (donor) in the second subject (recipient) 150. The replication of brain activity patterns, dependent on the stored patterns, typically seeks to stimulate or induce the brain of the second subject (recipient) by modulating a stimulus (or several stimuli) in a manner synchronized with the frequency, phase and/or waveform pattern represented in the brain activity patterns of the first subject (donor) in the sleep state. Typically, when the second subject (recipient) achieves the sleep state 160 (assuming that the first subject and second subject are physiologically compatible-a donor and a recipient should both be either human, or animals), the brain activity patterns of the first and second subject will be corresponding.

According to the present technology, the modulation of stimulation, which is, for example, a transcranial direct current stimulation (tDCS), whose waveform is modulated to correspond to the raw or processed brainwave pattern of the first subject (donor) for the brain region associated with the stimulation electrode.

For example, the brain activity pattern of the first subject (donor) is measured by EEG electrodes. In a sleep state, it may assume various wave patterns, over the range <1 Hz to about 25 Hz, which vary in amplitude, frequency, spatial location, and relative phase. For example, the first stage of sleep is initially dominated by alpha brainwaves with the frequency of 8 Hz to 13 Hz. Typically, brain activity pattern measurement from the first subject (donor) has a higher spatial resolution, e.g., 64 or 128 electrode EEGs, than the stimulator for the second subject (recipient), and the stimulus electrodes tends to be larger than the EEG electrode. The stimulus for the second subject (recipient) is therefore processed using a dimensionality (or spatial) reduction algorithm to account for these differences, which will tend to filter the stimulus signal. For example, tDCS stimulation typically uses minimum of two electrodes and maximum of 32 electrodes, requiring dimensionality reduction. The tDCS stimulation will tend to depolarize or hyperpolarize the resting membrane potential of cortical cells proximate to the electrode, and the treatment may modulate ion channels or cellular excitability. tDCS is typically applied at an intensity that avoids direct stimulation of action potentials of the cortical neurons. Therefore, by applying this stimulus modulated with the brain activity of the first subject (donor), the second subject (recipient) is made susceptible to synchronization with the brain activity pattern of the first subject (donor). For example, by temporally modulating the polarization level of the cells near the electrode, the cells will better couple to excitation stimuli in the brain of the second subject (recipient) having the characteristics of the brain activity pattern of the first subject (donor).

It is noted that stimulation distinct from tDCS may be used, such as pulsed electromagnetic fields (PEMF), tACS, visual stimulation, auditory stimulation, inertial simulation, etc. In any case, the goal is to couple the brain activity pattern of the second subject with the sleep pattern brain activity pattern of the first subject, to facilitate sleep in the second subject.

It will be understood by a person skilled in the art that any number of transcranial electric stimulation (TES) or transcranial magnetic stimulation (TMS). For example, TES may be transcranial direct current stimulation (tDCS), high definition transcranial direct current stimulation (HD-tDCS), transcranial oscillating direct current stimulation (osc-tDCS), transcranial direct current pulsing stimulation ("electrosleep"), transcranial alternating stimulation (tACS), as well as other less popular types of TES. In extreme cases (such as with Parkinson and epilepsy patients), the electric current stimulation may be applied to the electrodes implanted in the brain. Transcranial magnetic stimulation (TMS) may also be used.

Aside from TES or IMS, the donor's indigenous brainwaves may be modulated on light, sound, vibrations or any number of other stimuli amenable to frequency modulation. For example, donor's brainwaves may be modulated on ambient light, on binaural beats, or isochronic tones. The verification that the recipient has achieved the desired sleep state may optionally be done by visual observation, by EEG, EKG, measuring heart and/or respiration rate, body temperature or any number of other physiological parameters that will be well understood by a person skilled in the art. These measurements should be, preferably, done automatically via biosensors.

Figure 2:
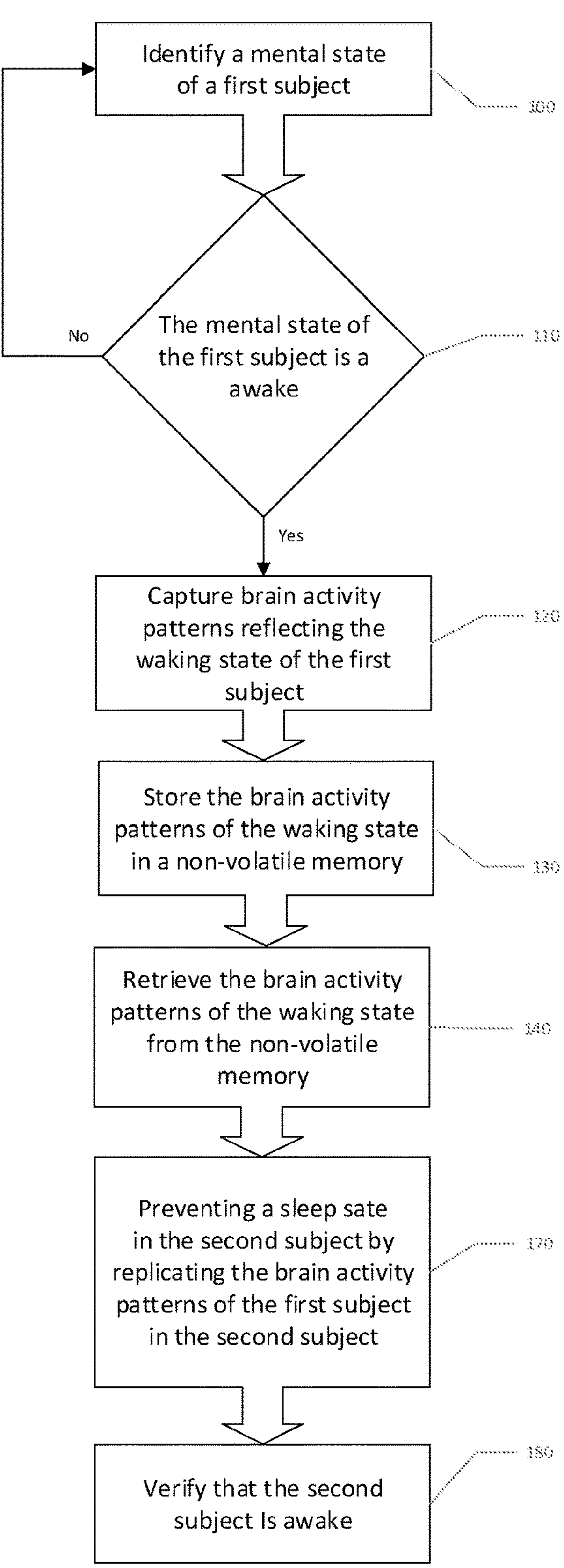
FIG. 2 shows a flowchart according to one embodiment of the invention illustrating a process of replicating a waking stage from one subject to another subject by recording and replicating brainwaves associated with the waking stage, according to one embodiment of the invention.

FIG. 2 shows a flowchart of the second embodiment according to the present invention. A first subject (donor), having a mental state, is interrogated, observed or sensed, to determine or identify of his or her mental state 100. The first subject is typically human, though this is not a limit of the invention (which equally applies to any animal). In this embodiment the interrogation seeks to identify a characteristic alert/awake pattern, and therefore the mental state of the first subject is monitored until an alert state occurs 111. When the first subject (donor) is awake, brain activity patterns reflecting or characterizing the waking state are captured 120, and stored in a non-volatile memory 130. For example, one may seek to capture the patterns that represent awakening, and therefore the monitoring commences on a sleeping subject. These stored patterns may be optionally processed, statistically aggregated, analyzed for perturbations or anomalies, filtered, compressed, etc. Stages of awakening may be determined. It is noted that the brain activity patterns change over time during awakening, and therefore the stored patterns may encompass one or more stages of the waking process.

The stored data from the first subject (donor) is then retrieved from the non-volatile memory 140 and used to "transplant" the state of alertness to prevent sleep, or maintain alertness, in a second subject (a recipient—also typically, but not necessarily, a human) by replicating the awake brain activity patterns of the first subject (donor), or sequences of brain activity patterns, in the second subject (recipient) 170. The replication of brain activity patterns, dependent on the stored patterns, typically seeks to stimulate or induce the brain of the second subject (recipient) by modulating indigenous brainwaves of the donor on a stimulus in a manner synchronized with the frequency, and preferably phase and/or waveform pattern represented in the brain activity patterns of the first subject (donor) in the awake or wakening state. Typically, when the second subject is awake or wakes up, 180, the brain activity patterns of the first and second subject will be corresponding.

Figure 3:
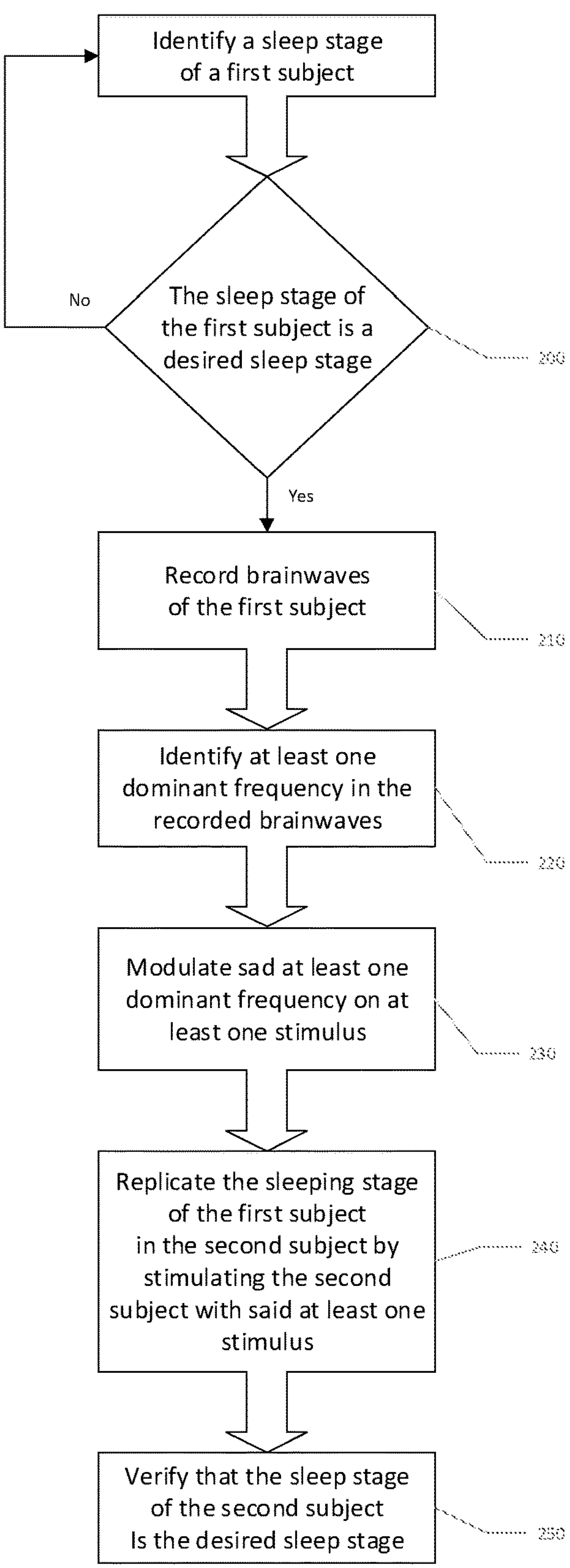
FIG. 3 shows a flowchart according to one embodiment of the invention illustrating a process of replicating a sleep stage from at least one first subject to another subject by recording electroencephalogram (EEG) of said least one first subject, extracting at least one dominant frequency from the EEG and replicating the sleep stage of said at least one first subject in a second subject by stimulating the second subject with stimuli having the dominant frequency associated with the desired sleep stage, according to one embodiment of the invention.

According to the third embodiment, the technology is generalized, as shown in the flowchart of FIG. 3. A first subject (donor), having a mental state, is interrogated, observed or sensed, to determine or identify his or her mental state 190. The mental state of the first subject is monitored until a desired state is achieved 200. When the first subject achieves that state, brain activity patterns reflecting or characterizing the state are captured 210 by, for example, recording EEG or MEG of the first subject, and optionally stored in a non-volatile memory. The brain activity pattern is, e.g., brainwaves (e.g., EEG) 210.

The brainwaves are analyzed using statistical data mining techniques such as principal component analysis (PCA) to determine a set of linearly-uncorrelated variables—principal components. At least one dominant frequency in the recorded brainwaves is identified 220. Optionally, secondary and higher harmonics may be identified as well. It will be well-understood by a person skilled in the art that any number of similar statistical data analysis technics may be used, such as signal processing, independent component analysis, network component analysis, correspondence analysis, multiple correspondence analysis, factor analysis, canonical correlation, functional principal component analysis, independent component analysis, singular spectrum analysis, weighted PCA, sparse PCA, principal geodesic analysis, eigenvector-based multivariate analyses, etc.

The stored data from the first subject is then retrieved, at least the dominant frequency is modulated on at least one stimulus and used to "transplant" the desired mental state of the donor in a second subject (recipient) by seeking to replicate the brain activity patterns of the first subject (donor), or sequences of brain activity patterns, in the second subject (recipient) 240. The second subject (recipient) is then monitored for induction of the desired mental state 250.

Figure 4:
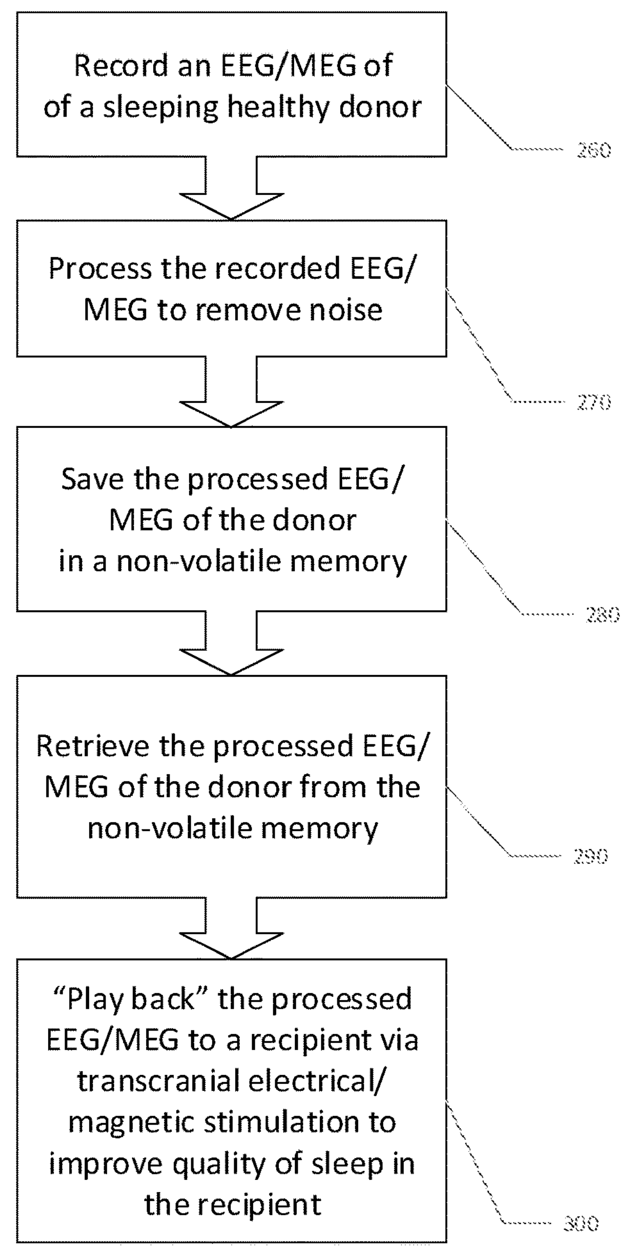
FIG. 4 shows a flowchart according to one embodiment of the invention illustrating a method of improving sleep in a recipient by recording EEG or MEG of a healthy donor and "playing it back" to the recipient via transcranial stimulation.

According to the fourth embodiment, reflected in the flowchart of FIG. 4, an EEG or EMG of a first subject (healthy donor), while in a state of sleep, is recorded 260, optionally processed to remove noise 270, and stored 280. The data may optionally be compressed. The stored data is retrieved 290 and decompressed as necessary. The data is then played back to a second subject (recipient), using transcranial electrical or magnetic stimulation to improve the quality of sleep 300.

Figure 5:
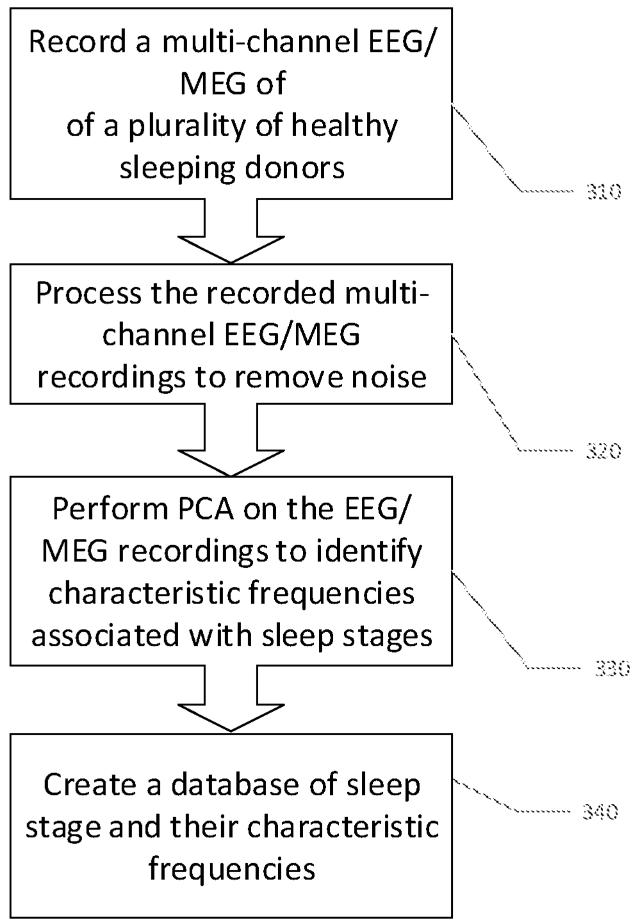
FIG. 5 shows a flowchart according to one embodiment of the invention illustrating creation of a database of sleep stages and their associated frequencies for later brain entrainment.
Figure 6:
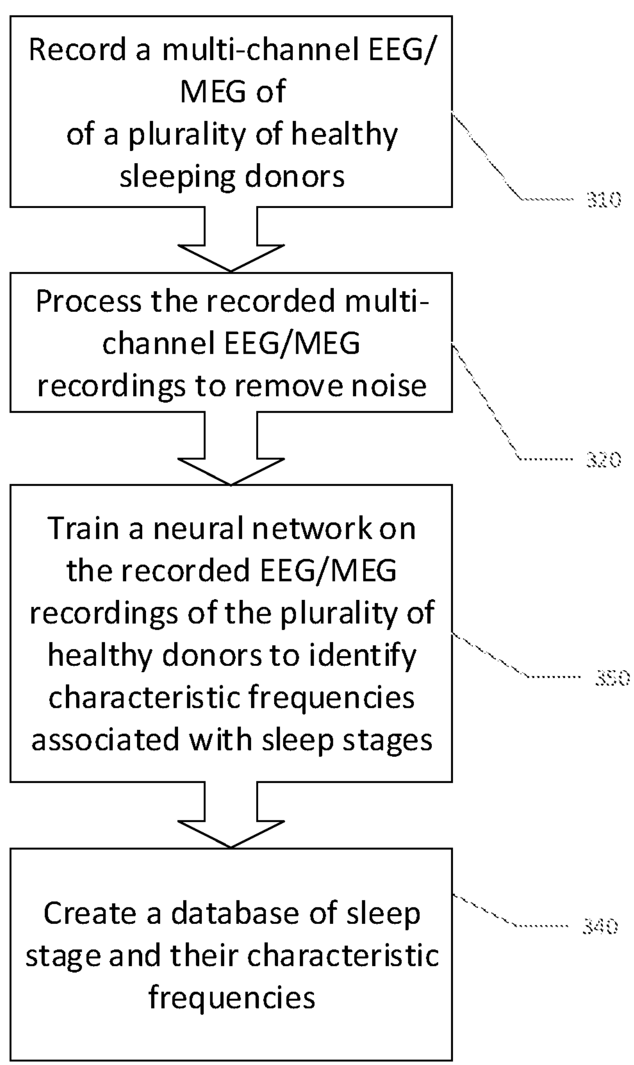
FIG. 6 shows a flowchart according to one embodiment of the invention illustrating using a neural network in the creation of a database of sleep stages and their associated frequencies for later brain entrainment.

According to the fifth embodiment, shown in the flowchart of FIG. 5, a multichannel EEG/EMG of a first subject (donor) is recorded 310, and processed to remove noise (and/or artifacts) and/or compress the data 320. It is optionally stored in a non-volatile memory. PCA analysis is performed on the data to determine characteristic frequencies associated with sleep stages 330. A database is created, storing the recorded EEG/MEG, the associated characteristic frequencies, and corresponding sleep stages, so that a characteristic frequency may be retrieved for any given sleep stage 340. This database can be a relational database or any other type of searchable database as will be readily understood by anyone skilled in the art. According to the sixth embodiment, a multichannel EEG/EMG of a first subject (donor) is recorded 310, and processed to remove noise (and/or artifacts) and/or compress the data 320. It is optionally stored in a non-volatile memory. An artificial neural network is trained on this data to determine characteristic frequencies associated with sleep stages 350. A deep neural network as well as other AI machine learning tools may be used as will be readily understood by a person skilled in the art. A database is created, storing the recording of the EEG/MEG, the associated characteristic frequencies, and corresponding sleep stages, so that a characteristic frequency may be retrieved for any given sleep stage 340.

Figure 7:
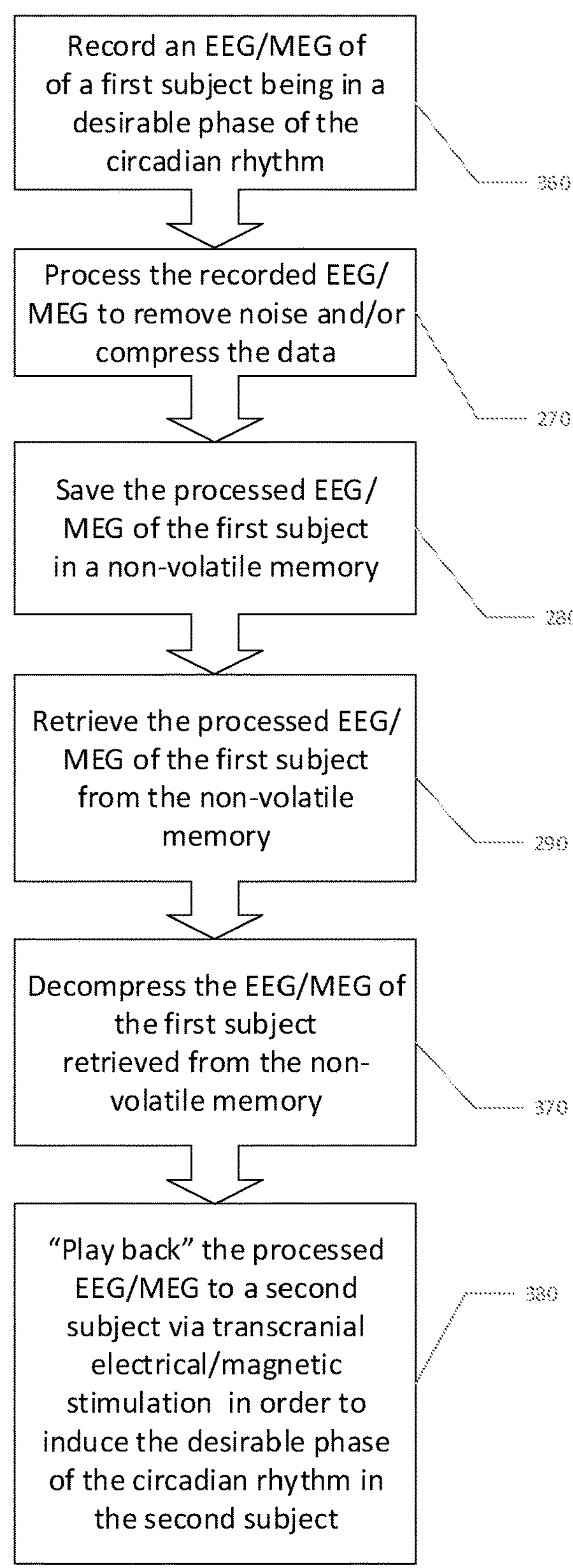
FIG. 7 shows a flowchart according to one embodiment of the invention illustrating a method of recording a mental state of a first subject in a desirable state of the subject's circadian rhythm and transplanting this mental state into another subject to replicated the desirable state of the circadian rhythm.

FIG. 7 shows a flowchart according to a further embodiment of the present invention illustrating a process in which a first subject (donor) is monitored with respect to phases of his or her circadian rhythm with his or her EEG or EMG recorded 360, processed to remove noise (and/or artifacts), and, optionally, compressed 270, and then stored in a non-volatile memory 280. In this case, the stored signals are tagged with the circadian cycle phase, unless only a single phase is captured, or pattern recognition used to identify the cycle stage. The stored data is then retrieved 290, decompressed 370, and played back to a second subject (recipient) 380, using transcranial electrical or magnetic stimulation, or other stimuli, to induce a desired circadian rhythm state. In this case, the technology may also be used to prolong states in the second subject, or hasten transition from one state to another. It may also be used to treat circadian rhythm disorders, by reinforcing healthy or normal circadian rhythm patterns in a second subject with an otherwise abnormal cycle. It will be well-understood by a person skilled in the art that, besides TES or TMS, a donor's circadian rhythms can be modulated on light, sounds, or other signals to be used as stimuli, to stimulate the recipient in order to induce the desired circadian rhythm phase in the recipient.

Figure 8:
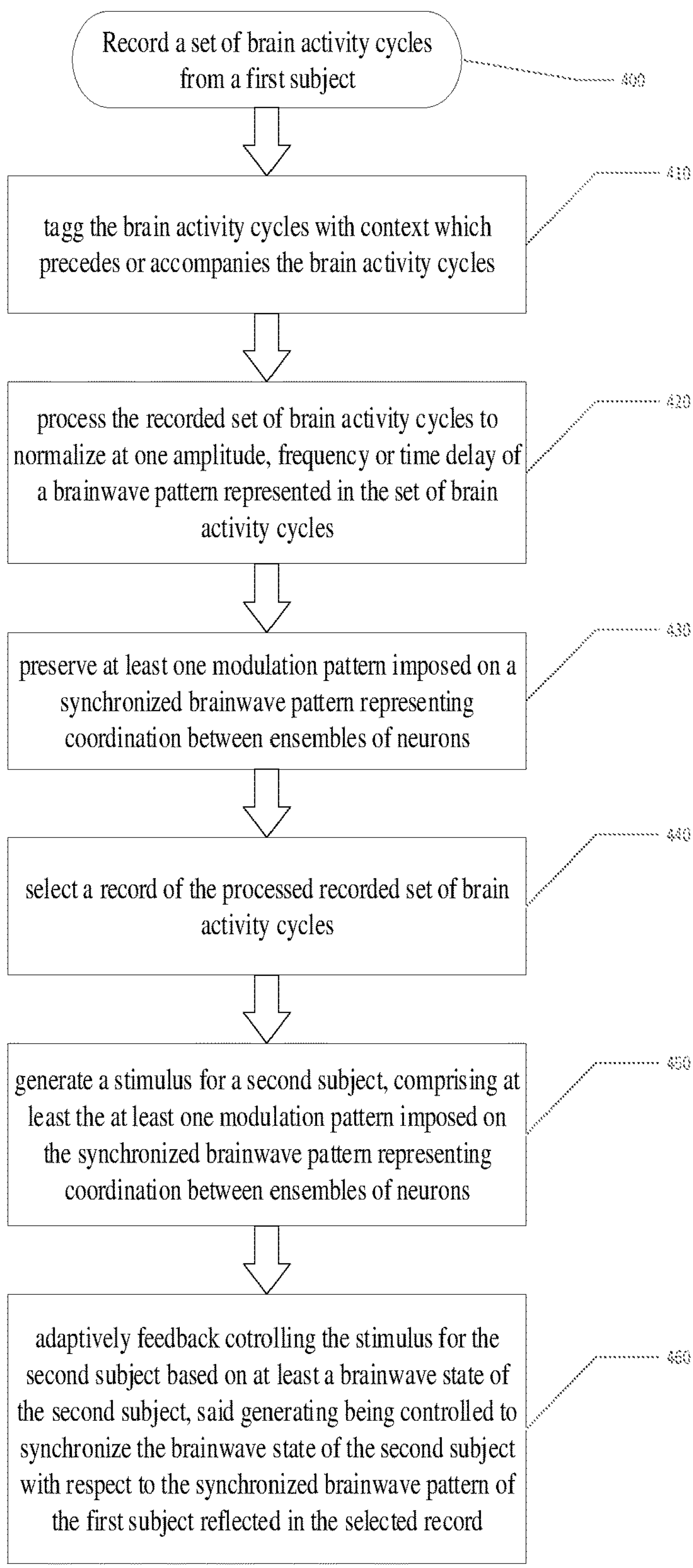
FIG. 8 shows a flowchart according to a further embodiment of the invention.
Figure 9:
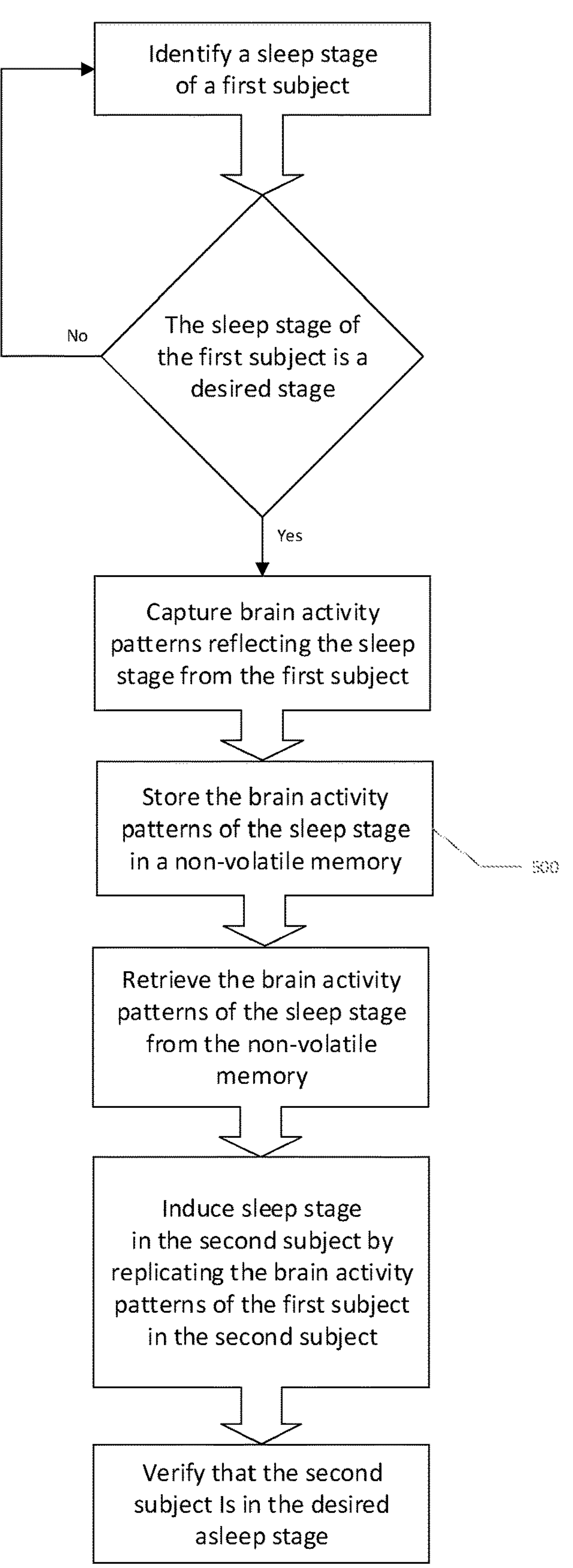
FIG. 9 shows a flowchart according to one embodiment of the invention illustrating a process of replicating a desired sleep stage from one subject to another subject.

FIG. 8 shows a flowchart according to a further embodiment of the present invention illustrating a process of replicating a desired sleep stage from one subject (donor) to another subject (recipient). In general, the sleep stage of the source subject is determined in a traditional manner, which may include brain signal analysis, other biometrics, and/or observation. The data may be acquired 400 over one or more sleep cycles, and during or after different types of environmental conditions or stimulation. For example, various types of music may be played, seeking to entrain a conscious or subconscious rhythm. Lights can flash, and various other sensory stimulation may occur. The brain signal readings are synchronized and tagged with the stimulation parameters 410, so that the stimulation is associated with its respective effect. Similarly, before sleep, the subject may be presented with certain experiences, such that during sleep the memory processing within the brain is dependent on these experiences.

After the various data is acquired from the subject 400, along with information about pre-sleep experience and or context 410, and sensory stimulation during sleep, a memory, database, statistical model, rule-based model is generated, and/or neural network is trained, reflecting the subject (donor). Data may be aggregated from a plurality of subjects (donors), but typically, these are processed for the particular subject before aggregation. Based on single or multiple subject data, a normalization process may occur 420. The normalization may be spatial and/or temporal. For example, the EEG electrodes between sessions or for different subject may be in different locations, leading to a distortion of the multichannel spatial arrangement. Further, head size and shape of different individuals is different, and this needs to be normalized and/or encoded as well. The size and shape of the head/skull and/or brain, may also lead to temporal differences in the signals, such as characteristic time delays, resonant or characteristic frequencies, etc.

One way to account for these effects is through use of a time-space transform, such as a wavelet-type transform. It is noted that, in a corresponding way that statistical processes are subject to frequency decomposition analysis through Fourier transforms, they are also subject to time-frequency decomposition through wavelet transforms. Typically, the wavelet transform is a discrete wavelet transform (DWT), though more complex and less regular transforms may be employed. As discussed above, principal component analysis (PCA) and spatial PCA may be used to analyze signals, presuming linearity (linear superposition) and statistical independence of components. However, these presumptions technically do not apply to brainwave data, and practically, one would normally expect interaction between brain wave components (non-independence) and lack of linearity (since "neural networks" by their nature are non-linear), defeating use of PCA or spatial PCA unmodified. However, a field of nonlinear dimensionality reduction provides various techniques to permit corresponding analyses under presumptions of non-linearity and non-independence. See, en.wikipedia.org/wiki/Nonlinear_dimensionality_reduction, www.image.ucar.edu/pub/toyIV/monahan_5_16.pdf (An Introduction to Nonlinear Principal Component Analysis, Adam Monahan), Nonlinear PCA toolbox for MATLAB (www.nlpca.org), Nonlinear PCA (www.comp.nus.edu.sg/~cs5240/lecture/nonlinear-pca.pdf), Nonlinear Principal Components Analysis: Introduction and Application (openaccess.leidenuniv.nl/bitstream/handle/1887/12386/Chapter2.pdf?sequence=10, 2007), Nonlinear Principal Component Analysis: Neural Network Models and Applications (pdfs.semanticscholar.org/9d31/23542031a227d2f4c4602066d8ebcaeb7a.pdf), Karl Friston, "Nonlinear PCA: characterizing interactions between modes of brain activity" (www.fil.ion.ucl.ac.uk/~karl/Nonlinear PCA.pdf, 2000), Howard et al., "Distinct Variation Pattern Discovery Using Alternating Nonlinear Principal Component Analysis", IEEE Trans Neural Network Learn Syst. 2018 January; 29(1):156-166. doi: 10.1109/TNNLS.2016.2616145. Epub 2016 Oct. 26 (www.ncbi.nlm.nih.gov/pubmed/27810837); Jolliffe, I. T., "Principal Component Analysis, Second Edition", Springer 2002, cda.psych.uiucedu/statistical_learning_course/Jolliffe I. Principal Component Analysis (2ed., Springer, 2002) (518s)_ MVsa_.pdf, Stone, James V. "Blind source separation using temporal predictability." Neural computation 13, no. 7 (2001):1559-1574; Barros, Allan Kardec, and Andrzej Cichocki. "Extraction of specific signals with temporal structure." Neural computation 13, no. 9 (2001): 1995-2003; Lee, Soo-Young. "Blind source separation and independent component analysis: A review." Neural Information Processing-Letters and Reviews 6, no. 1 (2005):1-57; Hyvärinen, Aapo, and Patrik Hoyer. "Emergence of phase-and shift-invariant features by decomposition of natural images into independent feature subspaces." Neural computation 12, no. 7 (2000): 1705-1720; Wahlund, Björn, Wlodzimierz Klonowski, Paweł Stepien, Robert Stepien, Tatiana von Rosen, and Dietrich von Rosen. "EEG data, fractal dimension and multivariate statistics." Journal of Computer Science and Engineering 3, no. 1 (2010): 10-14; Yu, Xianchuan, Dan Hu, and Jindong Xu. Blind source separation: theory and applications. John Wiley & Sons, 2013; Parida, Shantipriya, Satchidananda Dehuri, and Sung-Bae Cho. "Machine Learning Approaches for Cognitive State Classification and Brain Activity Prediction: A Survey." Current Bioinformatics 10, no. 4 (2015): 344-359; Friston, Karl J., Andrew P. Holmes, Keith J. Worsley, J-P. Poline, Chris D. Frith, and Richard S J Frackowiak. "Statistical parametric maps in functional imaging: a general linear approach." Human brain mapping 2, no. 4 (1994):189-210; Wang, Yan, Matthew T. Sutherland, Lori L. Sanfratello, and Akaysha C. Tang. "Single-trial classification of ERPS using second-order blind identification (SOB')." In Machine Learning and Cybernetics, 2004. Proceedings of 2004 International Conference on, vol. 7, pp. 4246-4251. IEEE, 2004; Jutten, Christian, and Massoud Babaie-Zadeh. "Source separation: Principles, current advances and applications." IAR Annu Meet Nancy Fr 110 (2006); Saproo, Sameer, Victor Shih, David C. Jangraw, and Paul Sajda. "Neural mechanisms underlying catastrophic failure in human-machine interaction during aerial navigation." Journal of neural engineering 13, no. 6 (2016): 066005; Valente, Giancarlo. "Separazione cieca di sorgenti in ambienti reali: nuovi algoritmi, applicazioni e implementazioni." (2006); Sapienza, La. "Blind Source Separation in real-world environments: new algorithms, applications and implementations."; Ewald, Arne. "Novel multivariate data analysis techniques to determine functionally connected networks within the brain from EEG or MEG data." (2014); Friston, Karl J. "Basic concepts and overview." SPMcourse, Short course; Crainiceanu, Ciprian M., Ana-Maria Staicu, Shubankar Ray, and Naresh Punjabi. "Statistical inference on the difference in the means of two correlated functional processes: an application to sleep EEG power spectra." Johns Hopkins University, Dept. of Biostatistics Working Papers (2011): 225; Konar, Amit, and Aruna Chakraborty. Emotion recognition: A pattern analysis approach. John Wiley & Sons, 2014; Kohl, Florian. "Blind separation of dependent source signals for MEG sensory stimulation experiments." (2013); Onken, Arno, Jian K. Liu, P P Chamanthi R. Karunasekara, Ioannis Delis, Tim Gollisch, and Stefano Panzeri. "Using matrix and tensor factorizations for the single-trial analysis of population spike trains." PLoS computational biology 12, no. 11 (2016): e1005189; Tressoldi, Patrizio, Luciano Pederzoli, Marco Bilucaglia, Patrizio Caini, Pasquale Fedele, Alessandro Ferrini, Simone Melloni, Diana Richeldi, Florentine Richeldi, and Agostino Accardo. "Brain-to-Brain (Mind-to-Mind) Interaction at Distance: A Confirmatory Study." (2014). f1000researchdata.s3.amazonaws.com/manuscripts/5914/

5adbf847-787a-4fc1-ac04-2e1cd61ca972_4336_-_patrizio_tressoldi_v3.pdf?doi=10.12688/f1000research.4336.3; Tsiaparas, Nikolaos N. "Wavelet analysis in coherence estimation of electroencephalographic signals in children for the detection of dyslexia-related abnormalities." PhD diss., 2006.

Therefore, statistical approaches are available for separating EEG signals from other signals, and for analyzing components of EEG signals themselves. According to the present invention, various components that might be considered noise in other contexts, e.g., according to prior technologies, such as a modulation pattern of a brainwave, are preserved. Likewise, interactions and characteristic delays between significant brainwave events are preserved. This information may be stored either integrated with the brainwave pattern in which it occurs, or as a separated modulation pattern that can then be recombined with an unmodulated brainwave pattern to approximate the original subject.

According to the present technology, lossy "perceptual" encoding (i.e., functionally optimized with respect to subjective response) of the brainwaves may be employed to process, store and communicate the brainwave information. In a testing scenario, the "perceptual" features may be tested, so that important information is preserved over information that does not strongly correspond to the effective signal. Thus, while one might not know a priori which components represent useful information, a genetic algorithm may empirically determine which features or data reduction algorithms or parameter sets optimize retention of useful information vs. information efficiency. It is noted that subjects may differ in their response to signal components, and therefore the "perceptual" encoding may be subjective with respect to the recipient. On the other hand, different donors may have different information patterns, and therefore each donor may also require individual processing. As a result, pairs of donor and recipient may require optimization, to ensure accurate and efficient communication of the relevant information. According to the present invention, sleep/wake mental states and their corresponding patterns are sought to be transferred. In the recipient, these patterns have characteristic brainwave patterns. Thus, the donor may be used, under a variety of alternate processing schemes, to stimulate the recipient, and the sleep/wake response of the recipient determined based on objective criteria, such as resulting brainwave patterns or expert observer reports, or subjective criteria, such as recipient self-reporting, survey or feedback. Thus, after a training period, an optimized processing of the donor, which may include filtering, dominant frequency resynthesis, feature extraction, etc., may be employed, which is optimized for both donor and recipient. In other cases, the donor characteristics may be sufficiently normalized, that only recipient characteristics need be compensated. In a trivial case, there is only one exemplar donor, and the signal is oversampled and losslessly recorded, leaving only recipient variation as a significant factor.

Because dominant frequencies tend to have low information content (as compared to the modulation of these frequencies and interrelation of various sources within the brain), one efficient way to encode the main frequencies is by location, frequency, phase, and amplitude. The modulation of a wave may also be represented as a set of parameters. By decomposing the brainwaves according to functional attributes, it becomes possible, during stimulation, to modify the sequence of "events" from the donor, so that the recipient need not experience the same events, in the same order, and in the same duration, as the donor. Rather, a high-level control may select states, dwell times, and transitions between states, based on classified patterns of the donor brainwaves. The extraction and analysis of the brainwaves of the donors, and response of the recipient, may be performed using statistical processes, such as principal components analysis (PCA), independent component analysis (ICA), and related techniques; clustering, classification, dimensionality reduction and related techniques; neural networks and other known technologies. These algorithms may be implemented on general purpose CPUs, array processors such as GPUs, and other technologies.

In practice, a brainwave pattern of the first subject may be analyzed by a PCA technique that respects the non-linearity and non-independence of the brainwave signals, to extract the major cyclic components, their respective modulation patterns, and their respective interrelation. The major cyclic components may be resynthesized by a waveform synthesizer, and thus may be efficiently coded. Further, a waveform synthesizer may modify frequencies or relationships of components from the donor based on normalization and recipient characteristic parameters. For example, the brain of the second subject (recipient) may have characteristic classified brainwave frequencies 3% lower than the donor (or each type of wave may be separately parameterized), and therefore the resynthesis may take this difference into account. The modulation patterns and interrelations may then be reimposed onto the resynthesized patterns. The normalization of the modulation patterns and interrelations may be distinct from the underlying major cyclic components, and this correction may also be made, and the normalized modulation patterns and interrelations included in the resynthesis. If the temporal modifications are not equal, the modulation patterns and interrelations may be decimated or interpolated to provide a correct continuous time sequence of the stimulator. The stimulator may include one or more stimulation channels, which may be implemented as electrical, magnetic, auditory, visual, tactile, or other stimulus, and/or combinations.

The stimulator is preferably feedback controlled. The feedback may relate to the brainwave pattern of the recipient, and/or context or ancillary biometric basis. For example, if the second subject (recipient) begins to awaken from sleep, which differs from the first subject (donor) sleep pattern, then the stimulator may resynchronize based on this finding. That is, the stimulator control will enter a mode corresponding to the actual state of the recipient, and seek to guide the recipient to a desired state from a current state, using the available range and set of stimulation parameters. The feedback may also be used to tune the stimulator, to minimize error from a predicted or desired state of the recipient subject based on the prior and current stimulation.

The control for the stimulator is preferably adaptive, and may employ a genetic algorithm to improve performance over time. For example, if there are multiple first subjects (donors), the second subject (recipient) may be matched with those donors from whose brainwave signals (or algorithmically modified versions thereof) the predicted response in the recipient is best, and distinguished from those donors from whose brainwave signals the predicted response in the recipient subject poorly corresponds. Similarly, if the donors have brainwave patterns determined over a range of time and context and stored in a database, the selection of alternates from the database may be optimized to ensure best correspondence of the recipient subject to the desired response.

It is noted that a resynthesizer-based stimulator is not required, if a signal pattern from a donor is available that properly corresponds to the recipient and permits a sufficiently low error between the desired response and the actual response. For example, if a donor and a recipient are the same subject at different times, a large database may be unnecessary, and the stimulation signal may be a minimally processed recording of the same subject at an earlier time. Likewise, in some cases, a deviation is tolerable, and an exemplar signal may be emitted, with relatively slow periodic correction. For example, a sleep signal may be derived from a single subject, and replayed with a periodicity of 90 minutes or 180 minutes, such as a light or sound signal, which may be useful in a dormitory setting, where individual feedback is unavailable or unhelpful.

In some cases, it is useful to provide a stimulator and feedback-based controller on the donor. This will better match the conditions of the donor and recipient, and further allow determination of not only the brainwave pattern of the donor, but also responsivity of the donor to the feedback. One difference between the donors and the recipients is that in the donor, the natural sleep pattern is sought to be maintained and not interrupted. Thus, the adaptive multi-subject database may include data records from all subject, whether selected ab initio as a useful exemplar or not. Therefore, the issue is whether a predictable and useful response can be induced in the recipient from the database record, and if so, that record may be employed. If the record would produce an unpredictable result, or a non-useful result, the use of that record should be avoided. The predictability and usefulness of the responses may be determined by a genetic algorithm, or other parameter-space searching technology.

Extending the sleep signal illumination example, an illuminator (e.g., red LED lightbulb) may have an intensity modulated based on a donors' brainwave pattern. The illuminator may have a flash memory module with tens or hundreds of different brainwave patterns available. The illuminator may further include a sensor, such as a camera or non-imaging optical or infrared sensor, and speech control, similar to Amazon Alexa. The illuminator may also include an associated speaker, to play synchronized sounds or music. When a sleep cycle is commenced, the illuminator begins displaying (and playing and associated audio) the brainwave pattern as a program, seeking to induce a predetermined sleep pattern. The sensors may be used to determine whether the recipient is in the predicted sleep state based on the program. If the recipient has a sleep state that deviates from the program, then the program may be reset to a portion that corresponds to the actual state of the recipient, or reset to a guiding state that seeks to guide the sleep state of the recipient back to the desired program. If the target subject cannot be efficiently synchronized or guided, then the illuminator may adopt a different source subject brainwave pattern. In this case, no electrical stimulation or electrical feedback is employed, and the entire operation may be non-contact.

Figure 10:
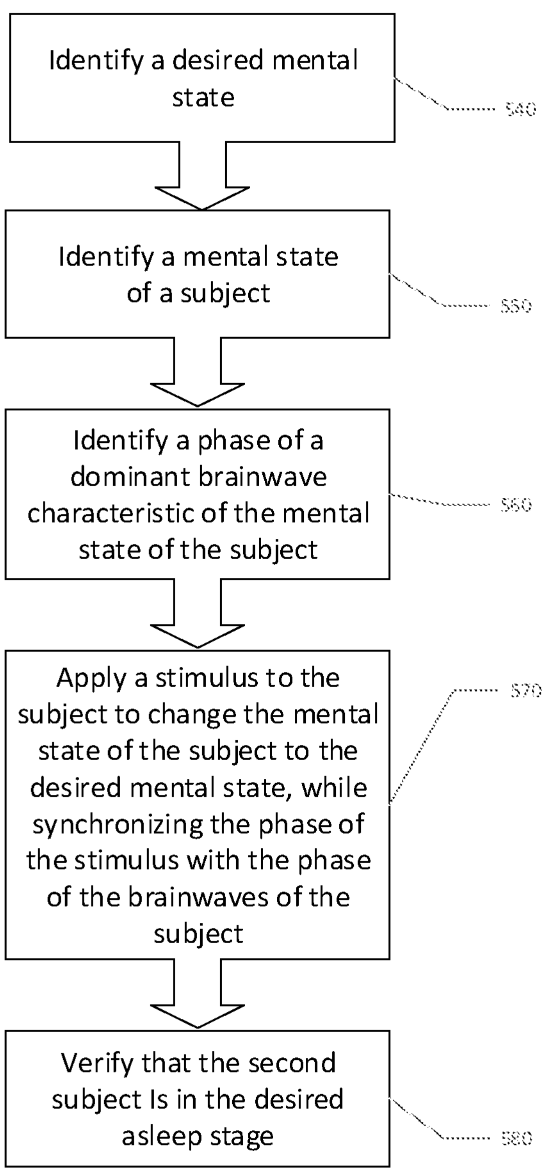
FIG. 10 shows a flowchart according to one embodiment of the invention illustrating a process of transferring a dominant brainwave with synchronized phase from a desired sleep stage from one subject to another subject.

As shown in FIG. 10, a human brain state or mental state in a subject is modified or altered. In some implementations, a current brainwave pattern of the subject, a phase of a characteristic wave of the current brainwave pattern of the subject, a characteristic timing of a stimulus-response dependent on the mental state, or temporal relationships in monitored neurological or motor patterns of the subject is determined. A desired change in the current brain wave pattern of the subject is determined or defined. A stimulus is applied, e.g., electrical, magnetic, acoustic or ultrasound, sensory, etc., which can be for determining the current state, changing the state, or both. For example, a characteristic timing of a stimulus-response dependent on the mental state may be extracted, or temporal relationships in monitored neurological or motor patterns of the subject determined. The stimulus may be asynchronous, or time-synchronized with respect to the phase state, or dependent on at least the determined temporal relationships. In a closed-loop excitation, the brain wave pattern of the subject after at least one stimulus is monitored or the response parameters, e.g., characteristic timing measured or assessed. The stimulus may be controlled dependent on the observed or monitored changes, indicative of an effective alteration or modification of the brain state or mental state in the subject.

Through the whole document, the term "connected to" or "coupled to" that is used to designate a connection or coupling of one element to another element includes both a case that an element is "directly connected or coupled to" another element and a case that an element is "electronically connected or coupled to" another element via still another element. Further, it is to be understood that the term "comprises or includes" and/or "comprising or including" used in the document means that one or more other components, steps, operation and/or existence or addition of elements are not excluded in addition to the described components, steps, operation and/or elements unless context dictates otherwise.

Through the whole document, the term "unit" or "module" includes a unit implemented by hardware or software and a unit implemented by both of them. One unit may be implemented by two or more pieces of hardware, and two or more units may be implemented by one piece of hardware.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

In this description, several preferred embodiments were discussed. Persons skilled in the art will, undoubtedly, have other ideas as to how the systems and methods described herein may be used. It is understood that this broad invention is not limited to the embodiments discussed herein. Rather, the invention is limited only by the following claims. The aspects of the invention are intended to be separable and may be implemented in combination, sub-combination, and with various permutations of embodiments. Therefore, the various disclosure herein, including that which is represented by acknowledged prior art, may be combined, sub-combined and permuted in accordance with the teachings hereof, without departing from the spirit and scope of the invention. All references and information sources cited herein are expressly incorporated herein by reference in their entirety.

What is claimed is:

1. A method of inducing a mental state in a subject comprising:

determining brainwave activity patterns of a human donor in the mental state;

processing the brainwave activity patterns with an automated processor to determine parameters of a modulation pattern of the brainwave activity patterns bearing information;

storing the parameters in a memory;

stimulating the subject with a sensory stimulus selected from the group consisting of one or more of auditory, visual, and haptic, the sensory stimulus being selectively modulated dependent on the stored parameters, wherein the parameters are stored prior to the stimulation, and the sensory stimulus comprises the information.

2. The method according to claim 1, wherein the parameters comprise a frequency and phase of the modulation pattern, and the sensory stimulus has characteristics corresponding to the frequency and phase.

3. The method according to claim 1, further comprising classifying the brainwave activity patterns with at least one of a statistical classifier and a neural network.

4. The method according to claim 1, wherein the mental state comprises a sleep stage.

5. The method according to claim 1, wherein the brainwave activity patterns are electroencephalographic patterns.

6. The method according to claim 1, wherein the sensory stimulation comprises auditory stimulation of the subject with binaural beats to entrain brainwaves of the subject with the bearing modulation pattern.

7. The method according to claim 1, wherein the sensory stimulation comprises visual stimulation of the subject to entrain brainwaves of the subject with the modulation pattern.

8. The method according to claim 1, wherein said processing the brainwave activity patterns with an automated processor to determine parameters of the modulation pattern of the brainwave activity patterns comprises processing a sequence of distinct brainwave activity patterns over time to determine sequential sets of parameters of respective modulation patterns of the sequence of distinct brainwave activity patterns.

9. The method according to claim 8, wherein the sequence of distinct brainwave activity patterns comprise brainwave patterns associated with a sequence of sleep stages.

10. The method according to claim 1, further comprising determining a brainwave pattern of the subject concurrent with the sensory stimulation, wherein the sensory stimulus is further selectively modulated further in dependence on the concurrent determined brainwave pattern of the subject.

11. The method according to claim 1, further comprising determining a mental state of the subject concurrent with the sensory stimulation, wherein the sensory stimulus is further selectively modulated further in dependence on the concurrent determined mental state of the subject.

12. A method of changing a mental state in a subject comprising:

determining a sequence of brainwave patterns of a human donor;

processing the sequence of brainwave patterns with an automated processor to determine sequential sets of parameters of respective modulation patterns of the sequence of brainwave patterns bearing information;

storing the sequential sets of parameters in a memory;

stimulating the subject with a sensory stimulus selectively modulated over time dependent on the stored sequential sets of parameters, wherein the sensory stimulus comprises the information associated with the sequence of brainwave patterns and the sequential sets of parameters are stored in the memory prior to said stimulating.

13. The method according to claim 12, wherein at least one set of the parameters comprises a frequency and phase of the respective modulation pattern, and the respective sensory stimulus associated with the modulation pattern has characteristics corresponding to the frequency and phase.

14. The method according to claim 12, further comprising classifying respective brainwave patterns with at least one of a statistical classifier and a neural network.

15. The method according to claim 12, wherein the sequence of brainwave patterns comprises electroencephalographic brainwave patterns associated with a series of sleep stages.

16. The method according to claim 12, wherein the sensory stimulation comprises auditory stimulation of the subject with binaural beats to entrain brainwaves of the subject with the respective information associated with the sequence of brainwave patterns.

17. The method according to claim 12, wherein the sensory stimulation comprises visual stimulation of the subject to entrain brainwaves of the subject with the information associated with the sequence of brainwave patterns.

18. The method according to claim 12, further comprising determining a brainwave pattern of the subject concurrent with the sensory stimulation, wherein the sensory stimulus is further selectively modulated further in dependence on the concurrent determined brainwave pattern of the subject.

19. A system for changing a mental state in a subject comprising:

an input port configured to receive a sequence of brainwave patterns of a human donor;

at least one automated processor configured to process the sequence of brainwave patterns to determine sequential sets of parameters of respective modulation patterns of the sequence of brainwave activity patterns bearing information;

a memory configured to store the sequential sets of parameters;

a sensory stimulator configured to stimulate the subject with a sensory stimulus selectively modulated over time dependent on the stored sequential sets of parameters, wherein the sensory stimulus comprises the information associated with the sequence of brainwave patterns and the sequential sets of parameters are stored in the memory prior to stimulation of the subject.

20. The system according to claim 19, wherein the sensory stimulator comprises an auditory stimulator configured to stimulate the subject with a binaural beats sensory stimulus.

* * * * *